(12) United States Patent
Zhou et al.

(10) Patent No.: US 12,172,989 B2
(45) Date of Patent: Dec. 24, 2024

(54) HISTONE ACETYLTRANSFERASE (HAT) INHIBITOR AND USE THEREOF

(71) Applicants: SHANGHAI INSTITUTE OF MATERIA MEDICA, CHINESE ACADEMY OF SCIENCES, Shanghai (CN); Suzhou Institute of Materia Medica, Jiangsu (CN)

(72) Inventors: Bing Zhou, Shanghai (CN); Cheng Luo, Shanghai (CN); Hualiang Jiang, Shanghai (CN); Yaxi Yang, Shanghai (CN); Lianghe Mei, Jiangsu (CN); Wenchao Lu, Shanghai (CN); Senhao Xiao, Shanghai (CN); Shijie Chen, Shanghai (CN); Shili Wan, Shanghai (CN); Gang Qiao, Jiangsu (CN); Rukang Zhang, Shanghai (CN)

(73) Assignees: SHANGHAI INSTITUTE OF MATERIA MEDICA, CHINESE ACADEMY OF SCIENCES, Shanghai (CN); SUZHOU INSTITUTE OF MATERIA MEDICA, Jiangsu (CN)

( * ) Notice: Subject to any disclaimer, the term of this patent is extended or adjusted under 35 U.S.C. 154(b) by 382 days.

(21) Appl. No.: 17/075,206

(22) Filed: Oct. 20, 2020

(65) Prior Publication Data

US 2021/0101891 A1 Apr. 8, 2021
US 2022/0002278 A9 Jan. 6, 2022

Related U.S. Application Data

(63) Continuation of application No. PCT/CN2019/083190, filed on Apr. 18, 2019.

(30) Foreign Application Priority Data

Apr. 20, 2018 (CN) .......................... 201810360078
Aug. 31, 2018 (CN) .......................... 201811012724

(51) Int. Cl.

| | | |
|---|---|---|
| *C07D 413/06* | (2006.01) | |
| *C07D 403/06* | (2006.01) | |
| *C07D 403/14* | (2006.01) | |
| *C07D 413/14* | (2006.01) | |
| *C07D 417/06* | (2006.01) | |
| *C07D 471/04* | (2006.01) | |
| *C07D 491/107* | (2006.01) | |
| *C07D 495/04* | (2006.01) | |
| *C07D 495/10* | (2006.01) | |
| *C07D 498/04* | (2006.01) | |
| *C07D 498/10* | (2006.01) | |

(Continued)

(52) U.S. Cl.
CPC ......... *C07D 413/06* (2013.01); *C07D 403/06* (2013.01); *C07D 403/14* (2013.01); *C07D 413/14* (2013.01); *C07D 417/06* (2013.01); *C07D 471/04* (2013.01); *C07D 491/107* (2013.01); *C07D 495/04* (2013.01); *C07D 495/10* (2013.01); *C07D 498/04* (2013.01); *C07D 498/10* (2013.01); *C07D 513/04* (2013.01); *A61K 45/06* (2013.01)

(58) Field of Classification Search
CPC .. C07D 413/06; C07D 413/14; C07D 417/06; C07D 403/06; C07D 403/14; C07D 498/04; C07D 498/10; C07D 491/107; C07D 471/04; C07D 495/04; C07D 513/04

See application file for complete search history.

(56) References Cited

U.S. PATENT DOCUMENTS

2022/0087996 A1* 3/2022 Fan ....................... A61K 31/422

FOREIGN PATENT DOCUMENTS

WO  WO 2016/044770 A1    3/2016
WO  WO-2020/108500 A1 * 6/2020 ........... C07D 235/02

OTHER PUBLICATIONS

"Database Registry CAS." Aug. 3, 2004, retrieved from STN Database accession No. RN-721420-67-3.

(Continued)

*Primary Examiner* — Laura L Stockton
(74) *Attorney, Agent, or Firm* — Reinhart Boerner Van Deuren P.C.

(57) ABSTRACT

Disclosed is a histone acetyltransferase (HAT) inhibitor. Provided are a compound represented by the general formula I, a pharmaceutically acceptable salt, a stereoisomer, an enantiomer, a diastereoisomer, an atropisomer, a racemate, a polymorph, a solvate or an isotope-labeled compound (including deuterium substitution) thereof, a preparation method therefor, a pharmaceutical composition comprising same and use thereof in the treatment of various HAT-related diseases or conditions.

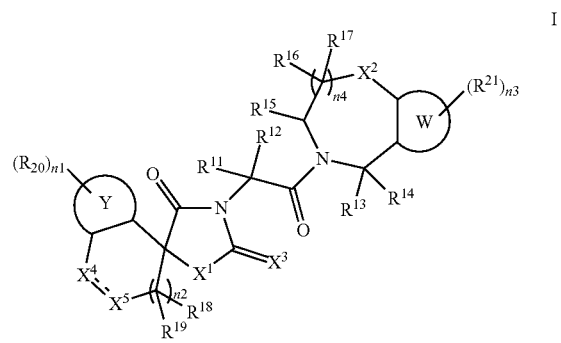

17 Claims, No Drawings

(51) Int. Cl.
*C07D 513/04* (2006.01)
*A61K 45/06* (2006.01)

(56) References Cited

OTHER PUBLICATIONS

"Database Registry CAS." Feb. 28, 2006, retrieved from STN Database accession No. RN-875422-74-5.
"Database Registry CAS." Mar. 24, 2006, retrieved from STN Database accession No. RN-877985-51-8.
"Database Registry CAS." Mar. 29, 2006, retrieved from STN Database accession No. RN-878458-26-5.
"Database Registry CAS." Mar. 29, 2006, retrieved from STN Database accession No. RN-878418-77-0.
"Database Registry CAS." Mar. 2, 2007, retrieved from STN Database accession No. RN-924417-81-2.
"Database Registry CAS." Sep. 21, 2008, retrieved from STN Database accession No. RN-1050766-02-3.
Aboeldahab et al., "Spirohydantoins and 1,2,4-triazole-3-carboxamide derivatives as inhibitors of histone deacetylase: Design, synthesis, and biological evaluation." *European Journal of Medicinal Chemistry*, Feb. 1, 2018, Amsterdam, NL, vol. 146, pp. 79-92.
Lasko et al., "Discovery of a selective catalytic p300/CBP inhibitor that targets lineage-specific tumors." *Nature*, Oct. 27, 2017, London, vol. 550, No. 7674, pp. 128-132.
Lopes Da Rosa et al., "A small molecule inhibitor of fungal histone acetyltransferase Rtt109." *Biorganic & Medicinal Chemistry Letters*, Apr. 4, 2013, Amsterdam, NL, vol. 23, No. 10, pp. 2853-2859.

* cited by examiner

HISTONE ACETYLTRANSFERASE (HAT) INHIBITOR AND USE THEREOF

CROSS REFERENCE TO RELATED APPLICATIONS

This application is a continuation of International Application No. PCT/CN2019/083190, filed Apr. 18, 2019, which claims priority to Chinese Application application Nos. 201810360078.2, filed Apr. 20, 2018, and 201811012724.2, filed Aug. 31, 2018.

TECHNICAL FIELD

The present invention relates to a histone acetyltransferase (HAT) inhibitor, and provides a compound represented by formula I, a pharmaceutically acceptable salt, stereoisomer, enantiomer, diastereomer, atropisomer, racemate, polymorphs, solvate or isotopically labeled compound (including deuterium substituted compound) thereof, a preparation method thereof, a pharmaceutical composition containing the same, and their use in treatment of various HAT-related diseases or disorders.

BACKGROUND OF ART

The DNA in the nucleus is wound and bound to histones in most of the time, and stored in the highly compressed chromatin at an inactive state. If the cell needs to activate some genes, the related genes (DNA fragments) are dissociated from histones with the aid of transcription factors.

One group of transcription factor families is histone acetyltransferases (HATs), which can be classified into five large families in terms of structure and activity:
  (1) PCAF/GNAT (p300/CBP associated factor, PCAF; GCN5-related N-acetyltransferases, GNAT), which is highly related to GCN5 in yeast HATs;
  (2) p300/CBP (including p270 and p470), which is a transcriptional coactivator;
  (3) TAF II p250 (TATA box-binding protein associated factor II), which is an important component of the basic transcription complex TAF II E;
  (4) SRC/ACTR (steroid hormone receptor coactivators, SRC; activator of the thyroid and retinoic-acid receptor, ACTR), which is a ligand-dependent nuclear receptor coactivator;
  (5) MYSF, including MOZ (monocytic leukemia zinc finger protein), Ybf2 (identical with something about silencing 2)/Sas3 (something about silencing 3), Sas2, Tip60 (trans-acting regulatory protein of HIV type 1 interacting protein 60 kDa) (Bazan, et al., Cell Cycle, 2008; Livengood, et al., journal of biological chemistry, 2002).

Among them, p300/CBP is one of the important macromolecular proteins in histone acetyltransferases. p300/CBP has a high degree of homology. Although p300/CBP is encoded by different genes, they have similar amino acid sequences and functions, belonging to the same class of proteins and are therefore considered to have the same function (Sadoul et al., Biochimie, 2008). p300/CBP interacts with a specific sequence activator and is absorbed into a promoter site, thereby participating in activation of many transcription factors (Chan et al., journal of cell science, 2001; Cook et al., Journal of Molecular Biology, 2011). p300/CBP itself also has acetyltransferase activity and can acetylate a variety of core histones and a variety of transcription factors.

It has been confirmed by more and more studies that p300/CBP mutation is closely related to a variety of human diseases, including diabetes, inflammation, and cardiac diseases (Karukurichi, et al., Bioorganic Chemistry, 2011). In particular, many malignant tumors discovered so far are accompanied with p300/CBP gene mutations to varying degrees (Gayther, et al., Nature Genetics, 2000). Therefore, p300/CBP has become an important potential medicinal target and has a high research and development enthusiasm in the industry, and many large domestic and foreign pharmaceutical companies have successively carried out research and development of new drugs targeting p300/CBP.

Recently, AbbVie Pharmaceuticals has developed a class of chiral spiro compounds (a representing compound thereof is A-485), which can compete with acetyl-CoA for binding to the catalytic active site of p300 and selectively inhibit proliferation of cell line-specific tumor cells such as castration resistant prostate cancer, showing excellent p300/CBP-targeting activity both in vivo and in vitro (References: Abbvie Inc., WO2016044770; Nature, 2017; ACS Med. Chem. Lett., 2018), this fully demonstrates the feasibility and great potential of p300/CBP target in drug development.

SUMMARY

An object of the present invention is to provide a histone acetyltransferase (HAT) inhibitor compound, a pharmaceutically acceptable salt, stereoisomer, enantiomer, diastereomer, atropisomer, racemate, polymorphs, solvate or isotopically labeled compound thereof.

Another object of the present invention is to provide a method of preparing the inhibitor compound.

Still another object of the present invention is to provide a pharmaceutical composition containing the inhibitor compound.

Still another object of the present invention is to provide use of the inhibitor compound in preparation of a medicament.

According to one embodiment of the present invention, provided is a compound represented by formula I, a pharmaceutically acceptable salt, stereoisomer, enantiomer, diastereomer, atropisomer, racemate, polymorphs, solvate or isotopically labeled compound thereof:

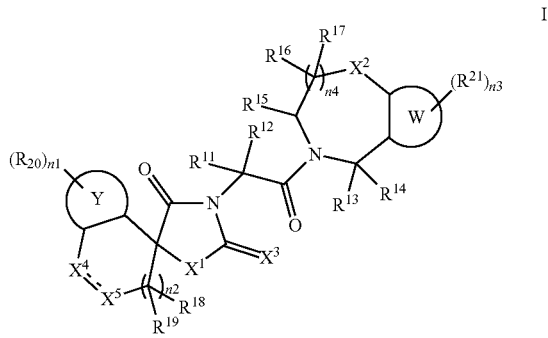

$X^1$ is independently —O—, —$NR^1$—, or —S—;
$R^1$ is independently hydrogen, $C_1$-$C_6$ alkyl, or $C_3$-$C_6$ cycloalkyl;
$X^2$ is independently —$C(R^2)(R^3)$—, —O—, —$N(R^4)$—, or —$S(O)_{n1}$—;
$R^2$ and $R^3$ are each independently hydrogen, deuterium, $C_1$-$C_6$ alkyl, $C_1$-$C_6$ haloalkyl, or $C_3$-$C_6$ cycloalkyl;

$R^4$ is independently hydrogen, $C_1$-$C_6$ alkyl, $C_3$-$C_6$ cycloalkyl, —C(=O)($C_1$-$C_6$ alkyl), —S(O)$_2$($C_1$-$C_6$ alkyl), —C(=O)($C_3$-$C_6$ cycloalkyl), or —S(O)$_2$($C_3$-$C_6$ cycloalkyl);

$X^3$ is independently O or NH;

~~~~~ is a single bond or a double bond, with the proviso that, when ~~~~~ is a single bond, $X^4$ is independently —C($R^5$)($R^6$)—, —O—, —C(=O)—, —N$R^7$—, or —S(O)$_{n1}$—; $X^5$ is independently —C($R^8$)($R^9$)—, —O—, —C(=O)—, —N$R^1$—, —S(O)$_{n1}$—, or not present; and when ~~~~~ is a double bond: $X^4$ is independently —C($R^5$)—; $X^5$ is independently —C(R')—;

$R^5$ and $R^6$ are each independently hydrogen, OH, halogen, CN, $C_1$-$C_6$ alkyl, $C_1$-$C_6$ haloalkyl, $C_3$-$C_6$ cycloalkyl, or $C_1$-$C_6$ alkoxy;

$R^8$ and $R^9$ are each independently hydrogen, OH, halogen, or $C_1$-$C_6$ alkyl;

$R^7$ is independently hydrogen, $C_1$-$C_6$ alkyl, or $C_3$-$C_6$ cycloalkyl;

$R^{10}$ is independently hydrogen, $C_1$-$C_6$ alkyl, or $C_3$-$C_6$ cycloalkyl;

Y is independently $C_6$-$C_{10}$ aromatic ring, $C_5$-$C_{10}$ heteroaromatic ring, and Y is independently unsubstituted or substituted with 1 or 2 $R^{20}$s;

$R^{11}$ and $R^{12}$ are each independently hydrogen, deuterium, $C_1$-$C_6$ alkyl, $C_1$-$C_6$ haloalkyl, or $C_3$-$C_6$ cycloalkyl;

$R^{13}$ and $R^{14}$ are each independently hydrogen, deuterium, $C_1$-$C_6$ alkyl, $C_1$-$C_6$ haloalkyl, or $C_3$-$C_6$ cycloalkyl;

$R^{16}$ and $R^{17}$ are each independently hydrogen, deuterium, $C_1$-$C_6$ alkyl, $C_1$-$C_6$ haloalkyl, or $C_3$-$C_6$ cycloalkyl;

$R^{18}$ and $R^{19}$ are each independently hydrogen, halogen, or $C_1$-$C_6$ alkyl;

$R^{15}$ is independently hydrogen, $C_1$-$C_6$ alkyl substituted with 0 to 2 $R^a$s, $C_1$-$C_6$ haloalkyl, or $M^a$;

wherein, $R^a$ is independently $C_1$-$C_6$ alkyl, $C_2$-$C_6$ alkenyl, $C_2$-$C_6$ alkynyl, halogen, $C_1$-$C_6$ haloalkyl, $C_1$-$C_6$ haloalkoxy, —CN, hydroxyl, —O$M^e$, —S$M^e$, —S(O)$_2$$M^e$, —C(O)N$M^f$$M^g$, —N$M^f$$M^g$, —N($M^e$)C(O)$M^h$, —N($M^e$)S(O)$_2$$M^h$, —N($M^e$)C(O)O$M^h$, —N($M^e$)C(O)N$M^f$$M^g$, or $M^b$ at each occurrence;

$R^{20}$ is independently hydrogen, halogen, —OH, —CN, —COOH, $C_1$-$C_6$ alkyl, $C_1$-$C_6$ alkoxy, $C_1$-$C_6$ haloalkoxy, $C_2$-$C_{10}$ alkoxyalkyl, $C_4$-$C_{20}$ alkoxyalkylalkynyl, $C_2$-$C_6$ haloalkoxyalkyl, $C_1$-$C_6$ hydroxyalkyl, $C_3$-$C_{10}$ hydroxyalkylalkynyl, $C_2$-$C_{10}$ hydroxyalkynyl, —B($R^b$)($R^d$), —S(O)$_{n1}$$R^c$, —N($R^c$)$_2$, —C(=O)N($R^c$)$_2$, —NHC(=O)$R^c$, —NHC(=O)O$R^c$, —NHC(=O)C(=O)N($R^c$)$_2$, —NHC(=O)C(=O)O$R^c$, —NHC(=O)N($R^c$)$_2$, —NHC(=O)N$R^c$C(=O)N($R^c$)$_2$, —NHC(=O)N$R^c$S(O)$_2$O$R^c$, —NHC(=O)N$R^c$S(O)$_2$N($R^c$)$_2$, —NHC(=S)N($R^c$)$_2$—NHC(=NC≡N)N$R^c$, —NHC(=NC≡N)S$R^c$, —NHS(O)$_{n1}$$R^c$, $M^c$, —($C_1$-$C_6$ alkylene)-B($R^b$)($R^d$), —($C_1$-$C_6$ alkylene)-S(O)$_{n1}$$R^c$, —($C_1$-$C_6$ alkylene)-N($R^c$)$_2$, —($C_1$-$C_6$ alkylene)-C(=O)N($R^c$)$_2$, —($C_1$-$C_6$ alkylene)-NHC(=O)$R^c$, —($C_1$-$C_6$ alkylene)-NHC(=O)O$R^c$, —($C_1$-$C_6$ alkylene)-NHC(=O)C(=O)N($R^c$)$_2$, —($C_1$-$C_6$ alkylene)-NHC(=O)N($R^c$)$_2$, —($C_1$-$C_6$ alkylene)-NHC(=O)N$R^c$C(=O)N($R^c$)$_2$, —($C_1$-$C_6$ alkylene)-NHC(=O)N$R^c$S(O)$_2$O$R^c$, —($C_1$-$C_6$ alkylene)-NHC(=O)N$R^c$S(O)$_2$N($R^c$)$_2$, —($C_1$-$C_6$ alkylene)-NHC(=S)N($R^c$)$_2$, —($C_1$-$C_6$ alkylene)-NHC(=N—C≡N)N$R^c$, —($C_1$-$C_6$ alkylene)-NHC(=N—C≡N)S$R^c$, —($C_1$-$C_6$ alkylene)-NHS(O)$_{n1}$$R^c$, —($C_1$-$C_6$ alkylene)-$M^c$, —CH=CH—($C_1$-$C_6$ alkyl), —CH=CH-$M^c$, —O$M^c$, —S$M^c$, or —N($R^c$)$M^c$ at each occurrence;

$R^b$ and $R^d$ are each independently hydrogen, hydroxyl, or $C_1$-$C_6$ alkyl;

$R^c$ is independently hydrogen, $C_1$-$C_6$ alkyl, $C_6$-$C_{10}$ aryl, 5-10 membered heteroaryl, 3-10 membered non-aromatic heterocyclic group, $C_3$-$C_{10}$ cycloalkyl, or $C_5$-$C_{10}$ cycloalkenyl, which are each independently unsubstituted or substituted with 1 or 2 groups of amino, hydroxyl, methoxy, $C_1$-$C_6$ alkyl, $C_3$-$C_{10}$ cycloalkyl, or CN;

$M^a$, $M^b$ and $M^c$ are each independently $C_6$-$C_{10}$ aryl, $C_5$-$C_{10}$ heteroaryl, $C_3$-$C_{10}$ non-aromatic heterocyclic group, $C_3$-$C_{10}$ cycloalkyl, or $C_3$-$C_{10}$ cycloalkenyl, which are each independently unsubstituted or substituted with 1-2$M^d$s;

$M^d$ is independently $C_1$-$C_6$ alkyl, $C_2$-$C_6$ alkenyl, $C_2$-$C_6$ alkynyl, halogen, $C_1$-$C_6$ haloalkyl, —CN, oxo, —O$M^e$, —OC(O)$M^h$, —OC(O)N$M^f$$M^g$, —S$M^e$, —S(O)$_2$$M^e$, —S(O)$_2$N$M^f$$M^g$, —C(O)$M^e$, —C(O)-5-10-membered monocyclic heterocyclic ring, —C(O)-5-10-membered monocyclic heteroaryl, —C(O)O$M^e$, —C(O)N$M^f$$M^g$, —N$M^f$$M^g$, —N($M^e$)C(O)$M^h$, —N($M^e$)S(O)$_2$$M^h$, —N($M^e$)C(O)O$M^h$, —N($M^e$)C(O)N$M^f$$M^g$, —($C_1$-$C_6$ alkylene)-O$M^e$, —($C_1$-$C_6$ alkylene)-OC(O)$M^h$, —($C_1$-$C_6$ alkylene)-OC(O)N$M^f$$M^g$, —($C_1$-$C_6$ alkylene)-S(O)$_2$$M^e$, —($C_1$-$C_6$ alkylene)-S(O)$_2$N$M^f$$M^g$, —($C_1$-$C_6$ alkylene)-C(O)$M^e$, —($C_1$-$C_6$ alkylene)-C(O)O$M^e$, —($C_1$-$C_6$ alkylene)-C(O)N$M^f$$M^g$, —($C_1$-$C_6$ alkylene)-N$M^f$$M^g$, —($C_1$-$C_6$ alkylene)-N($M^e$)C(O)$M^h$, —($C_1$-$C_6$ alkylene)-N($M^e$)S(O)$_2$$M^h$, —($C_1$-$C_6$ alkylene)-N($M^e$)C(O)O$M^h$, —($C_1$-$C_6$ alkylene)-N($M^e$)C(O)N$M^f$$M^g$, or —($C_1$-$C_6$ alkylene)-CN at each occurrence;

W is independently $C_6$-$C_{10}$ aromatic ring, $C_5$-$C_{10}$ heteroaromatic ring, and W is independently unsubstituted or substituted with 1, 2, or 3 $R^{21}$s;

$R^{21}$ is each independently $C_1$-$C_6$ alkyl, halogen, $C_1$-$C_6$ haloalkyl, $C_1$-$C_6$ haloalkoxy, $C_3$-$C_6$ cycloalkyl, —O$M^e$, —OC(O)$M^h$, —OC(O)N$M^f$$M^g$, —S$M^e$, —S(O)$_2$$M^e$, —S(O)$_2$N$M^f$$M^g$, —C(O)$M^e$, —C(O)O$M^e$, —C(O)N$M^f$$M^g$, —N$M^f$$M^g$, —N($M^e$)C(O)$M^h$, —N($M^e$)S(O)$_2$$M^h$, —N($M^e$)C(O)O$M^h$ and —N($M^e$)C(O)N$M^f$$M^g$ at each occurrence;

$M^e$, $M^f$, and $M^g$ are independently hydrogen, $C_1$-$C_6$ alkyl, $C_1$-$C_6$ haloalkyl, or $C_3$-$C_6$ cycloalkyl at each occurrence; and $M^h$ is independently $C_1$-$C_6$ alkyl, $C_1$-$C_6$ haloalkyl, or $C_3$-$C_6$ cycloalkyl at each occurrence;

n1 and n2 are independently 0, 1 or 2 at each occurrence;

n3 and n4 are independently 0, 1, 2 or 3 at each occurrence.

Preferably, the compound of formula I is selected from the group consisting of the compounds represented by formulae Ia and Ib:

Ia

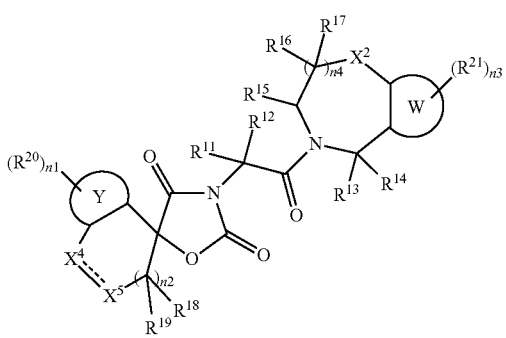
Ib

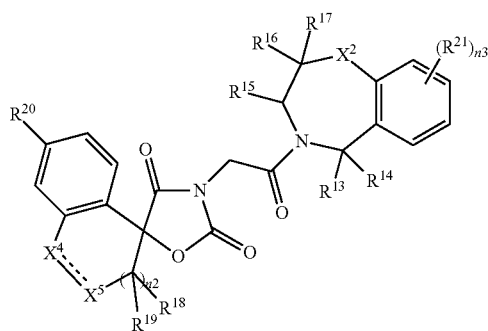
If wherein ~~~~ is a single bond or a double bond;

$R^{11}$ to $R^{21}$, $X^2$, Y, W, $X^4$, $X^5$, n1 to n4 are the same as defined in the formula I described above.

Preferably, the compound of formula I is selected from the group consisting of the compounds of formulae Ic, Id, Ie, and If:

wherein ~~~~ is a single bond or a double bond;

$R^{11}$ to $R^{21}$1, $X^2$, $X^4$, $X^5$, n1 to n4 are the same as defined in the formula I described above.

Preferably, the compound of formula I is selected from the group consisting of the compounds represented by formulae Ig and Ih:

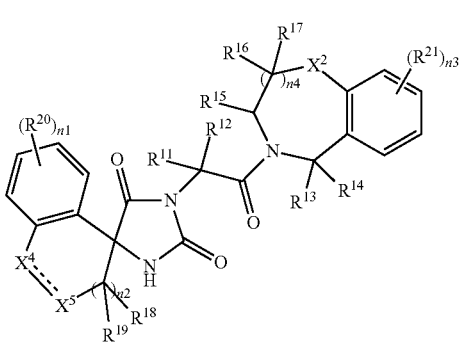
Ic

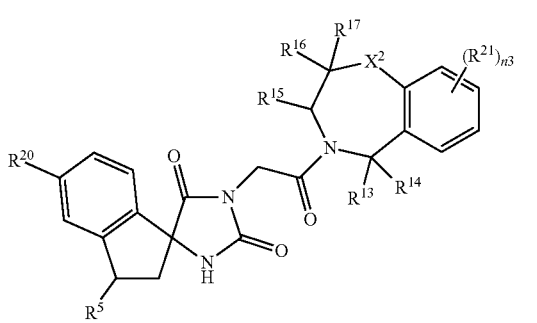
Ig

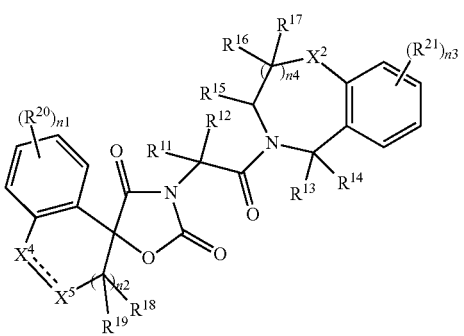
Id

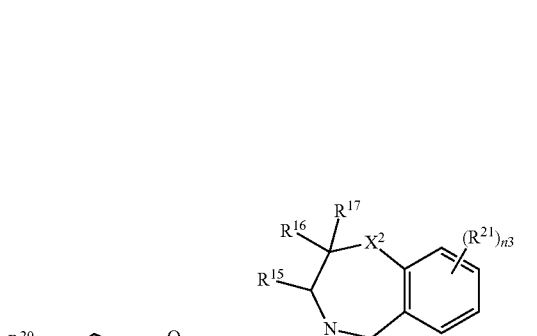
Ih

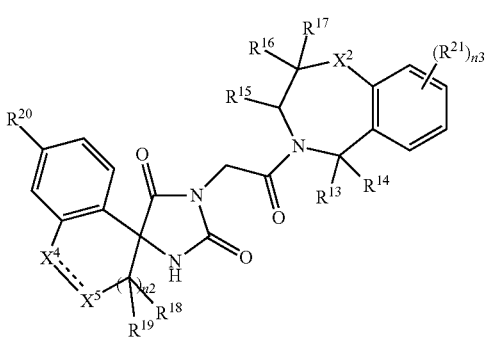
Ie wherein $R^5$ is hydrogen, halogen or $C_1$-$C_6$ alkyl;

$R^{13}$ to $R^{17}$, $R^{20}$, $R^{21}$, $X^2$, and n3 are the same as defined in the formula I described above.

Preferably, the compound of formula I is selected from the group consisting of the compounds represented by formulae Ii and Ij:

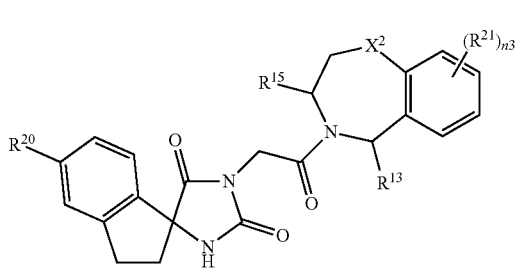

Ii

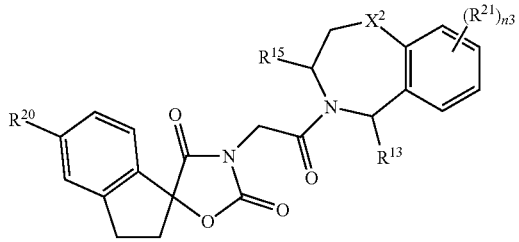

Ij wherein, $R^{13}$ is hydrogen, $C_1$-$C_6$ alkyl, or $C_3$-$C_6$ cycloalkyl;
$X^2$ is $CH_2$, O, —S(O)$_{n1}$—, or —N($R^4$)—;
$R^{15}$, $R^{20}$, $R^{21}$, $R^4$, n1 and n3 are the same as defined in the formula I described above.

Preferably, the compound of formula I is selected from the group consisting of the compounds represented by formulae Ik and Il:

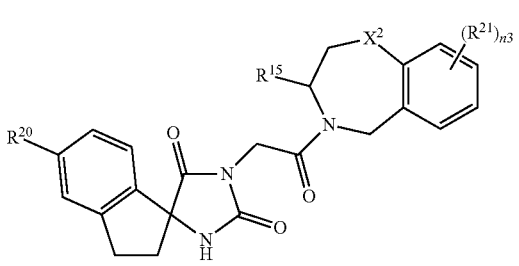

Ik

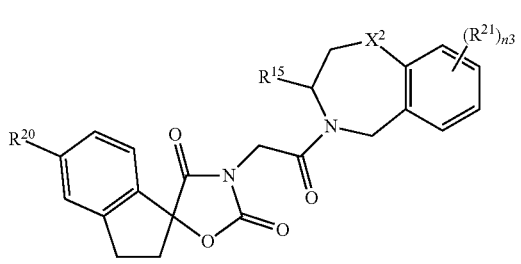

Il wherein, $X^2$ is $CH_2$, O, S or —N($M^e$)-;
$R^{21}$ is $C_1$-$C_6$ alkyl, halogen, $C_1$-$C_6$ haloalkyl, $C_1$-$C_6$ haloalkoxy, $C_1$-$C_6$ alkoxy, $C_3$-$C_6$ cycloalkyl;
n3 is 0, 1 or 2;
$R^{15}$ is $C_1$-$C_6$ alkyl, $C_3$-$C_6$ cycloalkyl, or $C_1$-$C_6$ haloalkyl;
$R^{20}$ is the same as defined in the formula I described above.

More preferably, in formulae Ik or Il,
$X^2$ is $CH_2$, O, S or —N(Me)-;
$R^{21}$ is halogen;
n3 is 0, 1 or 2;
$R^{15}$ is cyclopropyl, methyl, ethyl, propyl, isopropyl, or $CF_3$;

$R^{20}$ is

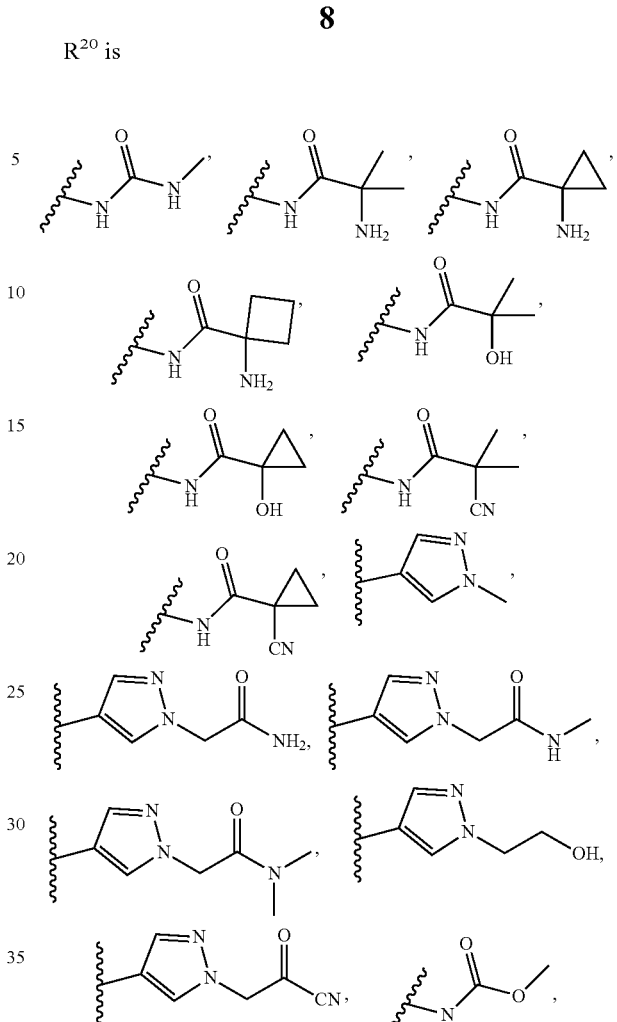

or —NHC(=O)($C_1$-$C_6$ alkyl).

Preferably, the compound of formula I is selected from the group consisting of the compounds of the formulae Im, In, Io, and Ip:

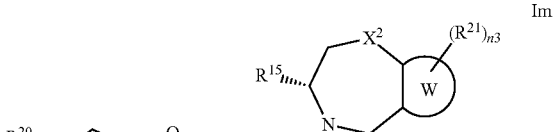

Im

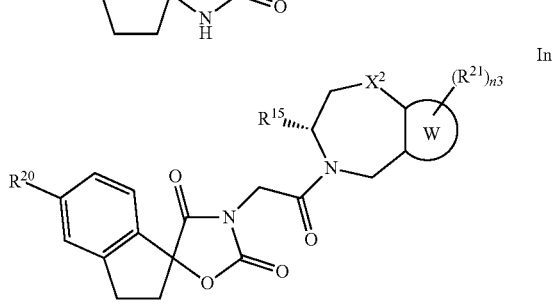

In

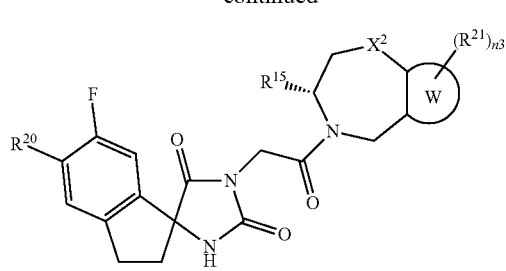
Io
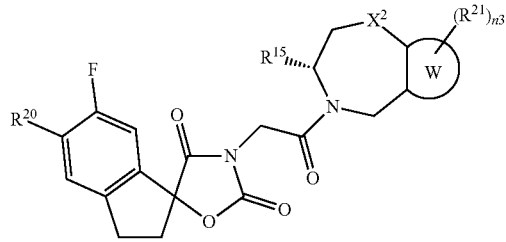
Ip
wherein, $X^2$ is $CH_2$, O, —S(O)$_{n1}$—, or —N(R$^4$)—;
R$^{15}$, R$^{20}$, R$^{21}$, R$^4$, n1 and n3 are the same as defined in the formula I described above;
W is a benzene ring or a $C_5$-$C_6$ heteroaromatic ring.
Preferably, the compound of formula I is selected from the group consisting of
SYY-B001
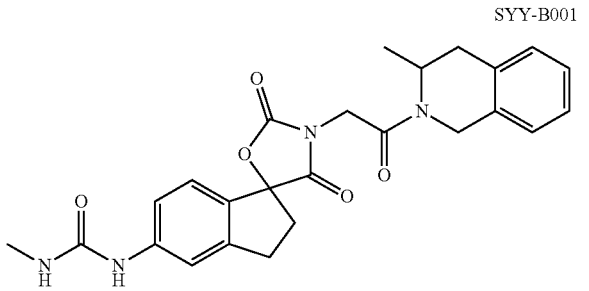
SYY-B003
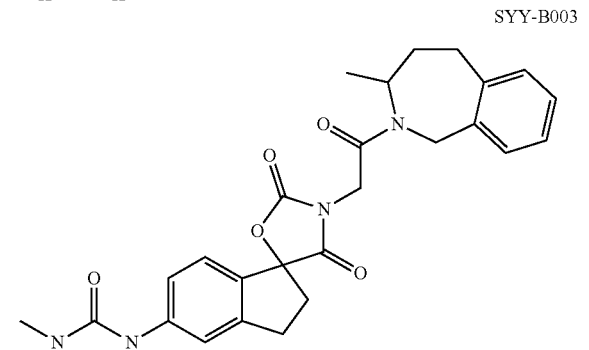
SYY-B009
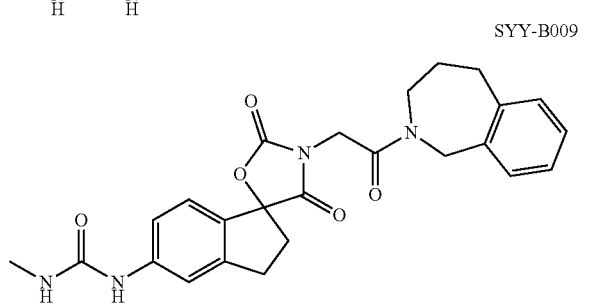
SYY-B010
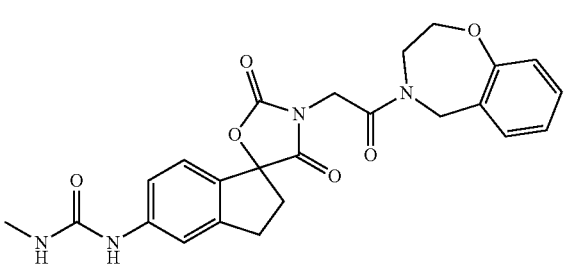
SYY-B012-1
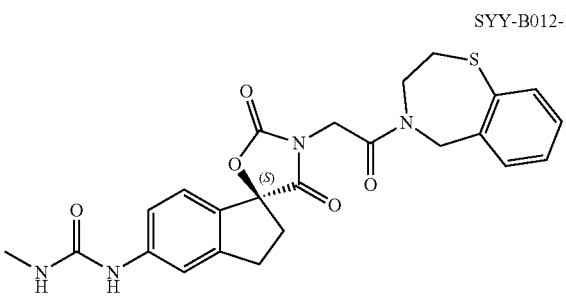
SYY-B012-2
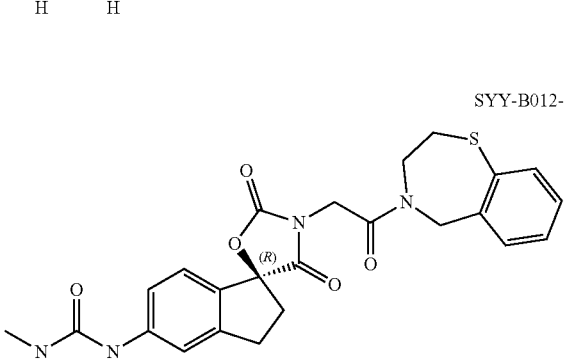
SYY-B013
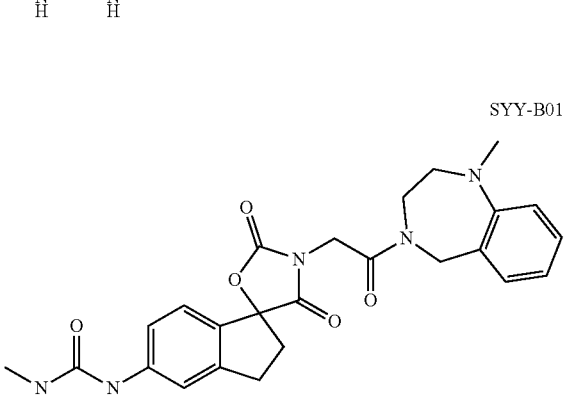
SYY-B014-1
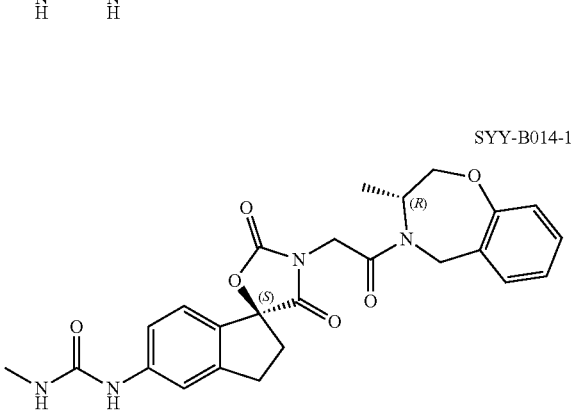

SYY-B014-2
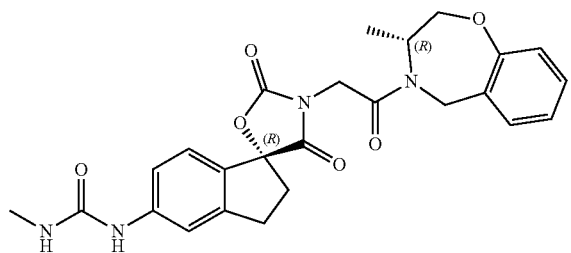
SYY-B015-1
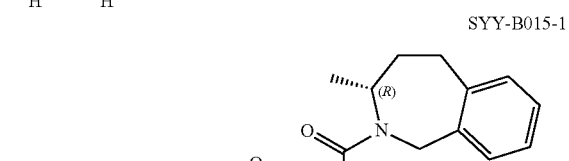
SYY-B015-2
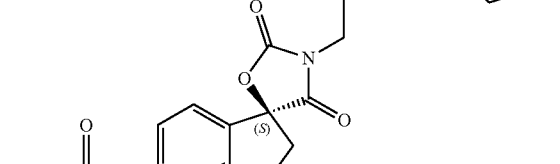
SYY-B016-1
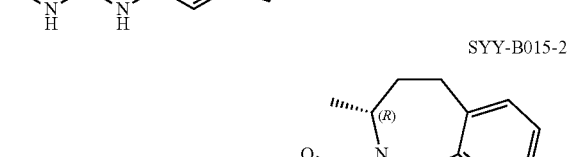
SYY-B016-2
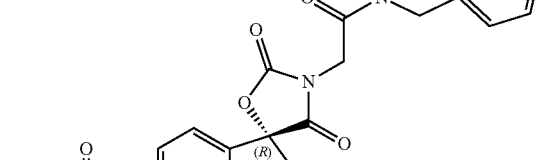
SYY-B017-1

SYY-B017-2
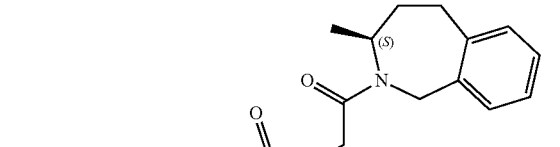
SYY-B018-1
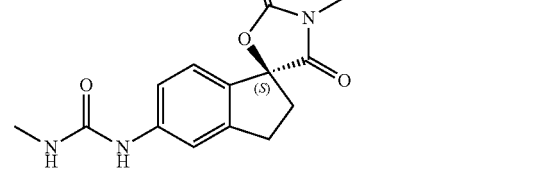
SYY-B018-2
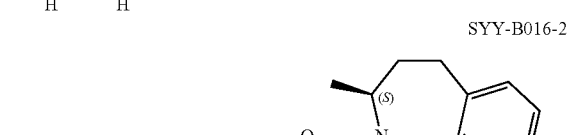

SYY-B019-1
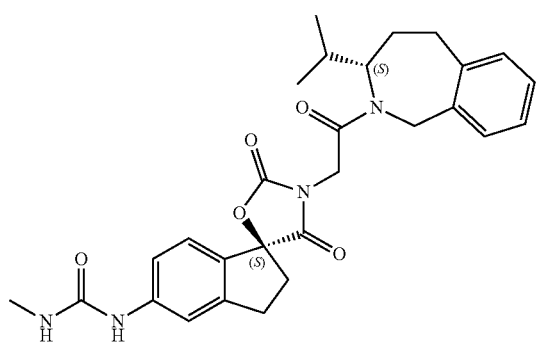
SYY-B021-1
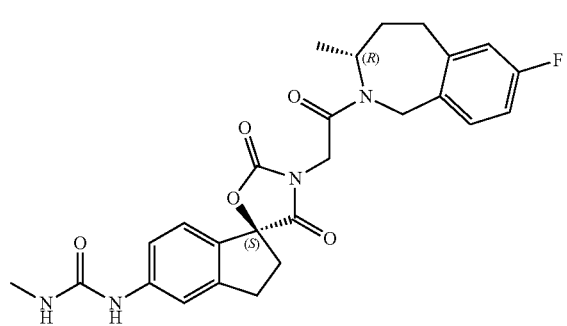
SYY-B019-2
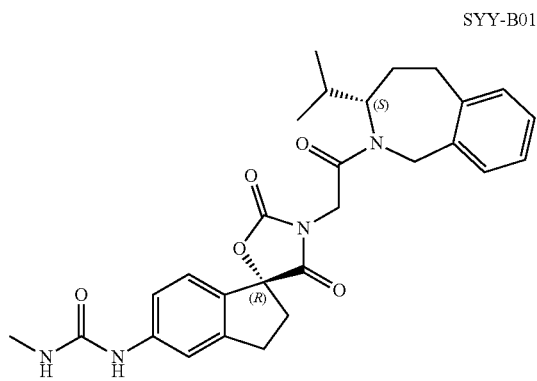
SYY-B021-2
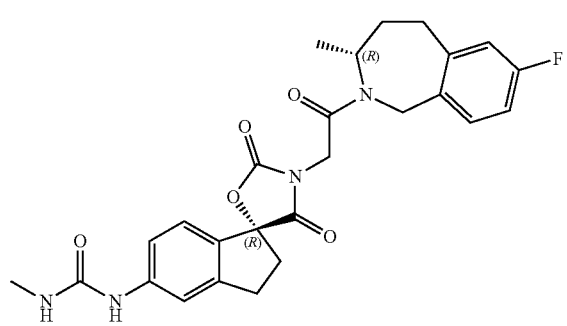
SYY-B020-1
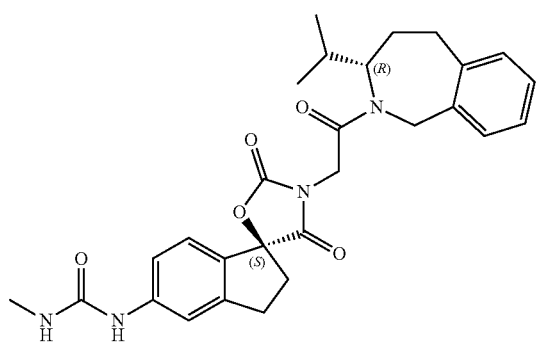
SYY-B022-1
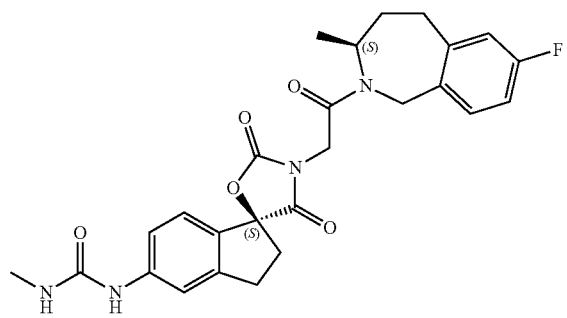
SYY-B020-2
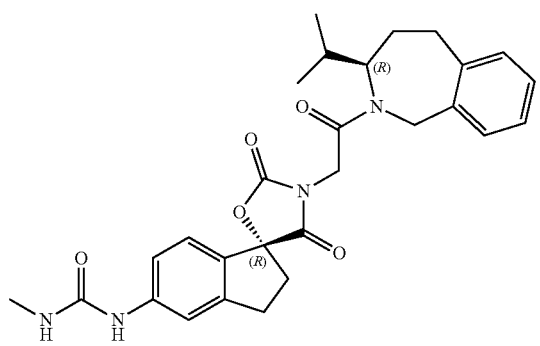
SYY-B022-2
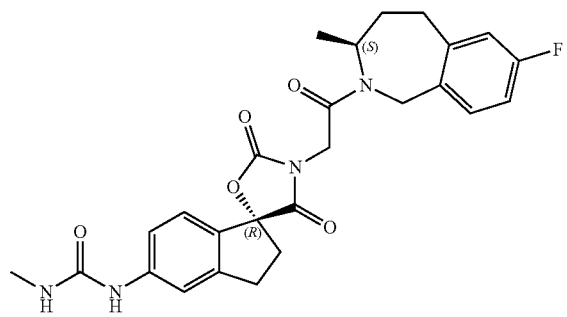

SYY-B023-1
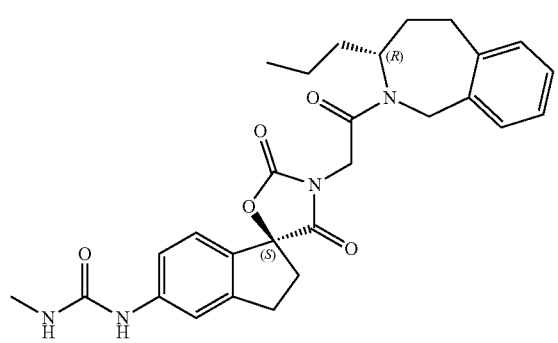
SYY-B025-1
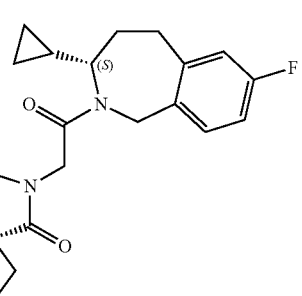
SYY-B023-2
SYY-B025-2
SYY-B024-1
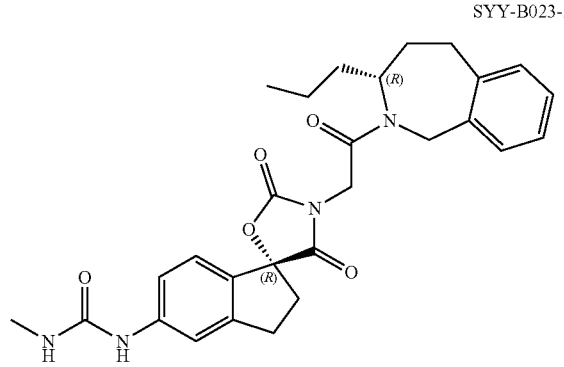
SYY-B026-1
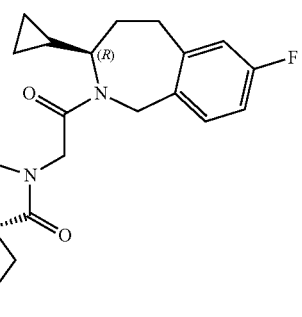
SYY-B024-2
SYY-B026-2
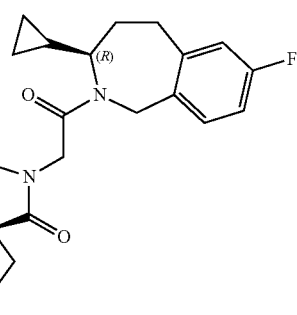
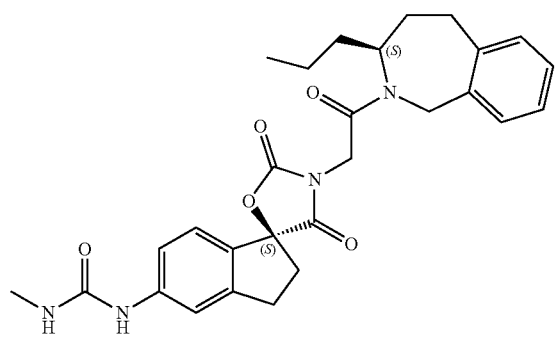

-continued
SYY-B027-1
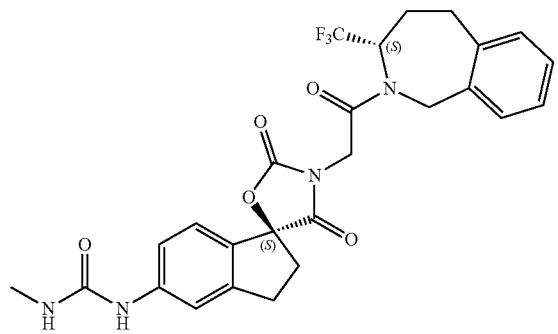
SYY-B029-1
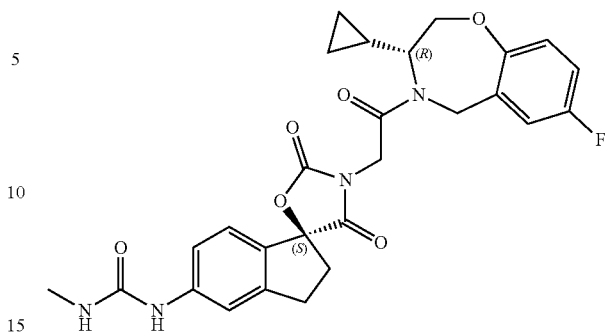
SYY-B027-2
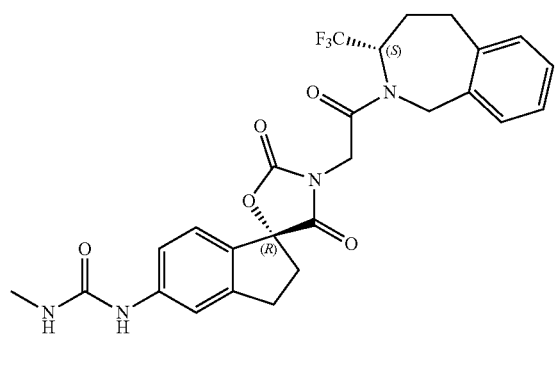
SYY-B029-2
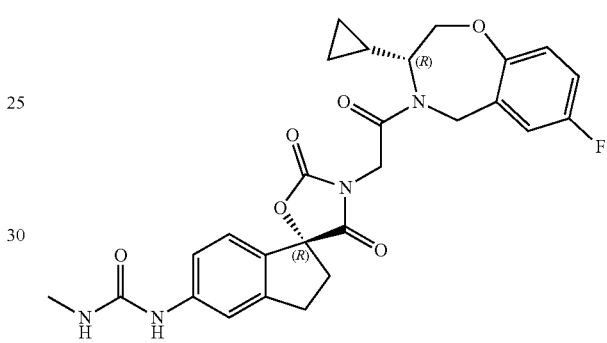
SYY-B028-1
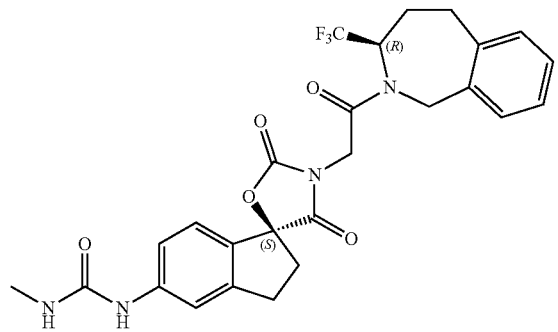
SYY-B030-1
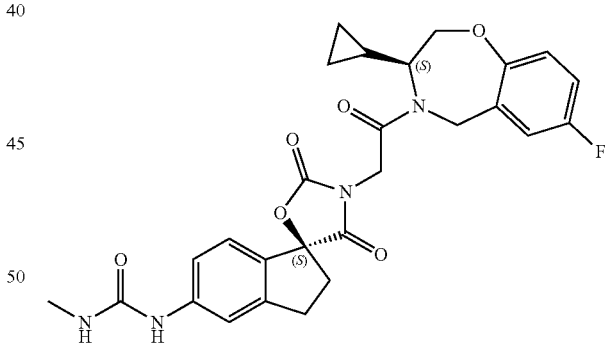
SYY-B028-2
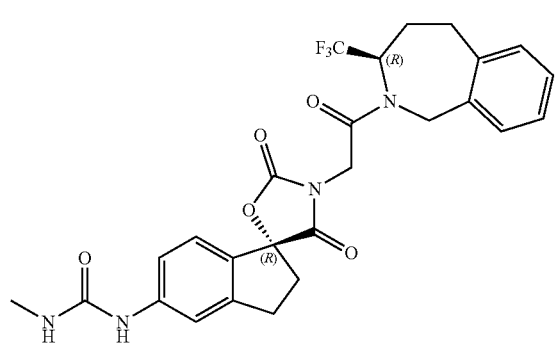
SYY-B030-2
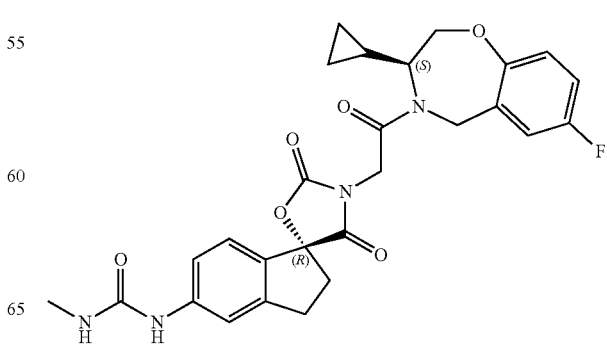

19
-continued
SYY-B031-1
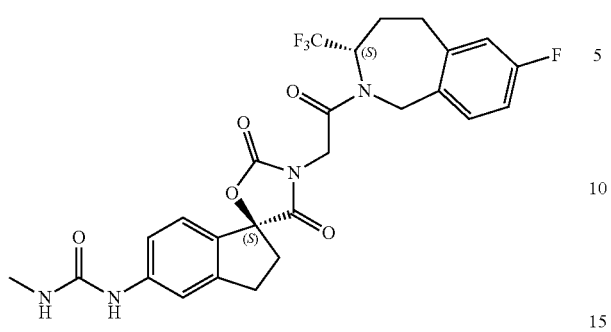
SYY-B031-2
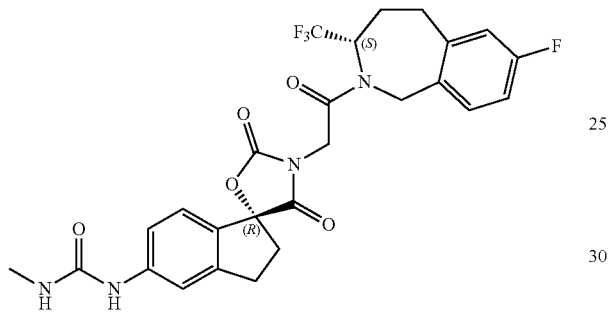
SYY-B032-1
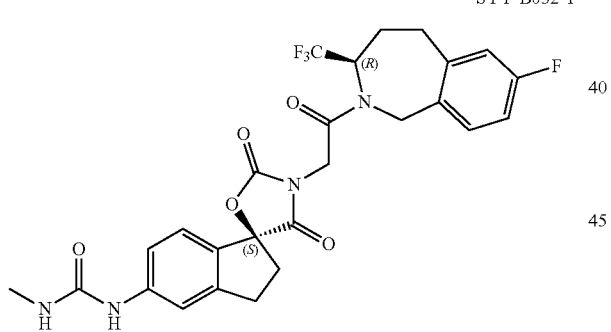
SYY-B032-2
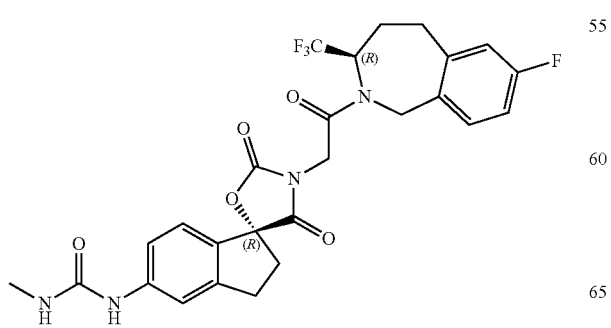
20
-continued
SYY-B033-1
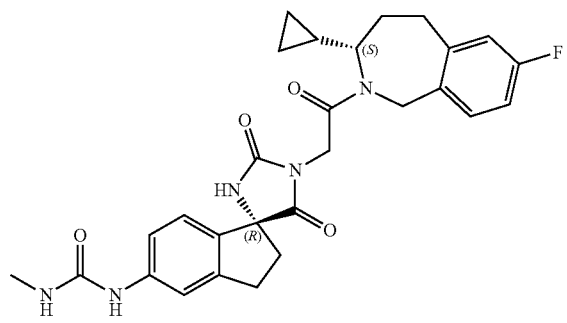
SYY-B033-2
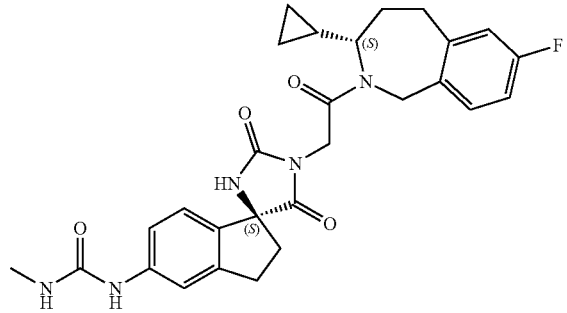
SYY-B034-1
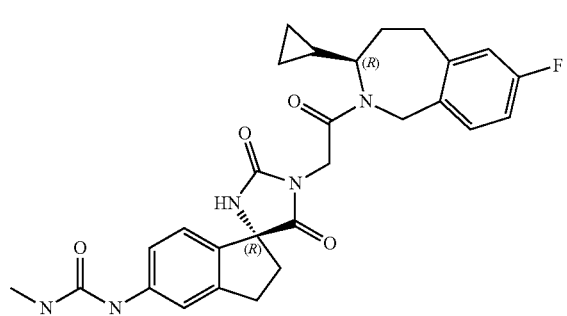
SYY-B034-2
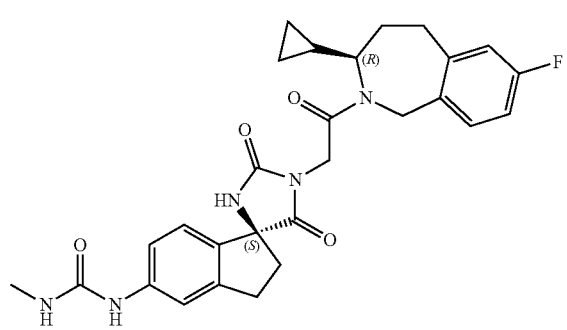

SYY-B035-1
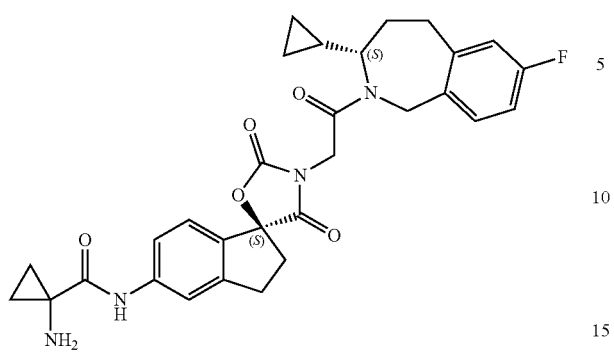
SYY-B037-1
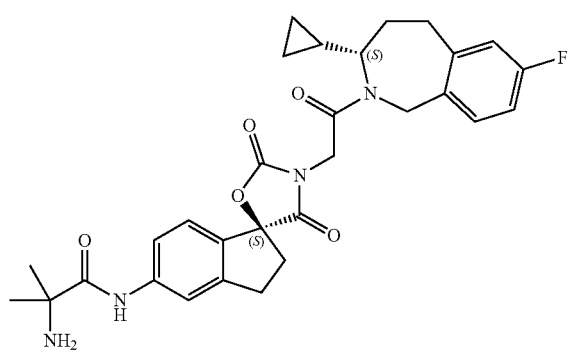
SYY-B035-2
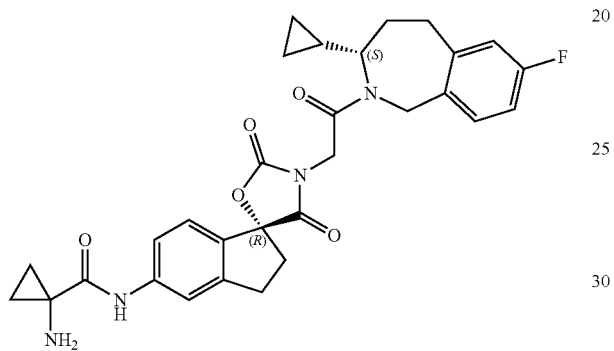
SYY-B037-2
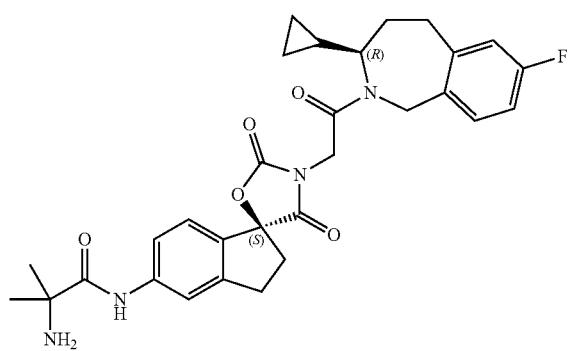
SYY-B036-1
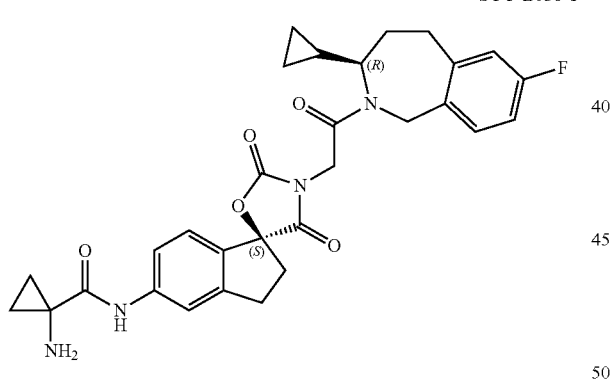
SYY-B038-1
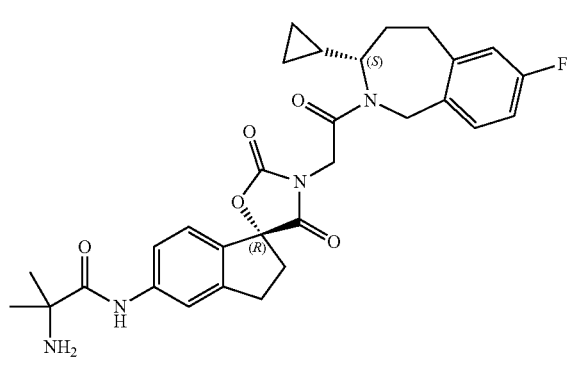
SYY-B036-2
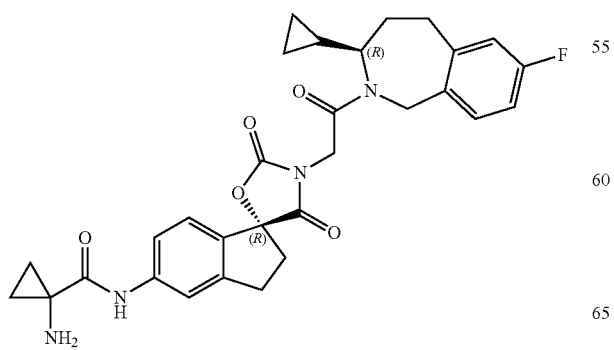
SYY-B038-2
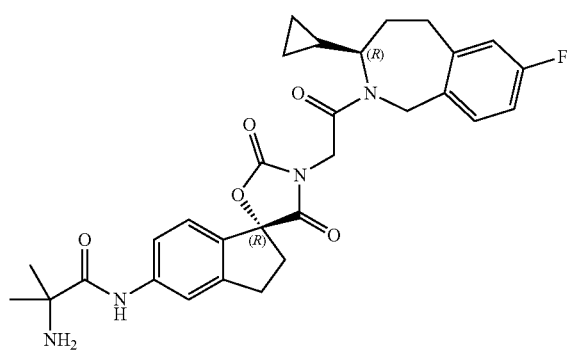

SYY-B039-1
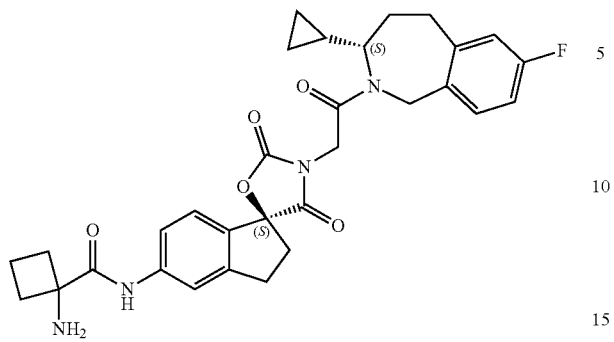
SYY-B041-1
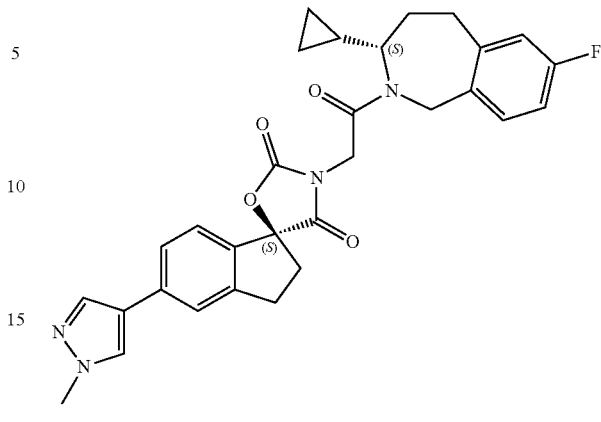
SYY-B039-2
SYY-B041-2
SYY-B040-1

SYY-B042-1
SYY-B040-2

-continued
SYY-B042-2
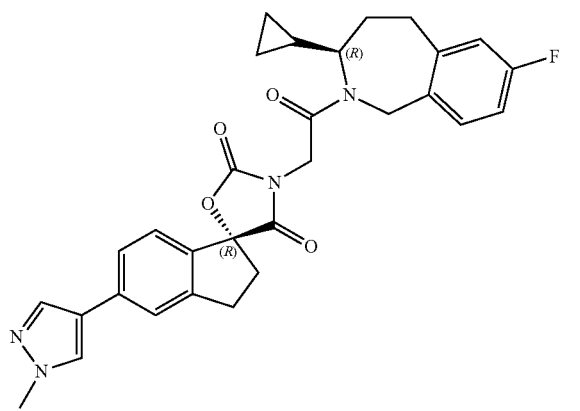
SYY-B043-1
SYY-B043-2

SYY-B044-1
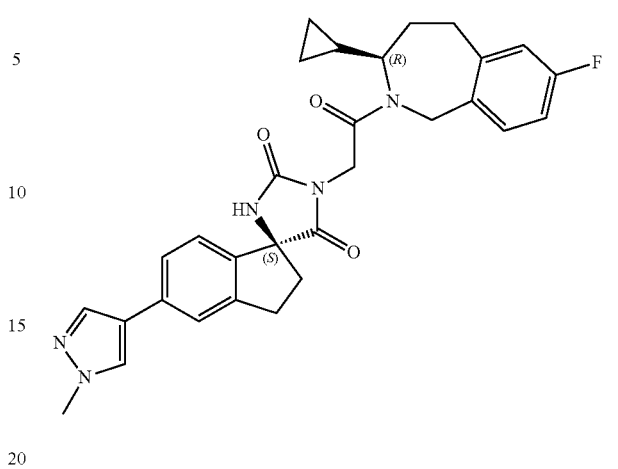
SYY-B044-2
SYY-B045
SYY-B046-1

SYY-B046-2
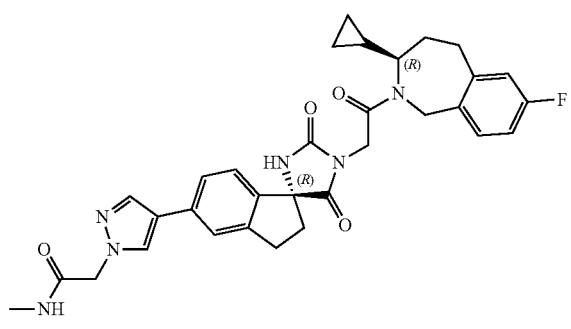
ZB-P-04
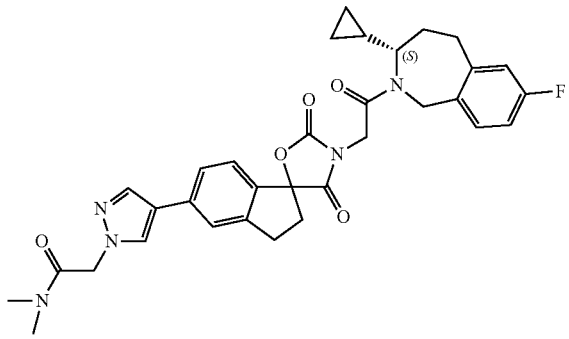
ZB-P-01
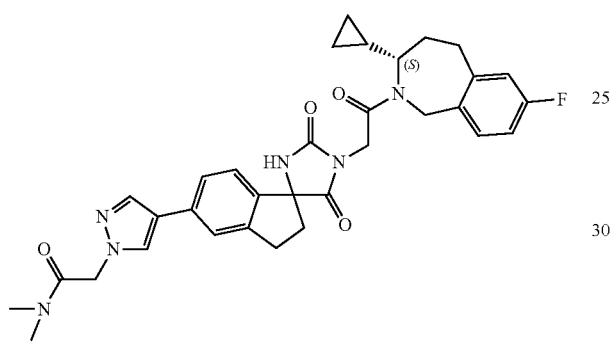
ZB-P-05
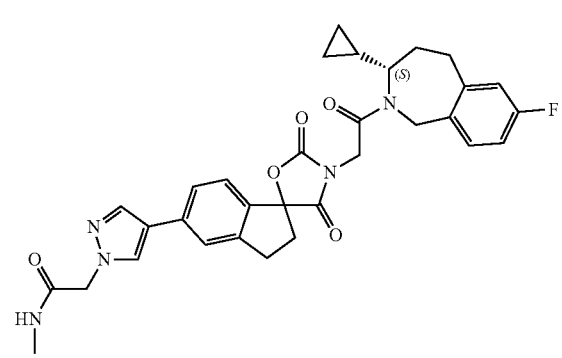
ZB-P-02
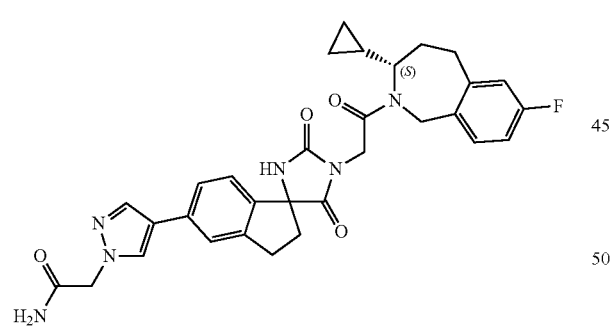
ZB-P-06
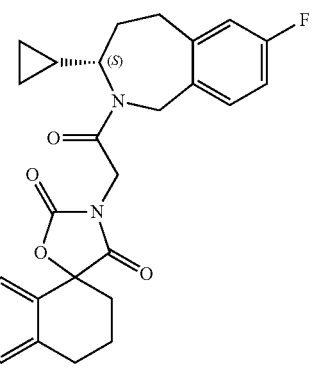
ZB-P-03
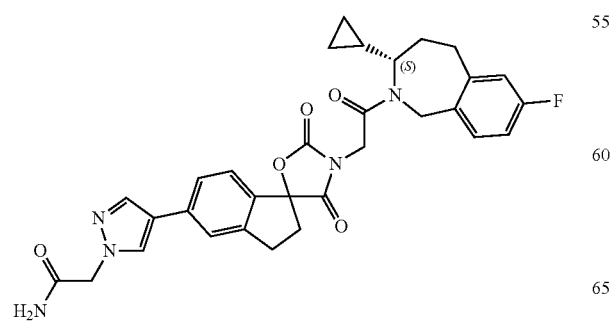
ZB-P-07
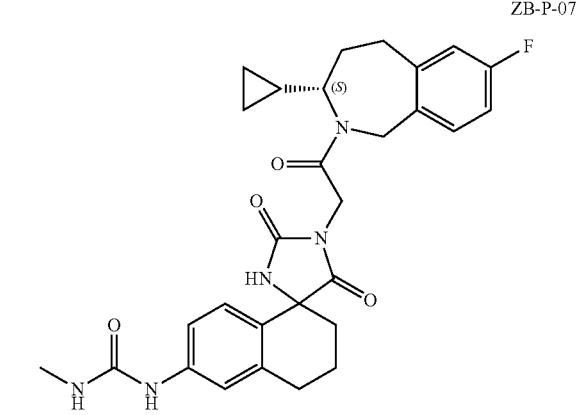

ZB-P-08
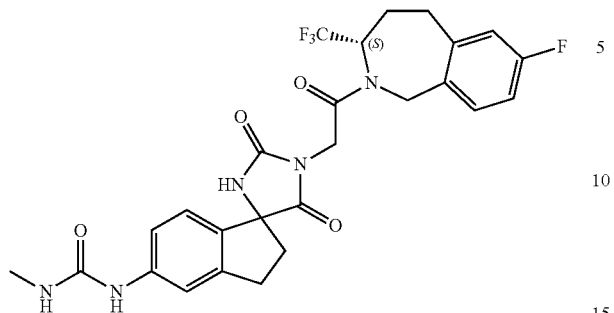
ZB-P-12
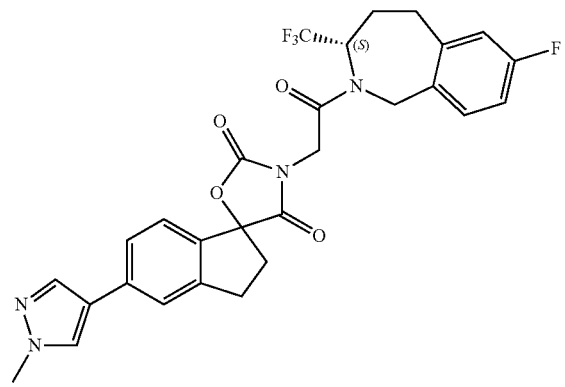
ZB-P-09
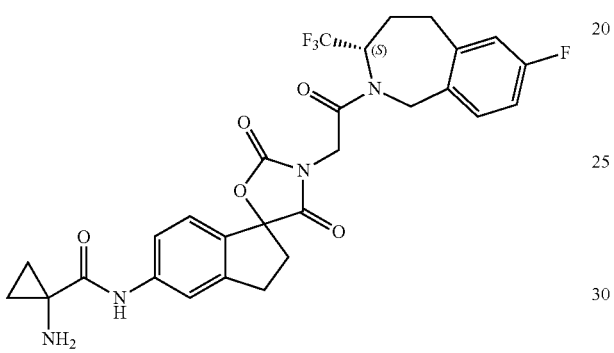
ZB-P-13
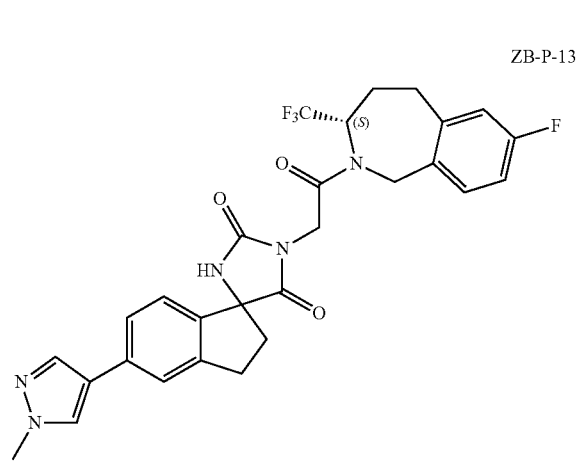
ZB-P-10
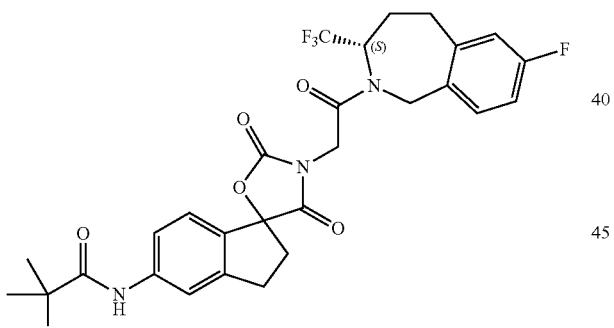
ZB-P-14
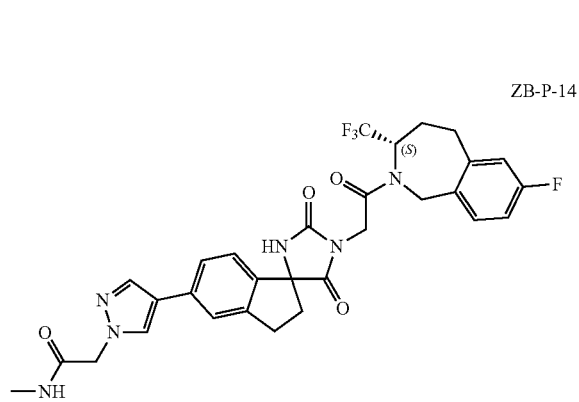
ZB-P-11
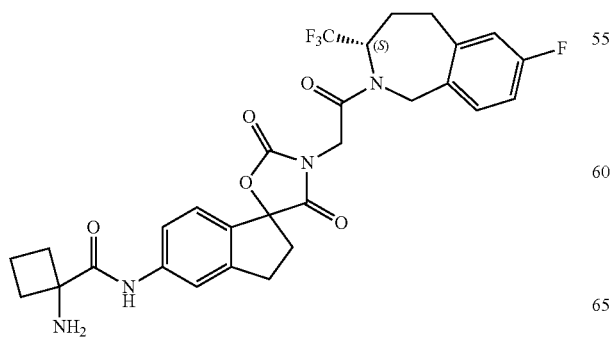
ZB-P-15
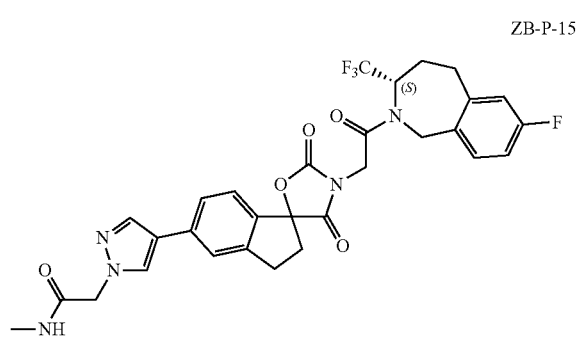

-continued
ZB-P-16
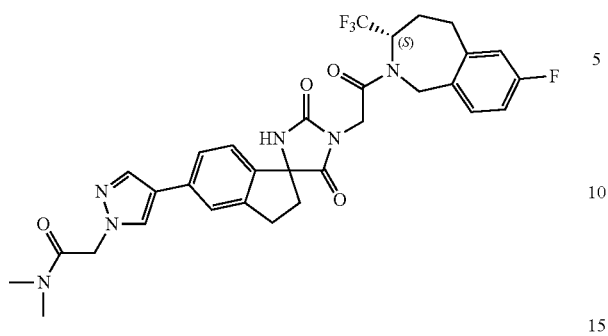
ZB-P-20
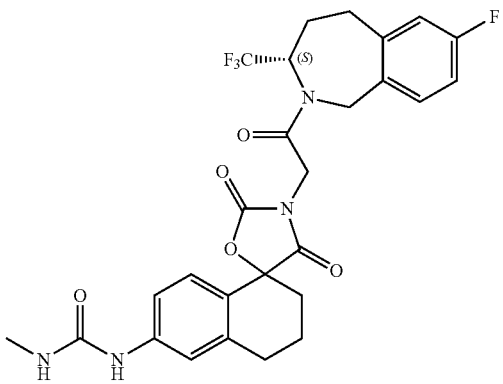
ZB-P-17
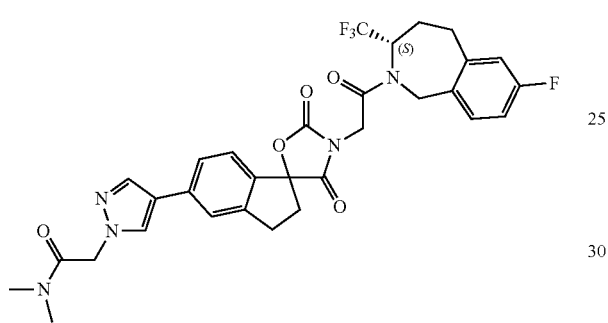
SYY-B033
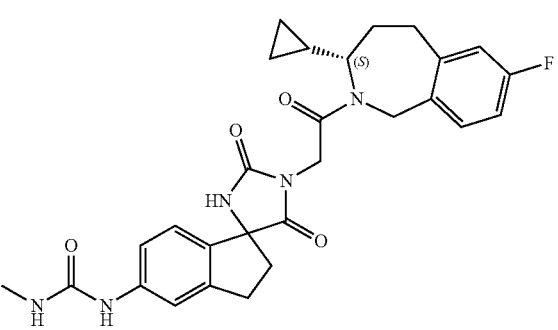
ZB-P-18
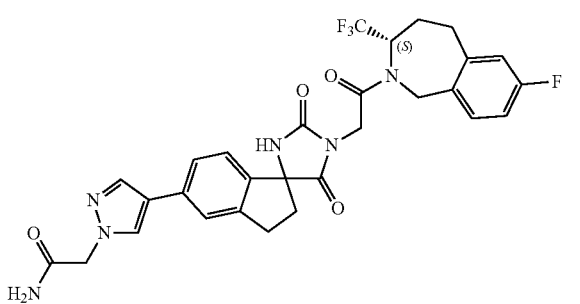
SYY-B043
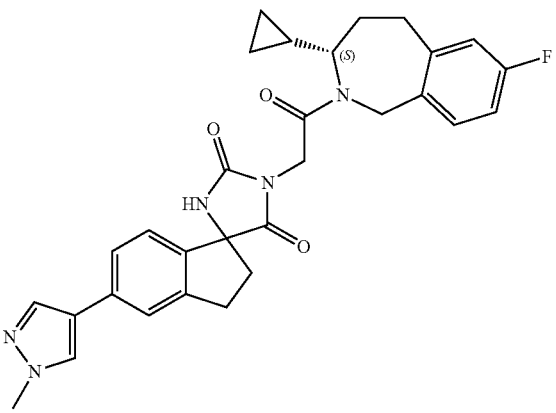
ZB-P-19
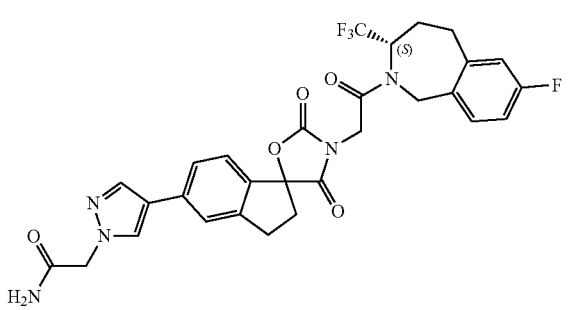
SYY-B045
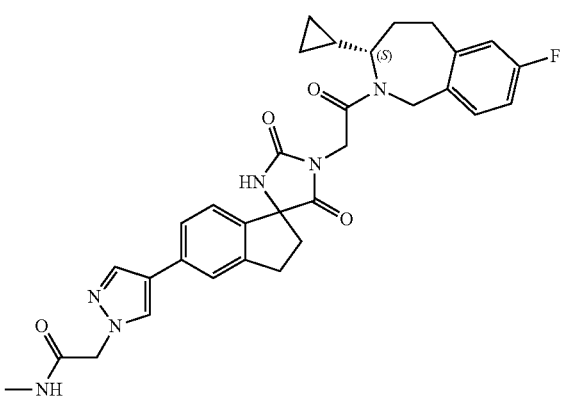

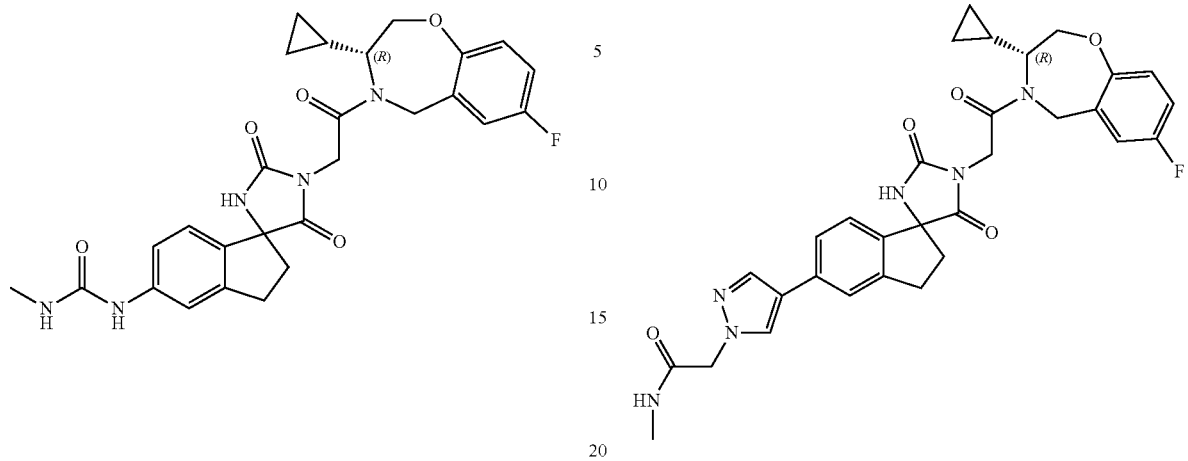
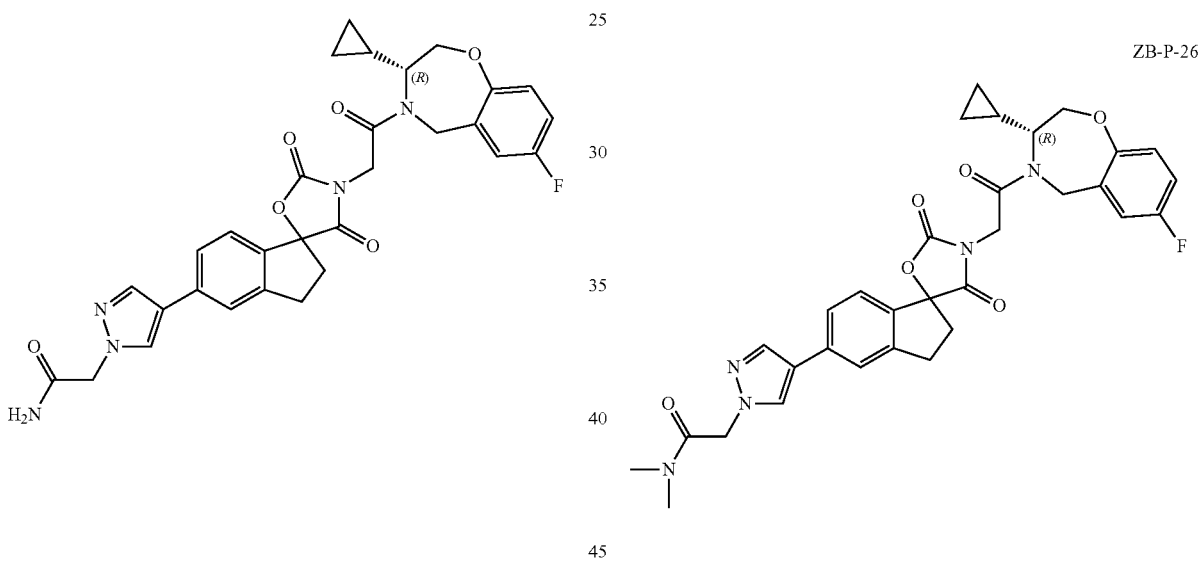
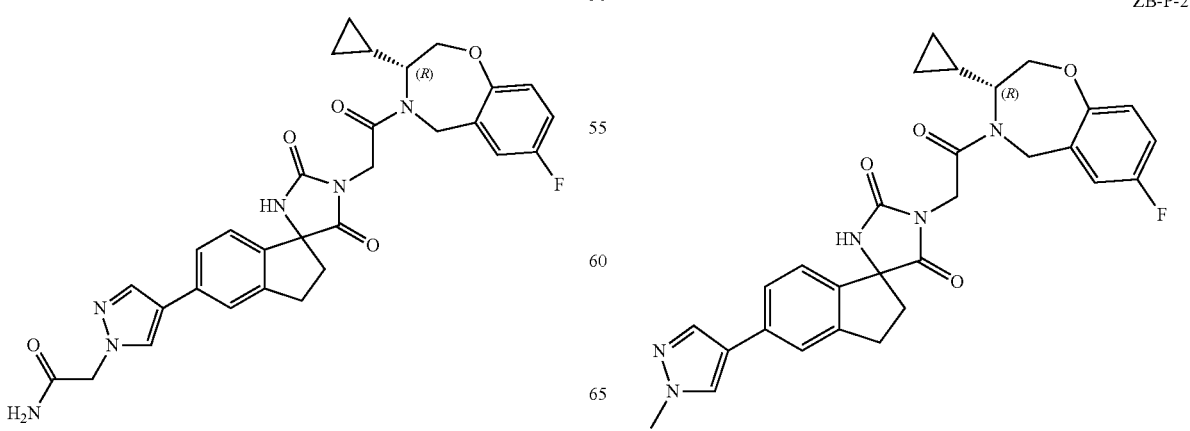

ZB-P-29
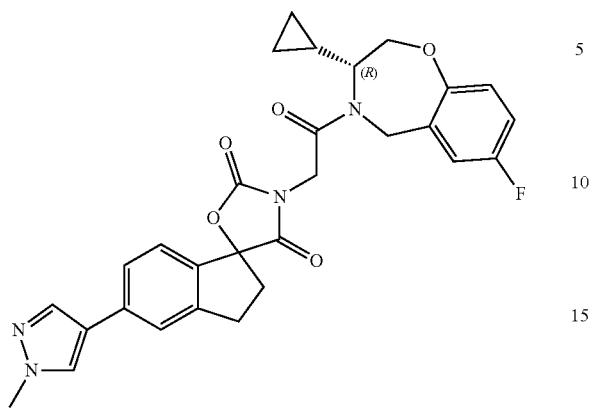
SYY-B045-2
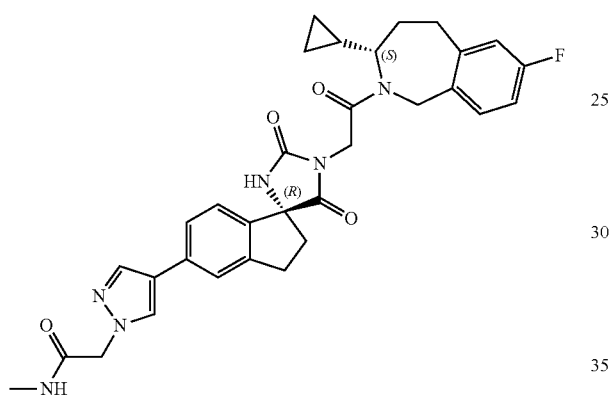
ZB-P-30
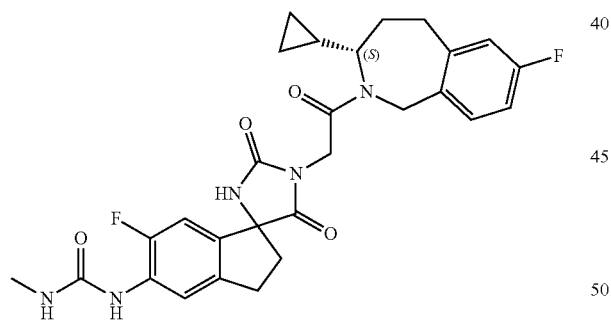
ZB-P-31
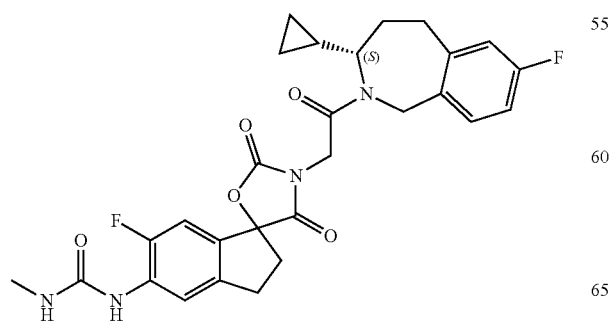
ZB-P-32
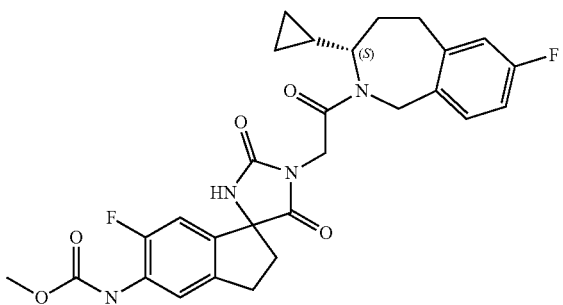
ZB-P-33
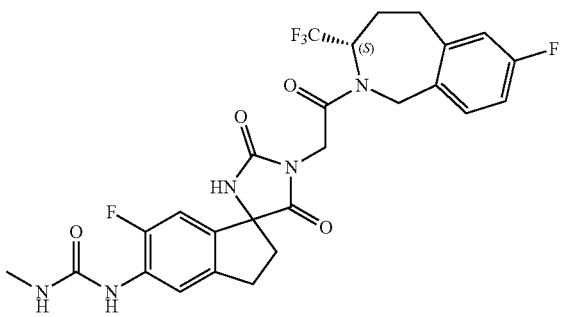
ZB-P-34
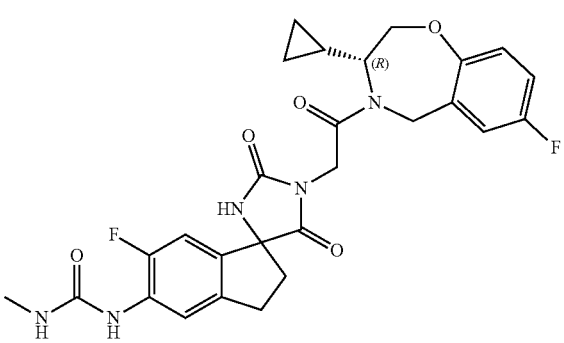
ZB-P-35
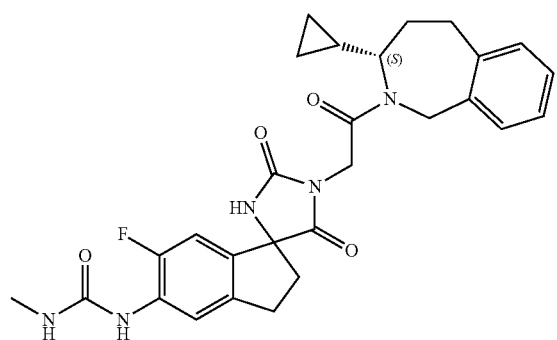

-continued
ZB-P-36
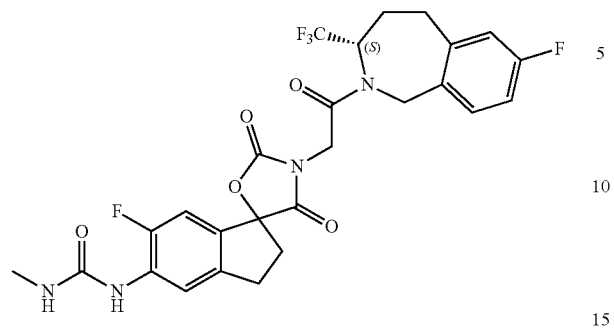
ZB-P-37
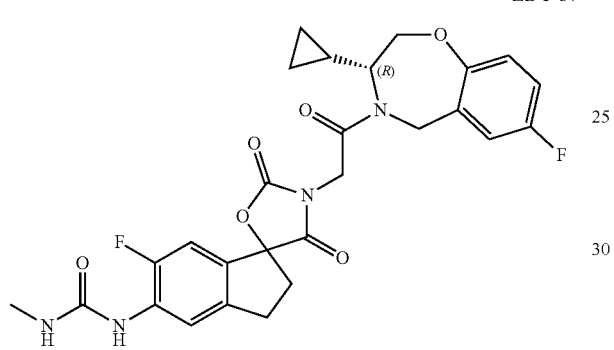
ZB-P-38
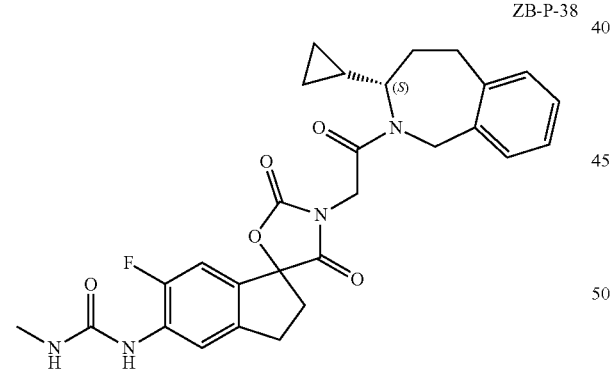
ZB-P-39
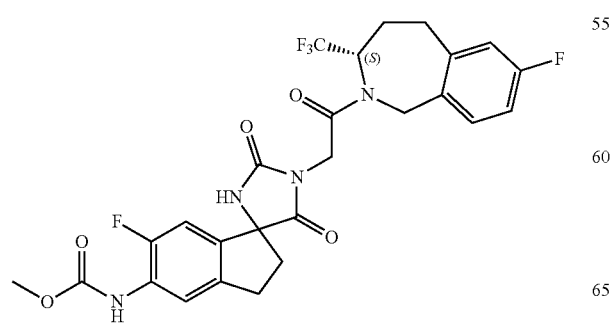
-continued
ZB-P-40
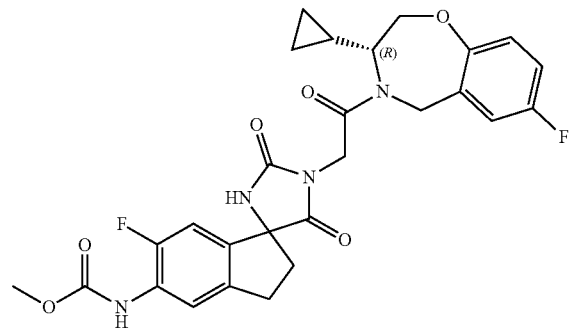
ZB-P-41
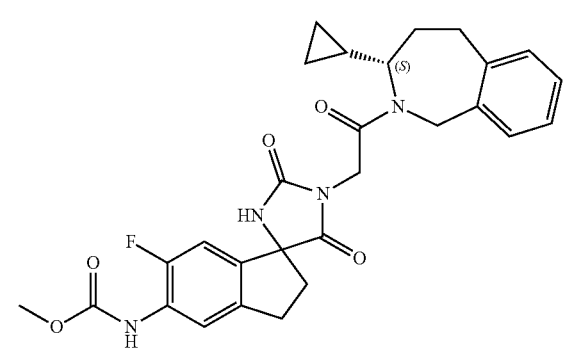
ZB-P-42
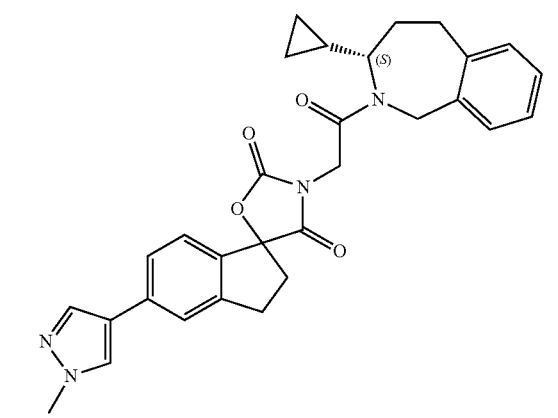
ZB-P-43
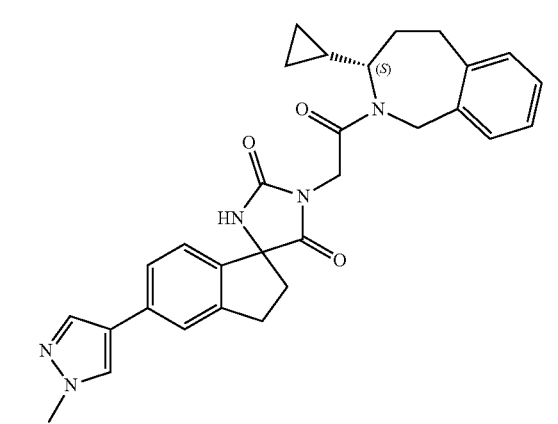

-continued
ZB-P-44
ZB-P-12-1
ZB-P-12-2
ZB-P-14-1
-continued
ZB-P-14-2
ZB-P-32-1
ZB-P-32-2
SYY-B041
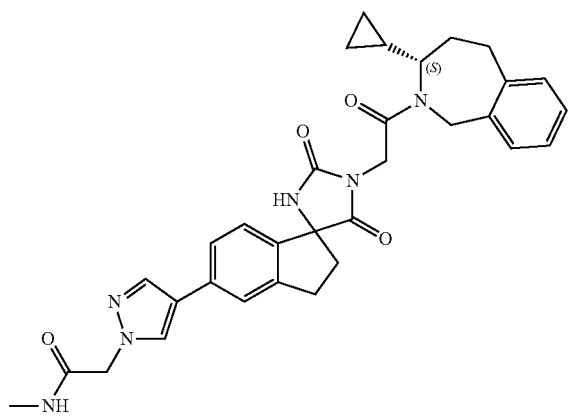
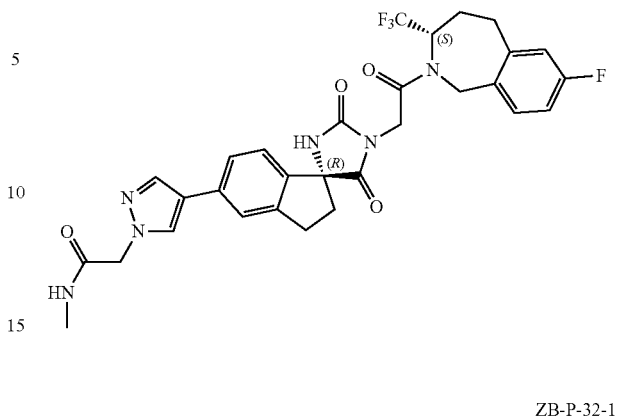

SYY-B057-1
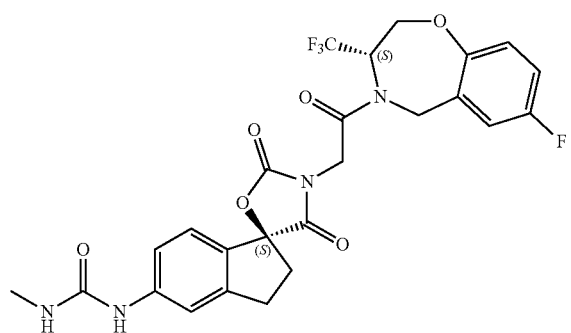
SYY-B083
SYY-B057-2
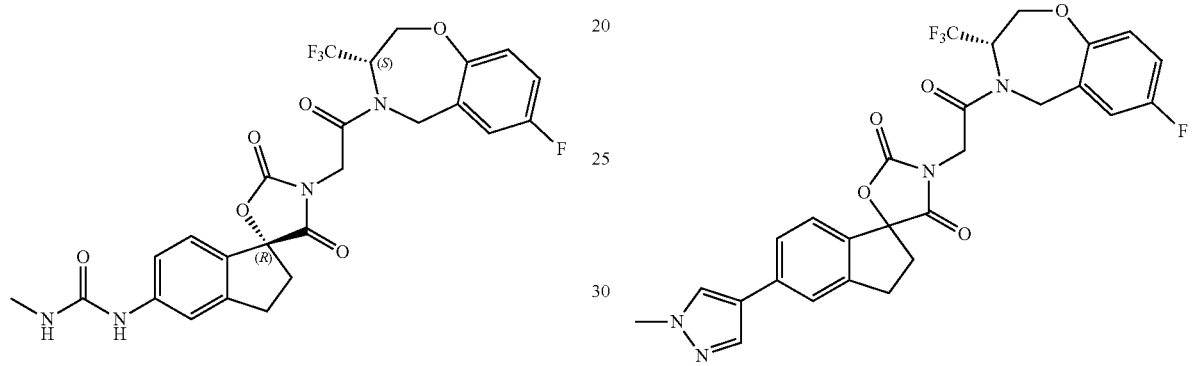
SYY-B084
SYY-B074
SYY-B085
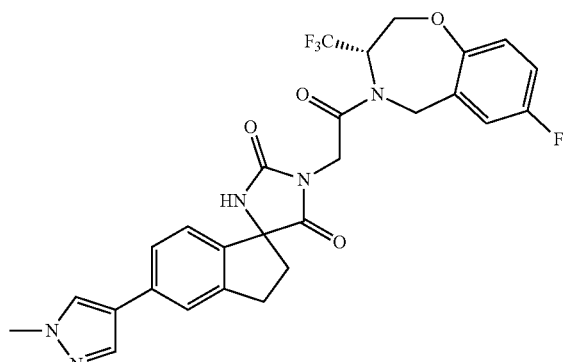
SYY-B077
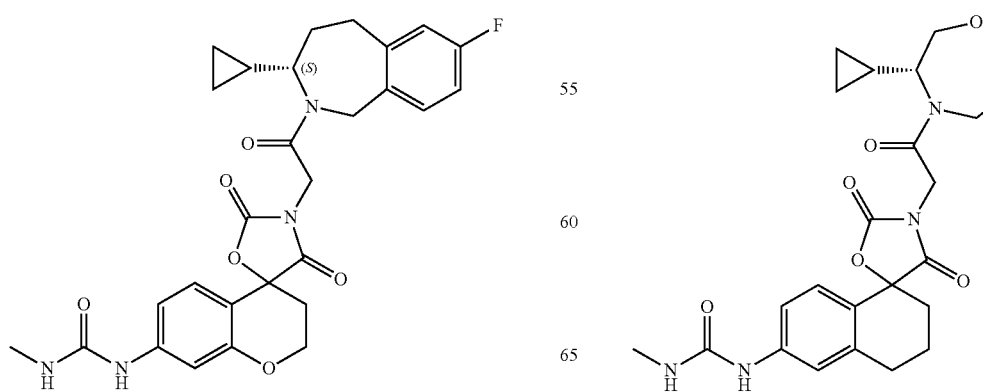
SYY-B086

SYY-B092
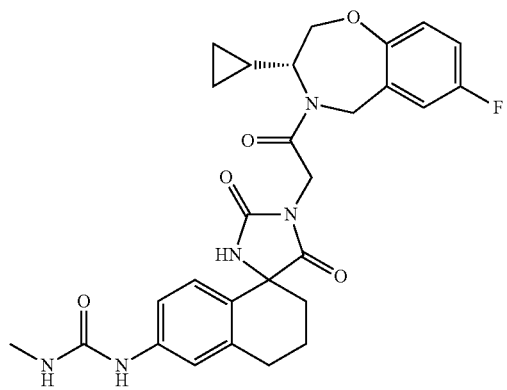
SYY-B093
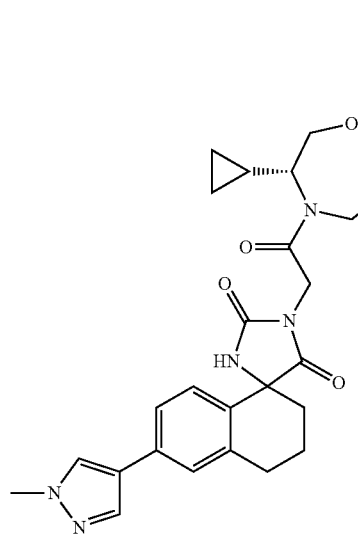
SYY-B094
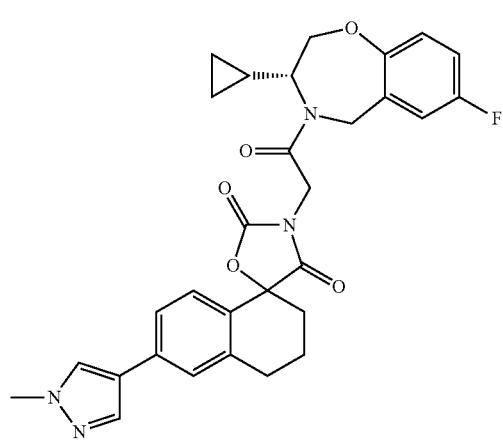
SYY-B099
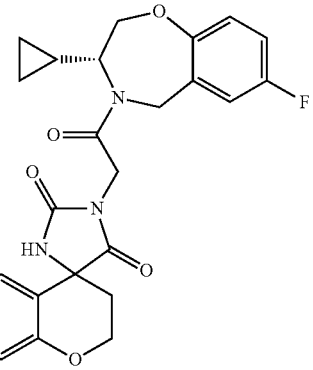
SYY-B100-1
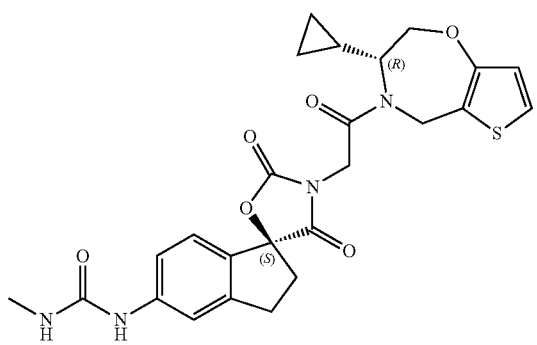
SYY-B100-2
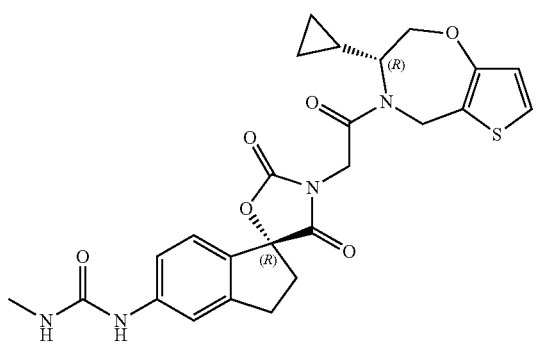
ZB-P-21-1
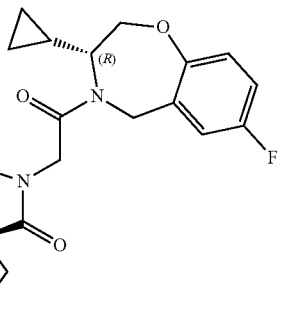

ZB-P-21-2
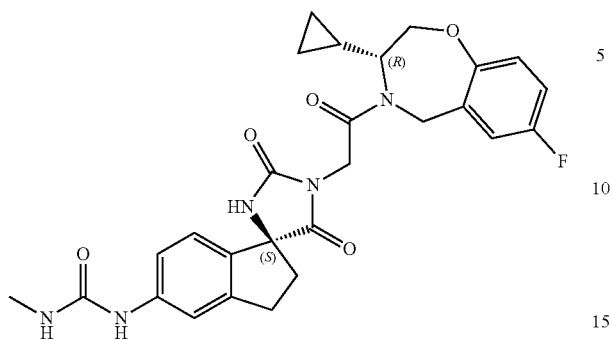
ZB-P-28-1
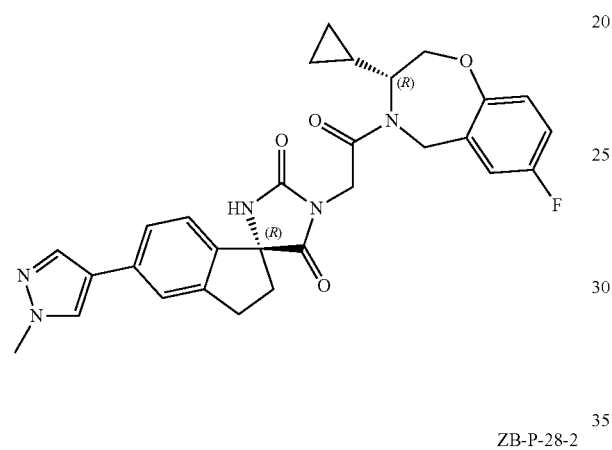
ZB-P-28-2
ZB-P-29-1
ZB-P-29-2
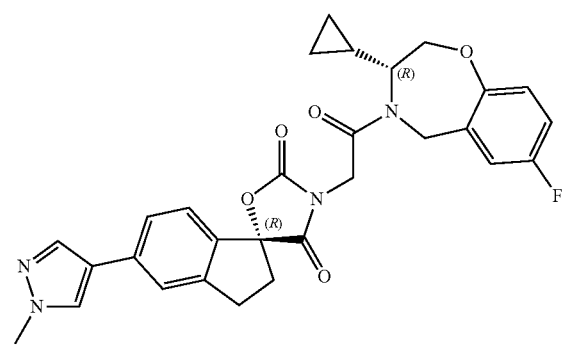
SYY-B074-1
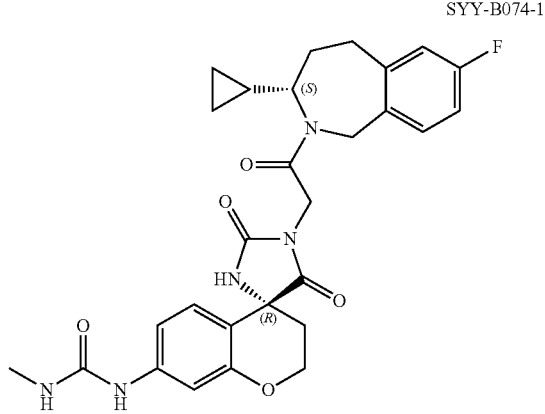
SYY-B074-2
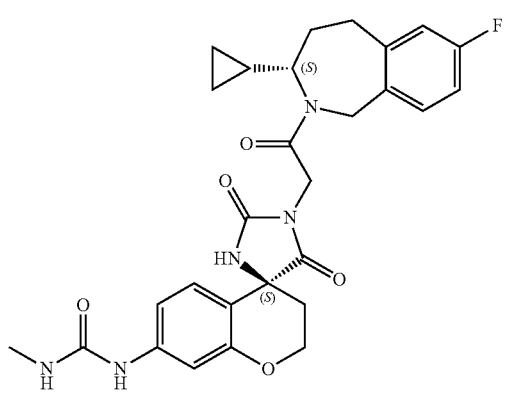
SYY-B077-1
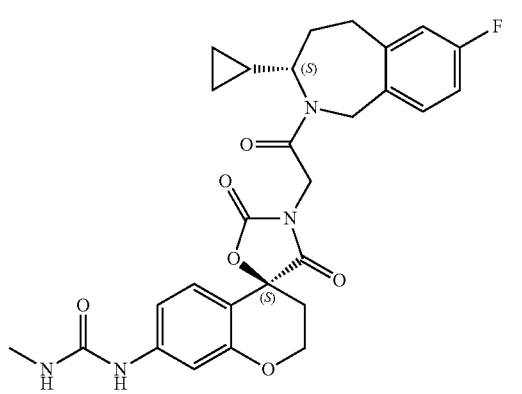

SYY-B077-2
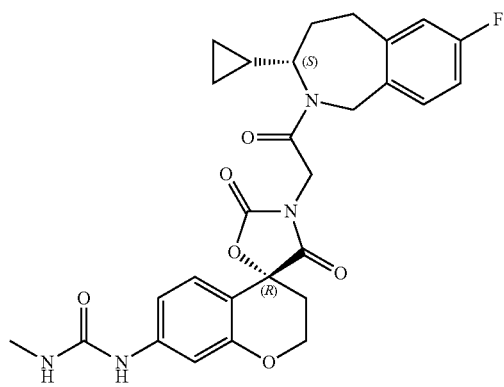
SYY-B083-1
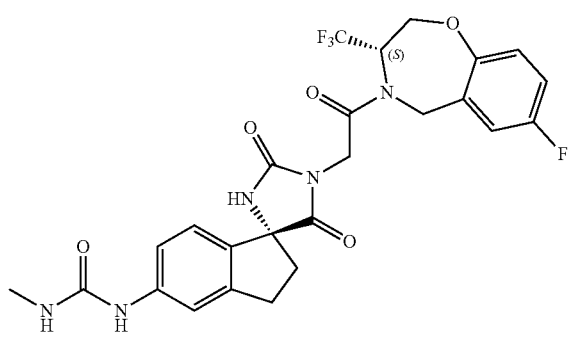
SYY-B083-2
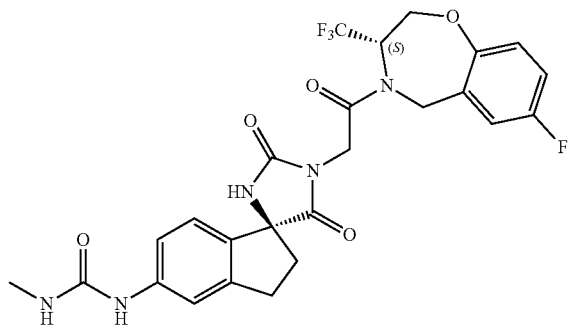
SYY-B084-1
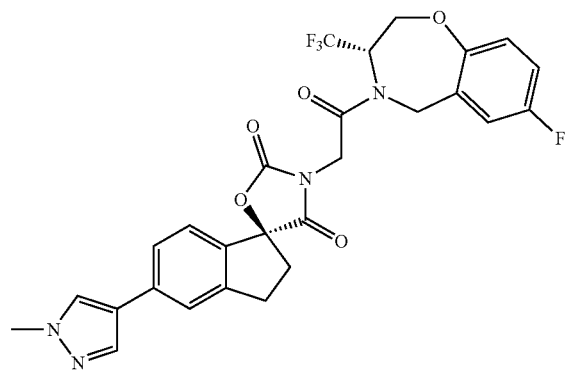
SYY-B084-2
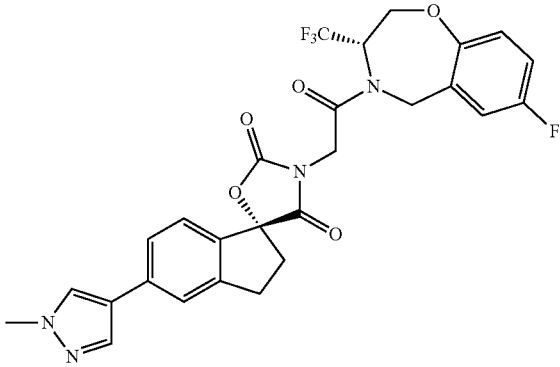
SYY-B085-1
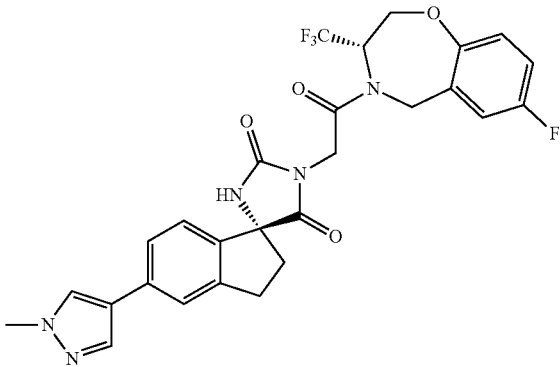
SYY-B085-2
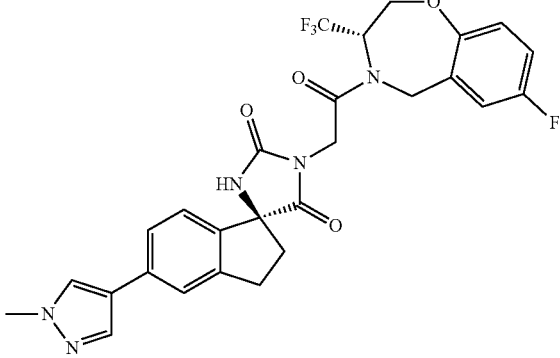
SYY-B086-1
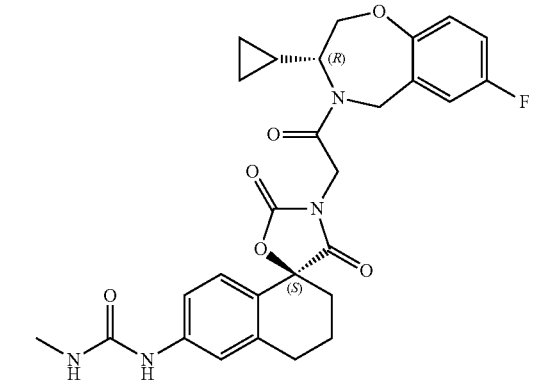

-continued
SYY-B086-2
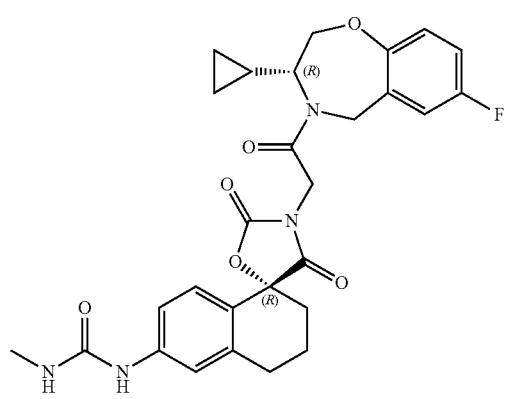
SYY-B092-1
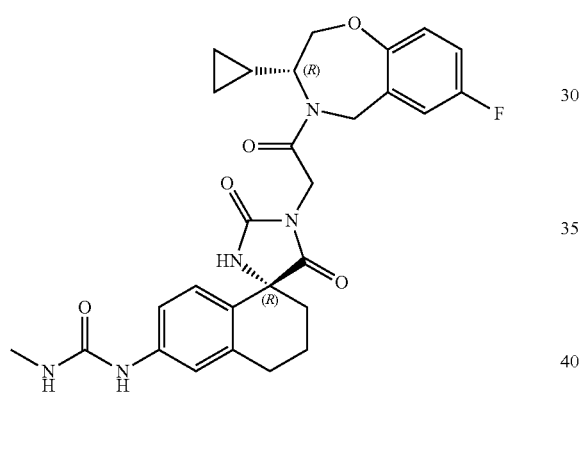
SYY-B092-2
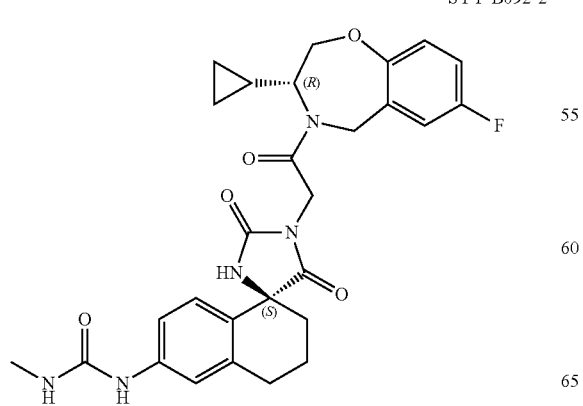
-continued
SYY-B093-1
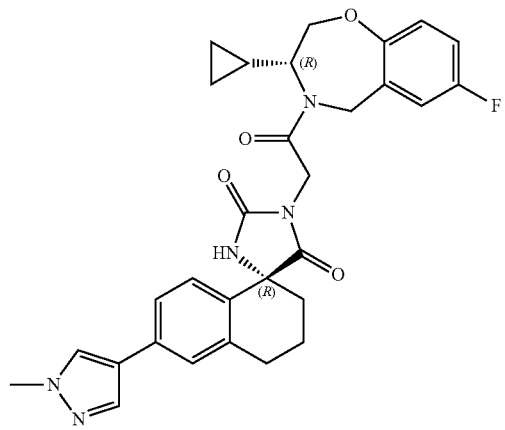
SYY-B093-2
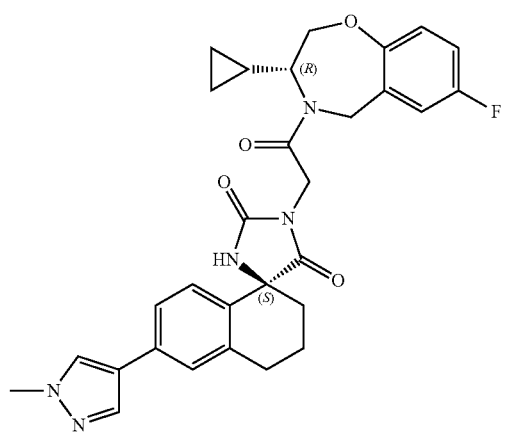
SYY-B094-1
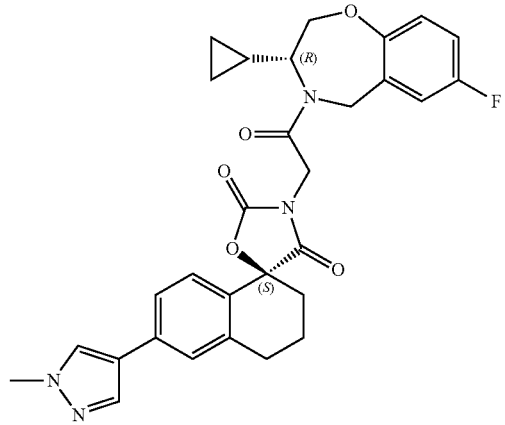

SYY-B094-2
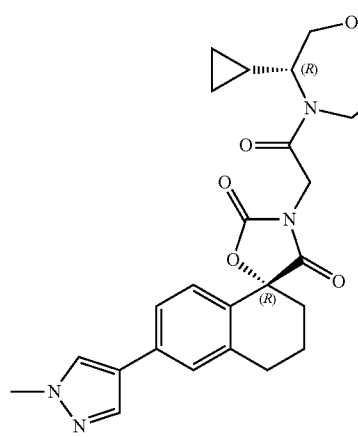
SYY-B099-1
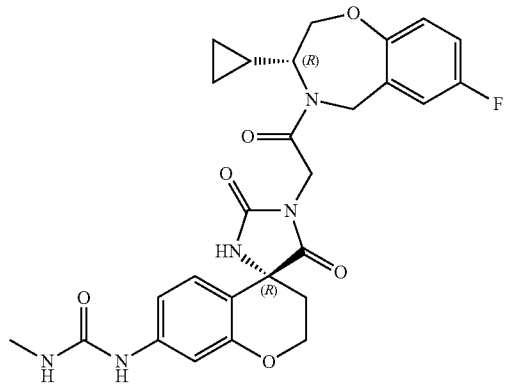
SYY-B099-2
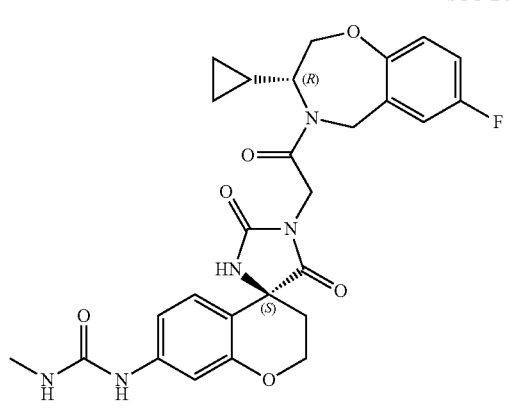
SYY-B081-1
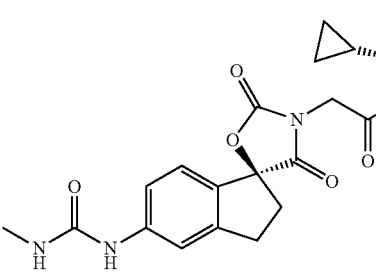
SYY-B081-2
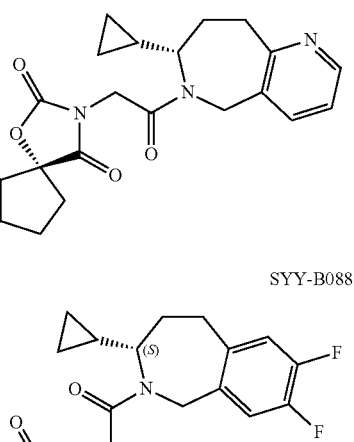
SYY-B088
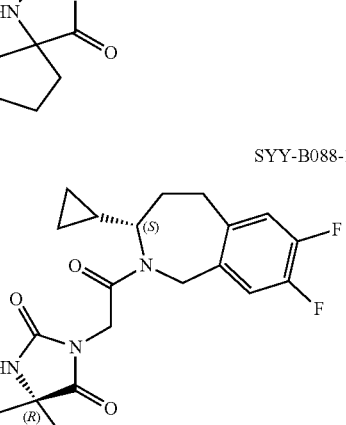
SYY-B088-1
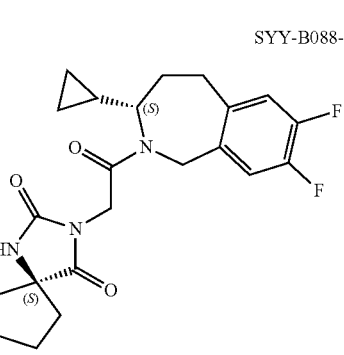
SYY-B088-2
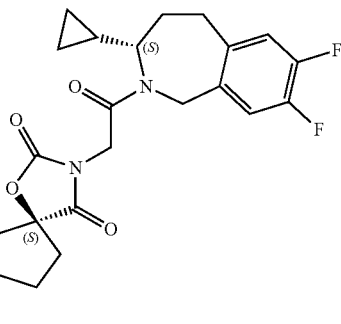
SYY-B090-1
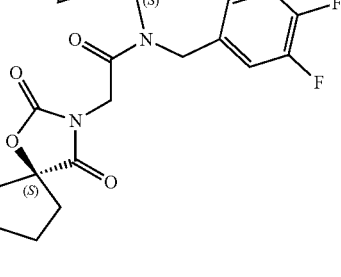

SYY-B090-2
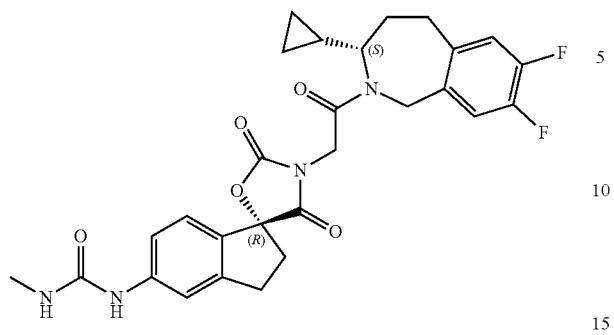
SYY-B095
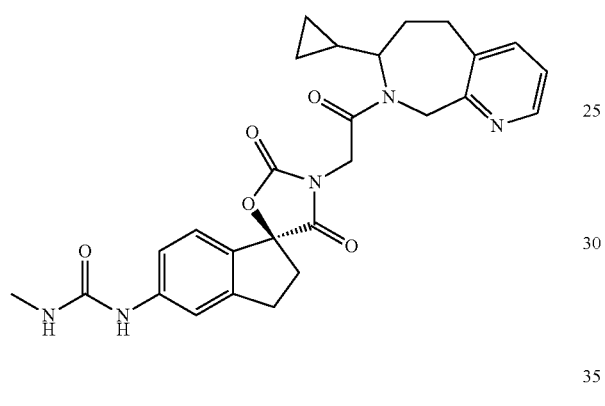
SYY-B095-1
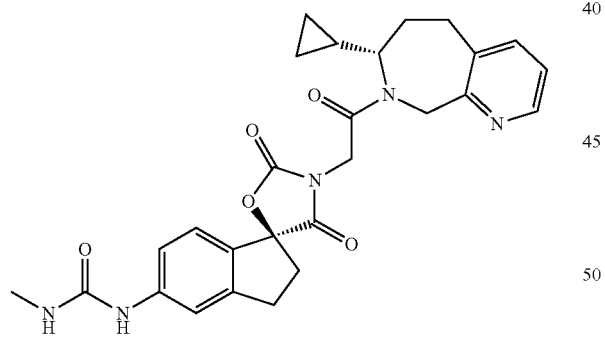
SYY-B095-2
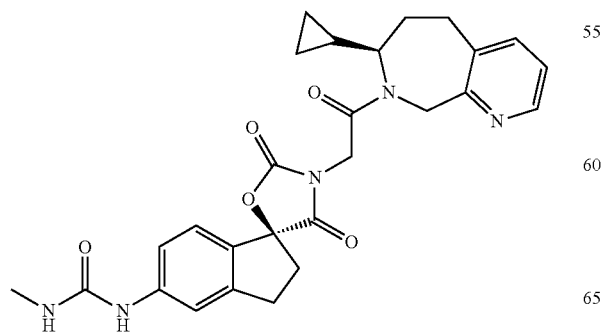
SYY-B096
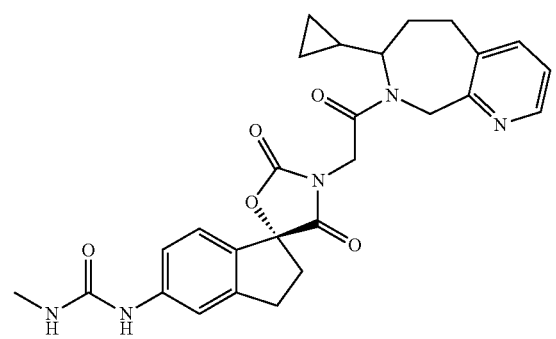
SYY-B096-1
SYY-B096-2
SYY-B097-1
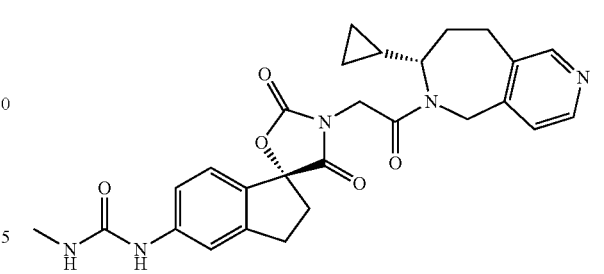
SYY-B097-2

SYY-B102-1

SYY-B102-2

SYY-B104

SYY-B104-1

SYY-B104-2

SYY-B106

SYY-B106-1

SYY-B106-2

-continued
SYY-B108
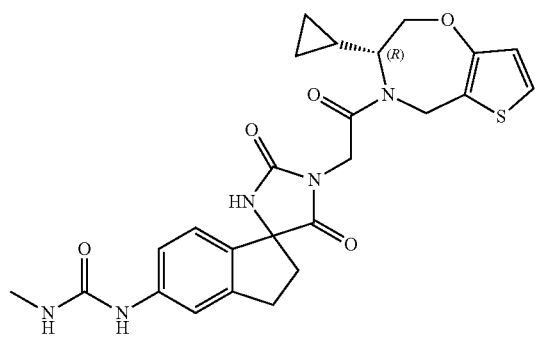
SYY-B108-1
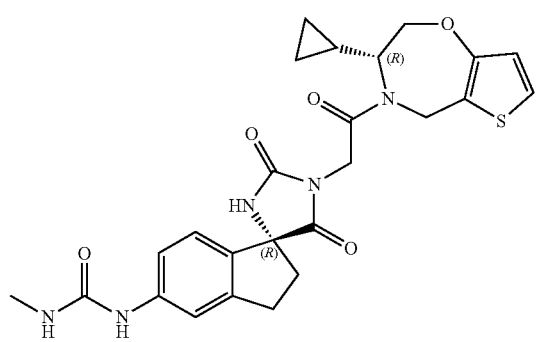
SYY-B108-2
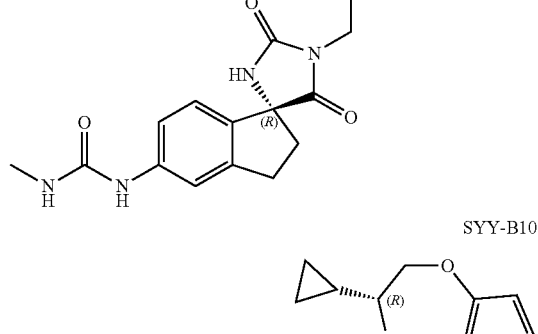
SYY-B082-1
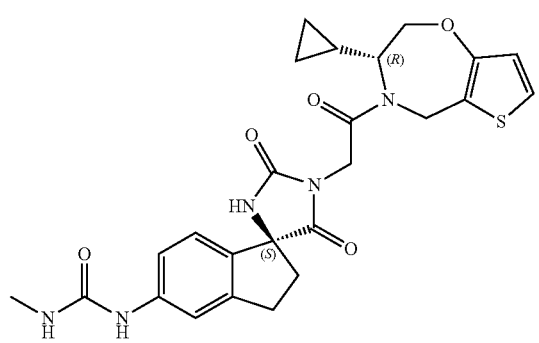
SYY-B082-2
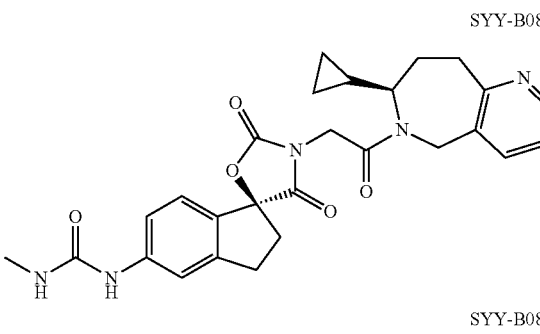
-continued
SYY-B098-1
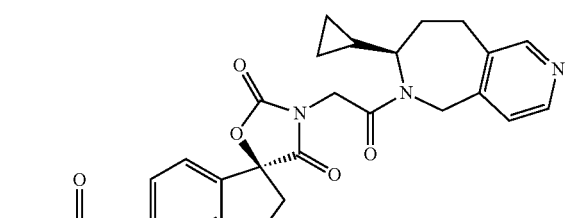
SYY-B098-2
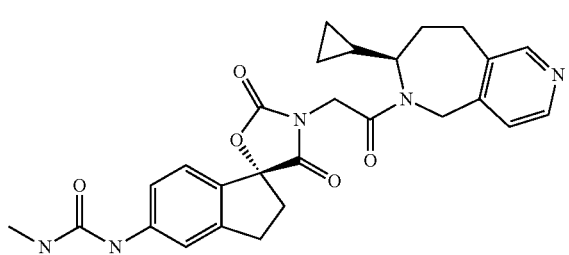
ZB-P-30-1
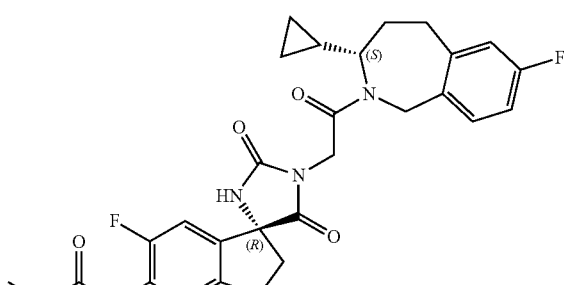
ZB-P-30-2
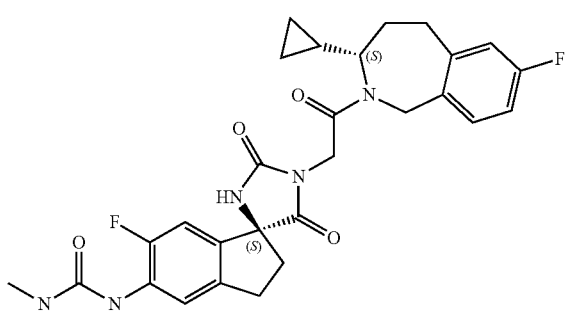
ZB-P-31-1
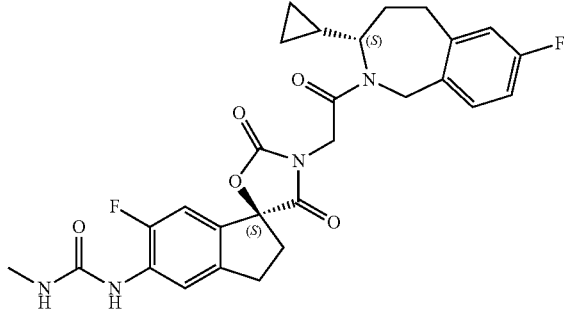

ZB-P-31-2
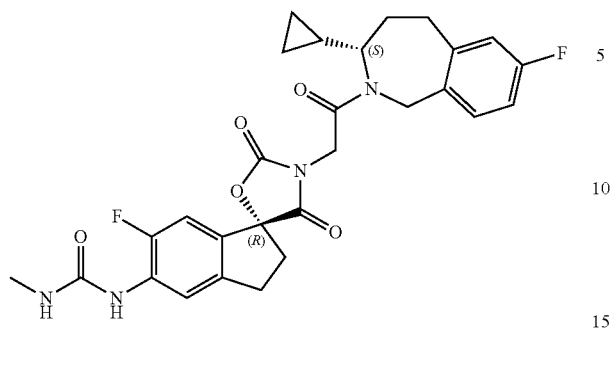
SYY-B110
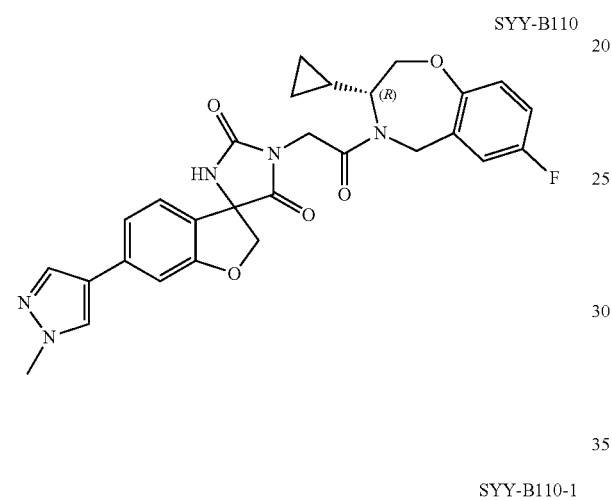
SYY-B110-1
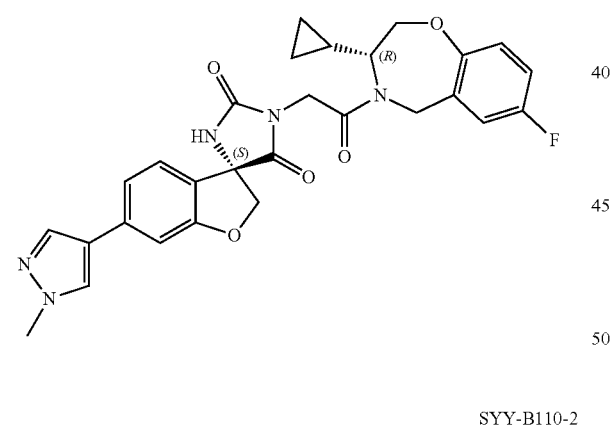
SYY-B110-2
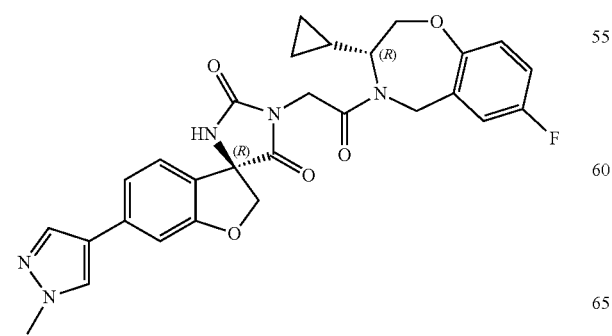
SYY-B112
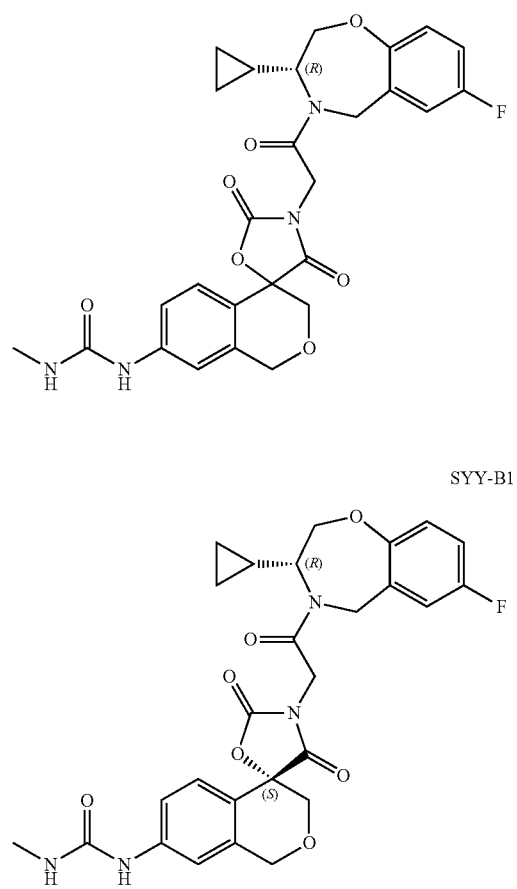
SYY-B112-1
SYY-B112-2
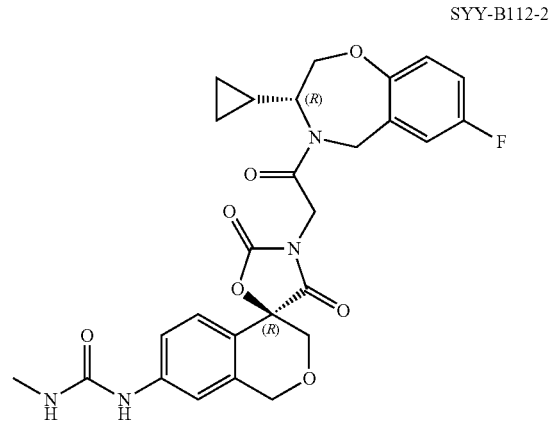
SYY-B116-1
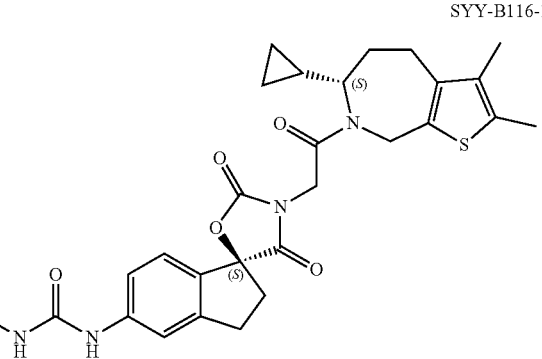

SYY-B116-2
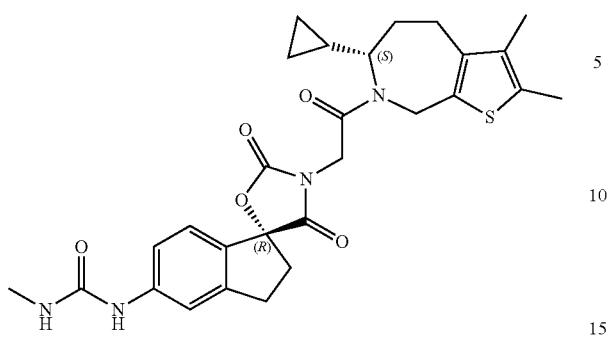
SYY-B122
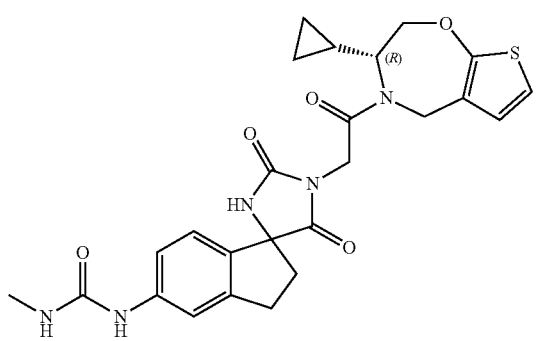
SYY-B118-2
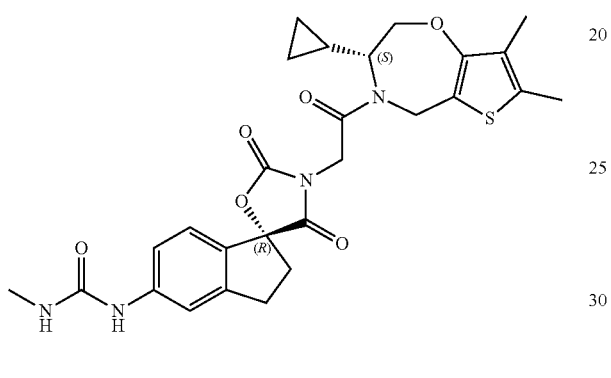
SYY-B122-1
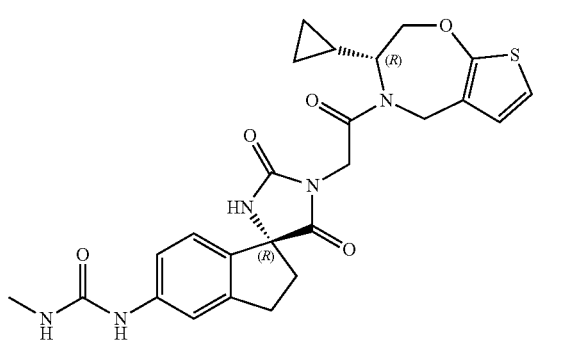
SYY-B120-1
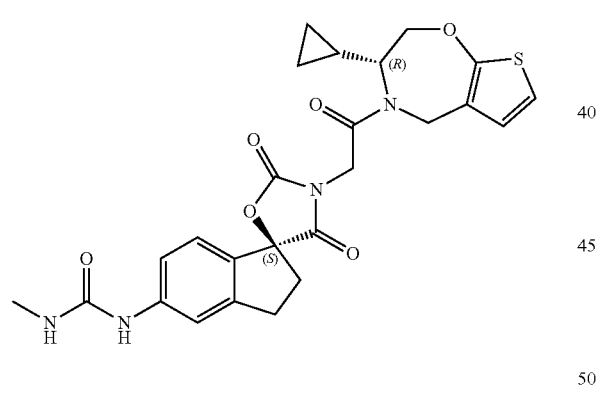
SYY-B122-2
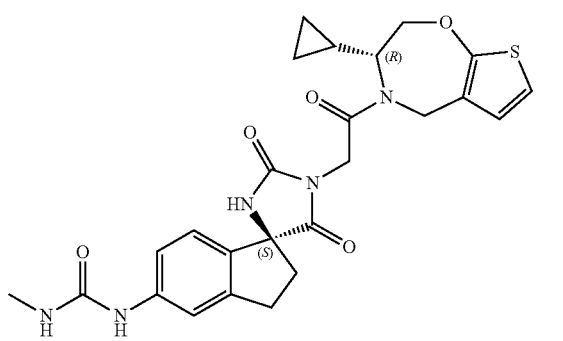
SYY-B120-2
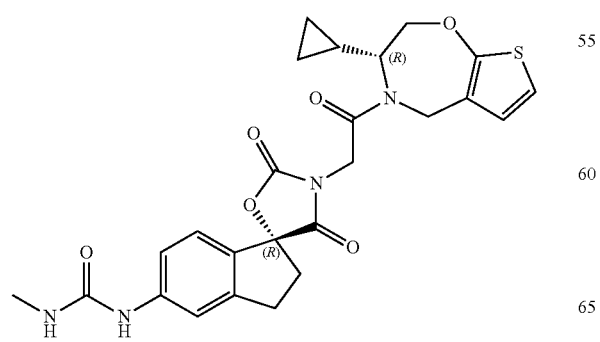
SYY-B124
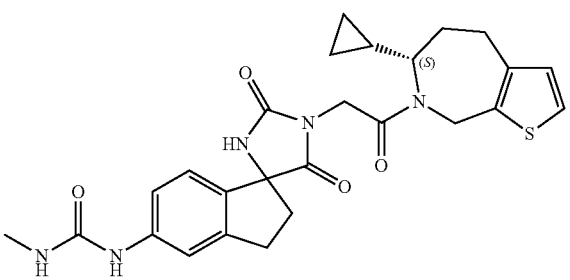

-continued
SYY-B124-1
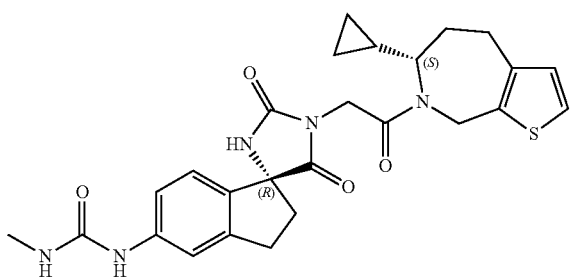
SYY-B124-2
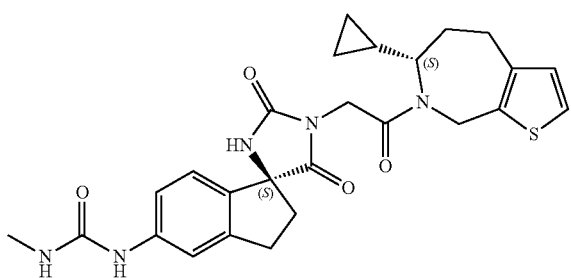
SYY-B126-1
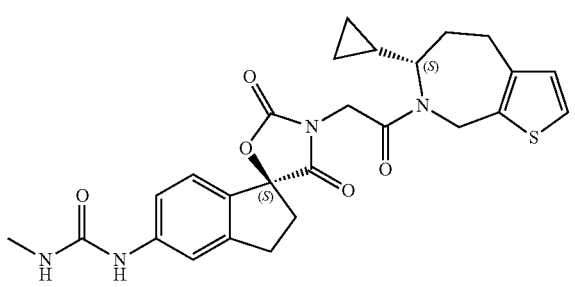
SYY-B126-2
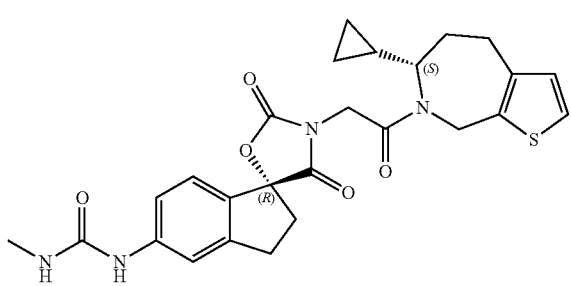
SYY-B130
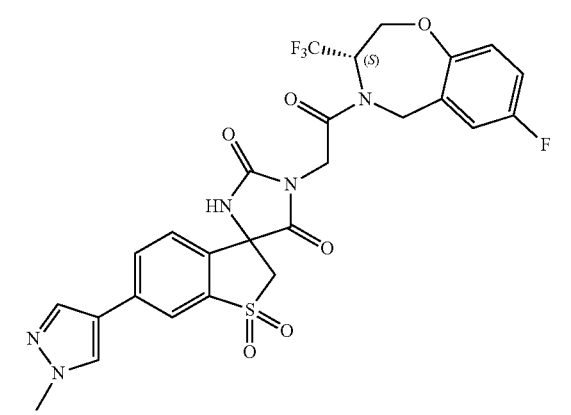
-continued
SYY-B130-1
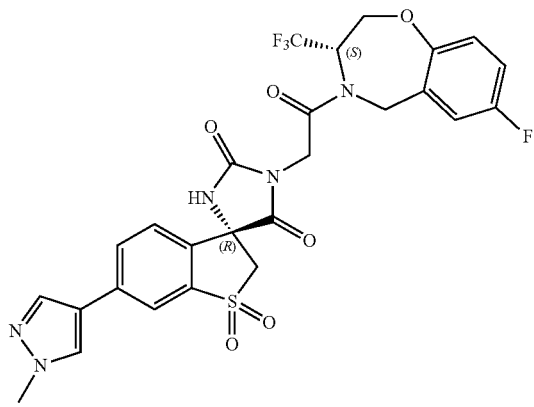
SYY-B130-2
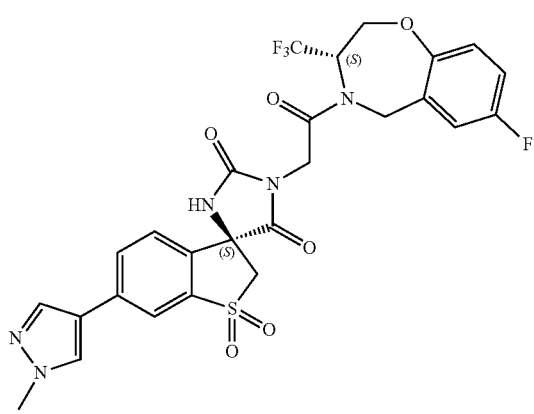
208-3
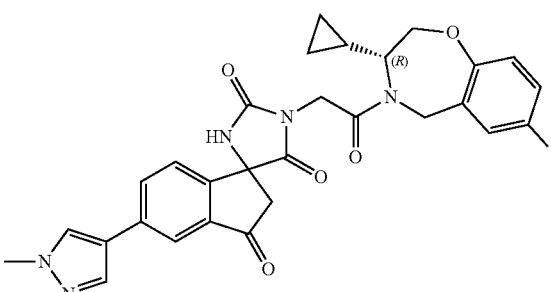
208-5-1
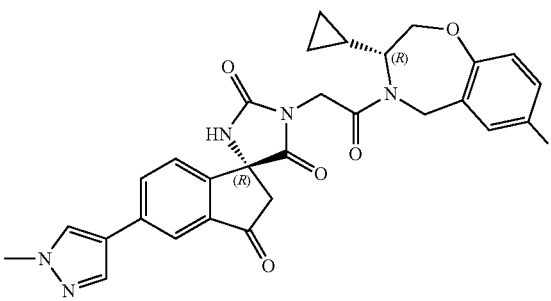

208-5-2
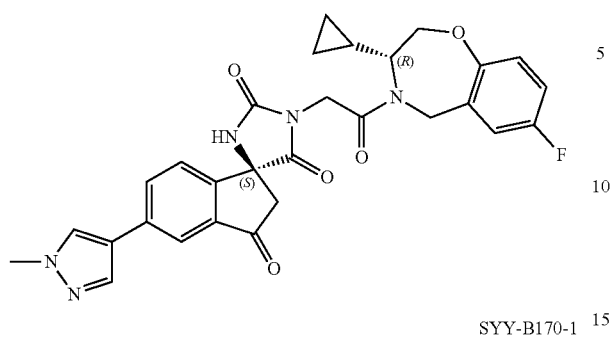
SYY-B136
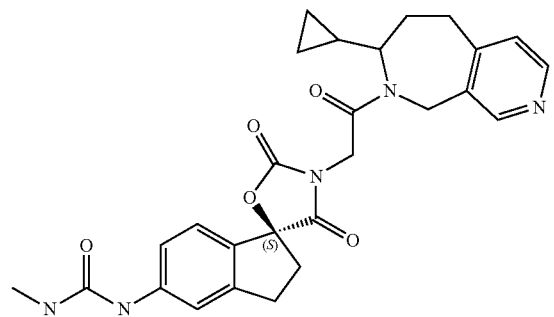
SYY-B170-1
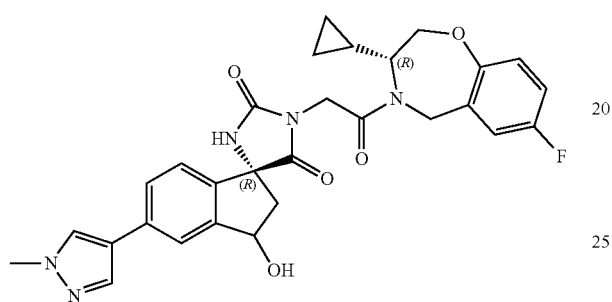
SYY-B170-2
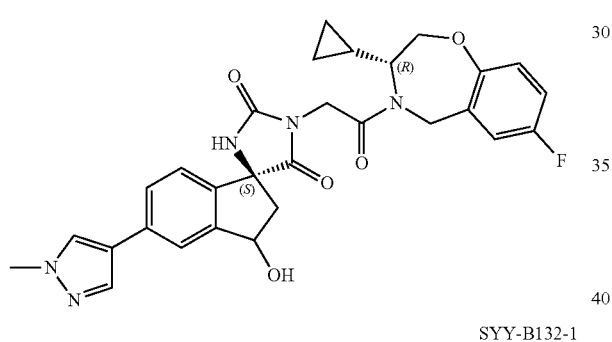
SYY-B136-1, SYY-B136-2
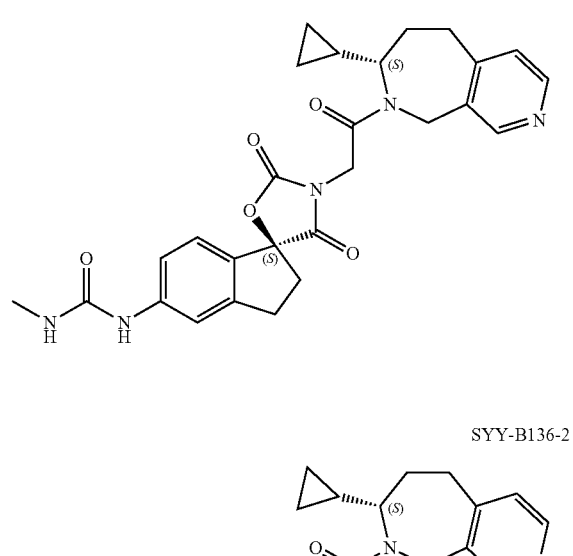
SYY-B132-1
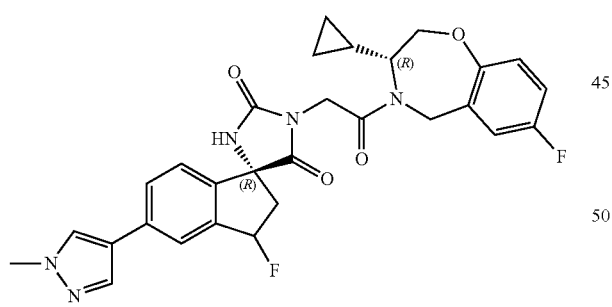
SYY-B132-2
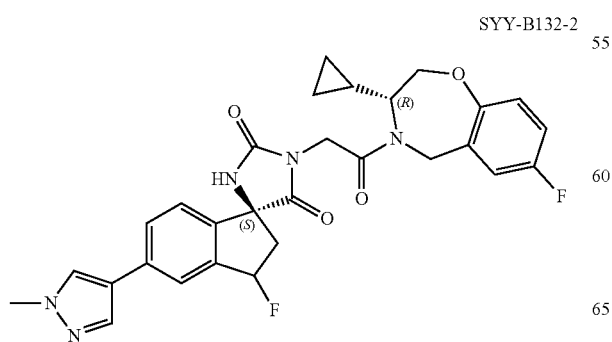
SYY-B137
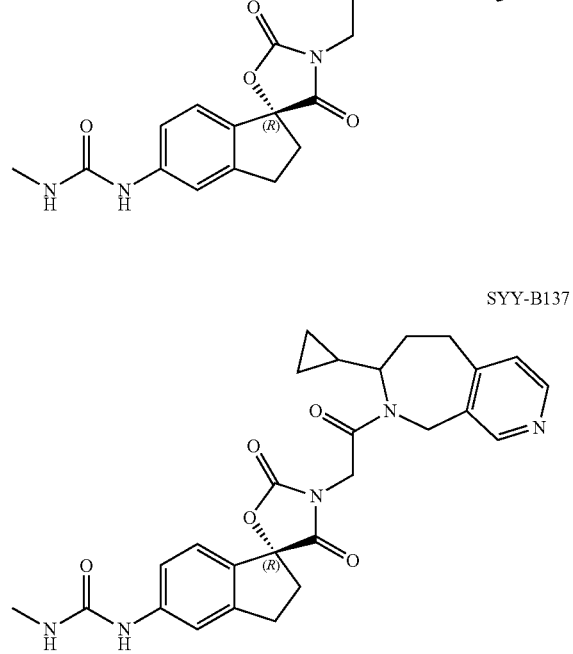

SYY-B137-1
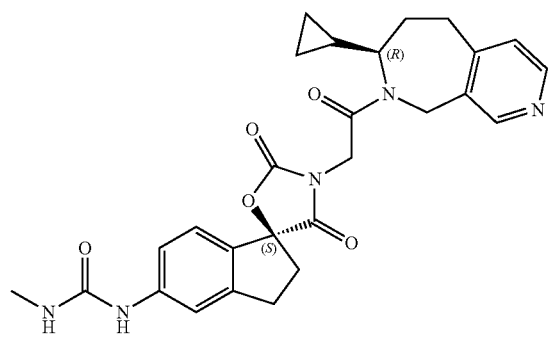
SYY-B138-2
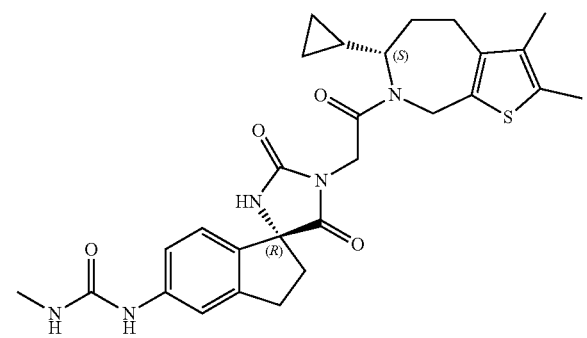
SYY-B137-2
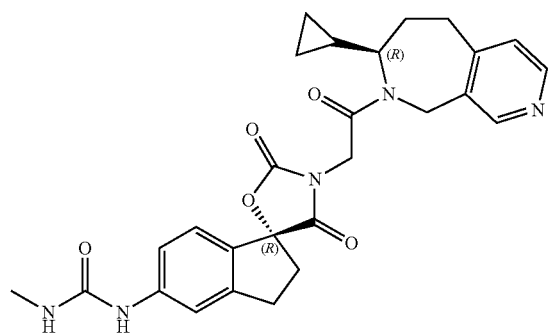
SYY-B140-1
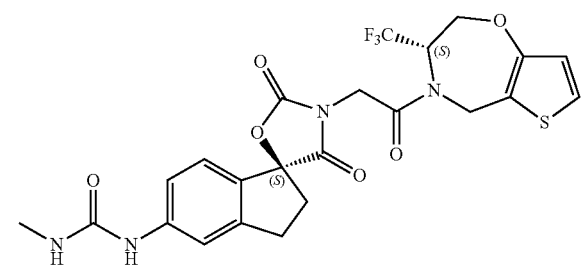
SYY-B138
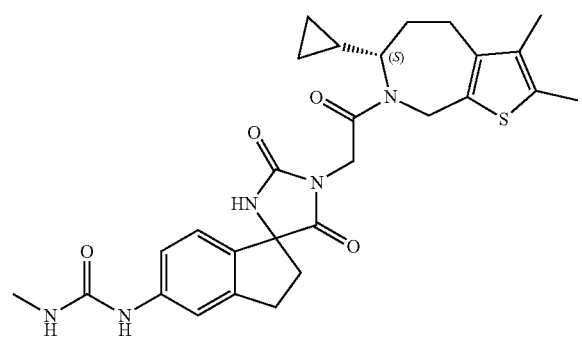
SYY-B140-2
SYY-B142
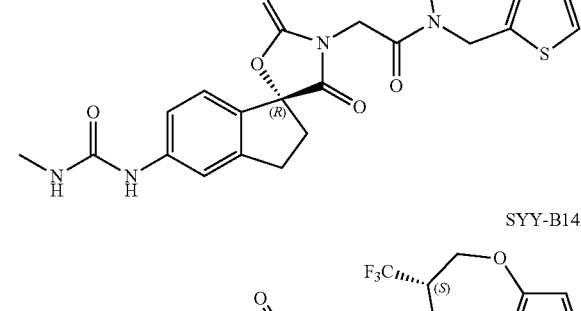
SYY-B138-1
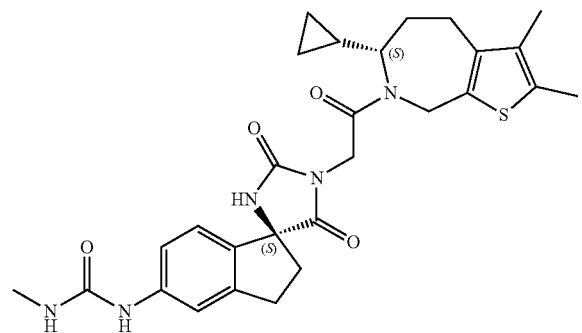
SYY-B142-1
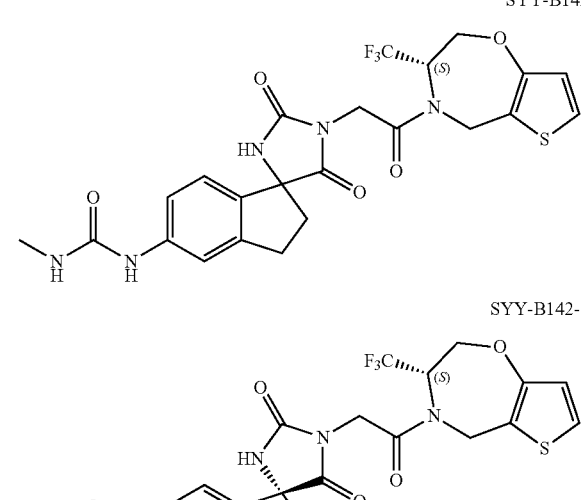

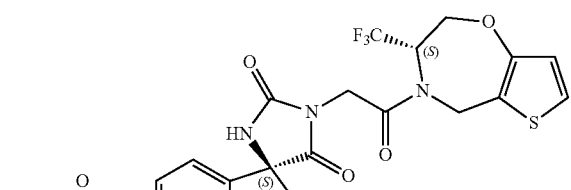
SYY-B142-2
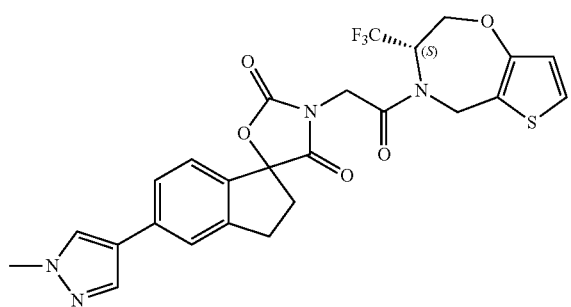
SYY-B144
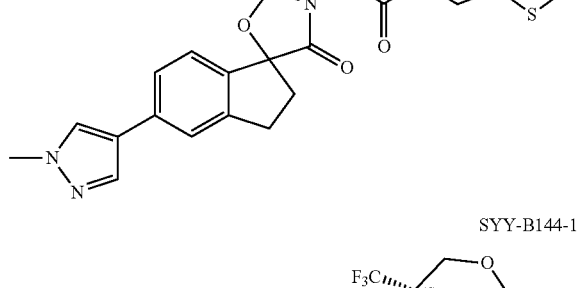
SYY-B144-1
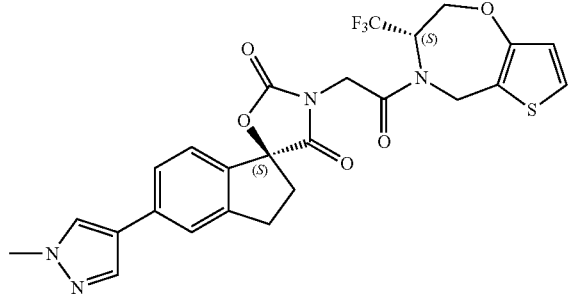
SYY-B144-2
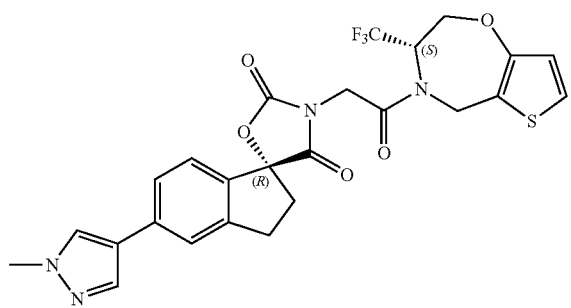
SYY-B146
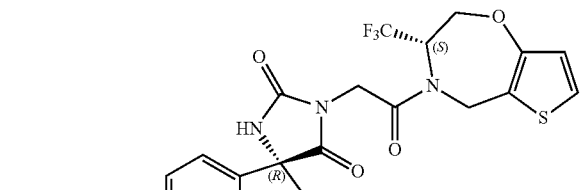
SYY-B146-1
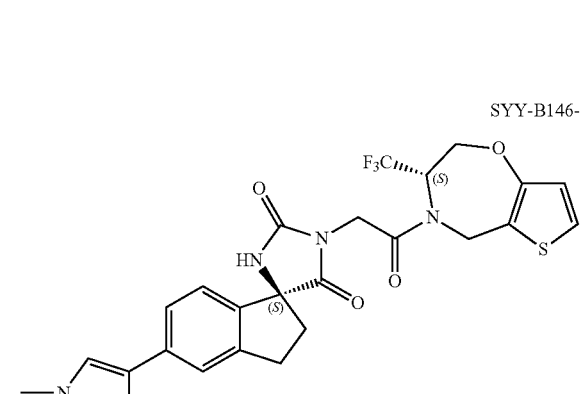
SYY-B146-2
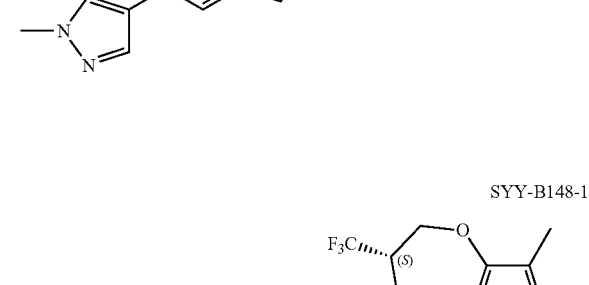
SYY-B148-1
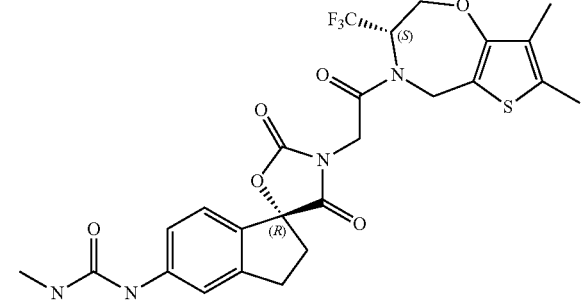
SYY-B148-2

-continued
SYY-B150
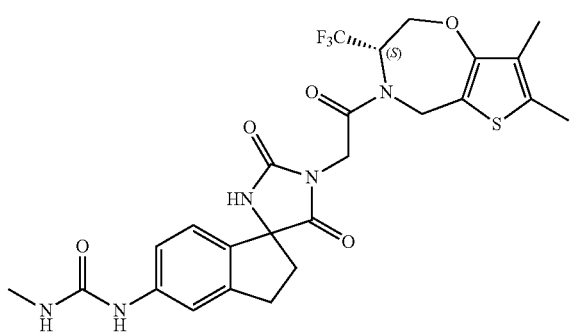
SYY-B150-1
SYY-B150-2
-continued
SYY-B152-1
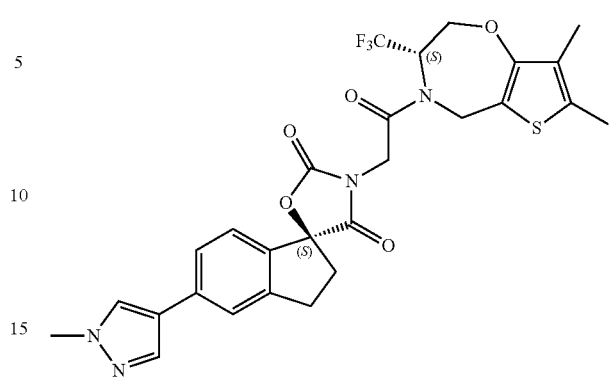
SYY-B152-2
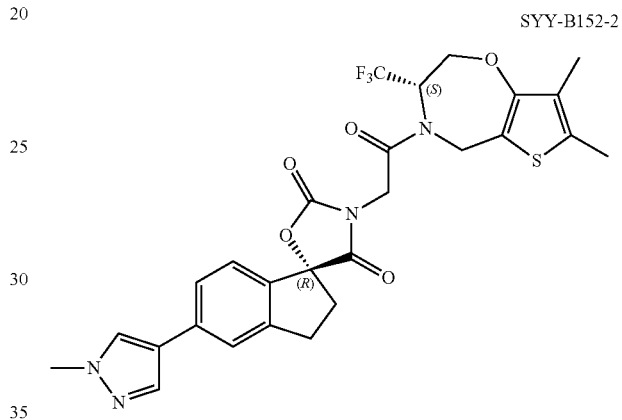
SYY-B154
SYY-B152
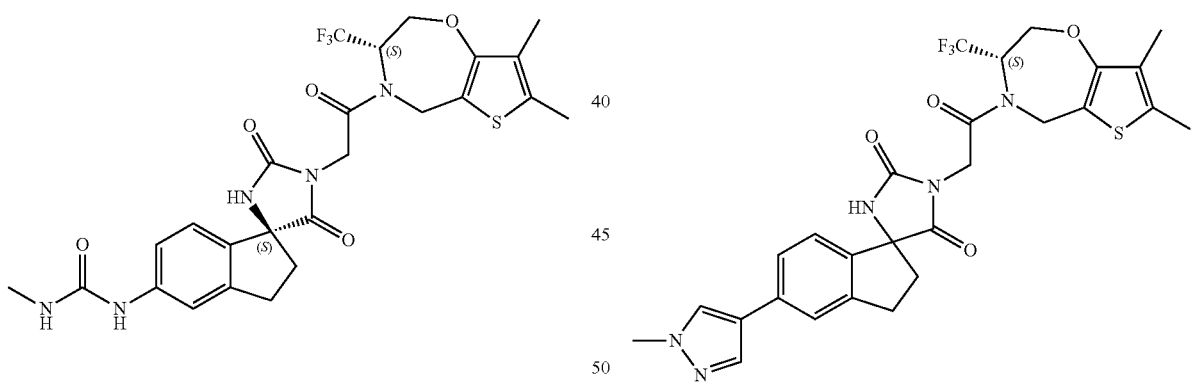
SYY-B154-1
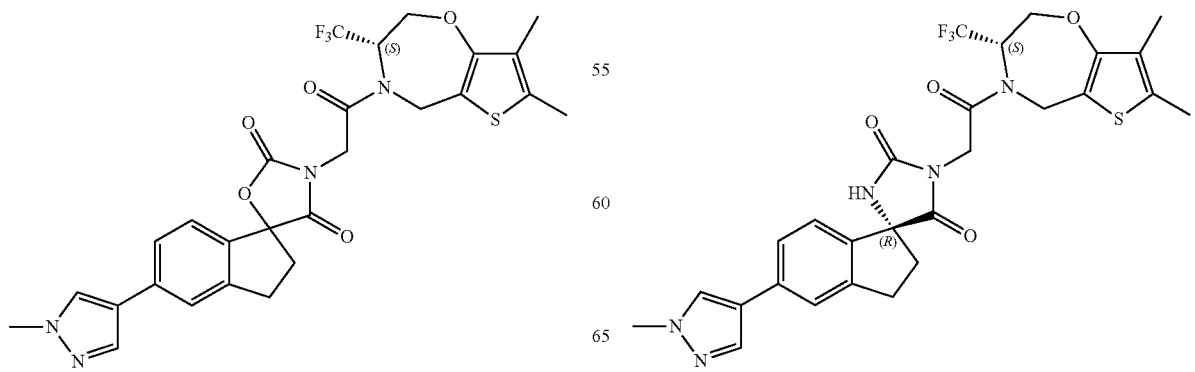

SYY-B154-2
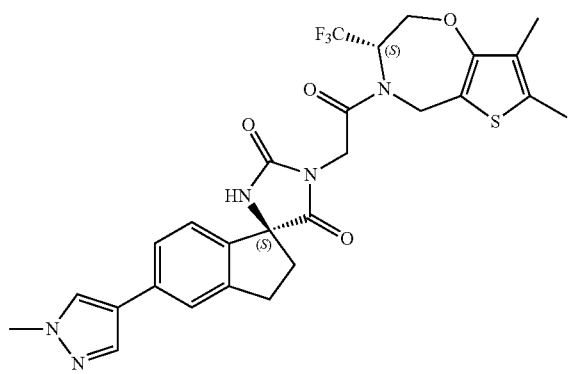
SYY-B156
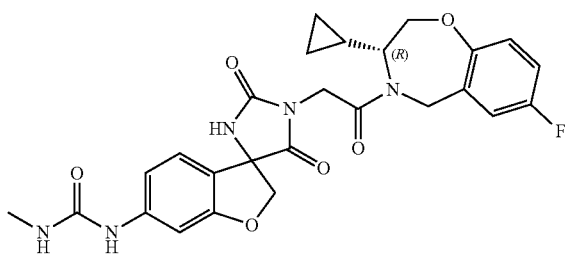
SYY-B155
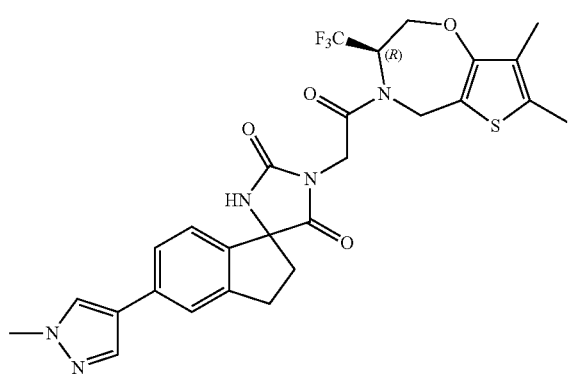
SYY-B156-1
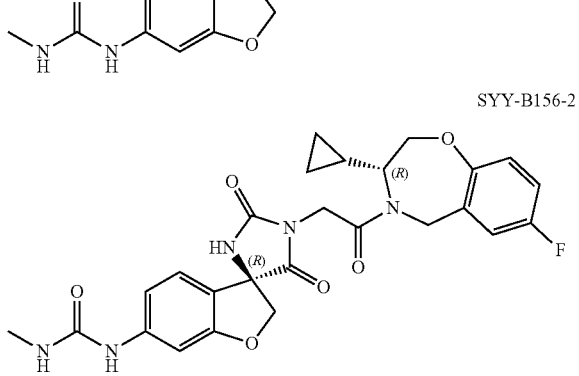
SYY-B155-1
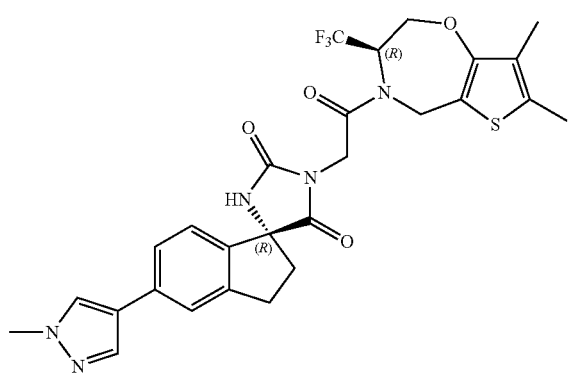
SYY-B156-2
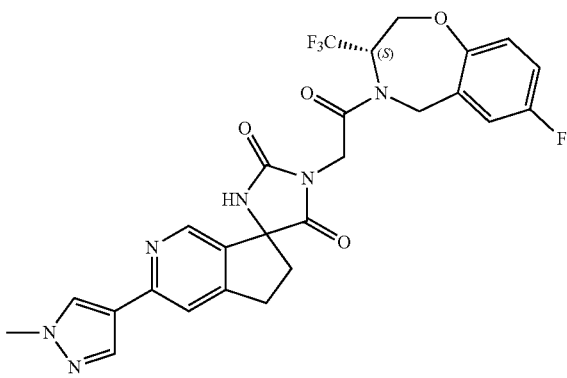
SYY-B155-2
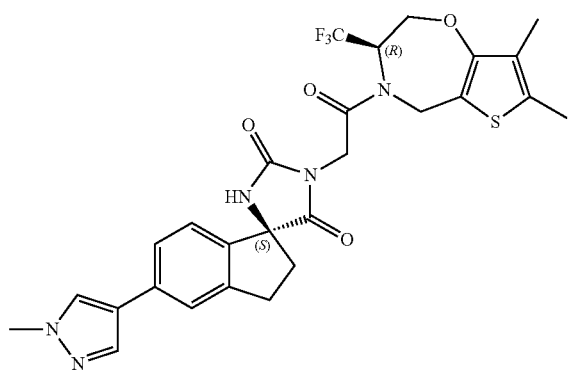
SYY-B161
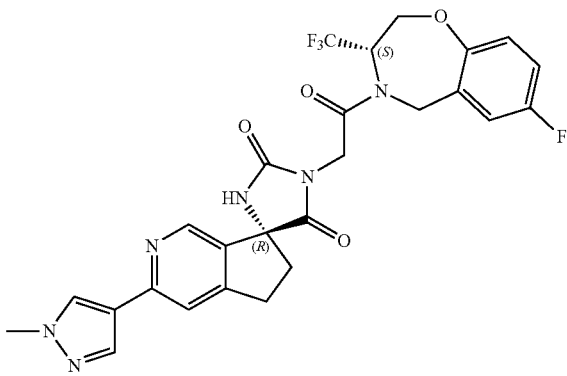
SYY-B161-1
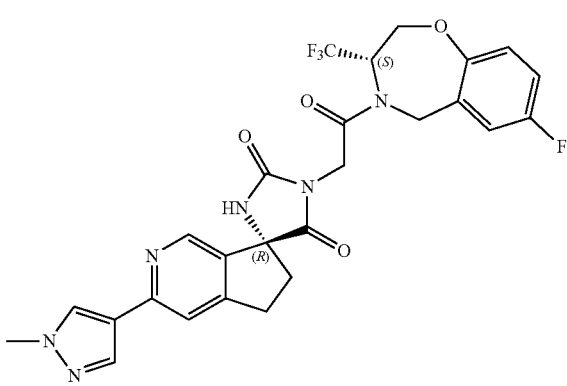

-continued

SYY-B161-2

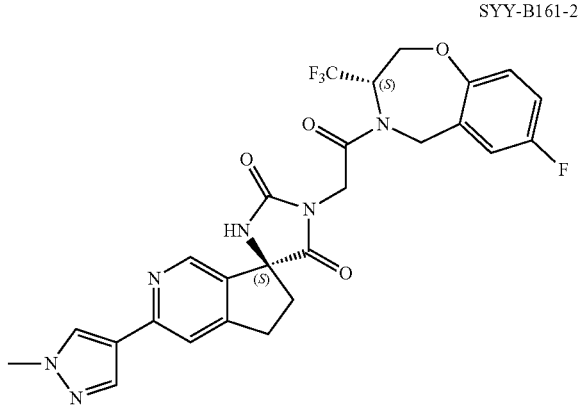

SYY-B163

SYY-B163-1

SYY-B163-2

-continued

SYY-B165

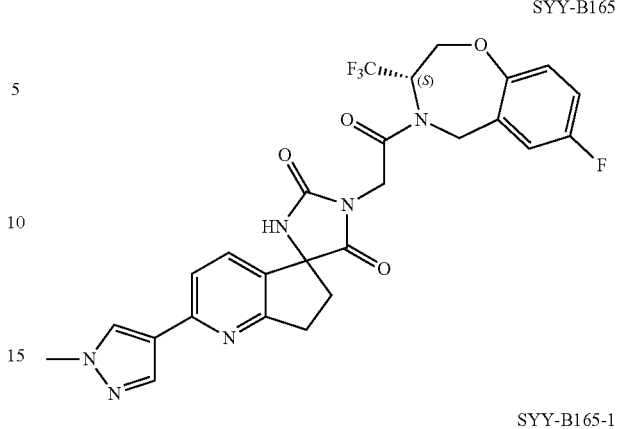

SYY-B165-1 and
SYY-B165-2

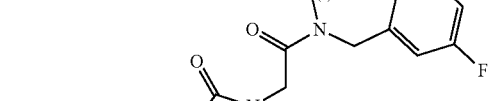

According to another embodiment of the present invention, provided is a pharmaceutical composition comprising a therapeutically effective amount of the compound of formula (I) described above, or a pharmaceutically acceptable salt, stereoisomer, enantiomer, diastereomer, atropisomer, racemate, polymorphs, solvate or isotopically labeled compound, and a pharmaceutically acceptable carrier, diluent or excipient.

Preferably, the pharmaceutical composition further comprises at least one other therapeutic agent. Preferably, the at least one other therapeutic agent comprised in the pharmaceutical composition is selected from the group consisting of other anticancer agents, immunomodulators, antiallergic agents, antiemetics, pain relievers, cytoprotective agents, and combinations thereof.

According to another embodiment of the present invention, provided is use of the compound, or a pharmaceutically acceptable salt, stereoisomer, enantiomer, diastereomer, atropisomer, racemate, polymorphs, solvate or isotopically labeled compound thereof, or the pharmaceutical composition in preparation of a medicament for treating a disease, disorder or condition in a subject.

Among others, the disease, disorder or condition is selected from the group consisting of acoustic neuroma, acute leukemia, acute lymphocytic leukemia, acute myeloid leukemia (monocytic, myeloblastic, adenocarcinoma, angiosarcoma, astrocytoma, myelomonocytic and promyelocytic), acute T-cell leukemia, basal cell carcinoma, cholangiocarcinoma, bladder cancer, brain cancer, breast cancer, bronchial cancer, Burkitt's lymphoma, cervical cancer, chondrosarcoma, chordoma, choriocarcinoma, chronic leukemia, chronic lymphocytic leukemia, chronic myeloid (granulocyte) leukemia, chronic myelogenous leukemia, colon cancer, colorectal cancer, craniopharyngioma, cystadenocarcinoma, diffuse large B-cell lymphoma, undesirable proliferative changes (dysplasia and metaplasia), embryonic cancer, endometrial cancer, epithelial cancer, erythroleukemia, esophageal cancer, estrogen receptor-positive breast cancer, essential thrombocythemia, Ewing's Sarcoma, fibrosarcoma, follicular lymphoma, germ cell testicular cancer, glioma, glioblastoma, gliosarcoma, heavy chain disease, hemangioblastoma, liver cancer, hepatocellular carcinoma, hormone-insensitive prostate cancer, leiomyosarcoma, leukemia, liposarcoma, lung cancer, lymphatic endothelial sarcoma, lymphangiosarcoma, lymphoblastic leukemia, Lymphoma (Hodgkin's and non-Hodgkin's), malignancies and hyperproliferative disorders of bladder, breast, colon, lung, ovary, pancreas, prostate, skin and uterus, T-cell or B-cell-derived lymphoid malignancies, leukemia, lymphoma, medullary carcinoma, medulloblastoma, melanoma, meningioma, mesothelioma, multiple myeloma, Myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinoma, papillary cancer, pineal gland tumor, polycythemia vera, prostate cancer, rectal cancer, renal cell carcinoma, retinoblastoma, rhabdomyosarcoma, sarcoma, sebaceous carcinoma, seminoma, skin cancer, small cell lung cancer, solid tumors (carcinoma and sarcoma), small cell lung cancer, stomach cancer, squamous cell carcinoma, synovial tumor, spiroma, thyroid cancer, primary macroglobulinemia, testicular tumor, uterine cancer and nephroblastoma, alternatively, the disease, disorder or condition is selected from the group consisting of a metabolic disease, a neurodegenerative disease or an inflammation.

According to another aspect of the present invention, provided is a method of preparing the compound of the present invention, wherein the method is as shown in the following Scheme 1:

Scheme 1

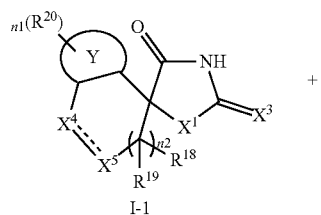

I-1

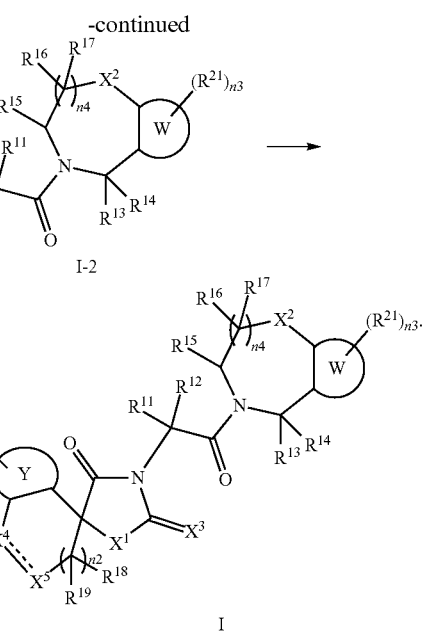

The method of preparing the compound of formula I is shown in Scheme 1. That is, in presence of a base, a spiro compound of formula I-1 and an α-haloamide compound of formula I-2 are reacted in an organic solvent, wherein, the spiro compound may be prepared by referring to known literatures (Abbvie Inc., WO2016044770; *Nature*, 2017, 550, 128-132; *ACS Med. Chem. Lett.*, 2018, 9, 28-33) or according to a conventional method well known in the art. Examples of the base include, but are not limited to, potassium carbonate, sodium carbonate, cesium carbonate, sodium hydroxide, potassium hydroxide, potassium tert-butoxide, sodium tert-butoxide, sodium hydrogen (NaH), triethylamine, diisopropylethylamine, pyridine, 1,5-diazabicyclo[5.4.0]undec-5-ene, 4-dimethylaminopyridine (DMAP), preferably potassium carbonate; the organic solvent includes, such as, but is not limited to, N,N-dimethylformamide (DMF), tetrahydrofuran (THF), acetonitrile, dioxane, dichloromethane (DCM), dichloroethane (DCE), chloroform, preferably N,N-dimethylformamide (DMF).

In Scheme 1, the definitions of $R^{11}$ to $R^{21}$, $X^1$, $X^2$, $X^3$, Y, W, $X^4$, $X^5$, n1, n3, n2, and n4 are the same as the previous text.

Preparation of Intermediate:

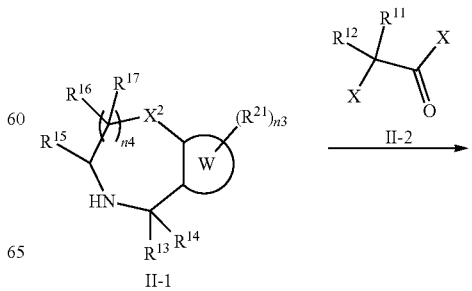

II-1

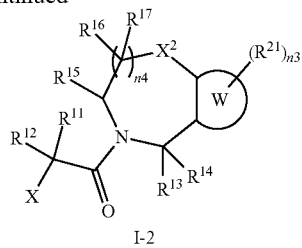

I-2

A method of preparing the α-haloamide compound of formula I-2 from the amine compound of formula II-1 is shown in the above scheme. That is, an amine compound of formula II-1 and a substituted halogenated acetylhalide of formula II-2 are reacted in an organic solvent, the organic solvent includes, such as, but is not limited to, dichloromethane (DCM), dichloroethane (DCE), chloroform, tetrahydrofuran (THF), acetonitrile, dioxane, preferably dichloromethane (DCM).

In the above scheme, X is halogen (Br, Cl, I, F). The amine compound of formula II-1 may be prepared by referring to known literatures or according to a conventional method well known in the art. The definitions of $R^{11}$ to $R^{17}$, $R^{21}$, $X^2$, W, n3, and n4 are the same as the previous text.

The compound of formula III-4 may be prepared using the general process shown in Scheme 2. That is, an aryl halide is treated with an aryl boronic acid containing a $R^{20}$ group or a derivative (for example, borate) thereof under Suzuki coupling condition. As shown in Scheme 2, a compound of formula III-1a, wherein the halogen may be Br, Cl, or I, is coupled with a compound of formula III-2, wherein $B^{III}$ may be a boric acid or a derivative (for example, a borate) thereof to provide a compound of formula III-3; or a compound of formula III-1b, wherein the halogen may be Br, Cl, or I, is coupled with a compound of formula III-2, wherein $B^{III}$ is a boric acid or a derivative (for example, a borate) thereof to provide a compound of formula III-4. Generally, the coupling reaction is carried out in the presence of a palladium catalyst and a base, and optionally a ligand, in a suitable solvent at an elevated temperature (for example, about 80° C. to 150° C.). The reaction can be promoted by microwave radiation. Examples of the palladium catalyst include, but are not limited to, tetrakistriphenylphosphine palladium(0), tris(dibenzylideneacetone)dipalladium(0), chlorinated allylpalladium(II) dimer, [1,1'-bis(diphenylphosphino)ferrocene]palladium dichloride ((dppf)PdCl$_2$) and palladium(II) acetate. Examples of the base suitable for use include, but are not limited to, carbonate or phosphate of sodium, potassium, and cesium, and cesium fluoride. Examples of the

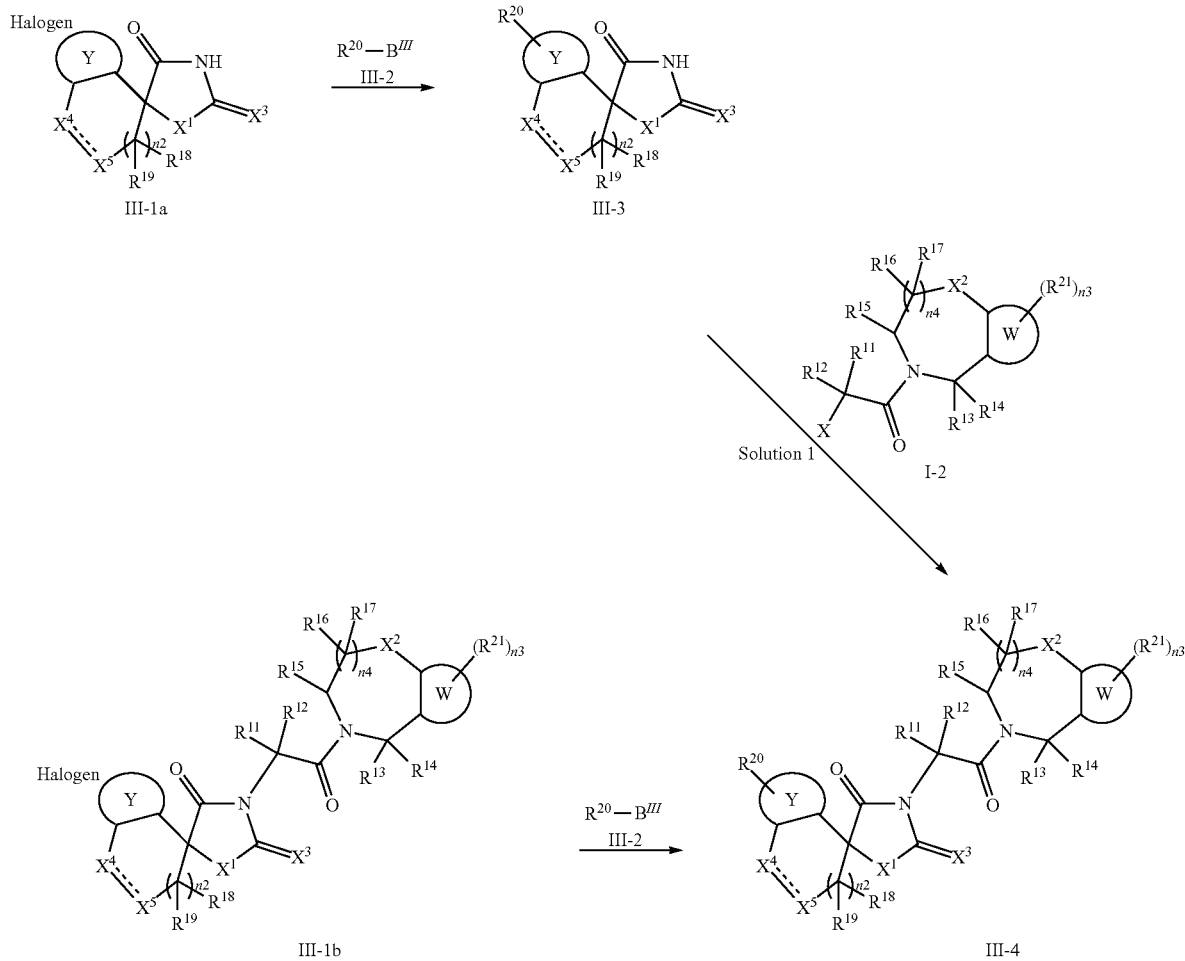

Scheme 2 suitable ligand include, but are not limited to, 2-dicyclohexylphosphino-2,4,6-triisopropylbiphenyl (X-phos), 1,3,5,7-tetramethyl-6-phenyl-2,4,8-trioxa-6-phosphaadamantane, sodium 2'-dicyclohexylphosphino-2,6-dimethoxy-1,1'-biphenyl-3-sulfonate hydrate and 1,1'-bis(diphenylphosphoryl)ferrocene. Non-limiting Examples of the suitable solvent include methanol, acetonitrile, dimethoxyethane, N,N-dimethylformamide, dimethyl sulfoxide, dioxane, tetrahydrofuran, ethylene glycol dimethyl ether, toluene, water, or mixtures thereof.

In addition, the compound of formula III-3 may be prepared by the general process shown in Scheme 1 into the compound of formula III-4.

In Scheme 2, the definitions of $R^{11}$ to $R^{19}$, $R^{21}$, $X^1$, $X^2$, $X^3$, Y, W, $X^4$, $X^5$, n2, n3 and n4 are the same as the previous text; and $R^{20}$ is Mc.

The optimal reaction conditions and time of each individual step can be varied according to the specific reactants used and the substituents present in all reactants. Unless otherwise specified, the solvent, temperature, and other reaction conditions can be easily selected by a person skilled in the art. The specific steps are provided in the Section for Synthetic Example. The reaction mixture can be further processed in a conventional manner, for example, by removing the solvent from the residue and further purifying according to a method generally known in the art, including, such as, but not limited to, crystallization, distillation, extraction, grinding and chromatography. Unless otherwise stated, starting materials and reactants are commercially available or can be prepared by a person skilled in the art from commercially available materials using methods described in chemical literatures.

Conventional experiments, including proper adjustment of the reaction conditions, the reactants and sequence of the synthetic route, the protection of any chemical functional group, which may not be compatible with the reaction conditions, and the deprotection at an appropriate point in the reaction sequence of the method, are all included in the scope of the present invention. Appropriate protecting groups and methods of using such appropriate protecting groups to protect or deprotect different substituents are well known to a person skilled in the art; examples thereof may be found in T. Greene and P. Wuts, Protecting Groups in Chemical Synthesis (third edition), John Wiley & Sons, NY (1999), which is incorporated herein by reference in its entirety. The synthesis of the compounds of the present invention can be achieved by methods similar to those described in the synthetic Schemes described above and in specific examples.

If a starting material is not commercial available, it may be prepared by steps selected from the following: standard organic chemistry techniques, techniques similar to the synthesis of known structural analogs, or techniques similar to the steps described in the above Scheme or Section for Synthetic Example. When an optically active form of the compound of the present invention is required, it can be obtained by performing one of the steps described herein using an optically active starting material (for example, asymmetrically induced preparation by appropriate reaction steps), or by resolving a stereoisomer mixture of the compound or intermediate by using a standard procedure such as chromatographic separation, recrystallization or enzymatic resolution.

Similarly, when a pure geometric isomer of the compound of the present invention is required, it can be obtained by performing one of the above steps using a pure geometric isomer as a starting material, or it can be obtained by resolving a geometric isomer mixture of the compound or intermediate by using a standard procedure such as chromatographic separation.

DETAILED EMBODIMENTS

The following embodiments may be used for illustration, and are only used to explain the technical solutions of the present invention, and not intended to limit the present invention.

Example 1 Synthesis of Amide AN-1

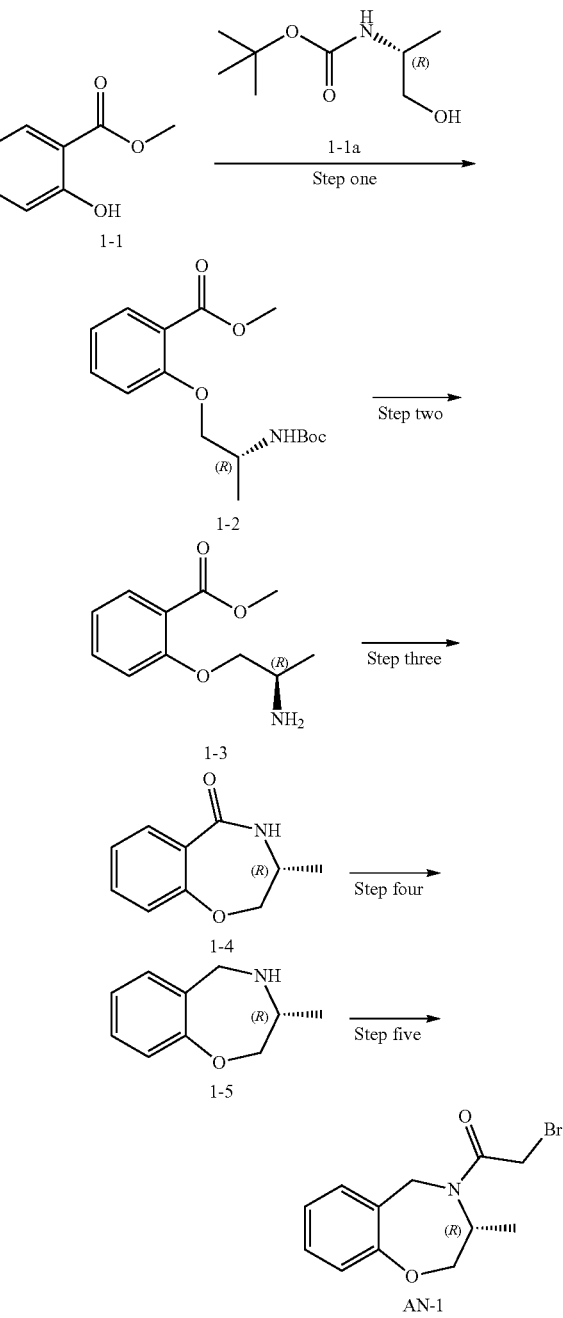

Step One:

Methyl salicylate (1-1, 5.0 g), N-Boc-D-alaninol (1-1a, 5.76 g), diisopropyl azodicarboxylate (7.30 g) and triphenylphosphine (9.48 g) were dissolved in anhydrous THF (50 mL) under nitrogen to react at room temperature overnight. TLC showed that the reaction was complete. The reaction mixture was quenched with water and extracted with ethyl acetate. The organic phased was dried over anhydrous sodium sulfate, filtered and rotary evaporated to dryness to obtain a crude, which is purified by column chromatography to give a light yellow liquid (1-2, 7.6 g). LC-MS: 332.2 [M+Na]*.

Step Two:

1-2 (3.0 g) was dissolved in dichloromethane (20 mL) and added with 4N hydrochloric acid/dioxane (20 mL) to react at room temperature overnight. TLC showed that the reaction was complete. The reaction mixture was quenched with water. The aqueous phase was washed with ethyl acetate, adjusted pH to 9 with 1M NaOH, and extracted with ethyl acetate. The organic phase was dried over anhydrous sodium sulfate, filtered and rotary evaporated to dryness to obtain a crude 1-3. LC-MS: 210.1 [M+H]$^+$.

Step Three:

1-3 (1.0 g) was dissolved in THF (10 mL) and added with TEA (2 mL) to react at 80° C. overnight. TLC showed that the reaction was complete. The reaction mixture was quenched with water, and extracted with ethyl acetate. The organic phase was dried over anhydrous sodium sulfate, filtered and rotary evaporated to dryness to obtain a crude, which is purified by column chromatography to give a light yellow liquid (1-4, 700 mg). LC-MS: 178.1 [M+H]$^+$.

Step Four:

1-4 (300 mg) was dissolved in anhydrous THF (10 mL) and added with lithium aluminum hydride (3.0 eq.) to react at 80° C. for 2 h. TLC showed that the reaction was complete. The reaction mixture was quenched with water and extracted with ethyl acetate. The organic phase was dried over anhydrous sodium sulfate, filtered and rotary evaporated to dryness to obtain a crude, which is purified by column chromatography to give a light yellow liquid (1-5, 230 mg).

Step Five:

A solution of bromoacetyl bromide (1.1 eq.) in dichloromethane was added dropwise to a solution of 1-5 (230 mg) and triethylamine (1.5 eq.) in dichloromethane under an ice bath to react at 0° C. for 1 h. TLC showed that the reaction was complete. The reaction mixture was added with a saturated sodium bicarbonate solution and extracted with dichloromethane. The organic phase was dried over anhydrous sodium sulfate, filtered and rotary evaporated to dryness to give a crude, which was purified by column chromatography to obtain a colorless oil (AN-1, 390 mg). LC-MS: 284.1 [M+H]$^+$.

Example 2 Synthesis of Amide AN-2

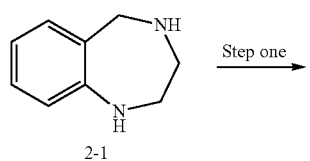

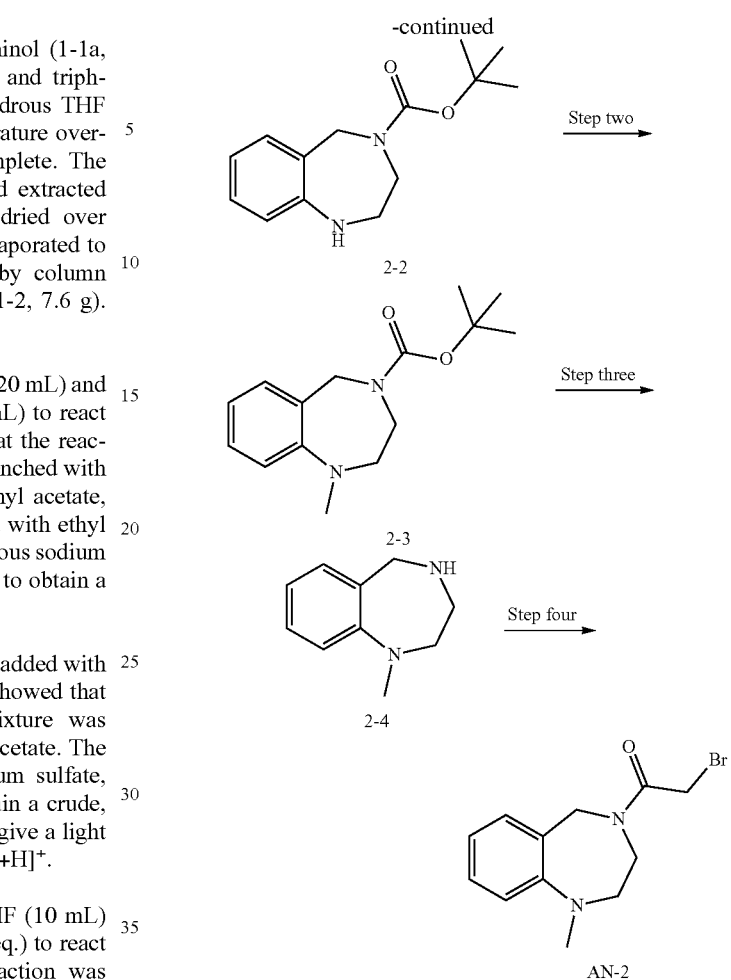

Step One:

2-1 (250 mg) was dissolved in dichloromethane (20 mL) and added with BOC anhydride (1.05 eq.). The reaction mixture was stirred at room temperature for 30 min and then rotary evaporated to dryness to obtain a crude (2-2, 420 mg), which was directly used in the next step.

Step Two:

2-2 (400 mg) was dissolved in methanol (20 mL) and added with acetic acid (150 mg) and 37% formaldehyde aqueous solution (55 mg). The reaction mixture was stirred at room temperature for 10 min, and then added with sodium cyanoborohydride (315 mg). After the reaction was complete, the reaction mixture was quenched with water, and extracted with ethyl acetate. The organic phase was dried, and rotary evaporated to dryness to obtain a crude (2-3, 300 mg).

Step Three:

2-3 (300 mg) was added with trifluoroacetic acid (2 mL), stirred for 20 min, and then distilled under reduced pressure to remove excess trifluoroacetic acid. After added with a 2 N sodium hydroxide aqueous solution (20 mL), the reaction mixture was extracted with dichloromethane. The organic phase was dried, rotary evaporated to dryness to give a crude (2-4, 150 mg).

Step Four:

2-4 (150 mg) was dissolved in anhydrous dichloromethane (20 mL), and added with bromoacetyl bromide (565 mg). The reaction mixture was stirred at room temperature for 0.5 h, quenched with water, and layered. The organic phase was subjected directly to column chromatography to give AN-2 (150 mg). LC-MS: 283.1 [M+H]+.

Example 3 Synthesis of Amide AN-3

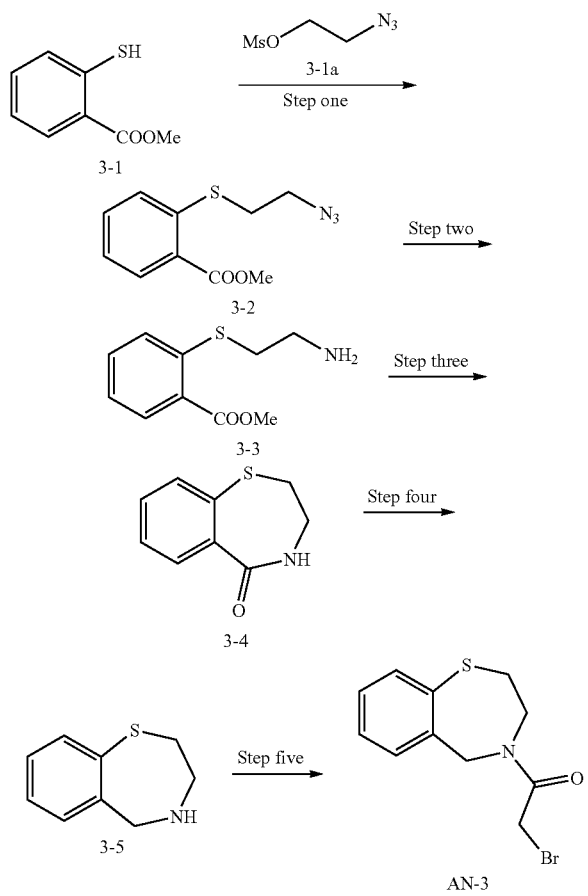

Step One:

Methyl thiosalicylate (3-1, 1.0 g) was dissolved in anhydrous DMF (10 mL), and added slowly with NaH (60%, 480 mg) under an ice bath. After stirred for 10 min, the reaction mixture was added with the azide 3-1a (1.11 g), warmed to room temperature and stirred for 0.5 h. TLC showed that the reaction was complete. The reaction mixture was quenched by slowly adding water under an ice-water bath, and extracted with ethyl acetate. The combined organic phase was washed with water and saturated brine, dried over anhydrous sodium sulfate, and concentrated to obtain 3-2 (700 mg) as an oil, which was used directly in the next step.

Step Two:

3-2 (700 mg) was dissolved in tetrahydrofuran (20 mL), added with triphenylphosphine (1.57 g), and stirred at 55° C. for 1 h. TLC detected disappearance of the raw material. The reaction solution was added with 5 mL of water and stirred for 2 h. TLC detected complete disappearance of the intermediate. The reaction solution was cooled to room temperature, poured into water, and extracted with ethyl acetate. The combined organic phase was washed with water and saturated brine, dried over anhydrous sodium sulfate, and concentrated to obtain 3-3 (415 mg) as a yellow solid.

Step Three:

3-3 (400 mg) was dissolved in anhydrous methanol (20 mL), added with sodium methoxide (810 mg) under an ice-water bath, and then stirred at room temperature overnight. TLC detected that the reaction was complete. The reaction solution was poured into ice water and extracted with ethyl acetate. The combined organic phase was washed with water and saturated brine, dried over anhydrous sodium sulfate, and concentrated to obtain 3-4 (320 mg) as a yellow oil, which was directly used in the next step.

Step Four:

At room temperature, 3-4 (320 mg) was dissolve in anhydrous tetrahydrofuran (20 mL), added batchwise with lithium aluminum tetrahydrogen (190 mg), heated to reflux and stirred for 3 h. TLC detected disappearance of the raw material. After cooled, the reaction solution was quenched by carefully adding water to precipitate a solid, which was filtered off. The filtrate was extracted with ethyl acetate. The combined organic phase was washed with water and saturated brine, dried over anhydrous sodium sulfate, and concentrated to obtain 3-5 (200 mg) as an oil, which was directly used in the next step.

Step Five:

3-5 (200 mg) was dissolved in anhydrous dichloromethane (20 mL), added with bromoacetyl bromide (505 mg) under an ice bath, and stirred at room temperature for 1 h. TLC detected that a small amount of the raw material was still unreacted. The reaction solution was supplemented with triethylamine (152 mg) and stirred for 0.5 h. TLC detected that the raw material was reacted completely. The reaction solution was quenched with water, and the organic phase was separated. The aqueous phase was extracted with dichloromethane. The combined organic phase was washed with water and saturated brine, dried over anhydrous sodium sulfate, and concentrated. The crude was purified by silica gel column chromatography to obtain the targeted AN-3 (215 mg) as a yellowish oil. LC-MS: 286.1 [M+H]+.

Example 4 Synthesis of Amide AN-4

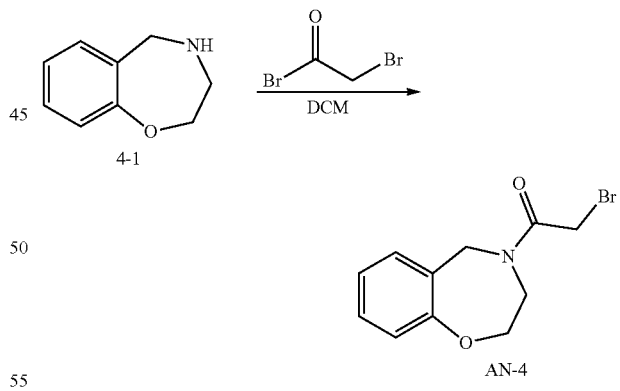

4-1 (120 mg) was dissolved in anhydrous methylene chloride (10 mL), added with bromoacetyl bromide (505 mg) at room temperature, and stirred for 30 min. TLC showed that the reaction was complete. The reaction solution was poured into ice water, and the organic phase was separated. The aqueous phase was extracted with dichloromethane. The combined organic phase was washed with water and saturated brine, dried over anhydrous sodium sulfate, and concentrated. The crude was purified by silica gel column chromatography to obtain AN-4 (150 mg). LC-MS: 270.1 [M+H]+.

Example 5 Synthesis of Amide AN-5

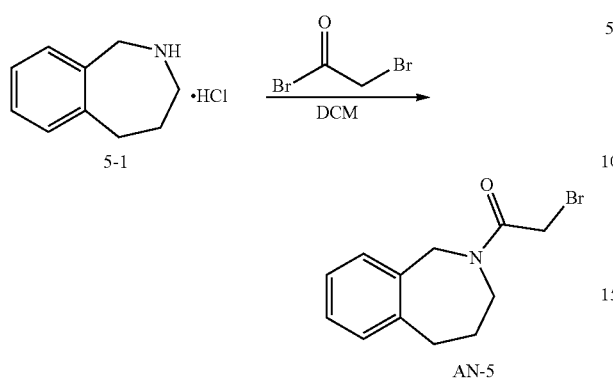

5-1 (400 mg, hydrochloride salt) was dissolved in water, adjusted pH to 11~12 with a 2N NaOH aqueous solution and extracted with dichloromethane. The combined organic phase was washed with water and saturated brine, dried and concentrated to about 20 mL. The reaction solution was added slowly with bromoacetyl bromide (1.2 g) under an ice-water bath, and stirred at room temperature for 30 min. TLC showed that the reaction was complete. The reaction solution was poured into ice water, and the organic phase was separated. The aqueous phase was extracted with dichloromethane. The combined organic phase was washed with water and saturated brine, dried over anhydrous sodium sulfate, and concentrated. The crude was purified by silica gel column chromatography to obtain AN-5 (416 mg). LC-MS: 268.1 $[M+H]^+$.

Example 6 Synthesis of Amide AN-6

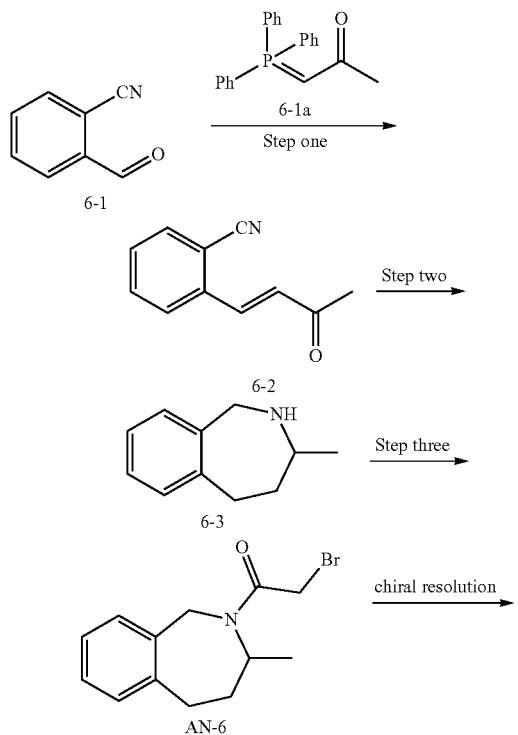

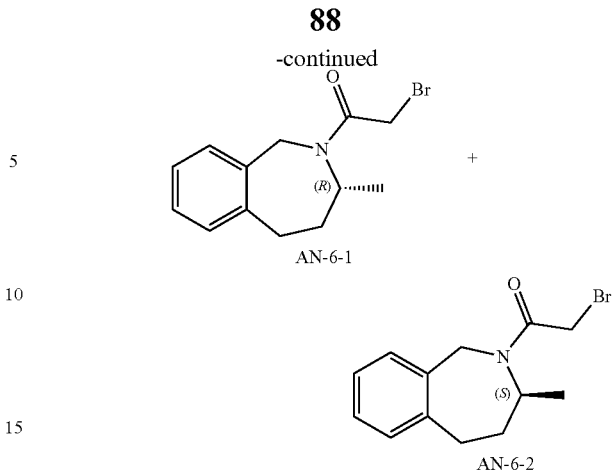

Step One:

2-cyanobenzaldehyde (6-1, 3.0 g) and 1-triphenylphos-phine-2-acetone (6-1a, 11.0 g) were added to anhydrous tetrahydrofuran (80 mL) at room temperature, and heated to 50° C. to react for 2 h. TLC showed that the reaction was complete. The reaction solution was cooled to room temperature, poured into ice water, and extracted with ethyl acetate. The combined organic phase was washed with water and saturated brine, dried over anhydrous sodium sulfate, and concentrated. The crude was purified and purified by column chromatography to obtain 6-2 (3.0 g) as a yellowish solid.

Step Two:

6-2 (3.0 g) and 10% Pd/C (600 mg) were dissolved in methanol (80 mL). After atmosphere was replaced with nitrogen 3 times and then with hydrogen 2 times, the reaction mixture was stirred under hydrogen (1.5 atm) for 2 days. TLC showed that the reaction was finished. The resultant was carefully filtered to remove Pd/C. The organic phase was concentrated directly to obtain a crude 6-3 (2.8 g), which is used directly in the next step. LC-MS: 162.2 $[M+H]^+$.

Step Three:

A solution of bromoacetyl bromide (3.5 g) in methylene chloride was added dropwise to a solution of 6-3 (2.8 g) in methylene chloride under an ice bath, and stirred for 3 h. TLC showed that the reaction was complete. The reaction mixture was rotary evaporated to dryness to obtain a crude, which was purified by column chromatography to obtain AN-6 (700 mg) as a yellowish oil. LC-MS: 282.1 $[M+H]^+$.

The racemate AN-6 was subjected to chiral resolution to obtain chiral amides AN-6-1 and AN-6-2.

Chiral resolution conditions: semi-preparative column was CHIRALPAK@OD-H, filler particle size (5 µm), inner diameter (30 mm), length (250 mm), flow rate: 20 mL/min, mobile phase: 90% n-hexane+10% ethanol, isogradient elution, wavelength: 220 nm, total time: 30 min; peak time is 21.8 min for peak 1, and 23.9 min for peak 2.

Example 7 Synthesis of Amide AN-7

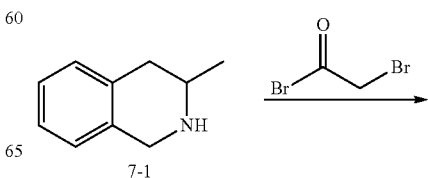

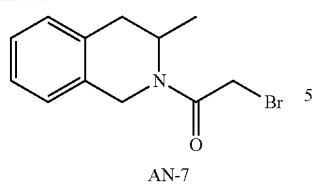

AN-7

7-1 (300 mg) was dissolved in anhydrous methylene chloride (15 mL), added with bromoacetyl bromide (1.21 g) at room temperature, and stirred for 1 h. TLC showed that the reaction was complete. The reaction solution was poured into ice water, and the organic phase was separated. The aqueous phase was extracted with dichloromethane. The combined organic phase was washed with water and saturated brine, dried over anhydrous sodium sulfate, and concentrated. The crude was purified by silica gel column chromatography to obtain AN-7 (355 mg). LC-MS: 268.1 [M+H]$^+$.

Example 8 Synthesis of Amides AN-8 and AN-12

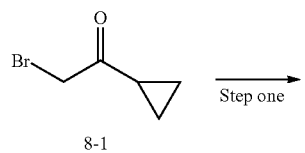

8-1

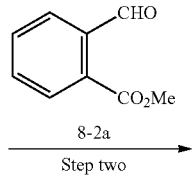

8-2

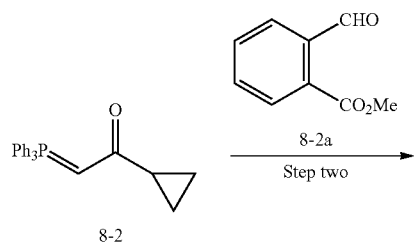

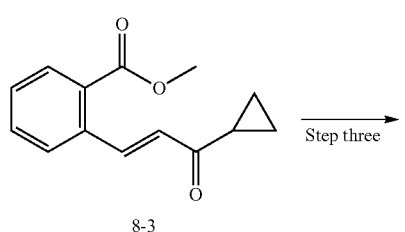

8-3

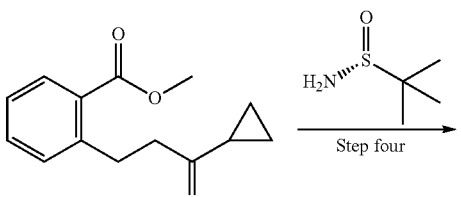

8-4

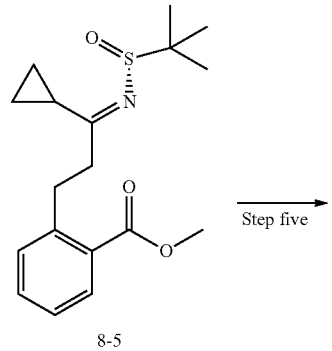

8-5

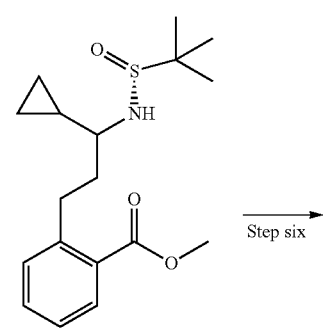

8-6

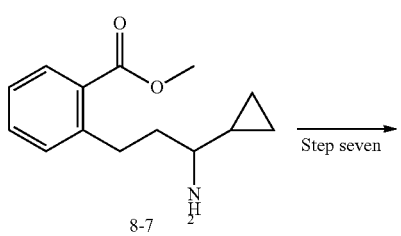

8-7

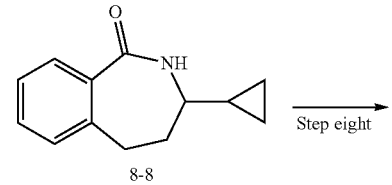

8-8

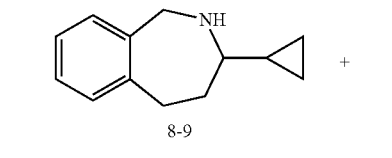

8-9

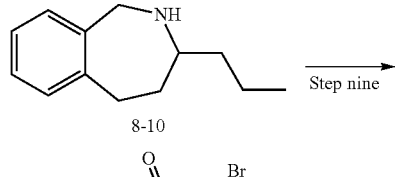

8-10

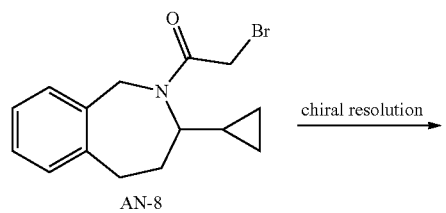

AN-8

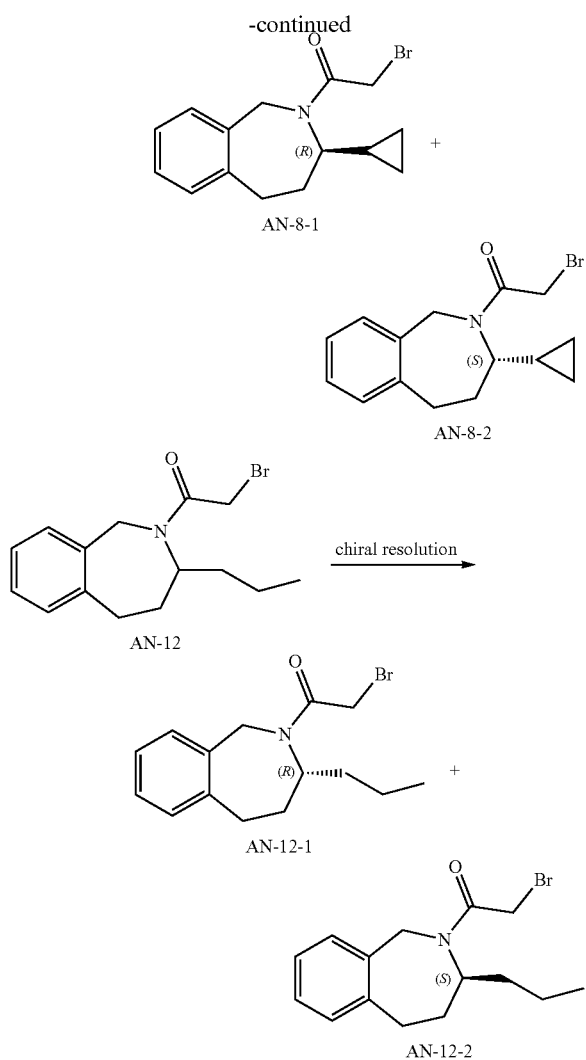

Step One:
Bromomethylcyclopropylketone (8-1, 15.0 g) and triphenylphosphine (28.5 g) were added to toluene (500 mL), and heated to reflux for 6 h. TLC showed that the reaction was complete. The reaction solution was cooled to room temperature to precipitate a solid, which was filtered off and washed with 200 mL of diethyl ether in batches. After the solid was dried, it was added to a mixture of 350 mL of dichloromethane and 200 mL of water, added with a 5N sodium hydroxide solution (250 mL), and stirred for 4 h at room temperature. The organic phase was separated and the aqueous phase was extracted with dichloromethane. The combined organic phase was washed with water and saturated brine, dried over anhydrous sodium sulfate, and concentrated to obtain 8-2 (23.2 g).

Step Two:
8-2 (20.0 g) and methyl 2-formylbenzoate (8-2a, 8.58 g) were added to 250 mL of tetrahydrofuran, and heated to reflux for 5 h. TLC showed that the reaction was complete. The reaction solution was concentrated to dryness. The crude was directly purified by silica gel column chromatography to obtain 8-3 (9.21 g).

Step Three:
8-3 (9.0 g) was dissolved in 100 mL of methanol and added with 10% Pd/C (1.0 g). After atmosphere was replaced with nitrogen 2 times and then with hydrogen 2 times, the reaction mixture was stirred at room temperature under hydrogen balloon overnight. TLC showed that the reaction was complete. Pd/C was removed by filtration and washed with methanol. The combined organic phase was concentrated to obtain a reduced product 8-4 (crude), which was directly used in the next step.

Step Four:
8-4 was dissolved in 100 mL of toluene, added with (R)-(+)-tert-butylsulfinamide (8-4a, 3.15 g) and tetraethyl titanate (7.84 g) in sequence, heated to reflux and stirred for 6 h. TLC showed that the reaction was complete. The reaction solution was poured into ice water, stirred for 30 min, and extracted with ethyl acetate. The combined organic phase was washed with water and saturated brine, dried over anhydrous sodium sulfate, and concentrated. The crude was purified by silica gel column chromatography to obtain 8-5 (2.5 g).

Step Five:
8-5 (2.5 g) was dissolved in methanol (30 mL), added slowly with sodium borohydride (568 mg) in an ice water bath, and stirred in an ice bath for 0.5 h. TLC showed that the raw material was reacted completely. The reaction solution was quenched by slow addition of water and extracted with ethyl acetate. The combined organic phase was washed with water and brine, dried over anhydrous sodium sulfate, and concentrated to obtain 8-6 (2.0 g), which was directly used in the next step.

Step Six:
8-6 (2.0 g) was dissolved in methanol (30 mL), added with saturated HCl (g)/methanol solution (10 mL), and stirred at room temperature for 0.5 h. TLC showed that the raw material was completely reacted. The reaction solution was rotary evaporated to dryness directly, alkalized with saturated sodium bicarbonate, and extracted with dichloromethane. The combined organic phase was washed with water and saturated brine, dried over anhydrous sodium sulfate, and concentrated to obtain the amine 8-7 (1.2 g), which was directly used in the next step. LC-MS: 234.4 $[M+H]^+$.

Step Seven:
8-7 (1.2 g) was dissolved in methanol (30 mL), slowly added with sodium methoxide (555 mg) at room temperature, and stirred at 70° C. for 3 h. TLC showed that the reaction was complete. The reaction solution was cooled to room temperature, and poured into ice water. The aqueous phase was extracted with ethyl acetate. The combined organic phase was washed with water and brine, dried over anhydrous sodium sulfate, and concentrated to obtain a crude 8-8 (830 mg), which was directly used in the next step. LC-MS: 202.2 $[M+H]^+$.

Step Eight:
8-8 (830 mg) was dissolved in anhydrous tetrahydrofuran (30 mL), added with lithium tetrahydroaluminum (380 mg), and stirred at 70° C. for 3 h. TLC showed that the reaction was complete. The reaction solution was cooled to room temperature, and quenched by slow addition of water. The aqueous phase was extracted with ethyl acetate. The combined organic phase was washed with water and brine, dried over anhydrous sodium sulfate, and concentrated to obtain a mixture of 8-9 and 8-10 (685 mg), which was directly used in the next step.

Step Nine:
The mixture of 8-9 and 8-10 (685 mg) was dissolved in anhydrous dichloromethane (30 mL), added slowly with bromoacetyl bromide (2.22 g) under an ice-water bath, and stirred at room temperature for 1 h. TLC showed that the reaction was complete. The reaction solution was poured into ice water, and extracted with ethyl acetate. The combined organic phase was washed with water and brine, dried over anhydrous sodium sulfate, and concentrated. The crude was purified by silica gel column chromatography to obtain AN-8 (240 mg), LC-MS: 308.1 [M+H]+; and AN-12 (440 mg), LC-MS: 310.1 [M+H]+.

The racemate AN-8 was subjected to chiral resolution to obtain chiral amides AN-8-1 and AN-8-2.

Chiral resolution conditions: semi-preparative column was CHIRALPAK@OD-H, filler particle size (5 μm), inner diameter (30 mm), length (250 mm), flow rate: 20 mL/min, mobile phase: 90% n-hexane+10% ethanol, isogradient elution, wavelength: 220 nm, total time: 30 min; peak time is 21.4 min for peak 1, and 25.9 min for peak 2.

The racemate AN-12 was subjected to chiral resolution to obtain chiral amides AN-12-1 and AN-12-2.

Chiral resolution conditions: semi-preparative column was CHIRALPAK@OD-H, filler particle size (5 μm), inner diameter (30 mm), length (250 mm), flow rate: 20 mL/min, mobile phase: 95% n-hexane+5% ethanol, isogradient elution, wavelength: 254 nm, total time: 40 min; peak time is 21.6 min for peak 1, and 24.9 min for peak 2.

Example 9 Synthesis of Amide AN-9

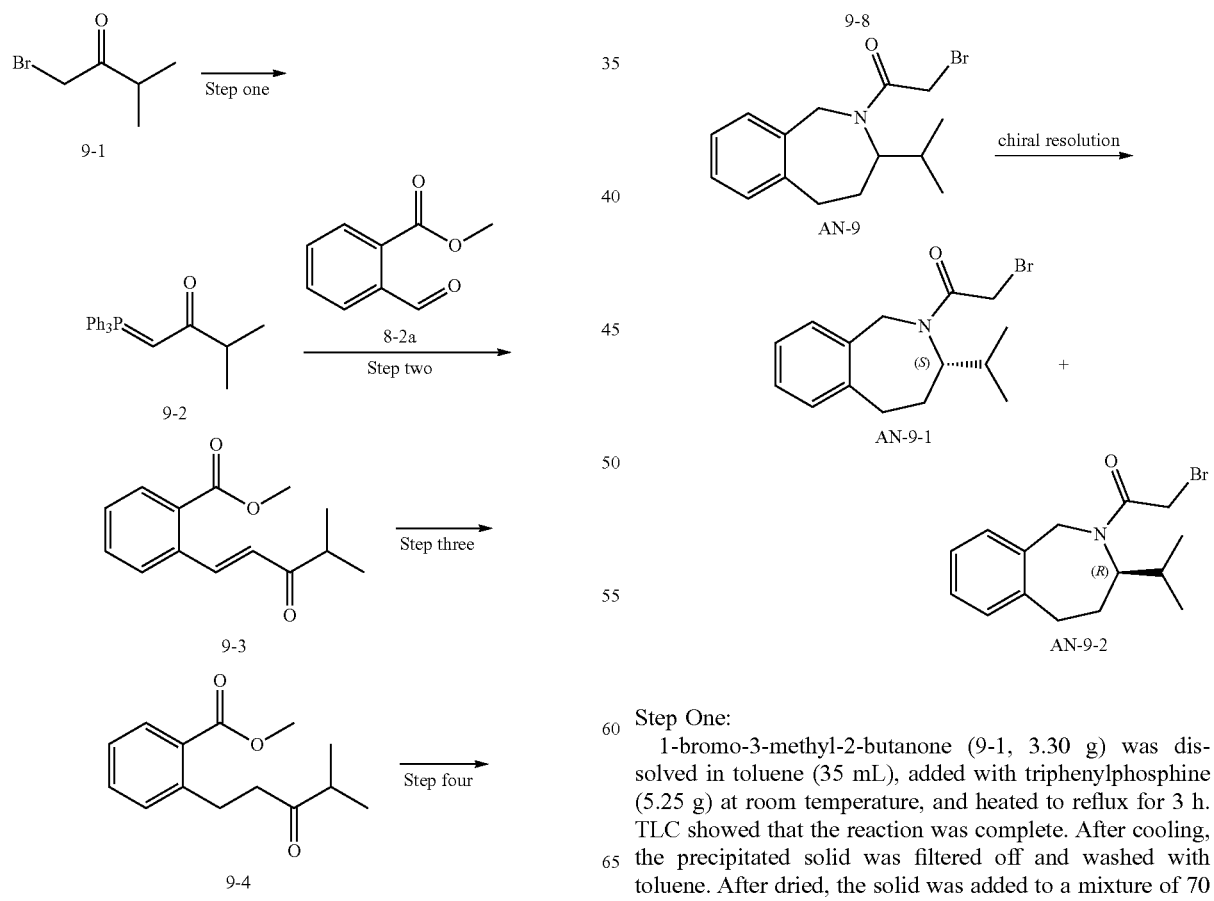

Step One:
1-bromo-3-methyl-2-butanone (9-1, 3.30 g) was dissolved in toluene (35 mL), added with triphenylphosphine (5.25 g) at room temperature, and heated to reflux for 3 h. TLC showed that the reaction was complete. After cooling, the precipitated solid was filtered off and washed with toluene. After dried, the solid was added to a mixture of 70 mL of dichloromethane and 40 mL of water, added with a 5

N sodium hydroxide solution (50 mL), and stirred for 4 h at room temperature. The organic phase was separated and the aqueous phase was extracted with dichloromethane. The combined organic phase was washed with water and saturated brine, dried over anhydrous sodium sulfate, and concentrated to obtain 9-2 (4.8 g) as a white solid.

Step Two:

Methyl 2-formylbenzoate (8-2a, 1.5 g) and 9-2 (4.80 g) were dissolved in tetrahydrofuran (20 mL), heated to reflux and stirred for 4 h. TLC showed that most of the raw material was reacted. The resultant was directly concentrated and the residue was purified by column chromatography to obtain a yellow oil (9-3, 1.34 g).

Step Three:

9-3 (1.34 g) was dissolved in 20 mL of methanol and 10% Pd/C (200 mg) was added. After atmosphere was replaced with nitrogen 2 times and then with hydrogen 2 times, the reaction solution was stirred at room temperature under hydrogen balloon overnight. TLC showed that the reaction was complete. Pd/C was removed by filtration, and washed with methanol. The combined organic phase was concentrated to obtain a crude 9-4 (1.34 g), which was directly used in the next step.

Step Four:

9-4 (5.00 g), tetraethyl titanate (7.0 g), and R-tert-butylsulfinamide (8-4a, 2.8 g) were added to toluene (100 mL), and stirred at 110° C. for 3 h. TLC detected that the reaction was complete. The reaction solution was cooled to room temperature, poured into ice water and filtered. The filter cake was washed with ethyl acetate. The aqueous phase was extracted with ethyl acetate. The combined organic phase was washed with a 2N dilute hydrochloric acid and saturated brine, dried and concentrated to obtain a crude. The crude was dissolved in methanol (60 mL), added with sodium borohydride (1.0 g) under an ice-water bath, stirred at room temperature for 30 min, and quenched by addition of saturated brine. The aqueous phase was extracted with ethyl acetate. The combined organic phase was washed with brine once, and concentrated to obtain a crude 9-5 (1.34 g), which was directly used in the next step.

Step Five:

9-5 was added to a solution (10 mL, 4M) of hydrogen chloride in methanol and stirred at room temperature for 30 min. TLC detected that the reaction was complete. The mixture was concentrated, added with water and ethyl acetate and stirred for 10 min. The organic phase was washed with water once. The combined aqueous phase was adjusted to be neutral and extracted with ethyl acetate. The combined organic phase was washed with water and saturated brine, dried over anhydrous sodium sulfate, and concentrated to obtain 9-6. LC-MS: 236.2 [M+H]$^+$.

Step Six:

9-6 (1.2 g) was dissolved in methanol (30 mL), added with sodium methoxide (2.75 g) at room temperature, heated to 60° C. and stirred for 3 h. TLC showed that the raw material was reacted completely. The reaction solution was cooled to room temperature, poured into water, and extracted with ethyl acetate. The combined organic phase was washed with water and saturated brine, dried over anhydrous sodium sulfate, and concentrated to obtain a cyclized product 9-7. LC-MS: 204.2 [M+H]$^+$.

Step Seven:

9-7 was dissolved in anhydrous tetrahydrofuran (20 mL), added with lithium aluminum tetrahydrogen (950 mg) under nitrogen, and heated to reflux for 36 h. TLC detected that part of the raw material was still unreacted. The reaction solution was cooled to room temperature, added with a 15% sodium hydroxide aqueous solution until no bubble emerges, added with water and ethyl acetate, and stirred and filtered. The filter cake was washed with ethyl acetate. The combined organic phase was added with a 4N hydrochloric acid and stirred for 10 min. The aqueous phase was adjusted to be neutral and extracted with ethyl acetate. The combined organic phase was washed with water and saturated brine, dried over anhydrous sodium sulfate, and concentrated to obtain a crude 9-8 (570 mg), which was directly used in the next step. LC-MS: 190.2 [M+H]$^+$.

Step Eight:

9-8 (570 mg, crude) was dissolved in dichloromethane (20 mL), added with bromoacetyl bromide (910 mg), and stirred at room temperature for 1 h. TLC detected that the reaction was complete. The reaction solution was poured into water, and the organic phase was separated. The aqueous phase was extracted with dichloromethane. The combined organic phase was washed with water and saturated brine, dried over anhydrous sodium sulfate, and concentrated. The crude was purified by column chromatography to obtain AN-9 (620 mg). LC-MS: 310.1 [M+H]$^+$.

The racemate AN-9 was subjected to chiral resolution to obtain chiral amides AN-9-1 and AN-9-2.

Chiral resolution conditions: semi-preparative column was CHIRALPAK@OD-H, filler particle size (5 μm), inner diameter (30 mm), length (250 mm), flow rate: 20 mL/min, mobile phase: 90% n-hexane+10% isopropanol, isogradient elution, wavelength: 220 nm, total time: 35 min; peak time is 21.7 min for peak 1, and 25.5 min for peak 2.

Example 10 Synthesis of Amide AN-10

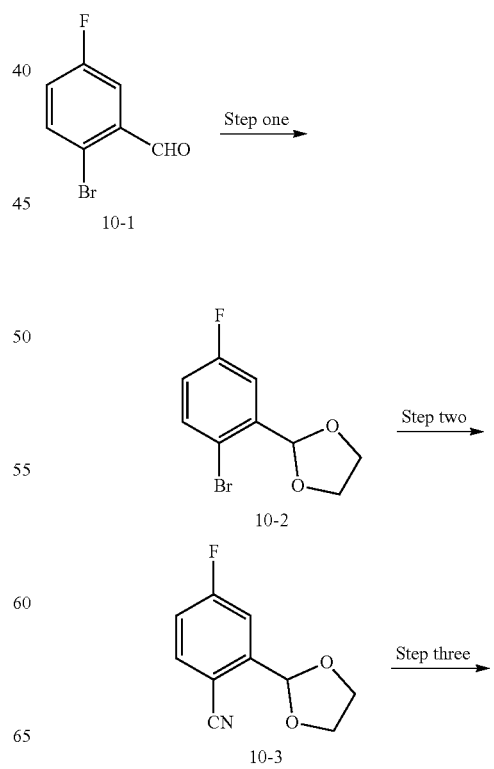

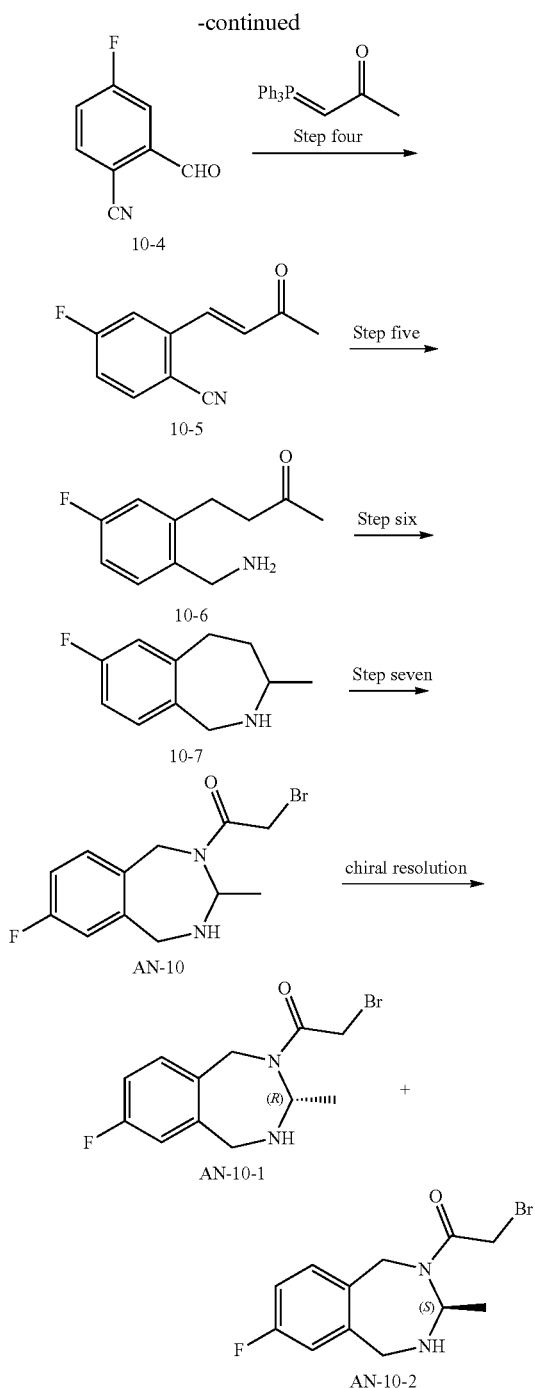

Step One:

2-Bromo-5-fluorobenzaldehyde (10-1, 50 g), ethylene glycol (150 mL) and p-toluenesulfonic acid (1.0 g) were dissolved in toluene (100 mL), heated to 100° C. and stirred for 5 h. TLC detected that the raw material was basically reacted. The reaction mixture was cooled to room temperature, diluted with ethyl acetate, added with brine, stirred and layered. The aqueous phase was extracted with ethyl acetate. The combined organic phase was washed with brine, dried over anhydrous sodium sulfate and concentrated. The crude was purified by silica gel column chromatography to obtain oil 10-2 (48.5 g).

Step Two:

10-2 (20.0 g), tris(dibenzylideneacetone) dipalladium (750 mg), triphenylphosphine (2.36 g) and zinc cyanide (19.1 g) were dissolved in anhydrous NMP (100 mL), and stirred at 100° C. for 3 h under nitrogen. TLC detected that the raw material was completely reacted. The reaction solution was cooled to room temperature and diluted with ethyl acetate. The solid was filtered off and washed with ethyl acetate. The organic phase was washed with water and saturated brine, dried over anhydrous sodium sulfate, and concentrated. The crude was purified by silica gel column chromatography to obtain 10-3 (8.72 g) as a white solid.

Step Three:

10-3 (8.72 g) was dissolved in 1,4-dioxane (100 mL), added with concentrated hydrochloric acid (33 mL), and stirred overnight at room temperature. TLC detected that the raw material was reacted completely. The reaction solution was poured into water and extracted with ethyl acetate. The combined organic phase was washed with water and saturated brine, dried over anhydrous sodium sulfate and concentrated. The crude was purified by silica gel column chromatography to obtain 10-4 (6.32 g).

Step Four:

10-4 (6.70 g) and the phosphorus ylide 10-4a (18.64 g) were dissolved in tetrahydrofuran (50 mL) and stirred under heating and refluxing for 2 h. TLC detected that the reaction was complete. The reaction solution was cooled and directly concentrated. The crude was purified by silica gel column chromatography to obtain 10-5 (7.67 g) as a yellowish liquid.

Step Five:

10-5 (5.71 g) was dissolved in methanol (80 mL) and added with 10% Pd/C (500 mg). After atmosphere was replaced with hydrogen, the reaction mixture was stirred overnight under hydrogen. After the reaction was complete, Pd/C was removed by suction filtration. The filter cake was washed with a small amount of methanol. The filtrate was combined and added with Raney nickel (800 mg) and TEA (0.5 mL). After atmosphere was replaced with hydrogen, the reaction mixture was stirred overnight at 40° C. under hydrogen. After the reaction was complete, the reaction mixture was filtered with suction, and the filter cake was washed with methanol. The filtrate was combined to obtain a solution of a crude 10-6 in methanol, which was directly used in the next step. LC-MS: 196.1 [M+H]$^+$.

Step Six:

The methanol solution of the crude 10-6 in the previous step was added with acetic acid (1 mL), and then added with sodium cyanoborohydride (3.14 g) at room temperature, and stirred at room temperature for 1 h. TLC indicated that the reaction was complete. The reaction solution was poured into ice water, alkalized with a 2N NaOH aqueous solution, and extracted with dichloromethane. The combined organic phase was washed with water and saturated brine, dried over anhydrous sodium sulfate, and concentrated to obtain a crude 10-7, which was used directly in the next step. LC-MS: 180.2 [M+H]$^+$.

Step Seven:

The crude 10-7 in the previous step was dissolved in dichloromethane (50 mL), added with bromoacetyl bromide (10.1 g) and stirred at room temperature for 1 h. TLC showed that the reaction was complete. The reaction solution was poured into water, and the organic phase was separated. The aqueous phase was extracted with dichloromethane. The combined organic phase was washed with water and saturated brine, dried over anhydrous sodium sulfate, and concentrated. The crude was purified by column chromatography to obtain AN-10 (2.2 g). LC-MS: 300.1 [M+H]+.

The racemate AN-10 was subjected to chiral resolution to obtain chiral amides AN-10-1 and AN-10-2.

Chiral resolution conditions: semi-preparative column was CHIRALPAK@OD-H, filler particle size (5 μm), inner diameter (30 mm), length (250 mm), flow rate: 20 mL/min, mobile phase: 90% n-hexane+10% ethanol, isogradient elution, wavelength: 220 nm, total time: 30 min; peak time is 18.8 min for peak 1, and 20.5 min for peak 2.

Example 11 Synthesis of Amide AN-11

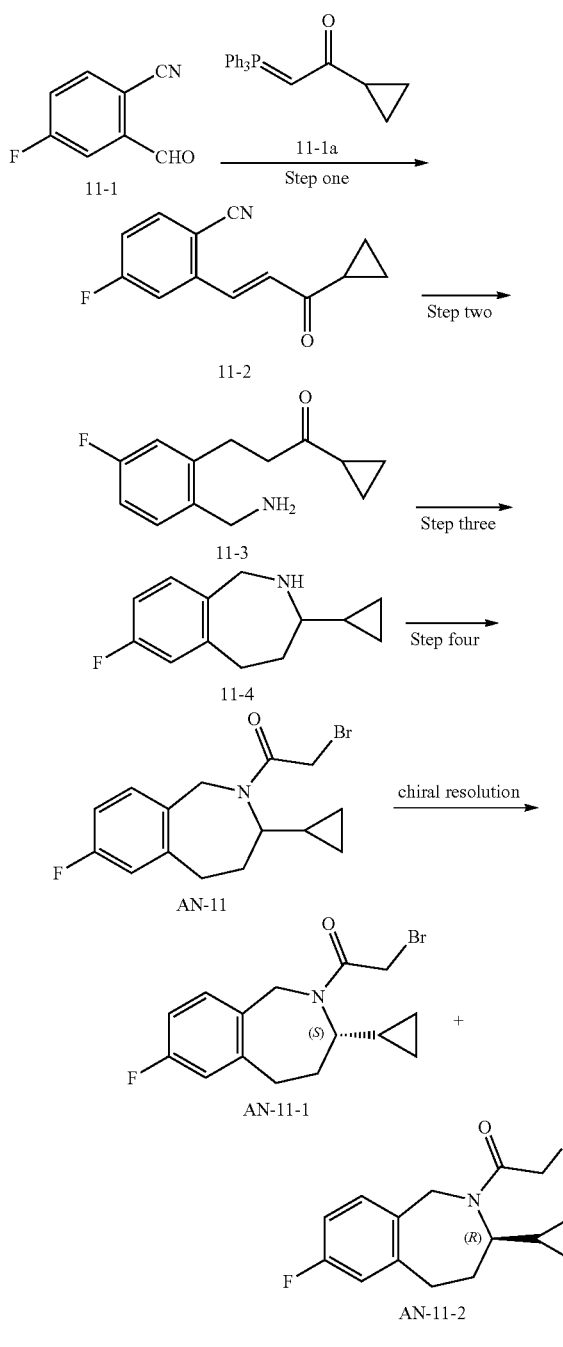

Step One:
11-1 (6.7 g) and the phosphorus ylide 11-1a (18.6 g) were dissolved in tetrahydrofuran (50 mL) and stirred under heating and refluxing for 2 h. TLC detected that the reaction was complete. The reaction solution was cooled and directly concentrated. The crude was purified by silica gel column chromatography to obtain 11-2 (7.67 g) as a yellowish liquid.

Step Two:
11-2 (5.71 g) was dissolved in methanol (80 mL) and add with 10% Pd/C (500 mg). After atmosphere was replaced with hydrogen, the reaction mixture was stirred overnight under hydrogen. After the reaction was complete, Pd/C was removed by suction filtration. The filter cake was washed with a small amount of methanol. The filtrate was combined and added with Raney nickel (800 mg) and triethylamine (0.5 mL). After atmosphere was replaced with hydrogen, the resultant was stirred overnight at 40° C. under hydrogen. After the reaction was complete, the resultant was filtered with suction. The filter cake was washed with methanol. The filtrate was combined to obtain a methanol solution of a crude 11-3, which was directly used in the next step.

Step Three:
The methanol solution of the crude 11-3 in the previous step was added with acetic acid (1 mL), and then added with sodium cyanoborohydride (3.14 g) room temperature, and stirred at room temperature for 1 h. TLC indicated that the reaction was complete. The reaction solution was poured into ice water, alkalized with a 2N NaOH aqueous solution, and extracted with dichloromethane. The combined organic phase was washed with water and saturated brine, dried over anhydrous sodium sulfate, concentrated to obtain a crude 11-4, which was used directly in the next step. LC-MS: 206.2 [M+H]+.

Step Four:
The crude 11-4 was dissolved in dichloromethane (50 mL), added with bromoacetyl bromide (10.09 g) and stirred at room temperature for 1 h. TLC showed that the reaction was complete. The reaction solution was poured into water, and the organic phase was separated. The aqueous phase was extracted with dichloromethane. The combined organic phase was washed with water and saturated brine, dried over anhydrous sodium sulfate, and concentrated. The crude was purified by column chromatography to obtain AN-11 (2.21 g). LC-MS: 326.1 [M+H]+.

The racemate AN-11 was subjected to chiral resolution to obtain chiral amides AN-11-1 and AN-11-2.

Chiral resolution conditions: semi-preparative column was CHIRALPAK@OD-H, filler particle size (5 μm), inner diameter (30 mm), length (250 mm), flow rate: 20 mL/min, mobile phase: 95% n-hexane+5% ethanol, isogradient elution, wavelength: 220 nm, total time: 30 min; peak time is 23.4 min for peak 1, and 26.3 min for peak 2.

Example 12 Synthesis of Amide AN-13

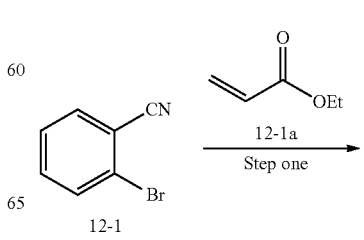

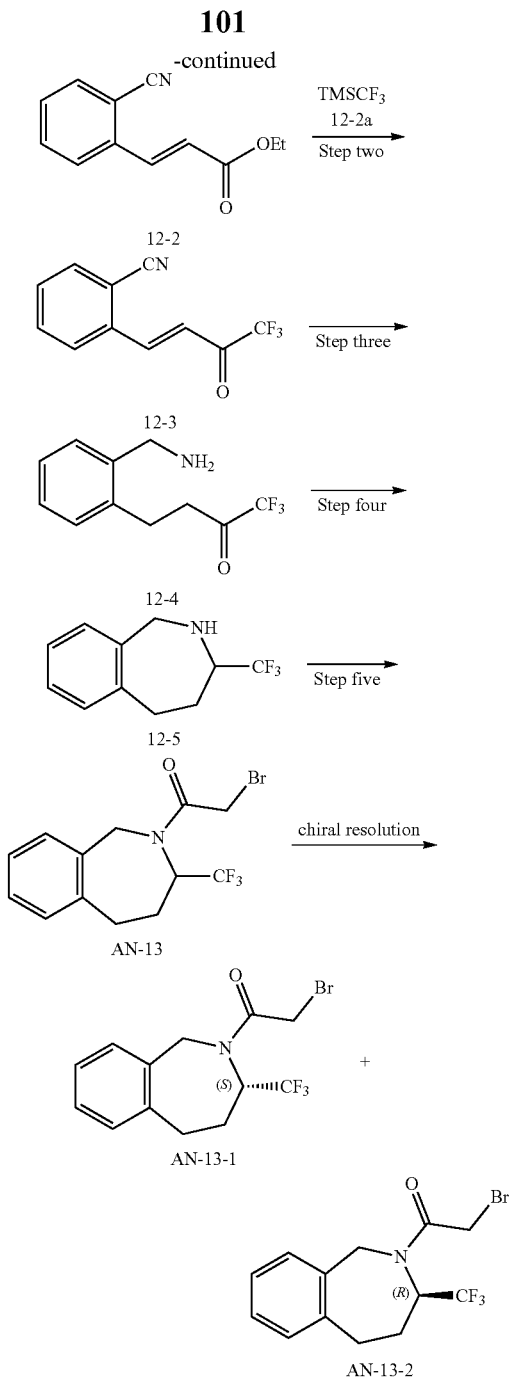

Step One:

2-Bromobenzonitrile (12-1, 20 g), ethyl acrylate (12-1a, 22.03 g) and diisopropylethylamine (42.6 g) were dissolved in dry DMF (100 mL), added with palladium acetate (494 mg) and tri-o-tolylphosphine (1.0 g), heated to 100° C. and stirred for 8 h under nitrogen. TLC showed that the reaction was complete. The reaction mixture was cooled to room temperature, poured into water, and extracted with ethyl acetate. The organic phase was washed with water and saturated brine, dried over anhydrous sodium sulfate, and concentrated. The residue was dissolved with a mixed solvent of petroleum ether (80 mL)/ethyl acetate (20 mL). The precipitated solid was filtered off, washed with a small amount of petroleum ether, and dried to obtain 12-2 (17.13 g).

Step Two:

12-2 (10.0 g) was dissolved in a mixed solvent of tetrahydrofuran and n-hexane (100 mL/50 mL), added with (trifluoromethyl)trimethylsilane (12-2a, 14.2 g) and 3 mL of a 3N tetrahydrofuran solution of TBAF, and reacted at room temperature overnight. The reaction solution was supplemented with (trifluoromethyl)trimethylsilane (14.2 g) and 3 mL of the 3N tetrahydrofuran solution of TBAF and react further for 3 h. TLC showed that the raw material was basically reacted. The reaction solution was poured into ice water, and extracted with ethyl acetate. The organic phase was washed with water and saturated brine, dried over anhydrous sodium sulfate, and concentrated. The crude was purified by silica gel column chromatography to obtain an intermediate (14.0 g). The crude was dissolved in tetrahydrofuran (30 mL), added with 4M HCl (30 mL) at room temperature, and stirred at 30° C. for 3 h. TLC showed that the reaction was complete. The resultant was quenched with water, and extracted with ethyl acetate. The organic phase was washed with water and saturated brine, dried over anhydrous sodium sulfate, and concentrated. The crude was purified by silica gel column chromatography to obtain 12-3 (6.5 g).

Step Three:

12-3 (3.50 g) was dissolved in methanol (100 mL), and added with 10% Pd/C (300 mg). After atmosphere was replaced with hydrogen, the reaction mixture was stirred overnight under hydrogen. After the reaction was completed, Pd/C was carefully removed by suction filtration. The filter cake was washed with a small amount of methanol. The combined filtrate was added with Raney nickel (200 mg) and TEA (0.5 mL). After atmosphere was replaced with hydrogen, the resultant was stirred overnight at 40° C. under hydrogen. After the reaction was complete, the resultant was filtered with suction. The filter cake was washed with a small amount of methanol. The filtrate was combined to obtain a methanol solution of 12-4, which was directly used in the next step.

Step Four:

The methanol solution of 12-4 was added with acetic acid (1 mL) and sodium cyanoborohydride (1.89 g) at room temperature, and stirred at room temperature for 1 h. TLC showed that the reaction was complete. The reaction solution was poured into ice water, adjusted pH to 1-2 with a 2N dilute hydrochloric acid, and extracted with ethyl acetate. The aqueous phase was alkalized with a 2N NaOH aqueous solution, and extracted with dichloromethane. The organic phase was washed with water and saturated brine, dried over anhydrous sodium sulfate, and concentrated to obtain a crude 12-5, which was used directly in the next step.

Step Five:

The crude 12-5 (700 mg) was dissolved in dichloromethane (50 mL), added with bromoacetyl bromide (1.41 g) and stirred at room temperature overnight. TLC showed that the reaction was complete. The resultant was quenched with water and layered, and the aqueous phase was extracted with dichloromethane. The organic phase was washed with water and saturated brine, dried and concentrated. The crude was purified by silica gel column chromatography to obtain AN-13 (420 mg). LC-MS: 336.0 [M+1]$^+$.

The racemate AN-13 was subjected to chiral resolution to obtain chiral amides AN-13-1 and AN-13-2.

Chiral resolution conditions: semi-preparative column was CHIRALPAK@OD-H, filler particle size (5 μm), inner diameter (30 mm), length (250 mm), flow rate: 20 mL/min, mobile phase: 90% n-hexane+10% ethanol, isogradient elution, wavelength: 220 nm, total time: 30 min; peak time is 15.1 min for peak 1, and 18.2 min for peak 2.

Example 13 Synthesis of Amide AN-14

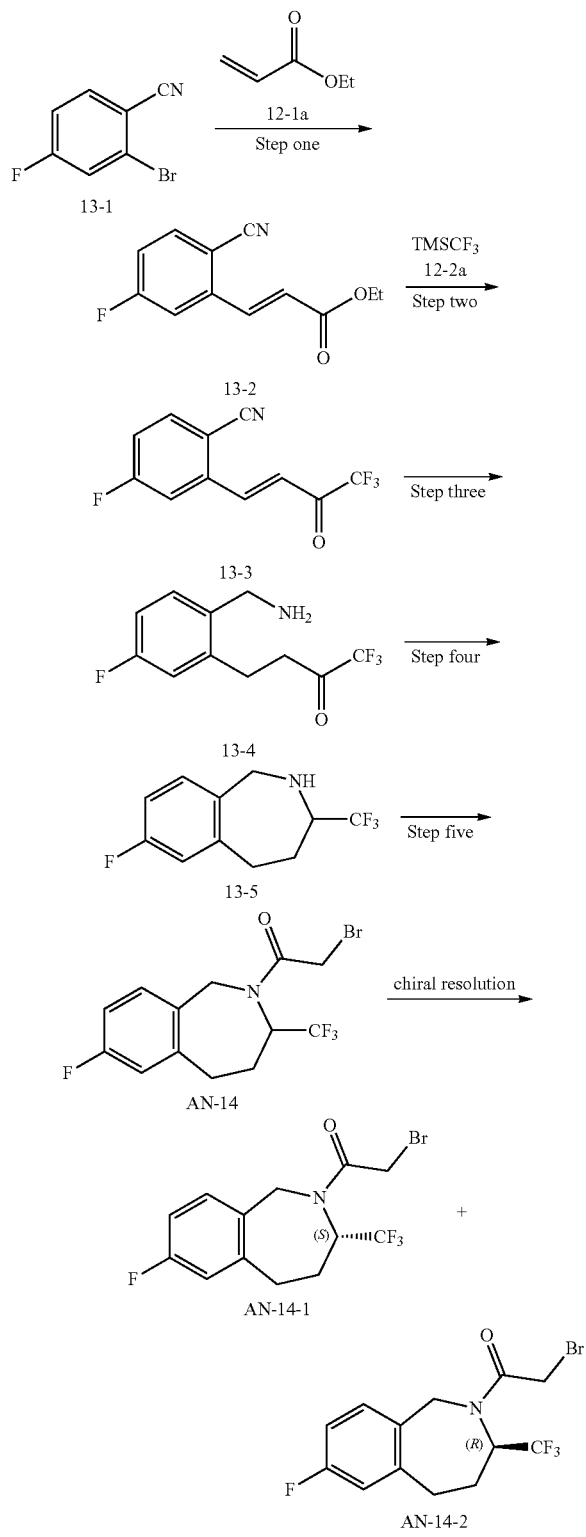

Step One:

2-Bromo-4-fluorobenzonitrile (13-1, 30.0 g) and ethyl acrylate (12-1a, 32 mL) were dissolved in dry DMF (200 mL), added with diisopropylethylamine (44 mL), palladium acetate (494 mg) and tri-o-tolylphosphine (1.0 g), heated to 100° C. and stirred for 4 h under nitrogen. TLC showed that the reaction was complete. The reaction solution was cooled to room temperature, poured into ice water, and extracted with ethyl acetate. The organic phase was washed with water and saturated brine, dried over anhydrous sodium sulfate, and concentrated. The crude was purified by silica gel column chromatography to obtain 13-2 (24.2 g).

Step Two:

13-2 (8.0 g) and (trifluoromethyl)trimethylsilane (12-2a, 7.82 g) were dissolved in a mixed solvent of tetrahydrofuran (100 mL) and n-hexane (50 mL) under nitrogen, slowly added dropwise with a TN TBAF solution in tetrahydrofuran (3 mL), and reacted at room temperature overnight. TLC showed that the reaction was not complete. The reaction solution was supplemented with (trifluoromethyl)trimethylsilane (7.82 g) and TN TBAF solution in tetrahydrofuran (3 mL), and continued to react at room temperature for 3 h. TLC showed that a small amount of the raw material remaining. The reaction solution was poured into ice water, and extracted with ethyl acetate. The organic phase was washed with water and saturated brine, dried over anhydrous sodium sulfate, and concentrated. The crude was purified by silica gel column chromatography to obtain an intermediate (3.0 g). The crude was dissolved in tetrahydrofuran (20 mL), added with a TFA aqueous solution (50%) (30 mL) at room temperature, and stirred at 30° C. for 3 h. TLC showed that the reaction was complete. The resultant was quenched with water, and extracted with ethyl acetate. The organic phase was washed with water and saturated brine, dried over anhydrous sodium sulfate, and concentrated. The crude was purified by silica gel column chromatography to obtain 13-3 (2.21 g).

Step Three:

13-3 (2.0 g) was dissolved in methanol (20 mL), and added with 10% Pd/C (200 mg). After atmosphere was replaced with hydrogen, the reaction mixture was stirred overnight under hydrogen. The Pd/C was carefully removed by suction filtration, and the filter cake was washed with a small amount of methanol. The filtrate was combined and added with raney nickel (200 mg) and TEA (0.5 mL). After atmosphere was replaced with hydrogen, the resultant was stirred overnight at 40° C. under hydrogen. After the reaction was complete, the resultant was filtered with suction. The filter cake was washed with a small amount of methanol. The filtrate was combined to obtain a methanol solution of 13-4, which was directly used in the next step.

Step Four:

The methanol solution of 13-4 was added with acetic acid (0.5 mL) and sodium cyanoborohydride (0.96 g) at room temperature, and stirred at room temperature for 1 h. TLC showed that the reaction was complete. The reaction solution was poured into ice water, adjusted pH to 1-2 with a 2N diluted hydrochloric acid, and extracted with ethyl acetate. The aqueous phase was alkalized with a 2N NaOH aqueous solution, and extracted with dichloromethane. The organic phase was washed with water and saturated brine, dried over anhydrous sodium sulfate, and concentrated to obtain a crude 13-5 (330 mg), which was used directly in the next step.

Step Five:

The crude 13-5 (330 mg) was dissolved in dichloromethane (50 mL), added with bromoacetyl bromide (705 mg) and stirred at room temperature overnight. TLC showed that the reaction was complete. The resultant was quenched with water and layered. The aqueous phase was extracted with dichloromethane. The organic phase was washed with water and saturated brine, dried and concentrated. The crude was purified by silica gel column chromatography to obtain AN-14 (360 mg). LC-MS: 354.1 [M+1]$^+$.

The racemate AN-14 was subjected to chiral resolution to obtain chiral amides AN-14-1 and AN-14-2.

Chiral resolution conditions: semi-preparative column was CHIRALPAK@OD-H, filler particle size (5 μm), inner diameter (30 mm), length (250 mm), flow rate: 20 mL/min, mobile phase: 97% n-hexane+3% ethanol, isogradient elution, wavelength 220 nm, total time: 30 min; peak time is 25.1 min for peak 1, and 29.3 min for peak 2.

Example 14 Synthesis of Amide AN-15

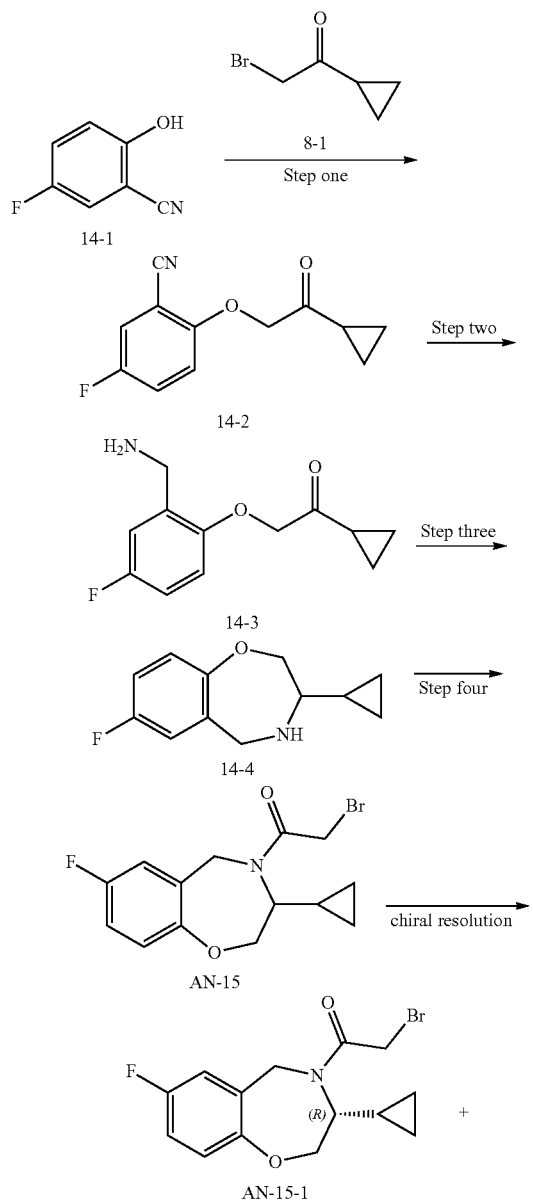

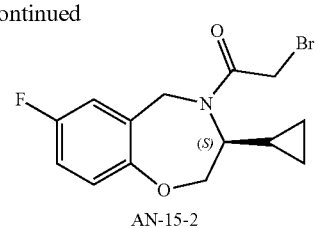

AN-15-2

Step One:

The 5-fluoro-2-hydroxybenzonitrile (14-1, 2.0 g), bromomethylcyclopropylketone (8-1, 4.76 g) and potassium carbonate (4.04 g) was dissolved in acetone (60 mL), and reacted at 50° C. for 3 h. TLC showed that the reaction was complete. The reaction solution was cooled to room temperature and filtered to remove salts, and the filtrate is rotary evaporated to dryness directly. The crude was purified by silica gel column chromatography to give 14-2 (3.01 g) as a white solid.

Step Two:

14-2 (3.00 g) and TEA (0.5 mL) were dissolved in methanol (60 mL), and added with raney nickel (880 mg). After atmosphere was replaced with hydrogen, the reaction mixture was stirred at 40° C. under hydrogen for 3 h. TLC showed that the reaction was complete. Raney nickel was removed by suction filtration. The filtrate was added with water, and acidized with HCl (1M). The aqueous phase was extracted with ethyl acetate, alkalized with a 1N NaOH solution, and extracted with ethyl acetate. The organic phase was washed with water and brine, dried over anhydrous sodium sulfate, concentrated to obtain a crude 14-3 (1.7 g) as a yellowish oil, which was directly used in the next step.

Step Three:

14-3 (1.7 g) was dissolved in methanol (50 mL), added with sodium cyanoborohydride (940 mg) and acetic acid (0.5 mL) at room temperature, and stirred for 30 min at room temperature. TLC showed that the reaction was complete. The reaction solution was poured into water, and acidized with a 1N dilute hydrochloric acid. The aqueous phase was extracted with ethyl acetate, alkalized with a 1N sodium hydroxide solution, and extracted again with ethyl acetate. The organic phase was washed with water and saturated brine, dried over anhydrous sodium sulfate, and concentrated to obtain 14-4 (1.1 g) as a yellowish oil, which was directly used in the next step.

Step Four:

14-4 (1.1 g) and triethylamine were dissolved in methylene chloride (30 mL). The bromoacetyl bromide (1.31 g) was added in an ice water bath, and reacted at room temperature for 30 min. TLC showed that the reaction was complete. The reaction solution was poured into ice water, and the organic phase was separated. The aqueous phase was extracted with dichloromethane. The combined organic phase was washed with water and saturated brine, dried over anhydrous sodium sulfate, and concentrated. The crude was purified by column chromatography to obtain AN-15 (610 mg). LC-MS: 328.1 [M+1]$^+$.

The racemate AN-15 was subjected to chiral resolution to obtain chiral amides AN-15-1 and AN-15-2.

Chiral resolution conditions: semi-preparative column was CHIRALPAK@OD-H, filler particle size (5 μm), inner diameter (30 mm), length (250 mm), flow rate: 20 mL/min, mobile phase: 96% n-hexane+4% ethanol, isogradient elu- Example 15 Synthesis of Spiro Ring SP-1

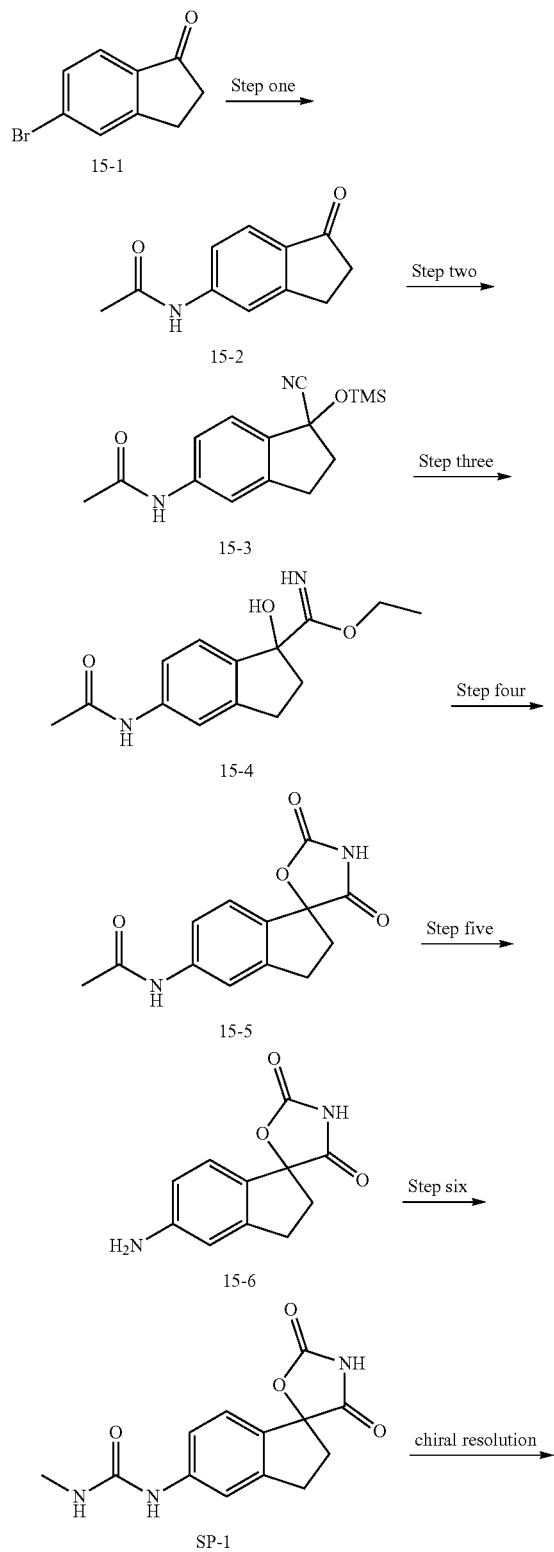

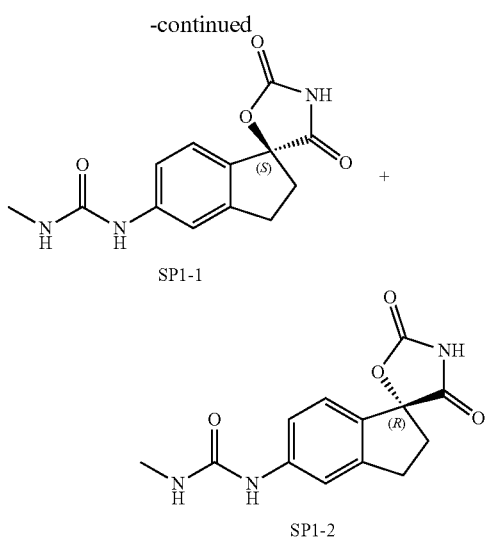

Step One:

5-Bromoindanone (15-1, 30.0 g), cesium carbonate (90.0 g), acetamide (16.7 g) were dissolved in anhydrous 1,4-dioxane (400 mL), added with 4,5-bis(diphenylphosphino)-9,9-dimethylxanthene (1.6 g), tris(dibenzylideneacetone) dipalladium (700 mg) under a nitrogen atmosphere, heated to 100° C. under nitrogen and stirred for 2 h. TLC showed disappearance of the raw material. The reaction solution was cooled to room temperature, and the solid was filtered off and washed with dichloromethane. The solvent was concentrated. The residue was poured into ice water and extracted with ethyl acetate. The combined organic phase was washed with water and saturated brine, dried over anhydrous sodium sulfate, and concentrated to obtain a crude 15-2 (26.0 g), which was directly used in the next step. LC-MS: 190.1 [M+H]$^+$.

Step Two:

The crude 15-2 (26.0 g) was dissolved in toluene (125 mL), added with acetonitrile (125 mL), then with trimethylsilyl cyanide (15.5 g) and zinc iodide (2.26 g) at room temperature, heated to 75° C. and stirred for 4 h. TLC showed that the reaction was complete. The reaction solution was cooled to room temperature, poured into ice water and extracted with ethyl acetate. The organic phase was washed with water and saturated brine, dried over anhydrous sodium sulfate, and concentrated. The crude was purified by silica gel column chromatography to obtain 15-3 (20.5 g). LC-MS: 289.1 [M+H]$^+$.

Step Three:

15-3 (20.5 g) was dissolved in absolute ethanol (100 mL), and introduced slowly with dry hydrogen chloride gas at 0° C. for 5 h. The resultant was distilled under reduced pressure at 30° C. to remove most of the ethanol, washed with diethyl ether, and rotary evaporated to dryness to obtain a crude 15-4, which was directly used in the next step.

Step Four:

The crude 15-4 was dissolved in anhydrous tetrahydrofuran (100 mL), added slowly and dropwise with triethylamine (18.52 g) at 0° C., added dropwise with triphosgene (5.97 g) dissolved in tetrahydrofuran (50 mL), stirred at 0° C. for 1 h, added with TN HCl (20 mL) and stirred further for 0.5 h. TLC showed that the reaction was complete. The reaction solution was poured into ice water and extracted with ethyl acetate. The organic phase was washed with saturated sodium bicarbonate. The aqueous phase was extracted with a small amount of ethyl acetate, adjusted pH to about 3-4 with TN HCl, and extracted with ethyl acetate. The organic phase was washed with water and brine, dried over anhydrous sodium sulfate, and concentrated to obtain a crude 15-5 (6.81 g). LC-MS: 259.1 [M−H]⁻.

Step Five:

15-5 (25.0 g) was dissolved in methanol (50 mL), added with 6N HCl (100 mL) and stirred at 75° C. for 3 h. TLC showed that the reaction was complete. The reaction solution was cooled to room temperature, adjusted pH to neutral with saturated sodium bicarbonate, and extracted with ethyl acetate. The organic phase was washed with water and brine, dried over anhydrous sodium sulfate, and concentrated. The crude was purified by silica gel column chromatography to obtain 15-6 (18.1 g).

Step Six:

15-6 (14.0 g) was dissolved in anhydrous tetrahydrofuran (100 mL), added with phenyl p-nitrochloroformate (14.2 g), and stirred at room temperature for 0.5 h. Methylamine hydrochloride (13.0 g) was dissolved in methanol (100 mL), added with TEA (32.5 g), stirred 10 min, added with the above reaction solution, and stirred at room temperature for 1 h. TLC showed that the reaction was complete. The reaction solution was poured into ice water, adjusted pH to 3~4 with 1N HCl, and extracted with ethyl acetate. The organic phase was washed with water and brine, dried over anhydrous sodium sulfate, and concentrated. The crude was purified by column chromatography to obtain SP-1 (10.2 g). LC-MS: 276.1 [M+H]⁺.

The racemate spiro ring SP-1 was subjected to chiral resolution to obtain chiral spiro rings SP-1-1 and SP-1-2.

Chiral resolution conditions: semi-preparative column was CHIRALPAK@AD-H, filler particle size (5 μm), inner diameter (20 mm), length (250 mm), flow rate: 15 m/min, mobile phase: 80% n-hexane+20% isopropanol, isogradient elution, wavelength 220 nm, total time 30 min; peak time is 13.6 min for peak 1, and 18.4 min for peak 2.

Example 16 Synthesis of Spiro Ring SP-2

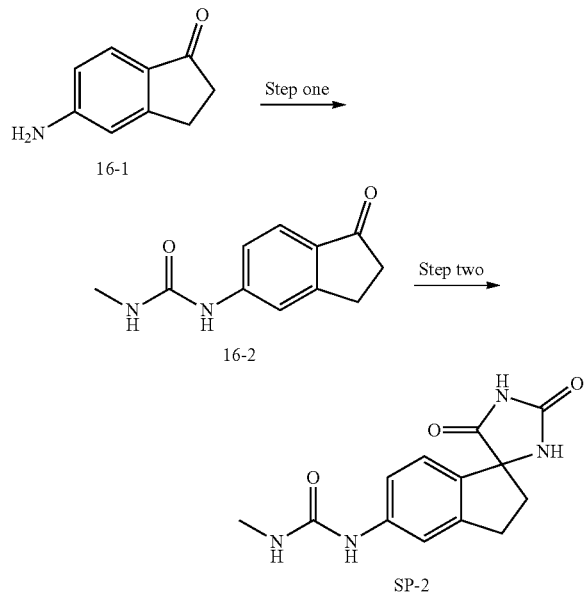

Step One:

5-Aminoindanone (16-1, 2.30 g) was dissolved in anhydrous tetrahydrofuran (20 mL), added with phenyl p-nitrochloroformate (3.63 g), and stirred at room temperature for 0.5 h. TLC showed that the reaction was complete. Methylamine hydrochloride (5.40 g) was dissolved in methanol (30 mL), added with triethylamine (8.10 g), stirred for 10 min at room temperature, added with the above reaction solution, and stirred at room temperature for 1 h. TLC showed that the reaction was complete. The reaction solution was poured into ice water, adjusted pH to 3~4 with 1N HCl, and extracted with ethyl acetate. The organic phase was washed with water and brine, dried over anhydrous sodium sulfate, and concentrated. The crude was purified by column chromatography to obtain 16-2 (1.52 g). LC-MS: 205.1 [M+H]⁺.

Step Two:

16-2 (1.52 g), trimethylsilyl cyanide (3.0 g), ammonium fluoride (3.0 g), and ammonium carbonate (7.50 g) were added in a mixture of ammonia (30 mL) and ethanol (60 mL) to react at 60° C. for 48 h. LC-MS showed that 30% of the raw material remained. The reaction solution was rotary evaporated to dryness to remove ethanol, and added with saturated sodium bicarbonate solution. The aqueous phase was extracted with ethyl acetate, adjusted pH to 3-4 with 1M HCl, extracted again with ethyl acetate. The organic phase was washed with water and brine, dried over anhydrous sodium sulfate, and concentrated to 20-30 mL to precipitate a solid, which was filtered to obtain SP-2 (580 mg) as a white solid. LC-MS: 275.1 [M+H]⁺.

Example 17 Synthesis of Spiro Ring SP-3

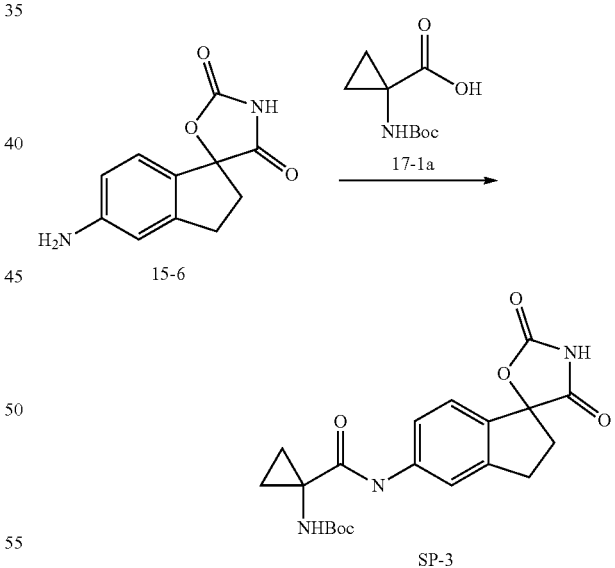

15-6 (550 mg), Boc-1-aminocyclopropylcarboxylic acid (17-1a, 600 mg), HATU (1.45 g) and triethylamine (405 mg) were dissolved in anhydrous DMF (15 mL), and stirred at room temperature overnight. TLC showed that the reaction was complete. The reaction solution was poured into water and extracted with ethyl acetate. The organic phase was washed with water and saturated brine, dried over anhydrous sodium sulfate, and concentrated. The crude was purified by column chromatography to obtain SP-3 (420 mg) as a yellowish solid. LC-MS: 402.2 [M+H]⁺.

Example 18 Synthesis of Spiro Rings SP-4-Boc-1 and SP-4-Boc-2

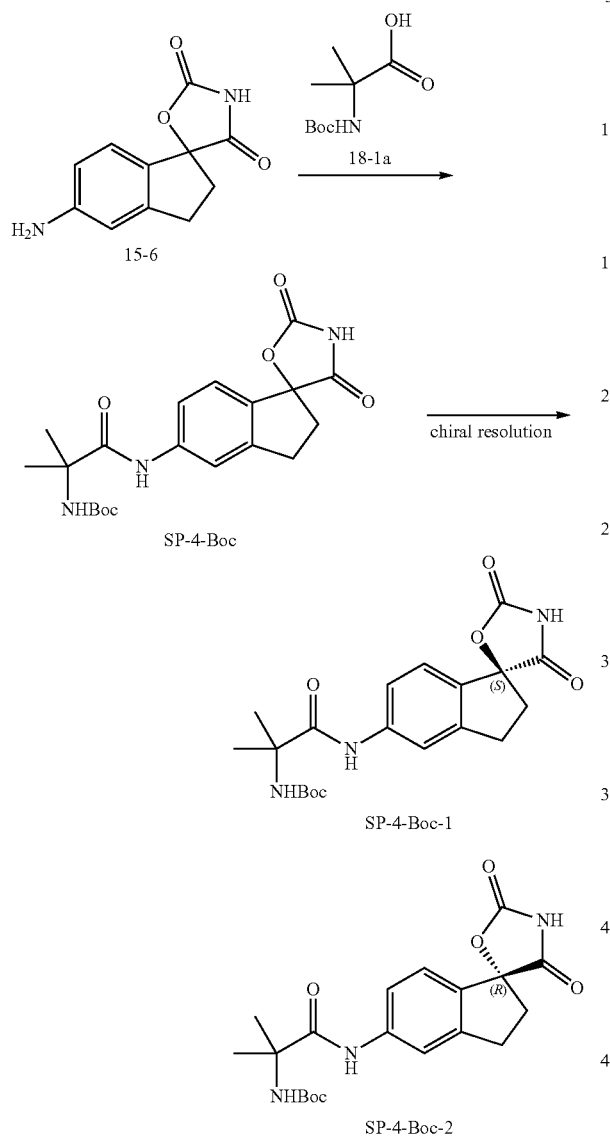

15-6 (550 mg), N-tert-butoxycarbonyl-2-methylalanine (18-1a, 610 mg), HATU (1.45 g) and triethylamine (405 mg) were dissolved in anhydrous DMF (15 mL) to stir at room temperature overnight. TLC showed that the reaction was complete. The reaction solution was poured into water and extracted with ethyl acetate. The organic phase was washed with water and saturated brine, dried over anhydrous sodium sulfate, and concentrated. The crude was purified by silica gel column chromatography to obtain SP-4-Boc (510 mg) as a yellowish solid. LC-MS: 404.2 [M+H]$^+$.

The racemate spiro ring SP-4-Boc was subjected to chiral resolution to obtain chiral spiro rings SP-4-Boc-1 and SP-4-Boc-2.

Chiral resolution conditions: semi-preparative column was CHIRALPAK@AD-H, filler particle size (5 μm), inner diameter (20 mm), length (250 mm), flow rate: 12 m/min, mobile phase: 65% n-hexane+35% isopropanol, isogradient elution, wavelength 254 nm, total time: 20 min; peak time is 8.7 min for peak 1, and 13.7 min for peak 2.

Example 19 Synthesis of Spiro Rings SP-5-Boc-1 and SP-5-Boc-2

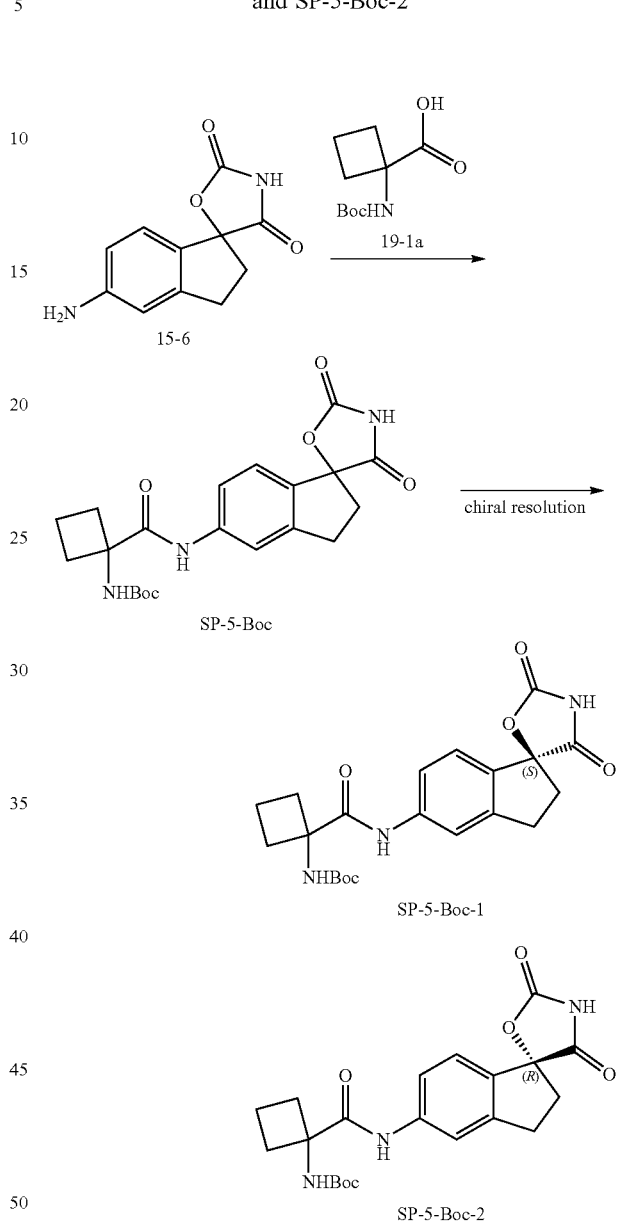

Boc-1-aminocyclobutanecarboxylic acid (19-1a, 740 mg) and triethylamine (405 mg) were dissolved in dry DMF (30 mL), added with HATU (1.31 g) at room temperature, stirred for 2 h, added with 15-6 (550 mg, 2.52 mmol), and stirred further at room temperature for 48 h. TLC showed that the reaction was complete. The reaction solution was poured into water and extracted with ethyl acetate. The organic phase was washed with water and saturated brine, dried over anhydrous sodium sulfate, and concentrated. The crude was purified by silica gel column chromatography to obtain SP-5-Boc (820 mg) as a yellowish solid. LC-MS: 416.2 [M+1]$^+$.

The racemate spiro ring SP-5-Boc was subjected to chiral resolution to obtain chiral spiro rings SP-5-Boc-1 and SP-5-Boc-2.

Chiral resolution conditions: semi-preparative column was CHIRALPAK@AD-H, filler particle size (5 μm), inner diameter (20 mm), length (250 mm), flow rate: 30 m/min, mobile phase: 65% n-hexane+35% isopropanol, isogradient elution, wavelength 254 nm, total time: 25 min; peak time is 17.6 min for peak 1, and 19.4 min for peak 2.

Example 20 Synthesis of Spiro Ring SP-6

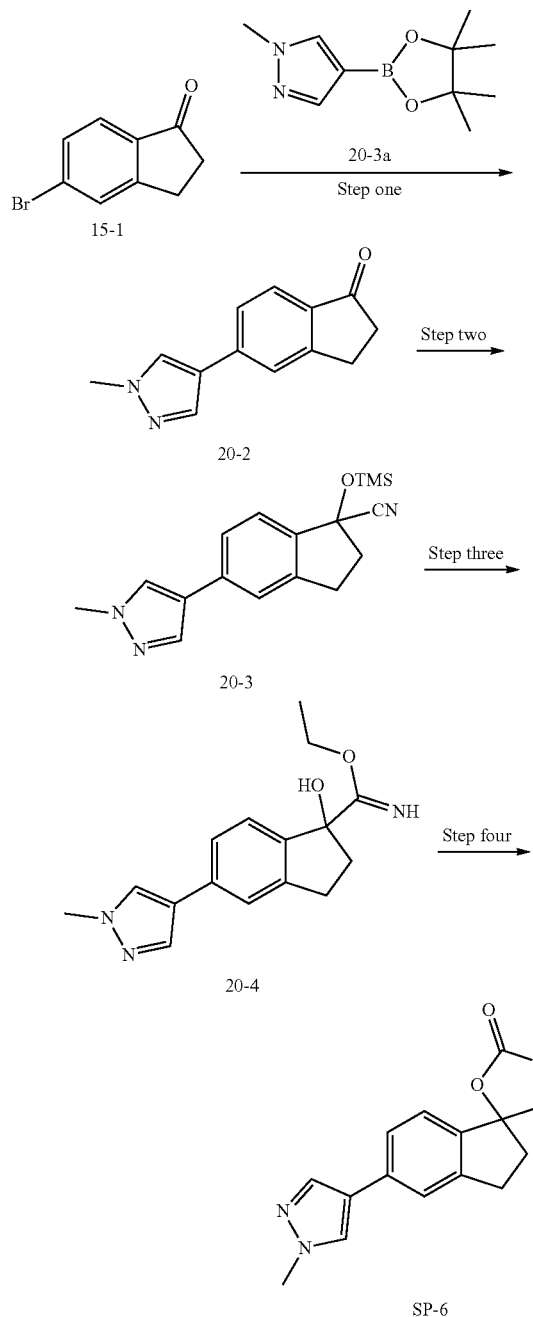

mixture was filtered, and the filter cake was washed with dichloromethane. The filtrate was added with water/dichloromethane and layered. The organic phase was dried, and rotary evaporated to dryness. The residue was passed a column to obtain 20 g of 20-2 as an oil.

Step Two:

20-2 (5 g), TMSCN (1.1 eq.), zinc iodide (0.05 eq.), toluene (50 mL) and acetonitrile (50 mL) were reacted at 75° C. for 3 h. TLC (DCM:MeOH=20:1) showed disappearance of the raw material. The system was added with water/ethyl acetate and layered. The organic phase was dried and concentrated. The residue was passed a column to obtain 20-3 (5 g) as an oil.

Step Three:

20-3 (5 g) was added with 150 mL of absolute ethanol, introduced with dry hydrogen chloride gas at 0° C. for 5 h, and then concentrated at 40° C. to obtain an oil. The oil was added with THF, slurried and filtered to obtain 20-4 as a solid, which was directly used in the next step.

Step Four:

20-4 was added with 50 mL of tetrahydrofuran and triethylamine (4 eq.), and then with triphosgene (2 eq.) at 0° C. The reaction mixture was not clear, and stirred under ice water for 30 min. TLC showed disappearance of the raw material. The reaction mixture was added with 50 mL dilute hydrochloric acid to become clear, stirred at room temperature for 30 min, and rotary evaporated to dryness. The residue was added with ethyl acetate/water, and layered. The organic layer was washed with water 3 times, and then with aqueous sodium hydroxide 2 times. The aqueous layer was washed with the organic solvent once. The aqueous layer was retained, acidized with a diluted hydrochloric acid, and extracted with the organic solvent 2 times. The organic layer was retained, washed with water and brine, dried and rotary evaporated to dryness to obtain 1.45 g of SP-6 as a yellow solid. LC-MS: [M+H]⁺=284.1.

Example 21 Synthesis of Spiro Ring SP-7

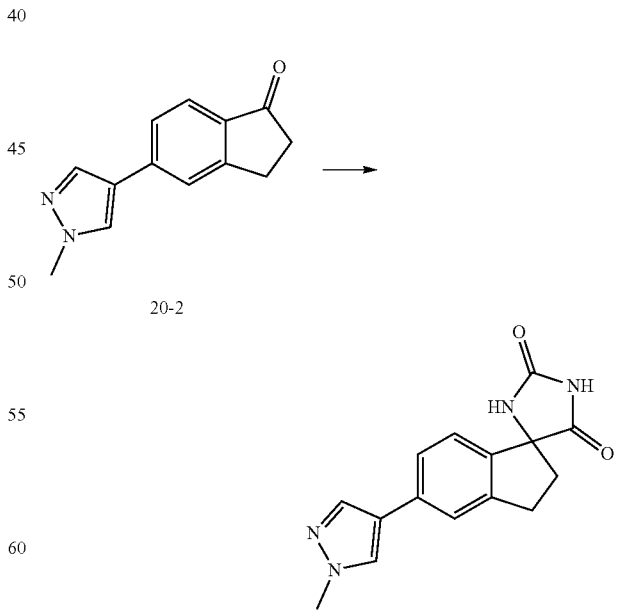

Step One:

15-1 (20 g), the borate 20-3a (23.6 g), Pd(dppf)Cl₂ (0.6 g), sodium carbonate (40 g), dioxane (200 mL) and water (20 mL) were reacted at 100° C. under nitrogen for 17 h. TCL showed disappearance of the raw material. The reaction The raw material (3.0 g), TMSCN (6.0 g), NH₄F (6.0 g) and (NH₄)₂CO₃ (15.0 g) were dissolved in a mixture of 30% ammonia (40 mL) and ethanol (100 mL) to react at 60° C. for 6 h. The ethanol was rotary evaporated off. The residue was added with saturated NaHCO₃ solution. The aqueous phase was extracted with ethyl acetate, adjusted pH to 3~4 with 1M HCl, and extracted again with ethyl acetate. The organic phase was washed with water and brine, dried over anhydrous sodium sulfate, and concentrated to precipitate a solid, which was filtered to obtain SP-7 as a white solid. LC-MS: [M+H]⁺=283.1.

Example 22 Synthesis of Spiro Ring SP-8

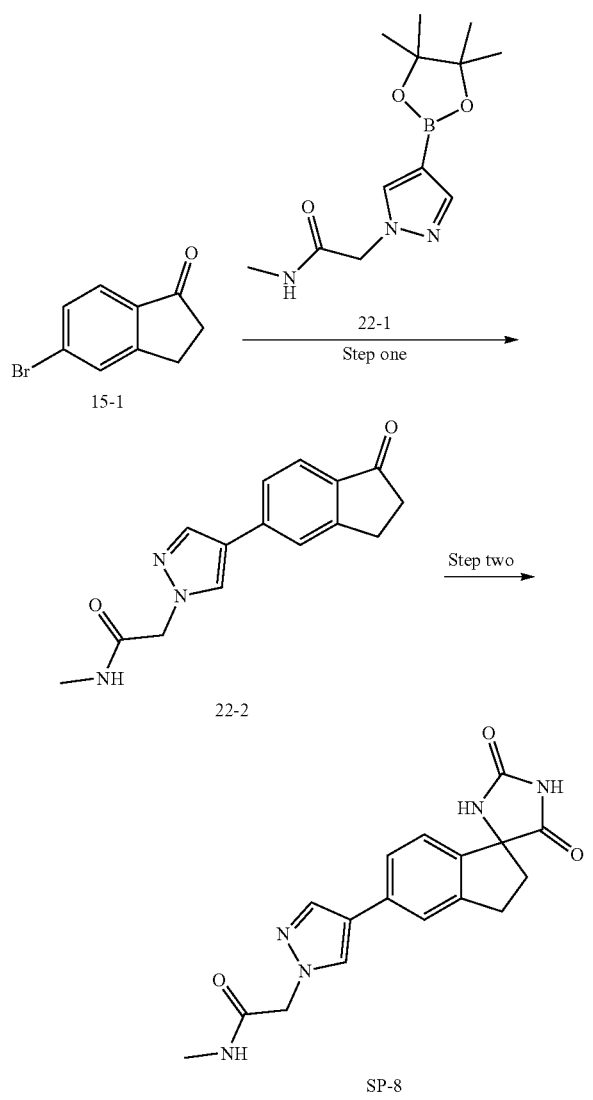

Step One:

15-1 (1.89 g) was dissolved in of DMF (70 mL) and water (10 mL), added with sodium carbonate (2.85 g) and 22-1a (2.5 g), and then with Pd(dppf)Cl₂ (660 mg) under nitrogen, and stirred at 100° C. for 5 h. LCMS showed that the reaction was complete. The resultant was added with water and extracted with ethyl acetate. The combined organic phase was washed with brine, dried over sodium sulfate, and rotary evaporated to dryness. The residue was purified by column chromatography to obtain 1.51 g of 22-2 as a gray solid. LC-MS: [M+H]⁺=270.1.

Step Two:

To a 250 mL single necked flask, were added 22-2 (1.50 g), absolute ethanol (100 mL), TMSCN (5.55 g), NH₄F (2.07 g), ammonium carbonate (8.08 g) and ammonia (8 mL) in sequence, and stirred at 80° C. for 5 h. TLC showed that a large amount of the raw material remained. The reaction mixture was supplemented with TMSCN (5.55 g), NH₄F (2.07 g), ammonium carbonate (8.08 g) and ammonia (8 mL) and reacted further at 80° C. for 6 h. TLC showed that some of the raw material still remained. The reaction mixture was supplemented with the same amount of the substances as above, and stirred at 65° C. for 8 h. TLC showed that the reaction was basically complete. The reaction solution was cooled to room temperature, added with water (200 mL), and extracted with ethyl acetate. The combined organic phase was dried over sodium sulfate and rotary evaporated to dryness. The residue was purified by column chromatography to obtain 850 mg of SP-8 as a yellow solid. LC-MS: [M+H]⁺=340.1.

Example 23 Synthesis of Spiro Ring SP-9

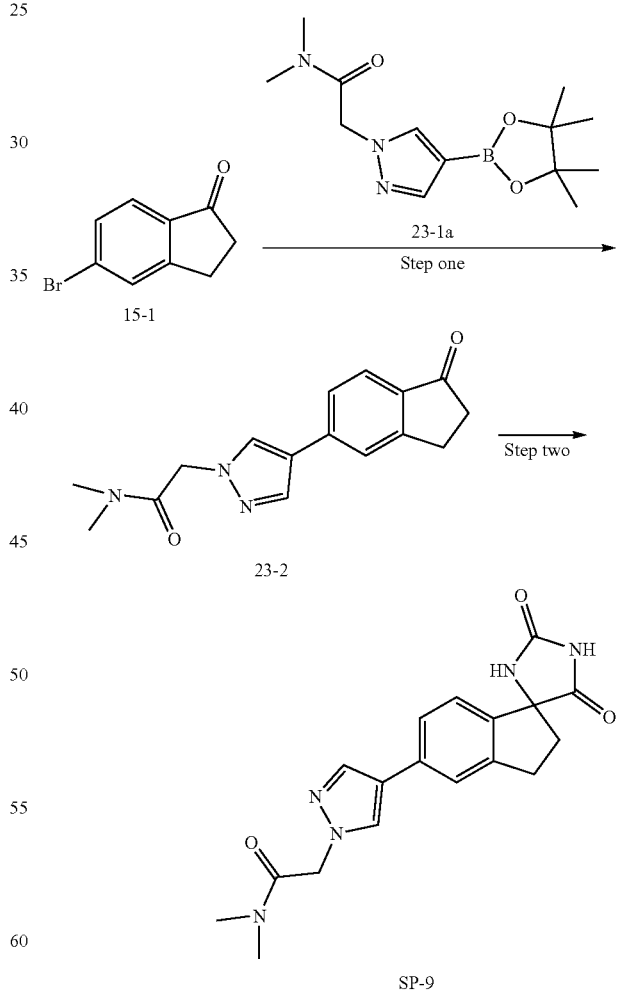

Step One:

15-1 (1.89 g) was dissolved in DMF (70 mL) and water (10 mL), added with sodium carbonate (2.85 g) and 23-1a (2.58 g), and then with Pd(dppf)Cl₂ (660 mg) under nitrogen, and stirred at 100° C. for 5 h. LCMS showed that the reaction was complete. The resultant was added with water and extracted with ethyl acetate. The combined organic phase was washed with brine, dried over sodium sulfate, and rotary evaporated to dryness. The residue was purified by column chromatography to obtain 23-2 as a solid. LC-MS: [M+H]$^+$=284.1.

Step Two:

To a 250 mL single necked flask, were added 23-2 (1.5 g), absolute ethanol (100 mL), TMSCN (5.6 g), NH$_4$F (2.07 g), ammonium carbonate (8.08 g) and ammonia (8 mL) in sequence, and stirred at 80° C. for 5 h. TLC showed that a large amount of the raw material remained. The reaction mixture was supplemented with TMSCN (5.55 g), NH$_4$F (2.07 g), ammonium carbonate (8.08 g) and ammonia (8 mL) and react at 80° C. for 6 h. TLC showed that some of the raw material still remained. The reaction mixture was further supplemented with the same amount of the substances as above and stirred at 65° C. for 8 h. TLC showed that the reaction was basically complete. The reaction solution was cooled to room temperature, added with water and extracted with ethyl acetate. The combined organic phase was dried and rotary evaporated to dryness. The residue was purified by column chromatography to obtain SP-9 as a solid. LC-MS: [M+H]$^+$=354.1.

Example 24 Synthesis of Spiro Ring SP-10

Step One:

15-1 (1.89 g) was dissolved in DMF (70 mL) and water (10 mL), added with sodium carbonate (2.85 g) and 24-1a (2.4 g), and then with Pd(dppf)Cl$_2$ (660 mg) under nitrogen, stirred at 100° C. for 5 h. LC-MS showed that the reaction was complete. The resultant was added with water and extracted with ethyl acetate. The combined organic phase was washed with brine, dried over sodium sulfate, and rotary evaporated to dryness. The residue was purified by column chromatography to obtain 24-2 as a solid. LC-MS: [M+H]$^+$=256.1.

Step Two:

To a 250 mL single necked flask, were added 24-2 (1.5 g), absolute ethanol (100 mL), TMSCN (5.6 g), NH$_4$F (2.07 g), ammonium carbonate (8.08 g) and ammonia (8 mL) in sequence, and stirred at 80° C. for 5 h. TLC showed that a large amount of the raw material remained. The reaction mixture was supplemented with TMSCN (5.55 g), NH$_4$F (2.07 g), ammonium carbonate (8.08 g) and ammonia (8 mL), and reacted further at 80° C. for 6 h. TLC showed that some of the raw material still remained. The reaction mixture was added with the same amount of the substances as above and stirred at 65° C. for 8 h. TLC showed that the reaction was basically complete. The reaction solution was cooled to room temperature, added with water and extracted with ethyl acetate. The combined organic phase was dried and rotary evaporated to dryness. The residue was purified by column chromatography to obtain SP-10 as a solid. LC-MS: [M+H]$^+$=326.1.

Example 25 Synthesis of Spiro Ring SP-11

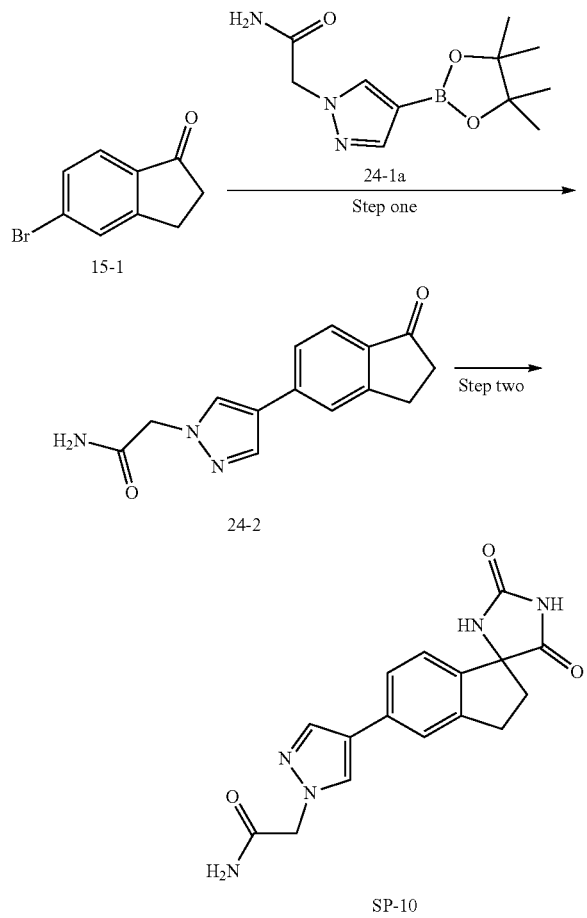

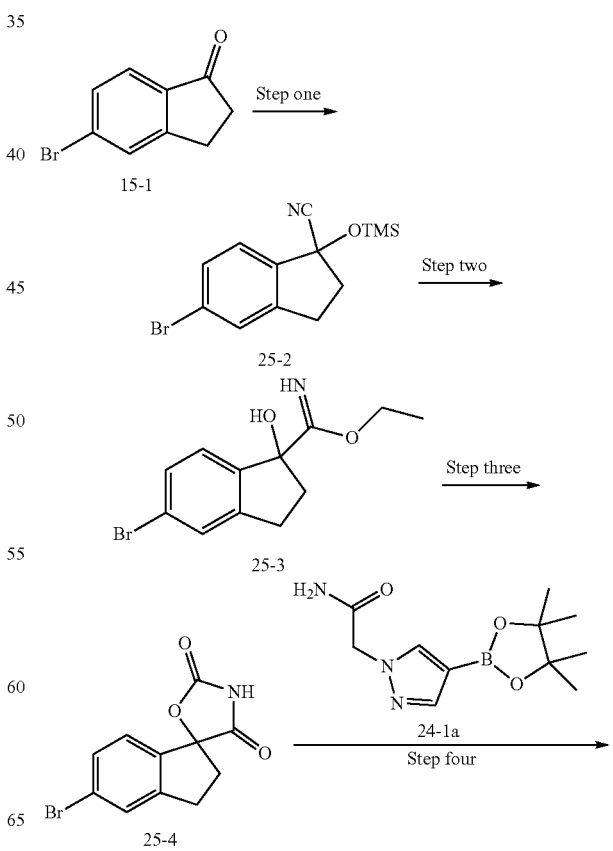

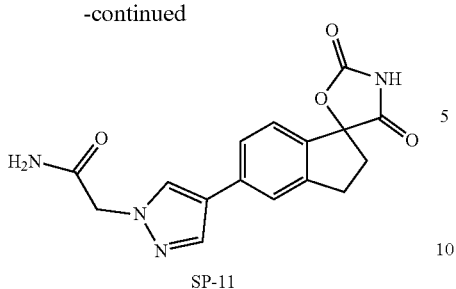

SP-11

Step One:

5-Bromo-indanone (3.0 g) dissolved in toluene (10 mL) was added with acetonitrile (10 mL), and then with trimethylsilyl cyanide (1.6 g) and zinc iodide (0.2 g) at room temperature, and heated to 75° C. to stir. TLC showed that the reaction was complete. The reaction solution was cooled to room temperature, poured into ice water and extracted with ethyl acetate. The organic phase was washed with water and saturated brine, dried over anhydrous sodium sulfate, and concentrated. The crude was purified by silica gel column chromatography to obtain 25-2. LC-MS: 310.1 [M+H]⁺.

Step Two:

25-2 (2 g) was dissolved in absolute ethanol (15 mL), introduced slowly with dry hydrogen chloride gas was at 0° C. for 5 h, distilled under reduced pressure at 30° C. to remove most of the ethanol, washed with diethyl ether, and rotary evaporated to dryness to obtain a crude 25-3, which was directly used in the next step.

Step Three:

The crude 25-3 was dissolved in anhydrous tetrahydrofuran (20 mL), slowly added dropwise with triethylamine at 0° C., and then added dropwise with triphosgene (5.1 g) dissolved in THF (10 mL), stirred at 0° C. for 1 h, added with 1N HCl (20 mL) and stirred for 0.5 h. TLC showed that the reaction was complete. The reaction solution was poured into ice water and extracted with ethyl acetate. The organic phase was washed with saturated sodium bicarbonate. The aqueous phase was extracted with a small amount of ethyl acetate, adjusted pH to about 3-4 with 1N HCl, and extracted again with ethyl acetate. The organic phase was washed with water and brine, dried over anhydrous sodium sulfate, and concentrated to obtain a crude 25-4.

Step Four:

25-4 (2 g), the borate 24-1a (2.3 g), Pd(dppf)Cl₂ (0.06 g), sodium carbonate (4 g), dioxane (200 mL) and water (20 mL) were reacted at 100° C. under nitrogen for 17 h. TCL showed disappearance of the raw material. The resultant was filtered. The filter cake was washed with dichloromethane. The filtrate was added with water/dichloromethane and layered. The organic layer was dried and rotary evaporated to dryness. The residue was purified by column chromatography to obtain SP-11. LC-MS: 327.1 [M+H]⁺.

Example 26 Synthesis of Spiro Ring SP-12

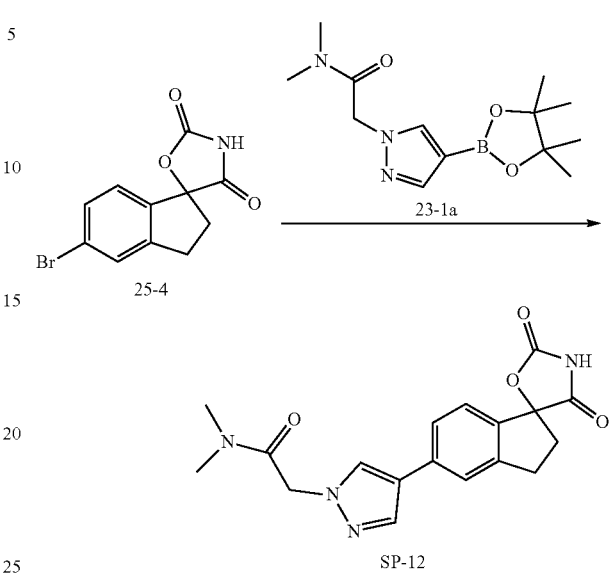

SP-12

25-4 (2 g), the borate 23-1a (2.5 g), Pd(dppf)Cl₂ (0.06 g), sodium carbonate (4 g), dioxane (200 mL) and water (20 mL) were reacted at 100° C. under nitrogen for 17 h. TCL showed disappearance of the raw material. The resultant was filtered. The filter cake was washed with DCM. The filtrate was added with water/dichloromethane and layered. The organic phase was dried and rotary evaporated to dryness. The residue was purified by column chromatography to obtain SP-12. LC-MS: 355.1 [M+H]⁺.

Example 27 Synthesis of Spiro Ring SP-13

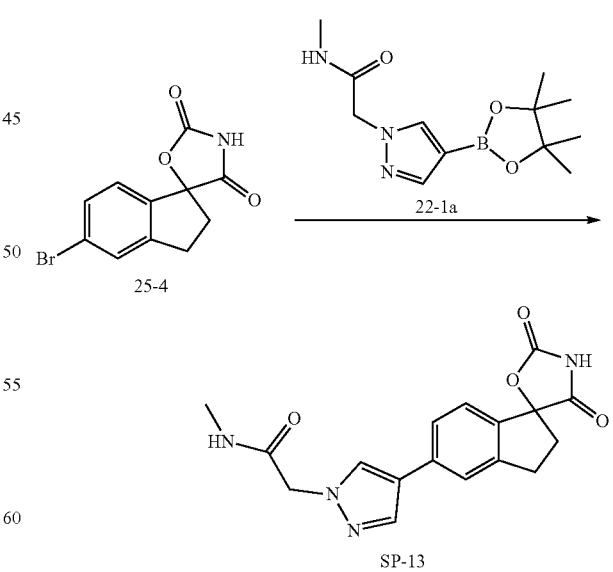

SP-13

25-4 (2 g), the borate 22-1a (2.4 g), Pd(dppf)Cl₂ (0.06 g), sodium carbonate (4 g), dioxane (200 mL) and water (20 mL) were reacted at 100° C. under nitrogen for 17 h. TCL showed disappearance of the raw material. The resultant was filtered. The filter cake was washed with dichloromethane. The filtrate was added with water/dichloromethane and layered. The organic phase was dried and rotary evaporated to dryness. The residue was purified by column chromatography to obtain SP-13. LC-MS: 341.1 [M+H]⁺.

Example 28 Synthesis of Spiro Ring SP-14

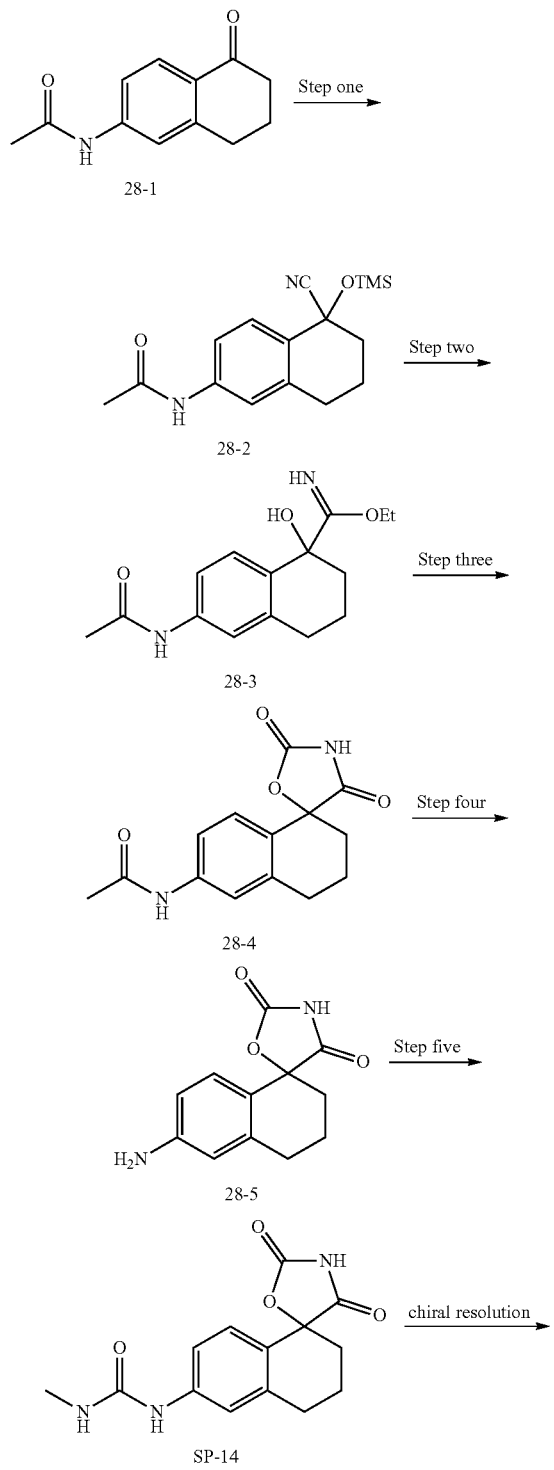

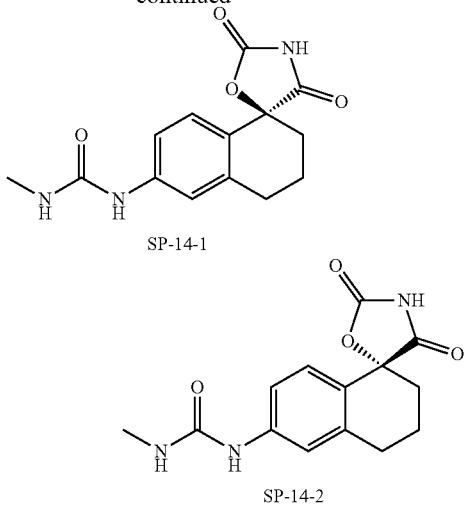

Step One:

The crude 28-1 dissolved in toluene was added with acetonitrile, and then with trimethylsilyl cyanide and zinc iodide at room temperature, heated to 75° C. and stirred for 4 h. TLC showed that the reaction was complete. The reaction solution was cooled to room temperature, poured into ice water and extracted with ethyl acetate. The organic phase was washed with water and saturated brine, dried over anhydrous sodium sulfate, and concentrated. The crude was purified by silica gel column chromatography to obtain 28-2.

Step Two:

28-2 dissolved in absolute ethanol was introduced slowly with dry hydrogen chloride gas at 0° C. for 5 h, distilled under reduced pressure to remove most of ethanol, washed with diethyl ether, and rotary evaporated to dryness to obtain a crude 28-3, which was directly used in the next step.

Step Three:

The crude 28-3 dissolved in anhydrous THF was slowly added with triethylamine at 0° C., and then added dropwise with triphosgene dissolved in THF, stirred at 0° C. for 1 h, added with 1N HCl and stirred for 0.5 h. TLC showed that the reaction was complete. The reaction solution was poured into ice water and extracted with ethyl acetate. The organic phase was washed with saturated sodium bicarbonate. The aqueous phase was extracted with a small amount of ethyl acetate, adjusted pH to about 3-4 with 1N HCl, and extracted again with ethyl acetate. The organic phase was washed with water and brine, dried over anhydrous sodium sulfate, and concentrated to obtain a crude 28-4.

Step Four:

28-4 dissolved in methanol was added with 6N HCl and stirred at 75° C. for 3 h. TLC showed that the reaction was complete. The reaction solution was cooled to room temperature, adjusted pH to neutral with saturated sodium bicarbonate, and extracted with ethyl acetate. The organic phase was washed with water and brine, dried over anhydrous sodium sulfate, and concentrated. The crude was purified by silica gel column chromatography to obtain 28-5. LC-MS: 233.1 [M+H]⁺.

Step Five:

28-5 dissolved in anhydrous THF was added with phenyl p-nitrochloroformate and stirred at room temperature for 0.5 h. Methylamine hydrochloride dissolved in methanol was added with TEA, stirred for 10 min, added with the above reaction solution, and stirred at room temperature for 1 h.

TLC showed that the reaction was complete. The reaction solution was poured into ice water, adjusted pH to 3~4 with 1N HCl, and extracted with ethyl acetate. The organic phase was washed with water and brine, dried over anhydrous sodium sulfate, and concentrated. The crude was purified by column chromatography to obtain SP-14. LC-MS: 290.1 [M+H]+.

Chiral resolution was performed to obtain intermediates SP-14-1 and SP-14-2: Preparative column was Daicel AD-H, filler particle size (5 μm), inner diameter (30 mm), length (250 mm), flow rate: 20 m/min, mobile phase: 80% n-hexane+20% isopropanol, isogradient elution, wavelength 254 nm, peak time is 16.82 min for peak 1, and 30.68 min for peak 2.

Example 29 Synthesis of Spiro Ring SP-15

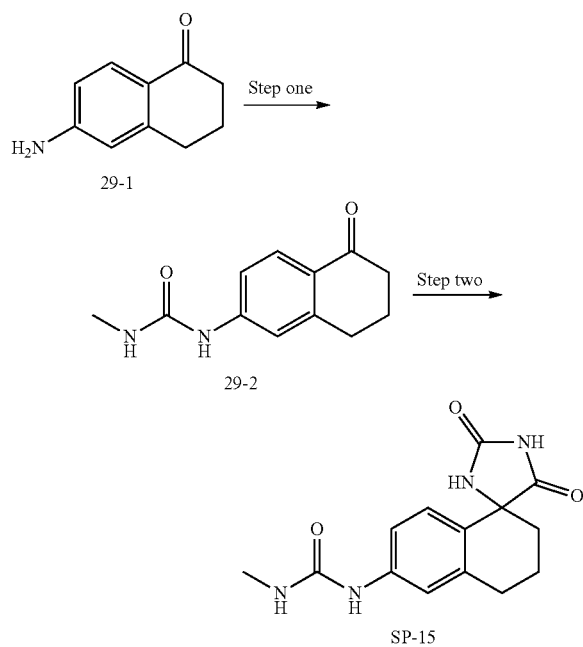

Step One:

29-1 (17.52 g) was weighed and dissolved in 250 mL of tetrahydrofuran, added dropwise with phenyl p-nitrochloroformate (10.0 g, pre-dissolved in 250 mL of tetrahydrofuran) solution, and reacted at room temperature for 2 h. Sampling analysis showed that the reaction was complete. The reaction mixture was added with methylamine hydrochloride (8.4 g), stirred at room temperature for 1 h, added with triethylamine (19.0 g) and stirred at room temperature for 2 h. Sampling analysis showed that the reaction was complete. The reaction solution was concentrated to dryness, added with water and ethyl acetate for extraction and layered. The organic phase was washed with saturated sodium bicarbonate solution to precipitate a large amount of solid. The solid was filtered off and dried to obtain 5.1 g of a solid. The organic phase was concentrated to dryness, added with 20 mL of a mixture (petroleum ether/ethyl acetate=2/1), slurried and filtered to obtain a solid, which was rinsed with water and dried to obtain 29-2 (3.2 g) as a solid.

Step Two:

To a 250 mL single necked flask, were added 29-2 (8.3 g), absolute ethanol (500 mL), TMSCN (37.7 g), NH4F (14.1 g), ammonium carbonate (55 g) and ammonia (30 mL) in sequence, and stirred at 80° C. for 10 h. TLC showed that the reaction was basically complete. The reaction solution was cooled to room temperature, added with water and extracted with ethyl acetate. The combined organic phase was dried and rotary evaporated to dryness. The residue was purified by column chromatography to obtain SP-15 as a solid. LC-MS: [M+H]+=289.1.

Example 30 Synthesis of SYY—B002

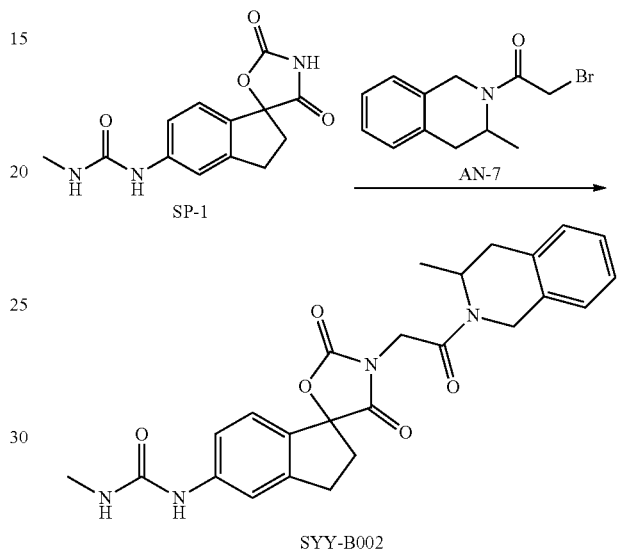

SP-1 (100 mg) dissolved in dry DMF (15 mL) was added with potassium carbonate (138 mg) and the amide fragment AN-7 (134 mg) at room temperature, and stirred at room temperature for 1 h. TLC showed that the reaction was complete. The reaction solution was poured into water and extracted with ethyl acetate. The organic phase was washed with water and saturated brine, dried over anhydrous sodium sulfate, and concentrated. The crude was purified by column chromatography to obtain the final product SYY—B002 (45 mg).

¹H NMR (400 MHz, DMSO-d6) δ 8.71 (brs, 1H), 7.56 (m, 1H), 7.35 (m, 1H), 7.25-7.21 (m, 5H), 6.08 (m, 1H), 4.97-4.48 (m, 5H), 4.30-4.10 (m, 1H), 3.20-3.00 (m, 3H), 2.65-2.49 (m, 5H), 1.15-0.99 (m, 3H). LC-MS: [2M+H]+ =925.3.

Example 31 Synthesis of SYY-B003

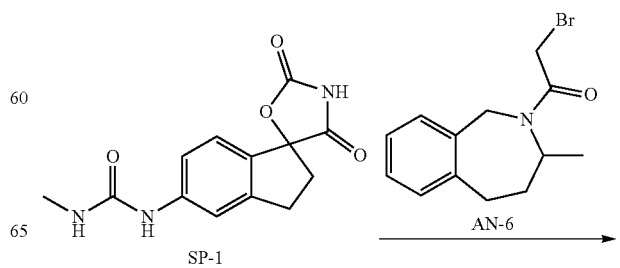

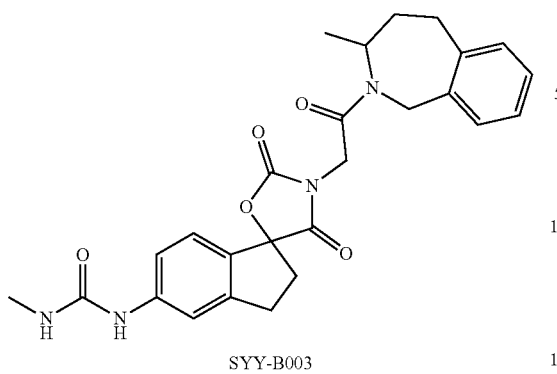

SYY-B003

SYY—B003 was prepared using the same method as that in Example 30, except that the amide fragment AN-6 was used instead of AN-7.

¹H NMR (400 MHz, DMSO-d₆) δ 8.71 (m, 1H), 7.56 (m, 1H), 7.35-7.11 (m, 6H), 6.08 (m, 1H), 4.92-4.58 (m, 3H), 4.42-3.77 (m, 3H), 3.17-2.96 (m, 3H), 2.65-2.49 (m, 5H), 2.07-1.82 (m, 2H), 1.35-1.18 (m, 3H). LC-MS: [M+H]⁺= 477.2.

Example 32 Synthesis of SYY—B009

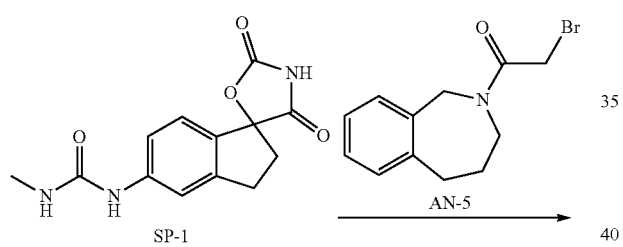

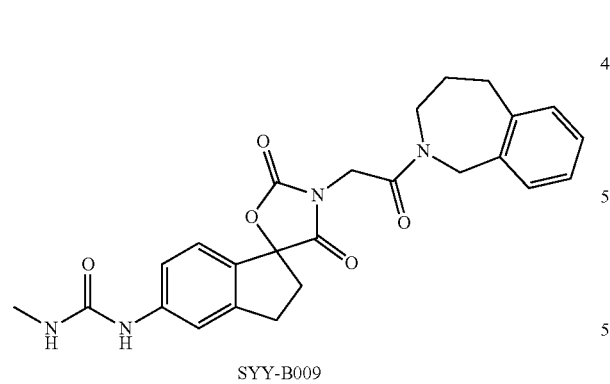

SYY-B009

SYY—B009 was prepared using the same method as that in Example 30, except that the amide fragment AN-5 was used instead of AN-7.

¹H NMR (400 MHz, DMSO-d₆) δ 8.69 (m, 1H), 7.53 (m, 1H), 7.41-7.11 (m, 6H), 6.07 (m, 1H), 4.73 (m, 1H), 4.57-4.44 (m, 3H), 3.82-3.79 (m, 2H), 3.14-2.94 (m, 4H), 2.65-2.57 (m, 4H), 2.44 (m, 1H), 1.82-1.67 (m, 2H). LC-MS: [2M+H]⁺=925.3.

Example 33 Synthesis of SYY-B010

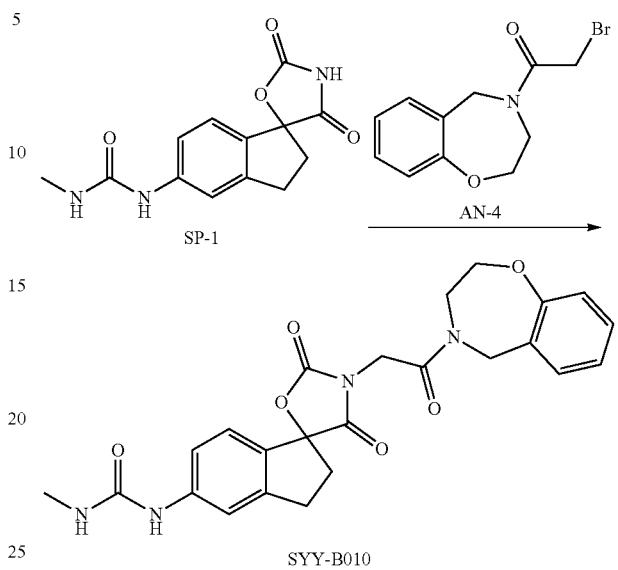

SYY-B010

SYY—B010 was prepared using the same method as that in Example 30, except that the amide fragment AN-4 was used instead of AN-7.

¹H NMR (400 MHz, DMSO-d₆) δ 8.71 (m, 1H), 7.53 (m, 1H), 7.29-7.20 (m, 4H), 7.09-6.98 (m, 2H), 6.08 (m, 1H), 4.77 (s, 1H), 4.67 (m, 1H), 4.53 (m, 2H), 4.22 (m, 1H), 4.11 (m, 1H), 3.95-3.91 (m, 2H), 3.15-2.94 (m, 2H), 2.65-2.61 (m, 4H), 2.49 (m, 1H). LC-MS: [M+H]⁺=465.2.

Example 34 Synthesis of SYY-B012-1 and SYY-B012-2

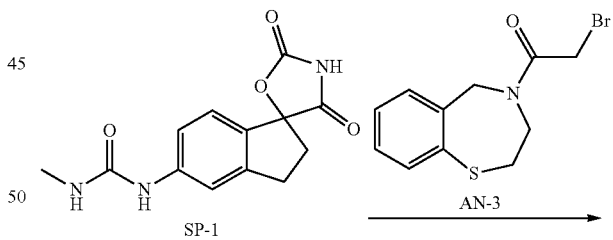

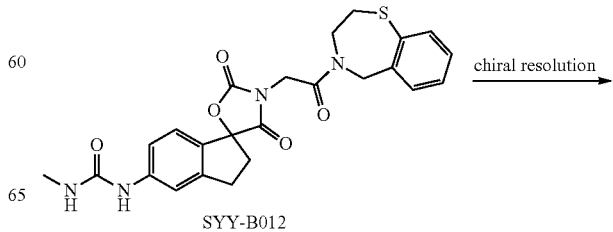

SYY-B012

127
-continued

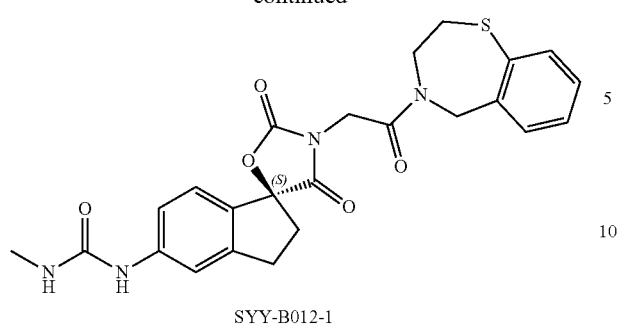

SYY-B012-1

SYY-B012-2

SYY—B012 was prepared using the same method as that in Example 30, except that the amide fragment AN-3 was used instead of AN-7.

The SYY—B012 was subjected to chiral resolution to obtain chiral products SYY-B012-1 and SYY-B012-2.

Chiral resolution conditions: semi-preparative column was CHIRALPAK@OD-H, filler particle size (5 μm), inner diameter (30 mm), length (250 mm), flow rate: 20 m/min, mobile phase: 75% n-hexane+25% ethanol, isogradient elution, wavelength 254 nm, total time: 60 min; peak time is 36 min for peak 1, and 45 min for peak 2.

SYY-B012-1: $^1$H NMR (400 MHz, DMSO-d$_6$) δ 8.72 (m, 1H), 7.58-7.44 (m, 3H), 7.35-7.22 (m, 4H), 6.10 (m, 1H), 4.87 (s, 1H), 4.66 (m, 1H), 4.52-4.48 (m, 2H), 4.00 (m, 2H), 3.08-2.92 (m, 4H), 2.64 (m, 4H), 2.49-2.44 (m, 1H). LC-MS: [M+H]$^+$=481.1.

SYY-B012-2: $^1$H NMR (400 MHz, DMSO-d$_6$) δ 8.71 (m, 1H), 7.58-7.44 (m, 3H), 7.35-7.21 (m, 4H), 6.09 (m, 1H), 4.88 (s, 1H), 4.66 (m, 1H), 4.53-4.44 (m, 2H), 4.01 (m, 2H), 3.04-2.92 (m, 4H), 2.64 (m, 4H), 2.40-2.44 (m, 1H). LC-MS: [M+H]$^+$=481.1.

Example 35 Synthesis of SYY-B013

128
-continued

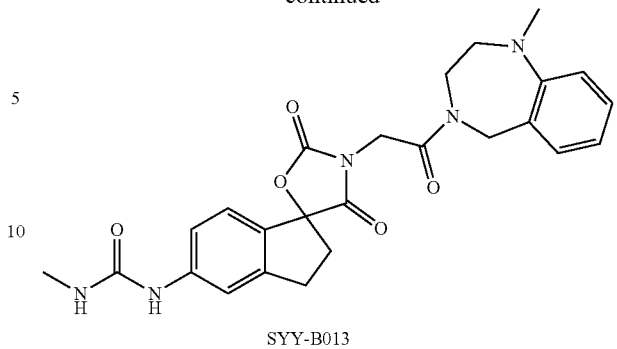

SYY-B013

SYY—B013 was prepared using the same method as that in Example 30, except that the amide fragment AN-2 was used instead of AN-7.

$^1$H NMR (400 MHz, DMSO-d$_6$) δ 8.85 (m, 1H), 7.54 (m, 1H), 7.30-7.21 (m, 4H), 6.97-6.83 (m, 2H), 6.18 (m, 1H), 4.64-4.49 (m, 4H), 3.72 (m, 2H), 3.16-3.07 (m, 4H), 2.88 (s, 3H), 2.64 (m, 4H), 2.48 (m, 1H). LC-MS: [M+H]$^+$=478.2.

Example 36 Synthesis of SYY-B014-1 and SYY-B014-2

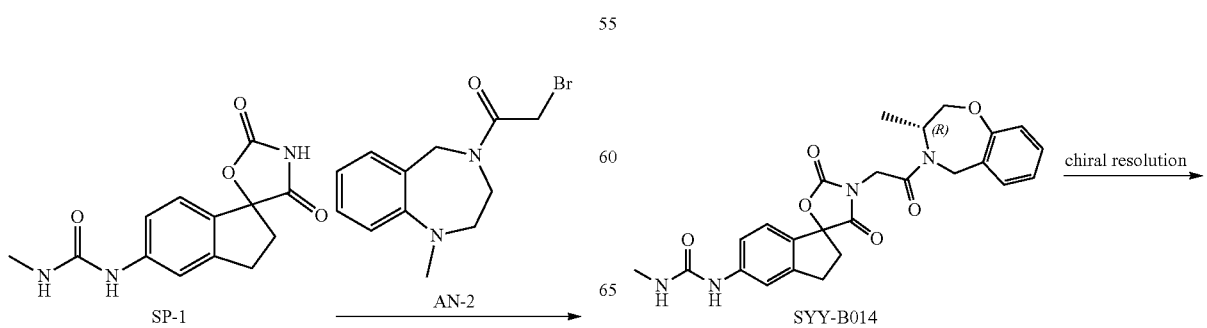

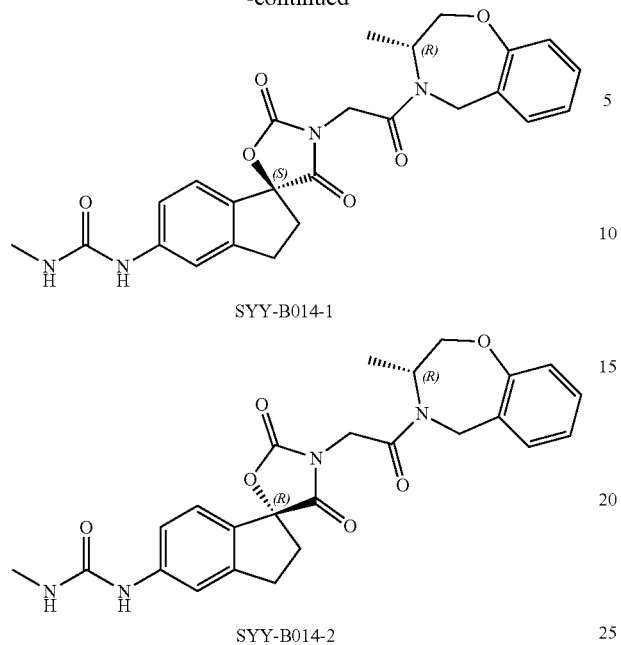

SYY-B014-1

SYY-B014-2

SYY—B014 was prepared using the same method as that in Example 30, except that the amide fragment AN-1 was used instead of AN-7.

The SYY—B014 was subjected to chiral resolution to obtain chiral products SYY-B014-1 and SYY-B014-2.

Chiral resolution conditions: semi-preparative column was CHIRALPAK@AY-H, filler particle size (5 μm), inner diameter (20 mm), length (250 mm), flow rate: 12 mL/min, mobile phase: 85% n-hexane+15% ethanol, isogradient elution, wavelength 254 nm, total time: 50 min; peak time is 18.5 min for peak 1, and 30 min for peak 2.

SYY-B014-1: $^1$H NMR (400 MHz, DMSO-d$_6$) δ 8.71 (m, 1H), 7.53 (m, 1H), 7.30-7.20 (m, 4H), 7.00-6.85 (m, 2H), 6.08 (m, 1H), 5.00-4.59 (m, 3H), 4.39-4.17 (m, 3H), 3.83 (m, 1H), 3.09-2.99 (m, 2H), 2.64-2.55 (m, 4H), 2.47 (m, 1H), 1.29-1.11 (m, 3H). LC-MS: [M+H]$^+$=479.2. [α]$_D^{20}$-24.9° (c 0.61, DCM:MeOH=9:1).

SYY-B014-2: $^1$H NMR (400 MHz, DMSO-d$_6$) δ 8.71 (m, 1H), 7.53 (m, 1H), 7.30-7.20 (m, 4H), 7.00-6.85 (m, 2H), 6.08 (m, 1H), 5.00-4.59 (m, 3H), 4.39-4.17 (m, 3H), 3.82 (m, 1H), 3.09-2.99 (m, 2H), 2.64-2.55 (m, 4H), 2.47 (m, 1H), 1.29-1.11 (m, 3H). LC-MS: [M+H]$^+$=479.2. [α]$_D^{20}$+26.8° (c 0.57, DCM:MeOH=9:1).

Example 37 Synthesis of SYY-B015-1

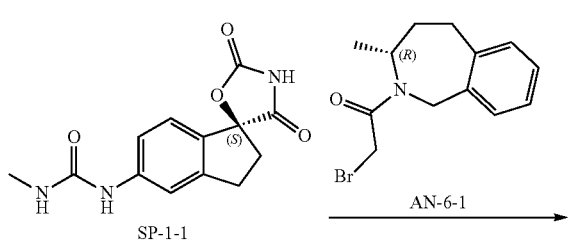

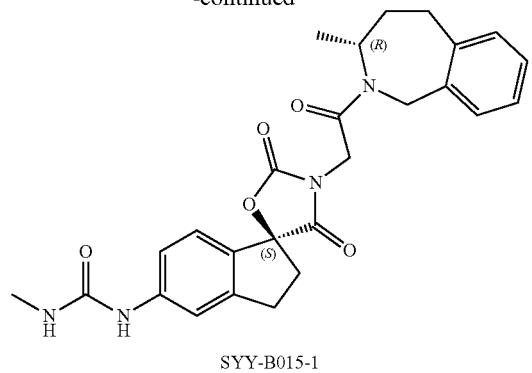

SYY-B015-1

SYY-B015-1 was prepared using the same method as that in Example 30, except that the spiro ring fragment SP-1-1 was used instead of SP-1 and the amide fragment AN-6-1 was used instead of AN-7.

$^1$H NMR (400 MHz, DMSO-d$_6$, 110° C.) δ 8.40 (brs, 1H), 7.49 (brs, 1H), 7.26 (m, 3H), 7.15 (m, 3H), 5.94 (m, 1H), 4.70-3.93 (m, 5H), 3.14-3.09 (m, 1H), 3.04-2.97 (m, 2H), 2.78-2.63 (m, 5H), 2.48-2.44 (m, 1H), 2.07-1.91 (m, 2H), 1.27 (m, 3H). LC-MS: [2M+H]$^+$=953.3. [α]$_D^{20}$-35.6° (c 0.72, DMSO).

Example 38 Synthesis of SYY-B015-2

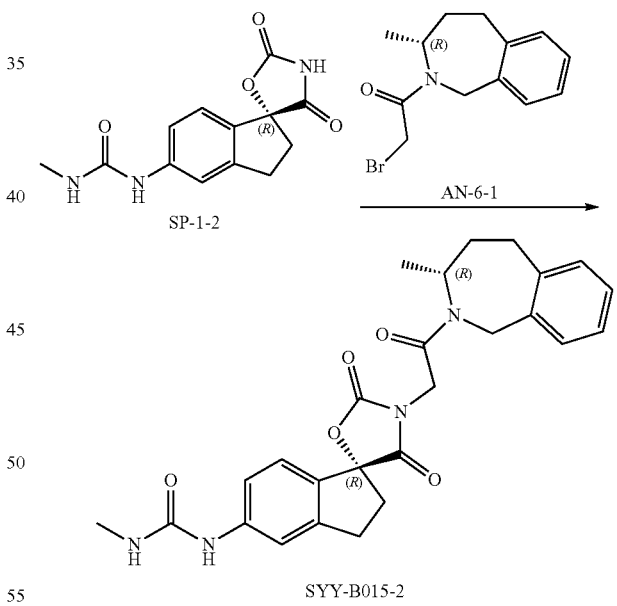

SYY-B015-2

SYY-B015-2 was prepared using the same method as that in Example 30, except that the spiro ring fragment SP-1-2 was used instead of SP-1 and the amide fragment AN-6-1 was used instead of AN-7.

$^1$H NMR (400 MHz, DMSO-d$_6$, 110° C.) δ 8.33 (brs, 1H), 7.49 (brs, 1H), 7.26 (m, 3H), 7.15 (m, 3H), 5.90 (m, 1H), 4.80-3.8 (m, 5H), 3.14-3.09 (m, 1H), 3.04-2.97 (m, 2H), 2.78-2.63 (m, 5H), 2.48-2.44 (m, 1H), 2.07-1.91 (m, 2H), 1.28 (m, 3H). LC-MS: [M+H]$^+$=477.2. [α]$_D^{20}$+31.6° (c 0.86, DMSO).

Example 39 Synthesis of SYY-B016-1

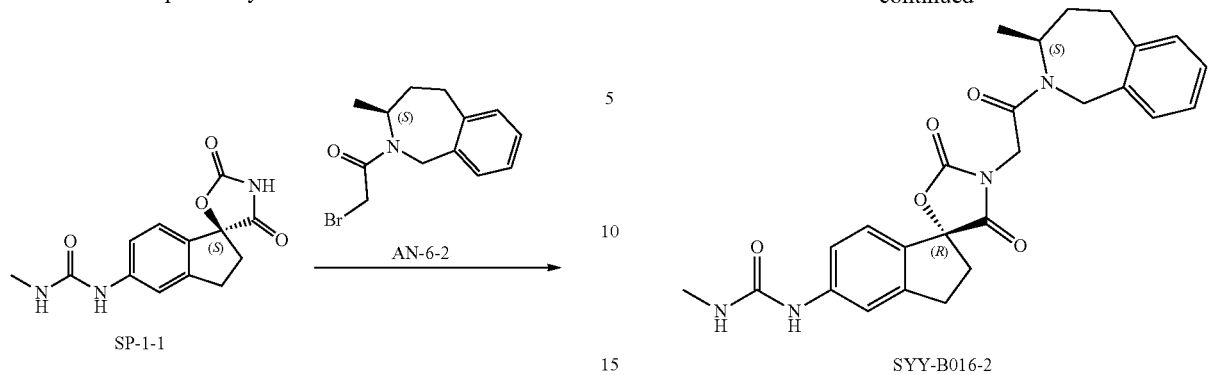

SYY-B016-1 was prepared using the same method as that in Example 30, except that the spiro ring fragment SP-1-1 was used instead of SP-1 and the amide fragment AN-6-2 was used instead of AN-7.

$^1$H NMR (400 MHz, DMSO-d$_6$) δ 8.71 (m, 1H), 7.53 (brs, 1H), 7.30-7.13 (m, 6H), 6.09 (m, 1H), 4.89-4.64 (m, 3H), 4.42-4.18 (m, 2H), 3.82 (m, 1H), 3.13-2.78 (m, 3H), 2.64-2.55 (m, 4H), 2.45 (m, 1H), 1.93-1.89 (m, 2H), 1.35-1.20 (m, 3H). LC-MS: [M+H]$^+$=477.2. $[α]_D^{20}$−35.7° (c 0.83, MeOH).

Example 40 Synthesis of SYY-B016-2

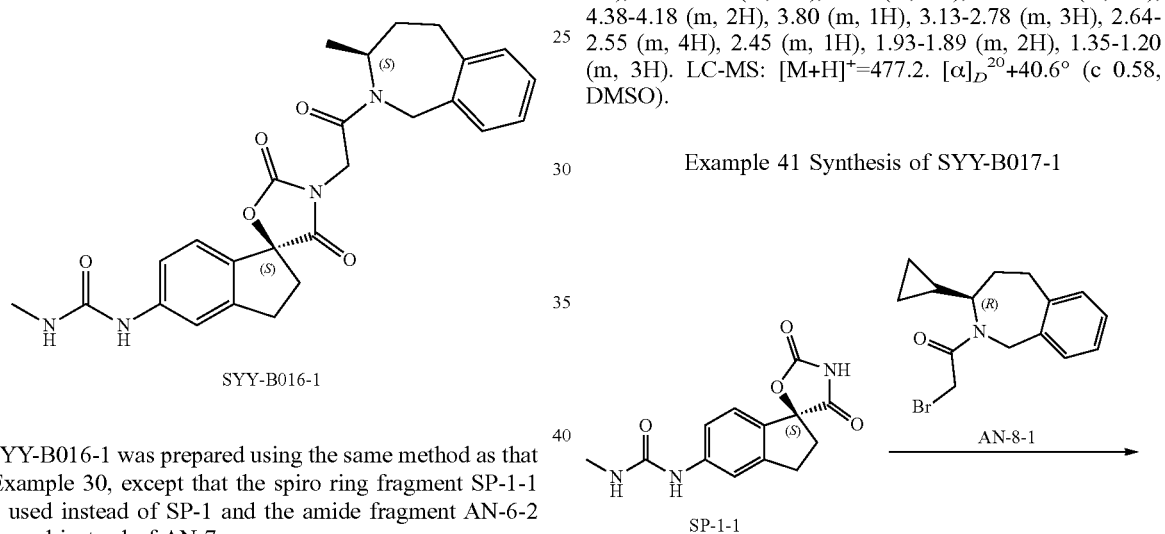

SYY-B016-2 was prepared using the same method as that in Example 30, except that the spiro ring fragment SP-1-2 was used instead of SP-1 and the amide fragment AN-6-2 was used instead of AN-7.

$^1$H NMR (400 MHz, DMSO-d$_6$) δ 8.72 (m, 1H), 7.53 (m, 1H), 7.30-7.12 (m, 6H), 6.10 (m, 1H), 4.91-4.58 (m, 3H), 4.38-4.18 (m, 2H), 3.80 (m, 1H), 3.13-2.78 (m, 3H), 2.64-2.55 (m, 4H), 2.45 (m, 1H), 1.93-1.89 (m, 2H), 1.35-1.20 (m, 3H). LC-MS: [M+H]$^+$=477.2. $[α]_D^{20}$+40.6° (c 0.58, DMSO).

Example 41 Synthesis of SYY-B017-1

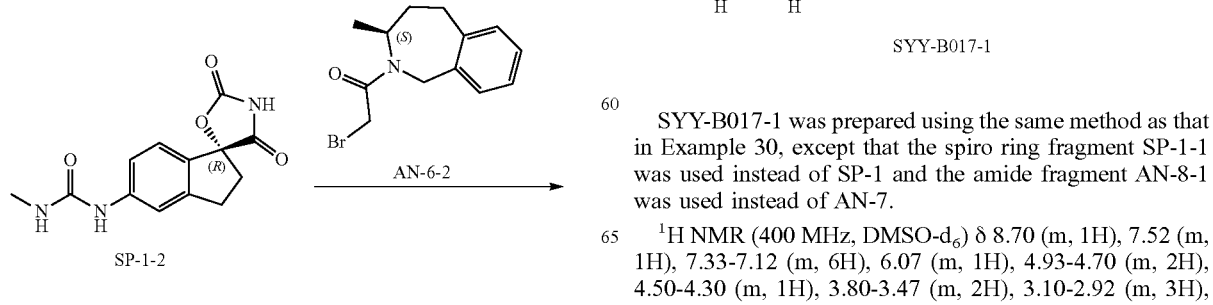

SYY-B017-1 was prepared using the same method as that in Example 30, except that the spiro ring fragment SP-1-1 was used instead of SP-1 and the amide fragment AN-8-1 was used instead of AN-7.

$^1$H NMR (400 MHz, DMSO-d$_6$) δ 8.70 (m, 1H), 7.52 (m, 1H), 7.33-7.12 (m, 6H), 6.07 (m, 1H), 4.93-4.70 (m, 2H), 4.50-4.30 (m, 1H), 3.80-3.47 (m, 2H), 3.10-2.92 (m, 3H), 2.73-2.56 (m, 5H), 2.45 (m, 1H), 1.99 (m, 2H), 1.42 (m, 1H), 0.57-0.29 (m, 4H). LC-MS: [M+H]$^+$=503.2. [α]$_D^{20}$–58.3° (c 0.51, MeOH).

Example 42 Synthesis of SYY-B017-2

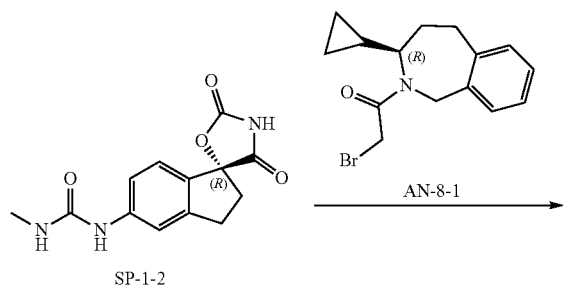

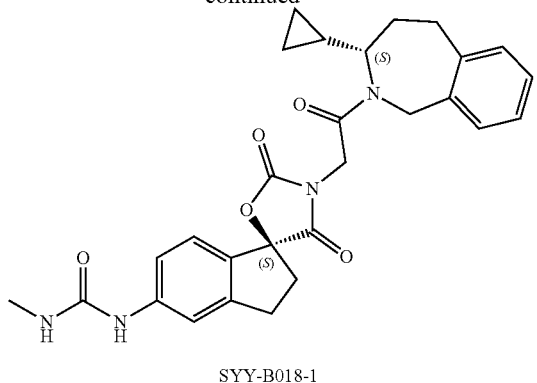

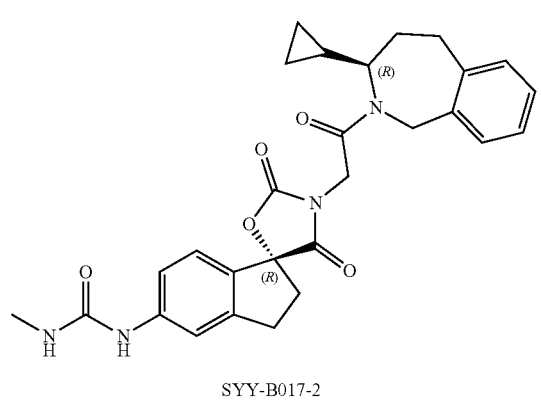

SYY-B017-2 was prepared using the same method as that in Example 30, except that the spiro ring fragment SP-1-2 was used instead of SP-1 and the amide fragment AN-8-1 was used instead of AN-7.

$^1$H NMR (400 MHz, DMSO-d$_6$) δ 8.70 (m, 1H), 7.52 (m, 1H), 7.33-7.12 (m, 6H), 6.07 (m, 1H), 4.93-4.70 (m, 2H), 4.50-4.30 (m, 1H), 3.80-3.47 (m, 2H), 3.10-2.92 (m, 3H), 2.73-2.56 (m, 5H), 2.45 (m, 1H), 1.99 (m, 2H), 1.47-1.25 (m, 1H), 0.57-0.29 (m, 4H). LC-MS: [M+H]$^+$=503.2. [α]$_D^{20}$+53.6° (c 0.53, MeOH).

Example 43 Synthesis of SYY-B018-1

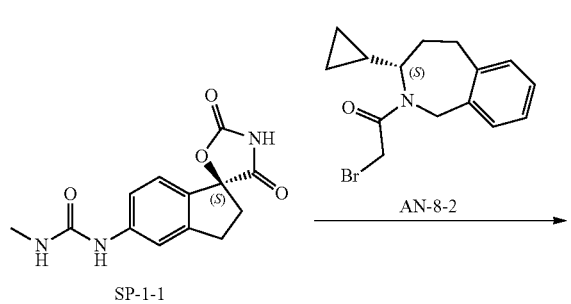

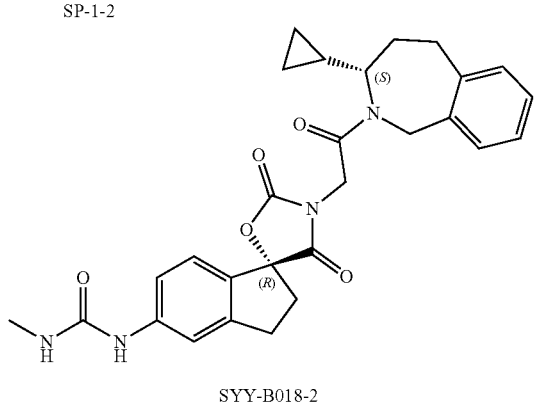

SYY-B018-1 was prepared using the same method as that in Example 30, except that the spiro ring fragment SP-1-1 was used instead of SP-1 and the amide fragment AN-8-2 was used instead of AN-7.

$^1$H NMR (400 MHz, DMSO-d$_6$, 110° C.) δ 8.33 (brs, 1H), 7.48 (brs, 1H), 7.30-7.17 (m, 6H), 5.90 (m, 1H), 4.76-3.58 (m, 5H), 3.14-3.09 (m, 2H), 3.04-2.97 (m, 1H), 2.72-2.62 (m, 5H), 2.47-2.43 (m, 1H), 2.09-2.00 (m, 2H), 1.28 (m, 1H), 0.62-0.37 (m, 4H). LC-MS: [M+H]$^+$=503.2. [α]$_D^{20}$–38.6° (c 0.42, DMSO).

Example 44 Synthesis of SYY-B018-2

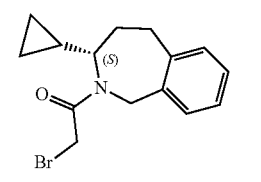

SYY-B018-2 was prepared using the same method as that in Example 30, except that the spiro ring fragment SP-1-2 was used instead of SP-1 and the amide fragment AN-8-2 was used instead of AN-7.

$^1$H NMR (400 MHz, DMSO-d$_6$, 110° C.) δ 8.31 (brs, 1H), 7.48 (brs, 1H), 7.30-7.17 (m, 6H), 5.89 (m, 1H), 4.76-3.58 (m, 5H), 3.14-3.09 (m, 2H), 3.04-2.97 (m, 1H), 2.72-2.61

(m, 5H), 2.47-2.43 (m, 1H), 2.09-2.00 (m, 2H), 1.32 (m, 1H), 0.63-0.38 (m, 4H). LC-MS: [M+H]$^+$=503.2. $[\alpha]_D^{20}$+46.3° (c 0.44, DMSO).

Example 45 Synthesis of SYY-B019-1

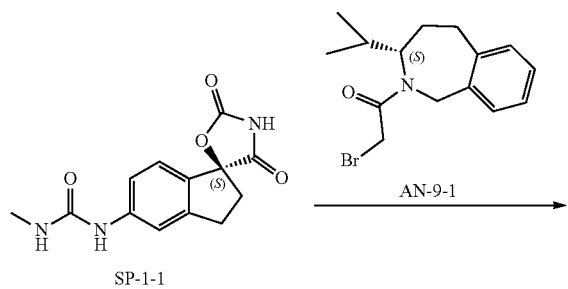

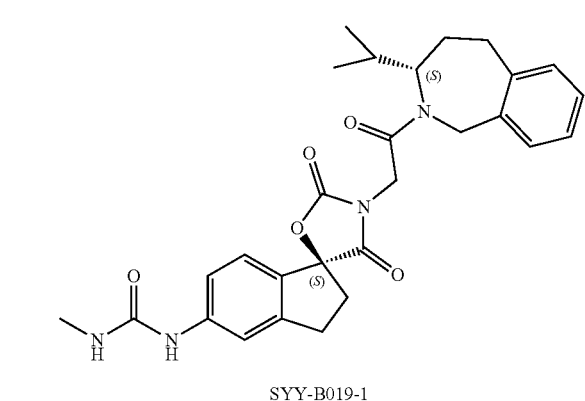

SYY-B019-1 was prepared using the same method as that in Example 30, except that the spiro ring fragment SP-1-1 was used instead of SP-1 and the amide fragment AN-9-1 was used instead of AN-7.

$^1$H NMR (400 MHz, DMSO-d$_6$, 110° C.) δ 8.35 (brs, 1H), 7.48 (brs, 1H), 7.30-7.10 (m, 6H), 5.91 (m, 1H), 4.90-4.24 (m, 4H), 3.86-3.68 (m, 1H), 3.14-3.09 (m, 1H), 3.03-2.94 (m, 2H), 2.79-2.62 (m, 5H), 2.47-2.43 (m, 1H), 2.20-2.11 (m, 1H), 2.02-1.86 (m, 2H), 1.08-0.88 (m, 6H). LC-MS: [M+H]$^+$=505.2. $[\alpha]_D^{20}$−34.4° (c 0.82, DCM:MeOH=10:1).

Example 46 Synthesis of SYY-B019-2

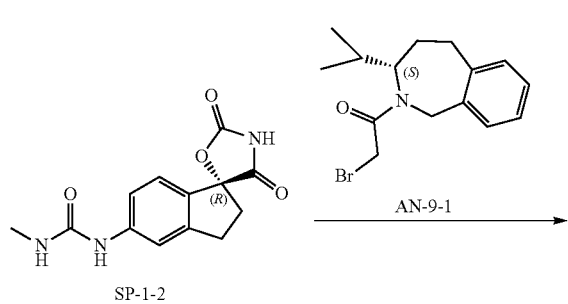

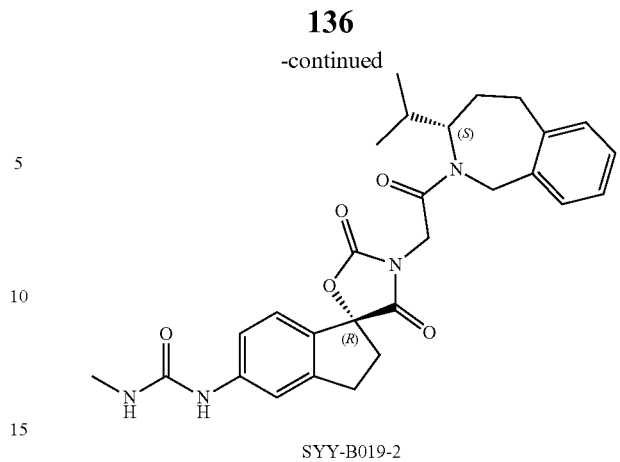

SYY-B019-2 was prepared using the same method as that in Example 30, except that the spiro ring fragment SP-1-2 was used instead of SP-1 and the amide fragment AN-9-1 was used instead of AN-7.

$^1$H NMR (400 MHz, DMSO-d$_6$, 110° C.) δ 8.32 (brs, 1H), 7.48 (brs, 1H), 7.30-7.11 (m, 6H), 5.89 (m, 1H), 4.90-4.24 (m, 4H), 3.86-3.68 (m, 1H), 3.13-3.08 (m, 1H), 3.01-2.95 (m, 2H), 2.80-2.60 (m, 5H), 2.47-2.43 (m, 1H), 2.20-2.11 (m, 1H), 2.03-1.84 (m, 2H), 1.02-0.90 (m, 6H). LC-MS: [M+H]$^+$=505.2. $[\alpha]_D^{20}$+62.9° (c 0.76, DCM:MeOH=10:1).

Example 47 Synthesis of SYY-B020-1

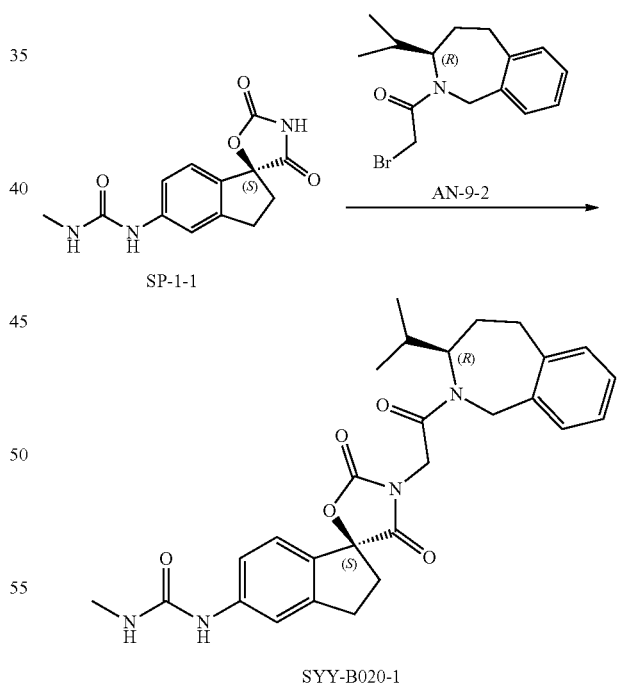

SYY-B020-1 was prepared using the same method as that in Example 30, except that the spiro ring fragment SP-1-1 was used instead of SP-1 and the amide fragment AN-9-2 was used instead of AN-7.

$^1$H NMR (400 MHz, DMSO-d$_6$) δ 8.73 (m, 1H), 7.53 (brs, 1H), 7.30-7.11 (m, 6H), 6.11 (m, 1H), 4.91-4.20 (m, 4H), 3.81-3.64 (m, 1H), 3.17-2.89 (m, 3H), 2.73-2.53 (m, 5H), 2.47-2.40 (m, 1H), 2.15-1.85 (m, 3H), 0.99-0.85 (m, 6H). LC-MS: [M+Na]⁺=527.3. $[\alpha]_D^{20}$−61.5° (c 0.78, MeOH).

Example 48 Synthesis of SYY-B020-2

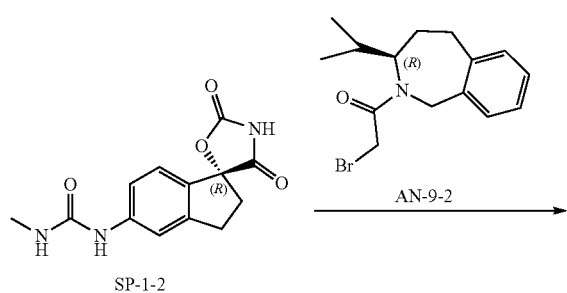

SP-1-2

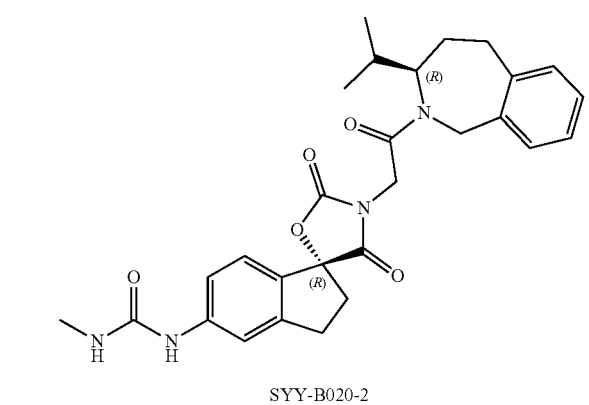

SYY-B020-2

SYY-B020-2 was prepared using the same method as that in Example 30, except that the spiro ring fragment SP-1-2 was used instead of SP-1 and the amide fragment AN-9-2 was used instead of AN-7.

¹H NMR (400 MHz, DMSO-d₆) δ 8.70 (m, 1H), 7.53 (m, 1H), 7.30-7.10 (m, 6H), 6.08 (m, 1H), 4.93-4.02 (m, 4H), 3.77 (m, 1H), 3.09-2.89 (m, 3H), 2.74-2.53 (m, 5H), 2.47-2.40 (m, 1H), 2.15-1.85 (m, 3H), 0.99-0.85 (m, 6H). LC-MS: [M+H]⁺=505.2. $[\alpha]_D^{20}$+23.3° (c 0.64, MeOH).

Example 49 Synthesis of SYY-B021-1

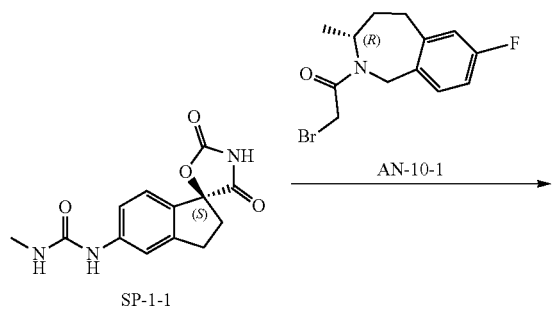

SP-1-1

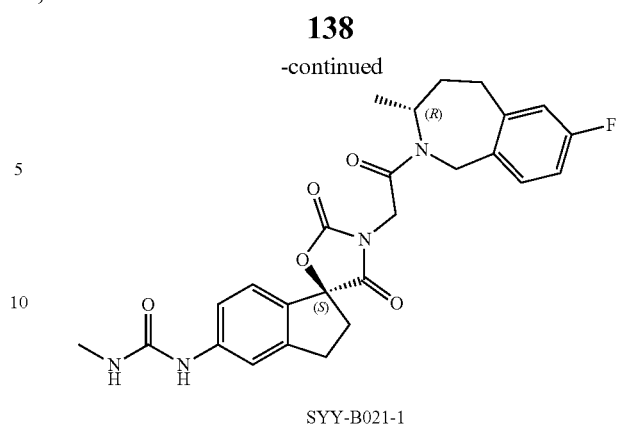

SYY-B021-1

SYY-B021-1 was prepared using the same method as that in Example 30, except that the spiro ring fragment SP-1-1 was used instead of SP-1 and the amide fragment AN-10-1 was used instead of AN-7.

¹H NMR (400 MHz, DMSO-d₆) δ 8.83 (m, 1H), 7.53 (m, 1H), 7.38-7.21 (m, 3H), 7.07-6.94 (m, 2H), 6.17 (m, 1H), 4.90-4.64 (m, 3H), 4.38-3.76 (m, 2H), 3.13-2.94 (m, 3H), 2.64-2.57 (m, 5H), 2.44 (m, 1H), 2.02-1.90 (m, 2H), 1.35-1.19 (m, 3H). LC-MS: [M+H]⁺=495.2. $[\alpha]_D^{20}$−11.4° (c 0.64, MeOH).

Example 50 Synthesis of SYY-B021-2

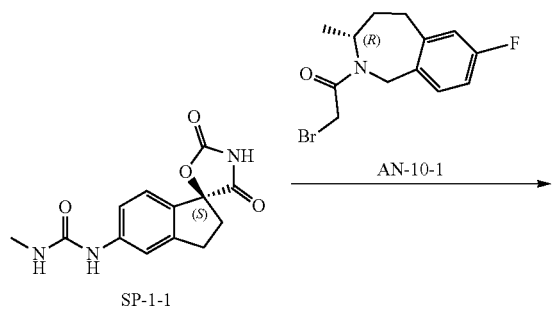

SYY-B021-2 was prepared using the same method as that in Example 30, except that the spiro ring fragment SP-1-2 was used instead of SP-1 and the amide fragment AN-10-1 was used instead of AN-7.

¹H NMR (400 MHz, DMSO-d₆) δ 8.71 (m, 1H), 7.52 (m, 1H), 7.38-7.21 (m, 3H), 7.07-6.94 (m, 2H), 6.09 (m, 1H), 4.88-4.64 (m, 3H), 4.41-3.79 (m, 2H), 3.13-2.94 (m, 3H), 2.64-2.57 (m, 5H), 2.45 (m, 1H), 2.02-1.88 (m, 2H), 1.34-1.19 (m, 3H). LC-MS: [M+H]⁺=495.2. $[\alpha]_D^{20}$+31.6° (c 0.68, MeOH).

Example 51 Synthesis of SYY-B022-1

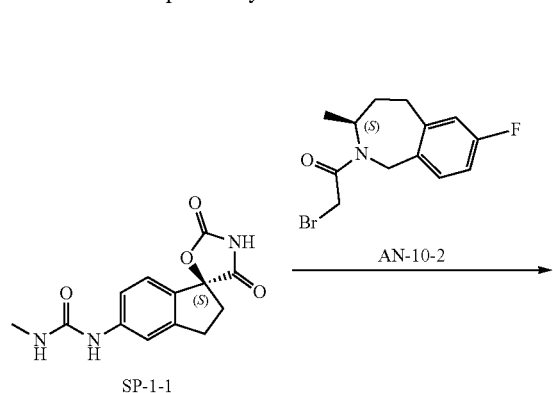

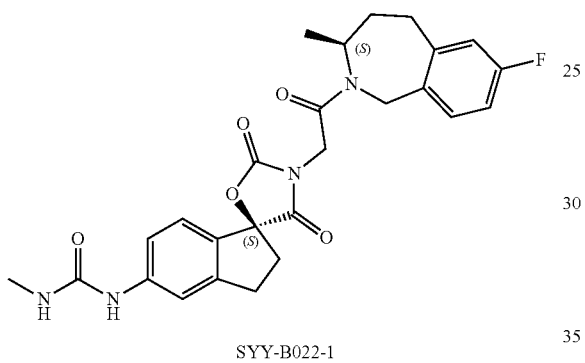

SYY-B022-1 was prepared using the same method as that in Example 30, except that the spiro ring fragment SP-1-1 was used instead of SP-1 and the amide fragment AN-10-2 was used instead of AN-7.

¹H NMR (400 MHz, DMSO-$d_6$) δ 8.70 (m, 1H), 7.52 (m, 1H), 7.38-7.19 (m, 3H), 7.07-6.91 (m, 2H), 6.09 (m, 1H), 4.88-4.64 (m, 3H), 4.42-3.79 (m, 2H), 3.13-2.94 (m, 3H), 2.64-2.57 (m, 5H), 2.45 (m, 1H), 2.02-1.88 (m, 2H), 1.34-1.19 (m, 3H). LC-MS: [M+H]⁺=495.2. $[\alpha]_D^{20}$=37.8° (c 0.41, MeOH).

Example 52 Synthesis of SYY-B022-2

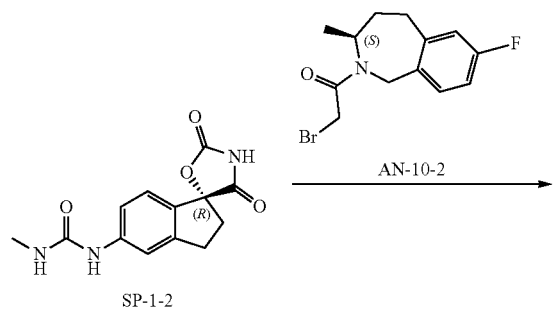

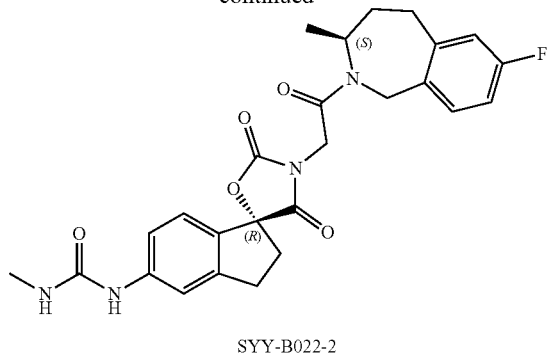

SYY-B022-2 was prepared using the same method as that in Example 30, except that the spiro ring fragment SP-1-2 was used instead of SP-1 and the amide fragment AN-10-2 was used instead of AN-7.

¹H NMR (400 MHz, DMSO-$d_6$) δ 8.71 (m, 1H), 7.52 (m, 1H), 7.37-7.20 (m, 3H), 7.08-6.91 (m, 2H), 6.08 (m, 1H), 4.90-4.64 (m, 3H), 4.37-3.77 (m, 2H), 3.15-2.94 (m, 3H), 2.64-2.57 (m, 5H), 2.45 (m, 1H), 2.02-1.88 (m, 2H), 1.35-1.19 (m, 3H). LC-MS: [M+H]⁺=495.2.

Example 53 Synthesis of SYY-B023-1

SYY-B023-1 was prepared using the same method as that in Example 30, except that the spiro ring fragment SP-1-1 was used instead of SP-1 and the amide fragment AN-12-1 was used instead of AN-7.

¹H NMR (400 MHz, DMSO-$d_6$, 110° C.) δ 8.34 (brs, 1H), 7.48 (brs, 1H), 7.31-7.12 (m, 6H), 5.91 (m, 1H), 4.86-3.86 (m, 5H), 3.14-3.09 (m, 1H), 3.02-2.97 (m, 2H), 2.79-2.62 (m, 5H), 2.47-2.43 (m, 1H), 2.11-1.44 (m, 6H), 1.01 (m, 3H). LC-MS: [M+H]⁺=505.2.

Example 54 Synthesis of SYY-B023-2

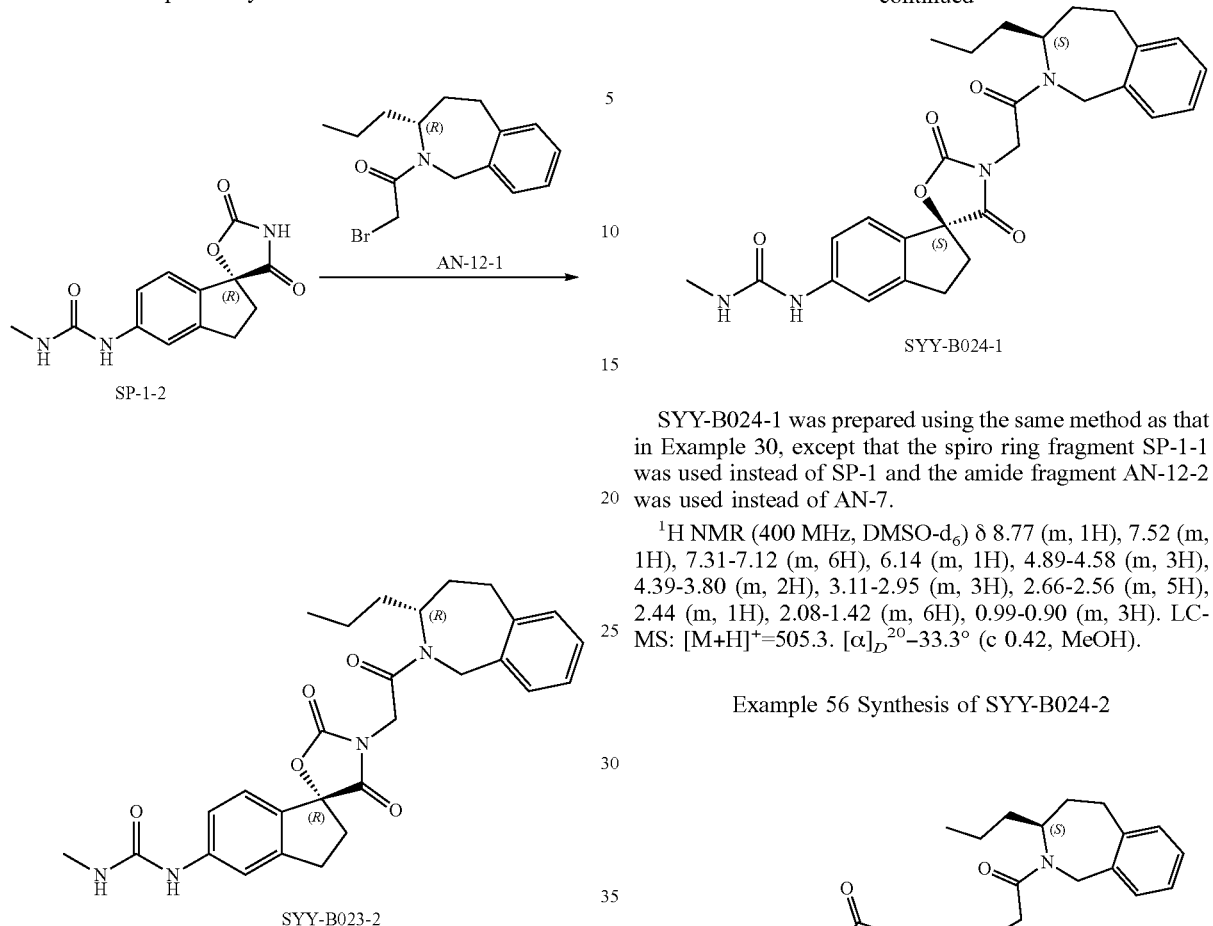

SYY-B023-2 was prepared using the same method as that in Example 30, except that the spiro ring fragment SP-1-2 was used instead of SP-1 and the amide fragment AN-12-1 was used instead of AN-7.

$^1$H NMR (400 MHz, DMSO-$d_6$) δ 8.72 (m, 1H), 7.52 (m, 1H), 7.31-7.12 (m, 6H), 6.07 (m, 1H), 4.90-4.58 (m, 3H), 4.39-3.80 (m, 2H), 3.12-2.94 (m, 3H), 2.66-2.56 (m, 5H), 2.44 (m, 1H), 2.08-1.42 (m, 6H), 0.99-0.90 (m, 3H). LC-MS: [M+H]$^+$=505.2. [α]$_D^{20}$+28.9° (c 0.81, DCM:MeOH=10:1).

Example 55 Synthesis of SYY-B024-1

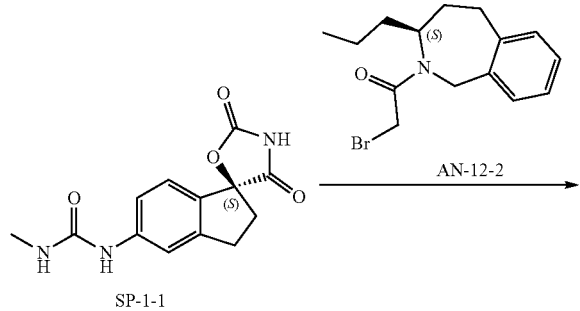

SYY-B024-1 was prepared using the same method as that in Example 30, except that the spiro ring fragment SP-1-1 was used instead of SP-1 and the amide fragment AN-12-2 was used instead of AN-7.

$^1$H NMR (400 MHz, DMSO-$d_6$) δ 8.77 (m, 1H), 7.52 (m, 1H), 7.31-7.12 (m, 6H), 6.14 (m, 1H), 4.89-4.58 (m, 3H), 4.39-3.80 (m, 2H), 3.11-2.95 (m, 3H), 2.66-2.56 (m, 5H), 2.44 (m, 1H), 2.08-1.42 (m, 6H), 0.99-0.90 (m, 3H). LC-MS: [M+H]$^+$=505.3. [α]$_D^{20}$−33.3° (c 0.42, MeOH).

Example 56 Synthesis of SYY-B024-2

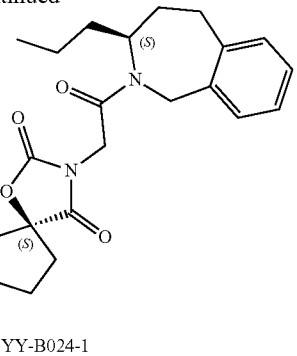

SYY-B024-2 was prepared using the same method as that in Example 30, except that the spiro ring fragment SP-1-2 was used instead of SP-1 and the amide fragment AN-12-2 was used instead of AN-7.

$^1$H NMR (400 MHz, DMSO-$d_6$) δ 8.73 (m, 1H), 7.52 (m, 1H), 7.31-7.12 (m, 6H), 6.10 (m, 1H), 4.92-4.61 (m, 3H), 4.36-3.77 (m, 2H), 3.12-2.94 (m, 3H), 2.66-2.56 (m, 5H), 2.44 (m, 1H), 2.05-1.38 (m, 6H), 1.00-0.89 (m, 3H). LC-MS: [M+H]$^+$=505.2. [α]$_D^{20}$+48.6° (c 0.57, MeOH).

Example 57 Synthesis of SYY-B025-1

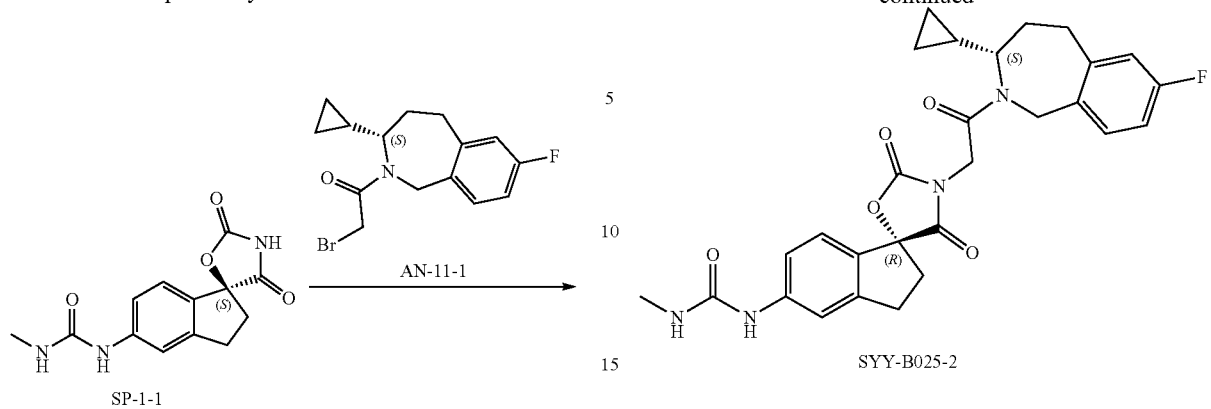

SYY-B025-1 was prepared using the same method as that in Example 30, except that the spiro ring fragment SP-1-1 was used instead of SP-1 and the amide fragment AN-11-1 was used instead of AN-7.

$^1$H NMR (400 MHz, DMSO-d$_6$, 110° C.) δ 8.34 (brs, 1H), 7.48 (brs, 1H), 7.33-7.21 (m, 3H), 6.98 (m, 2H), 5.91 (m, 1H), 4.75-3.88 (m, 5H), 3.14-3.09 (m, 2H), 3.02-2.97 (m, 1H), 2.73-2.62 (m, 5H), 2.48-2.43 (m, 1H), 2.05 (m, 2H), 1.30 (m, 1H), 0.62-0.40 (m, 4H). LC-MS: [M+H]$^+$=521.2.

Example 58 Synthesis of SYY-B025-2

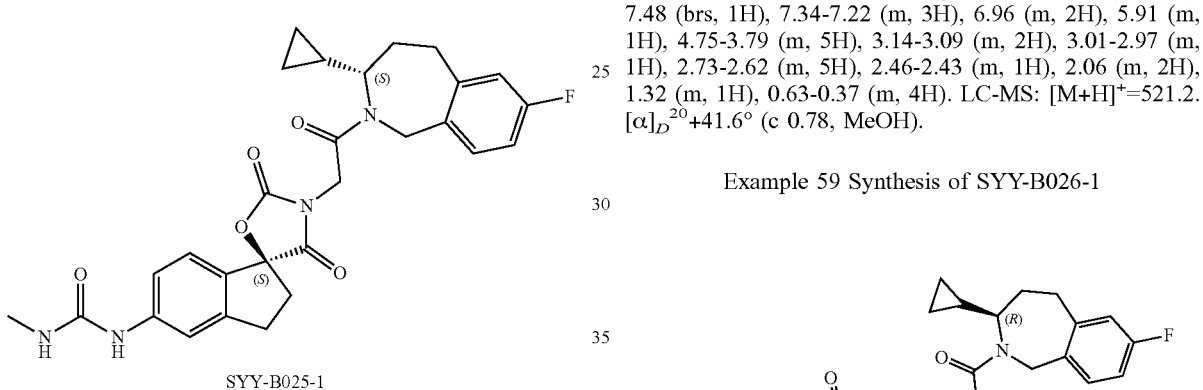

SYY-B025-2 was prepared using the same method as that in Example 30, except that the spiro ring fragment SP-1-2 was used instead of SP-1 and the amide fragment AN-11-1 was used instead of AN-7.

$^1$H NMR (400 MHz, DMSO-d$_6$, 110° C.) δ 8.32 (brs, 1H), 7.48 (brs, 1H), 7.34-7.22 (m, 3H), 6.96 (m, 2H), 5.91 (m, 1H), 4.75-3.79 (m, 5H), 3.14-3.09 (m, 2H), 3.01-2.97 (m, 1H), 2.73-2.62 (m, 5H), 2.46-2.43 (m, 1H), 2.06 (m, 2H), 1.32 (m, 1H), 0.63-0.37 (m, 4H). LC-MS: [M+H]$^+$=521.2. $[\alpha]_D^{20}$+41.6° (c 0.78, MeOH).

Example 59 Synthesis of SYY-B026-1

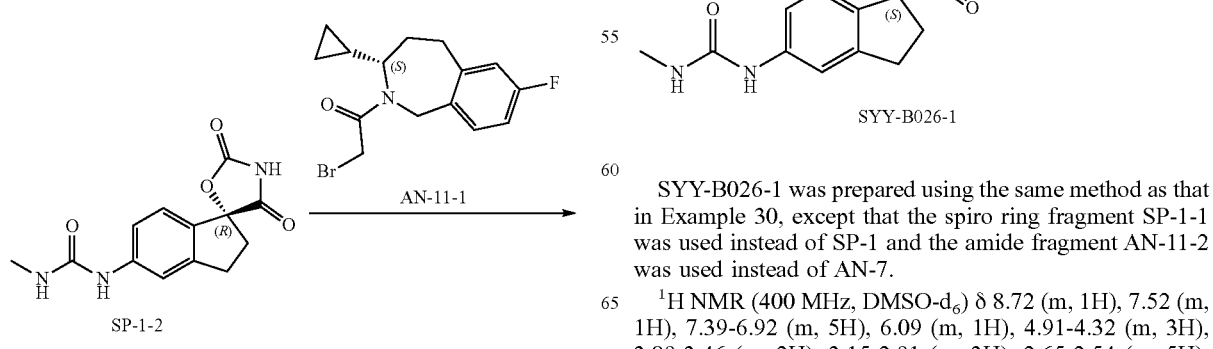

SYY-B026-1 was prepared using the same method as that in Example 30, except that the spiro ring fragment SP-1-1 was used instead of SP-1 and the amide fragment AN-11-2 was used instead of AN-7.

$^1$H NMR (400 MHz, DMSO-d$_6$) δ 8.72 (m, 1H), 7.52 (m, 1H), 7.39-6.92 (m, 5H), 6.09 (m, 1H), 4.91-4.32 (m, 3H), 3.89-3.46 (m, 2H), 3.15-2.91 (m, 3H), 2.65-2.54 (m, 5H), 2.47-2.41 (m, 1H), 2.08-1.95 (m, 2H), 1.49-1.32 (m, 1H), 0.66-0.41 (m, 4H). LC-MS: [M+H]⁺=521.2. $[\alpha]_D^2$ −38.6° (c 0.6, MeOH).

Example 60 Synthesis of SYY-B026-2

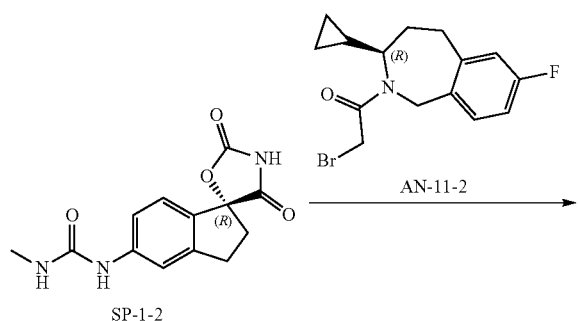

SYY-B026-2 was prepared using the same method as that in Example 30, except that the spiro ring fragment SP-1-2 was used instead of SP-1 and the amide fragment AN-11-2 was used instead of AN-7.

¹H NMR (400 MHz, DMSO-d₆) δ 8.69 (m, 1H), 7.53 (m, 1H), 7.37-6.99 (m, 5H), 6.08 (m, 1H), 4.94-4.30 (m, 3H), 3.89-3.46 (m, 2H), 3.13-2.93 (m, 3H), 2.65-2.54 (m, 5H), 2.47-2.41 (m, 1H), 2.09-1.96 (m, 2H), 1.50-1.33 (m, 1H), 0.63-0.39 (m, 4H). LC-MS: [M+H]⁺=521.2.

Example 61 Synthesis of SYY-B027-1

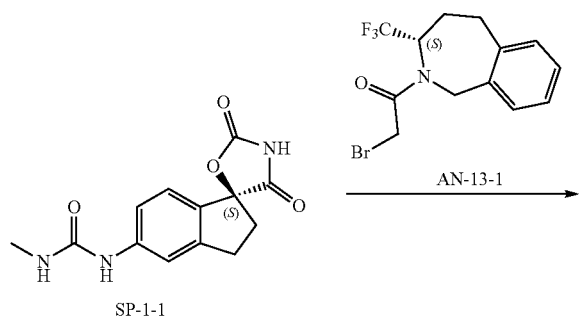

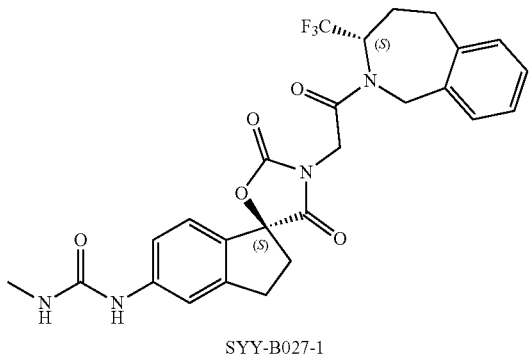

SYY-B027-1 was prepared using the same method as that in Example 30, except that the spiro ring fragment SP-1-1 was used instead of SP-1 and the amide fragment AN-13-1 was used instead of AN-7.

¹H NMR (400 MHz, DMSO-d₆) δ 8.74 (m, 1H), 7.54 (m, 1H), 7.29-7.16 (m, 6H), 6.09 (m, 1H), 5.26-4.32 (m, 4H), 3.80 (m, 1H), 3.13-2.89 (m, 3H), 2.73-2.54 (m, 5H), 2.50-2.30 (m, 3H). LC-MS: [M+H]⁺=531.2.

Example 62 Synthesis of SYY-B027-2

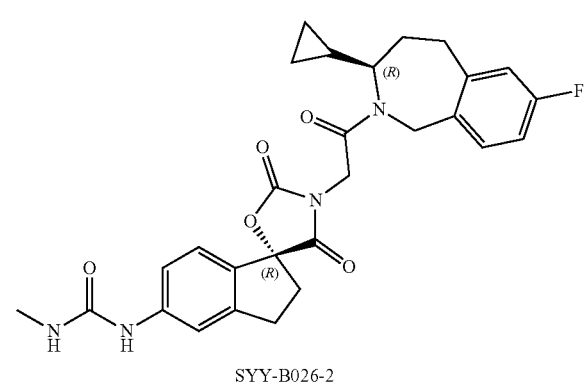

SYY-B027-2 was prepared using the same method as that in Example 30, except that the spiro ring fragment SP-1-2 was used instead of SP-1 and the amide fragment AN-13-1 was used instead of AN-7.

¹H NMR (400 MHz, DMSO-d₆) δ 8.71 (m, 1H), 7.52 (m, 1H), 7.31-7.17 (m, 6H), 6.10 (m, 1H), 5.29-3.81 (m, 4H), 3.13-2.91 (m, 4H), 2.79-2.56 (m, 5H), 2.49-2.31 (m, 3H). LC-MS: [M+H]⁺=531.2. $[\alpha]_D^{20}$+101.3° (c 0.67, MeOH).

Example 63 Synthesis of SYY-B028-1

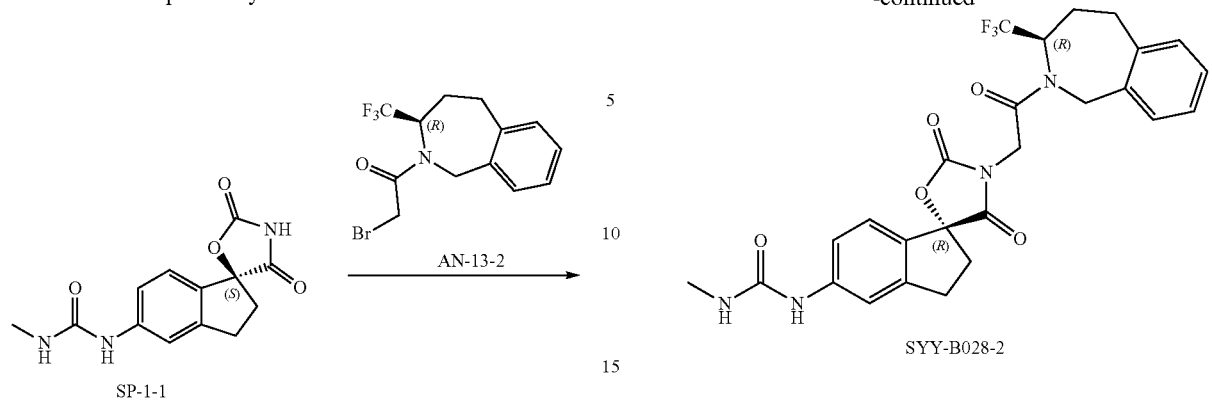

SYY-B028-1 was prepared using the same method as that in Example 30, except that the spiro ring fragment SP-1-1 was used instead of SP-1 and the amide fragment AN-13-2 was used instead of AN-7.

$^1$H NMR (400 MHz, DMSO-d$_6$) δ 8.71 (m, 1H), 7.52 (m, 1H), 7.31-7.17 (m, 6H), 6.08 (m, 1H), 5.27-3.81 (m, 5H), 3.12-2.91 (m, 3H), 2.74-2.56 (m, 5H), 2.50-2.31 (m, 3H). LC-MS: [M+H]$^+$=531.2. [α]$_D^{20}$ −102.6° (c 1.0, MeOH).

Example 64 Synthesis of SYY-B028-2

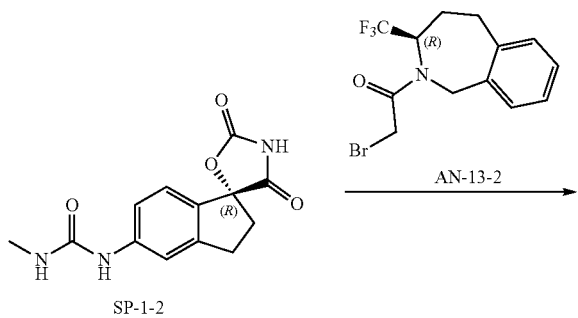

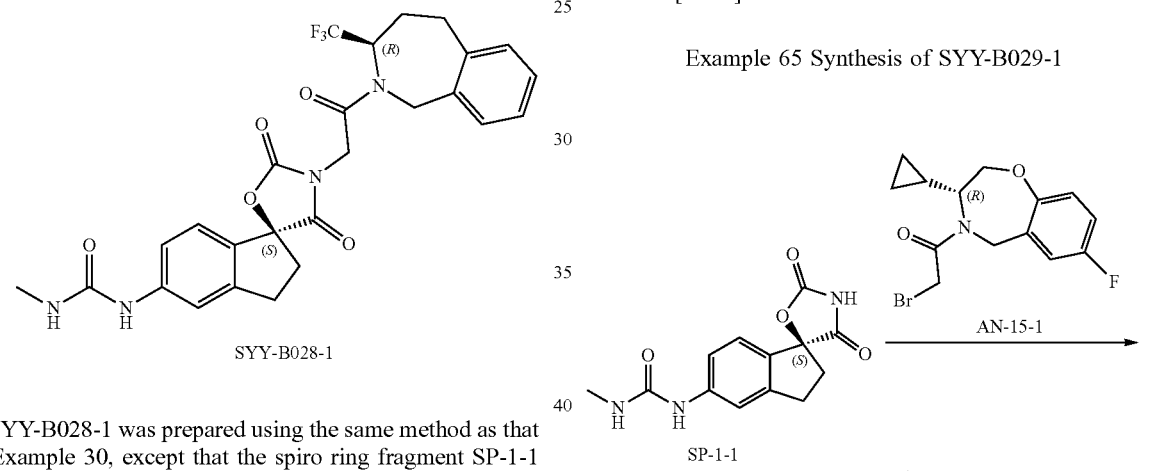

SYY-B028-2 was prepared using the same method as that in Example 30, except that the spiro ring fragment SP-1-2 was used instead of SP-1 and the amide fragment AN-13-2 was used instead of AN-7.

$^1$H NMR (400 MHz, DMSO-d$_6$) δ 8.71 (m, 1H), 7.52 (m, 1H), 7.31-7.17 (m, 6H), 6.10 (m, 1H), 5.29-3.78 (m, 5H), 3.14-2.89 (m, 3H), 2.79-2.56 (m, 5H), 2.49-2.31 (m, 3H). LC-MS: [M+H]$^+$=531.2.

Example 65 Synthesis of SYY-B029-1

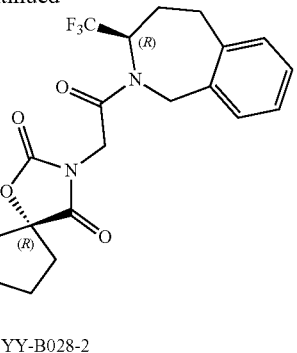

SYY-B029-1 was prepared using the same method as that in Example 30, except that the spiro ring fragment SP-1-1 was used instead of SP-1 and the amide fragment AN-15-1 was used instead of AN-7.

$^1$H NMR (400 MHz, DMSO-d$_6$) δ 8.72 (m, 1H), 7.53 (m, 1H), 7.26-6.92 (m, 5H), 6.10 (m, 1H), 5.07-4.06 (m, 6H), 3.83 (m, 1H), 3.15-2.94 (m, 2H), 2.64-2.56 (m, 4H), 2.49-2.43 (m, 1H), 1.15 (m, 1H), 0.65-0.33 (m, 4H). LC-MS: [M+H]$^+$=523.2. [α]$_D^{20}$ −46.1° (c 0.81, MeOH).

Example 66 Synthesis of SYY-B029-2

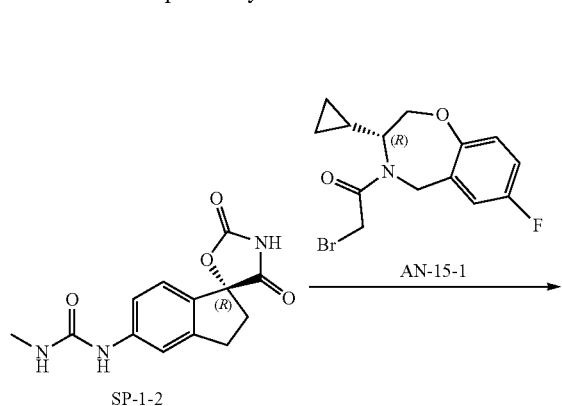

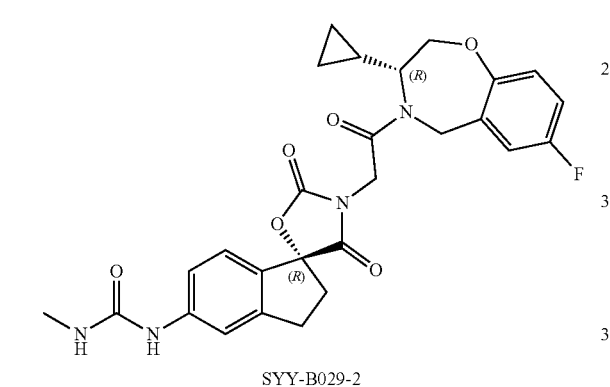

SYY-B029-2 was prepared using the same method as that in Example 30, except that the spiro ring fragment SP-1-2 was used instead of SP-1 and the amide fragment AN-15-1 was used instead of AN-7.

$^1$H NMR (400 MHz, DMSO-$d_6$) δ 8.72 (m, 1H), 7.53 (m, 1H), 7.25-6.91 (m, 5H), 6.10 (m, 1H), 5.07-4.05 (m, 6H), 3.85 (m, 1H), 3.14-2.92 (m, 2H), 2.65-2.55 (m, 4H), 2.49-2.42 (m, 1H), 1.16 (m, 1H), 0.63-0.33 (m, 4H). LC-MS: [M+H]$^+$=523.2. [α]$_D^{20}$+40.2° (c 0.74, MeOH).

Example 67 Synthesis of SYY-B030-1

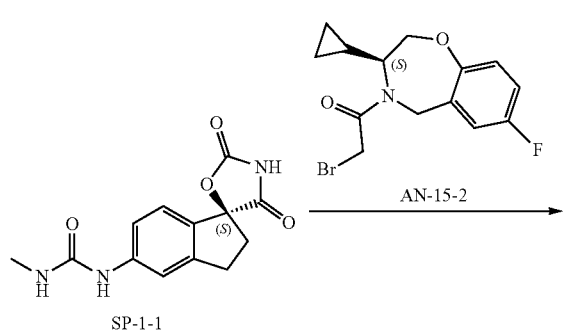

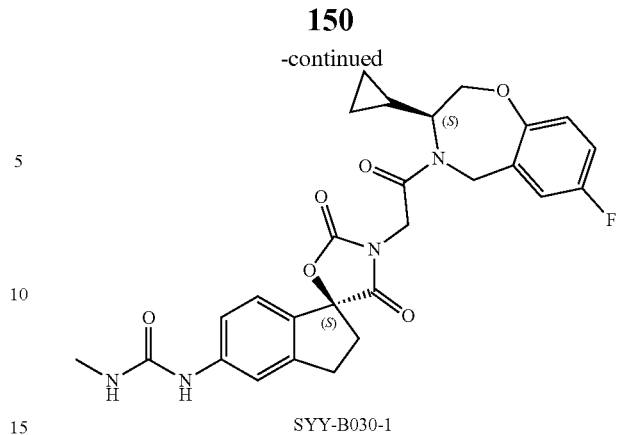

SYY-B030-1 was prepared using the same method as that in Example 30, except that the spiro ring fragment SP-1-1 was used instead of SP-1 and the amide fragment AN-15-2 was used instead of AN-7.

$^1$H NMR (400 MHz, DMSO-$d_6$) δ 8.72 (m, 1H), 7.53 (m, 1H), 7.26-6.92 (m, 5H), 6.10 (m, 1H), 5.07-4.06 (m, 6H), 3.83 (m, 1H), 3.15-2.94 (m, 2H), 2.64-2.56 (m, 4H), 2.49-2.43 (m, 1H), 1.35-1.12 (m, 1H), 0.65-0.33 (m, 4H). LC-MS: [M+H]$^+$=523.2. [α]$_D^{20}$-44.8° (c 0.61, MeOH).

Example 68 Synthesis of SYY-B030-2

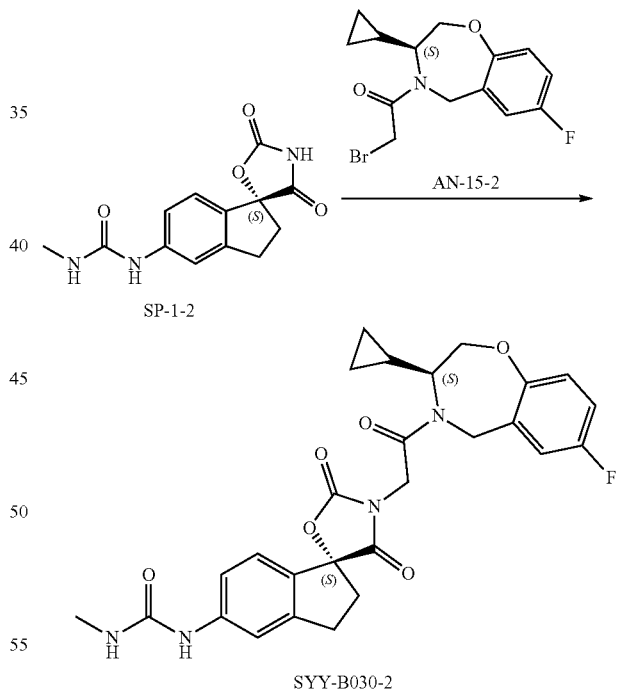

SYY-B030-2 was prepared using the same method as that in Example 30, except that the spiro ring fragment SP-1-2 was used instead of SP-1 and the amide fragment AN-15-2 was used instead of AN-7.

$^1$H NMR (400 MHz, DMSO-$d_6$) δ 8.73 (m, 1H), 7.54 (m, 1H), 7.26-6.90 (m, 5H), 6.10 (m, 1H), 5.07-4.06 (m, 6H), 3.83 (m, 1H), 3.15-2.94 (m, 2H), 2.64-2.56 (m, 4H), 2.49-2.43 (m, 1H), 1.35-1.12 (m, 1H), 0.65-0.33 (m, 4H). LC-MS: [M+H]$^+$=523.2. [α]$_D^{20}$+45.4° (c 0.61, MeOH).

Example 69 Synthesis of SYY-B031-1

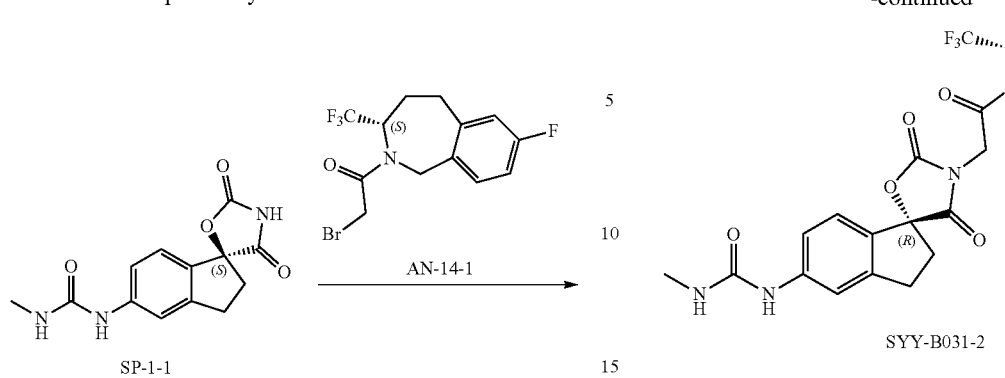

SYY-B031-1 was prepared using the same method as that in Example 30, except that the spiro ring fragment SP-1-1 was used instead of SP-1 and the amide fragment AN-14-1 was used instead of AN-7.

$^1$H NMR (400 MHz, DMSO-d$_6$, 110° C.) δ 8.38 (brs, 1H), 7.49 (brs, 1H), 7.34-7.20 (m, 3H), 7.02 (m, 2H), 5.93 (m, 1H), 5.26-3.91 (m, 5H), 3.16-3.09 (m, 2H), 3.02-2.97 (m, 1H), 2.79-2.62 (m, 5H), 2.48-2.44 (m, 1H), 2.36 (m, 2H). LC-MS: [M+H]$^+$=549.2.

Example 70 Synthesis of SYY-B031-2

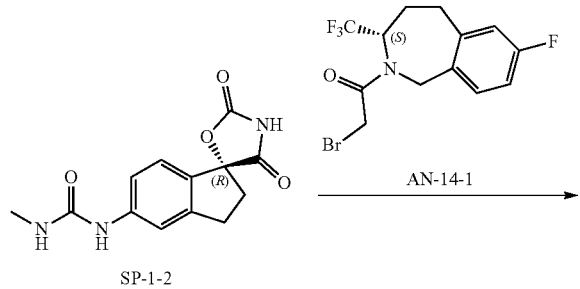

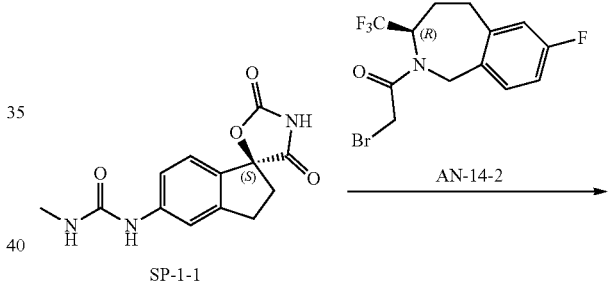

SYY-B031-2 was prepared using the same method as that in Example 30, except that the spiro ring fragment SP-1-2 was used instead of SP-1 and the amide fragment AN-14-1 was used instead of AN-7.

$^1$H NMR (400 MHz, DMSO-d$_6$) δ 8.73 (m, 1H), 7.51 (m, 1H), 7.35-7.03 (m, 5H), 6.09 (m, 1H), 5.24-3.79 (m, 5H), 3.12-2.91 (m, 3H), 2.73-2.56 (m, 5H), 2.49-2.25 (m, 3H). LC-MS: [M+H]$^+$=549.2. [α]$_D^{20}$+92.8° (c 0.71, MeOH).

Example 71 Synthesis of SYY-B032-1

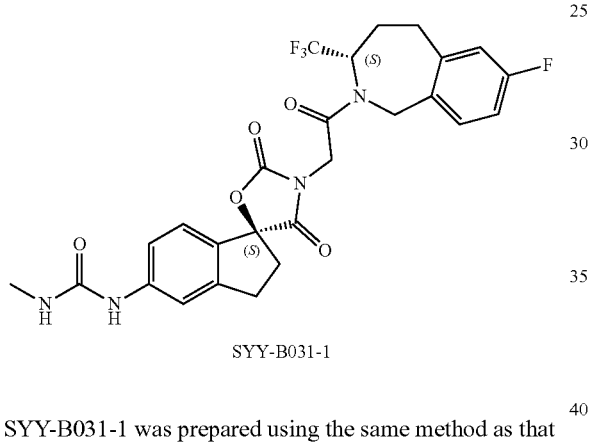

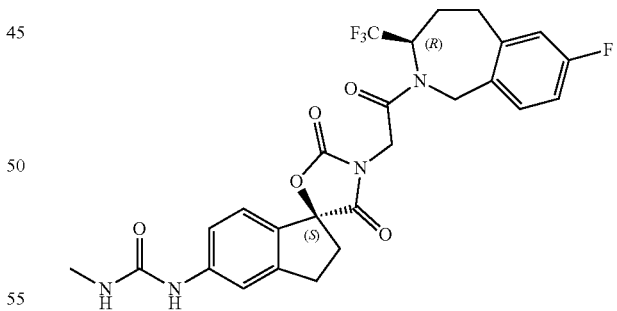

SYY-B032-1 was prepared using the same method as that in Example 30, except that the spiro ring fragment SP-1-1 was used instead of SP-1 and the amide fragment AN-14-2 was used instead of AN-7.

$^1$H NMR (400 MHz, DMSO-d$_6$) δ 8.71 (m, 1H), 7.52 (m, 1H), 7.35-6.96 (m, 5H), 6.09 (m, 1H), 5.25-3.80 (m, 5H), 3.14-2.91 (m, 3H), 2.73-2.56 (m, 5H), 2.49-2.27 (m, 3H). LC-MS: [M+H]$^+$=549.2. [α]$_D^{20}$−88.7° (c 0.67, MeOH).

Example 72 Synthesis of SYY-B032-2

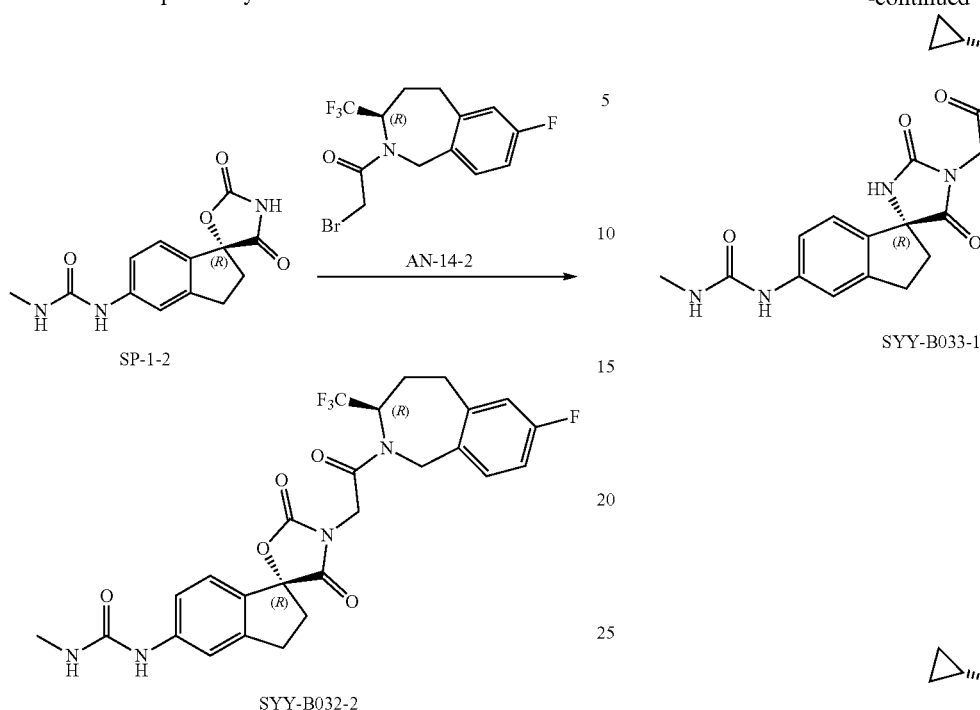

SYY-B032-2 was prepared using the same method as that in Example 30, except that the spiro ring fragment SP-1-2 was used instead of SP-1 and the amide fragment AN-14-2 was used instead of AN-7.

$^1$H NMR (400 MHz, DMSO-$d_6$) δ 8.76 (m, 1H), 7.54 (m, 1H), 7.34-6.96 (m, 5H), 6.10 (m, 1H), 5.29-3.80 (m, 5H), 3.15-2.93 (m, 3H), 2.75-2.56 (m, 5H), 2.49-2.29 (m, 3H). LC-MS: [M+H]$^+$=549.2.

Example 73 Synthesis of SYY-B033-1 and SYY-B033-2

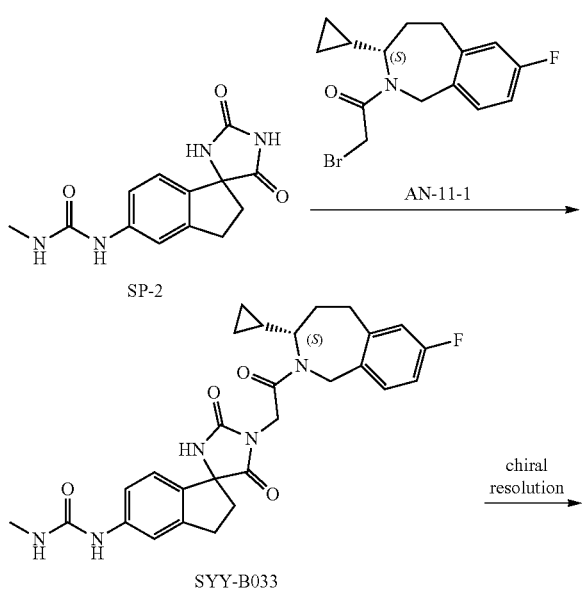

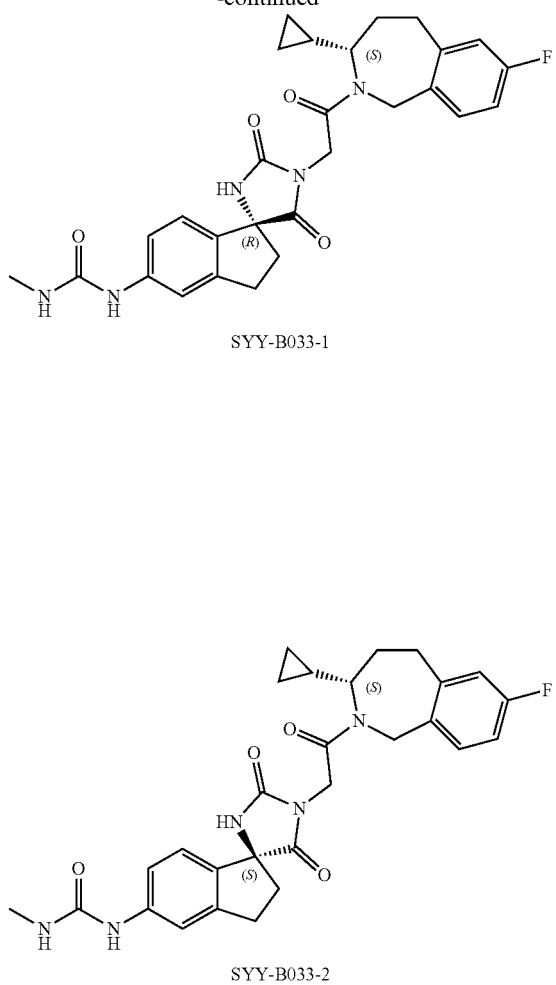

SYY—B033 was prepared using the same method as that in Example 30, except that the spiro ring fragment SP-2 was used instead of SP-1 and the amide fragment AN-11-1 was used instead of AN-7.

The SYY—B033 was subjected to chiral resolution to obtain chiral products SYY-B033-3 and SYY-B033-2.

Chiral resolution conditions: semi-preparative column was CHIRALPAK@AD-H, filler particle size (5 μm), inner diameter (20 mm), length (250 mm), flow rate: 12 m/mi, mobile phase: 60% n-hexane+40% isopropanol, isogradient elution, wavelength 254 nm, total time: 60 min; peak time is 15.2 min for peak 1, and 20.5 min for peak 2.

SYY-B033-1: $^1$H NMR (400 MHz, DMSO-$d_6$) δ 8.66 (m, 1H), 8.55 (m, 1H), 7.42-7.14 (m, 3H), 7.06-6.94 (m, 3H), 6.02 (m, 1H), 4.85-4.65 (m, 2H), 4.40-4.14 (m, 1H), 3.87-3.43 (m, 2H), 3.17-2.88 (m, 3H), 2.75-2.55 (m, 4H), 2.44 (m, 1H), 2.16-1.92 (m, 3H), 1.33 (m, 1H), 0.65-0.23 (m, 4H). LC-MS: [M+H]$^+$=520.2.

SYY-B033-2: H NMR (400 MHz, DMSO-$d_6$) δ 8.66 (m, 1H), 8.54 (m, 1H), 7.42-7.14 (m, 3H), 7.06-6.89 (m, 3H), 6.01 (m, 1H), 4.84-4.66 (m, 2H), 4.40-4.14 (m, 1H), 3.86-3.43 (m, 2H), 3.17-2.88 (m, 3H), 2.74-2.55 (m, 4H), 2.44 (m, 1H), 2.16-1.92 (m, 3H), 1.33 (m, 1H), 0.65-0.23 (m, 4H). LC-MS: [M+H]$^+$=520.2.

Example 74 Synthesis of SYY-B034-1 and SYY-B034-2

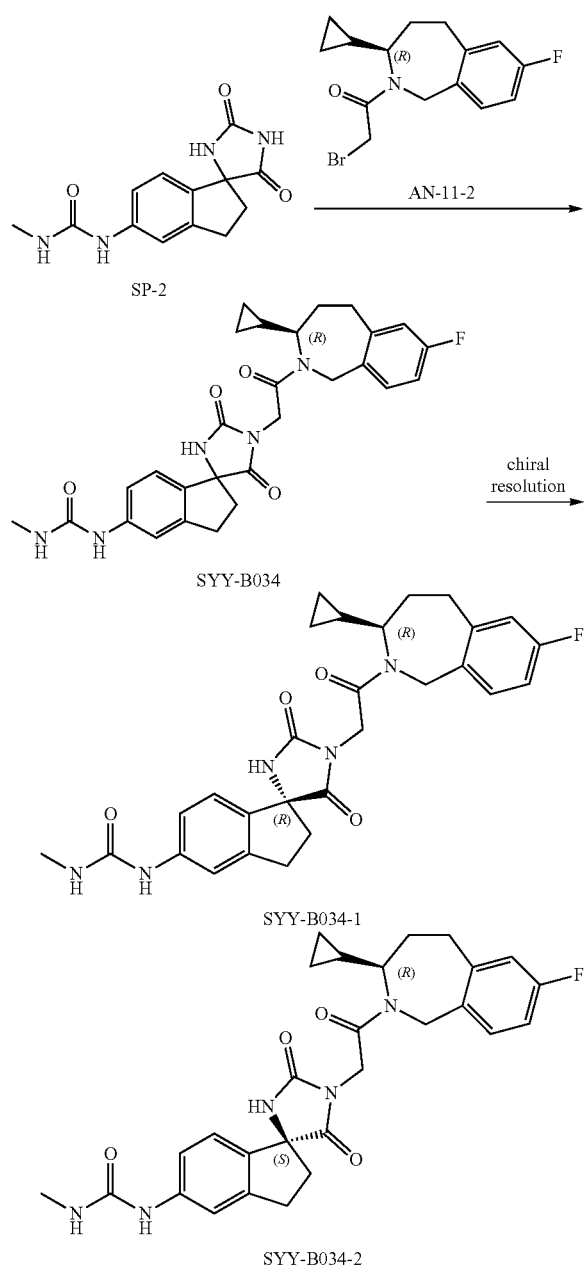

SYY—B034 was prepared using the same method as that in Example 30, except that the spiro ring fragment SP-2 was used instead of SP-1 and the amide fragment AN-11-2 was used instead of AN-7.

The SYY—B034 was subjected to chiral resolution to obtain chiral products SYY-B034-1 and SYY-B034-2.

Chiral resolution conditions: semi-preparative column was CHIRALPAK@OD-H, filler particle size (5 μm), inner diameter (30 mm), length (250 mm), flow rate: 20 mL/min, mobile phase: 70% n-hexane+30% ethanol, isogradient elution, wavelength 254 nm, total time: 60 min; peak time is 41.6 min for peak 1, and 51.4 min for peak 2.

SYY-B034-1: $^1$H NMR (400 MHz, DMSO-d$_6$) δ 8.66 (m, 1H), 8.54 (m, 1H), 7.42-7.14 (m, 3H), 7.06-6.89 (m, 3H), 6.01 (m, 1H), 4.84-4.66 (m, 2H), 4.40-4.14 (m, 1H), 3.87-3.43 (m, 2H), 3.17-2.88 (m, 3H), 2.75-2.55 (m, 4H), 2.44 (m, 1H), 2.16-1.92 (m, 3H), 1.33 (m, 1H), 0.65-0.23 (m, 4H). LC-MS: [M+H]$^+$=520.3.

SYY-B034-2: $^1$H NMR (400 MHz, DMSO-d$_6$) δ 8.66 (m, 1H), 8.54 (m, 1H), 7.42-7.14 (m, 3H), 7.06-6.89 (m, 3H), 6.01 (m, 1H), 4.84-4.66 (m, 2H), 4.40-4.14 (m, 1H), 3.87-3.43 (m, 2H), 3.17-2.88 (m, 3H), 2.75-2.55 (m, 4H), 2.44 (m, 1H), 2.16-1.92 (m, 3H), 1.33 (m, 1H), 0.65-0.23 (m, 4H). LC-MS: [M+H]$^+$=520.2.

Example 75 Synthesis of SYY-B035-Boc-1 and SYY-B035-Boc-2

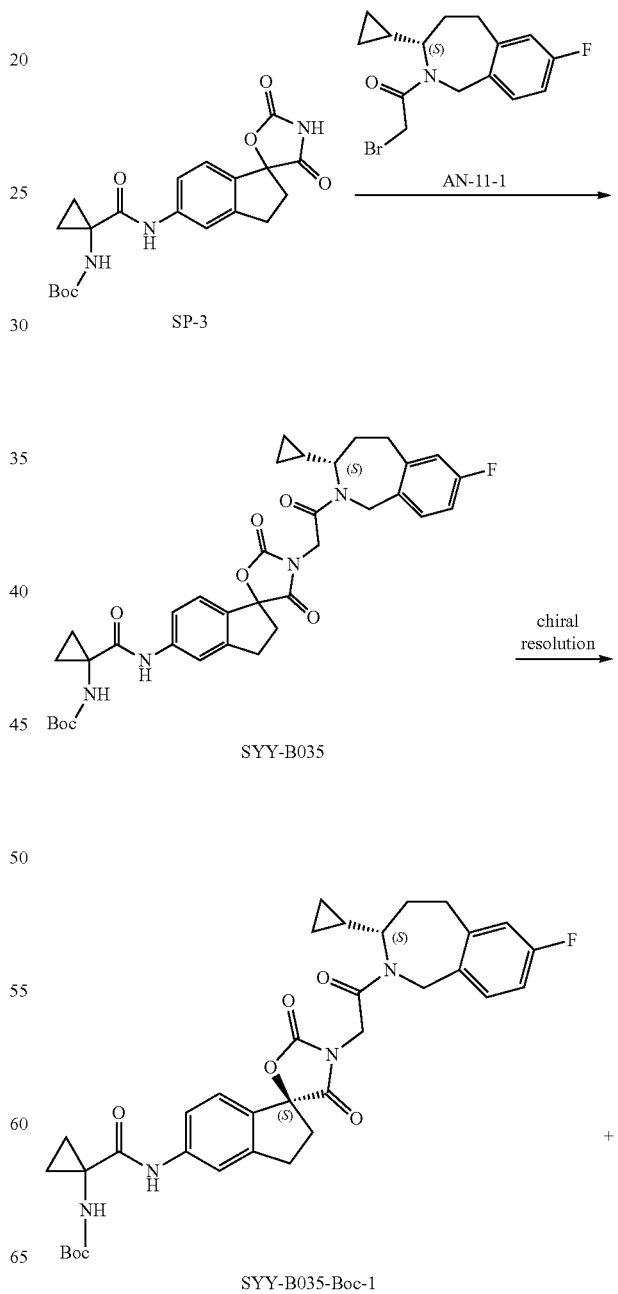

-continued

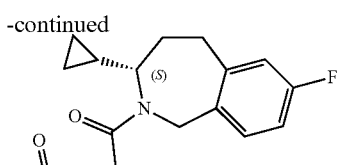

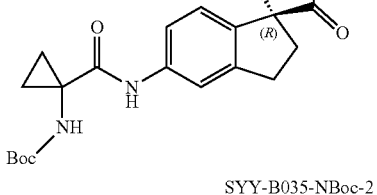

SYY-B035-NBoc-2

SYY—B035 was prepared using the same method as that in Example 30, except that the spiro ring fragment SP-3 was used instead of SP-1 and the amide fragment AN-11-1 was used instead of AN-7.

The SYY—B035 was subjected to chiral resolution to obtain chiral products SYY-B035-Boc-1 and SYY-B035-Boc-2.

Chiral resolution conditions: semi-preparative column was CHIRALPAK@AD-H, filler particle size (5 μm), inner diameter (30 mm), length (250 mm), flow rate: 20 mL/min, mobile phase: 70% n-hexane+30% ethanol, isogradient elution, wavelength 254 nm, total time: 65 min; peak time is 43.7 min for peak 1, and 55.2 min for peak 2.

Example 76 Synthesis of SYY-B035-1

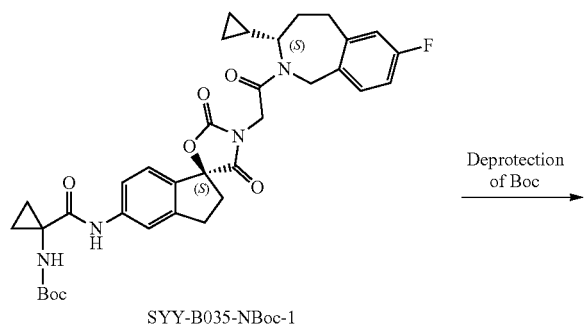

SYY-B035-Boc-1 was dissolved in a solution of TFA (5 mL) in dichloromethane (10 mL) and stirred at room temperature for 2 h. TLC showed that the reaction was complete. The reaction solution was rotary evaporated to dryness to obtain SYY-B035-1 as a trifluoroacetate. $^1$H NMR (400 MHz, CD$_3$OD) δ 7.68 (m, 1H), 7.46-7.28 (m, 3H), 6.98-6.83 (m, 2H), 4.89 (m, 1H), 4.87-4.47 (m, 2H), 4.09-3.47 (m, 2H), 3.25-3.04 (m, 3H), 2.88-2.50 (m, 3H), 2.13 (m, 2H), 1.76 (m, 2H), 1.49 (m, 2H), 1.31 (m, 1H), 0.69-0.42 (m, 4H). LC-MS: [M+H]$^+$=547.3.

Example 77 Synthesis of SYY-B035-2

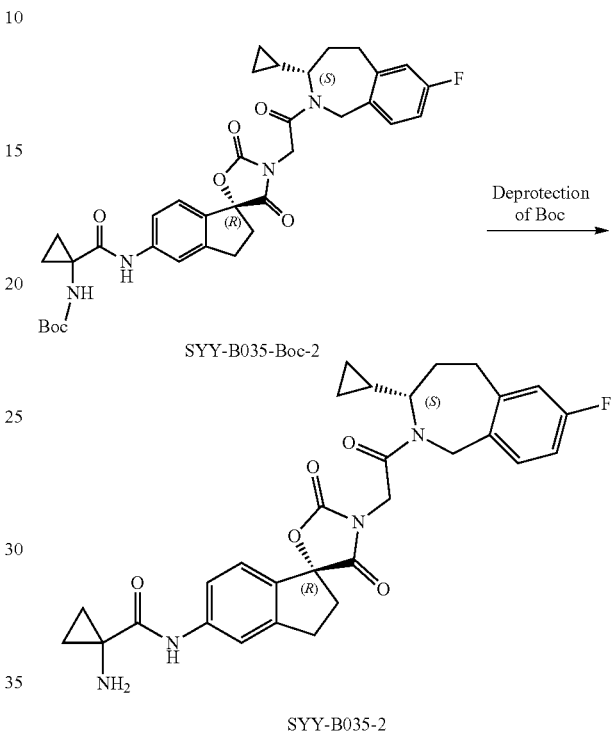

SYY-B035-Boc-2 was dissolved in a solution of TFA (5 mL) in dichloromethane (10 mL) and stirred at room temperature for 2 h. TLC showed that the reaction was complete. The reaction solution was rotary evaporated to dryness to obtain SYY-B035-2 as a trifluoroacetate. $^1$H NMR (400 MHz, CD$_3$OD) δ 7.68 (m, 1H), 7.46-7.28 (m, 3H), 6.98-6.83 (m, 2H), 4.92 (m, 1H), 4.84-4.40 (m, 2H), 4.09-3.47 (m, 2H), 3.25-3.04 (m, 3H), 2.88-2.50 (m, 3H), 2.13 (m, 2H), 1.76 (m, 2H), 1.49 (m, 2H), 1.31 (m, 1H), 0.69-0.41 (m, 4H). LC-MS: [M+H]$^+$=547.3.

Example 78 Synthesis of SYY-B036-Boc-1 and SYY-B036-Boc-2

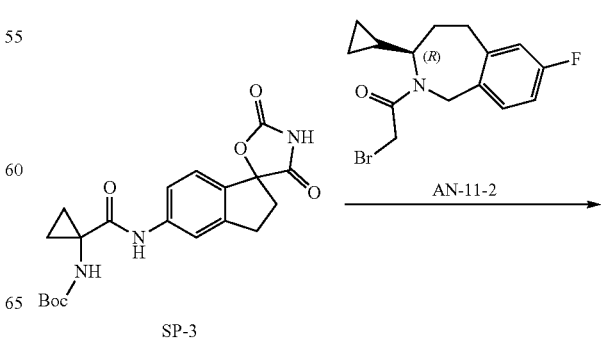

-continued

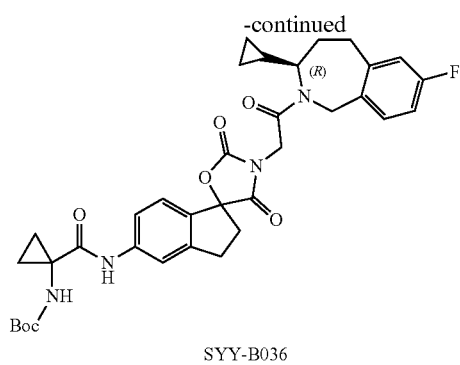

SYY-B036

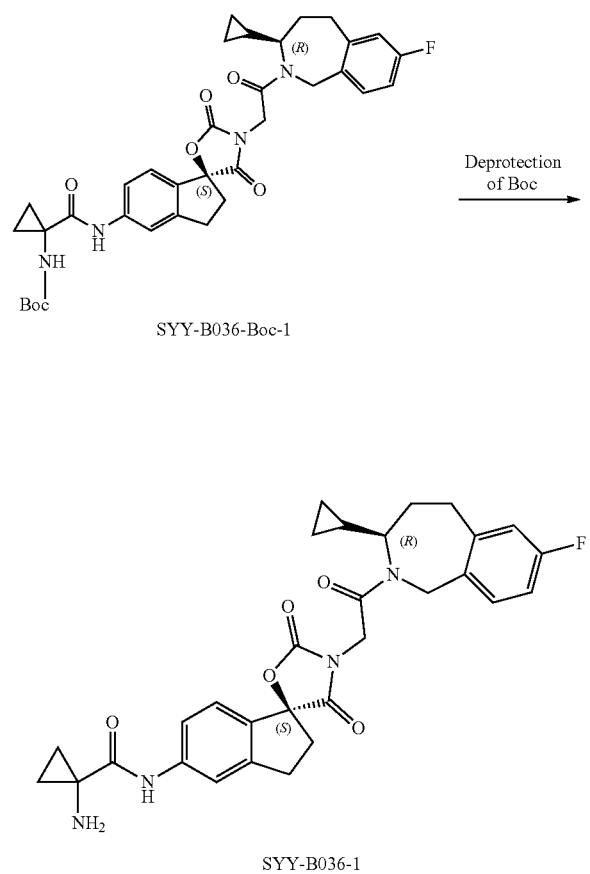

SYY—B036 was prepared using the same method as that in Example 30, except that the spiro ring fragment SP-3 was used instead of SP-1 and the amide fragment AN-11-2 was used instead of AN-7.

The SYY—B036 was subjected to chiral resolution to obtain chiral products SYY-B036-Boc-1 and SYY-B036-Boc-2.

Chiral resolution conditions: semi-preparative column was CHIRALPAK@AD-H, filler particle size (5 μm), inner diameter (30 mm), length (250 mm), flow rate: 40 mL/min, mobile phase: 65% n-hexane+35% ethanol, isogradient elution, wavelength 254 nm, total time: 35 min; peak time is 21.3 min for peak 1, and 28.7 min for peak 2.

Example 79 Synthesis of SYY-B036-1

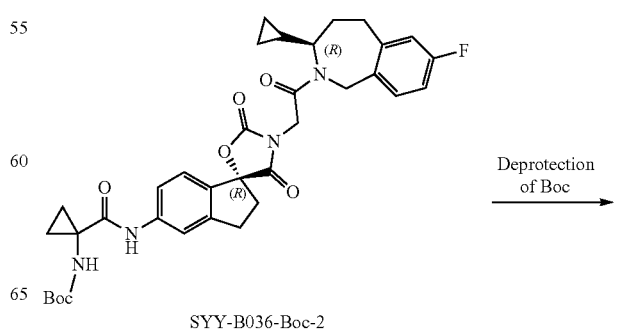

SYY-B036-Boc-1 was dissolved in a solution of TFA (5 mL) in dichloromethane (10 mL) and stirred at room temperature for 2 h. TLC showed that the reaction was complete. The reaction solution was rotary evaporated to dryness to obtain SYY-B036-1 as a trifluoroacetate. $^1$H NMR (400 MHz, CD$_3$OD δ 7.68 (m, 1H), 7.46-7.28 (m, 3H), 6.98-6.83 (m, 2H), 4.92 (m, 1H), 4.85-4.47 (m, 2H), 4.09-3.47 (m, 2H), 3.25-3.04 (m, 3H), 2.88-2.50 (m, 3H), 2.13 (m, 2H), 1.76 (m, 2H), 1.49 (m, 2H), 1.31 (m, 1H), 0.69-0.41 (m, 4H). LC-MS: [M+H]$^+$=547.3.

Example 80 Synthesis of SYY-B036-2

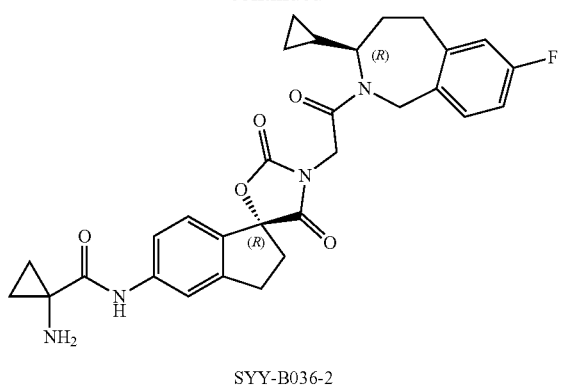

SYY-B036-2

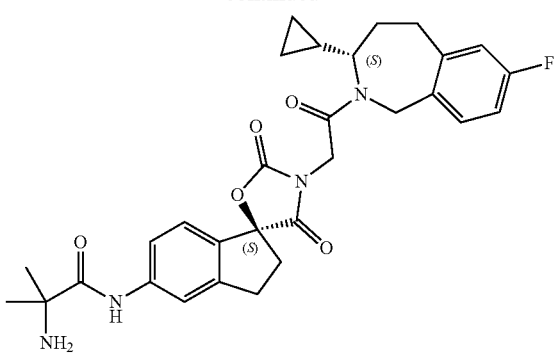

SYY-B037-1

SYY-B036-Boc-2 was dissolved in a solution of TFA (5 mL) in dichloromethane (10 mL) and stirred at room temperature for 2 h. TLC showed that the reaction was complete. The reaction solution was rotary evaporated to dryness to obtain SYY-B036-2 as a trifluoroacetate. $^1$H NMR (400 MHz, CD$_3$OD) δ 7.68 (m, 1H), 7.46-7.28 (m, 3H), 6.98-6.83 (m, 2H), 4.92 (m, 1H), 4.85-4.47 (m, 2H), 4.06-3.48 (m, 2H), 3.25-3.04 (m, 3H), 2.87-2.50 (m, 3H), 2.13 (m, 2H), 1.76 (m, 2H), 1.49 (m, 2H), 1.31 (m, 1H), 0.69-0.41 (m, 4H). LC-MS: [M+H]$^+$=547.3.

Example 81 Synthesis of SYY-B037-1

SYY-B037-Boc-1 was prepared using the same method as that in Example 30, except that the spiro ring fragment SP-4-Boc-1 was used instead of SP-1 and the amide fragment AN-11-1 was used instead of AN-7.

SYY-B037-Boc-1 was dissolved in a solution of TFA (5 mL) in dichloromethane (10 mL) and stirred at room temperature for 2 h. TLC showed that the reaction was complete. The reaction solution was rotary evaporated to dryness to obtain SYY-B037-1 as a trifluoroacetate. $^1$H NMR (400 MHz, CD$_3$OD) δ 7.73 (m, 1H), 7.50-7.27 (m, 3H), 6.98-6.81 (m, 2H), 4.92 (m, 1H), 4.85-4.40 (m, 2H), 4.05-3.48 (m, 2H), 3.25-3.05 (m, 3H), 2.87-2.50 (m, 3H), 2.13 (m, 2H), 1.53 (s, 6H), 1.31 (m, 1H), 0.68-0.41 (m, 4H). LC-MS: [M+H]$^+$=549.3. $[\alpha]_D^{20}$ −43.5° (c 0.91, MeOH).

Example 82 Synthesis of SYY-B037-2

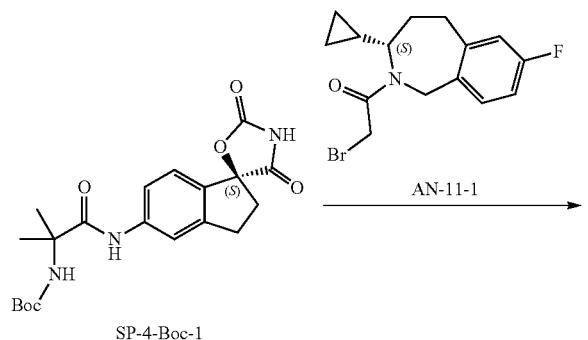

SP-4-Boc-1

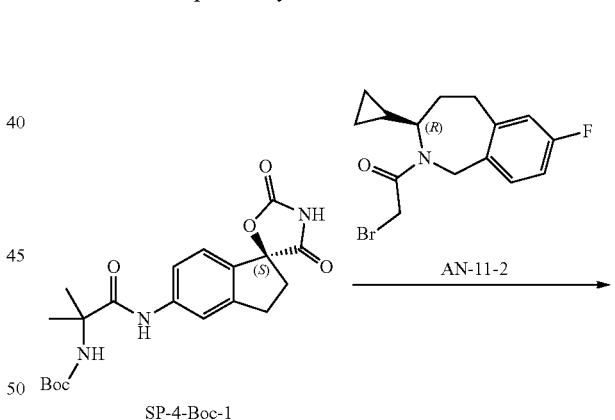

SP-4-Boc-1

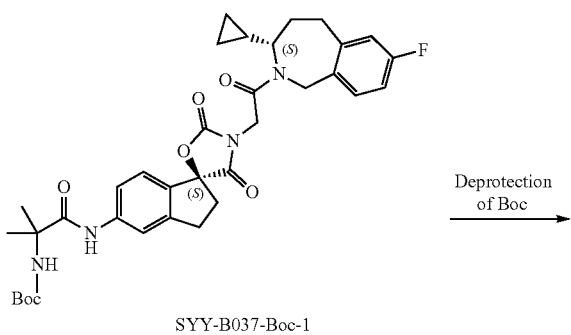

SYY-B037-Boc-1

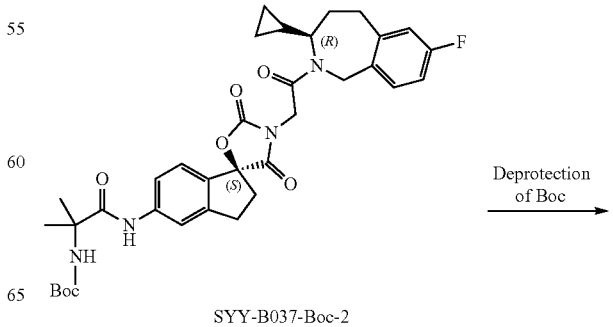

SYY-B037-Boc-2

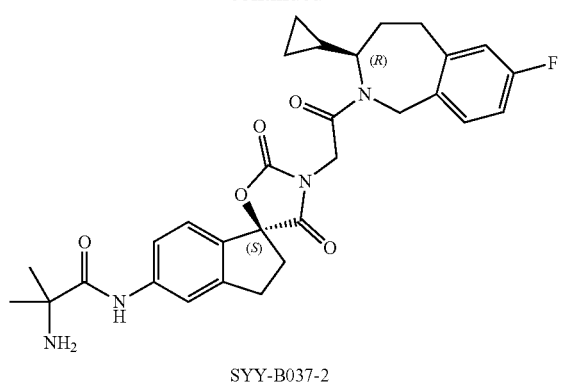

SYY-B037-2

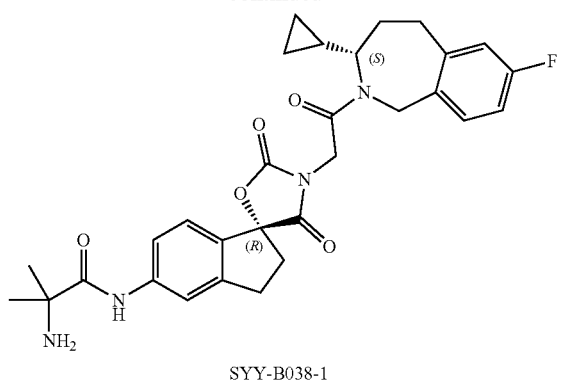

SYY-B038-1

SYY-B037-Boc-2 was prepared using the same method as that in Example 30, except that the spiro ring fragment SP-4-Boc-1 was used instead of SP-1 and the amide fragment AN-11-2 was used instead of AN-7.

SYY-B037-Boc-2 was dissolved in a solution of TFA (5 mL) in dichloromethane (10 mL) and stirred at room temperature for 2 h. TLC showed that the reaction was complete. The reaction solution was rotary evaporated to dryness to obtain SYY-B037-2 as a trifluoroacetate. $^1$H NMR (400 MHz, CD$_3$OD) δ 7.73 (m, 1H), 7.50-7.27 (m, 3H), 6.98-6.81 (m, 2H), 4.93 (m, 1H), 4.85-4.46 (m, 2H), 4.08-3.48 (m, 2H), 3.25-3.05 (m, 3H), 2.87-2.50 (m, 3H), 2.13 (m, 2H), 1.51 (s, 6H), 1.30 (m, 1H), 0.68-0.42 (m, 4H). LC-MS: [M+H]$^+$=549.3. $[\alpha]_D^{20}$ −32.6° (c 0.79, MeOH).

SYY-B038-Boc-1 was prepared using the same method as that in Example 30, except that the spiro ring fragment SP-4-Boc-2 was used instead of SP-1 and the amide fragment AN-11-1 was used instead of AN-7.

SYY-B038-Boc-1 was dissolved in a solution of TFA (5 mL) in dichloromethane (10 mL) and stirred at room temperature for 2 h. TLC showed that the reaction was complete. The reaction solution was rotary evaporated to dryness to obtain SYY-B038-1 as a trifluoroacetate. $^1$H NMR (400 MHz, CD$_3$OD) δ 7.73 (m, 1H), 7.50-7.27 (m, 3H), 6.98-6.81 (m, 2H), 4.97-4.93 (m, 1H), 4.87-4.47 (m, 2H), 4.09-3.48 (m, 2H), 3.25-3.05 (m, 3H), 2.87-2.50 (m, 3H), 2.13 (m, 2H), 1.70 (s, 6H), 1.31 (m, 1H), 0.68-0.41 (m, 4H). LC-MS: [M+H]$^+$=549.3. $[\alpha]_D^{20}$ +28.2° (c 0.54, MeOH).

Example 83 Synthesis of SYY-B038-1

Example 84 Synthesis of SYY-B038-2

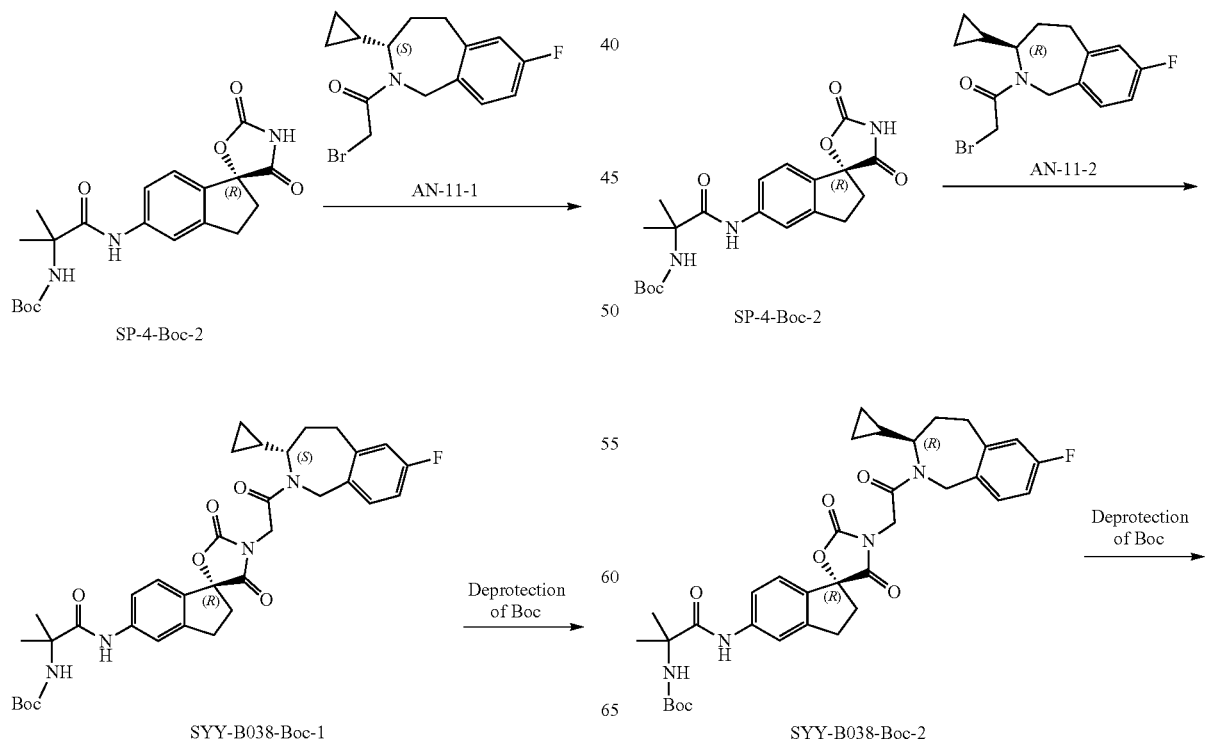

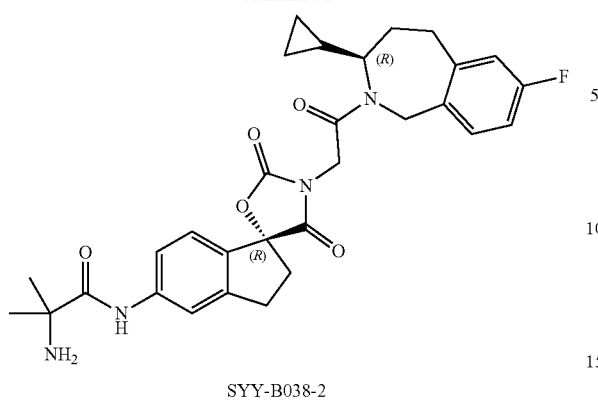

SYY-B038-2

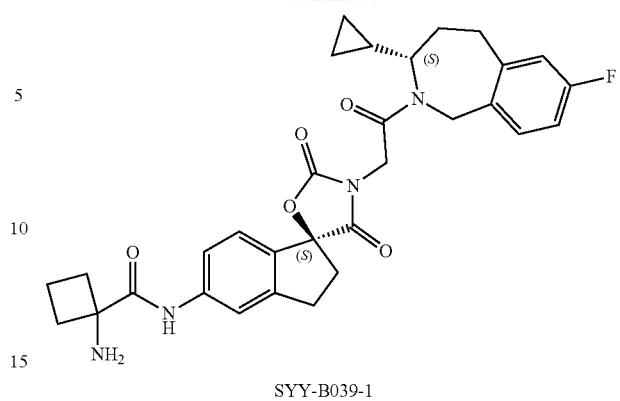

SYY-B039-1

SYY-B038-Boc-2 was prepared using the same method as that in Example 30, except that the spiro ring fragment SP-4-Boc-2 was used instead of SP-1 and the amide fragment AN-11-2 was used instead of AN-7.

SYY-B038-Boc-2 was dissolved in a solution of TFA (5 mL) in dichloromethane (10 mL) and stirred at room temperature for 2 h. TLC showed that the reaction was complete. The reaction solution was rotary evaporated to dryness to obtain SYY-B038-2 as a trifluoroacetate. $^1$H NMR (400 MHz, CD$_3$OD) δ 7.73 (m, 1H), 7.50-7.27 (m, 3H), 6.98-6.81 (m, 2H), 4.92 (m, 1H), 4.87-4.40 (m, 2H), 4.06-3.48 (m, 2H), 3.25-3.05 (m, 3H), 2.87-2.50 (m, 3H), 2.13 (m, 2H), 1.71 (s, 6H), 1.31 (m, 1H), 0.68-0.41 (m, 4H). LC-MS: [M+H]$^+$=549.3. $[\alpha]_D^{20}$+35.3° (c 0.61, MeOH).

SYY-B039-Boc-1 was prepared using the same method as that in Example 30, except that the spiro ring fragment SP-5-Boc-1 was used instead of SP-1 and the amide fragment AN-11-1 was used instead of AN-7.

SYY-B039-Boc-1 was dissolved in a solution of TFA (5 mL) in dichloromethane (10 mL) and stirred at room temperature for 2 h. TLC showed that the reaction was complete. The reaction solution was rotary evaporated to dryness to obtain SYY-B039-1 as a trifluoroacetate. $^1$H NMR (400 MHz, CD$_3$OD) δ 7.75 (m, 1H), 7.56-7.27 (m, 3H), 6.98-6.81 (m, 2H), 4.92 (m, 1H), 4.87-4.41 (m, 2H), 4.06-3.48 (m, 2H), 3.25-3.07 (m, 3H), 2.94-2.71 (m, 4H), 2.61-2.52 (m, 1H), 2.46-2.34 (m, 3H), 2.31-2.11 (m, 3H), 1.31 (m, 1H), 0.68-0.41 (m, 4H). LC-MS: [M+H]$^+$=561.3.

Example 85 Synthesis of SYY-B039-1

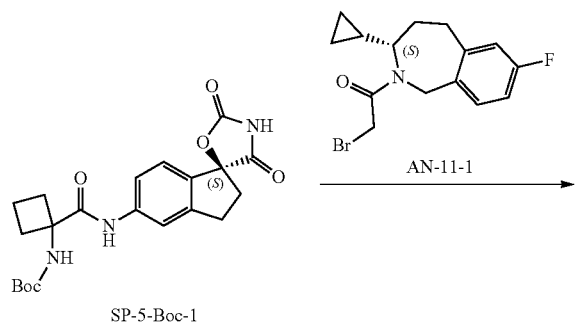

SP-5-Boc-1

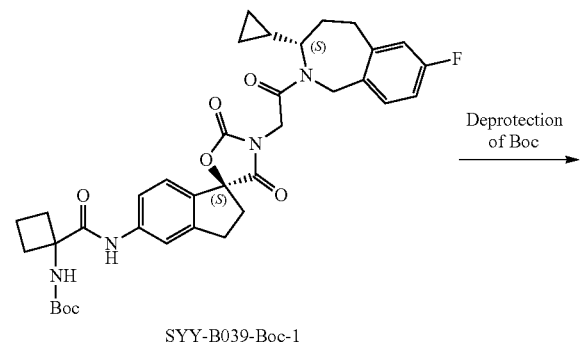

SYY-B039-Boc-1

Example 86 Synthesis of SYY-B039-2

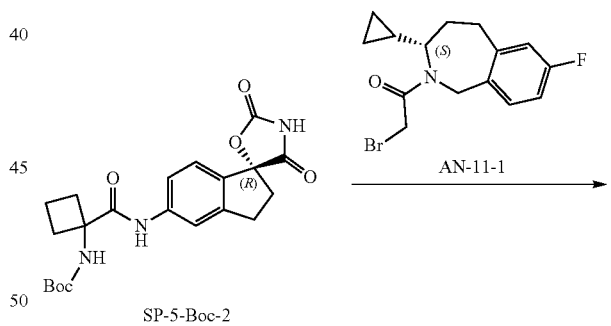

SP-5-Boc-2

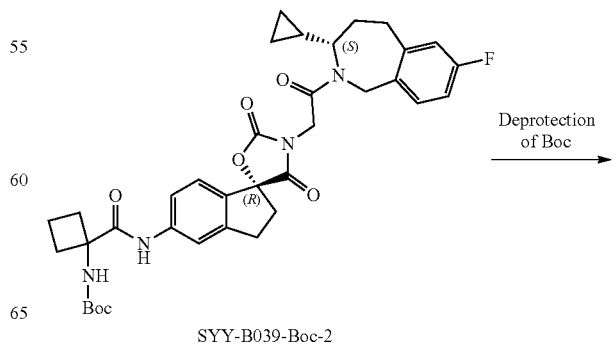

SYY-B039-Boc-2

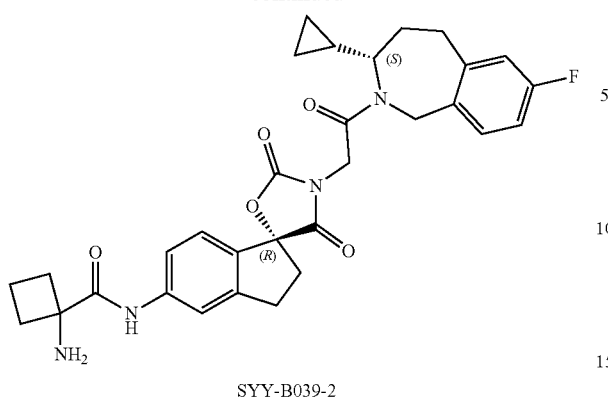

SYY-B039-2

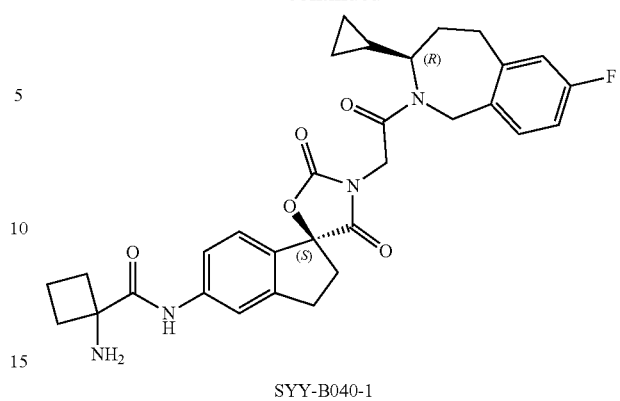

SYY-B040-1

SYY-B039-Boc-2 was prepared using the same method as that in Example 30, except that the spiro ring fragment SP-5-Boc-2 was used instead of SP-1 and the amide fragment AN-11-1 was used instead of AN-7.

SYY-B039-Boc-2 was dissolved in a solution of TFA (5 mL) in dichloromethane (10 mL) and stirred at room temperature for 2 h. TLC showed that the reaction was complete. The reaction solution was rotary evaporated to dryness to obtain SYY-B039-2 as a trifluoroacetate. $^1$H NMR (400 MHz, CD$_3$OD δ 7.76 (m, 1H), 7.56-7.27 (m, 3H), 6.98-6.81 (m, 2H), 4.93 (m, 1H), 4.87-4.47 (m, 2H), 4.09-3.46 (m, 2H), 3.25-3.07 (m, 3H), 2.94-2.71 (m, 4H), 2.61-2.52 (m, 1H), 2.46-2.34 (m, 3H), 2.31-2.11 (m, 3H), 1.31 (m, 1H), 0.68-0.41 (m, 4H). LC-MS: [M+H]$^+$=561.3.

SYY-B040-Boc-1 was prepared using the same method as that in Example 30, except that the spiro ring fragment SP-5-Boc-1 was used instead of SP-1 and the amide fragment AN-11-2 was used instead of AN-7.

SYY-B040-Boc-1 was dissolved in a solution of TFA (5 mL) in dichloromethane (10 mL) and stirred at room temperature for 2 h. TLC showed that the reaction was complete. The reaction solution was rotary evaporated to dryness to obtain SYY-B040-1 as a trifluoroacetate. $^1$H NMR (400 MHz, CD$_3$OD δ 7.74 (m, 1H), 7.58-7.27 (m, 3H), 6.98-6.81 (m, 2H), 4.92 (m, 1H), 4.87-4.41 (m, 2H), 4.09-3.46 (m, 2H), 3.25-3.07 (m, 3H), 2.94-2.71 (m, 4H), 2.61-2.52 (m, 1H), 2.46-2.34 (m, 3H), 2.31-2.11 (m, 3H), 1.31 (m, 1H), 0.68-0.41 (m, 4H). LC-MS: [M+H]$^+$=561.3.

Example 87 Synthesis of SYY-B040-1

Example 88 Synthesis of SYY-B040-2

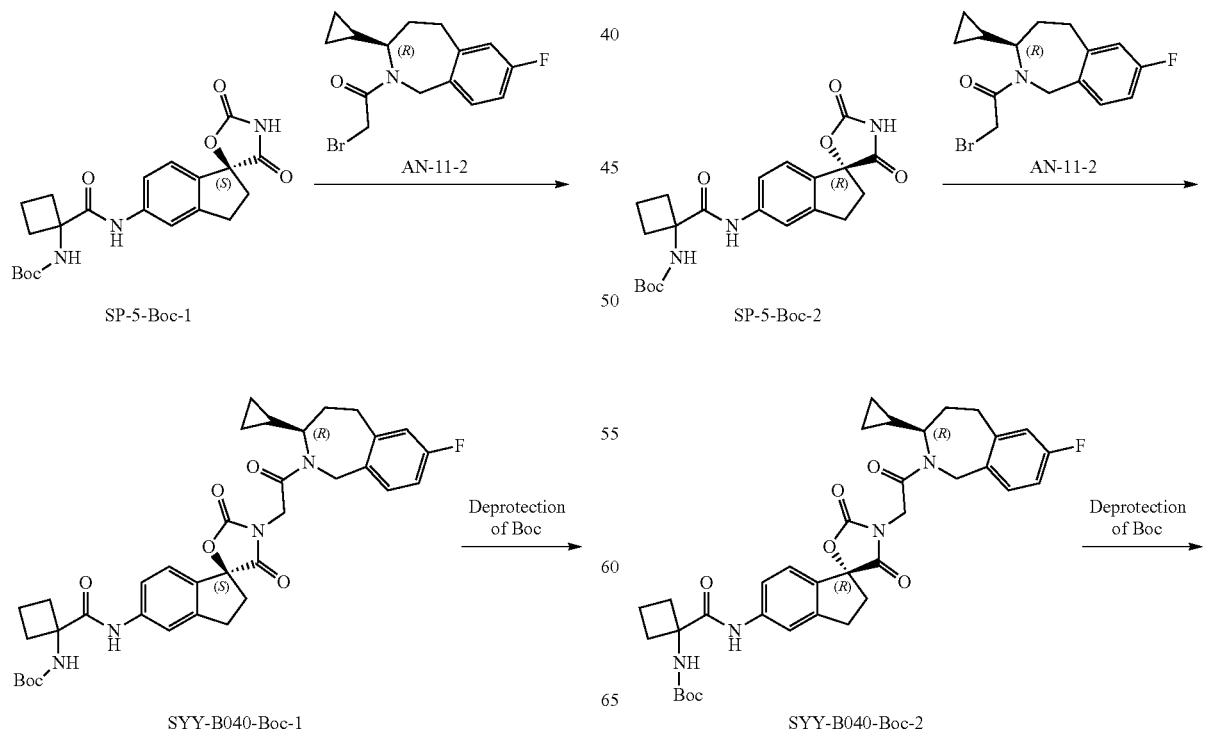

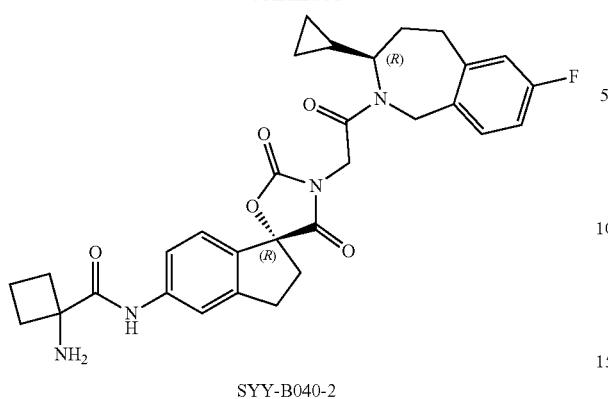

SYY-B040-2

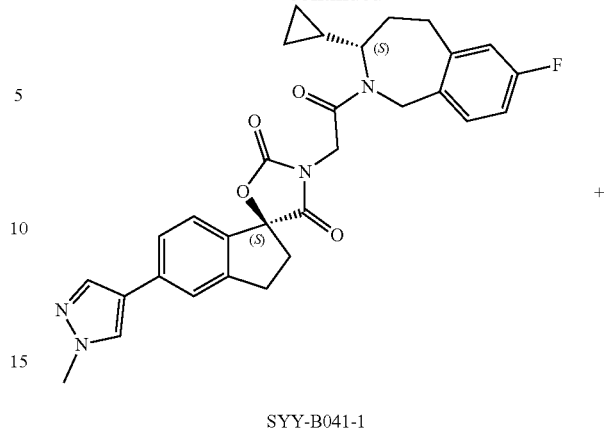

SYY-B041-1

SYY-B040-Boc-2 was prepared using the same method as that in Example 30, except that the spiro ring fragment SP-5-Boc-2 was used instead of SP-1 and the amide fragment AN-11-2 was used instead of AN-7.

SYY-B040-Boc-2 was dissolved in a solution of TFA (5 mL) in dichloromethane (10 mL) and stirred at room temperature for 2 h. TLC showed that the reaction was complete. The reaction solution was rotary evaporated to dryness to obtain SYY-B040-2 as a trifluoroacetate. $^1$H NMR (400 MHz, CD$_3$OD) δ 7.75 (m, 1H), 7.56-7.27 (m, 3H), 6.98-6.81 (m, 2H), 4.92 (m, 1H), 4.87-4.41 (m, 2H), 4.09-3.46 (m, 2H), 3.25-3.07 (m, 3H), 2.94-2.71 (m, 4H), 2.61-2.52 (m, 1H), 2.46-2.34 (m, 3H), 2.31-2.11 (m, 3H), 1.31 (m, 1H), 0.68-0.41 (m, 4H). LC-MS: [M+H]$^+$=561.3.

Example 89 Synthesis of SYY-B041-1 and SYY-B041-2

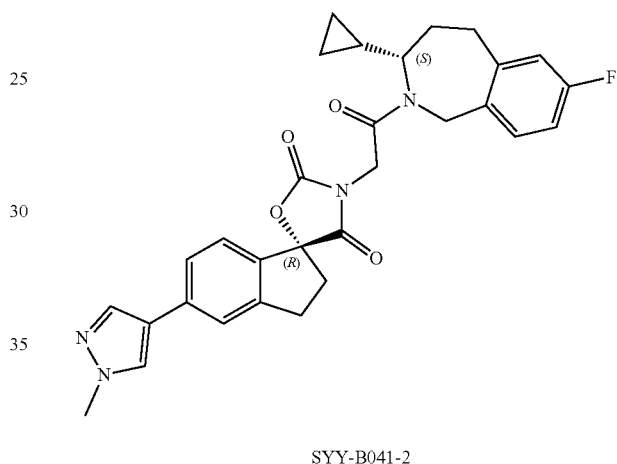

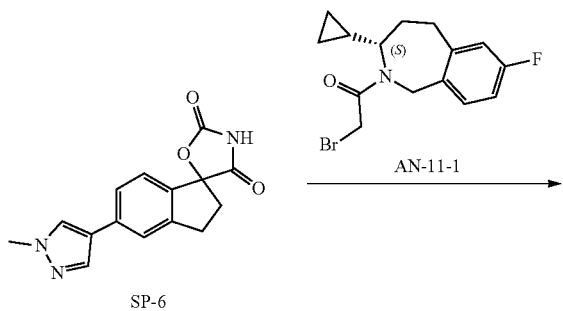

SP-6

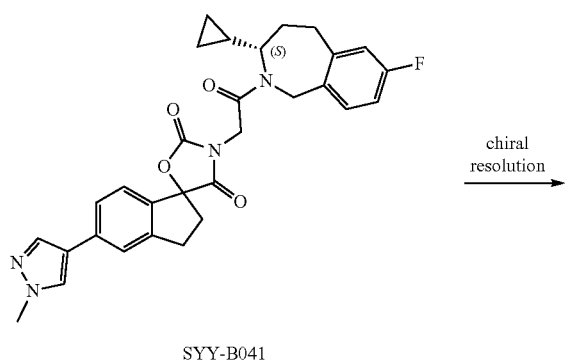

SYY-B041

SYY—B041 was prepared using the same method as that in Example 30, except that the spiro ring fragment SP-6 was used instead of SP-1 and the amide fragment AN-11-1 was used instead of AN-7.

The SYY—B041 was subjected to chiral resolution to obtain chiral products SYY-B041-1 and SYY-B041-2.

Chiral resolution conditions: semi-preparative column was CHIRALPAK@AD-H, filler particle size (5 μm), inner diameter (30 mm), length (250 mm), flow rate: 30 mL/min, mobile phase: 60% n-hexane+40% isopropanol, isogradient elution, wavelength 254 nm, total time: 60 min; peak time is 37.0 min for peak 1, and 41.7 min for peak 2.

SYY-B041-1: $^1$H NMR (400 MHz, DMSO-d$_6$) δ 8.17 (m, 1H), 7.89 (m, 1H), 7.57-7.50 (m, 2H), 7.41-7.25 (m, 2H), 7.08-6.89 (m, 2H), 4.94-4.29 (m, 4H), 3.87-3.45 (m, 4H), 3.18-2.98 (m, 3H), 2.76-2.53 (m, 2H), 2.44 (m, 1H), 2.02 (m, 2H), 1.22 (m, 1H), 0.55-0.23 (m, 4H). LC-MS: [M+H]$^+$= 529.3. [α]$_D^{20}$−60° (c 0.96, MeOH).

SYY-B041-2: $^1$H NMR (400 MHz, DMSO-d$_6$) δ 8.17 (m, 1H), 7.89 (m, 1H), 7.57-7.49 (m, 2H), 7.41-7.25 (m, 2H), 7.08-6.89 (m, 2H), 4.91-4.32 (m, 4H), 3.87-3.45 (m, 4H), 3.18-2.98 (m, 3H), 2.76-2.53 (m, 2H), 2.44 (m, 1H), 2.02 (m, 2H), 1.22 (m, 1H), 0.55-0.23 (m, 4H). LC-MS: [M+H]$^+$= 529.3. [α]$_D^{20}$+45.9° (c 0.81, MeOH).

Example 90 Synthesis of SYY-B042-1 and SYY-B042-2

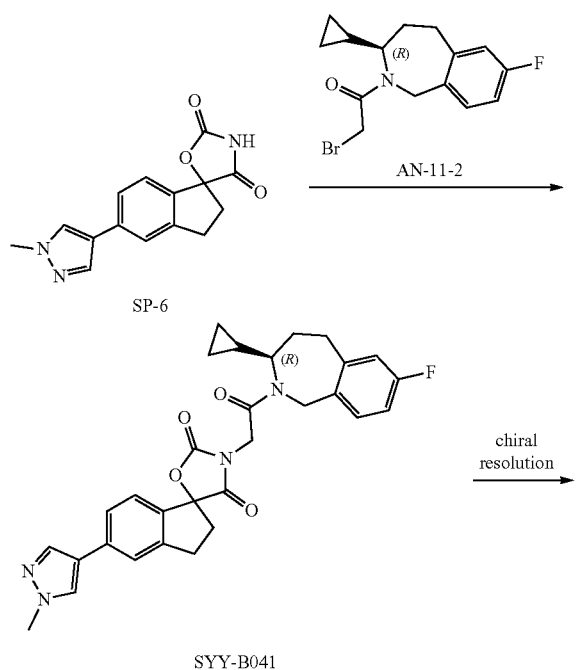

SYY—B042 was prepared using the same method as that in Example 30, except that the spiro ring fragment SP-6 was used instead of SP-1 and the amide fragment AN-11-2 was used instead of AN-7.

The SYY—B042 was subjected to chiral resolution to obtain chiral products SYY-B042-1 and SYY-B042-2.

Chiral resolution conditions: semi-preparative column was CHIRALPAK@AS-H, filler particle size (10 μm), inner diameter (30 mm), length (250 mm), flow rate: 35 mL/min, mobile phase: 70% n-hexane+30% ethanol, isogradient elution, wavelength 254 nm, total time: 65 min; peak time is 52.4 min for peak 1, and 58.2 min for peak 2.

SYY-B042-1: $^1$H NMR (400 MHz, DMSO-d$_6$) δ 8.18 (s, 1H), 7.90 (s, 1H), 7.59-7.52 (m, 2H), 7.43-7.27 (m, 2H), 7.09-6.90 (m, 2H), 4.96-4.31 (m, 4H), 3.87-3.45 (m, 4H), 3.18-2.98 (m, 3H), 2.76-2.53 (m, 2H), 2.44 (m, 1H), 2.02 (m, 2H), 0.86 (m, 1H), 0.55-0.23 (m, 4H). LC-MS: [M+H]$^+$= 529.2.

SYY-B042-2: $^1$H NMR (400 MHz, DMSO-d$_6$) δ 8.17 (m, 1H), 7.89 (m, 1H), 7.59-7.50 (m, 2H), 7.41-7.25 (m, 2H), 7.08-6.89 (m, 2H), 4.91-4.33 (m, 4H), 3.87-3.45 (m, 4H), 3.18-2.98 (m, 3H), 2.76-2.53 (m, 2H), 2.44 (m, 1H), 2.02 (m, 2H), 0.86 (m, 1H), 0.55-0.23 (m, 4H). LC-MS: [M+H]$^+$= 529.2.

Example 91 Synthesis of SYY-B043-1 and SYY-B043-2

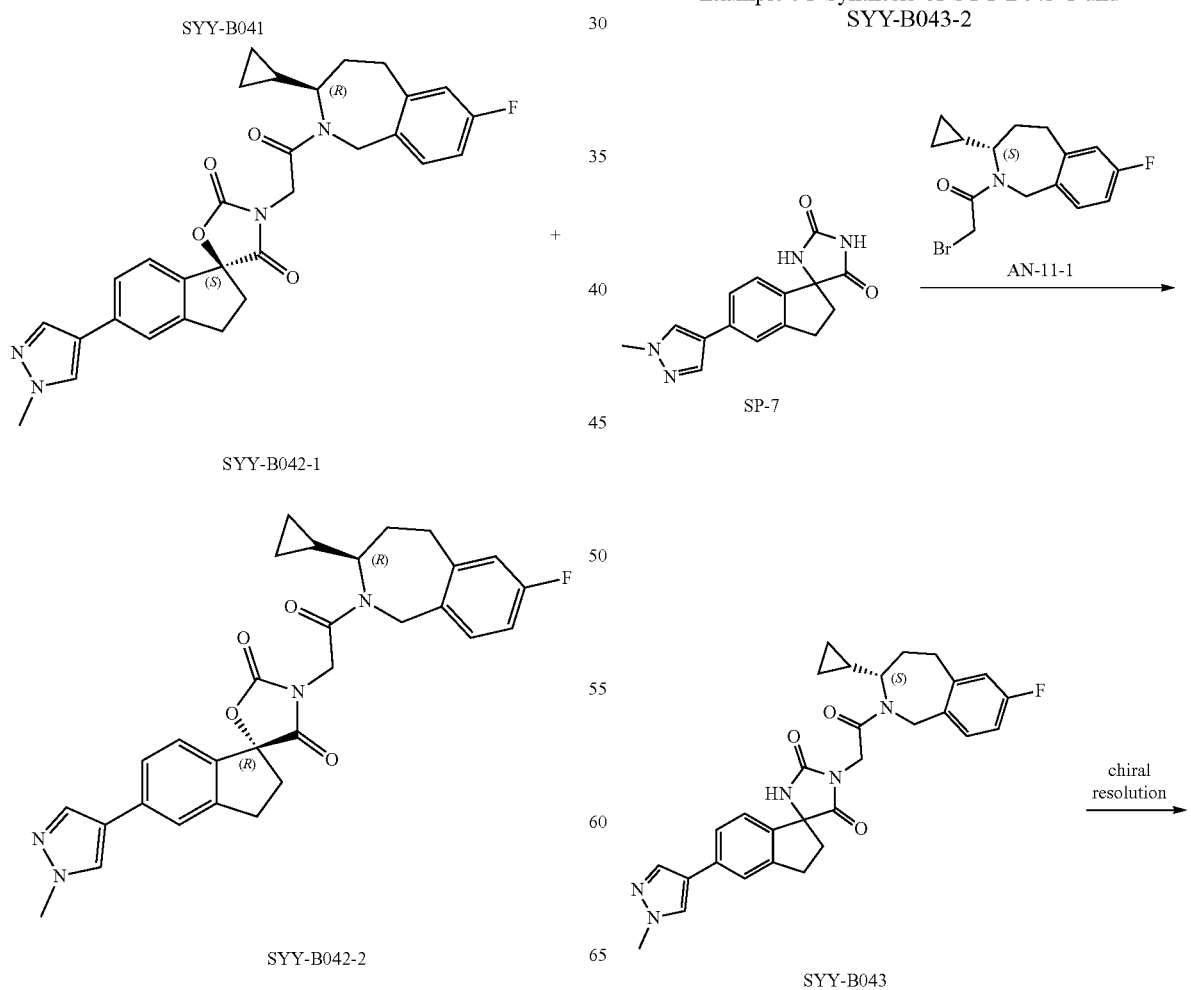

173
-continued

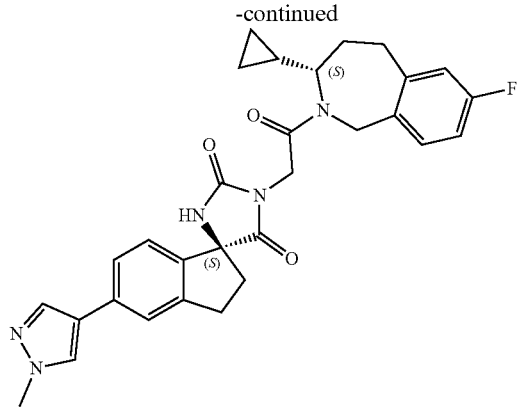

SYY-B043-1

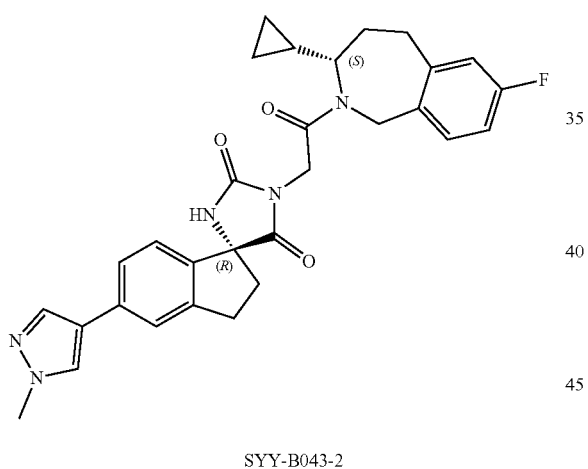

SYY-B043-2

SYY—B043 was prepared using the same method as that in Example 30, except that the spiro ring fragment SP-7 was used instead of SP-1 and the amide fragment AN-11-1 was used instead of AN-7: $^1$H NMR (400 MHz, DMSO-$d_6$) δ 8.70 (m, 1H), 8.10 (m, 1H), 7.83 (m, 1H), 7.47-6.92 (m, 6H), 4.73-4.14 (m, 3H), 3.87-3.45 (m, 5H), 2.98 (m, 3H), 2.68 (m, 2H), 2.15-1.90 (m, 3H), 1.35 (m, 1H), 0.55-0.27 (m, 4H). LC-MS: [M+H]$^+$=528.2.

The SYY—B043 was subjected to chiral resolution to obtain chiral products SYY-B043-1 and SYY-B043-2.

Chiral resolution conditions: analytical column was CHIRALPAK@AD-H, filler particle size (5 μm), inner diameter (4.6 mm), length (250 mm), flow rate: 1 mL/min, mobile phase: 60% n-hexane+40% isopropanol, isogradient elution, wavelength 254 nm, total time: 20 min; peak time is 10.45 min for peak 1, and 12.08 min for peak 2.

174
Example 92 Synthesis of SYY-B044-1 and SYY-B044-2

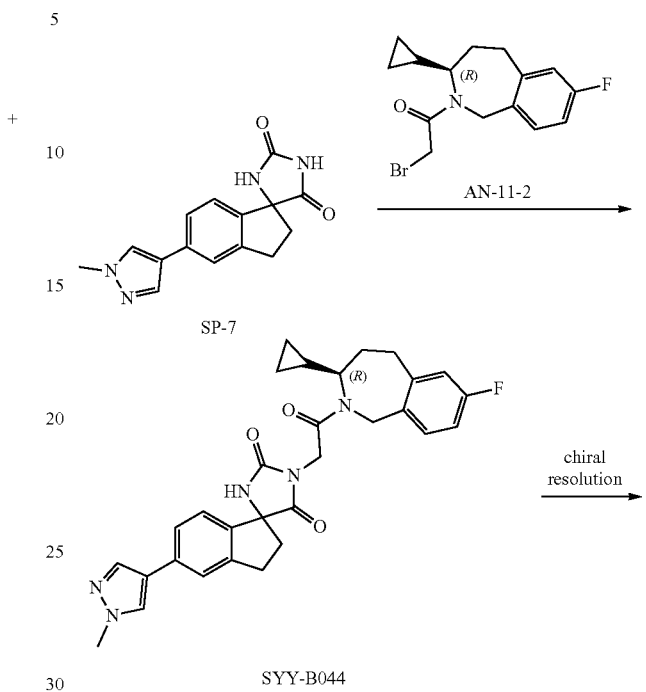

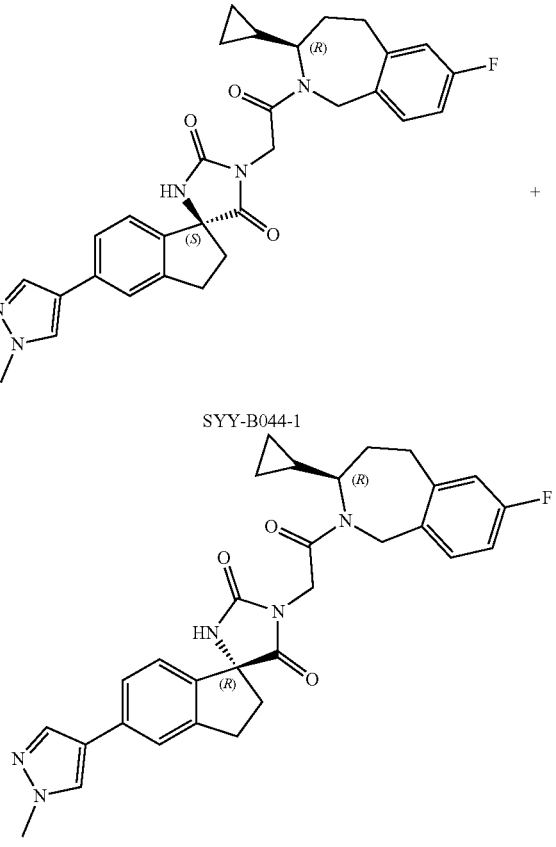

SYY-B044-2

SYY—B044 was prepared using the same method as that in Example 30, except that the spiro ring fragment SP-7 was used instead of SP-1 and the amide fragment AN-11-2 was used instead of AN-7: $^1$H NMR (400 MHz, DMSO-$d_6$) δ 8.72 (m, 1H), 8.13 (m, 1H), 7.85 (m, 1H), 7.49-6.90 (m, 6H), 4.85-4.15 (m, 3H), 3.87-3.45 (m, 5H), 3.18-2.98 (m, 3H), 2.76-2.53 (m, 2H), 2.21-1.94 (m, 3H), 1.34 (m, 1H), 0.55-0.23 (m, 4H). LC-MS: [M+H]$^+$=528.2.

The SYY—B044 was subjected to chiral resolution to obtain chiral products SYY-B044-1 and SYY-B044-2.

Chiral resolution conditions: semi-preparative column was CHIRALPAK@AS-H, filler particle size (10 μm), inner diameter (30 mm), length (250 mm), flow rate: 30 mL/min, mobile phase: 70% n-hexane+30% ethanol, isogradient elution, wavelength 254 nm, total time: 65 min; peak time is 12.1 min for peak 1, and 30.6 min for peak 2.

Example 93 Synthesis of SYY-B045

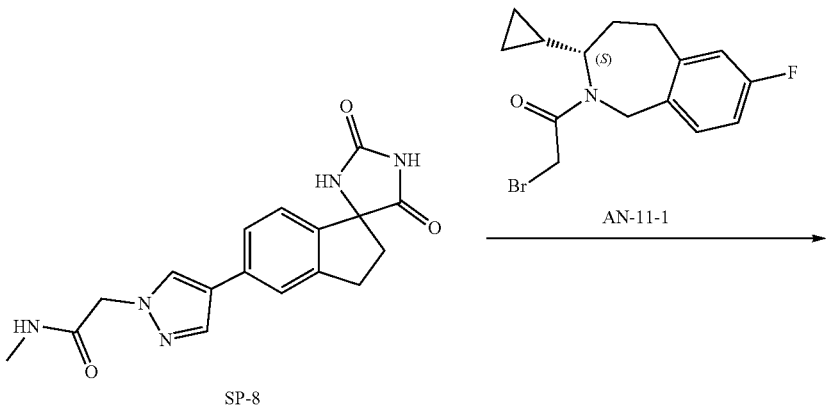

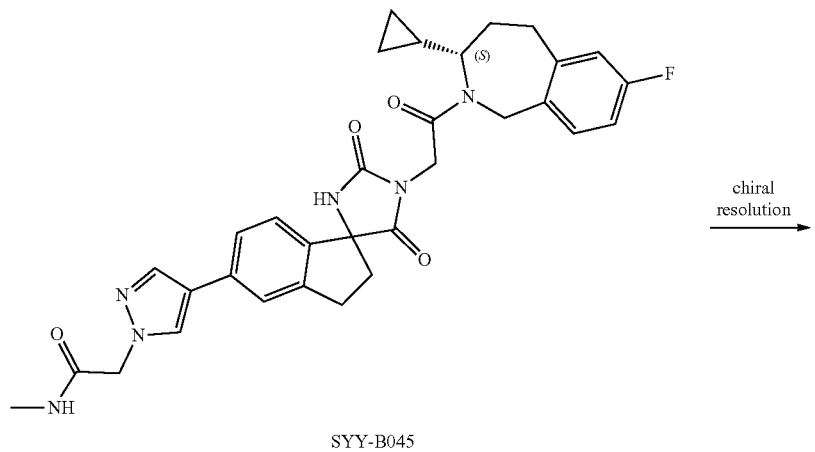

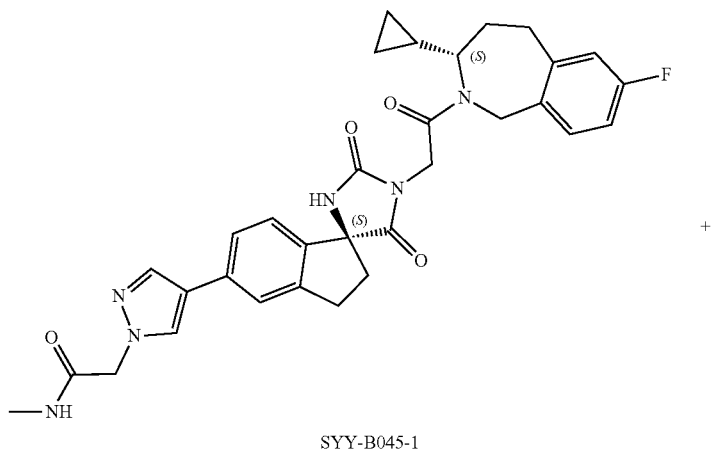

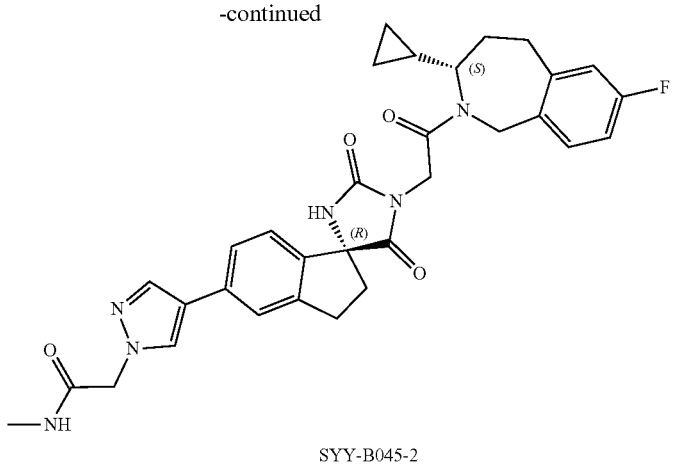

SYY-B045-2

SYY—B045 was prepared using the same method as that in Example 30, except that the spiro ring fragment SP-8 was used instead of SP-1 and the amide fragment AN-11-1 was used instead of AN-7: $^1$H NMR (400 MHz, DMSO-$d_6$) δ 8.72 (m, 1H), 8.14-7.89 (m, 3H), 7.52-7.01 (m, 6H), 4.76-4.70 (m, 5H), 4.39-3.45 (m, 3H), 3.12-2.98 (m, 3H), 2.73-2.53 (m, 4H), 2.21-1.94 (m, 3H), 1.42 (m, 1H), 0.55-0.25 (m, 4H). LC-MS: [M+H]$^+$=585.3.

The SYY—B045 was subjected to chiral resolution to obtain chiral products SYY-B045-1 and SYY-B045-2.

Chiral resolution conditions: analytical column was CHI-RALPAK@ OD-H, filler particle size (5 μm), inner diameter (4.6 mm), length (250 mm), flow rate: 1.0 mL/min, mobile phase: 60% n-hexane+40% ethanol, isogradient elution, wavelength 210 nm, total time: 30 min; peak time is 10.23 min for peak 1, and 16.08 min for peak 2.

Example 94 Synthesis of SYY-B046-1 and SYY-B046-2

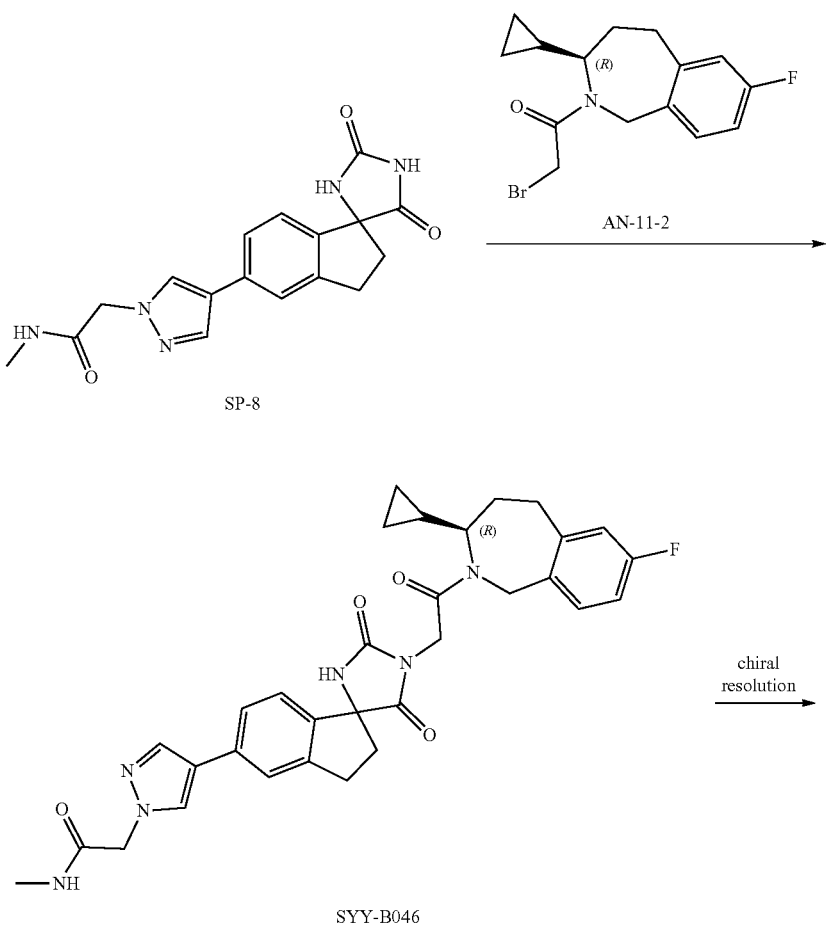

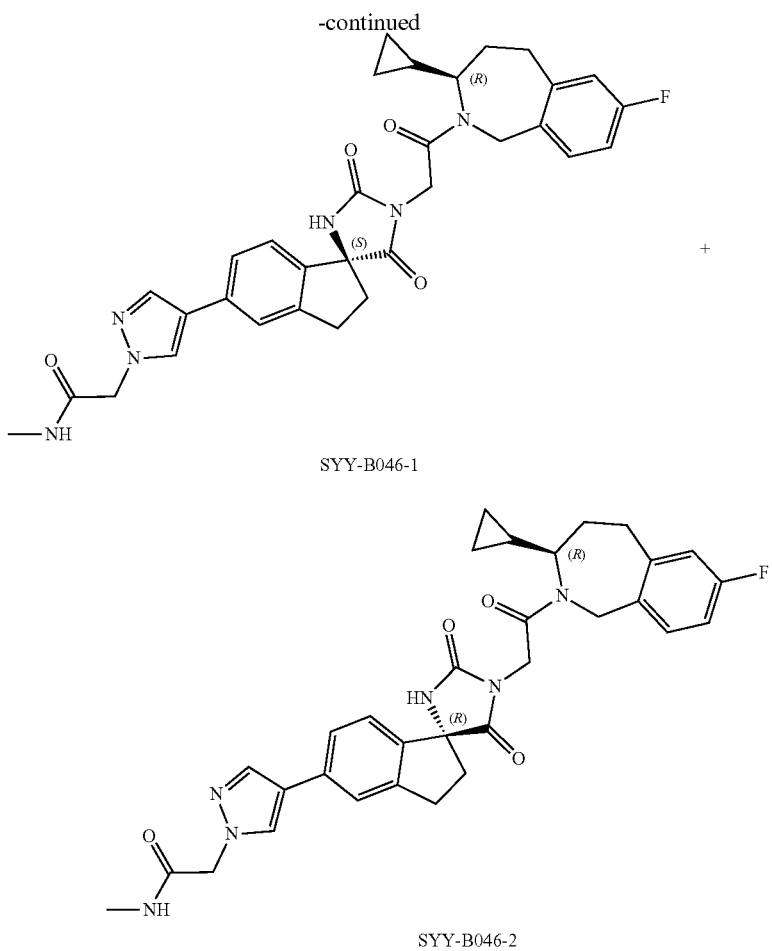

SYY-B046-1

SYY-B046-2

SYY—B046 was prepared using the same method as that in Example 30, except that the spiro ring fragment SP-8 was used instead of SP-1 and the amide fragment AN-11-2 was used instead of AN-7: $^1$H NMR (400 MHz, DMSO-d$_6$) δ 8.73 (m, 1H), 8.14-7.90 (m, 3H), 7.52-6.98 (m, 6H), 4.85-4.68 (m, 5H), 4.41-3.45 (m, 3H), 3.12-2.98 (m, 3H), 2.73-2.53 (m, 4H), 2.21-1.94 (m, 3H), 1.47 (m, 1H), 0.55-0.25 (m, 4H). LC-MS: [M+H]$^+$=585.3.

The SYY—B046 was subjected to chiral resolution to obtain chiral products SYY-B046-1 and SYY-B046-2.

Chiral resolution conditions: analytical column was CHIRALPAK@ AS-H, filler particle size (5 μm), inner diameter (4.6 mm), length (250 mm), flow rate: 1 mL/min, mobile phase: 60% n-hexane+40% ethanol, isogradient elution, wavelength 210 nm, total time: 30 min; peak time is 6.44 min for peak 1, and 11.33 min for peak 2.

Example 95 Synthesis of ZB—P-01

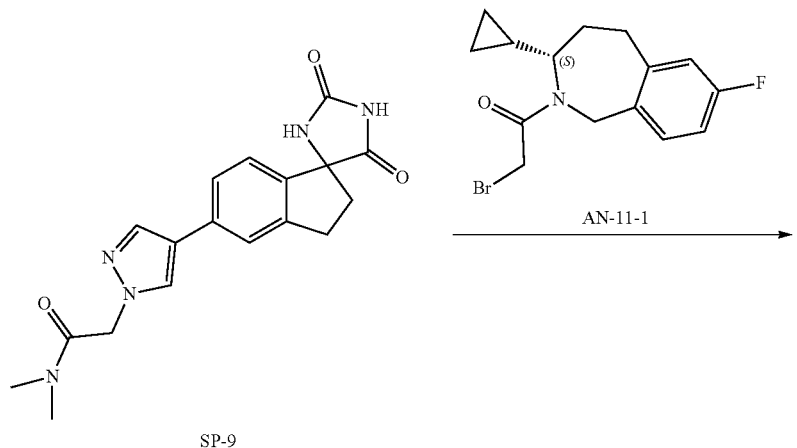

SP-9    AN-11-1

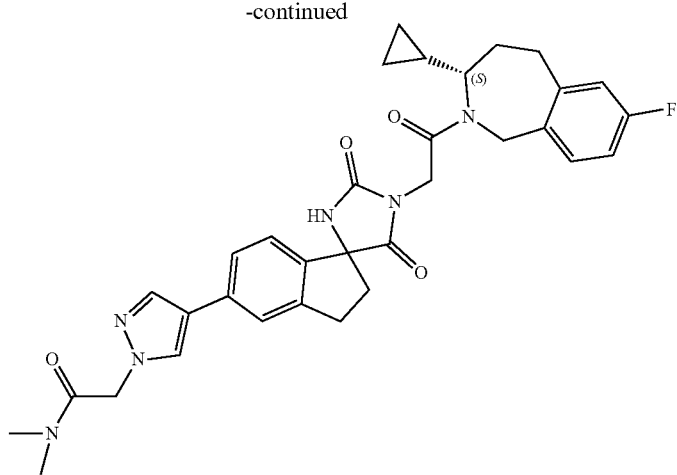

ZB-P-01

ZB—P-01 was prepared using the same method as that in Example 30, except that the spiro ring fragment SP-9 was used instead of SP-1 and the amide fragment AN-11-1 was used instead of AN-7: LC-MS: [M+H]$^+$=599.2.

Example 96 Synthesis of ZB—P-02

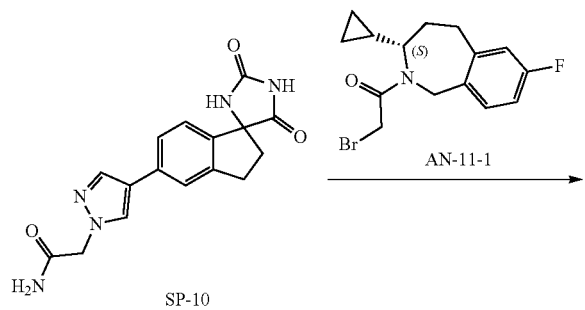

SP-10     AN-11-1

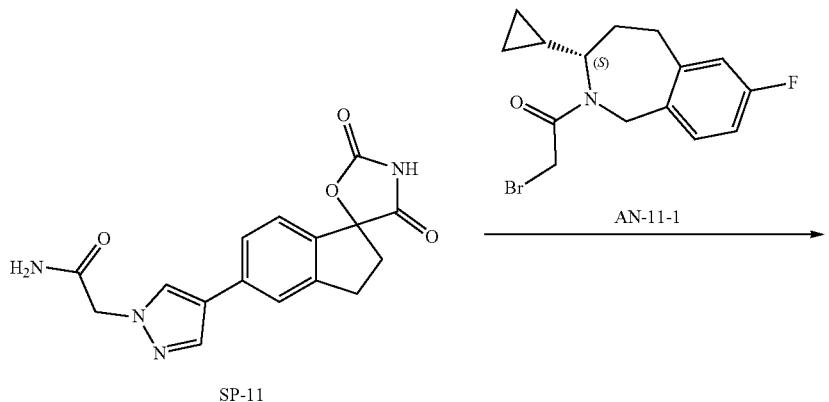

ZB-P-02

ZB—P-02 was prepared using the same method as that in Example 30, except that the spiro ring fragment SP-10 was used instead of SP-1 and the amide fragment AN-11-1 was used instead of AN-7: LC-MS: [M+H]$^+$=571.2.

Example 97 Synthesis of ZB—P-03

SP-11     AN-11-1

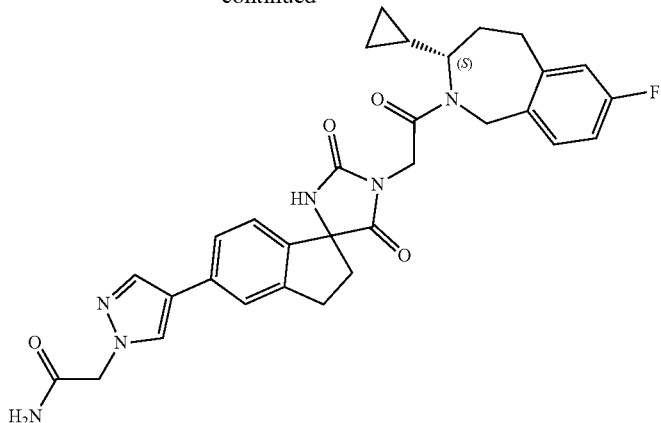
ZB-P-03
ZB—P-03 was prepared using the same method as that in Example 30, except that the spiro ring fragment SP-11 was used instead of SP-1 and the amide fragment AN-11-1 was used instead of AN-7: LC-MS: [M+H]$^+$=572.2.
Example 98 Synthesis of ZB—P-04
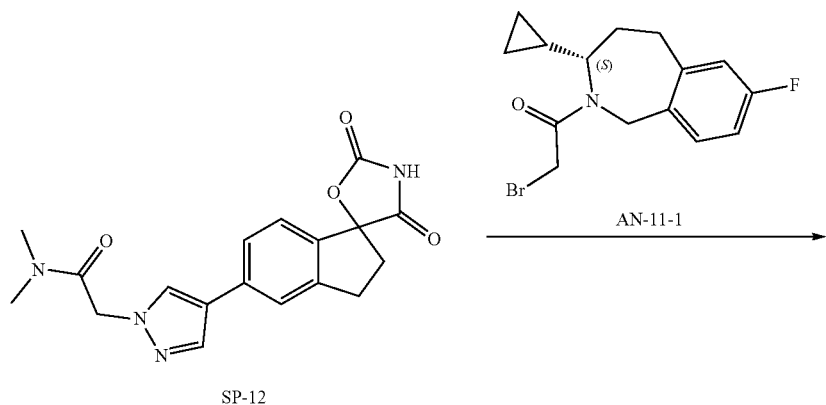
SP-12
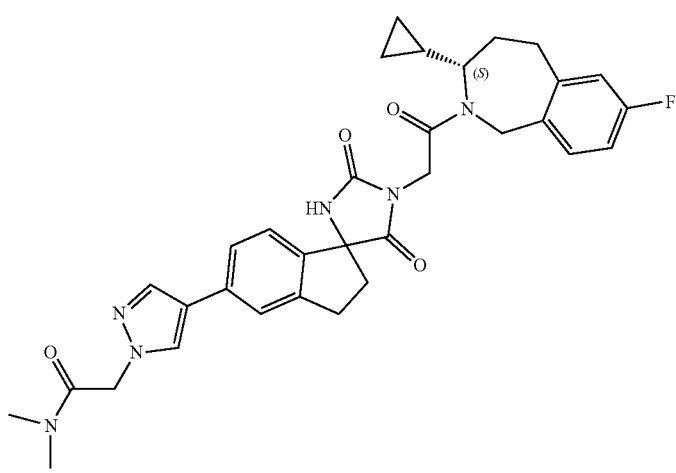
ZB-P-04

ZB—P-04 was prepared using the same method as that in Example 30, except that the spiro ring fragment SP-12 was used instead of SP-1 and the amide fragment AN-11-1 was used instead of AN-7: LC-MS: [M+H]$^+$=600.2.

Example 99 Synthesis of ZB—P-05

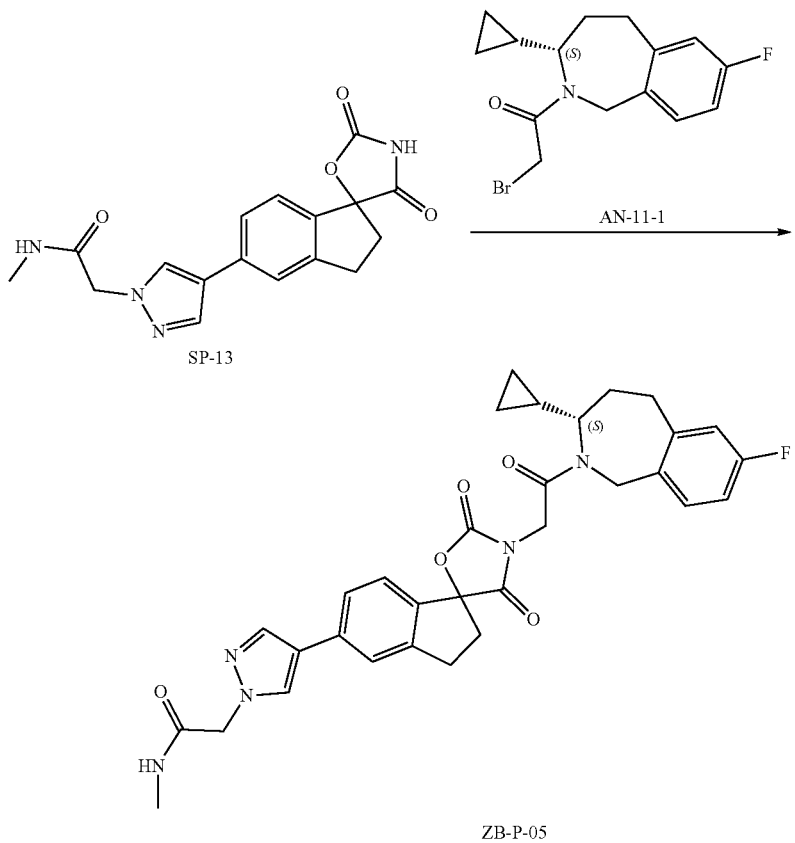

ZB—P-05 was prepared using the same method as that in Example 30, except that the spiro ring fragment SP-13 was used instead of SP-1 and the amide fragment AN-11-1 was used instead of AN-7: $^1$H NMR (400 MHz, DMSO-d$_6$) δ 8.20 (m, 1H), 8.04 (m, 1H), 7.94 (m, 1H), 7.61-7.54 (m, 2H), 7.43-7.26 (m, 2H), 7.10-6.91 (m, 2H), 4.96-3.47 (m, 7H), 3.20-2.98 (m, 3H), 2.79-2.51 (m, 6H), 2.07-1.99 (m, 2H), 1.49-1.23 (m, 1H), 0.59-0.27 (m, 4H). LC-MS: [M+H]$^+$= 586.2.

Example 100 Synthesis of ZB—P-06

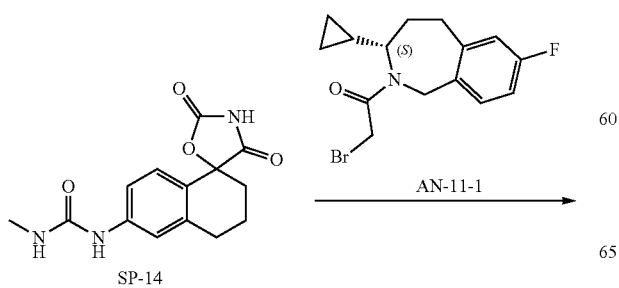

-continued

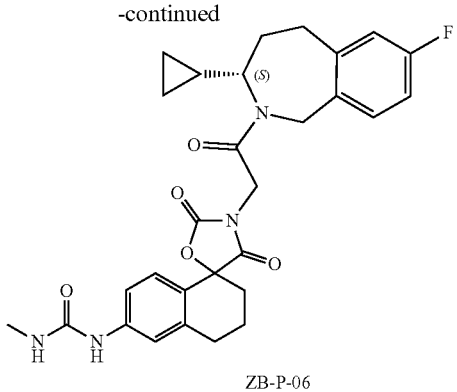

ZB—P-06 was prepared using the same method as that in Example 30, except that the spiro ring fragment SP-14 was used instead of SP-1 and the amide fragment AN-11-1 was used instead of AN-7: LC-MS: [M+H]$^+$=535.2.

Example 101 Synthesis of ZB—P-07

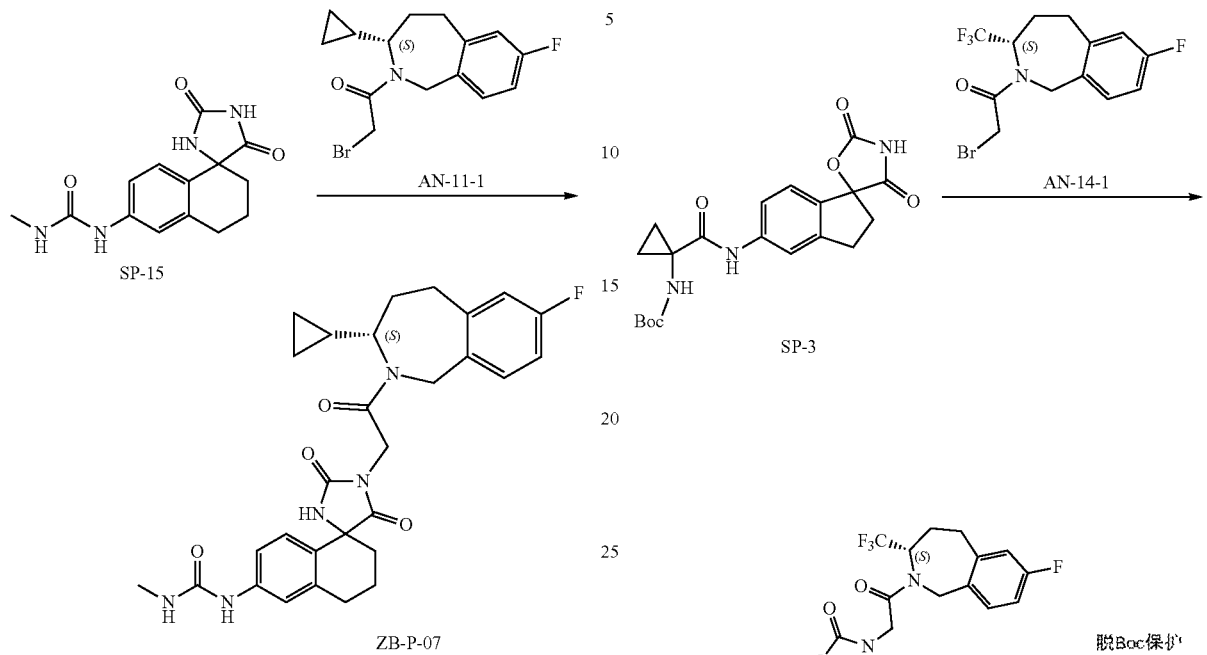

ZB—P-07 was prepared using the same method as that in Example 30, except that the spiro ring fragment SP-15 was used instead of SP-1 and the amide fragment AN-11-1 was used instead of AN-7: LC-MS: [M+H]⁺=534.2.

Example 102 Synthesis of ZB—P-08

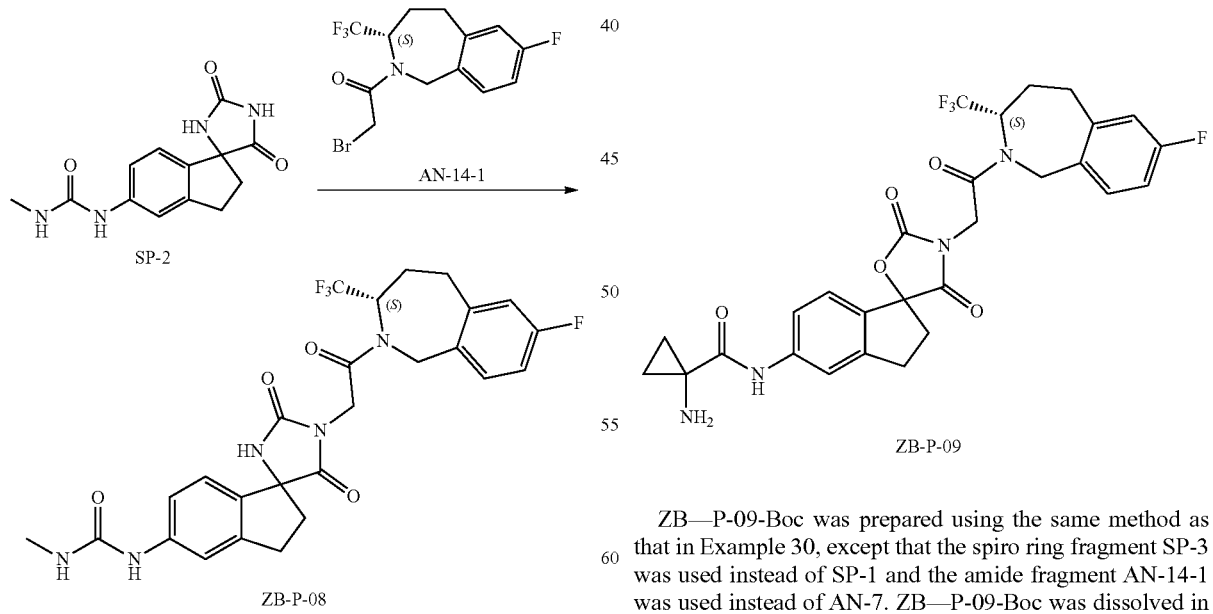

ZB—P-08 was prepared using the same method as that in Example 30, except that the spiro ring fragment SP-2 was used instead of SP-1 and the amide fragment AN-14-1 was used instead of AN-7: LC-MS: [M+H]⁺=548.2.

Example 103 Synthesis of ZB—P-09

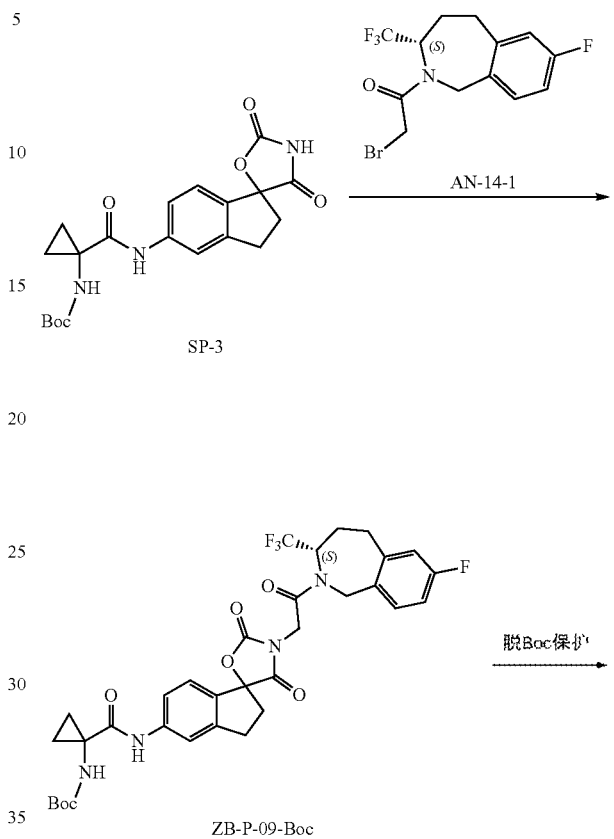

ZB—P-09-Boc was prepared using the same method as that in Example 30, except that the spiro ring fragment SP-3 was used instead of SP-1 and the amide fragment AN-14-1 was used instead of AN-7. ZB—P-09-Boc was dissolved in dichloromethane (3 mL), added with TFA (1 mL), and stirred at room temperature for 2 h. TLC showed that the reaction was complete. The reaction solution was rotary evaporated to dryness to obtain ZB—P-09. LC-MS: [M+H]⁺= 575.2.

Example 104 Synthesis of ZB—P-10

Example 105 Synthesis of ZB—P-11

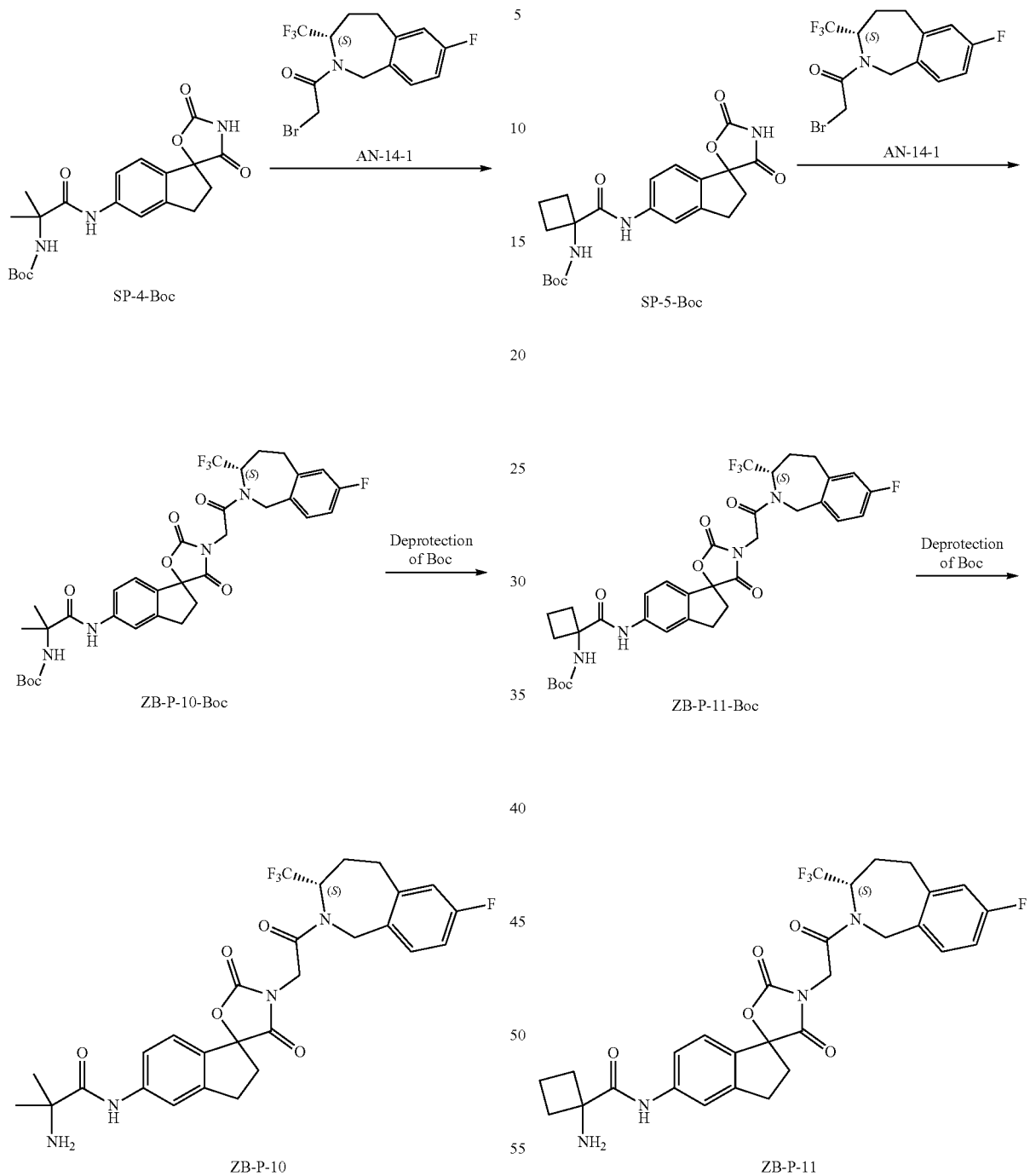

ZB—P-10-Boc was prepared using the same method as that in Example 30, except that the spiro ring fragment SP-4-Boc was used instead of SP-1 and the amide fragment AN-14-1 was used instead of AN-7. ZB—P-10-Boc was dissolved in dichloromethane (3 mL), added with TFA (1 mL), and stirred at room temperature for 2 h. TLC showed that the reaction was complete. The reaction solution was rotary evaporated to dryness to obtain ZB—P-10. LC-MS: [M+H]$^+$=577.2.

ZB—P-11-Boc was prepared using the same method as that in Example 30, except that the spiro ring fragment SP-5-Boc was used instead of SP-1 and the amide fragment AN-14-1 was used instead of AN-7. ZB—P-11-Boc was dissolved in dichloromethane (3 mL), added with TFA (1 mL), and stirred at room temperature for 2 h. TLC showed that the reaction was complete. The reaction solution was rotary evaporated to dryness to obtain ZB—P-11. LC-MS: [M+H]$^+$=589.2.

Example 106 Synthesis of ZB—P-12

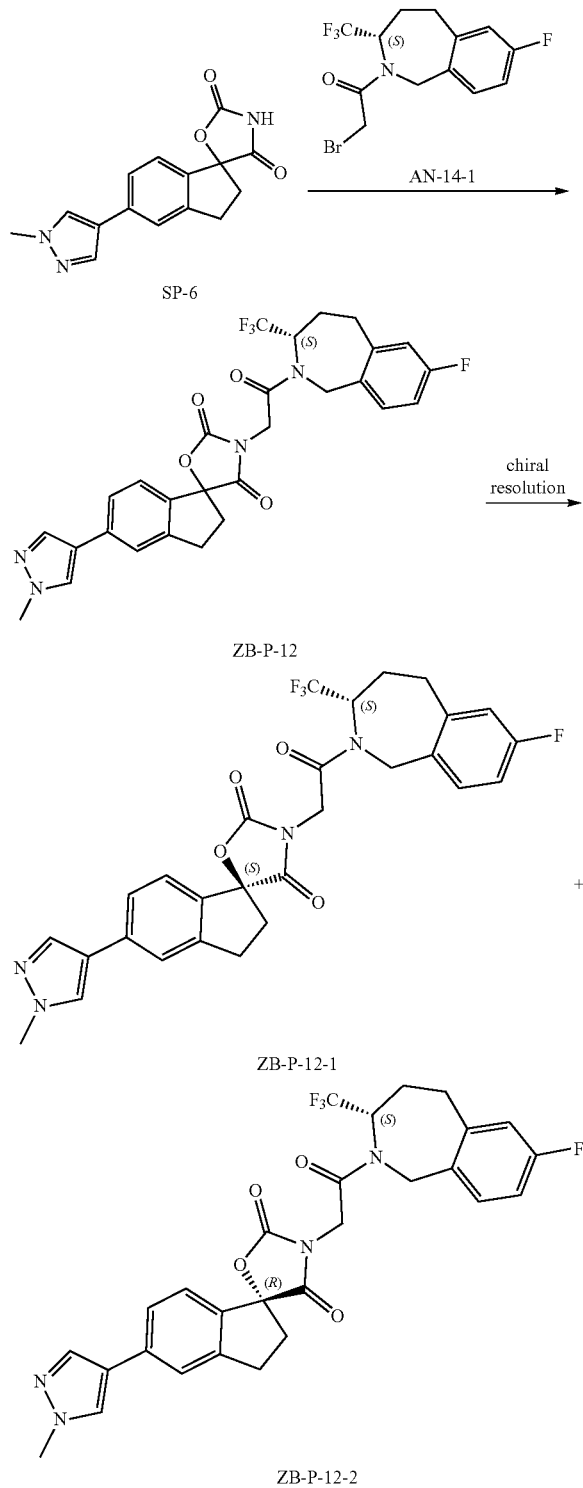

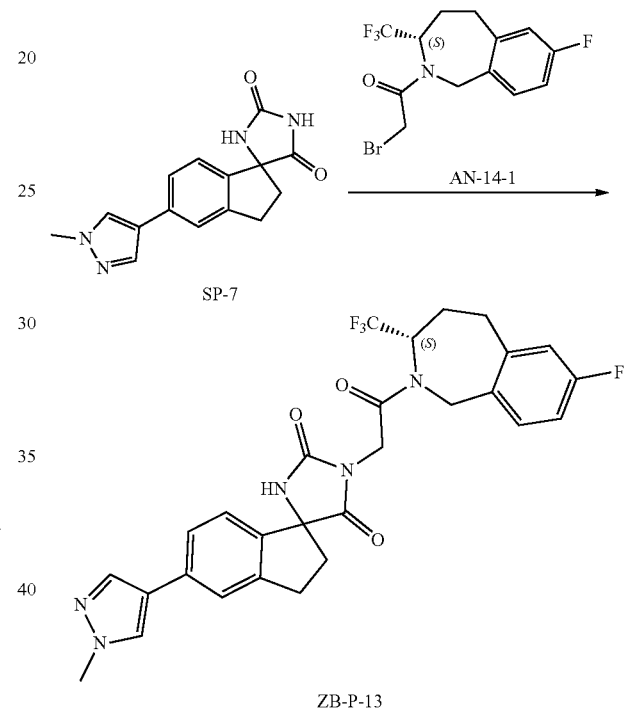

ZB—P-12 was prepared using the same method as that in Example 30, except that the spiro ring fragment SP-6 was used instead of SP-1 and the amide fragment AN-14-1 was used instead of AN-7: ¹H NMR (400 MHz, DMSO-$d_6$) δ 8.19 (m, 1H), 7.91 (m, 1H), 7.60-7.51 (m, 2H), 7.41-7.27 (m, 2H), 7.11-6.98 (m, 2H), 5.23-4.31 (m, 5H), 3.86 (s, 3H), 3.15-3.06 (m, 3H), 2.75-2.52 (m, 2H), 2.47-2.28 (m, 3H). LC-MS: [M+H]$^+$=557.2.

The ZB—P-12 was subjected to chiral resolution to obtain chiral products ZB—P-12-1 and ZB—P-12-2.

Chiral resolution conditions: analytical column was NANOMICRO OD-5H, filler particle size (5 μm), inner diameter (4.6 mm), length (250 mm), flow rate: 1 mL/min, mobile phase: 70% n-hexane+30% isopropanol, isogradient elution, wavelength 254 nm, total time 60 min; peak time is 29.12 min for peak 1, and 33.97 min for peak 2.

Example 107 Synthesis of ZB—P-13

ZB—P-13 was prepared using the same method as that in Example 30, except that the spiro ring fragment SP-7 was used instead of SP-1 and the amide fragment AN-14-1 was used instead of AN-7: LC-MS: [M+H]$^+$=556.2.

Example 108 Synthesis of ZB—P-14

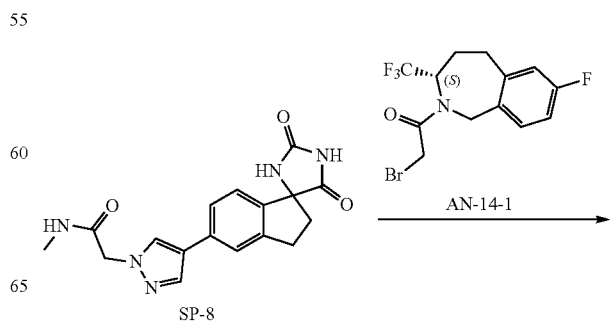

Example 109 Synthesis of ZB—P-15

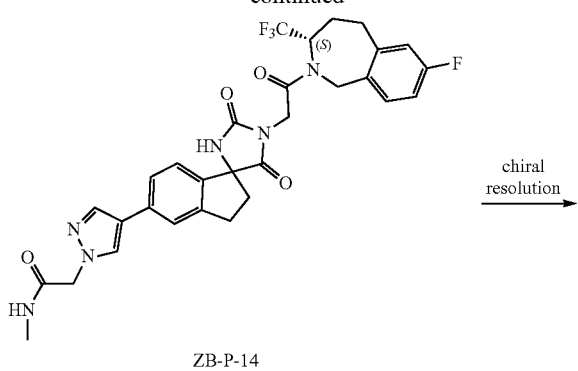

ZB-P-14

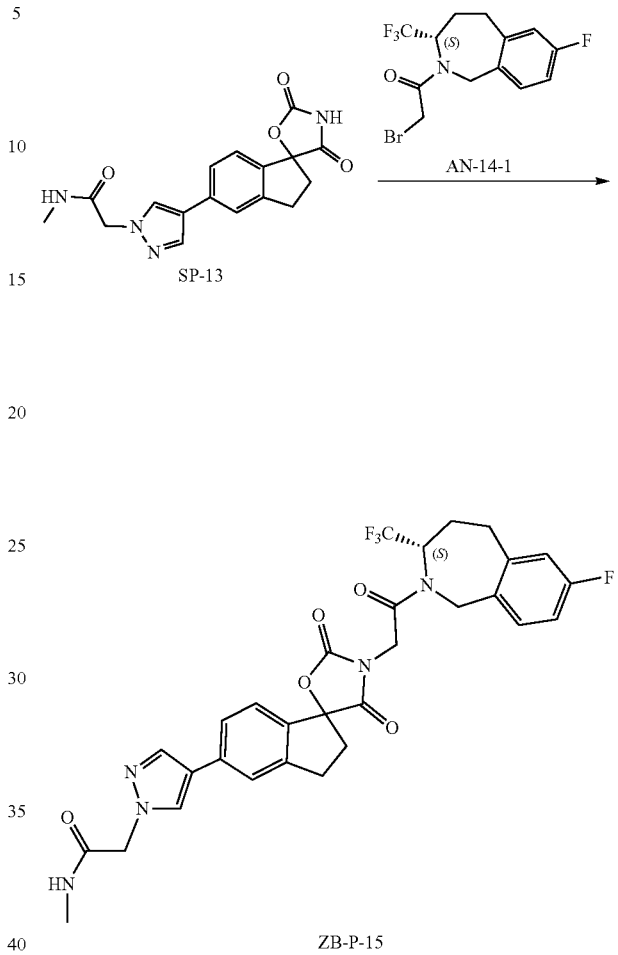

ZB-P-14-1

ZB-P-14-2

ZB—P-14 was prepared using the same method as that in Example 30, except that the spiro ring fragment SP-8 was used instead of SP-1 and the amide fragment AN-14-1 was used instead of AN-7: $^1$H NMR (400 MHz, DMSO-d$_6$) δ 8.80 (m, 1H), 8.14 (m, 1H), 8.04 (m, 1H), 7.90 (m, 1H), 7.52-7.46 (m, 2H), 7.36-7.19 (m, 2H), 7.10-7.02 (m, 2H), 5.22-3.67 (m, 7H), 3.02-2.98 (m, 3H), 2.75-2.52 (m, 4H), 2.42-2.15 (m, 4H). LC-MS: [M+H]$^+$=613.2.

The ZB—P-14 was subjected to chiral resolution to obtain chiral products ZB—P-14-1 and ZB—P-14-2.

Chiral resolution conditions: analytical column was CHIRALPAK@ OD-H, filler particle size (5 μm), inner diameter (4.6 mm), length (250 mm), flow rate: 1 mL/min, mobile phase: 60% n-hexane+40% ethanol, isogradient elution, wavelength 210 nm, total time: 30 min; peak time is 7.98 min for peak 1, and 10.69 min for peak 2.

ZB—P-15 was prepared using the same method as that in Example 30, except that the spiro ring fragment SP-13 was used instead of SP-1 and the amide fragment AN-14-1 was used instead of AN-7: $^1$H NMR (400 MHz, DMSO-d$_6$) δ 8.20 (m, 1H), 8.04 (m, 1H), 7.94 (m, 1H), 7.62-7.53 (m, 2H), 7.43-7.26 (m, 2H), 7.13-6.92 (m, 2H), 5.26-3.78 (m, 7H), 3.21-3.01 (m, 3H), 2.78-2.52 (m, 6H), 2.45-2.27 (m, 2H). LC-MS: [M+H]$^+$=614.2.

Example 110 Synthesis of ZB—P-16

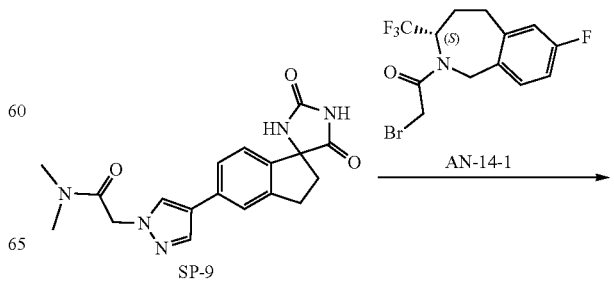

-continued

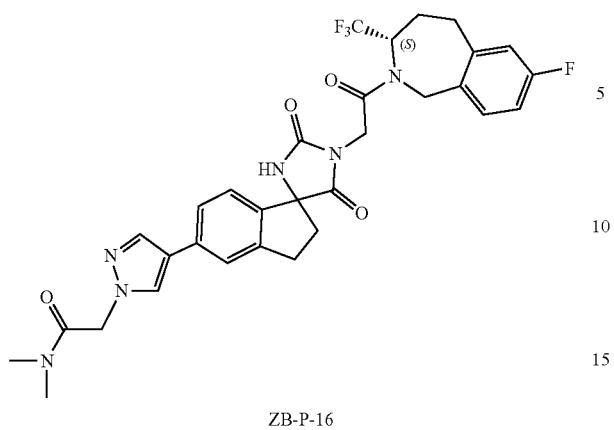

ZB-P-16

ZB—P-16 was prepared using the same method as that in Example 30, except that the spiro ring fragment SP-9 was used instead of SP-1 and the amide fragment AN-14-1 was used instead of AN-7: LC-MS: [M+H]$^+$=627.2.

Example 111 Synthesis of ZB—P-17

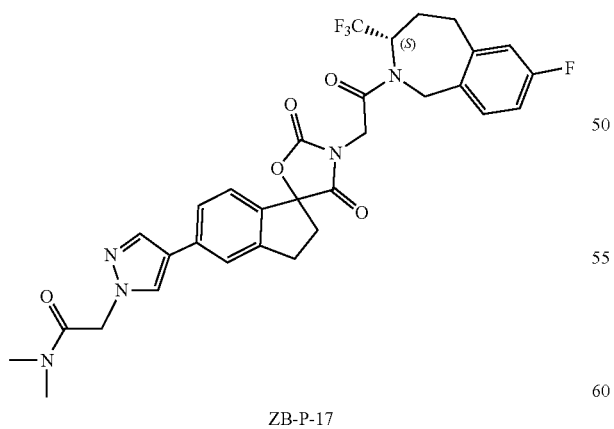

ZB-P-17

ZB—P-17 was prepared using the same method as that in Example 30, except that the spiro ring fragment SP-12 was used instead of SP-1 and the amide fragment AN-14-1 was used instead of AN-7: LC-MS: [M+H]$^+$=628.2.

Example 112 Synthesis of ZB—P-18

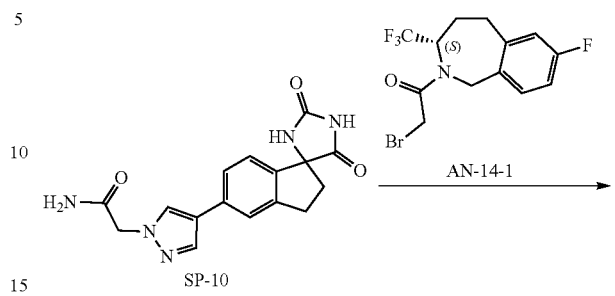

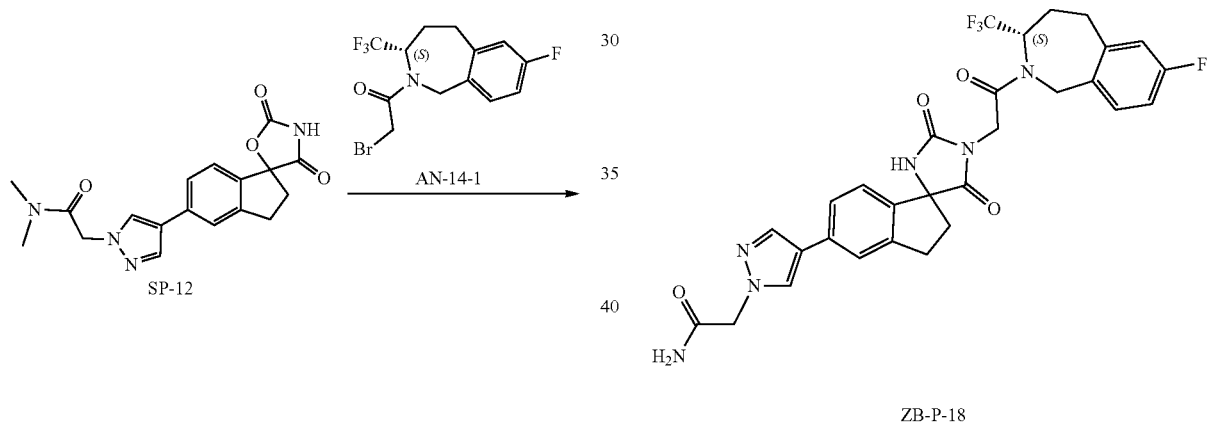

ZB-P-18

ZB—P-18 was prepared using the same method as that in Example 30, except that the spiro ring fragment SP-10 was used instead of SP-1 and the amide fragment AN-14-1 was used instead of AN-7: LC-MS: [M+H]$^+$=599.2.

Example 113 Synthesis of ZB—P-19

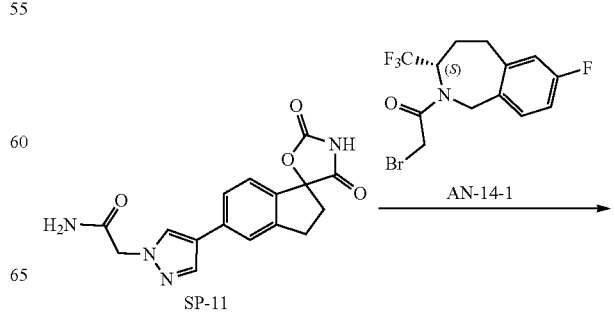

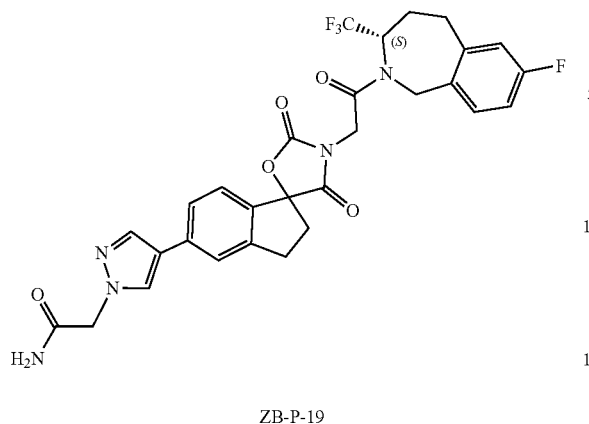

ZB-P-19

ZB—P-19 was prepared using the same method as that in Example 30, except that the spiro ring fragment SP-11 was used instead of SP-1 and the amide fragment AN-14-1 was used instead of AN-7: LC-MS: [M+H]⁺=600.2.

Example 114 Synthesis of ZB—P-20

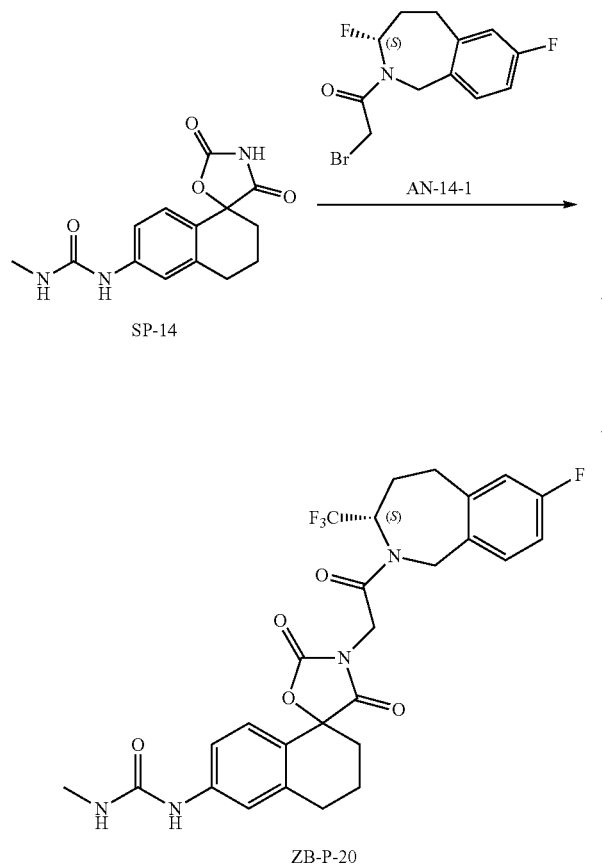

ZB-P-20

ZB—P-20 was prepared using the same method as that in Example 30, except that the spiro ring fragment SP-14 was used instead of SP-1 and the amide fragment AN-14-1 was used instead of AN-7: LC-MS: [M+H]⁺=563.2.

Example 115 Synthesis of ZB—P-21

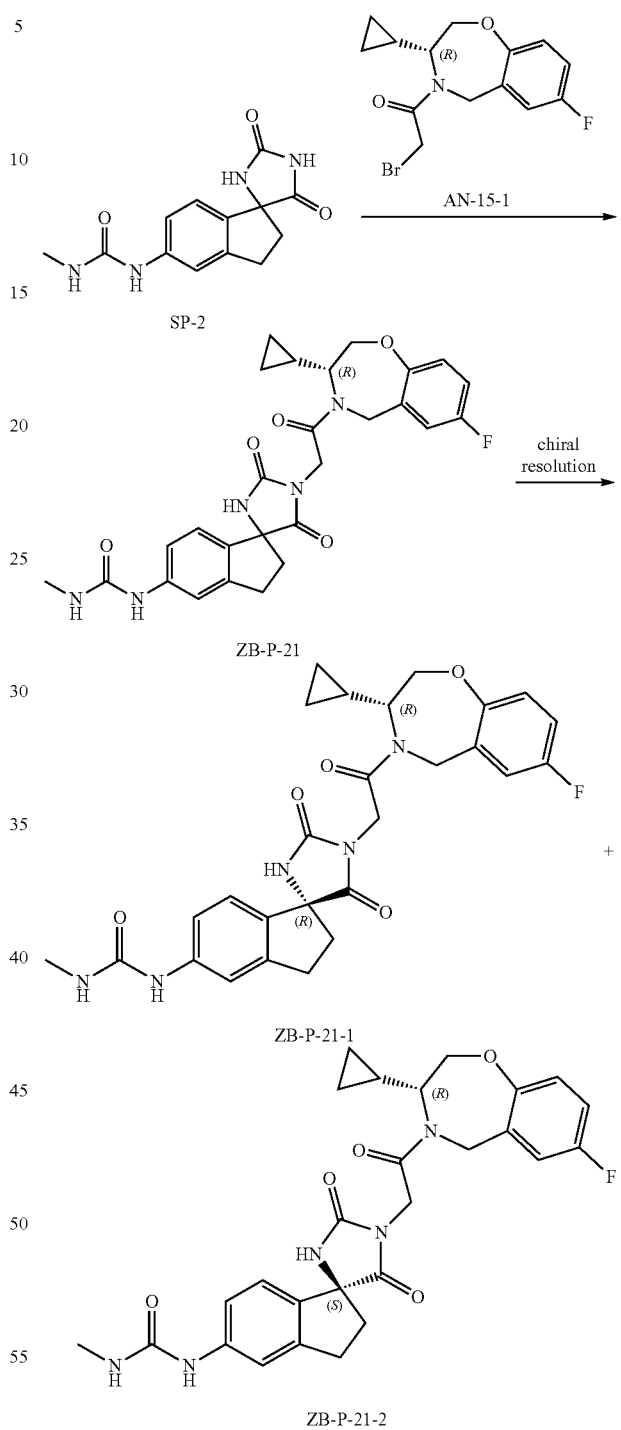

ZB—P-21 was prepared using the same method as that in Example 30, except that the spiro ring fragment SP-2 was used instead of SP-1 and the amide fragment AN-15-1 was used instead of AN-7: $^1$H NMR (400 MHz, DMSO-d$_6$) δ 8.70 (m, 1H), 8.55 (m, 1H), 7.41 (m, 1H), 7.24-6.88 (m, 5H), 6.01 (m, 1H), 5.01-3.70 (m, 7H), 2.93 (m, 2H), 2.62 (m, 3H), 2.44 (m, 1H), 2.14 (m, 1H), 1.33 (m, 1H), 0.55-0.30 (m, 4H). LC-MS: [M+H]⁺=522.2.

Chiral resolution was performed to obtain ZB—P-21-1 and ZB—P-21-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 12.54 min for peak 1, and 38.69 min for peak 2.

Example 116 Synthesis of ZB—P-22

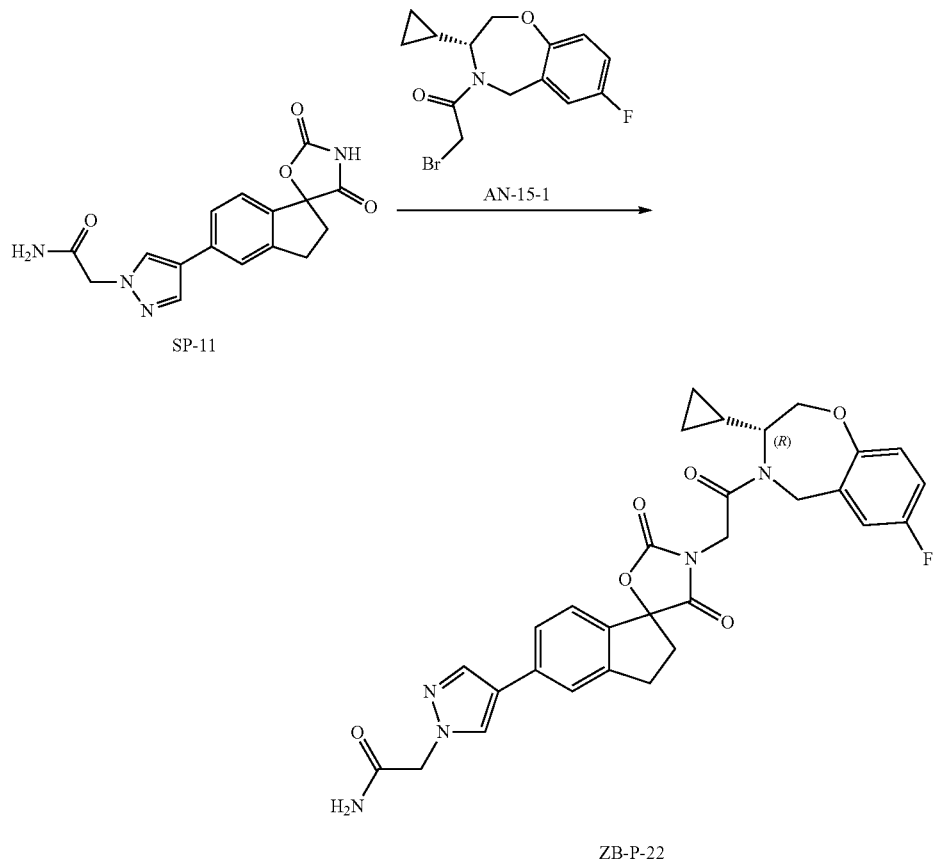

ZB—P-22 was prepared using the same method as that in Example 30, except that the spiro ring fragment SP-11 was used instead of SP-1 and the amide fragment AN-15-1 was used instead of AN-7: LC-MS: [M+H]$^+$=574.2.

Example 117 Synthesis of ZB—P-23

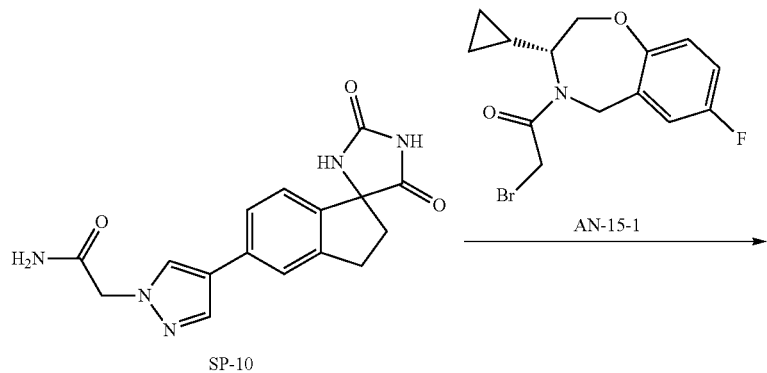

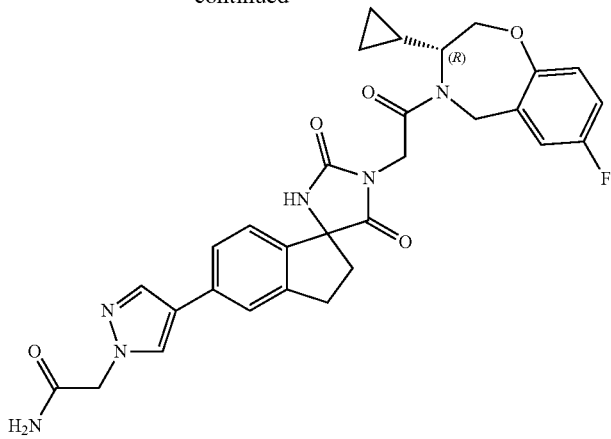
ZB-P-23
ZB—P-23 was prepared using the same method as that in Example 30, except that the spiro ring fragment SP-10 was used instead of SP-1 and the amide fragment AN-15-1 was used instead of AN-7: LC-MS: [M+H]$^+$=573.2.
Example 118 Synthesis of ZB—P-24
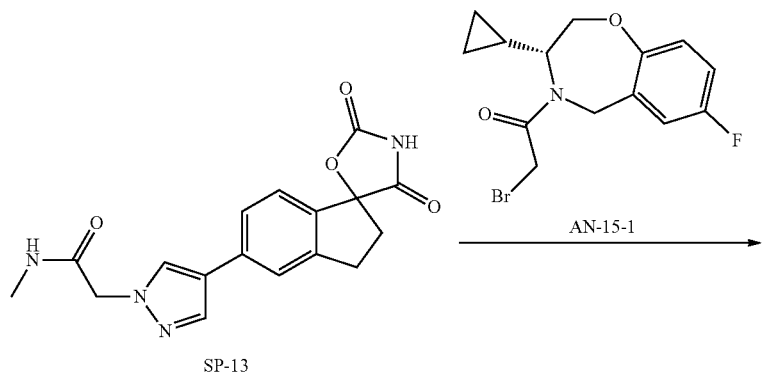
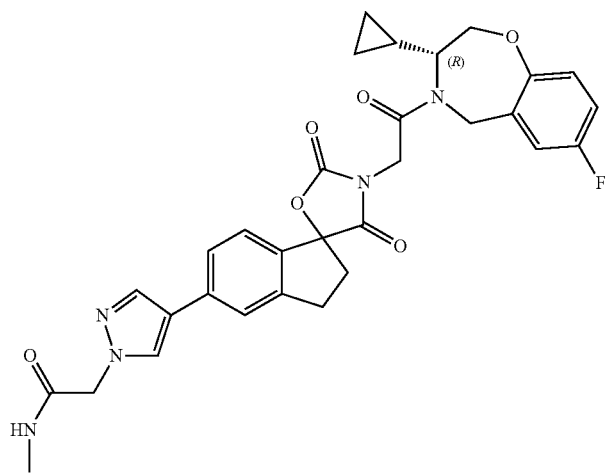
ZB-P-24

ZB—P-24 was prepared using the same method as that in Example 30, except that the spiro ring fragment SP-13 was used instead of SP-1 and the amide fragment AN-15-1 was used instead of AN-7: LC-MS: [M+H]$^+$=588.2.

Example 119 Synthesis of ZB—P-25

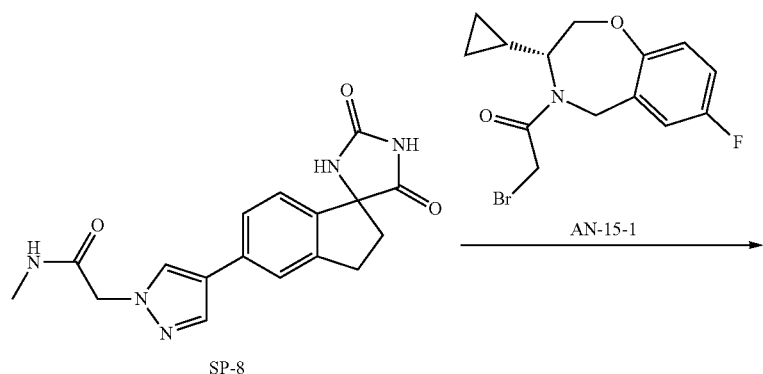

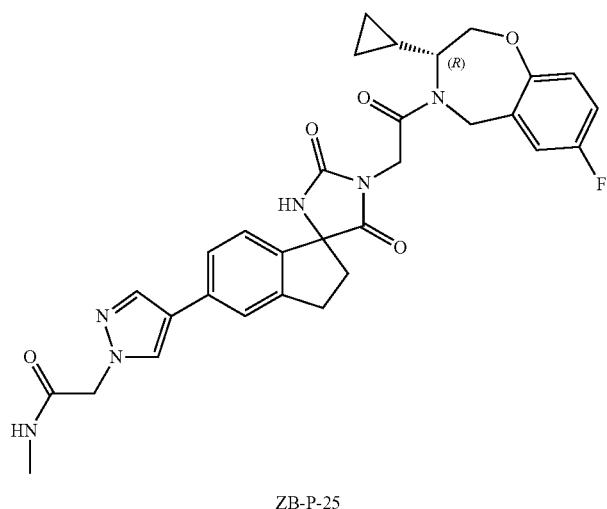

ZB—P-25 was prepared using the same method as that in Example 30, except that the spiro ring fragment SP-8 was used instead of SP-1 and the amide fragment AN-15-1 was used instead of AN-7: LC-MS: [M+H]$^+$=587.2.

Example 120 Synthesis of ZB—P-26

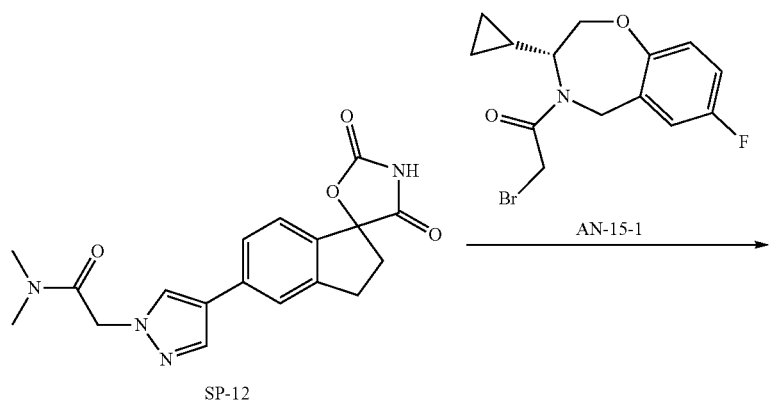

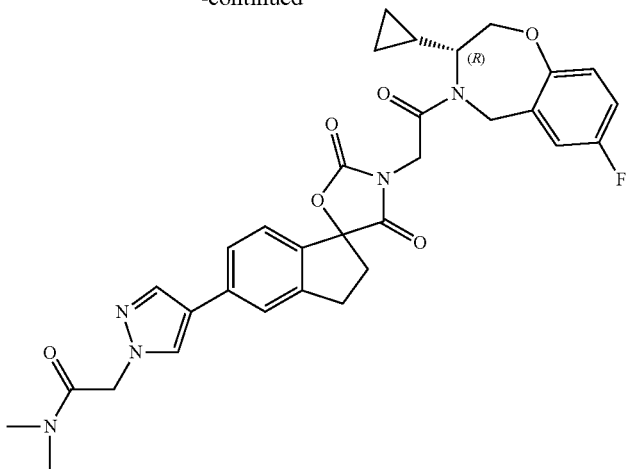
ZB-P-26
ZB—P-26 was prepared using the same method as that in Example 30, except that the spiro ring fragment SP-12 was used instead of SP-1 and the amide fragment AN-15-1 was used instead of AN-7: LC-MS: [M+H]$^+$=602.2.
Example 121 Synthesis of ZB—P-27
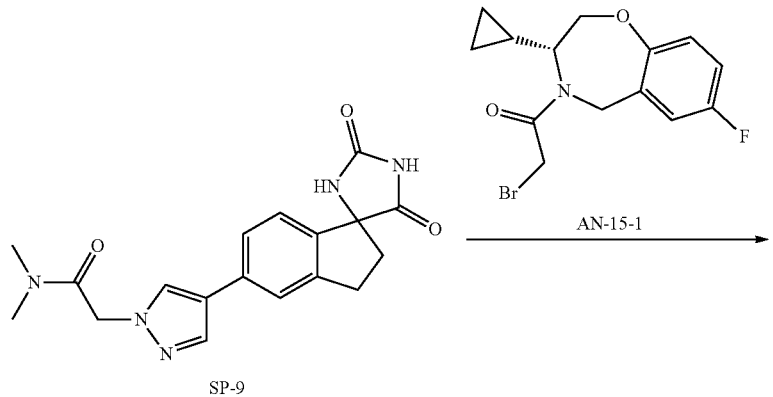
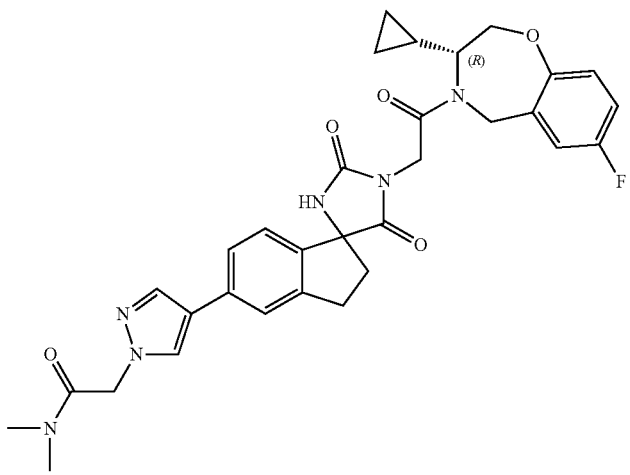
ZB-P-27

ZB—P-27 was prepared using the same method as that in Example 30, except that the spiro ring fragment SP-9 was used instead of SP-1 and the amide fragment AN-15-1 was used instead of AN-7: LC-MS: [M+H]$^+$=601.2.

Example 122 Synthesis of ZB—P-28

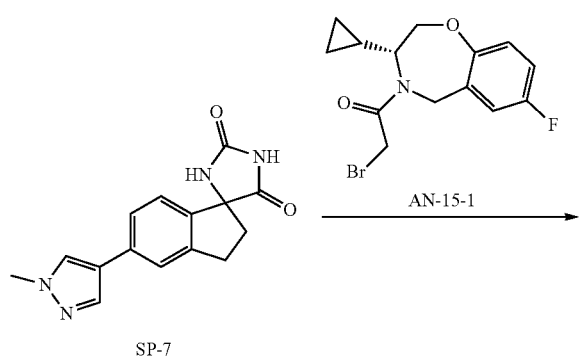
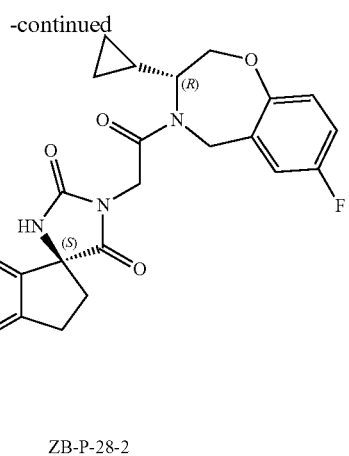
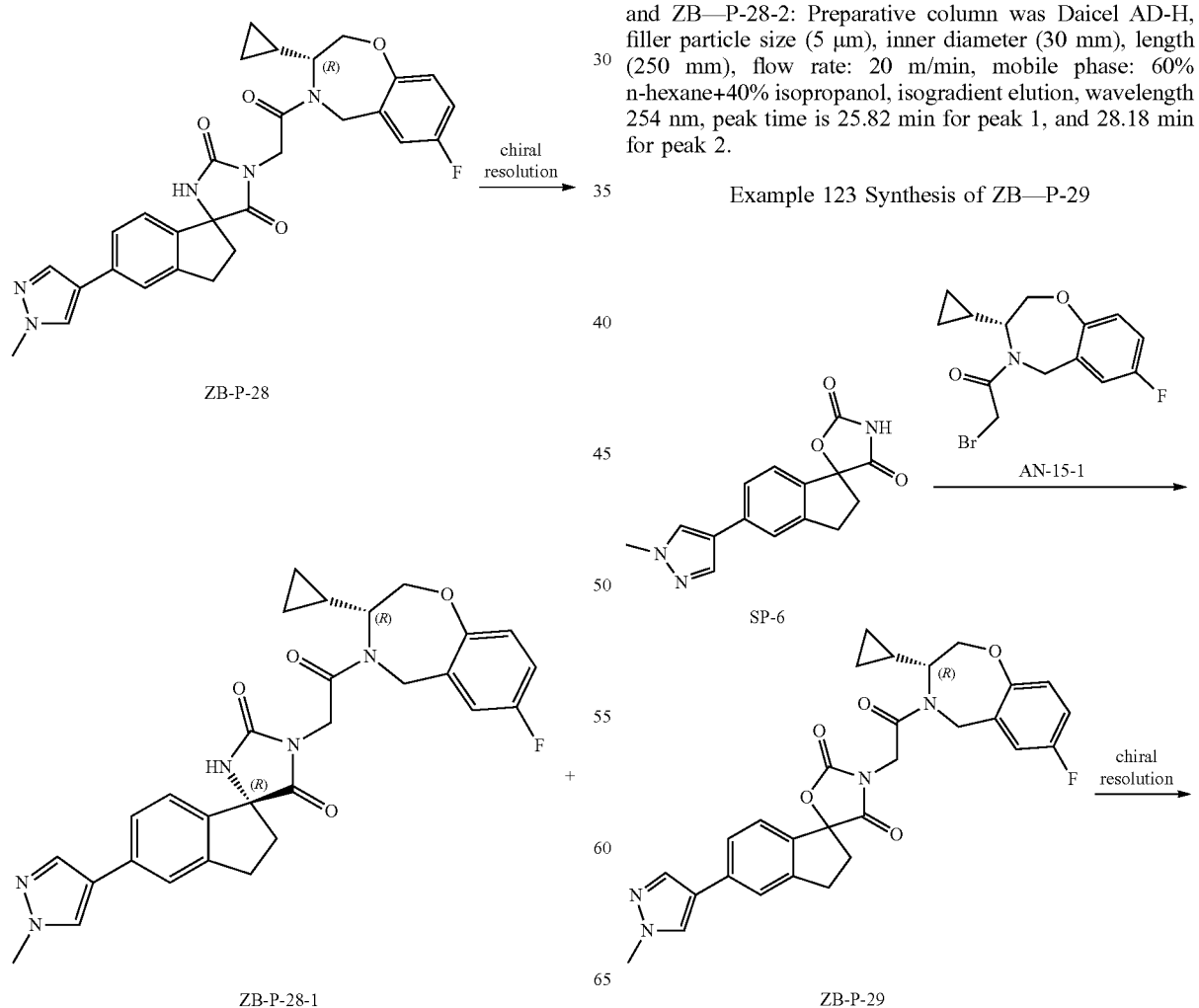

ZB—P-28 was prepared using the same method as that in Example 30, except that the spiro ring fragment SP-7 was used instead of SP-1 and the amide fragment AN-15-1 was used instead of AN-7: $^1$H NMR (400 MHz, DMSO-d$_6$) δ 8.76 (m, 1H), 8.13 (m, 1H), 7.86 (m, 1H), 7.46 (m, 2H), 7.25-6.90 (m, 4H), 5.02-3.73 (m, 10H), 3.01 (m, 2H), 2.53 (m, 1H), 2.22-1.98 (m, 1H), 1.33-1.18 (m, 1H), 0.60-0.35 (m, 4H). LC-MS: [M+H]$^+$=530.2.

Chiral resolution was performed to obtain ZB—P-28-1 and ZB—P-28-2: Preparative column was Daicel AD-H, filler particle size (5 μm), inner diameter (30 mm), length (250 mm), flow rate: 20 m/min, mobile phase: 60% n-hexane+40% isopropanol, isogradient elution, wavelength 254 nm, peak time is 25.82 min for peak 1, and 28.18 min for peak 2.

Example 123 Synthesis of ZB—P-29

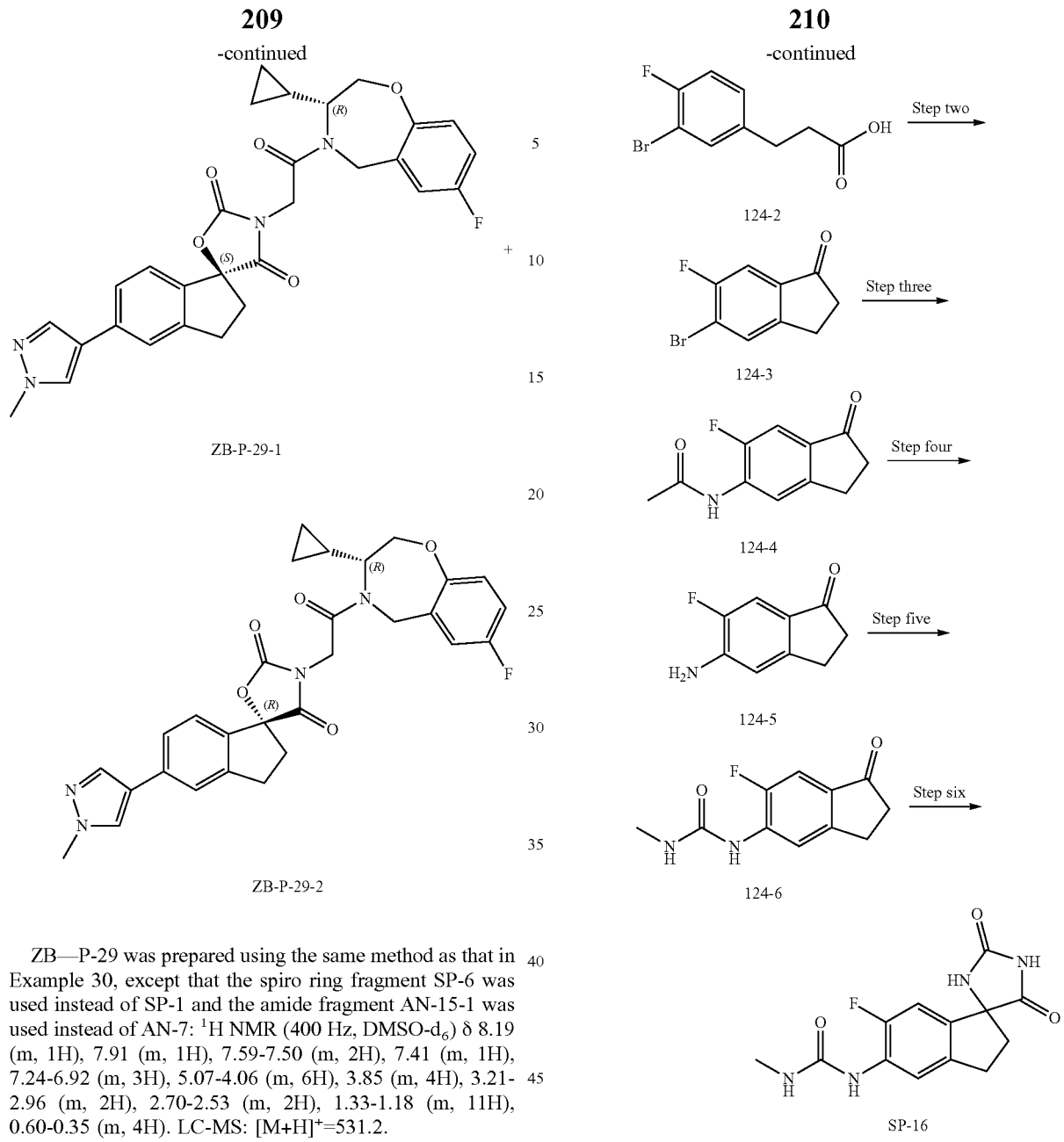

ZB-P-29-1

ZB-P-29-2

ZB—P-29 was prepared using the same method as that in Example 30, except that the spiro ring fragment SP-6 was used instead of SP-1 and the amide fragment AN-15-1 was used instead of AN-7: $^1$H NMR (400 Hz, DMSO-d$_6$) δ 8.19 (m, 1H), 7.91 (m, 1H), 7.59-7.50 (m, 2H), 7.41 (m, 1H), 7.24-6.92 (m, 3H), 5.07-4.06 (m, 6H), 3.85 (m, 4H), 3.21-2.96 (m, 2H), 2.70-2.53 (m, 2H), 1.33-1.18 (m, 11H), 0.60-0.35 (m, 4H). LC-MS: [M+H]$^+$=531.2.

Chiral resolution was performed to obtain ZB—P-29-1 and ZB—P-29-2: Preparative column was NANOMICRO OD-5H, filler particle size (5 μm), inner diameter (30 mm), length (250 mm), flow rate: 20 mL/min, mobile phase: 60% n-hexane+40% ethanol, isogradient elution, wavelength 254 nm, peak time is 29.51 min for peak 1, and 33.99 min for peak 2.

Example 124 Synthesis of Spiro Ring SP-16

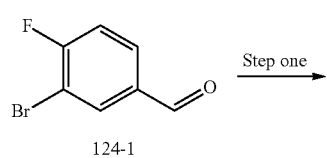

124-1

Step One:
Triethylamine (33.2 mL) was slowly added to formic acid (22.4 mL) at 0° C., stirred for 15 min, and slowly added into a solution of 3-bromo-4-fluorobenzaldehyde (124-1, 40.0 g) and cyclic-isopropylidene malonate (28.4 g) in DMF (200 mL). The reaction solution was slowly heated to 100° C. and stirred for 24 h. TCL showed disappearance of the raw material. The reaction solution was cooled to room temperature, alkalized with a 1N NaOH aqueous solution under an ice-water bath, and extracted with ethyl acetate. The aqueous layer was adjusted pH to 1-2 with 4N HCl, and extracted with ethyl acetate. The combined organic phase was washed with water and saturated brine, dried over anhydrous sodium sulfate, and concentrated. The crude was purified by silica gel column chromatography to obtain target product 124-2 (25.1 g). LC-MS: [M−H]$^−$=245.0.

Step Two:
124-2 (24.7 g) was dissolved in 1,2-dichloroethane (100 mL), added slowly with thionyl chloride (10 mL) and dry DMF (0.5 mL) at room temperature, heated at 70° C. and stirred for 3 h, and rotary evaporated to dryness directly. The crude was dissolved in dry dichloromethane (100 mL), slowly added dropwise into a solution of anhydrous aluminum chloride (40.0 g) in dichloromethane at room temperature, and reacted at 40° C. for 3 h. The reaction solution was cooled to room temperature, slowly poured into a cold ice hydrochloric acid, and extracted with dichloromethane. The combined organic phase was washed with water and saturated brine, dried over anhydrous sodium sulfate, and concentrated. The crude was purified by silica gel column chromatography to obtain the targeted 124-3 (13.2 g). LC-MS: [M+H]⁺=229.0.

Step Three:

124-3 (8.0 g), acetamide (4.0 g) and cesium carbonate (22.0 g) were dissolved in dry 1,4-dioxane (200 mL), added with tris(dibenzylideneacetone)dipalladium (Pd$_2$(dba)$_3$, 300 mg) and 4,5-bis(diphenylphosphino)-9,9-dimethylxanthene (Xantphos, 400 mg) under nitrogen, and reacted at 100° C. for 3 h under nitrogen. TLC showed disappearance of the raw material. The reaction solution was cooled to room temperature, poured into ice water and extracted with ethyl acetate. The combined organic phase was washed with water and saturated brine, dried over anhydrous sodium sulfate, and concentrated to obtain a crude 124-4, which was directly used in the next step. LC-MS: [M+H]⁺=208.1.

Step Four:

The crude 124-4 was dissolved in 6N HCl (40 mL)/methanol (100 mL), and stirred at 70° C. for 2 h. TLC showed that the reaction was complete. The reaction solution was cooled to room temperature, adjusted to neutral with 1N NaOH under an ice water bath, and extracted with ethyl acetate. The combined organic phase was washed with water and saturated brine, dried over anhydrous sodium sulfate, and concentrated to obtain a crude 124-5 (3.2 g, crude), which was directly used in the next step. LC-MS: [M+H]⁺=166.1.

Step Five:

The crude 124-5 was dissolved in THF (50 mL), added with p-nitrophenyl chloroformate (4.28 g) at room temperature, and reacted at room temperature for 1 h. Methylamine hydrochloride (2.6 g) was dissolved in methanol (100 mL), added with TEA (5 mL), stirred for 10 min, added slowly with the above reaction solution, and reacted at room temperature for 1 h. The reaction solution was poured into ice water and extracted with ethyl acetate. The combined organic phase was washed with water and saturated brine, dried over anhydrous sodium sulfate, and concentrated. The crude was purified by silica gel column chromatography to obtain the targeted 124-6 (3.11 g). LC-MS: [M+H]⁺=223.1.

Step Six:

124-6 (1.50 g), TMSCN (3.0 g), NH$_4$F (3.0 g), (NH$_4$)$_2$CO$_3$ (6.0 g) were dissolved in ammonia (20 mL)/ethanol (50 mL), and heated to 70° C. for 70 h. LCMS showed that the reaction was complete. The reaction solution was cooled to room temperature, rotary evaporated to dryness to remove ethanol, and added with saturated sodium bicarbonate solution. The aqueous phase was extracted with ethyl acetate, adjusted pH to 3~4 with 1M HCl, and extracted again with ethyl acetate. The organic phase was washed with water and brine, dried over sodium sulfate, and concentrated to precipitate a solid, which was filtered to obtain SP-16 (1.53 g) as a white solid, LC-MS: [M+H]⁺=293.1.

Example 125 Synthesis of Spiro Ring SP-17

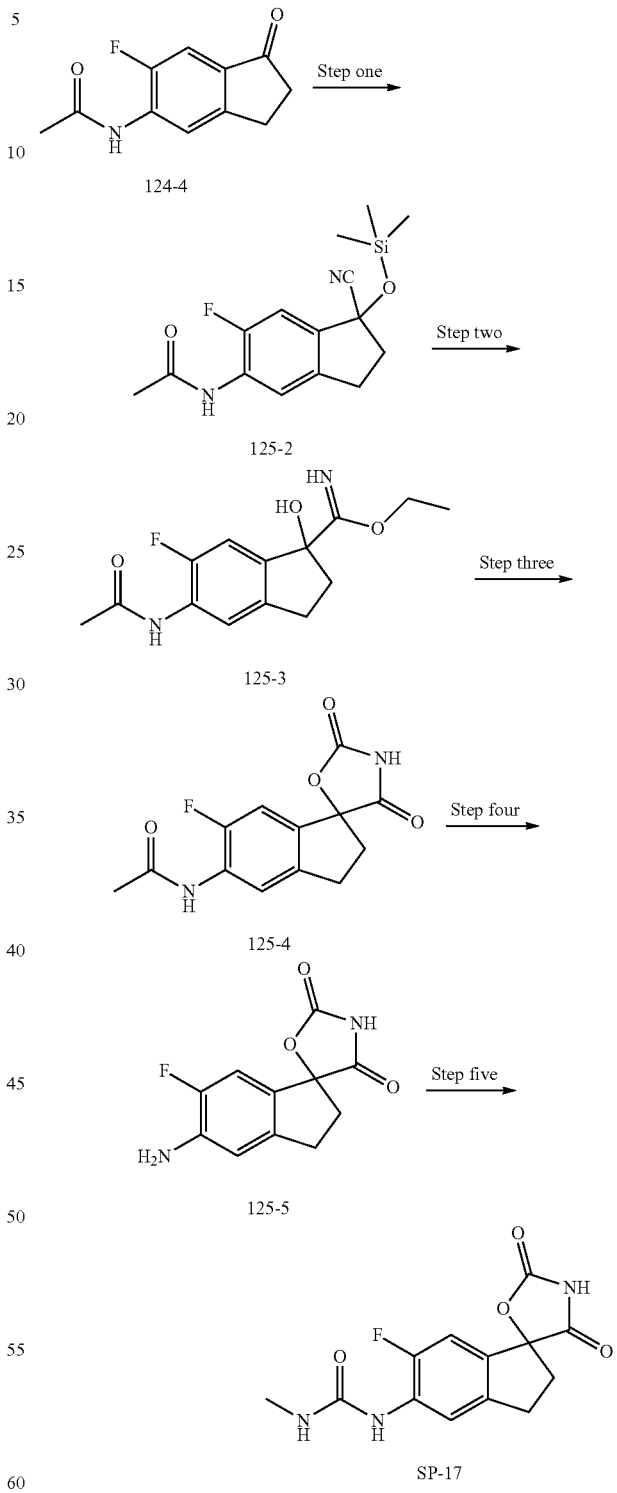

Step One:

124-4 (6.10 g), TMSCN (3.1 g), zinc iodide (0.4 g) were dissolved in toluene (50 mL)/acetonitrile (50 mL), and stirred at 75° C. for 4 h. TLC showed that the reaction was complete. The reaction solution was directly rotary evaporated to dryness. The residue was purified by column chromatography to obtain 125-2 (4.7 g) as an oil.

Step Two:

125-2 (4.71 g) was dissolved in absolute ethanol (70 mL), introduced with dry hydrogen chloride gas at 0° C. for 5 h, and rotary evaporated to dryness to obtain an oil, which was added with 20 mL of THF to be ultrasonically treated. The supernatant was discarded, and 125-3 as an oil was obtained and used in the next step.

Step Three:

125-3 was dissolved in anhydrous THF (50 mL), slowly added dropwise with TEA (1.5 g) at 0° C., added dropwise with triphosgene (8.90 g) dissolved in THF (50 mL), stirred at 0° C. for 1 h, added with 1N HCl (20 mL) and stirred further for 0.5 h. TLC showed that the reaction was complete. The reaction solution was poured into ice water and extracted with ethyl acetate. The organic phase was washed with saturated sodium bicarbonate 2 times. The aqueous phase was extracted with a small amount of ethyl acetate 2 times, adjusted pH to about 3-4 with 1N HCl, and extracted with ethyl acetate 3 times. The organic phase was washed with water and brine, dried over anhydrous sodium sulfate, and concentrated to obtain a crude 125-4 (1.11 g). LC-MS: $[M+H]^+=279.1$.

Step Four:

125-4 (1.1 g) was added with 30 mL of 6N HCl and 30 mL of methanol, heated to 75° C., and stirred for 3 h. The reaction mixture changed from turbidity to clear. TLC showed disappearance of the raw material. The resultant was adjusted to neutral with NaOH, extracted with ethyl acetate and layered. The organic phase was dried and rotary evaporated to dryness to obtain a crude 125-5 (0.9 g), which was used directly in the next step. LC-MS: $[M+H]^+=237.1$.

Step Five:

The crude 125-5 was dissolved in anhydrous THF (30 mL), added with phenyl p-nitrochloroformate (0.92 g, 4.1 mmol), and stirred at room temperature for 0.5 h to be ready for use. Methylamine hydrochloride (0.52 g) was dissolved in methanol (50 mL), added with TEA (0.70 g), stirred for 10 min, added with the above reaction solution, and stirred further at room temperature for 1 h. TLC showed that the reaction was complete. The reaction solution was poured into ice water, adjusted pH to 3~4 with 1N HCl, and extracted with ethyl acetate. The organic phase was washed with water and brine, dried over anhydrous sodium sulfate, and concentrated. The crude was purified by silica gel column chromatography to obtain SP-17 (680 mg). LC-MS: $[M+H]^+=294.1$.

Example 126 Synthesis of Spiro Ring SP-18

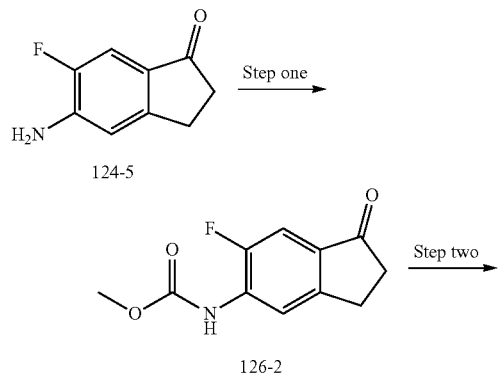

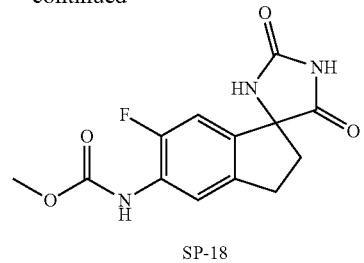

Step One:

124-5 (1 g) was dissolved in a mixed solution of ethyl acetate/water (volume ratio 2:1), added with solid sodium bicarbonate (1.14 g), cooled to 0° C. and stirred, added dropwise with methyl chloroformate (0.52 mL), stirred at 0° C. for 15 min, and warmed to room temperature to react overnight. The reaction solution was diluted with ethyl acetate, washed with 1M dilute hydrochloric acid, and layered. The organic phase was washed with saturated brine and layered. The organic phase was dried and concentrated. The residue was purified by column chromatography to obtain 126-2 (0.8 g). LC-MS: $[M+H]^+=224.1$.

Step Two:

126-2 (1.50 g), TMSCN (3.0 g), NH$_4$F (3.0 g), (NH$_4$)$_2$CO$_3$ (6.0 g) were dissolved in ammonia (20 mL)/ethanol (50 mL), and heated to 70° C. to react for 70 h. LCMS showed that the reaction was complete. The reaction solution was cooled to room temperature, rotary evaporated to dryness to remove ethanol, and added with saturated sodium bicarbonate solution. The aqueous phase was extracted with ethyl acetate, adjusted pH to 3~4 with 1M HCl, and extracted again with ethyl acetate. The organic phase was washed with water and brine, dried over anhydrous sodium sulfate, and concentrated to precipitate a solid, which was filtered to obtain SP-18 as a white solid, LC-MS: $[M+H]^+=294.1$.

Example 127 Synthesis of ZB—P-30

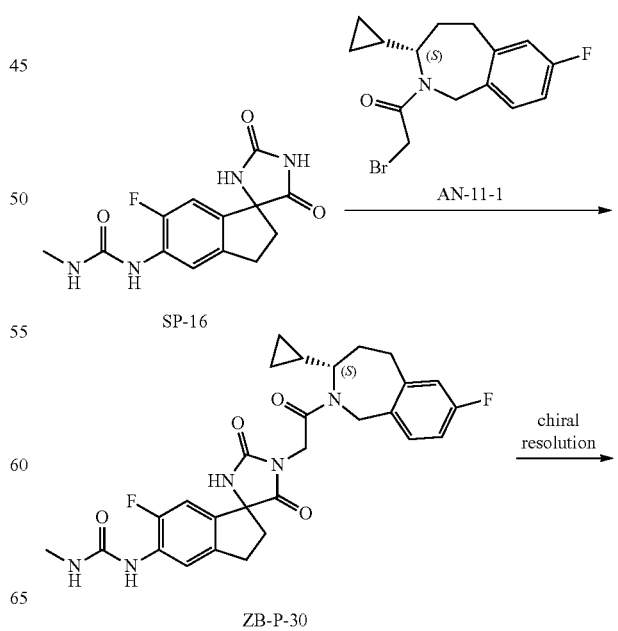

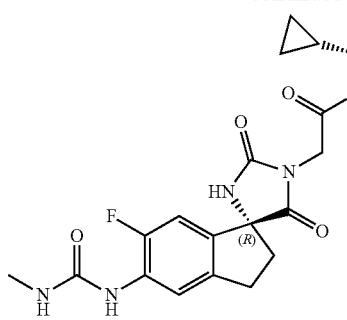

ZB-P-30-1

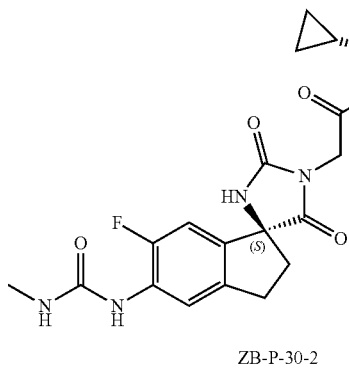

ZB-P-30-2

ZB—P-30 was prepared using the same method as that in Example 30, except that the spiro ring fragment SP-16 was used instead of SP-1 and the amide fragment AN-11-1 was used instead of AN-7:

$^1$H NMR (400 MHz, DMSO-d$_6$) δ 8.74 (m, 1H), 8.32 (m, 1H), 8.05 (m, 1H), 7.39-6.88 (m, 4H), 6.50-4.14 (m, 3H), 4.92-3.41 (m, 5H), 3.10 (m, 3H), 2.68 (m, 2H), 2.15-1.90 (m, 3H), 1.30 (m, 1H), 0.60-0.24 (m, 4H). LC-MS: [M+H]$^+$= 538.2.

Chiral resolution was performed to obtain ZB-P30-1 and ZB-P30-2: Preparative column was NANOMICRO OD-5H, filler particle size (5 μm), inner diameter (30 mm), length (250 mm), flow rate: 30 mL/min, mobile phase: 85% n-hexane+15% ethanol, isogradient elution, wavelength 254 nm, peak time is 62.18 min for peak 1, and 78.65 min for peak 2.

Example 128 Synthesis of ZB—P-31

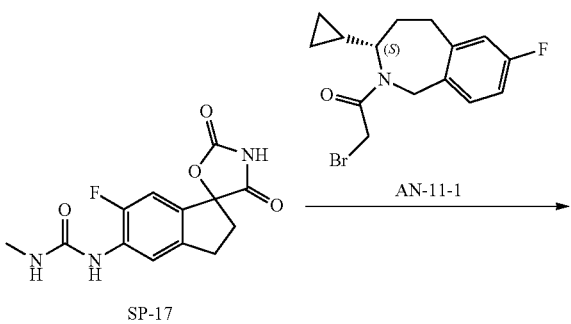

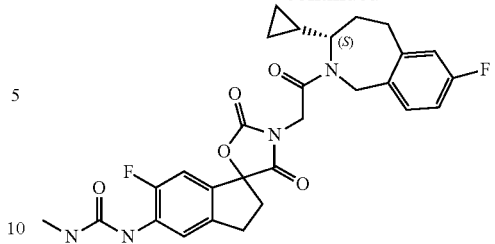

ZB-P-31

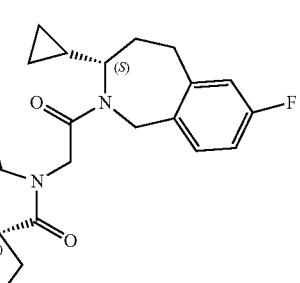

ZB-P-31-1

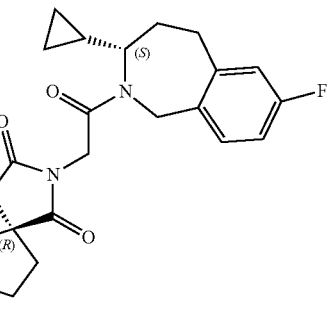

ZB-P-31-2

ZB—P-31 was prepared using the same method as that in Example 30, except that the spiro ring fragment SP-17 was used instead of SP-1 and the amide fragment AN-11-1 was used instead of AN-7:

$^1$H NMR (400 MHz, DMSO-d$_6$) δ 8.46 (m, 1H), 8.18 (m, 1H), 7.38-6.90 (m, 4H), 6.58 (m, 1H), 4.95-3.48 (m, 5H), 3.10-1.98 (m, 11H), 1.30 (m, 1H), 0.60-0.24 (m, 4H). LC-MS: [M+H]$^+$=539.2.

Chiral resolution was performed to obtain ZB-P31-1 and ZB-P31-2: Preparative column was NANOMICRO OD-5H, filler particle size (5 μm), inner diameter (30 mm), length (250 mm), flow rate: 20 mL/min, mobile phase: 80% n-hexane+20% ethanol, isogradient elution, wavelength 254 nm, peak time is 28.10 min for peak 1, and 31.59 min for peak 2.

Example 129 Synthesis of ZB—P-32

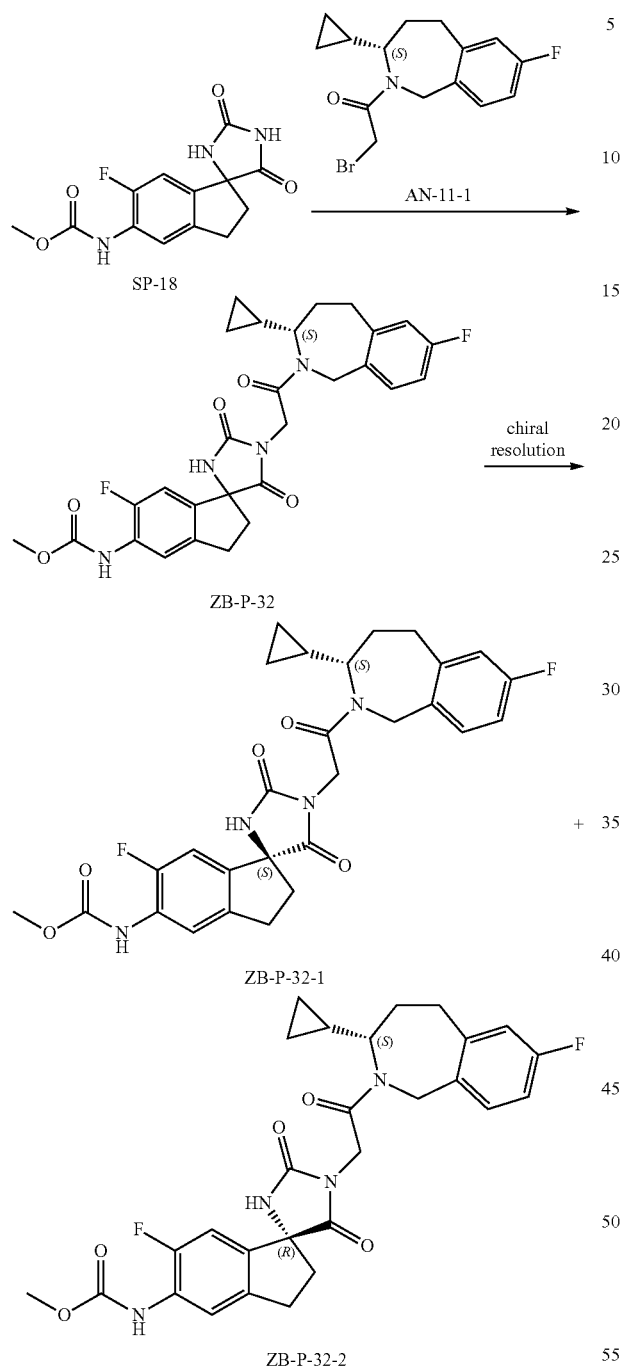

Chiral resolution conditions: analytical column was NANOMICRO OD-5H, filler particle size (5 μm), inner diameter (4.6 mm), length (250 mm), flow rate: 1 mL/min, mobile phase: 60% n-hexane+40% isopropanol, isogradient elution, wavelength 254 nm, total time: 40 min; peak time is 7.54 min for peak 1, and 14.94 min for peak 2.

Example 130 Synthesis of ZB—P-33

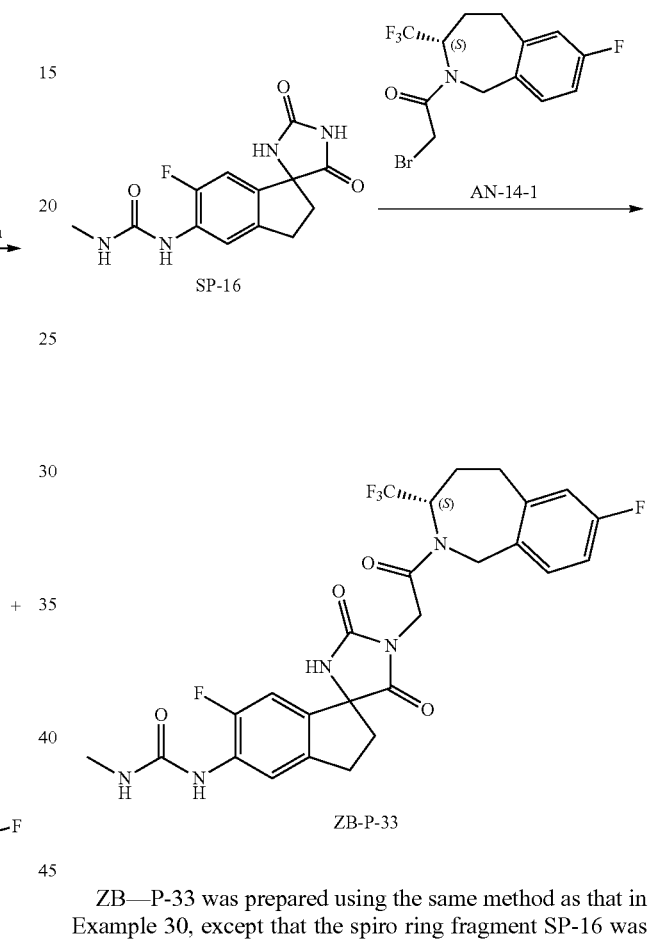

ZB—P-32 was prepared using the same method as that in Example 30, except that the spiro ring fragment SP-18 was used instead of SP-1 and the amide fragment AN-11-1 was used instead of AN-7: $^1$H NMR (400 MHz, DMSO-$d_6$) δ 9.36 (m, 1H), 8.80 (m, 1H), 7.55 (m, 1H), 7.38-7.23 (m, 2H), 7.08-6.90 (m, 2H), 4.85-3.45 (m, 8H), 3.20-2.93 (m, 3H), 2.74-2.51 (m, 2H), 2.21-1.96 (m, 3H), 1.48-1.31 (m, 1H), 0.63-0.22 (m, 4H). LC-MS: [M+H]$^+$=539.2.

The ZB—P-32 was subjected to chiral resolution to obtain chiral products ZB—P-32-1 and ZB—P-32-2.

ZB—P-33 was prepared using the same method as that in Example 30, except that the spiro ring fragment SP-16 was used instead of SP-1 and the amide fragment AN-14-1 was used instead of AN-7: LC-MS: [M+H]$^+$=566.2.

Example 131 Synthesis of ZB—P-34

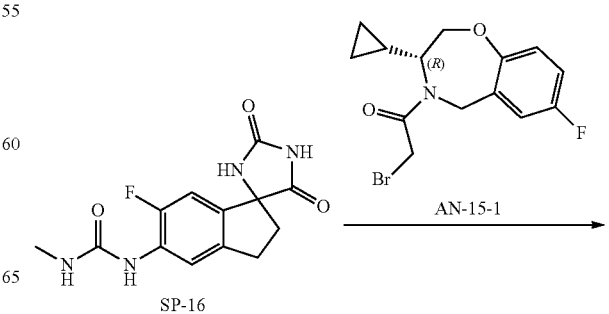

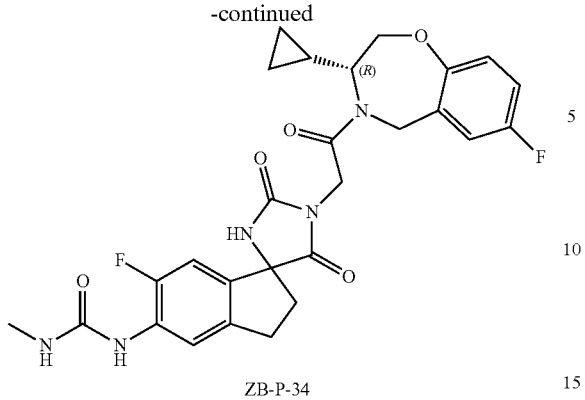

ZB-P-34

ZB—P-34 was prepared using the same method as that in Example 30, except that the spiro ring fragment SP-16 was used instead of SP-1 and the amide fragment AN-15-1 was used instead of AN-7: LC-MS: [M+H]⁺=540.2.

Example 132 Synthesis of ZB—P-35

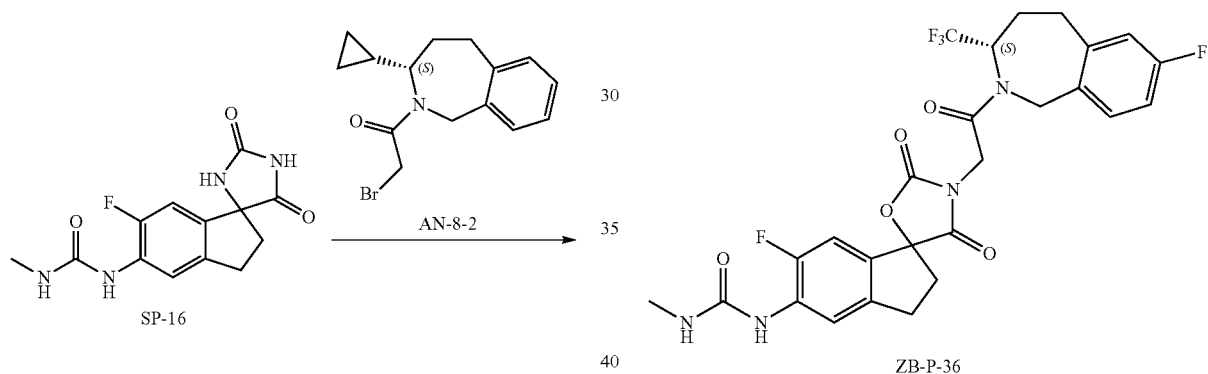

ZB-P-35

ZB—P-35 was prepared using the same method as that in Example 30, except that the spiro ring fragment SP-16 was used instead of SP-1 and the amide fragment AN-8-2 was used instead of AN-7: LC-MS: [M+H]⁺=520.2.

Example 133 Synthesis of ZB—P-36

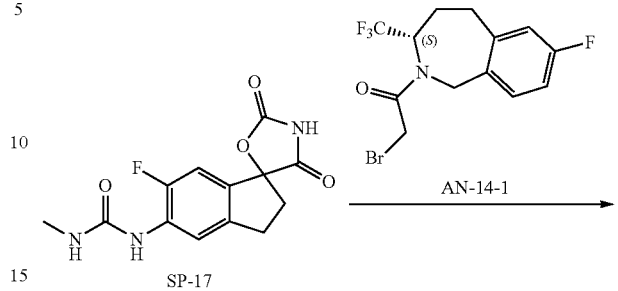

SP-17

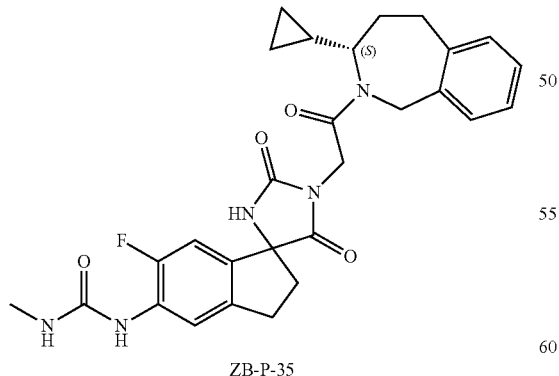

ZB-P-36

ZB—P-36 was prepared using the same method as that in Example 30, except that the spiro ring fragment SP-17 was used instead of SP-1 and the amide fragment AN-14-1 was used instead of AN-7: LC-MS: [M+H]⁺=567.2.

Example 134

Synthesis of ZB—P-37

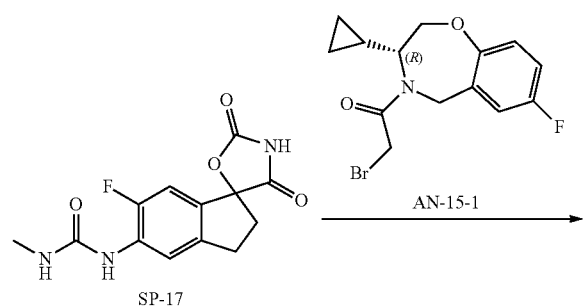

SP-17

-continued

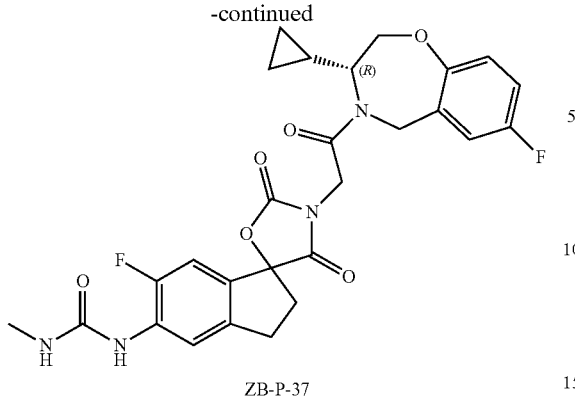

ZB-P-37

ZB—P-37 was prepared using the same method as that in Example 30, except that the spiro ring fragment SP-17 was used instead of SP-1 and the amide fragment AN-15-1 was used instead of AN-7: LC-MS: [M+H]$^+$=541.2.

Example 135 Synthesis of ZB—P-38

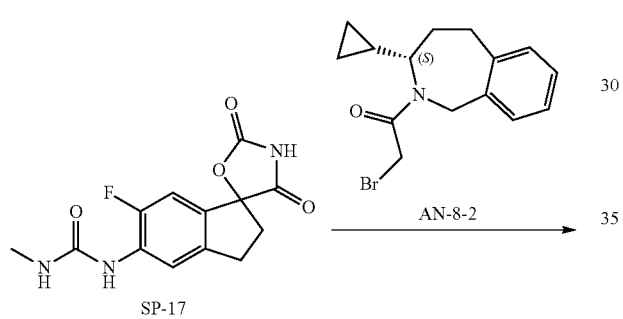

ZB-P-38

ZB—P-38 was prepared using the same method as that in Example 30, except that the spiro ring fragment SP-17 was used instead of SP-1 and the amide fragment AN-8-2 was used instead of AN-7: LC-MS: [M+H]$^+$=521.2.

Example 136 Synthesis of ZB—P-39

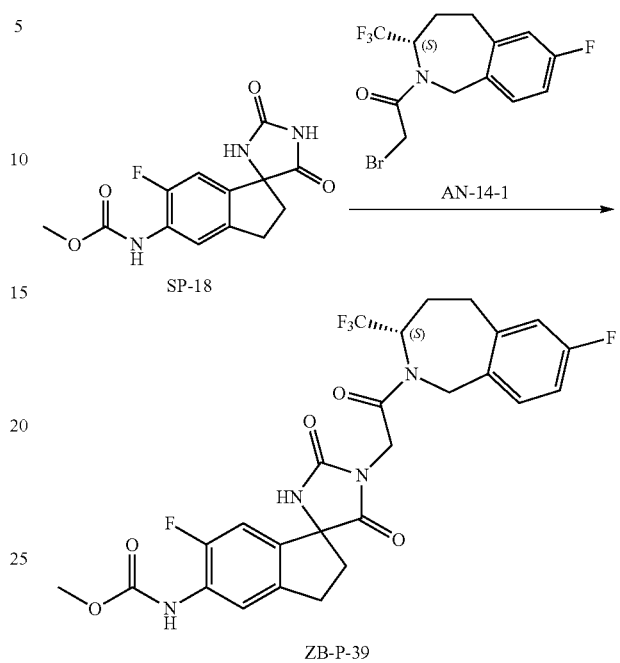

ZB-P-39

ZB—P-39 was prepared using the same method as that in Example 30, except that the spiro ring fragment SP-18 was used instead of SP-1 and the amide fragment AN-14-1 was used instead of AN-7: LC-MS: [M+H]$^+$=567.2.

Example 137 Synthesis of ZB—P-40

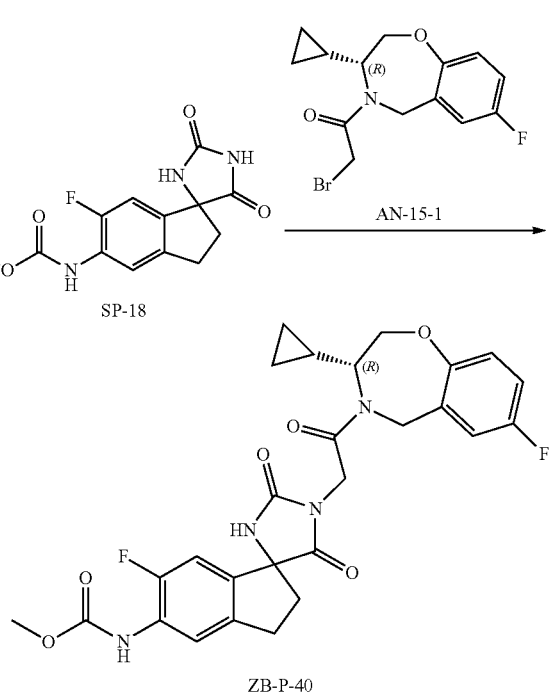

ZB-P-40

ZB—P-40 was prepared using the same method as that in Example 30, except that the spiro ring fragment SP-18 was used instead of SP-1 and the amide fragment AN-15-1 was used instead of AN-7: LC-MS: [M+H]⁺=541.2.

Example 138 Synthesis of ZB—P-41

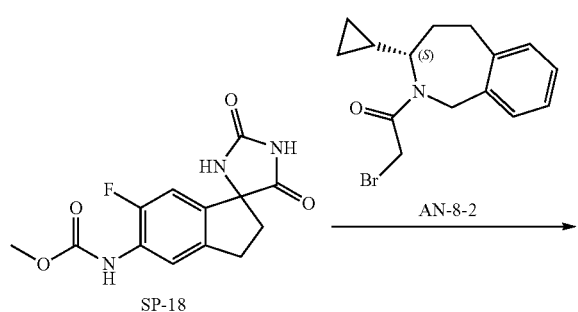

ZB—P-41 was prepared using the same method as that in Example 30, except that the spiro ring fragment SP-18 was used instead of SP-1 and the amide fragment AN-8-2 was used instead of AN-7: LC-MS: [M+H]⁺=521.2.

Example 139 Synthesis of ZB—P-42

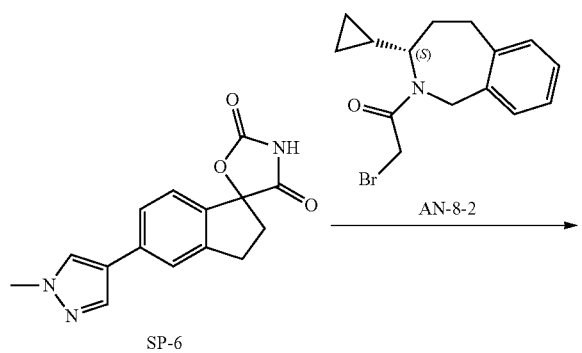

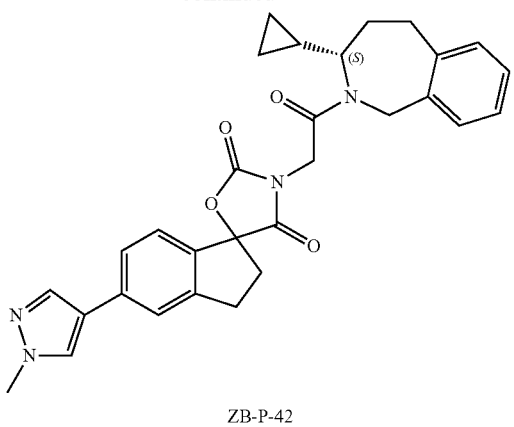

ZB—P-42 was prepared using the same method as that in Example 30, except that the spiro ring fragment SP-6 was used instead of SP-1 and the amide fragment AN-8-2 was used instead of AN-7: LC-MS: [M+H]⁺=511.2.

Example 140 Synthesis of ZB—P-43

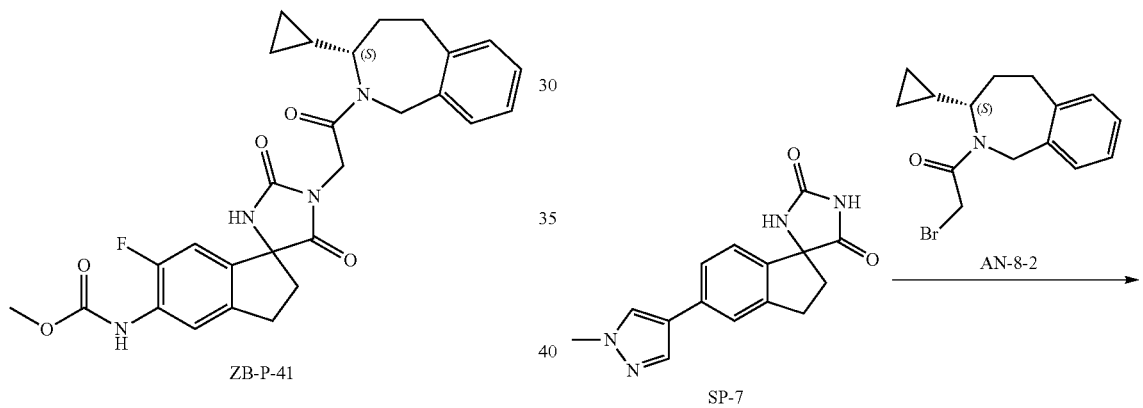

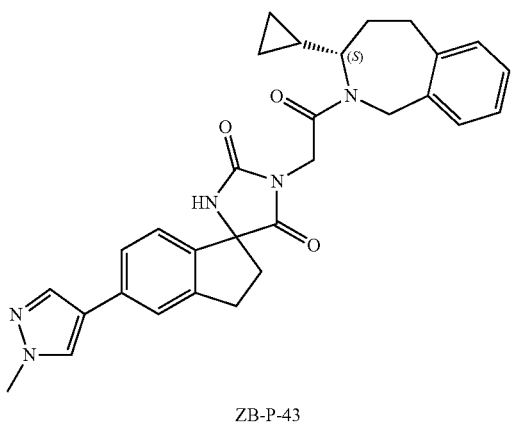

ZB—P-43 was prepared using the same method as that in Example 30, except that the spiro ring fragment SP-7 was used instead of SP-1 and the amide fragment AN-8-2 was used instead of AN-7: LC-MS: [M+H]⁺=510.2.

Example 141 Synthesis of ZB—P-44

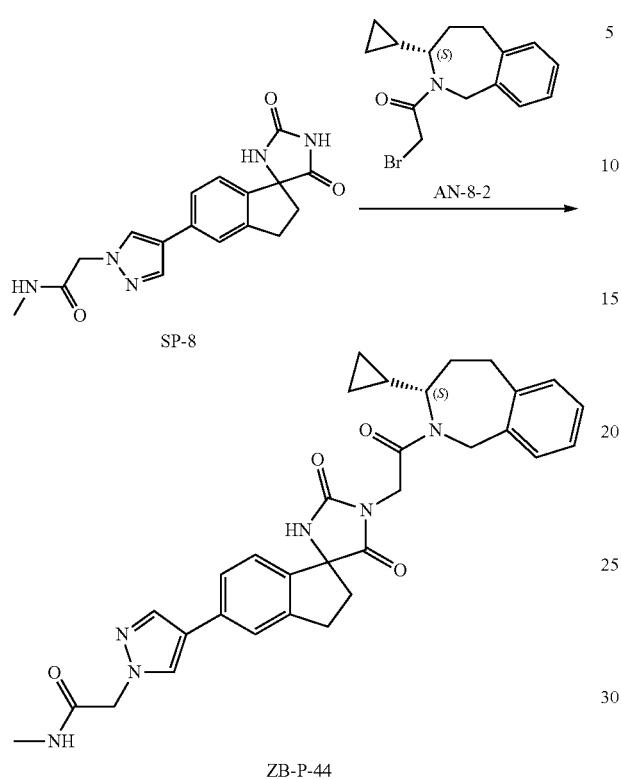

ZB—P-44 was prepared using the same method as that in Example 30, except that the spiro ring fragment SP-8 was used instead of SP-1 and the amide fragment AN-8-2 was used instead of AN-7: LC-MS: [M+H]$^+$=567.2.

Example 142 Synthesis of Amide AN-16

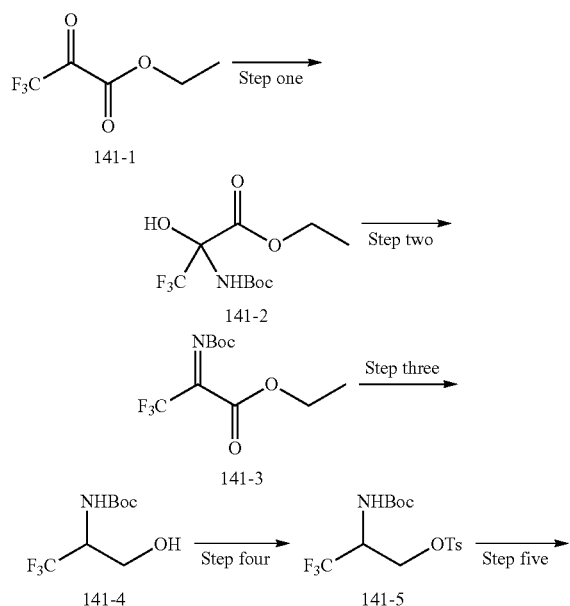

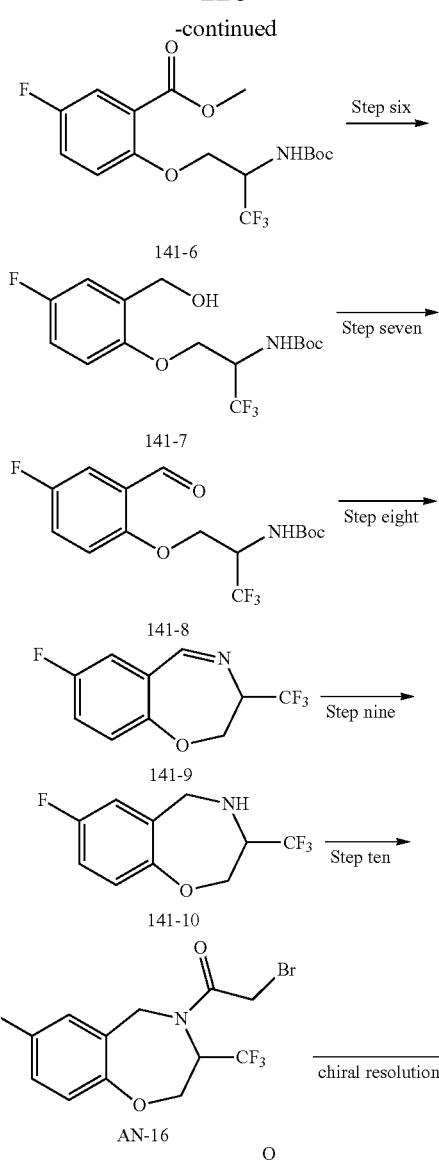

Step One:

Ethyl 3,3,3-trifluoropyruvate (25.0 g, 0.147 mol) was dissolved in dichloromethane (100 mL) under nitrogen, added with tert-butyl carbamate (13.5 g, 0.115 mol), and stirred at room temperature for 16 h. TLC showed that the reaction was complete. The resultant was concentrated and dried to obtain a crude 141-2 (32.4 g) as a white solid.

227

Step Two:

141-2 (32.4 g) and pyridine (55 mL, 0.452 mol) were added to diethyl ether (400 mL) under nitrogen, added slowly with trifluoroacetic anhydride (56.7 g, 0.226 mol) under an ice bath, and stirred at room temperature for 16 h. TLC showed that the reaction was complete. The reaction solution was filtered, and the filter cake was washed with diethyl ether. The solid was dried, dissolved in dichloromethane, washed with water and saturated brine, dried over anhydrous sodium sulfate, and concentrated to obtain a crude 141-3 (30 g) as a yellowish semi-solid, which was used directly in the next step.

Step Three:

141-3 (30 g, crude) was dissolved in anhydrous tetrahydrofuran (300 mL), cooled in an ice-water bath, added batchwise with lithium aluminum tetrahydrogen (7.7 g, 0.2 mol) under nitrogen, slowly raised to room temperature, and stirred for 16 h. TLC showed that the reaction was complete. The reaction solution was quenched by slowly adding 15% sodium hydroxide solution in an ice water bath, added with water and extracted with ethyl acetate. The organic phase was washed with water and saturated brine, dried over anhydrous sodium sulfate and concentrated to obtain a crude 141-4 (15 g) as a yellowish solid, which was used directly in the next step.

Step Four:

141-4 (11.0 g) was dissolved in dichloromethane (200 mL), added with p-toluenesulfonyl chloride (15.2 g, 80 mmol), triethylamine (12.3 g, 122 mmol) and 4-dimethylaminopyridine (7.44 g, 61 mmol), and stirred for 3 h. TLC showed that the raw material was completely reacted. The reaction solution was quenched by slowly adding water and extracted with dichloromethane. The combined organic phase was washed with water and brine, dried over anhydrous sodium sulfate, and concentrated. The crude was purified by silica gel column chromatography to obtain 141-5 (10.2 g).

Step Five:

Methyl 5-fluoro-2-hydroxybenzoate (6.00 g, 35.3 mmol) was dissolved in dry DMF (30 mL), added with 141-5 (13.5 g, 35.3 mmol) and potassium carbonate (9.67 g, 70 mmol), and stirred at room temperature for 12 h. TLC showed that the raw material was completely reacted. The reaction solution was poured into ice water and extracted with ethyl acetate. The combined organic phase was washed with water and brine, dried over anhydrous sodium sulfate, and concentrated. The crude was purified by silica gel column chromatography to obtain 141-6 (2.52 g).

Step Six:

141-6 (2.52 g, 3.93 mmol) was dissolved in anhydrous tetrahydrofuran (50 mL), slowly added with lithium aluminum tetrahydrogen (500 mg, 13.16 mmol) at room temperature, and stirred at room temperature for 1 h. Then TLC showed that the reaction was complete. The reaction solution was added slowly with a 15% sodium hydroxide solution, and then with water and extracted with ethyl acetate. The organic phase was washed with water and saturated brine, dried over anhydrous sodium sulfate, and concentrated to obtain 141-7 (2.05 g, crude), which was used directly in the next step. LC-MS: 376.1 [M+Na]$^+$.

Step Seven:

141-7 (1.60 g, crude) was dissolved in dichloromethane (200 mL), added with active manganese dioxide (8.0 g), and stirred at room temperature for 2 h. TLC showed that the reaction was complete. The reaction solution was filtered and concentrated to obtain a crude 141-8 (1.2 g), LC-MS: 374.1 [M+Na]$^+$.

228

Step Eight:

141-8 (1.2 g) was dissolved in trifluoroacetic acid (15 mL) and stirred at room temperature for 30 min. TLC showed that the reaction was complete. The reaction solution was concentrated to obtain a crude 141-9, which was used directly in the next step.

Step Nine:

141-9 was dissolved in dichloromethane (20 mL), added with sodium cyanoborohydride (204 mg), and stirred for 30 min at room temperature. TLC showed that the reaction was complete. The reaction solution was poured into ice water, and extracted with dichloromethane. The organic phase was washed with saturated brine, dried over anhydrous sodium sulfate, and concentrated. The crude was purified by silica gel column chromatography to obtain 141-10 (440 mg). LC-MS: 236.1 [M+H]$^+$.

Step Ten:

141-10 (440 mg, 1.87 mmol) was dissolved in anhydrous dichloromethane (20 mL), added with bromoacetyl bromide, and stirred at room temperature overnight. TLC showed that the reaction was complete. After treatment and purification, the targeted AN-16 (506 mg, yield 76%) was obtained. LC-MS: 356.0 [M+H]$^+$.

AN-16 was subjected to chiral resolution to obtain chiral products AN-16-1 and AN-16-2.

Chiral resolution conditions: preparative column was NANOMICRO OD-5H, filler particle size (5 μm), inner diameter (30 mm), length (250 mm), flow rate: 20 mL/min, mobile phase: 80% n-hexane+20% ethanol, isogradient elution, wavelength 220 nm, total time: 20 min; peak time is 12.9 min for peak 1, and 16.2 min for peak 2.

Example 143 Synthesis of Spiro Ring SP-19

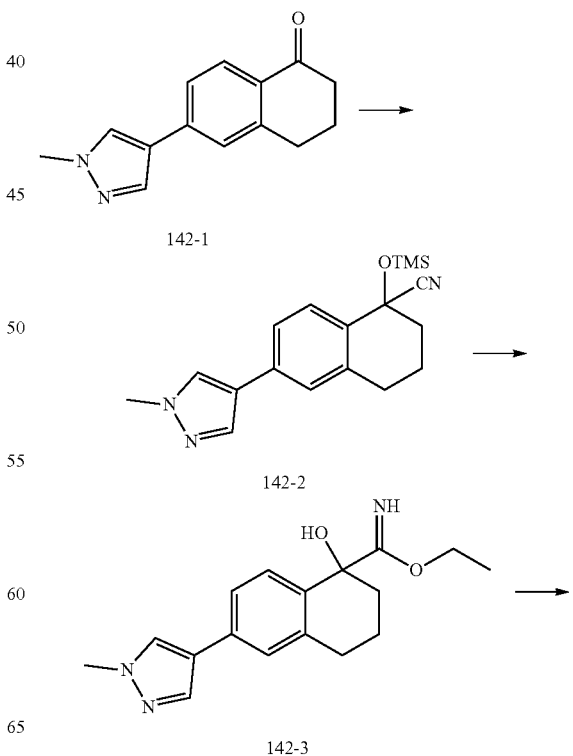

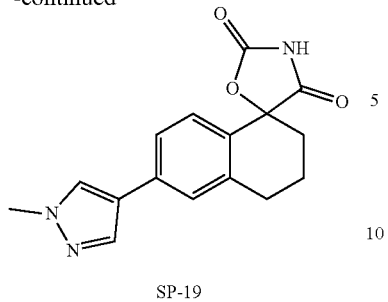

SP-19

Step One:

142-1 (4.7 g, 20.7 mmol) was dissolved in a mixed solvent of toluene/acetonitrile (50/50 mL), added with TMSCN (6.2 g, 42.9 mmol) and $ZnI_2$ (1.4 g, 1.44 mmol) at room temperature, heated to 80° C. to react for 18 h. TLC showed that the reaction was complete. The reaction solution was cooled to room temperature, quenched with water and extracted with ethyl acetate. The combined organic phase was washed with water and saturated brine, dried over anhydrous sodium sulfate, and concentrated to obtain a crude, which was purified by silica gel column chromatography to obtain 142-2 (6.21 g).

Step Two:

142-2 (6.2 g, 19.1 mmol) was dissolved in absolute ethanol (30 mL), cooled to below 0° C., and continuously introduced with dry HCl gas for 6 h. The resultant was concentrated at 35° C., slurried in THF and filtered. The filter cake was dried to obtain 142-3 (crude), which was directly used in the next step.

Step Three:

The crude 142-3 was dissolved in anhydrous tetrahydrofuran (10 mL), added with triethylamine (5.79 g, 57.2 mmol), and then with Triphosgene (2.27 g, 7.64 mmol) under an ice bath, and stirred for 10 min. TLC showed that the reaction was complete. The reaction mixture was adjusted pH to 5-6 with concentrated hydrochloric acid and stirred for 30 min. TLC showed that the reaction was complete. The reaction solution was poured into ice water, and extracted with ethyl acetate twice. The organic phase was stirred with 4N NaOH for 10 min. The organic phase was separated, and the aqueous phase was adjusted to be weakly acidic with concentrated hydrochloric acid to precipitate a solid. The solid was purified by column chromatography to obtain the targeted SP-19 (750 mg). LCMS: 298.1 [M+H]⁺.

Example 144 Synthesis of Spiro Ring SP-20

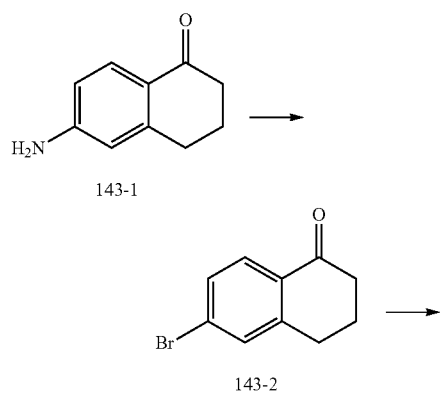

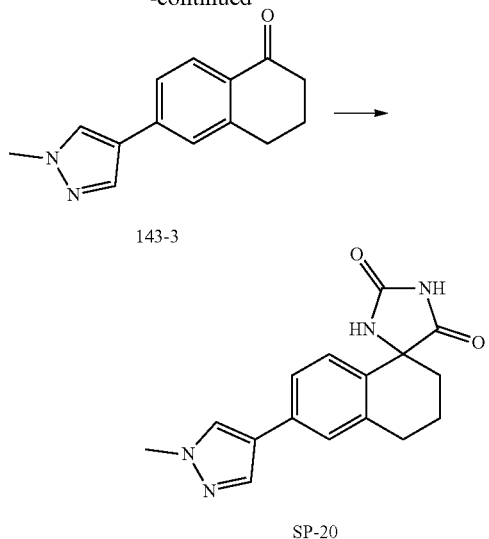

SP-20

Step One:

6-Amino-1,2,3,4-tetrahydro-1-naphthone (143-1, 10.0 g, 62.0 mmol) was dissolved in 48% aqueous hydrobromic acid solution (120 mL), slowly added dropwise with a solution of $NaNO_2$ (4.70 g, 68.2 mmol) in $H_2O$ (50 mL) at −5 to 5° C., and reacted at the temperature for 30 min. The reaction solution was slowly added into a mixture of CuBr (19.5 g, 136.4 mmol)/HBr (20 mL), and stirred at room temperature for 30 min. TLC showed that the reaction was complete. The resultant was extracted with ethyl acetate. The combined organic phase was washed with water, saturated sodium bicarbonate solution and saturated brine, dried over anhydrous sodium sulfate, and concentrated. The crude was purified by silica gel column chromatography to obtain the targeted 143-2 (5.2 g). ¹H-NMR: (CDCl₃, 400 MHz): δ 2.13-2.19 (m, 2H), 2.67 (t, J=6.8 Hz, 2H), 2.97 (t, J=6.0 Hz, 2H), 7.46-7.48 (m, 2H), 7.90-7.92 (m, 1H).

Step Two:

143-2 (8.3 g, 36.9 mmol) and 1-methyl-H-pyrazole-4-boronic acid, pinacol ester (11.62 g, 55.4 mmol) were dissolved in dry DMF (50 ml), and added with water (5 mL), sodium carbonate (7.8 g, 73.8 mmol) and Pd(dppf)Cl₂ (400 mg, 3.69 mmol) at room temperature. After atmosphere was replaced with nitrogen three times, the reaction mixture was reacted at 70° C. for 3 h under nitrogen. TLC showed that the reaction was complete. The reaction solution was cooled to room temperature, poured into ice water, and extracted with ethyl acetate. The organic phase was washed with water and saturated brine, dried over anhydrous sodium sulfate, and concentrated. The crude was purified by silica gel column chromatography to obtain 143-3 (4.7 g). LC-MS: 227.1 [M+H]⁺.

Step Three:

143-3 (1.0 g, 4.4 mmol) was dissolved in EtOH (20 mL) at room temperature, added with TMSCN (4.4 g, 44 mmol), ammonium fluoride (1.6 g, 44 mmol), ammonium carbonate (6.4 g, 66 mmol) and ammonia (10 mL) at room temperature, and heated to 60° C. to react for 18 h. TLC showed that some of the raw material was remaining. The reaction solution was supplemented with ammonium carbonate (3.2 g, 33 mmol), and reacted further for 6 h. The reaction solution was cooled to room temperature, quenched with water and extracted with ethyl acetate. The combined organic phase was washed with saturated brine, dried over anhydrous sodium sulfate, and concentrated. The crude was purified by silica gel column chromatography to obtain SP-20 (340 mg). LCMS: 295.1[M–H]⁻.

Example 145 Synthesis of Spiro Ring SP-21

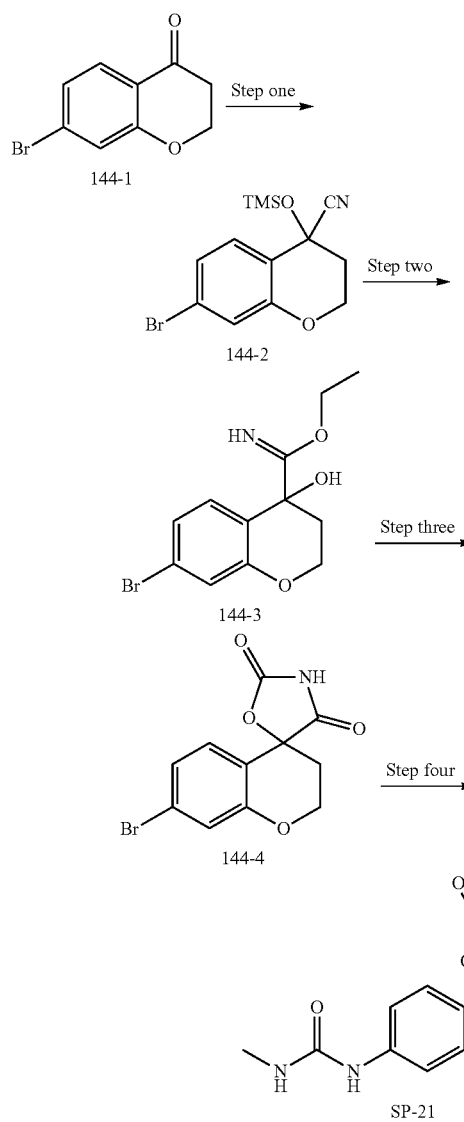

(6.8 g, 68.3 mmol) under ice bath. After the reaction was finished, the reaction mixture was adjusted to be weakly acidic with a diluted HCl to become clear, stirred at room temperature for 30 min, and concentrated. The residue was added with water and extracted with ethyl acetate. The organic phase was washed with aqueous sodium hydroxide solution, and the aqueous phase was extracted again with ethyl acetate. The aqueous phase was remained, acidized with dilute hydrochloric acid, and extracted with ethyl acetate. The organic phase was remained, washed with water and saturated brine, dried, and concentrated to obtain 144-4 (890 mg) as a white solid. LC-MS: 296.0 [M+H]⁺.

Step Four:

144-4 (890 mg, 2.9 mmol), methylurea (443 mg, 5.8 mmol), Pd$_2$(dba)$_3$ (3.27 mg, 0.03 mmol), xantphos (34 mg, 0.06 mmol) and cesium carbonate (2 g, 5.8 mmol) were dissolved in dioxane (50 mL) and reacted under nitrogen. After the reaction was complete, the resultant was added with water and extracted with ethyl acetate. The organic phase was dried and concentrated. The residue was purified by silica gel column chromatography to obtain 160 mg of SP-21.

Example 146 Synthesis of Spiro Ring SP-22

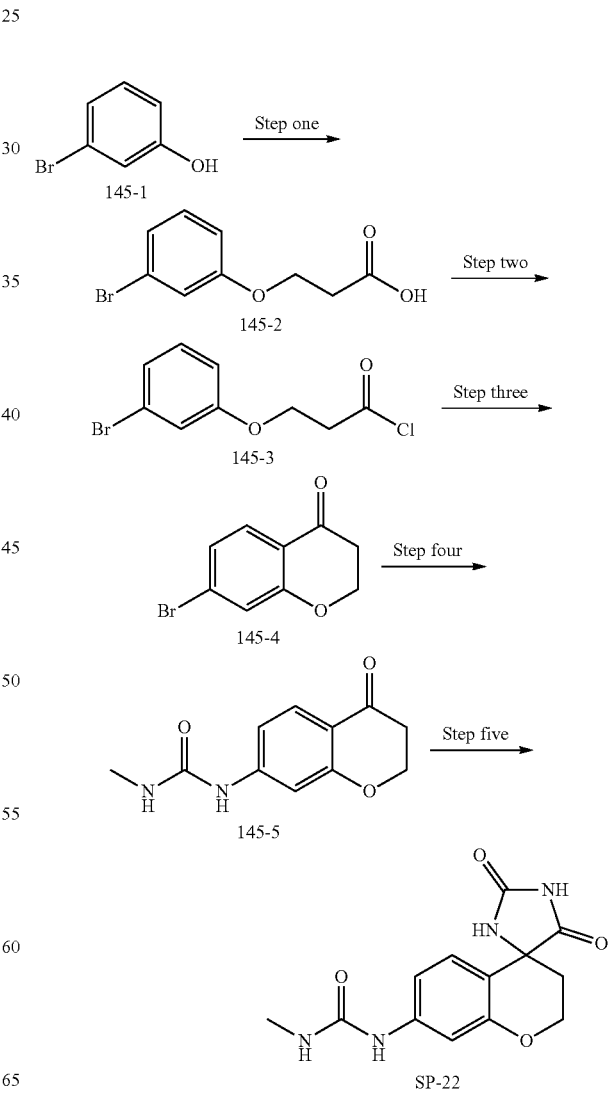

Step One:

144-1 (12.0 g, 52.8 mmol) was dissolved in a mixed solvent of toluene (100 mL) and acetonitrile (100 mL), added with TMSCN (5.7 g, 58.1 mmol) and zinc iodide (0.8 g, 2.6 mmol), and reacted at 75° C. for 3 h. The reaction solution was concentrated and the residue was purified by silica gel column chromatography to obtain 144-2 (7.4 g).

Step Two and Step Three:

144-2 (7.4 g, 22.7 mmol) was dissolved in absolute ethanol (150 mL), introduced with dry HCl gas at 0° C. to react for 5 h, and concentrated at 38° C. to obtain a crude 144-3 as a white solid. 144-3 was dissolved in tetrahydrofuran (20 mL), treated ultrasonically for 5 min, and filtered. The filter cake was dissolved in tetrahydrofuran (50 mL), added with triphosgene (6.7 g, 22.7 mmol) and triethylamine

Step One:

m-Bromophenol (145-1, 34.6 g, 0.2 mol) was dissolved in 3-chloropropionic acid (21.7 g, 0.2 mol), added dropwise with a solution of sodium hydroxide (19.2 g, 0.48 mol) in water (100 mL), and stirred at 70° C. for 72 h. The reaction solution was cooled to room temperature, adjusted to be weakly acidic with a diluted hydrochloric acid under an ice-water bath, and extracted with ethyl acetate. The organic phase was washed with water and brine, dried over anhydrous sodium sulfate, and concentrated. The crude was purified by column chromatography to obtain 145-2 (13.6 g) as a yellow solid. LC-MS: 243.1 [M–H]⁻.

Step Two:

145-2 (13.6 g, 55.5 mmol) was dissolved in thionyl chloride (100 mL), added with a catalytic amount of DMF, and refluxed at 70° C. for 2 h. TLC sampling detection in methanol showed that the raw material was completely reacted. The reaction solution was concentrated to obtain a crude 145-3, which was used directly in the next step.

Step Three:

145-3 was dissolved in dichloromethane (200 mL), added slowly with aluminum trichloride (22.4 g, 0.167 mol), and refluxed at 40° C. for 3 h. TLC showed that the reaction was complete. The reaction solution was poured into ice dilute hydrochloric acid (2N, 100 mL), and extracted with dichloromethane. The organic phase was washed with water and saturated brine, dried and concentrated. The crude was purified by silica gel column chromatography to obtain a yellowish crude 145-4 (8.4 g).

Step Four:

145-4 (3.0 g, 13.2 mol) was dissolved in 1,4-dioxane (150 mL), added with N-methylurea (1.90 g, 26.4 mol), Cs₂CO₃ (8.6 g, 26.4 mmol), Xantphos (153 mg, 0.264 mmol) and Pd₂(dba)₃ (120 mg, 0.132 mmol), and reacted at 100° C. for 3 h under nitrogen. TLC detected that the raw material was completely reacted. The reaction mixture was diluted with ethyl acetate and filtered. The filtrate was concentrated and the residue was purified by silica gel column chromatography to obtain 1.22 g of 145-5 as a yellowish solid.

Step Five:

145-5 (1.8 g, 8.18 mmol) was dissolved in ethanol (60 mL), added with ammonium carbonate (9.1 g, 94.8 mol), ammonium fluoride (3.6 g, 97.3 mol), ammonia (24 mL) and TMSCN (3.6 g, 36.4 mol), and reacted at 65° C. for 2 days. TLC detected that a small amount of the raw material was unreacted. The resultant was added with saturated brine and extracted with ethyl acetate. The organic phase was washed with saturated brine, dried and concentrated. The residue was slurried in dichloromethane and filtered to obtain SP-22 (1.1 g) as a white solid. LC-MS: 291.1[M+H]⁺.

Example 147 Synthesis of Amide AN-17

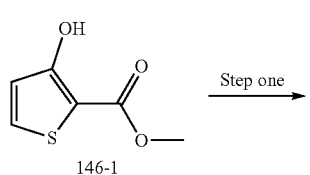

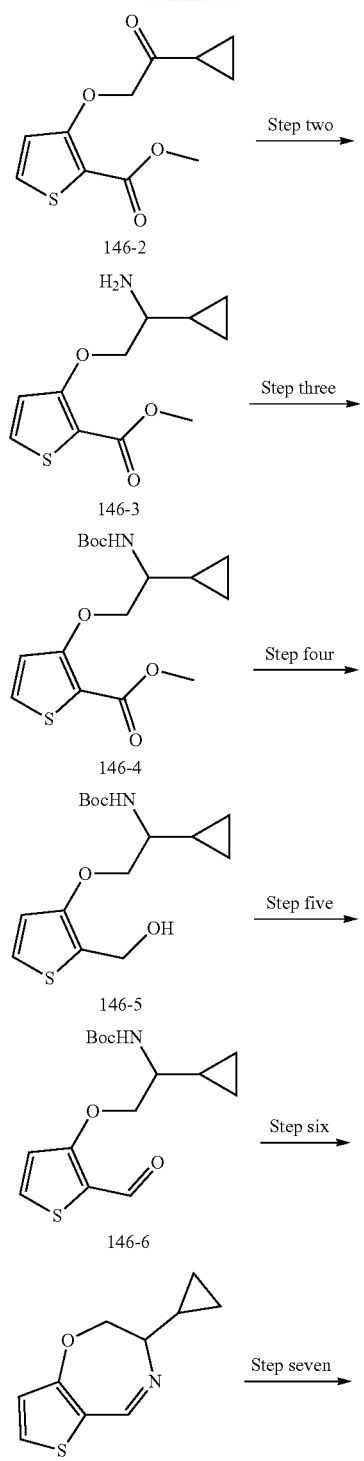

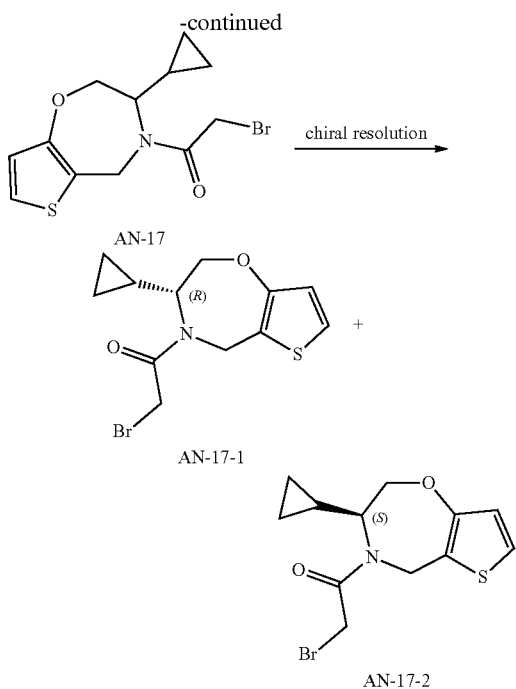

Step One:

Methyl 3-hydroxy-2-thiophenecarboxylate (146-1, 10 g, 63.2 mmol) was dissolved in DMF (100 mL), added with solid potassium carbonate (17.4 g, 126.4 mmol), stirred at room temperature to react for 10 min, added with bromomethyl cyclopropyl ketone (15.4 g, 94.8 mmol), and stirred at room temperature to react for 2 h. TLC detected that the reaction was complete. The reaction solution was poured into ice water and extracted with ethyl acetate. The combined organic phase was washed with water and saturated brine, dried over anhydrous sodium sulfate, and concentrated to obtain 146-2 (17.2 g), which was directly used in the next step. $^1$HNMR: (CDCl$_3$, 400 MHz): 1.01-1.05 (m, 2H), 1.13-1.17 (m, 2H), 2.45-2.50 (m, 1H), 3.86 (s, 3H), 4.81 (s, 2H), 6.73 (d, J=5.6 Hz, 1H), 7.42 (d, J=5.6 Hz, 1H).

Step Two:

146-2 (17.2 g, crude) was dissolved in n-butanol (120 mL), added with ammonium acetate (48.7 g, 632 mmol) and sodium cyanoborohydride (19.8 g, 316 mmol), and heated to 60° C. to react for 1 h. TLC detected that the reaction was complete. The reaction solution was cooled to room temperature, poured into ice water and extracted with dichloromethane. The combined organic phase was washed with water and saturated brine, dried over anhydrous sodium sulfate, and concentrated. The crude was purified by column chromatography to obtain 146-3 (11.2 g) as a white solid.

Step Three:

146-3 (3.0 g, 12.43 mmol) was dissolved in dichloromethane (60 mL), added with TEA (1.9 g, 18.64 mmol), cooled to 0° C., added dropwise with a solution of Boc anhydride (3.0 g, 13.7 mmol) in dichloromethane, warmed to room temperature and stirred for 2 h. TLC detected that the reaction was complete. The reaction solution was cooled to room temperature, poured into ice water and extracted with dichloromethane. The combined organic phase was washed with 1N hydrochloric acid solution, water and saturated brine, dried over anhydrous sodium sulfate, and concentrated to obtain targeted 146-4 (4.03 g) as a yellowish oil, which was used directly in the next step. LC-MS: 364.1 [M+Na]$^+$.

Step Four:

146-4 (4.03 g, crude) was dissolved in THF (80 mL), cooled to about 0° C. under nitrogen, added dropwise with a tetrahydrofuran solution of lithium aluminum tetrahydrogen (7.4 mL, 18.64 mmol, 2.5 mol/L), and stirred for 1 h at 0° C. TLC detected that the reaction was complete. The reaction solution were successively added dropwise with water (0.7 mL), 15% sodium hydroxide aqueous solution (0.7 mL) and water (2.1 mL) at 0° C., stirred vigorously for 0.5 h and filtered. The filtrate was concentrated to obtain a crude. The crude was dissolved in ethyl acetate, washed with water and saturated brine, dried over anhydrous sodium sulfate, and concentrated to obtain the targeted 146-5 (2.71 g) as a yellowish oil, which was used directly in the next step.

Step Five:

The crude 146-5 (2.71 g) was dissolved in dichloromethane (50 mL), added with manganese dioxide (15.0 g, 172.25 mmol), and heated to reflux for 2 h. TLC detected that the reaction was complete. The reaction solution was cooled, and filtered. The filtrate was concentrated to obtain 146-6 (2.3 g) as a yellowish oil, which was used directly in the next step. LC-MS: 334.1 [M+Na]$^+$.

Step Six:

The crude 146-6 (2.3 g) was dissolved in dichloromethane (30 mL), added with trifluoroacetic acid (5 mL), and stirred at room temperature for 0.5 h. LCMS detected that the reaction was complete. The reaction solution was directly concentrated to obtain a crude 146-7 as a yellow solid, which was used directly in the next step. LC-MS: 194.1 [M+H]$^+$.

Step Seven:

The crude 146-7 (1.81 g) was dissolved in methanol (50 mL), added with sodium borohydride (378 mg, 10 mmol) at 0° C., and stirred for 0.5 h. TLC detected that the reaction was complete. The reaction solution was poured into 1N aqueous hydrochloric acid solution, and extracted with dichloromethane. The combined organic phase was washed with water and saturated brine, dried over anhydrous sodium sulfate, and concentrated. The crude was purified by column chromatography to obtain 146-8 (1.31 g). $^1$H-NMR: (CDCl$_3$, 400 MHz): 0.36-0.39 (m, 2H), 0.58-0.64 (m, 2H), 0.84-0.88 (m, 1H), 2.26-2.31 (m, 1H), 3.78-3.83 (m, 1H), 3.91 (d, J=15.2 Hz, 1H), 4.04 (d, J=15.6 Hz, 1H), 4.37 (d, J=2 Hz, 0.5H), 4.40 (d, J=2 Hz, 0.5H), 6.70 (d, J=5.6 Hz, 1H), 6.90 (d, J=5.6 Hz, 1H).

Step Eight:

The 146-8 (700 mg, 3.58 mmol) was dissolved in dichloromethane (35 mL), added with TEA (543 mg, 5.37 mmol), cooled to 0° C. under nitrogen, added dropwise with a solution of bromoacetyl bromide (867 mg, 4.3 mmol) in dichloromethane, and reacted for 1 h at 0° C. TLC detected that the reaction was basically complete. The reaction solution was quenched with ice water, and extracted with dichloromethane. The organic phase was washed with water and brine, dried over anhydrous sodium sulfate, and concentrated. The crude was purified by column chromatography to obtain the amide AN-17 (610 mg). LC-MS: 316.0 [M+H]$^+$.

The amide AN-17 was subjected to chiral resolution. Resolution conditions: Preparative column was NANOMICRO OD-5H, filler particle size (5 μm), inner diameter (30 mm), length (250 mm), flow rate: 30 mL/min, mobile phase: 95% n-hexane+5% ethanol, isogradient elution, wavelength 254 nm, peak time is 20.19 min for peak 1, and 24.60 min for peak 2.

Example 148 Synthesis of SYY-B057-1

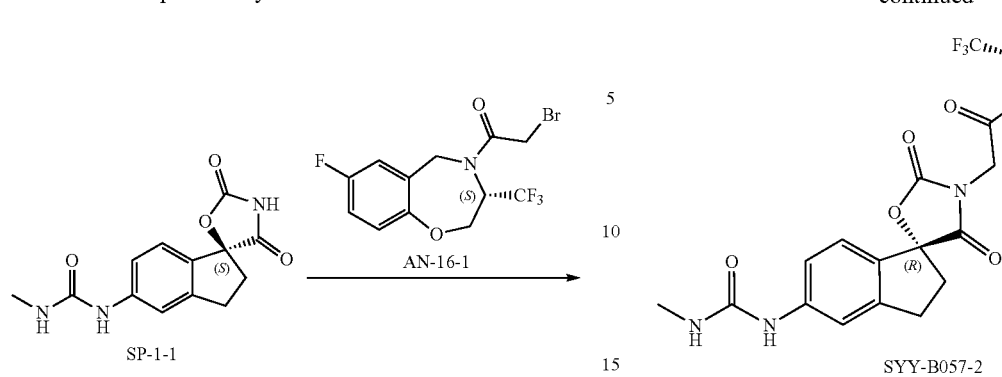

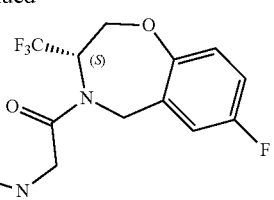

SYY-B057-1 was prepared using the same method as that in Example 30, except that the spiro ring fragment SP-1-1 was used instead of SP-1 and the amide fragment AN-16-1 was used instead of AN-7: $^1$H NMR (400 MHz, DMSO-$d_6$) δ 8.70 (m, 1H), 7.54 (m, 1H), 7.23-6.97 (m, 5H), 6.08 (m, 1H), 5.58 (m, 1H), 5.16-3.91 (m, 6H), 3.13-2.90 (m, 2H), 2.64-2.56 (m, 4H), 2.49-2.43 (m, 1H). LC-MS: [M+H]$^+$= 551.1.

Example 149 Synthesis of SYY-B057-2

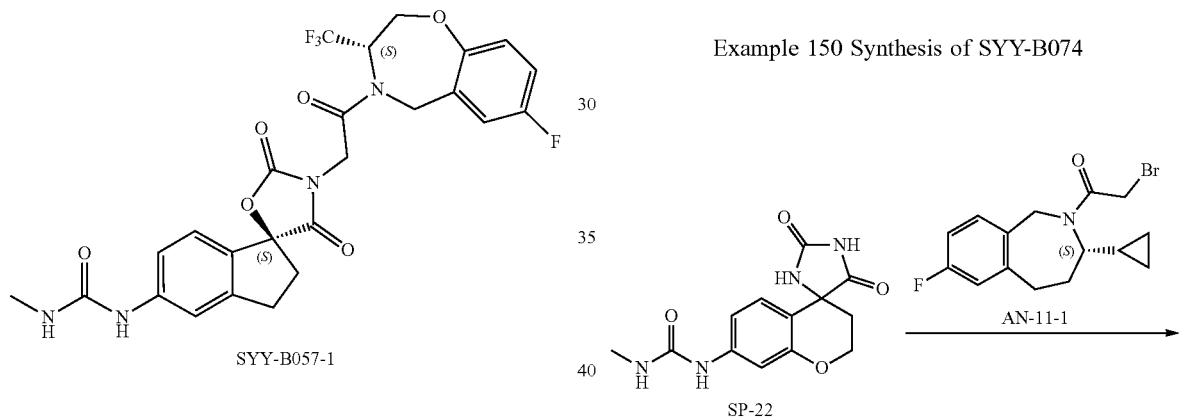

SYY-B057-2 was prepared using the same method as that in Example 30, except that the spiro ring fragment SP-1-2 was used instead of SP-1 and the amide fragment AN-16-1 was used instead of AN-7: $^1$H NMR (400 MHz, DMSO-$d_6$) δ 8.75 (m, 1H), 7.53 (m, 1H), 7.26-6.96 (m, 5H), 6.11 (m, 1H), 5.59 (m, 1H), 5.13-3.93 (m, 6H), 3.14-2.90 (m, 2H), 2.65-2.56 (m, 4H), 2.49-2.43 (m, 1H). LC-MS: [M+H]$^+$= 551.2.

Example 150 Synthesis of SYY-B074

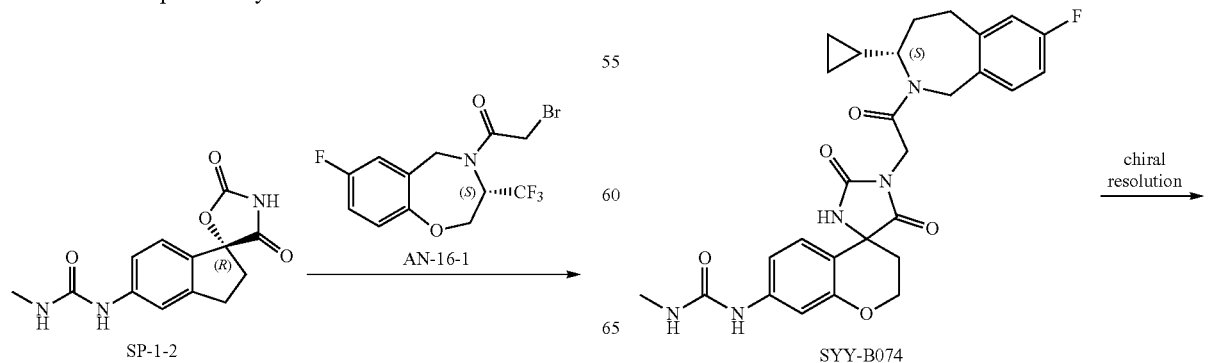

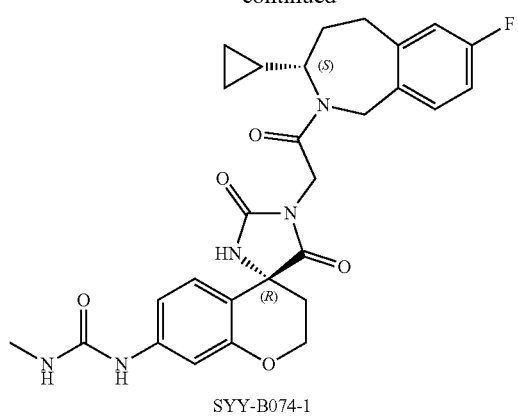

SYY-B074-1

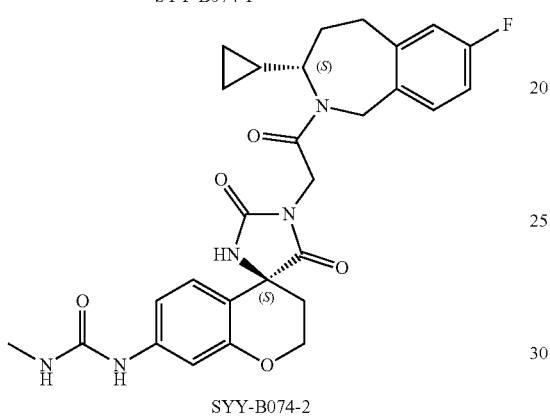

SYY-B074-2

SYY—B074 was prepared using the same method as that in Example 30, except that the spiro ring fragment SP-22 was used instead of SP-1 and the amide fragment AN-11-1 was used instead of AN-7: $^1$H NMR (400 MHz, DMSO-$d_6$) δ 8.86 (m, 1H), 8.54 (m, 1H), 7.40-6.79 (m, 6H), 6.01 (m, 1H), 4.84-4.68 (m, 2H), 4.40-3.43 (m, 5H), 3.17-3.05 (m, 1H), 2.73-2.56 (m, 4H), 2.44-2.00 (m, 4H), 1.40-1.33 (m, 1H), 0.60-0.24 (m, 4H). LC-MS: [M+H]$^+$=536.2.

Chiral resolution was performed to obtain SYY-B074-1 and SYY-B074-2: Preparative column was Daicel AD-H, filler particle size (5 μm), inner diameter (30 mm), length (250 mm), flow rate: 20 mL/min, mobile phase: 60% n-hexane+40% isopropanol, isogradient elution, wavelength 254 nm, peak time is 8.29 min for peak 1, and 17.13 min for peak 2.

Example 151 Synthesis of SYY—B077

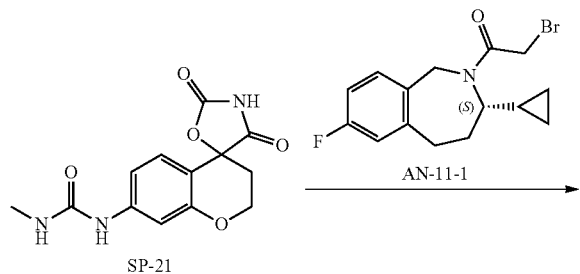

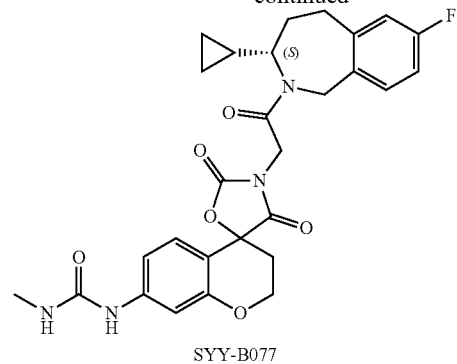

SYY-B077

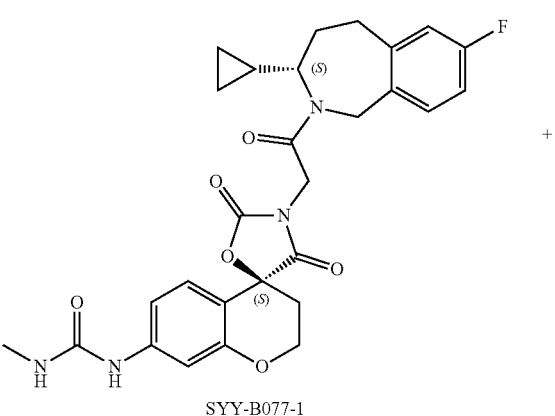

SYY-B077-1

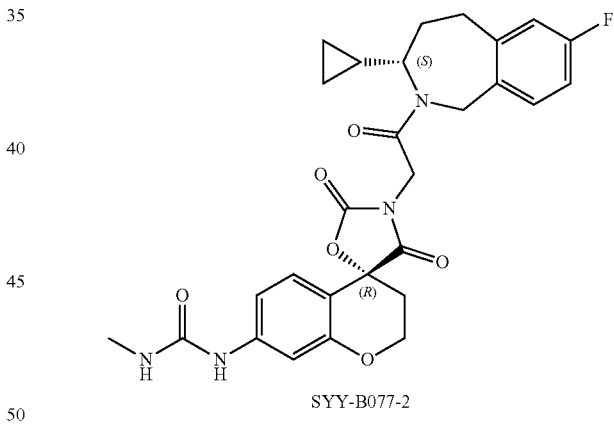

SYY-B077-2

SYY—B077 was prepared using the same method as that in Example 30, except that the spiro ring fragment SP-21 was used instead of SP-1 and the amide fragment AN-11-1 was used instead of AN-7: $^1$H NMR (400 MHz, DMSO-$d_6$) δ 8.68 (m, 1H), 7.38-6.83 (m, 6H), 6.09 (m, 1H), 4.92-4.78 (m, 2H), 4.47-3.43 (m, 5H), 3.18-3.05 (m, 1H), 2.78-2.54 (m, 4H), 2.39-2.29 (m, 2H), 2.08-1.96 (m, 2H), 1.40-1.33 (m, 1H), 0.64-0.26 (m, 4H). LC-MS: [M+H]$^+$=537.2.

Chiral resolution was performed to obtain SYY-B077-1 and SYY-B077-2: Preparative column was Daicel AD-H, filler particle size (5 μm), inner diameter (30 mm), length (250 mm), flow rate: 30 mL/min, mobile phase: 70% n-hexane+30% ethanol, isogradient elution, wavelength 254 nm, peak time is 34.32 min for peak 1, and 48.67 min for peak 2.

Example 152 Synthesis of SYY—B083

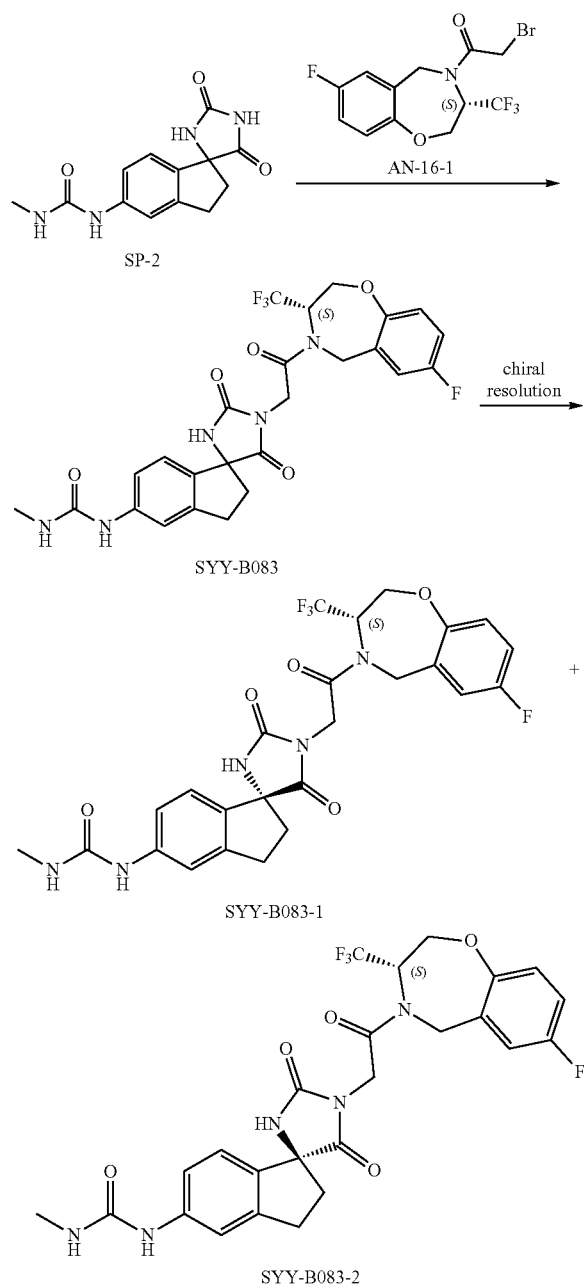

SYY—B083 was prepared using the same method as that in Example 30, except that the spiro ring fragment SP-2 was used instead of SP-1 and the amide fragment AN-16-1 was used instead of AN-7: $^1$H NMR (400 MHz, DMSO-d$_6$) δ 8.75 (m, 1H), 8.55 (m, 1H), 7.42 (m, 1H), 7.24-6.94 (m, 5H), 6.01 (m, 1H), 5.55 (m, 1H), 5.10-4.48 (m, 5H), 3.78 (m, 1H), 2.97-2.91 (m, 2H), 2.62 (m, 3H), 2.49-2.43 (m, 1H), 2.15 (m, 1H). LC-MS: [M+H]$^+$=550.2.

Chiral resolution was performed to obtain SYY-B083-1 and SYY-B083-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 8.56 min for peak 1, and 26.33 min for peak 2.

Example 153 Synthesis of SYY—B084

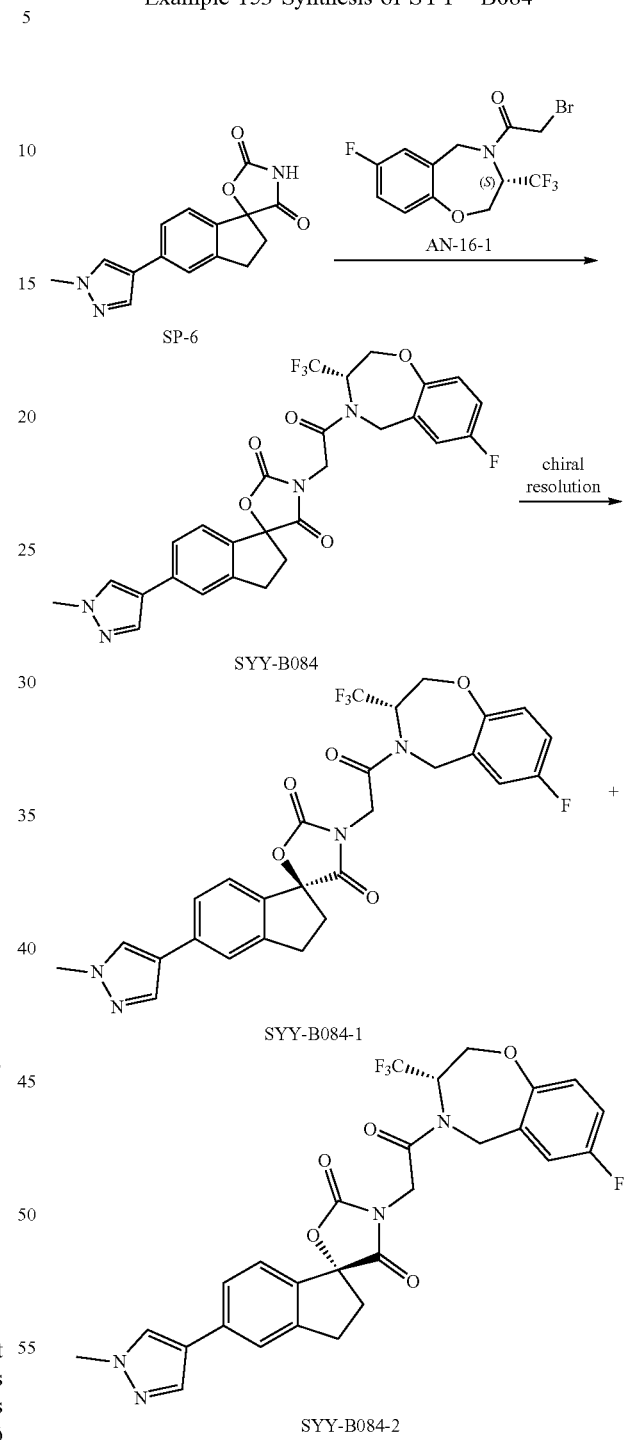

SYY—B084 was prepared using the same method as that in Example 30, except that the spiro ring fragment SP-6 was used instead of SP-1 and the amide fragment AN-16-1 was used instead of AN-7: $^1$H NMR (400 MHz, DMSO-d$_6$) δ 8.18 (m, 1H), 7.90 (m, 1H), 7.60-7.54 (m, 2H), 7.38 (m, 1H), 7.21 (m, 1H), 6.99 (m, 2H), 5.59 (m, 1H), 5.10-3.86 (m, 9H), 3.21-3.01 (m, 2H), 2.68-2.50 (m, 2H). LC-MS: [M+H]$^+$=559.2.

Chiral resolution was performed to obtain SYY-B084-1 and SYY-B084-2: Preparative column was NANOMICRO OD-5H, filler particle size (5 μm), inner diameter (30 mm), length (250 mm), flow rate: 20 mL/min, mobile phase: 70% n-hexane+30% isopropanol, isogradient elution, wavelength 254 nm, peak time is 68.20 min for peak 1, and 77.29 min for peak 2.

Example 154 Synthesis of SYY—B085

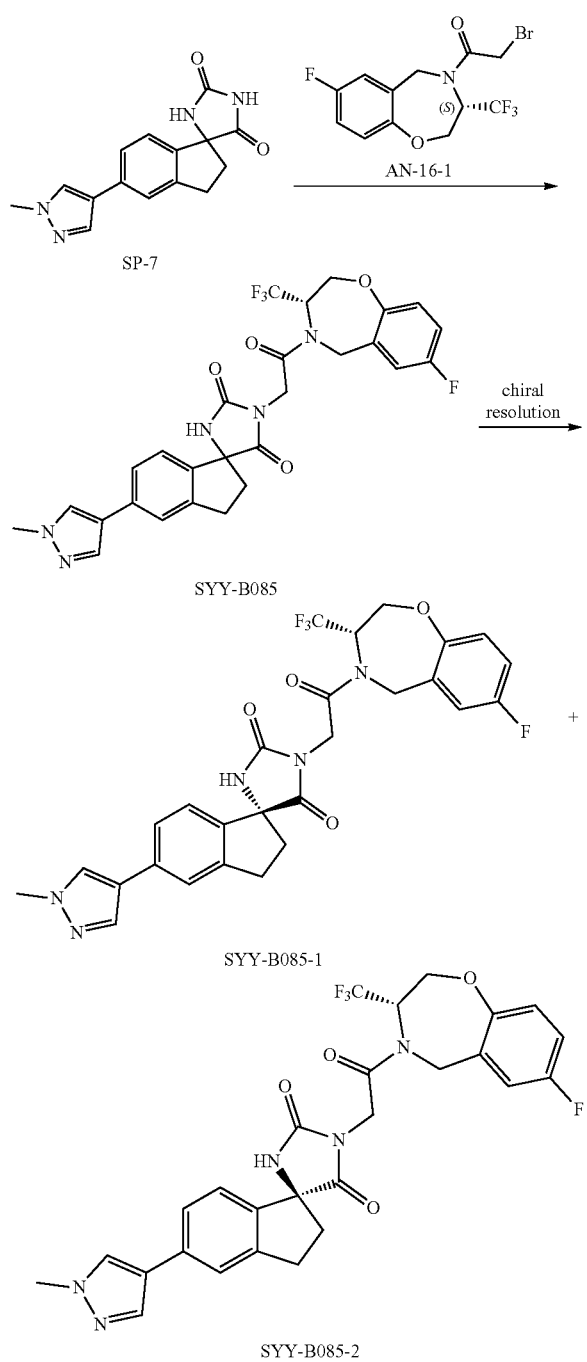

SYY—B085 was prepared using the same method as that in Example 30, except that the spiro ring fragment SP-7 was used instead of SP-1 and the amide fragment AN-16-1 was used instead of AN-7: $^1$H NMR (400 MHz, DMSO-d$_6$) δ 8.82 (m, 1H), 8.13 (m, 1H), 7.86 (m, 1H), 7.47 (m, 2H), 7.20 (m, 2H), 7.10-6.92 (m, 2H), 5.55 (m, 1H), 5.12-3.80 (m, 9H), 3.02 (m, 2H), 2.55 (m, 1H), 2.22 (m, 1H). LC-MS: [M+H]$^+$=558.2.

Chiral resolution was performed to obtain SYY-B085-1 and SYY-B085-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 32.11 min for peak 1, and 42.08 min for peak 2.

Example 155 Synthesis of SYY-B086-1 and SYY-B086-2

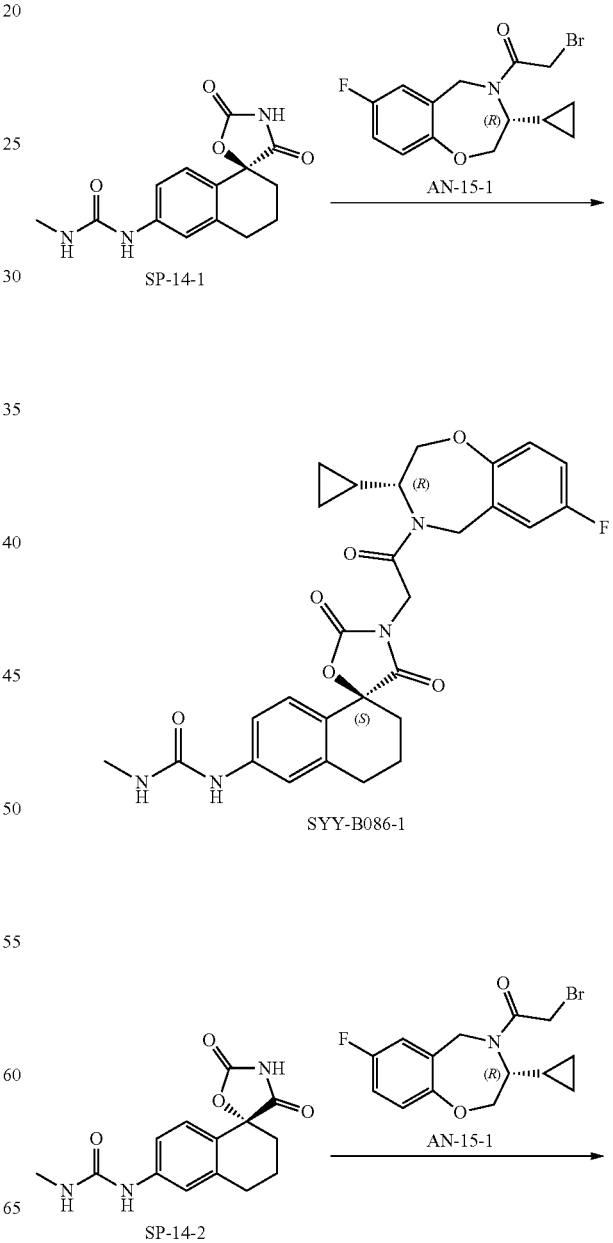

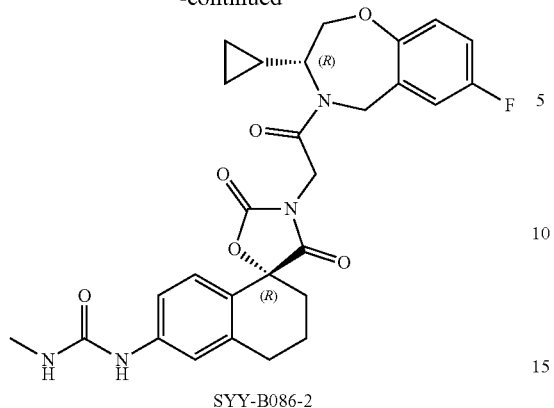

SYY-B086-2

SYY-B086-1 and SYY-B086-2 was prepared using the same method as that in Example 30, except that the spiro ring fragment SP-14-1 and SP-14-2 were used instead of SP-1 and the amide fragment AN-15-1 was used instead of AN-7: LC-MS: [M+H]$^+$=537.2.

Example 156 Synthesis of SYY-B092

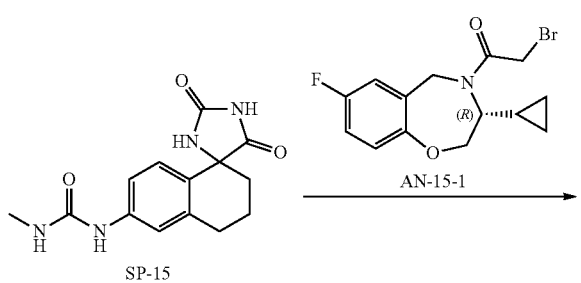

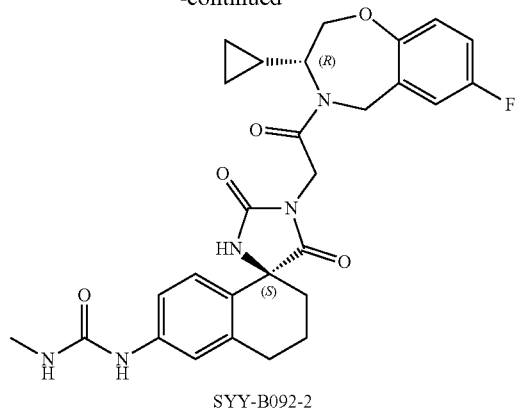

SYY-B092-2

SYY—B092 was prepared using the same method as that in Example 30, except that the spiro ring fragment SP-15 was used instead of SP-1 and the amide fragment AN-15-1 was used instead of AN-7: $^1$H NMR (400 MHz, DMSO-d$_6$) δ 8.79 (m, 1H), 8.47 (m, 1H), 7.25-6.88 (m, 6H), 6.00 (m, 1H), 5.02-4.92 (m, 1H), 4.76-4.68 (m, 2H), 4.45-3.71 (m, 4H), 2.68-2.61 (m, 5H), 2.02 (m, 2H), 1.85 (m, 2H), 1.40-1.33 (m, 1H), 0.58-0.24 (m, 4H). LC-MS: [M+H]$^+$=536.2.

Chiral resolution was performed to obtain SYY-B092-1 and SYY-B092-2: Preparative column was Daicel AD-H, filler particle size (5 μm), inner diameter (30 mm), length (250 mm), flow rate: 20 m/min, mobile phase: 60% n-hexane+40% isopropanol, isogradient elution, wavelength 254 nm, peak time is 11.23 min for peak 1, and 21.82 min for peak 2.

Example 157 Synthesis of SYY-B093

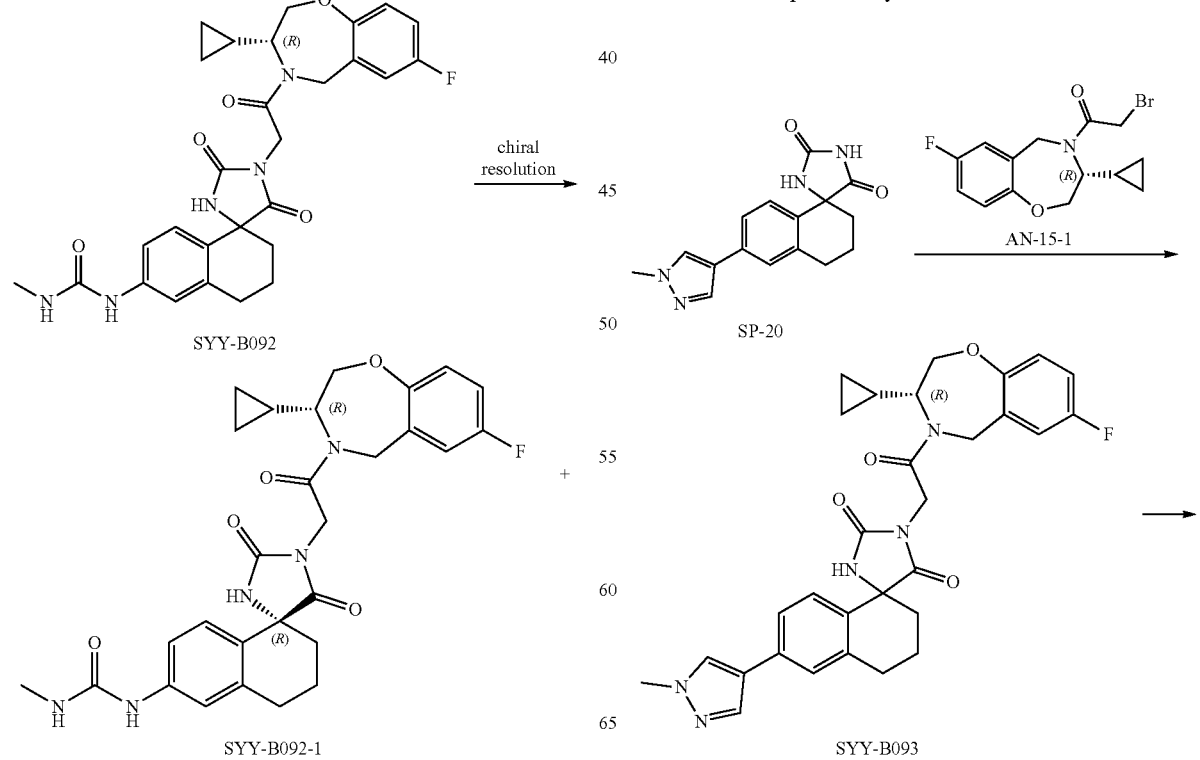

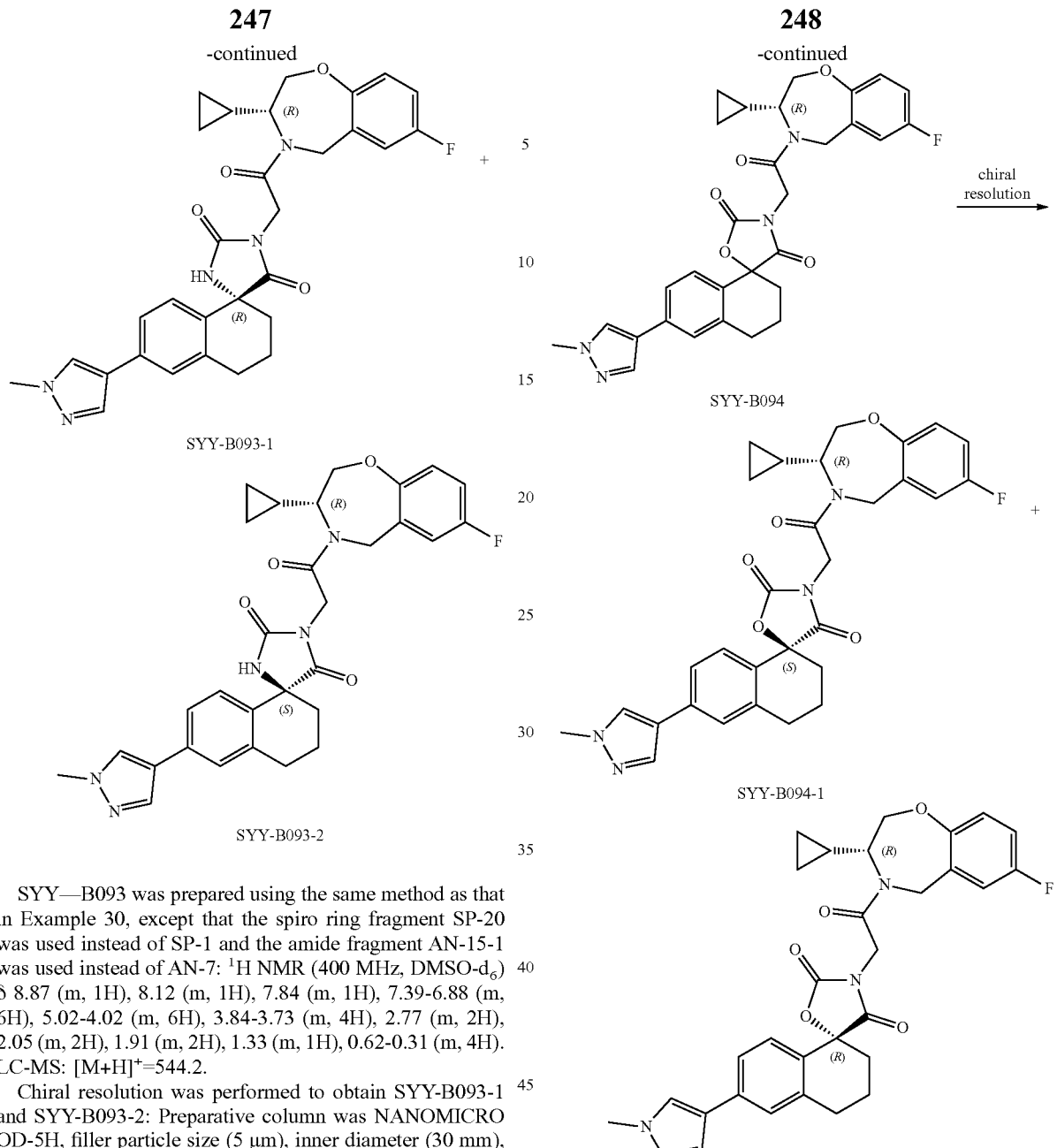

SYY—B093 was prepared using the same method as that in Example 30, except that the spiro ring fragment SP-20 was used instead of SP-1 and the amide fragment AN-15-1 was used instead of AN-7: $^1$H NMR (400 MHz, DMSO-$d_6$) δ 8.87 (m, 1H), 8.12 (m, 1H), 7.84 (m, 1H), 7.39-6.88 (m, 6H), 5.02-4.02 (m, 6H), 3.84-3.73 (m, 4H), 2.77 (m, 2H), 2.05 (m, 2H), 1.91 (m, 2H), 1.33 (m, 1H), 0.62-0.31 (m, 4H). LC-MS: [M+H]$^+$=544.2.

Chiral resolution was performed to obtain SYY-B093-1 and SYY-B093-2: Preparative column was NANOMICRO OD-5H, filler particle size (5 μm), inner diameter (30 mm), length (250 mm), flow rate: 30 mL/min, mobile phase: 60% n-hexane+40% ethanol, isogradient elution, wavelength 254 nm, peak time is 21.27 min for peak 1, and 31.24 min for peak 2.

Example 158 Synthesis of SYY-B094

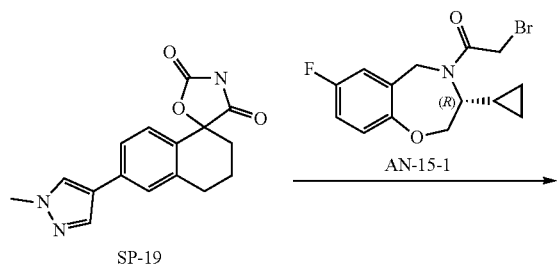

SYY—B094 was prepared using the same method as that in Example 30, except that the spiro ring fragment SP-19 was used instead of SP-1 and the amide fragment AN-15-1 was used instead of AN-7: $^1$H NMR (400 MHz, DMSO-$d_6$) δ 8.19 (m, 1H), 7.88 (m, 1H), 7.47-7.39 (m, 3H), 7.25-7.19 (m, 1H), 7.07-6.88 (m, 2H), 5.07-4.52 (m, 3H), 4.48-4.04 (m, 3H), 3.99-3.74 (m, 4H), 2.85 (m, 2H), 2.22 (m, 2H), 2.00 (m, 1H), 1.82 (m, 1H), 1.18 (m, 1H), 0.59-0.36 (m, 4H). LC-MS: [M+H]$^+$=545.2.

Chiral resolution was performed to obtain SYY-B094-1 and SYY-B094-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 60.88 min for peak 1, and 76.10 min for peak 2.

Example 159 Synthesis of SYY—B099

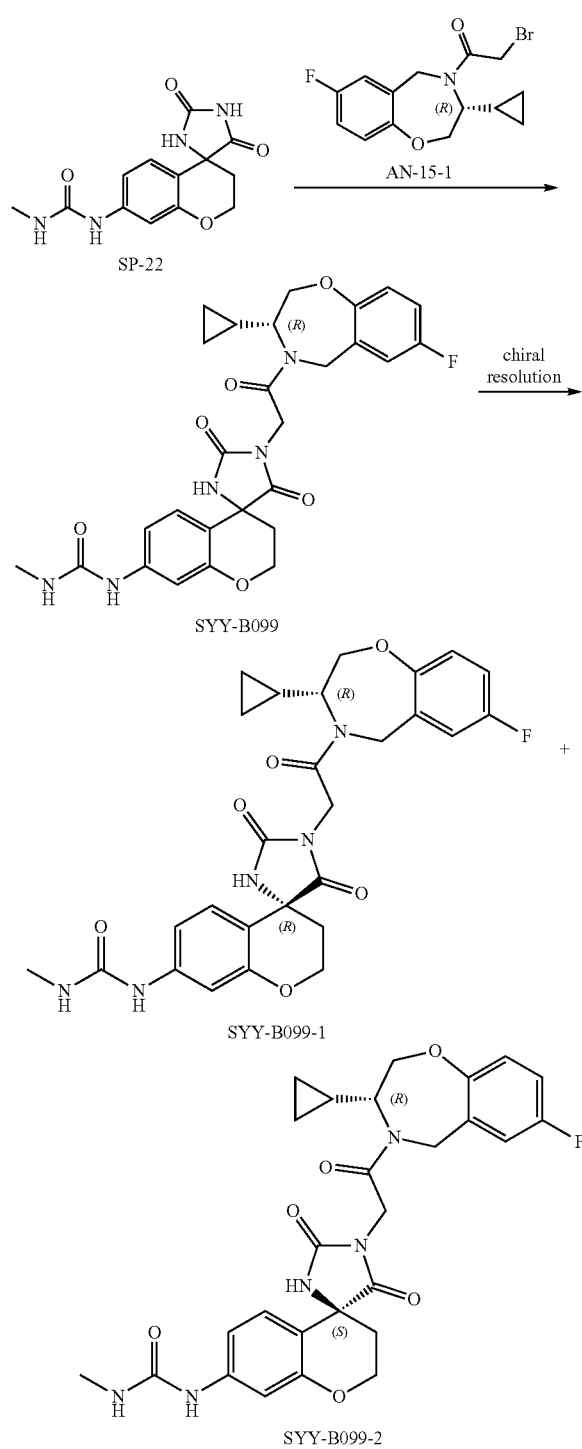

SYY—B099 was prepared using the same method as that in Example 30, except that the spiro ring fragment SP-22 was used instead of SP-1 and the amide fragment AN-15-1 was used instead of AN-7: $^1$H NMR (400 MHz, DMSO-$d_6$) δ 8.88 (m, 1H), 8.54 (m, 1H), 7.24-6.79 (m, 6H), 6.01 (m, 1H), 5.02-4.92 (m, 1H), 4.78-4.68 (m, 2H), 4.40-3.43 (m, 6H), 2.62 (m, 3H), 2.25-2.00 (m, 2H), 1.40-1.33 (m, 1H), 0.60-0.24 (m, 4H). LC-MS: [M+H]$^+$=538.2.

Chiral resolution was performed to obtain SYY-B099-1 and SYY-B099-2: Preparative column was Daicel AD-H, filler particle size (5 μm), inner diameter (30 mm), length (250 mm), flow rate: 20 mL/min, mobile phase: 60% n-hexane+40% ethanol, isogradient elution, wavelength 220 nm, peak time is 12.0 min for peak 1, and 21.15 min for peak 2.

Example 160 Synthesis of SYY-B100-1

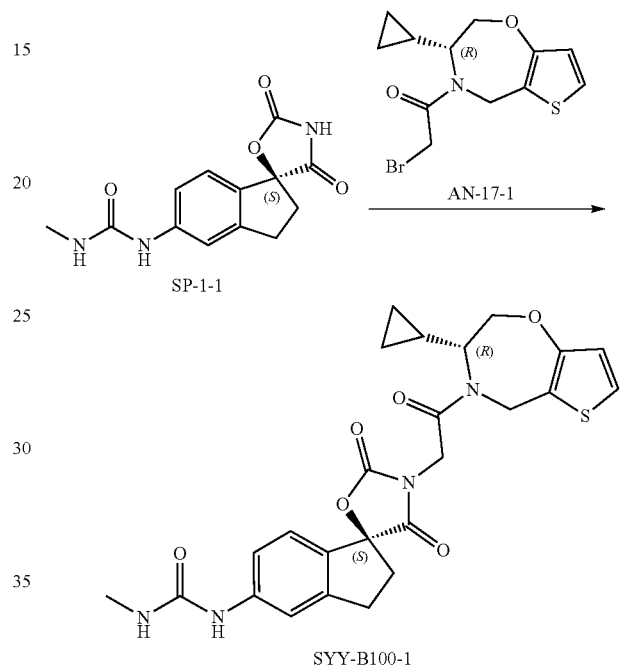

SYY-B100-1 was prepared using the same method as that in Example 30, except that the spiro ring fragment SP-1-1 was used instead of SP-1 and the amide fragment AN-17-1 was used instead of AN-7: $^1$H NMR (400 MHz, DMSO-$d_6$) δ 8.79 (m, 1H), 7.53 (m, 1H), 7.27-7.21 (m, 3H), 6.66 (m, 1H), 6.16 (m, 1H), 5.12-3.90 (m, 7H), 3.14-2.93 (m, 2H), 2.65-2.56 (m, 4H), 2.49-2.43 (m, 1H), 1.10 (m, 1H), 0.63-0.32 (m, 4H). LC-MS: [M+H]$^+$=511.2.

Example 161 Synthesis of SYY-B100-2

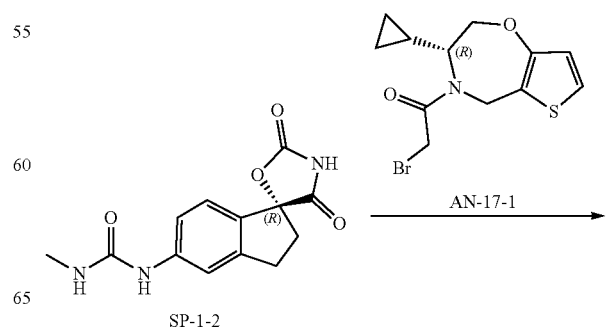

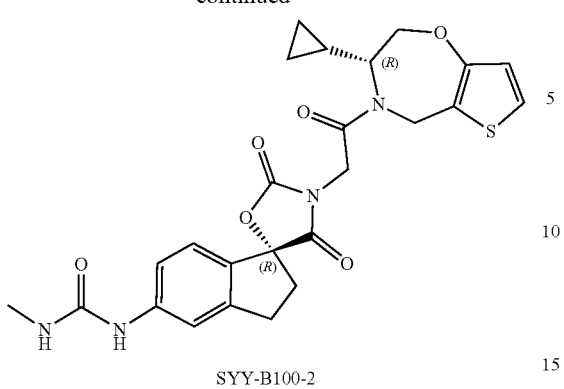

SYY-B100-2

SYY-B100-2 was prepared using the same method as that in Example 30, except that the spiro ring fragment SP-1-2 was used instead of SP-1 and the amide fragment AN-17-1 was used instead of AN-7: $^1$H NMR (400 MHz, DMSO-$d_6$) δ 8.81 (m, 1H), 7.53 (m, 1H), 7.26-7.21 (m, 3H), 6.66 (m, 1H), 6.15 (m, 1H), 5.13-3.93 (m, 7H), 3.14-2.93 (m, 2H), 2.65-2.56 (m, 4H), 2.49-2.43 (m, 1H), 1.08 (m, 1H), 0.63-0.32 (m, 4H). LC-MS: [M+H]$^+$=511.2.

Example 162 Synthesis of Amine AN-18

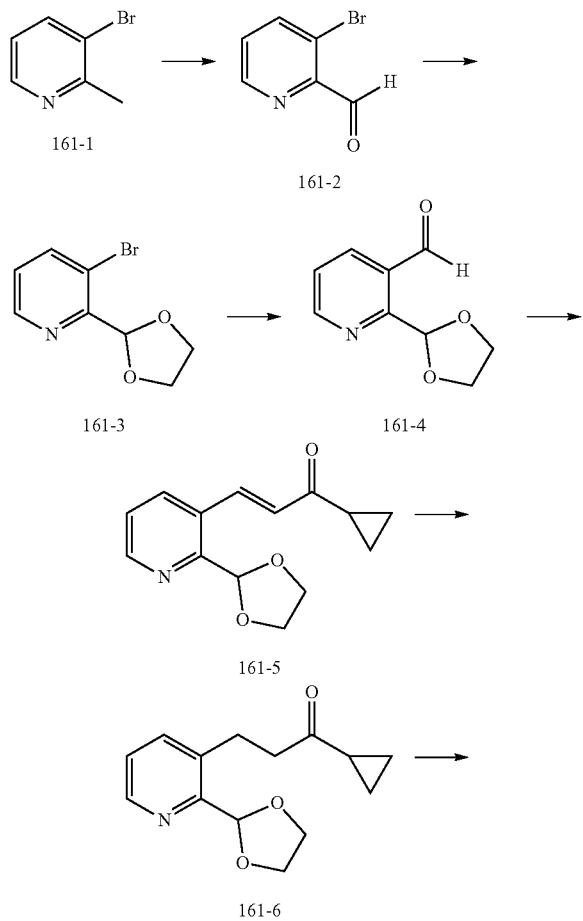

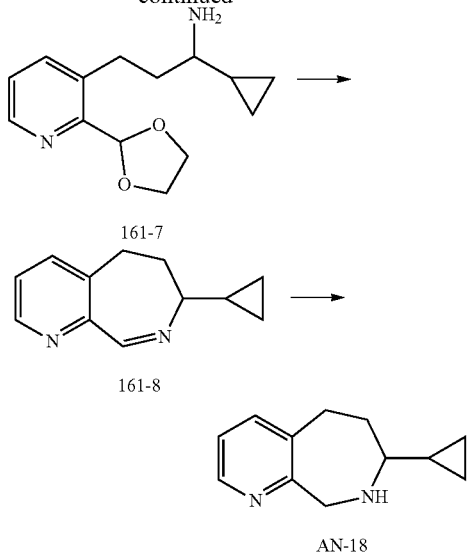

AN-18

Step 1:

2-Methyl-3-bromopyridine (161-1, 20.0 g, 116.3 mmol) was dissolved in a mixed solvent of 1,4-dioxane (200 mL) and water (20 mL), added with selenium dioxide (26.0 g, 234.3 mmol), heated to 110° C. for 7 h, added with selenium dioxide (13.0 g, 117.2 mmol), and continually heated to react overnight. TLC detected that most of the raw material was reacted. The reaction solution was cooled to room temperature, and filtered. The filtrate was concentrated. The residue was dissolved with ethyl acetate, washed with water and saturated brine, dried over anhydrous sodium sulfate, and concentrated. The crude was purified by silica gel column chromatography to obtain 161-2 (9.12 g) as a yellowish solid. $^1$H-NMR: (CDCl$_3$, 400 MHz): δ 10.23 (s, 1H), 8.75 (dd, J1=4.8 Hz, J2=1.6 Hz, 1H), 8.04 (dd, J1=8.0 Hz, J2=1.2 Hz, 1H), 7.38 (q, J=3.6 Hz, 1H).

Step 2:

161-2 (2.8 g, 15.05 mmol) was dissolved in toluene (50 mL), successively added with ethylene glycol (1.9 g, 30.1 mmol) and p-toluenesulfonic acid (500 mg, 3.01 mmol), and heated to 130° C. to separate water for 3 h. TLC detected that the reaction was complete. The reaction solution was cooled to room temperature, poured into an iced sodium carbonate aqueous solution, and extracted with ethyl acetate. The organic phase was washed, dried, and concentrated to obtain 3.2 g of 161-3 as a yellow oil, which was directly used for the next reaction.

Step 3:

161-3 (3.2 g, crude) was dissolved in tetrahydrofuran (30 mL), cooled to about −70° C. under nitrogen, and added dropwise with a n-butyl lithium solution (6.1 mL, 15.3 mmol), stirred at −70° C. for 1 h, added with a THF solution of DMF (5.1 g, 69.55 mmol), and continually stirred for 1 h. TLC detected that the reaction was basically complete. The reaction solution was quenched with saturated aqueous ammonium chloride solution, and extracted. The organic phase was washed, dried and concentrated. The crude was purified by column chromatography to obtain 161-4 (512 mg) as a yellow oil. $^1$H-NMR: (CDCl$_3$, 400 MHz): 10.57 (s, 1H), 8.78 (dd, J1=4.8 Hz, J2=1.6 Hz, 1H), 8.26 (dd, J1=8.0 Hz, J2=1.6 Hz, 1H), 7.48 (q, J=2.8 Hz, 1H), 6.16 (s, 1H), 4.28-4.24 (m, 2H), 4.16-4.12 (m, 2H).

Step 4:

161-4 (3.6 g, 20.1 mmol) and Wittig reagent (7.6 g, 22.1 mmol) were heated in tetrahydrofuran (50 mL) to reflux for 1 h. TLC detected that the reaction was basically complete. The reaction solution was concentrated and the residue was purified by silica gel column chromatography to obtain 161-5 (4.2 g) as a yellow oil.

Step 5:

161-5 (350 mg, 1.43 mmol) was dissolved in methanol (10 mL), and added with Pd/C (100 mg). After atmosphere was replaced with hydrogen three times, the reaction mixture was stirred at room temperature for 2 h. LC-MS detected that the reaction was complete. The resultant was filtered and concentrated to obtain 161-6 (300 mg) as a yellowish oil.

Step 6:

161-6 (500 mg, 2.02 mmol) was dissolved in n-butanol (10 mL), added with solid ammonium acetate (1.6 g, 20.2 mmol), and then with solid sodium cyanoborohydride (638 mg, 10.1 mmol) under stirring, further added with n-butanol (10 mL), and heated to 80° C. to react for 1.5 h. TLC detected that the reaction was complete. The reaction solution was concentrated to dryness, diluted with water and extracted with dichloromethane. The mother liquor was extracted with dichloromethane and isopropanol twice. The organic phase was washed with saturated brine, dried over anhydrous sodium sulfate, and concentrated to obtain 161-7 (390 mg) as a colorless oil. LC-MS: 249.2 [M+1]$^+$.

Step 7:

161-7 (390 mg, 1.57 mmol) was heated to 60° C. in concentrated hydrochloric acid (10 mL) to react for 2 h. TLC detected that the reaction was complete. The reaction solution was concentrated to a small amount, neutralized with sodium carbonate, and extracted with dichloromethane and isopropanol twice. The organic phase was washed with saturated brine, dried over anhydrous sodium sulfate, and concentrated to obtain 161-8 (190 mg) as a yellow oil. LC-MS: 187.2 [M+1]$^+$.

Step 8:

161-8 (190 mg, 1.02 mmol) was dissolved in methanol (5 mL), and added with Pd/C (100 mg). After atmosphere was replaced with hydrogen three times, the reaction mixture was stirred at room temperature for 1 h. TLC detected that the reaction was complete. The reaction solution was filtered, and the filtrate was concentrated to obtain the amine AN-18 (140 mg) as a yellowish oil. LC-MS: 189.2 [M+1]$^+$.

Example 163 Synthesis of Amide AN-19

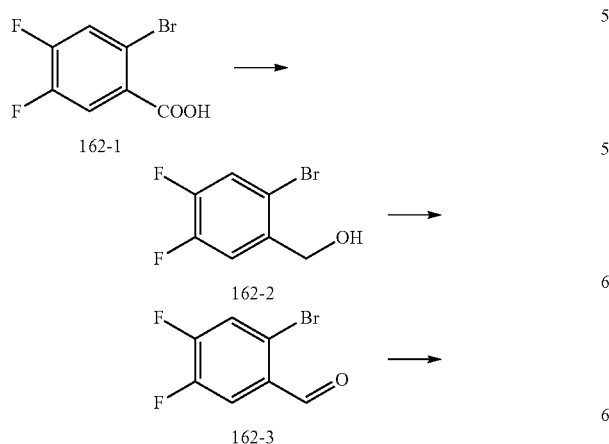

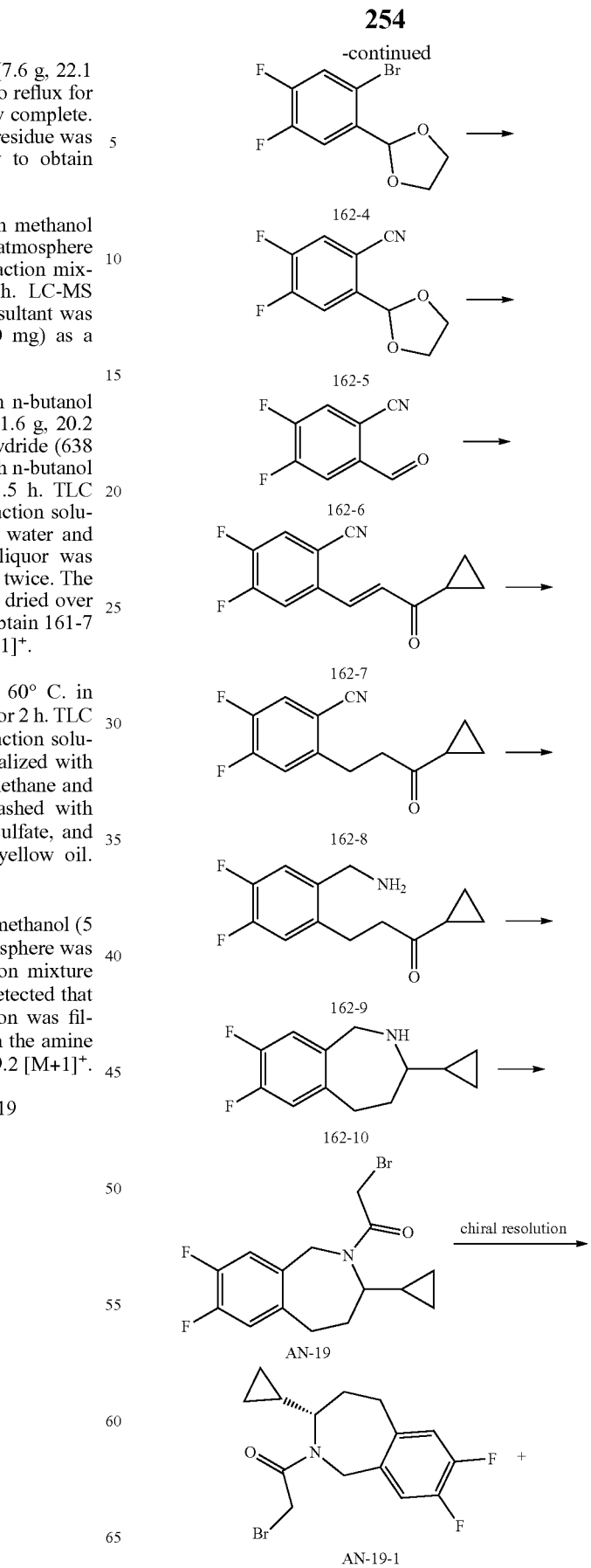

-continued

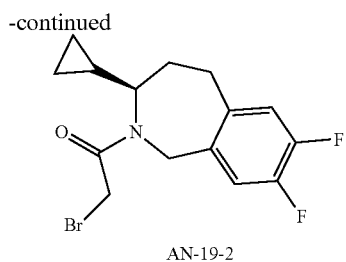

AN-19-2

Step 1:

2-Bromo-4,5-difluorobenzoic acid (162-1, 30.0 g, 0.127 mol) was dissolved in tetrahydrofuran (150 mL), added with a tetrahydrofuran solution of borane (140 mL, 0.139 mol) under ice bath, heated to 80° C. and refluxed for 2 h. TLC detected that the reaction was complete. The reaction solution was cooled to room temperature, added with 2N potassium hydroxide solution (66 mL) dropwise under an ice bath, diluted with ethyl acetate, and filtered. The combined organic phase was washed with saturated brine, concentrated and dried to obtain 162-2 (28.2 g) as a white solid. $^1$H-NMR (400 MHz, CDCl$_3$): δ 7.42-7.38 (m, 2H), 4.70 (s, 2H), 2.18 (brs, 1H).

Step 2:

162-2 (28.2 g) was dissolved in dichloromethane (300 mL), added with manganese dioxide (110 g, 1.27 mol) at room temperature, and reacted for 16 h at room temperature. TLC detected that the reaction was complete. The reaction solution was filtered through celite. The filter cake was washed with dichloromethane. The filtrate was dried and concentrated to obtain 162-3 (27.6 g) as a white solid. $^1$H-NMR (400 MHz, CDCl$_3$): δ 10.24 (d, J=3.2 Hz, 1H), 7.81-7.76 (m, 1H), 7.55-7.51 (m, 1H).

Step 3:

162-3 (27.6 g, crude) was dissolved in toluene (200 mL), added with ethylene glycol (200 mL) and p-toluenesulfonic acid (1.0 g, 5.8 mmol) at room temperature, and heated to 100° C. to react for 24 h. TLC detected that the reaction was complete. The reaction solution was cooled to room temperature, and extracted with ethyl acetate. The combined organic phase was washed with water and saturated brine, dried and concentrated. The crude was purified by silica gel column chromatography to obtain 162-4 (18.1 g) as a yellow oil.

Step 4:

162-4 (18.1 g, 68.4 mol) was dissolved in dry NMP (150 mL), added with Pd$_2$(dba)$_3$ (1.8 g, 2.05 mol), triphenylphosphine (1.8 g, 6.84 mol) and zinc cyanide (16.0 g, 0.137 mol) at room temperature under nitrogen, and heated to 100° C. to react for 16 h. The reaction solution was cooled to room temperature, diluted with ethyl acetate, and filtered. The filtrate was washed with water and saturated brine, dried and concentrated. The crude was purified by silica gel column chromatography to obtain 162-5 (5.08 g) as a white solid. $^1$H-NMR (400 MHz, CDCl$_3$): δ 7.58-7.47 (m, 2H), 5.98 (s, 1H), 4.25-4.10 (m, 4H).

Step 5:

162-5 (5.00 g, 23.7 mmol) was dissolved in dioxane (100 mL), added with hydrochloric acid (33 mL, 12N) at room temperature, and stirred at room temperature for 1 h. TLC detected that the reaction was complete. The resultant was added with water and extracted with ethyl acetate. The combined organic phase was washed with saturated brine, dried over anhydrous sodium sulfate, and concentrated to obtain 162-6, which was directly used in the next step.

$^1$H-NMR (400 MHz, CDCl$_3$): δ 10.29 (d, J=2.4 Hz, 1H), 7.92-7.88 (m, 1H), 7.73-7.69 (m, 1H),

Step 6:

162-6 was dissolved in tetrahydrofuran (150 mL), added with the phosphorus ylide (12.3 g, 35.9 mmol) at room temperature, and heated to 80° C. to reflux for 2 h. TLC detected that the reaction was complete. The reaction solution was concentrated, and the residue was purified by silica gel column chromatography to obtain 162-7 (5.1 g) as a yellow solid. $^1$H-NMR (400 MHz, CDCl$_3$): δ 7.79 (dd, J1=16.0 Hz, J2=1.2 Hz, 1H), 7.63-7.55 (m, 2H), 6.92 (d, J=16.0 Hz, 1H), 2.34-2.28 (m, 1H), 1.24-1.20 (m, 2H), 1.10-1.05 (m, 2H). LC-MS: [M+1]: 234.1.

Step 7:

162-7 (5.1 g, 21.9 mmol) was dissolved in methanol (100 mL) and added with 10% Pd/C (1.0 g) at room temperature. After atmosphere was replaced with hydrogen 3 times, the reaction was conducted at room temperature for 3 h. TLC detected that the reaction was complete. The reaction solution was filtered. The filter cake was washed with methanol, and the filtrate containing 162-8 was directly used in the next step.

Step 8:

The filtrate containing 162-8 obtained in the previous step was added with Raney nickel (800 mg) and TEA (2 mL, 14.4 mmol) at room temperature. After atmosphere was replaced with hydrogen 3 times, the reaction was performed at room temperature for 16 h. TLC detected that the reaction was complete. The reaction solution was filtered. The filter cake was washed with methanol, and the filtrate containing 162-9 was directly used in the next step. LCMS: [M+1]$^+$ 240.1.

Step 9:

The filtrate containing 162-9 obtained in the previous step was added with acetic acid (1 mL) and sodium cyanoborohydride (2.6 g, 43.8 mmol) at room temperature, and reacted at room temperature for 1 h. TLC detected that the reaction was complete. The resultant was quenched with saturated brine, and extracted with ethyl acetate. The combined organic phase was washed with saturated brine, dried over anhydrous sodium sulfate, and concentrated to obtain 162-10, which was directly used in the next step. LC-MS: [M+1]$^+$ 224.2.

Step 10

162-10 was dissolved in dichloromethane (100 mL), added with bromoacetyl bromide (4 mL, 47.4 mmol) at room temperature, and reacted for 3 h at room temperature. TLC detected that the raw material was completely reacted. The reaction mixture was added with saturated sodium bicarbonate solution (20 mL), stirred for 10 min, and extracted with dichloromethane. The combined organic phase was washed with saturated brine, dried over anhydrous sodium sulfate, and concentrated. The crude was purified by pre-HPLC to obtain AN-19 (1.5 g) as a yellow oil. LC-MS: [M+1]: 344.1.

Chiral resolution was performed to obtain AN-19-1 and AN-19-2. Method: Daicel AD-H, filler particle size (5 μm), inner diameter (30 mm), length (250 mm), flow rate: 20 mL/min, mobile phase: 95% n-hexane+5% isopropanol, isogradient elution, wavelength 254 nm, peak time is 28.85 min for peak 1, and 38.65 min for peak 2.

Example 164 Synthesis of Amine AN-20

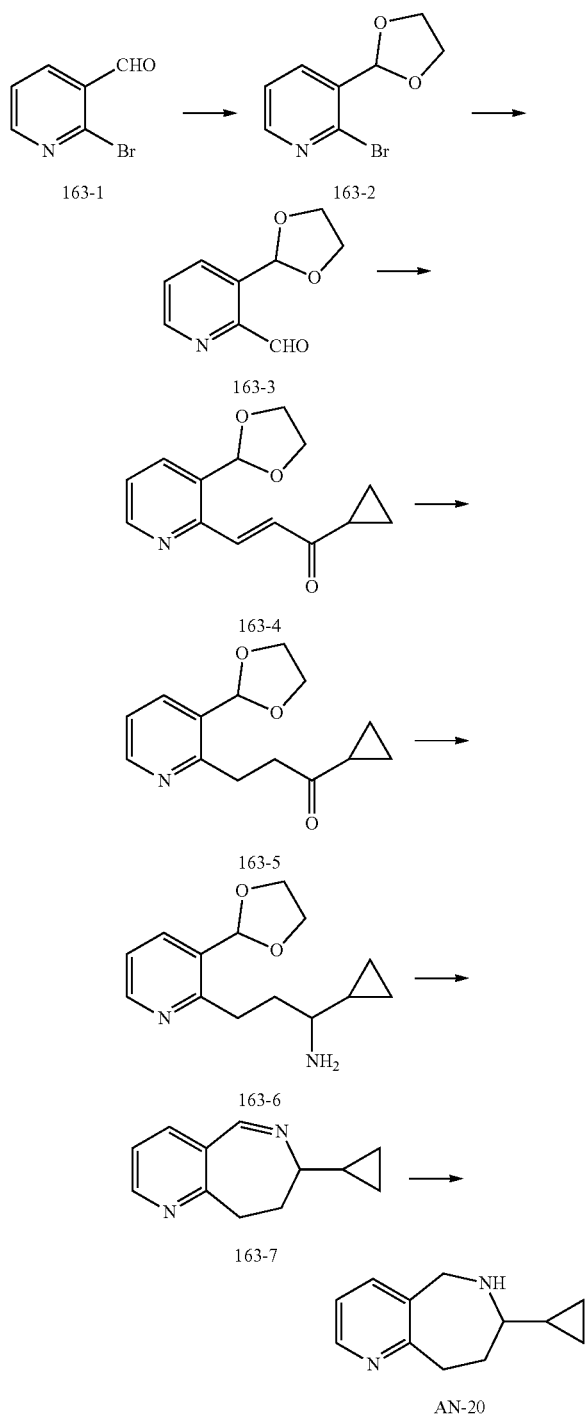

Step 1:

2-Bromo-3-pyridinecarboxaldehyde (163-1, 20.0 g, 108 mmol), p-toluenesulfonic acid (4.0 g) and ethylene glycol (50 mL) were dissolved in toluene (150 mL), heated to 100° C. and stirred for 4 h. TLC detected that the raw material was basically reacted. The reaction solution was cooled to room temperature, poured into ice water and extracted with EtOAc. The combined organic phase was washed with water and saturated brine, dried over anhydrous sodium sulfate, and concentrated. The crude was purified by silica gel column chromatography to obtain 163-2 (21.51 g). LC-MS: 230.0 [M+1]$^+$

Step 2:

163-2 (21.52 g, 93.54 mmol) was dissolved in 300 mL of tetrahydrofuran. After atmosphere was replaced with nitrogen three times, the reaction mixture was cooled to −65° C. under a dry ice bath, slowly added with butyl lithium (59 mL, 148 mmol) dropwise, stirred for 1 h, added with dry DMF (11 mL, 148 mmol), warmed to room temperature and stirred for another 30 min, and then quenched with water. The aqueous phase was extracted with EtOAc. The combined organic phase was washed with water and saturated brine, dried over anhydrous sodium sulfate, and concentrated to obtain 163-3 (18.2 g), which was used directly in the next step. LC-MS: 180.1 [M+1]$^+$

Step 3:

163-3 (18.2 g) and the phosphorus ylide (27.0 g, 80 mmol) were dissolved in tetrahydrofuran (200 mL), and heated to 70° C. to stir for 1 h. TLC detected that the reaction was complete. The reaction solution was cooled to room temperature and concentrated directly. The crude was purified by silica gel column chromatography to obtain 163-4 (10.63 g).

Step 4:

163-4 (10.0 g, 40 mmol) was dissolved in ethyl acetate (250 mL), and added with 10% Pd/C (1.7 g). After atmosphere was replaced with hydrogen, the reaction mixture was stirred under hydrogen (1 atm) at room temperature for 2 h. TLC detected that the reaction was complete. The reaction solution was filtered through celite, and the filter cake was washed with ethyl acetate. The combined organic phase was dried, and concentrated to obtain 163-5 (9.65 g), which was used for the next product directly.

Step 5:

The crude 163-5 (9.65 g) was dissolved in methanol (150 mL), added with ammonium acetate (31 g, 400 mmol) and sodium cyanoborohydride (12 g, 200 mmol), and reacted at room temperature for 16 h. TLC detected that the raw material was completely reacted. The reaction solution was quenched with water and extracted with EtOAc. The combined organic phase was washed with water and saturated brine, dried over anhydrous sodium sulfate, and concentrated. The crude was purified by silica gel column chromatography to obtain 163-6 (4.12 g). LCMS: 249.2 [M+1]$^+$.

Step 6:

163-6 (4.12 g, 16.6 mmol) was dissolved in 40 mL of TFA, added with 10 mL of water, and reacted at 80° C. for 4 h. TLC showed that the reaction was complete. The resultant was concentrated. The crude was poured into water, alkalized with 1N NaOH, and extracted with ethyl acetate. The combined organic phase was washed with water and saturated brine, dried over anhydrous sodium sulfate, and concentrated to obtain 163-7 (1.51 g, crude) which was used directly in the next step. LC-MS: 187.1 [M+1]$^+$.

Step 7:

163-7 was dissolved in 15 mL of methanol, added with 0.5 mL of acetic acid and sodium cyanoborohydride (2.0 g, 30 mmol), and reacted at room temperature for 2 h. TLC showed that the reaction was complete. The resultant was concentrated. The crude was poured into water and extracted with ethyl acetate. The combined organic phase was washed with water and saturated brine, dried over anhydrous sodium sulfate, and concentrated to obtain the amine AN-20 (628 mg) as a white solid. LC-MS: 189.2 [M+1]$^+$.

Example 165 Synthesis of Amine AN-21

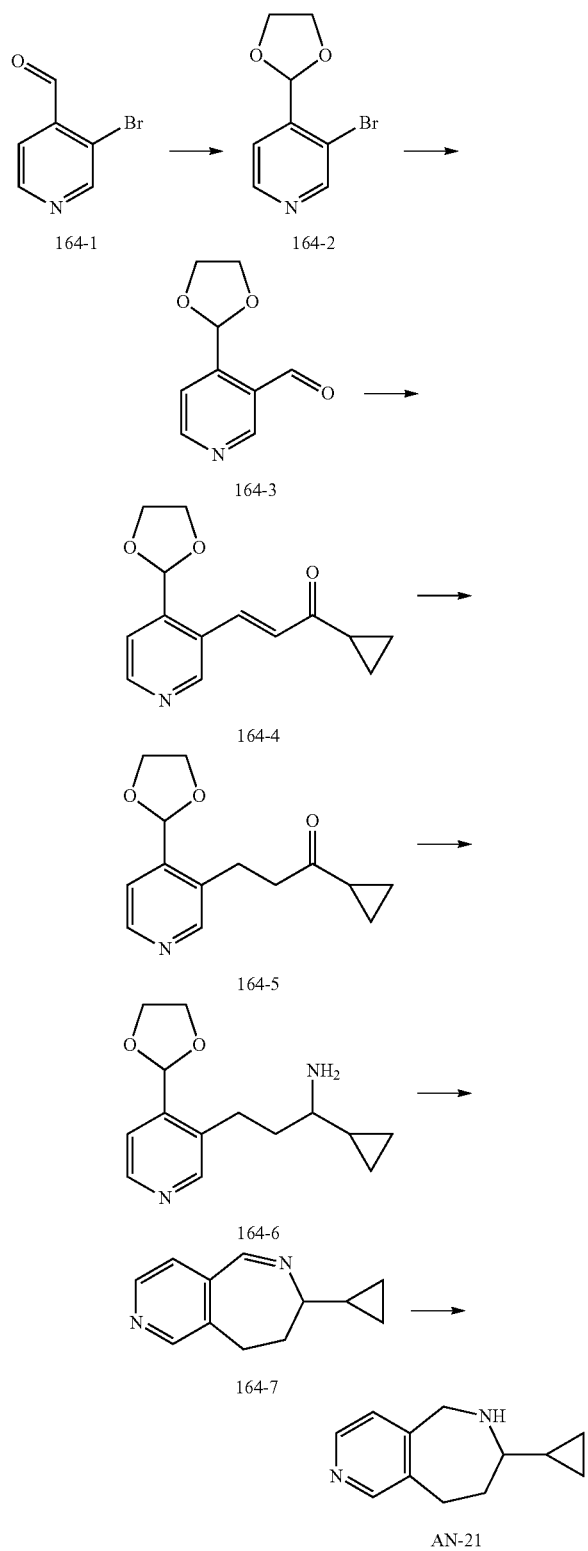

Step 1:

3-Bromo-4-pyridinecarbaldehyde (164-1, 22.0 g, 118 mmol), ethylene glycol (14.7 g, 236 mmol) and TsOH (6.1 g, 35 mmol) were added to toluene (150 mL), and heated to reflux to separate water and react for 3 h. TLC showed that the raw material was completely reacted. The reaction solution was cooled to room temperature, poured into ice water and extracted with ethyl acetate. The combined organic phase was washed with water and saturated brine, dried over anhydrous sodium sulfate, and concentrated to obtain 164-2 as a yellow oil, which was directly used in the next step.

Step 2:

164-2 (26.7 g) was dissolved in anhydrous THF (400 mL) under nitrogen, added dropwise with n-BuLi (51 ml, 0.12 mol) at −65° C., stirred for 1 h, added with dry DMF (42.4 g, 0.58 mol), stirred for 30 min, slowly warmed to room temperature, and stirred for another 30 min. The reaction solution was quenched with water, and the aqueous phase was extracted with EtOAc. The combined organic phase was washed with water and saturated brine, dried over anhydrous sodium sulfate, and concentrated. The crude was purified by silica gel column chromatography to obtain 164-3 (8 g). LC-MS: 180.1 [M+1]$^+$. $^1$H-NMR (400 MHz, CDCl$_3$): δ 10.44 (s, 1H), 9.09 (s, 1H), 8.84 (d, J=4.2 Hz, 1H), 7.66 (d, J=4.2 Hz, 1H), 6.44 (s, 1H), 4.12 (br, 4H).

Step 3:

164-3 (10.8 g, 60.33 mmol) and the phosphorus ylide (23 g, 66.36 mmol) were dissolved in anhydrous THF (200 mL) under nitrogen, and stirred at 75° C. for 1.5 h. TLC showed that the raw material was completely reacted. The reaction solution was cooled to room temperature and concentrated directly. The crude was purified by silica gel column chromatography to obtain 164-4 (9.5 g) as a yellowish oil. LC-MS: 246.2 [M+1]$^+$.

Step 4:

164-4 (9.5 g, 38.7 mmol) was dissolved in methanol (200 mL) and added with 10% Pd/C (2.0 g). After atmosphere was replaced with hydrogen, the reaction mixture was stirred under hydrogen (1 atm) at room temperature for 2 h. TLC detected that the reaction was complete. The reaction solution was filtered through celite, and the filter cake was washed with ethyl acetate. The combined organic phase was dried and concentrated to obtain 164-5 (9.4, crude), which was used for the next product directly.

Step 5:

164-5 (9.4 g, crude) was dissolved in methanol (150 mL), added with ammonium acetate (31 g, 400 mmol) and sodium cyanoborohydride (12 g, 200 mmol), and reacted at room temperature for 16 h. TLC detected that the raw material was completely reacted. The reaction solution was quenched with water and extracted with EtOAc. The combined organic phase was washed with water and saturated brine, dried over anhydrous sodium sulfate, and concentrated. The crude was purified by silica gel column chromatography to obtain 164-6 (1.61 g). LC-MS: 249.2[M+1]$^+$.

Step 6:

164-6 (1.61 g, 6.45 mmol) was dissolved in 20 mL concentrated hydrochloric acid and reacted at 60° C. for 2 h. TLC showed that the reaction was complete. The resultant was concentrated. The crude was poured into water, alkalized with saturated sodium carbonate, and extracted. The organic phase was washed with brine, dried over anhydrous sodium sulfate, and concentrated to dryness to obtain 164-7 (1.05 g, crude), which was used directly in the next step.

Step 7:

164-7 (1.05 g, crude) was dissolved in methanol (40 mL) and added with 10% Pd/C (600 mg). After atmosphere was replaced with hydrogen 3 times, the reaction mixture was stirred under hydrogen (1 atm) at room temperature for 2 h.

TLC detected that the reaction was complete. The reaction solution was filtered through celite, and the filter cake was washed with ethyl acetate. The combined organic phase was dried and concentrated. The crude was purified by silica gel column chromatography to obtain the amine AN-21 (730 mg). LC-MS: 189.2 [M+1]$^+$.

Example 166 Synthesis of SYY-B081-1 and SYY-B082-1

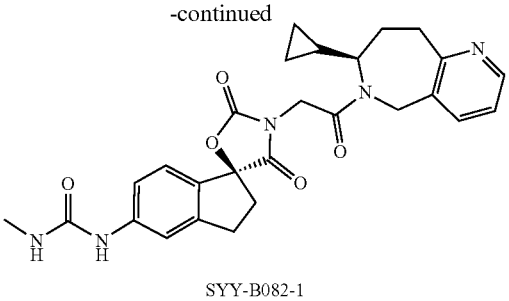

SYY-B082-1

Step 1:

SP-1-1 (130 mg, 0.472 mmol) was dissolved in DMF (4 mL), added with benzyl 2-bromoacetate (162 mg, 0.698 mmol) and potassium carbonate (130 mg, 0.942 mmol) at room temperature, and reacted at room temperature for 1 h. TLC detected that the reaction was complete. The resultant was added with water and extracted with ethyl acetate. The organic phase was washed with saturated brine, dried over anhydrous sodium sulfate, and concentrated. The crude was purified by silica gel column chromatography to obtain 165-2 (300 mg).

Step 2:

165-2 (300 mg) was dissolved in methanol (10 mL) and added with Pd/C (82 mg) at room temperature. After atmosphere was replaced with hydrogen, the reaction was conducted at room temperature for 2 h. TLC detected that the reaction was complete. The resultant was filtered through celite, and the filtrate was concentrated to obtain 165-3 (160 mg).

Step 3:

165-3 (160 mg, 0.480 mmol) and the amine AN-20 (90 mg, 0.478 mmol) were dissolved in dry DMF (5 mL), added with DIPEA (150 mg, 0.96 mmol) and HATU (300 mg, 0.789 mmol) at room temperature, and reacted at room temperature for 1 h under nitrogen. TLC detected that the reaction was complete. The resultant was added with water and extracted with ethyl acetate. The organic phase was washed with saturated brine, dried over anhydrous sodium sulfate, and concentrated. The crude was purified by silica gel column chromatography to obtain SYY—B081/082-1 (40 mg). $^1$H NMR (400 MHz, CD$_3$OD δ 8.37-8.28 (m, 1H), 7.28-7.74 (m, 1H), 7.50-7.18 (m, 4H), 5.01-3.57 (m, 7H), 3.22-3.10 (m, 2H), 3.07-2.85 (m, 3H), 2.74-2.68 (m, 1H), 2.53 (m, 1H), 2.24 (m, 2H), 1.48 (m, 1H), 0.72-0.38 (m, 4H). LC-MS: [M+H]$^+$=504.2.

Chiral resolution was performed to obtain SYY-B081-1 and SYY-B082-1. Preparation method: chiral column was Daicel AD-H, filler particle size (5 μm), inner diameter (30 mm), length (250 mm), flow rate: 20 mL/min, mobile phase: 60% n-hexane+40% ethanol, isogradient elution, wavelength 254 nm, peak time is 15.07 min for peak 1, and 30.56 min for peak 2.

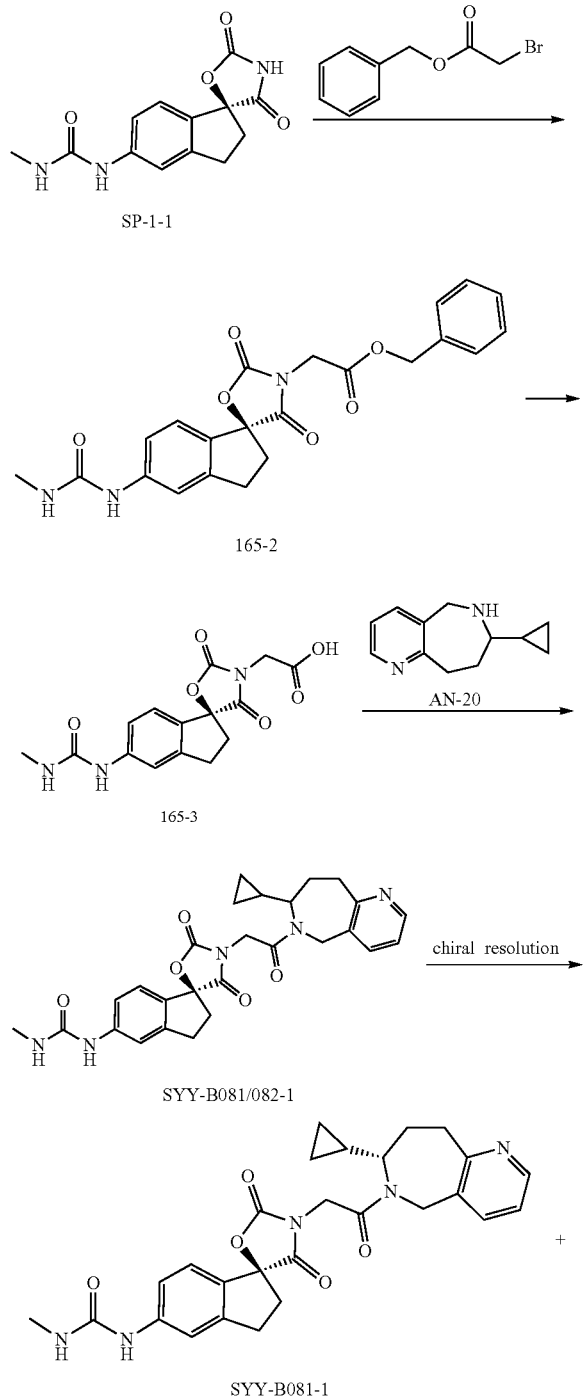

Example 167 Synthesis of SYY-B081-2 and SYY-B082-2

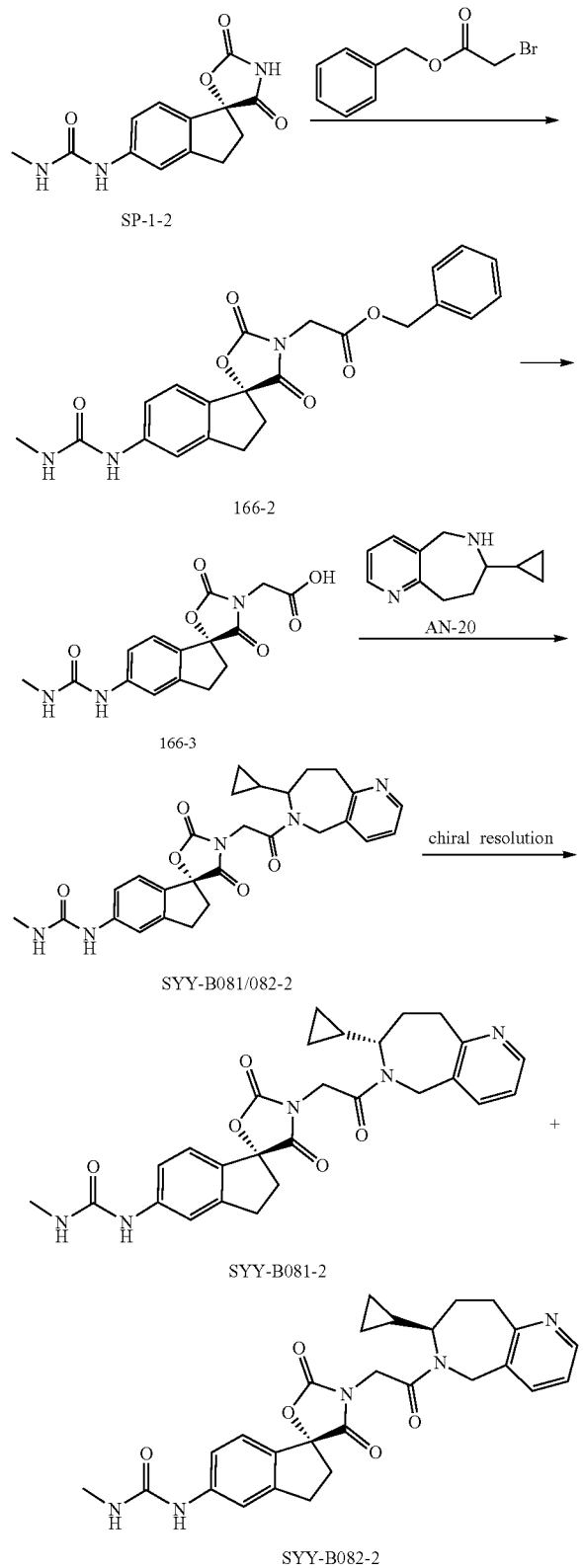

Step 1:

SP-1-2 (200 mg) was dissolved in DMF (5 mL), added with benzyl 2-bromoacetate (183 mg) and potassium carbonate (150 mg) at room temperature, and reacted at room temperature for 1 h. TLC detected that the reaction was complete. The resultant was added with water and extracted with ethyl acetate. The organic phase was washed with saturated brine, dried over anhydrous sodium sulfate, and concentrated. The crude was purified by silica gel column chromatography to obtain 166-2 (250 mg).

Step 2:

166-2 (250 mg) was dissolved in methanol (10 mL) and added with Pd/C (100 mg) at room temperature. After atmosphere was replaced with hydrogen, the reaction was conducted at room temperature for 2 h. TLC detected that the reaction was complete. The resultant was filtered through celite, and the filtrate was concentrated to obtain 166-3 (160 mg).

Step 3:

166-3 (160 mg) and the amine AN-20 (90 mg) were dissolved in dry DMF (5 mL), added with DIPEA (150 mg) and HATU (300 mg) at room temperature, and reacted at room temperature for 1 h under nitrogen. TLC detected that the reaction was complete. The resultant was added with water and extracted with ethyl acetate. The organic phase was washed with saturated brine, dried over anhydrous sodium sulfate, and concentrated. The crude was purified by silica gel column chromatography to obtain SYY—B081/082-2 (35 mg). $^1$H NMR (400 MHz, CD$_3$OD $\delta$ 8.37-8.28 (m, 1H), 7.28-7.74 (m, 1H), 7.50-7.18 (m, 4H), 5.01-3.57 (m, 7H), 3.22-3.10 (m, 2H), 3.07-2.85 (m, 3H), 2.74-2.68 (m, 1H), 2.53 (m, 1H), 2.24 (m, 2H), 1.48 (m, 1H), 0.72-0.38 (m, 4H). LC-MS: [M+H]$^+$=504.2.

Chiral resolution was performed to obtain SYY-B081-2 and SYY-B082-2. Preparation method: chiral column was Daicel AD-H, filler particle size (5 μm), inner diameter (20 mm), length (250 mm), flow rate: 20 mL/min, mobile phase: 80% n-hexane+20% ethanol, isogradient elution, wavelength 254 nm, peak time is 14.10 min for peak 1, and 18.93 min for peak 2.

Example 168 Synthesis of SYY-B088

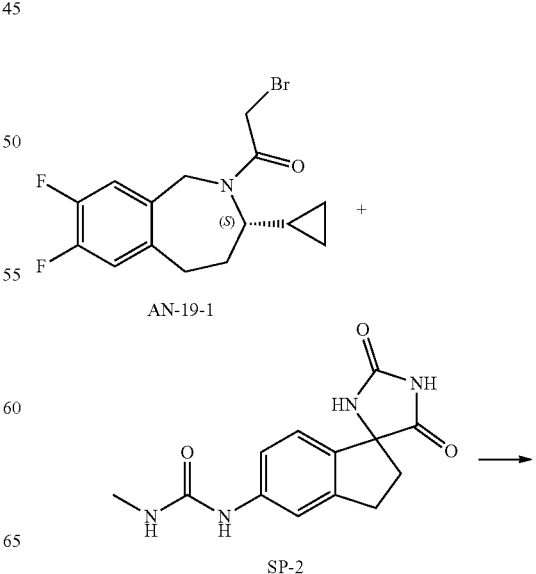

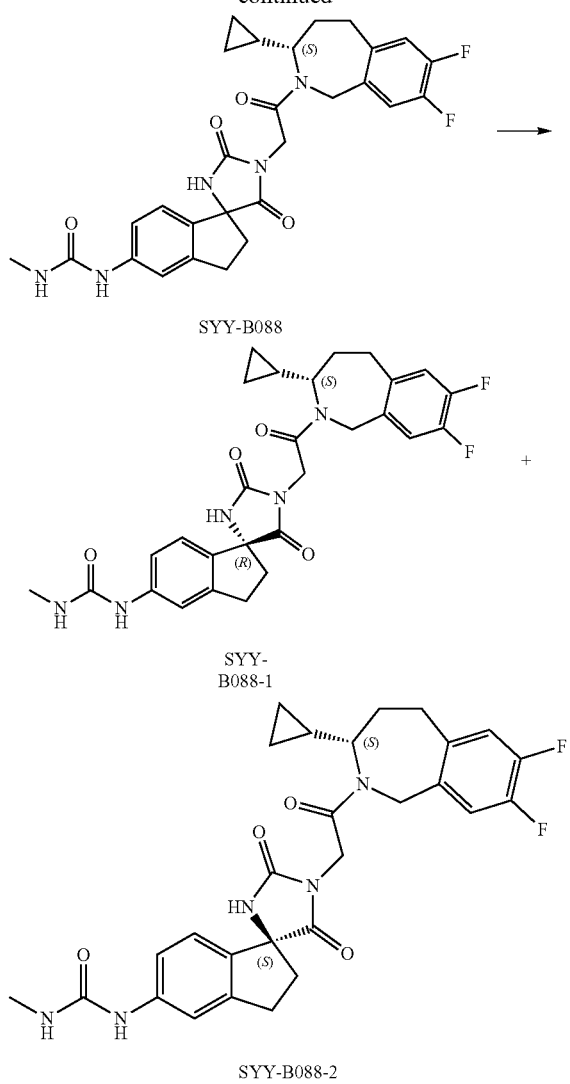

SYY-B088

SYY-B088-1

SYY-B088-2

The chiral amide AN-19-1 (100 mg, 0.290 mmol) was dissolved in DMF (6 mL), added with the spiro ring SP-2 (100 mg, 0.364 mmol) and potassium carbonate (80 mg, 0.579 mmol) at room temperature, and reacted at room temperature for 16 h. TLC detected that the raw material was reacted completely. The resultant was diluted with saturated brine, and extracted with ethyl acetate. The combined organic phase was dried over anhydrous sodium sulfate, and concentrated. The crude was purified by silica gel column chromatography to obtain SYY—B088 (170 mg) as a white solid. $^1$H NMR (400 MHz, DMSO-d$_6$) δ 8.68-8.54 (m, 2H), 7.48-7.00 (m, 5H), 6.01 (m, 1H), 4.88-3.44 (m, 5H), 3.11-2.91 (m, 3H), 2.71-2.52 (m, 4H), 2.46 (m, 1H), 2.14 (m, 1H), 2.02 (m, 2H), 1.42 (m, 1H), 0.65-0.27 (m, 4H). LC-MS: [M+H]$^+$=538.3.

Chiral resolution was performed to obtain SYY-B088-1, and the SYY-B088-2. Preparation method: Daicel AD-H, filler particle size (5 μm), inner diameter (30 mm), length (250 mm), flow rate: 20 mL/min, mobile phase: 60% n-hexane+40% isopropanol, isogradient elution, wavelength 254 nm, peak time is 9.46 min for peak 1, and 15.27 min for peak 2.

Example 169 Synthesis of SYY-B090-1

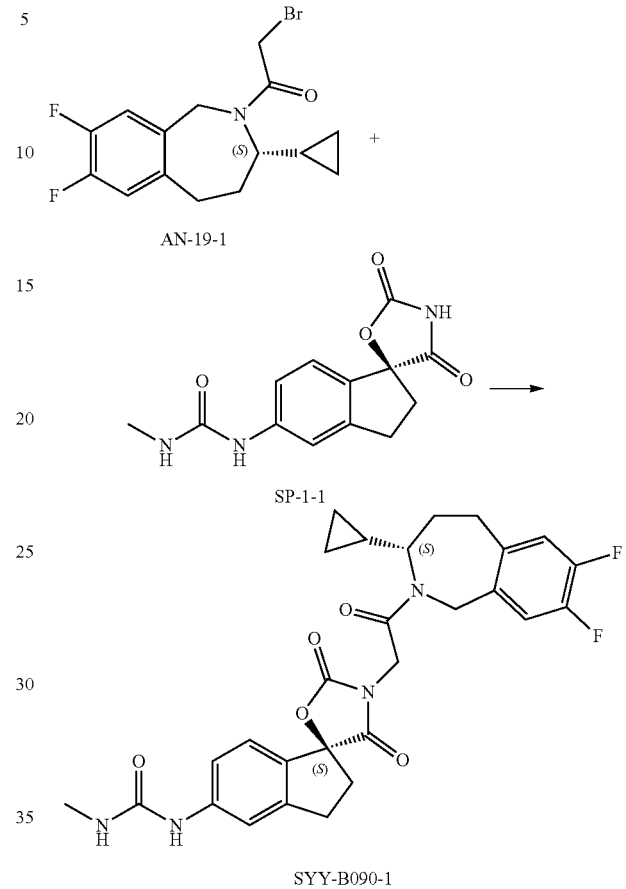

AN-19-1

SP-1-1

SYY-B090-1

AN-19-1 (70 mg, 0.203 mmol) was dissolved in DMF (6 mL), added with SP-1-1 (70 mg, 0.254 mmol) and potassium carbonate (80 mg, 0.579 mmol) at room temperature, and reacted at room temperature for 16 h. TLC detected that the reaction was complete. The resultant was diluted with saturated brine, and extracted with ethyl acetate. The combined organic phase was dried over anhydrous sodium sulfate and concentrated. The crude was purified by silica gel column chromatography to obtain SYY-B090-1 (90 mg) as a white solid. $^1$H NMR (400 MHz, DMSO-d$_6$) δ 8.72 (m, 1H), 7.52-7.18 (m, 5H), 6.09 (m, 1H), 4.85-3.48 (m, 5H), 3.13-2.91 (m, 3H), 2.74-2.52 (m, 4H), 2.43 (m, 1H), 2.14 (m, 1H), 2.02 (m, 2H), 1.42 (m, 1H), 0.66-0.27 (m, 4H). LC-MS: [M+H]$^+$=539.2.

Example 170 Synthesis of SYY-B090-2

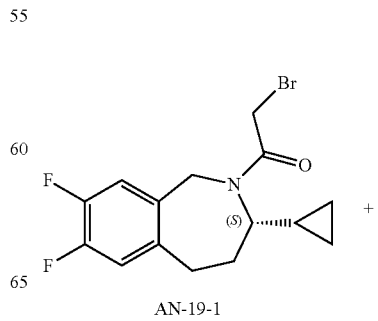

AN-19-1

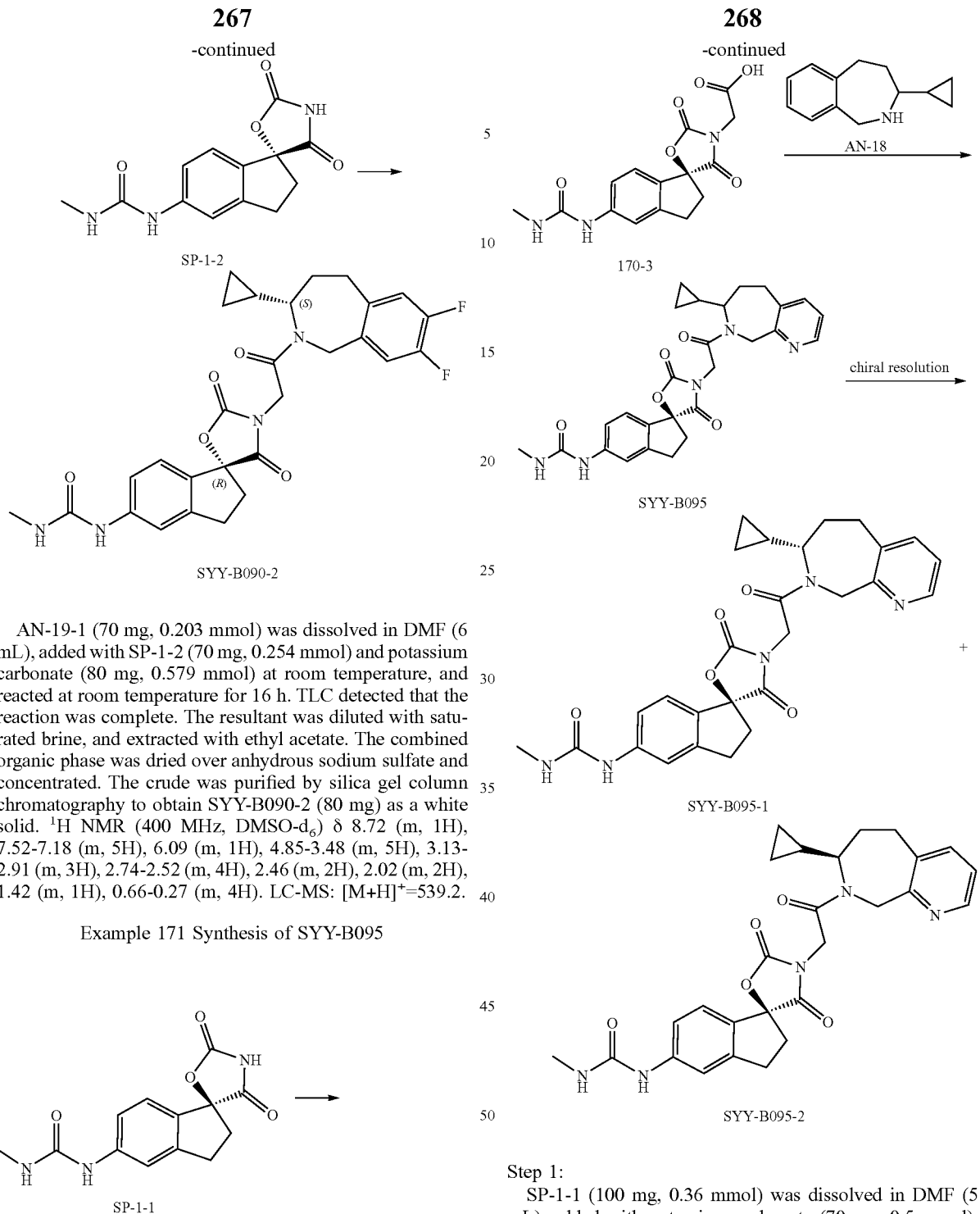

AN-19-1 (70 mg, 0.203 mmol) was dissolved in DMF (6 mL), added with SP-1-2 (70 mg, 0.254 mmol) and potassium carbonate (80 mg, 0.579 mmol) at room temperature, and reacted at room temperature for 16 h. TLC detected that the reaction was complete. The resultant was diluted with saturated brine, and extracted with ethyl acetate. The combined organic phase was dried over anhydrous sodium sulfate and concentrated. The crude was purified by silica gel column chromatography to obtain SYY-B090-2 (80 mg) as a white solid. $^1$H NMR (400 MHz, DMSO-$d_6$) δ 8.72 (m, 1H), 7.52-7.18 (m, 5H), 6.09 (m, 1H), 4.85-3.48 (m, 5H), 3.13-2.91 (m, 3H), 2.74-2.52 (m, 4H), 2.46 (m, 2H), 2.02 (m, 2H), 1.42 (m, 1H), 0.66-0.27 (m, 4H). LC-MS: [M+H]$^+$=539.2.

Example 171 Synthesis of SYY-B095

Step 1:

SP-1-1 (100 mg, 0.36 mmol) was dissolved in DMF (5 mL), added with potassium carbonate (70 mg, 0.5 mmol), stirred for 10 min, added with benzyl 2-bromoacetate (91 mg, 0.40 mmol), and stirred at room temperature to react for 1 h. TLC detected that the reaction was complete. The reaction solution was quenched with water and extracted with ethyl acetate. The organic phase was washed with saturated brine, dried over anhydrous sodium sulfate, and concentrated to obtain 170-2 (200 mg, crude) as a yellow viscous oil.

Step 2:

170-2 (200 mg) was dissolved in methanol (15 mL), and added with Pd/C (100 mg). After atmosphere was replaced with hydrogen three times, the reaction mixture was stirred at room temperature for 1 h. TLC detected that the reaction was complete. The reaction solution was filtered, and concentrated to obtain 170-3 (98 mg) as a solid.

Step 3:

170-3 (98 mg, 0.29 mmol) and amine AN-18 (150 mg) were dissolved in DMF (5 mL), added with DIPEA (75 mg, 0.58 mmol) and then with HATU (165 mg, 0.44 mmol), and stirred at room temperature to react for 1 h. TLC detected that the reaction was complete. The reaction solution was added with water and extracted with ethyl acetate. The organic phase was washed with saturated brine, dried over anhydrous sodium sulfate, and concentrated. The crude was purified by Pre-TLC to obtain a yellow solid (70 mg). $^1$H NMR (400 MHz, DMSO-d$_6$) (8.72 (m, 1H), 8.33 (m, 1H), 7.62-7.51 (m, 2H), 7.25-7.16 (m, 3H), 6.08 (m, 1H), 5.06-3.52 (m, 6H), 3.03 (m, 3H), 2.76-2.54 (m, 4H), 2.42 (m, 1H), 2.02 (m, 2H), 1.46 (m, 1H), 0.62-0.28 (m, 4H). LC-MS: [M+H]$^+$=504.2.

Chiral resolution was performed to obtain SYY-B095-1, and SYY-B095-2. Preparation method: Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 20.38 min for peak 1, and 57.16 min for peak 2.

Example 172 Synthesis of SYY-B096

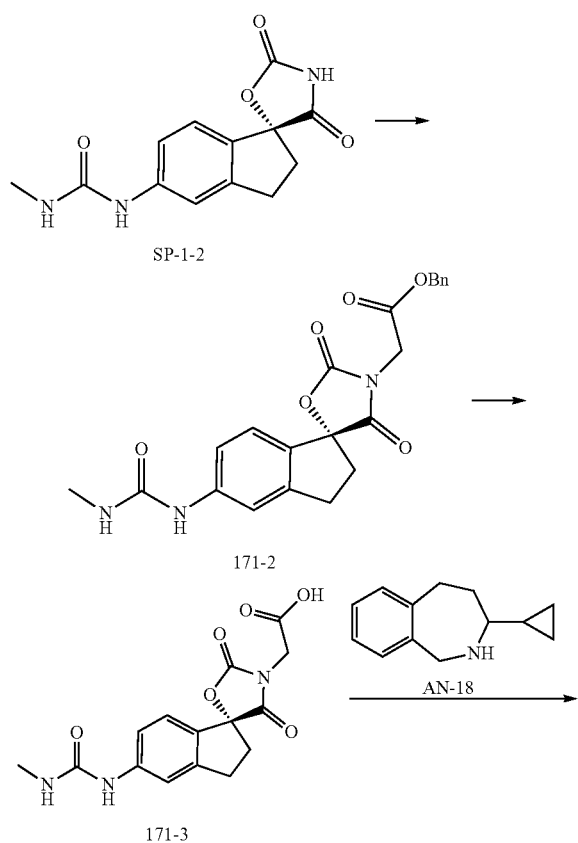

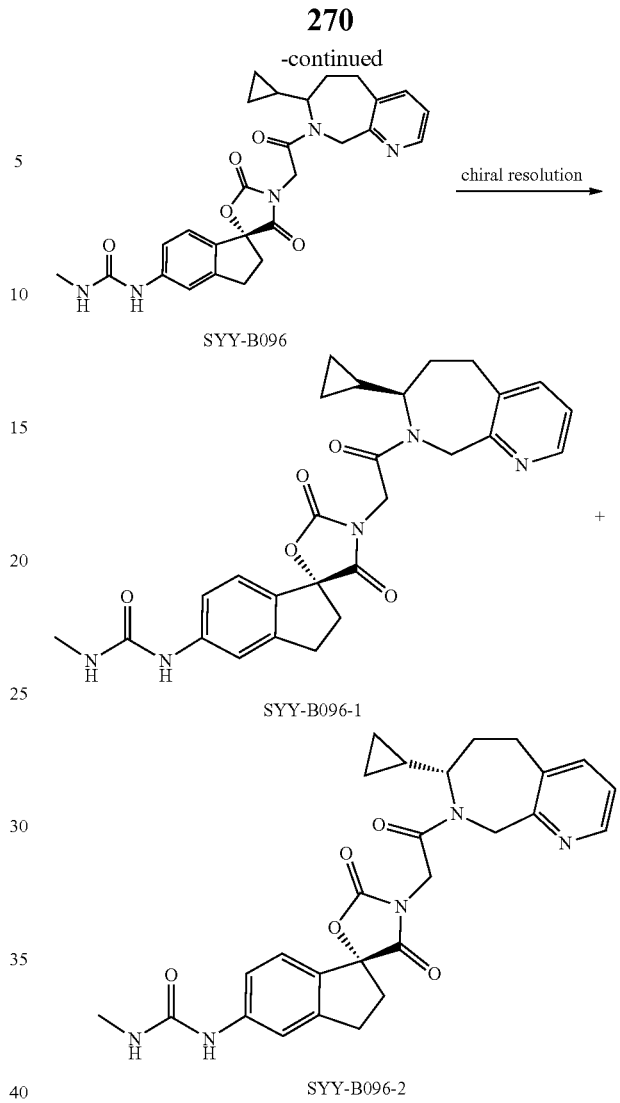

Step 1:

SP-1-2 (250 mg) was dissolved in DMF (10 mL), added with potassium carbonate (176 mg), stirred for 10 min, added with benzyl 2-bromoacetate (228 mg), and stirred at room temperature to react for 1 h. TLC detected that the reaction was complete. The reaction solution was quenched with water and extracted with ethyl acetate. The organic phase was washed with saturated brine, dried over anhydrous sodium sulfate, and concentrated to obtain 171-2 (430 mg) as a yellow viscous oil.

Step 2:

171-2 (430 mg) was dissolved in methanol (15 mL), and added with Pd/C (100 mg). After atmosphere was replaced with hydrogen three times, the reaction mixture was stirred at room temperature for 1 h. TLC detected that the reaction was complete. The reaction solution was filtered, and concentrated to obtain 171-3 (280 mg) as a solid.

Step 3:

171-3 (150 mg) and amine AN-18 (169 mg) were dissolved in DMF (10 mL), added with DIPEA (116 mg) and then with HATU (257 mg), and stirred at room temperature to react for 1 h. TLC detected that the reaction was complete. The reaction solution was added with water and extracted with ethyl acetate. The organic phase was washed with saturated brine, dried over anhydrous sodium sulfate, and concentrated. The crude was purified by Pre-TLC to obtain a yellow solid (80 mg). $^1$H NMR (400 MHz, DMSO-$d_6$) δ 8.72 (m, 1H), 8.33 (m, 1H), 7.62-7.51 (m, 2H), 7.25-7.16 (m, 3H), 6.08 (m, 1H), 5.06-3.52 (m, 6H), 3.03 (m, 3H), 2.76-2.54 (m, 4H), 2.42 (m, 1H), 2.02 (m, 2H), 1.46 (m, 1H), 0.62-0.28 (m, 4H). LC-MS: [M+H]$^+$=504.2.

Chiral resolution was performed to obtain SYY-B096-1 and SYY-B096-2. Preparation method: Daicel AD-H, filler particle size (5 μm), inner diameter (30 mm), length (250 mm), flow rate: 30 mL/min, mobile phase: 70% n-hexane+ 30% ethanol, isogradient elution, wavelength 254 nm, peak time is 64.99 min for peak 1, and 82.02 min for peak 2.

Example 173 Synthesis of SYY-B097-1 and SYY-B098-1

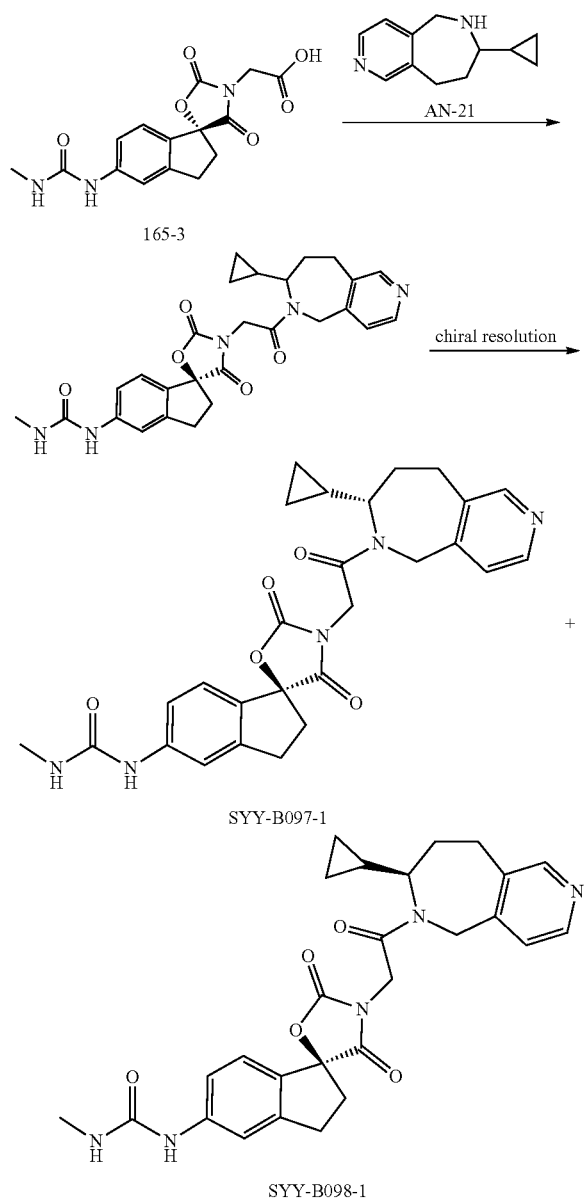

165-3 (89 mg, 0.26 mmol) and racemic amine AN-21 (50 mg, 0.26 mmol) were dissolved in DMF (5 mL) under nitrogen, added with DIPEA (68 mg, 0.52 mmol) and HATU (150 mg, 0.39 mmol) at room temperature, and reacted at room temperature for 1 h. TLC detected that the reaction was complete. The resultant was added with water and extracted with ethyl acetate. The organic phase was washed with saturated brine, dried over anhydrous sodium sulfate, and concentrated. The crude was purified by silica gel column chromatography to obtain a product (110 mg). $^1$H NMR (400 MHz, DMSO-$d_6$) δ 8.68 (m, 1H), 8.39-8.30 (m, 2H), 7.52-7.19 (m, 4H), 6.07 (m, 1H), 4.93-3.52 (m, 6H), 3.03 (m, 3H), 2.76-2.54 (m, 4H), 2.42 (m, 1H), 2.02 (m, 2H), 1.46 (m, 1H), 0.62-0.28 (m, 4H). LC-MS: [M+H]$^+$=504.2.

Chiral resolution was performed to obtain SYY-B097-1 and SYY-B098-1. Preparation method: Daicel AD-H, filler particle size (5 μm), inner diameter (30 mm), length (250 mm), flow rate: 30 mL/min, mobile phase: 70% n-hexane+ 30% ethanol, isogradient elution, wavelength 254 nm, peak time is 34.31 min for peak 1, and 49.21 min for peak 2.

Example 174 Synthesis of SYY-B097-2 and SYY-B098-2

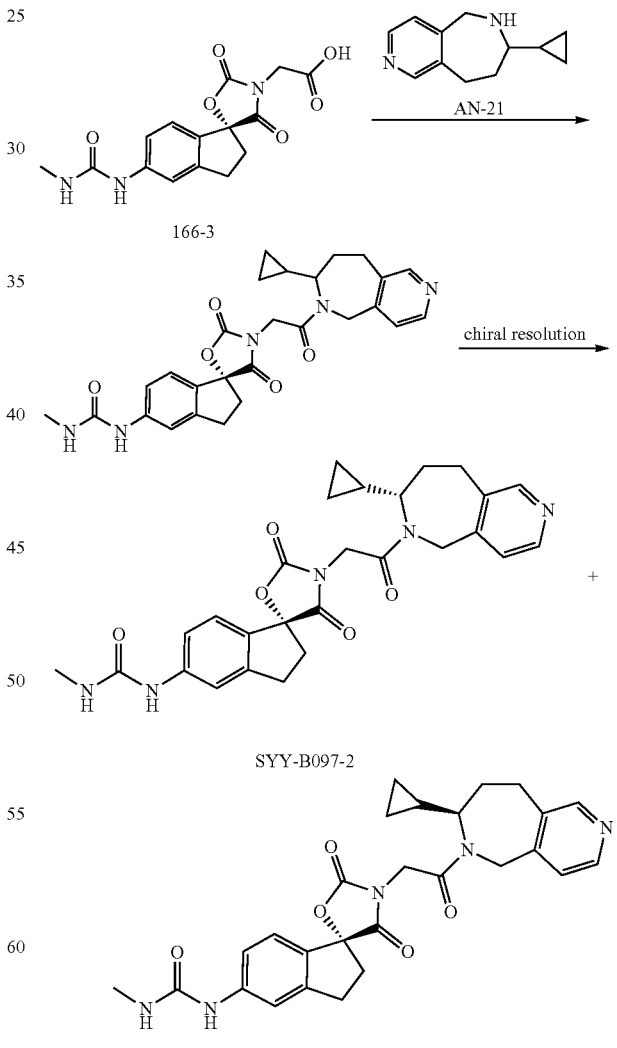

166-3 (143 mg) and racemic amine AN-21 (81 mg) were dissolved in DMF (10 mL) under nitrogen, added with DIPEA (111 mg) and HATU (245 mg) at room temperature, and reacted at room temperature for 1 h. TLC detected that the reaction was complete. The resultant was added with water and extracted with ethyl acetate. The organic phase was washed with saturated brine, dried over anhydrous sodium sulfate, and concentrated. The crude was purified by silica gel column chromatography to obtain a product (60 mg). $^1$H NMR (400 MHz, DMSO-d$_6$) δ 8.77 (m, 1H), 8.39-8.30 (m, 2H), 7.52-7.19 (m, 4H), 6.07 (m, 1H), 4.93-3.52 (m, 6H), 3.03 (m, 3H), 2.76-2.54 (m, 4H), 2.42 (m, 1H), 2.02 (m, 2H), 1.46 (m, 1H), 0.62-0.28 (m, 4H). LC-MS: [M+H]$^+$=504.2.

Chiral resolution was performed to obtain SYY-B097-2 and SYY-B098-2. Preparation method: Daicel AD-H, filler particle size (5 μm), inner diameter (30 mm), length (250 mm), flow rate: 30 mL/min, mobile phase: 60% n-hexane+ 40% isopropanol, isogradient elution, wavelength 254 nm, peak time is 15.26 min for peak 1, and 25.10 min for peak 2.

Example 175 Synthesis of Amide AN-22

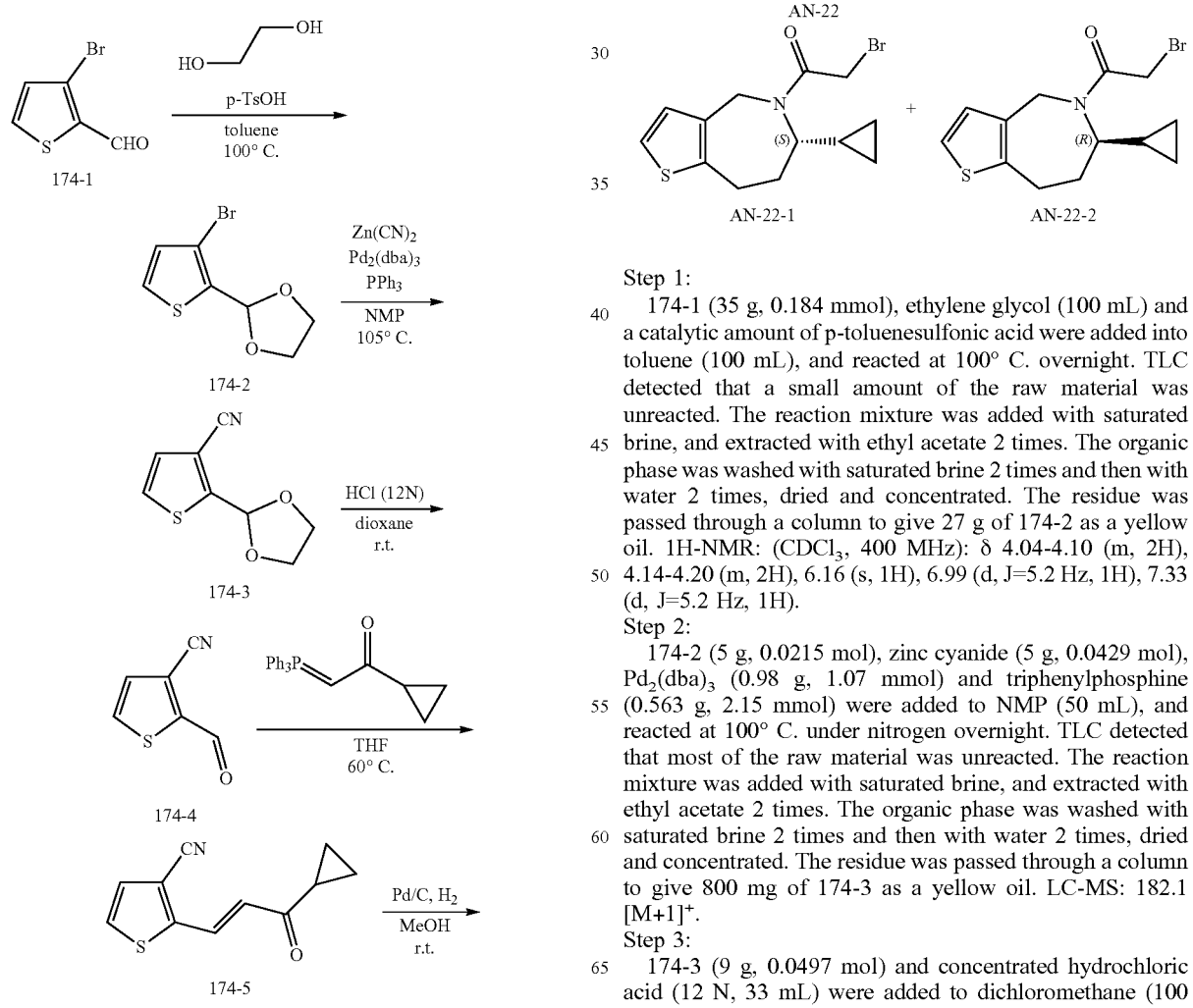

Step 1:
174-1 (35 g, 0.184 mmol), ethylene glycol (100 mL) and a catalytic amount of p-toluenesulfonic acid were added into toluene (100 mL), and reacted at 100° C. overnight. TLC detected that a small amount of the raw material was unreacted. The reaction mixture was added with saturated brine, and extracted with ethyl acetate 2 times. The organic phase was washed with saturated brine 2 times and then with water 2 times, dried and concentrated. The residue was passed through a column to give 27 g of 174-2 as a yellow oil. 1H-NMR: (CDCl$_3$, 400 MHz): δ 4.04-4.10 (m, 2H), 4.14-4.20 (m, 2H), 6.16 (s, 1H), 6.99 (d, J=5.2 Hz, 1H), 7.33 (d, J=5.2 Hz, 1H).

Step 2:
174-2 (5 g, 0.0215 mol), zinc cyanide (5 g, 0.0429 mol), Pd$_2$(dba)$_3$ (0.98 g, 1.07 mmol) and triphenylphosphine (0.563 g, 2.15 mmol) were added to NMP (50 mL), and reacted at 100° C. under nitrogen overnight. TLC detected that most of the raw material was unreacted. The reaction mixture was added with saturated brine, and extracted with ethyl acetate 2 times. The organic phase was washed with saturated brine 2 times and then with water 2 times, dried and concentrated. The residue was passed through a column to give 800 mg of 174-3 as a yellow oil. LC-MS: 182.1 [M+1]$^+$.

Step 3:
174-3 (9 g, 0.0497 mol) and concentrated hydrochloric acid (12 N, 33 mL) were added to dichloromethane (100 mL), and stirred for 1 h at room temperature. LCMS detected that the raw material was completely reacted. The resultant was diluted with saturated brine, and extracted with ethyl acetate 2 times. The combined organic phase was washed with saturated brine 2 times, dried over anhydrous sodium sulfate, and concentrated to give 174-4, which was used directly in the next step.

Step 4:

The product in the previous step (6.8 g) was dissolved in tetrahydrofuran (200 mL), added with the phosphorus ylide (20 g, 0.0581 mol), and stirred at 60° C. for 2 h. TLC detected that the reaction was complete. The resultant was directly concentrated, and the residue was passed through a column to obtain 11 g of 174-5 as a white solid. $^1$H-NMR: (CDCl$_3$, 400 MHz): δ 1.05-1.08 (m, 2H), 1.21-1.23 (m, 2H), 2.27-2.31 (m, 1H), 6.91 (d, J=16 Hz, 1H), 7.30 (d, J=5.2 Hz, 1H), 7.45 (d, J=5.2 Hz, 1H), 7.83 (d, J=16 Hz, 1H).

Step 5:

174-5 (11 g, 0.478 mol) and Pd/C (2 g) were added to methanol (150 mL), and stirred for 6 h under hydrogen. TLC detected that most of the raw material was reacted. The resultant was filtered, and the filtrate was used directly in the next step.

Step 6:

Raney nickel (2 g) and triethylamine (2 mL) were added to the filtrate in the previous step, and stirred for 7 h under hydrogen. TLC detected that most of the raw material was reacted. The resultant was filtered, and the filtrate was used directly in the next step.

Step 7:

Sodium cyanoborohydride and acetic acid (2 mL) were added to the filtrate in the previous step, and stirred at room temperature for 1 h. TLC detected that the raw material was completely reacted. The resultant was quenched with saturated brine, and extracted with ethyl acetate 2 times. The combined organic phase was washed with saturated brine 2 times, dried over anhydrous sodium sulfate, and concentrated to give 174-8, which was used directly in the next step.

Step 8:

Dichloromethane was added to the concentrated product in the previous step, slowly added with bromoacetyl bromide dropwise, and stirred overnight at room temperature. The resultant was added with water, stirred for 0.5 h, and extracted with dichloromethane 2 times. The combined organic phase was washed with saturated sodium bicarbonate solution 2 times, dried and concentrated. The residue was passed through a column to give 2.4 g of AN-22 as a yellowish oil. LC-MS: [M+1]$^+$314.0.

Chiral resolution was performed to obtain AN-22-1 and AN-22-2: Preparative column was Daicel AD-H, filler particle size (5 μm), inner diameter (30 mm), length (250 mm), flow rate: 30 mL/min, mobile phase: 95% n-hexane+5% ethanol, isogradient elution, wavelength 254 nm, peak time is 19.33 min for peak 1, and 34.96 min for peak 2.

Example 176 Synthesis of SYY-B102-1

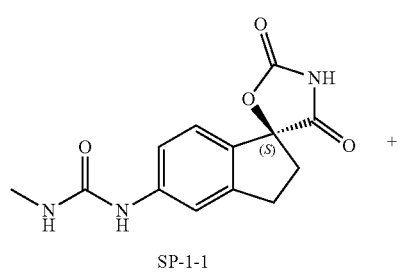

SP-1-1

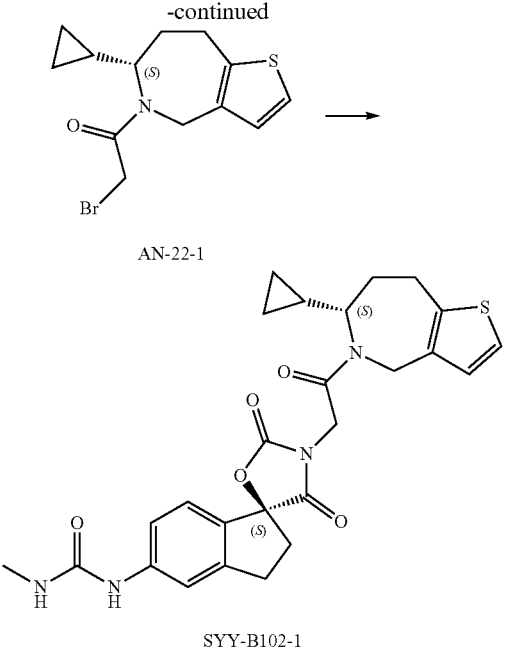

AN-22-1

SYY-B102-1

AN-22-1 (50 mg, 0.159 mmol), spiro ring SP-1-1 (53 mg, 0.193 mmol) and potassium carbonate (66 mg, 0.477 mmol) were dissolved in dry DMF (5 mL) at room temperature to react for 2 h. TLC detected that most of the raw material was reacted. The reaction solution was poured into ice water and extracted with ethyl acetate. The organic phase was washed with water and saturated brine, dried over anhydrous sodium sulfate, and concentrated. The residue was purified to obtain targeted SYY-B102-1 (21 mg) as a white solid.

$^1$H NMR (400 MHz, DMSO-d$_6$) δ 8.72 (m, 1H), 7.53 (m, 1H), 7.27-7.15 (m, 3H), 6.90 (m, 1H), 6.10 (m, 1H), 5.01-3.58 (m, 5H), 3.18-2.92 (m, 3H), 2.65-2.56 (m, 4H), 2.49-2.43 (m, 2H), 2.12 (m, 2H), 1.28 (m, 1H), 0.55-0.31 (m, 4H). LC-MS: [M+H]$^+$=509.2.

Example 177 Synthesis of SYY-B102-2

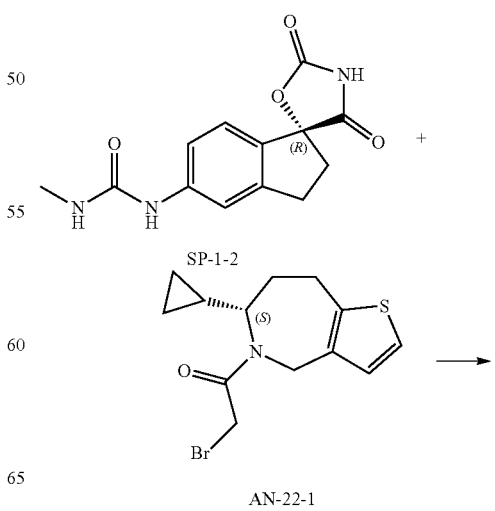

SP-1-2

AN-22-1

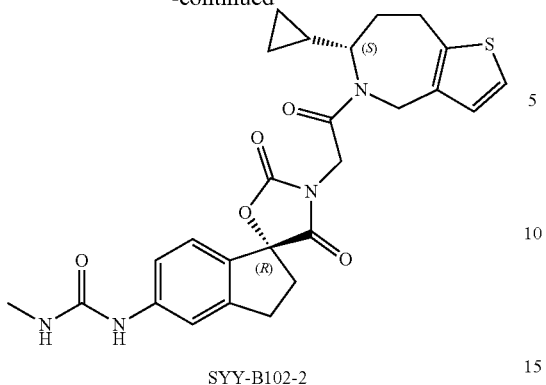

Thiophene fused 7-membered ring amide AN-22-1 (70 mg, 0.223 mmol), spiro ring SP-1-2 (70 mg, 0.254 mmol) and potassium carbonate (100 mg, 0.723 mmol) were added to dry DMF (6 mL) at room temperature, and stirred for 3 h at room temperature. TLC detected that most of the raw material was reacted. The reaction solution was poured into ice water and extracted with ethyl acetate. The organic phase was washed with water and saturated brine, dried over anhydrous sodium sulfate, and concentrated. The residue was purified to obtain targeted SYY-B102-2 (40 mg) as a white solid. $^1$H NMR (400 MHz, DMSO-$d_6$) δ 8.71 (m, 1H), 7.52 (m, 1H), 7.27-7.15 (m, 3H), 6.90 (m, 1H), 6.09 (m, 1H), 5.05-3.58 (m, 5H), 3.18-2.92 (m, 3H), 2.65-2.56 (m, 4H), 2.49-2.43 (m, 2H), 2.12 (m, 2H), 1.28 (m, 1H), 0.55-0.31 (m, 4H). LC-MS: [M+H]$^+$=509.2.

Example 178 Synthesis of SYY—B104

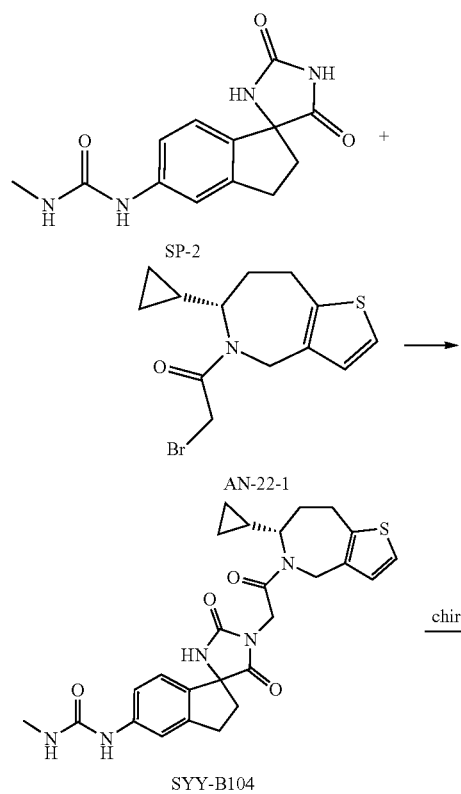

Thiophene fused 7-membered ring amide AN-22-1 (150 mg, 0.479 mmol), racemic spiro ring SP-2 (150 mg, 0.545 mmol) and potassium carbonate (198 mg, 1.437 mmol) were successively added to dry DMF (6 mL) at room temperature, and stirred for 3 h at room temperature. TLC detected that most of the raw material was reacted. The reaction solution was poured into ice water and extracted with ethyl acetate. The organic phase was washed with water and saturated brine, dried over anhydrous sodium sulfate, and concentrated. The residue was purified to obtain targeted SYY—B104 (180 mg) as a white solid. Chiral resolution was performed to obtain SYY-B104-1 and the SYY-B104-2: Preparative column was Daicel AD-H, filler particle size (5 μm), inner diameter (30 mm), length (250 mm), flow rate: 30 mL/min, mobile phase: 60% n-hexane+40% ethanol, iso-gradient elution, wavelength 254 nm, peak time is 9.75 min for peak 1, and 50.31 min for peak 2.

Example 179 Synthesis of Spiro Ring SP-23

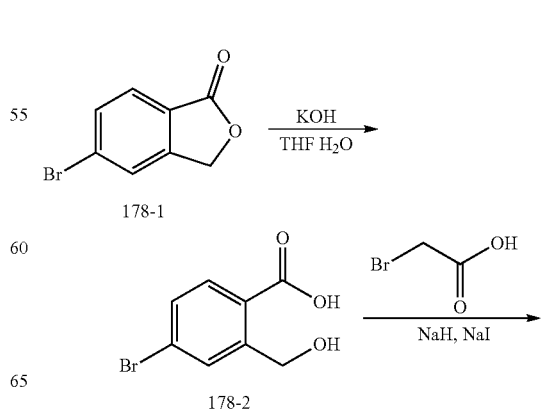

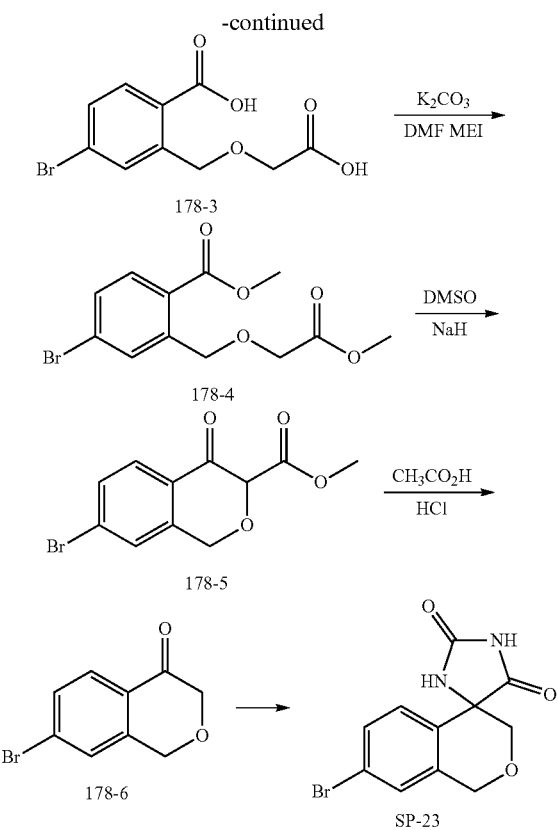

Step One:

5-Bromo phthalide (178-1, 100.0 g, 0.469 mmol) was dissolved in tetrahydrofuran (350 ml)/methanol (50 ml), added with 140 g of a KOH solution (40 g of potassium hydroxide dissolved in 100 ml of water) at room temperature, and stirred at room temperature for 5 h. TLC showed that the reaction was complete. The reaction mixture was distilled under reduced pressure to remove most of the organic solvents, adjusted pH to 12 with 2N hydrochloric acid under an ice-water bath to precipitate a solid. The solid was suction filtered, washed with water and dried to obtain the targeted 178-2 (100.2 g, crude) as a yellow solid, which was used directly in the next step. LC-MS: 231.0 [M+1]$^+$.

Step Two:

NaH (60%, 80.0 g) was slowly added to absolute ethanol (800 ml) under an ice-water bath, added dropwise under an ice-water bath with 178-2 (100.2 g, crude) and bromoacetic acid (90.0 g, 0.647 mmol) dissolved in anhydrous tetrahydrofuran (900 ml), stirred at room temperature for 0.5 h, added with sodium iodide (10 g) and heated to 80° C. to stir for 24 h. The reaction mixture was cooled to room temperature and poured into ice water, adjust pH with 2N hydrochloric acid to 1 to 2, and extracted with ethyl acetate 2 times. The organic phase was washed with water and brine, dried over anhydrous sodium sulfate, and concentrated to obtain 178-3 (180.2 g, crude). LC-MS: 289.0 [M+1]$^+$.

Step Three:

178-3 (180.2 g, crude) was dissolved in dry DMF (400 ml), added with methyl iodide (100 ml, 1.61 mmol) and potassium carbonate (200.0 g, 1.45 mmol) at room temperature, and stirred overnight at room temperature. The reaction solution was poured into ice water and extracted with ethyl acetate. The organic phase was washed with water and saturated NaCl solution, dried over anhydrous sodium sulfate, and concentrated. The crude was purified by silica gel column chromatography to obtain 178-4 (80.4 g, yield in 3 steps: 54%) as a template product. LC-MS: 317.0 [M+1]$^+$.

Step Four:

Sodium hydride (60%, 12.0 g) was dissolved in dry DMSO (200 ml), stirred at room temperature for 2 h, slowly added with 178-4 (80.4 g, 0.254 mmol) dissolved in dry DMSO (200 ml), and stirred overnight at 50° C. TLC showed that the reaction was basically complete. The reaction solution was slowly poured into a dilute hydrochloric acid under ice-water cooling to precipitate a solid, which was filtered by suction, washed and dried to obtain 178-5 (60.5 g, crude) as a yellow solid.

Step Five:

178-5 (50.0 g, crude) was dissolved in acetic acid (400 ml), added with concentrated hydrochloric acid (37%, 150 ml) at room temperature, and stirred at 60° C. for 1 h. The reaction system was changed from turbidity to clear. TLC showed that the reaction was complete. The resultant was treated and dried to obtain a crude 178-6 (26 g), which was directly used in the next step. $^1$H-NMR: (400 MHz, DMSO-d$_6$): 7.82-7.80 (m, 1H), 7.89-7.67 (m, 2H), 4.89 (s, 2H), 4.37 (s, 2H).

Step Six:

178-6 (5.0 g, crude) was dissolved in ethanol (100 ml), added with ammonia (20 ml), ammonium carbonate (21.1 g, 0.22 mmol), ammonium fluoride (4.0 eq) and TMSCN (21.8 g, 0.22 mmol) at room temperature, and stirred overnight at 60° C. The reaction mixture was vacuum distilled to remove most of ethanol, and extracted with ethyl acetate several times. The organic phase was washed with brine, dried over anhydrous sodium sulfate, and concentrated. The crude was purified by column chromatography to obtain the targeted SP-23 (1.5 g), LC-MS: 297.0 [M+1]$^+$.

Example 180 Synthesis of SYY—B106

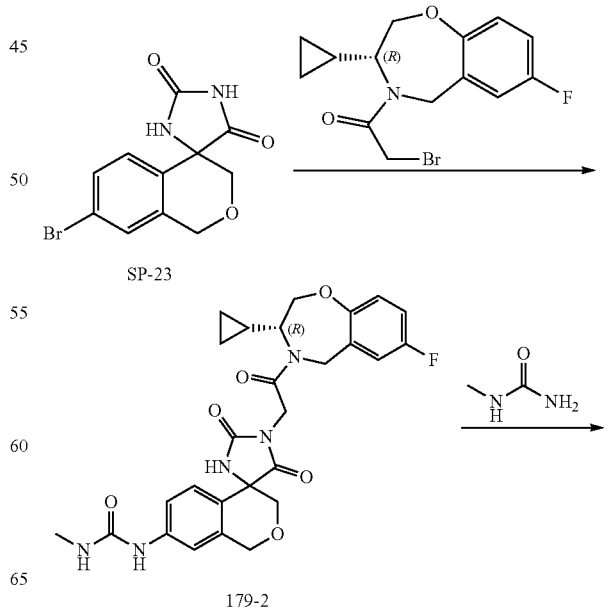

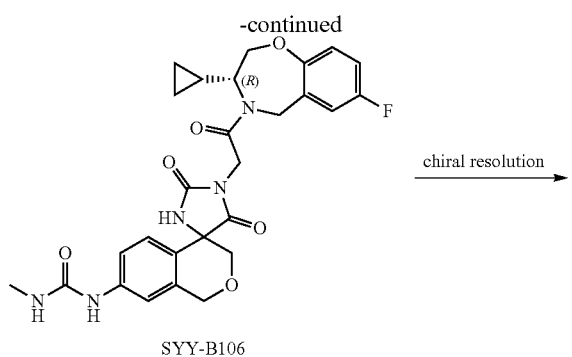

ethyl acetate. The organic phase was washed with water and saturated brine, dried over anhydrous sodium sulfate, and concentrated. The crude was purified by silica gel column chromatography to obtain SYY—B106 (200 mg). LC-MS: 538.2 [M+1]$^+$.

Chiral resolution was performed to obtain SYY-B106-1 and SYY-B106-2. Preparative column: Daicel AD-H (30*250 mm), filler particle size (5 μm), inner diameter (30 mm), length (250 mm), flow rate: 30 mL/min, mobile phase: 60% n-hexane+40% ethanol, isogradient elution, wavelength 254 nm, peak time is 18.64 min for peak 1, and 87.83 min for peak 2.

Example 181 Synthesis of SYY—B108

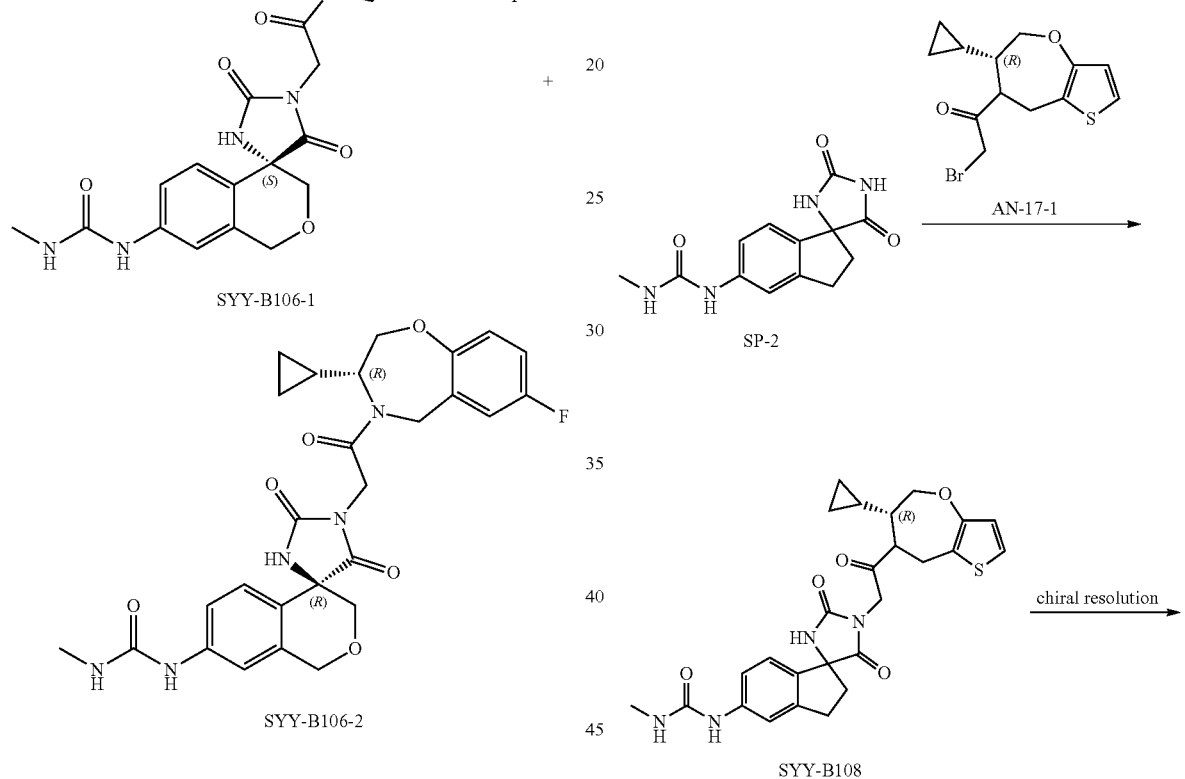

Step 1:

The racemic spiro ring SP-23 (300 mg, 1 mmol) and the amide AN-15-1 (300 mg, 0.91 mmol) were dissolved in DMF (6 mL), added with potassium carbonate (300 mg, 2.1 mmol), and reacted at room temperature for 3 h. The reaction solution was poured into 50 ml of ice water, stirred for 10 min, and filtered. The filter cake was washed with water and petroleum ether, dissolved with ethyl acetate, washed with water and saturated brine, dried and concentrated. The crude was purified by silica gel column chromatography to obtain targeted 179-2 (310 mg, 63%) as a white solid. LC-MS: 544.1 [M+1]$^+$.

Step 2:

179-2 (310 mg, 0.56 mmol) was dissolved in dioxane (30 ml), added with methylurea (168 mg, 2.2 mmol) and cesium carbonate (367 mg, 1.1 mmol), and finally added with Pd$_2$(dba)$_3$ (30 mg, 0.056 mmol) and xantphos (60 mg, 0.056 mmol). The atmosphere was replaced with nitrogen, the reaction mixture was reacted at 100° C. for 3 h, cooled to room temperature, poured into ice water and extracted with

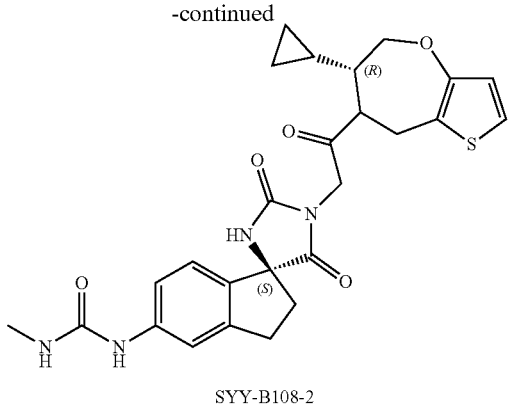

SYY-B108-2

SYY—B108 was prepared using the same method as that in Example 30, except that the spiro ring fragment SP-2 was used instead of SP-1 and the amide fragment AN-17-1 was used instead of AN-7. $^1$H NMR (400 MHz, DMSO-d$_6$) δ 8.71-8.54 (m, 2H), 7.42 (m, 1H), 7.25-7.04 (m, 3H), 6.65 (m, 1H), 6.01 (m, 1H), 5.09-3.80 (m, 7H), 2.93 (m, 2H), 2.62 (m, 3H), 2.49-2.43 (m, 1H), 2.16 (m, 1H), 1.08 (m, 1H), 0.53-0.35 (m, 4H). LC-MS: [M+H]$^+$=510.1.

Chiral resolution was performed to obtain SYY-B108-1 and SYY-B108-2. Preparative column: Daicel AD-H (30*250 mm), filler particle size (5 μm), inner diameter (30 mm), length (250 mm), flow rate: 30 mL/min, mobile phase: 60% n-hexane+40% ethanol, isogradient elution, wavelength 254 nm, peak time is 20.03 min for peak 1, and 86.35 min for peak 2.

Example 182 Synthesis of Spiro Ring SP-24

Step One:

178-6 (13.0 g, 57.3 mmol) was dissolved in anhydrous dichloromethane (80 mL), added with N-methylmorpholine-N-oxide (4.02 g, 34.3 mmol) and trimethylsilyl cyanide (18.0 g, 181 mmol), and stirred at room temperature for 2 h. TLC showed that the reaction was complete. The reaction mixture was added with petroleum ether (200 mL), distilled off most of the dichloromethane under reduced pressure, added with petroleum ether (200 mL), stirred for 15 min, filtered with suction, and concentrated to obtain 181-2 (9.2 g, crude) as an intermediate.

Step Two:

The intermediate 181-2 (9.2 g, crude) was dissolved in absolute ethanol (70 mL), introduced with dry hydrogen chloride gas at 0° C. for 5.5 h, and rotary evaporated under reduced pressure at 30° C. to obtain a crude, which was dissolved in tetrahydrofuran and directly used in the next step. The obtained solid was added into anhydrous tetrahydrofuran (100 mL), slowly added with triethylamine (17.4 g, 172 mmol) dropwise at 0° C., dropwise added with triphosgene (8.6 g, 29 mmol) dissolved in tetrahydrofuran, stirred at 0° C. for 1 h, added with 1N hydrochloric acid and further stirred for 0.5 h. TLC showed that the reaction was complete. The reaction mixture was extracted with ethyl acetate. The resulting ethyl acetate was washed with saturated sodium bicarbonate, and the resulting aqueous solution was extracted with ethyl acetate again. The aqueous phase was adjusted pH with 1N hydrochloric acid to about 3-4, and extracted with ethyl acetate. The combined organic phase was dried, rotary evaporated to dryness to obtain SP-24 (4.1 g). LC-MS: 298.0 [M+1]$^+$. $^1$H-NMR (400 MHz, DMSO-d$_6$) (12.43 (br, 1H), 7.56-7.53 (m, 2H), 7.29 (d, J=8.0 Hz, 1H), 4.86 (d, J=15.6 Hz, 1H), 4.73 (d, J=12.8 Hz, 1H), 4.03 (d, J=12.8 Hz, 1H).

Example 183 Synthesis of Spiro Ring SP-25

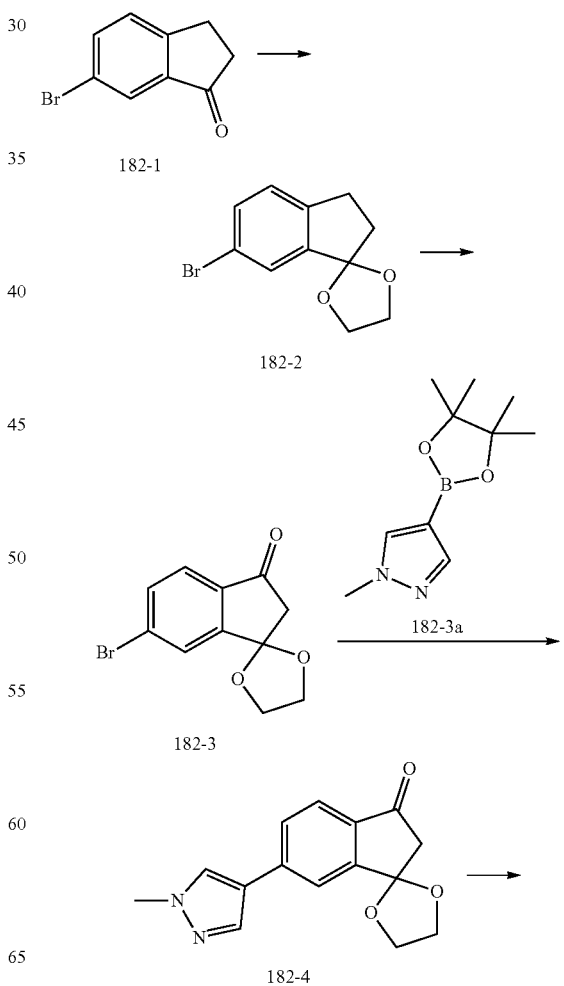

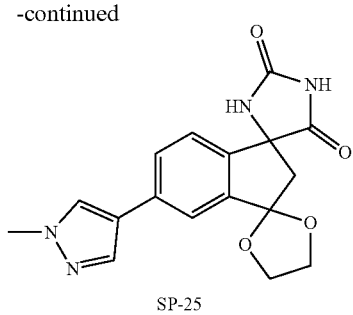

SP-25

Step 1:

6-Bromoindanone (182-1, 10.0 g, 47.38 mmol), ethylene glycol (30.0 g, 483.3 mmol) and p-toluenesulfonic acid (80 mg, 0.46 mmol) were dissolved in toluene (300 mL), heated to reflux (125° C.) to separate water overnight. The water separation was complete. TLC detected that the reaction was complete. The reaction solution was cooled to room temperature, concentrated to remove the solvent, neutralized with saturated sodium carbonate aqueous solution, and extracted with ethyl acetate. The combined organic phase was washed with water and saturated brine, dried over anhydrous sodium sulfate, and concentrated. The crude was purified by silica gel column chromatography to obtain 182-2 (10.5 g) as a yellow oil. $^1$H-NMR: (CDCl$_3$, 400 MHz): δ 2.31 (t, J=7.2 Hz, 2H), 2.90 (t, J=7.2 Hz, 2H), 4.07-4.11 (m, 2H), 4.18-4.22 (m, 2H), 7.12 (d, J=8.0 Hz, 1H), 7.43 (dd, J$_1$=8.4 Hz, J$_2$=2.0 Hz, 1H), 7.48 (d, J=2.0 Hz, 1H).

Step 2:

The oil 182-2 (2.8 g, 10.98 mmol) was dissolved in acetone (120 mL), successively added with potassium permanganate (17.3 g, 109.5 mmol) and an aqueous solution (16 mL) of magnesium sulfate (4.0 g, 33.23 mmol), and heated to 65° C. to react overnight. TLC detected the raw material remaining. The reaction solution was cooled to room temperature and filtered through celite. The filter cake was washed, and the filtrate was concentrated. The crude was dissolved with ethyl acetate, washed with water and saturated brine, dried over anhydrous sodium sulfate, and concentrated. The residue was purified by silica gel column chromatography to obtain 182-3 (680 mg) as a white solid. $^1$H-NMR: (CDCl$_3$, 400 MHz): 2.93 (s, 2H), 4.12-4.15 (m, 2H), 4.26-4.29 (m, 2H), 7.59-7.61 (m, 1H), 7.66-7.68 (m, 1H), 7.78 (d, J=1.2 Hz, 1H).

Step 3:

182-3 (1.7 g, 6.32 mmol), 182-3a (2.0 g, 10.30 mmol) as a pyrazole borate and sodium carbonate (1.4 g, 13.21 mmol) were dispersed in dioxane (30 mL) and water (5 mL), and added with [1,1'-bis(diphenylphosphino)ferrocene]palladium dichloride dichloromethane complex (258 mg, 0.32 mmol). After atmosphere was replaced with nitrogen 3 times, the reaction mixture was heated to 100° C. to react for 2 h. TLC detected that the reaction was complete. The reaction solution was cooled to room temperature, added with water and extracted with ethyl acetate. The combined organic phase was washed with water and saturated brine, dried over anhydrous sodium sulfate, and concentrated. The crude was purified by silica gel column chromatography to obtain 182-4 (1.8 g) as a yellowish solid. LC-MS: 271.1 [M+1]$^+$.

$^1$H-NMR: (CDCl$_3$, 400 MHz): δ 2.94 (s, 2H), 3.96 (s, 3H), 4.13-4.19 (m, 2H), 4.27-4.33 (m, 2H), 7.62-7.64 (m, 1H), 4.68-4.73 (m, 3H), 7.85 (s, 1H).

Step 4:

The crude 182-4 (1.8 g), ammonium fluoride (2.8 g, 75.59 mmol), ammonium carbonate (7.0 g, 72.85 mmol) and trimethylsilyl cyanide (2.8 g, 28.22 mmol) were dispersed in 30% ammonia (18 mL) and ethanol (54 mL), and heated to 60° C. to react overnight. TLC detected that the reaction was complete. The reaction solution was cooled to room temperature, and concentrated. The residue was adjusted pH to about 6 with 1N hydrochloric acid, and extracted with dichloromethane and isopropanol (3.5V/1V). The combined organic phase was washed with water and saturated brine, dried over anhydrous sodium sulfate, and concentrated to obtain 2.2 g of a red-brown crude, which was purified by silica gel column chromatography to obtain SP-25 (1.4 g) as an orange solid. LC-MS: 341.2 [M+1]$^+$.

Example 184 Synthesis of Spiro Ring SP-26

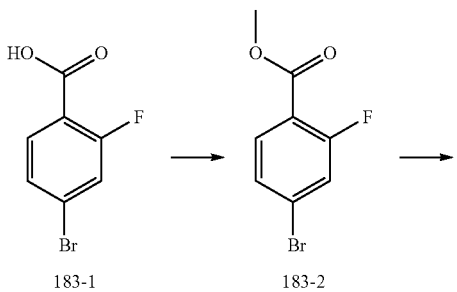

183-1          183-2

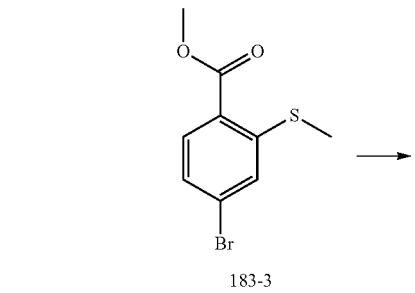

183-3

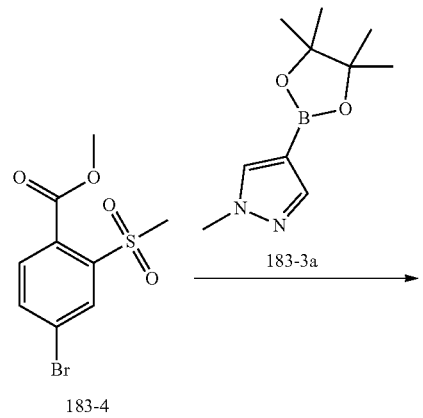

183-4

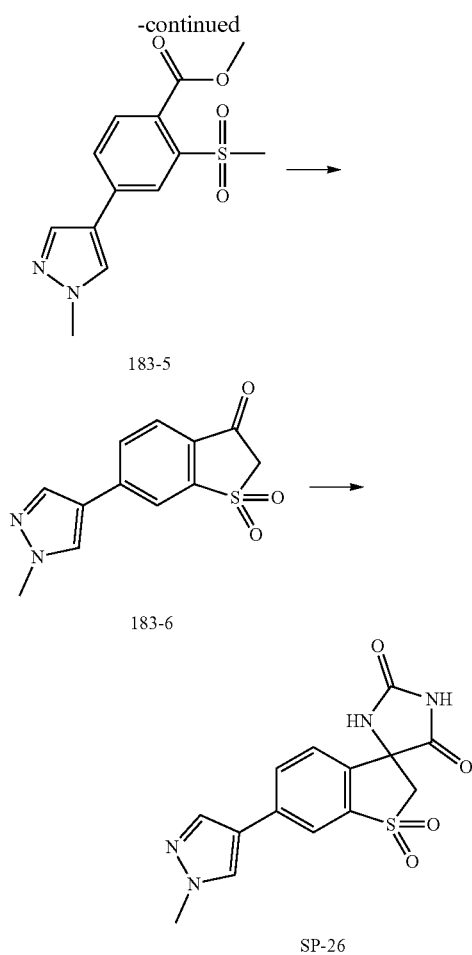

Step 1:

4-Bromo-2-fluorobenzoic acid (183-1, 20.0 g, 91.32 mmol) was dissolved in absolute methanol (330 mL), decreased to 0° C., added dropwise with thionyl chloride (33.0 g, 277.4 mmol), and heated to reflux for 3 h. The reaction solution was cooled to room temperature and concentrated. The crude was dissolved in ethyl acetate and washed with saturated sodium carbonate aqueous solution. The combined organic phase was washed with water and saturated brine, dried over anhydrous sodium sulfate, and concentrated to obtain 183-2 (20.5 g) as a white solid.

Step 2:

The crude solid 183-2 (24.0 g) was dissolved in anhydrous tetrahydrofuran (240 mL), added with sodium methanethiolate (10.8 g, 154.1 mmol) in batches at room temperature, and heated to reflux for 6 h. The reaction solution was cooled to room temperature, added with water, and concentrated to remove tetrahydrofuran. The aqueous phase was extracted with ethyl acetate. The combined organic phase was washed with water and saturated brine, dried over anhydrous sodium sulfate, and concentrated to obtain 183-3 (20 g) as a white solid. $^1$H NMR (400 MHz, DMSO-d$_6$) δ 7.81 (d, J=8.3 Hz, 1H), 7.47 (d, J=1.8 Hz, 1H), 7.43 (dd, J=8.3, 1.9 Hz, 1H), 3.82 (s, 3H), 2.45 (s, 3H).

Step 3:

The crude 183-3 (20.0 g) was dissolved in dioxane/water (400 mL/200 mL), added with potassium hydrogen persulfate (Oxone$^@$, 142 g, 231.0 mmol) in batches, and stirred overnight at room temperature. The reaction solution was filtered, and washed with ethyl acetate. The filtrate was concentrated, diluted with water and extracted with ethyl acetate. The combined organic phase was washed with saturated sodium thiosulfate solution, dried over anhydrous sodium sulfate, and concentrated to obtain 183-4 (23.8 g) as a white solid. $^1$H NMR (400 MHz, DMSO-d$_6$) δ 8.13 (d, J=1.8 Hz, 1H), 8.08 (dd, J=8.1, 1.9 Hz, 1H), 7.72 (d, J=8.2 Hz, 1H), 3.87 (s, 3H), 3.42 (s, 3H).

Step 4:

183-4 (6.0 g), 1-methyl-4-(4,4,5,5-tetramethyl-1,3,2-dioxaborolan-2-yl)-1H-pyrazole 182-3a (5.12 g, 24.61 mmol), sodium carbonate (6.51 g, 61.42 mmol) and [1,1'-bis(diphenylphosphino)ferrocene]dichloropalladium dichloromethane complex (837 mg, 1.02 mmol) were dissolved in 1,4-dioxane/water (60 mL/50 mL), and heated to 100° C. to react for 3 h. The reaction solution was cooled to room temperature, concentrated, poured into water and extracted with dichloromethane. The combined organic phase was washed with water and saturated brine, dried over anhydrous sodium sulfate, and concentrated. The crude was purified by silica gel column chromatography to obtain 183-5 (5.16 g) as a yellow solid. $^1$H-NMR (400 MHz, DMSO-d$_6$) δ 8.37 (s, 1H), 8.11 (d, J=1.7 Hz, 1H), 8.01 (d, J=0.7 Hz, 1H), 7.98 (dd, J=8.0, 1.8 Hz, 1H), 7.72 (d, J=8.0 Hz, 1H), 3.87 (s, 3H), 3.84 (s, 3H), 3.39 (s, 3H).

Step 5:

The 183-5 (5.97 g, 20.28 mmol) was dissolved in anhydrous tetrahydrofuran (100 mL), added with sodium hydride (60%, 2.44 g, 61 mmol) in batches in an ice-water bath, and heated to reflux for 6 h. The reaction solution was cooled to room temperature, quenched by dropwise addition of 1N dilute hydrochloric acid, adjusted pH to 8, concentrated to remove tetrahydrofuran, and filtered off the precipitated solid. The filter cake was washed with water, and dried to obtain 183-6 (6.0 g) as a yellow solid. LC-MS: 263.1 [M+1]$^+$. $^1$H-NMR (400 MHz, DMSO-d$_6$) δ 8.55 (s, 1H), 8.35 (d, J=1.1 Hz, 1H), 8.23 (d, J=0.6 Hz, 1H), 8.12 (dd, J=8.2, 1.5 Hz, 1H), 7.95 (d, J=8.4 Hz, 1H), 4.55 (s, 2H), 3.88 (s, 3H).

Step 6:

183-6 (3.0 g), ammonium fluoride (4.87 g, 131.5 mmol), ammonium carbonate (12.1 g, 126.0 mmol) and trimethylsilyl cyanide (5.67 g, 57.15 mmol) were added in sequence to ethanol (75 mL) and 30% ammonia water (30 mL), and heated to 60° C. to react for 23 h. The reaction solution was cooled to room temperature, and concentrated. The crude was added with water and extracted with ethyl acetate. The combined organic phase was washed with water and saturated brine, dried over anhydrous sodium sulfate, and concentrated. The crude was purified by silica gel column chromatography to obtain SP-26 (1.56 g) as a golden yellow solid. LC-MS: 333.1 [M+1]$^+$. $^1$H-NMR (400 MHz, DMSO-d$_6$) δ 11.31 (s, 1H), 8.78 (s, 1H), 8.39 (s, 1H), 8.10-8.04 (m, 2H), 7.98 (dd, J=8.3, 1.7 Hz, 1H), 7.53 (d, J=8.2 Hz, 1H), 4.11 (d, J=14.5 Hz, 1H), 3.86 (s, 3H), 3.72 (d, J=14.5 Hz, 1H).

Example 185 Synthesis of Spiro Ring SP-27

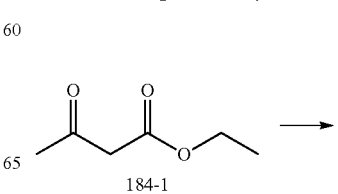

-continued

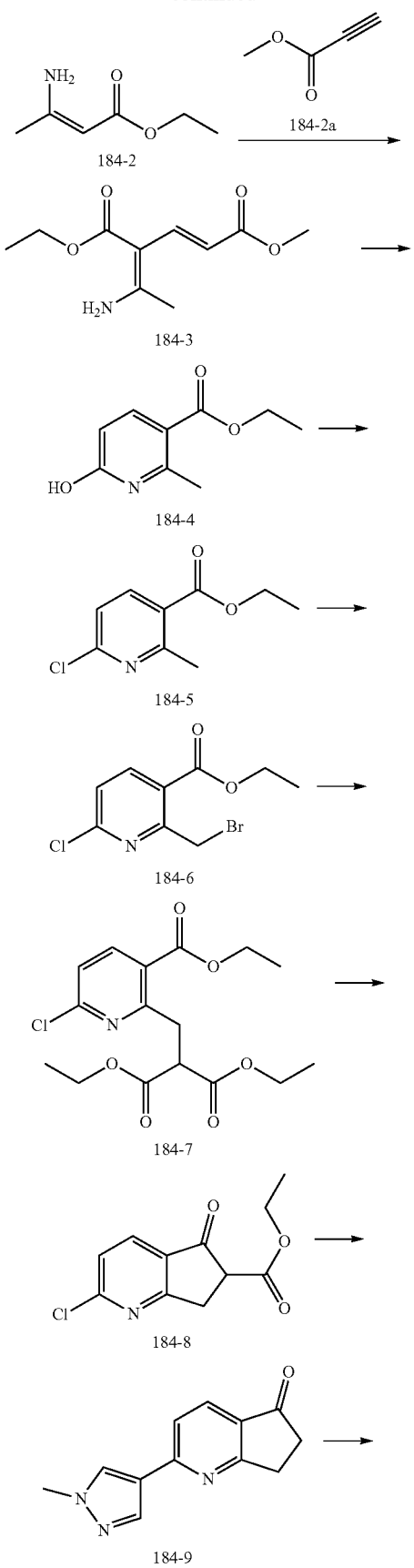

-continued

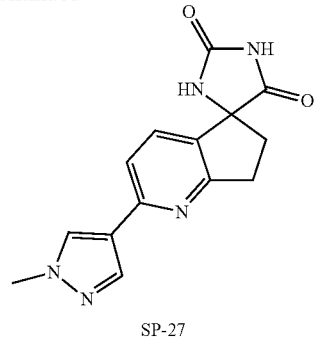

SP-27

Step 1:
A mixture of ethyl acetoacetate (35.0 g, 268.9 mmol) and silica gel (2.7 g) was slowly dropped into a 28% ammonia solution (19.4 g, 0.32 mol), and stirred overnight at room temperature. TLC showed that the reaction was complete. The reaction solution was filtered. The filter cake was washed with ethyl acetate. The filtrate was added with water and extracted with ethyl acetate. The combined organic phase was washed with saturated brine, dried over anhydrous sodium sulfate, and concentrated to obtain anhydrous 184-2 (32.0 g) as a transparent oil.

Step 2:
The crude 184-2 (67.5 g) and methyl propiolate (184-2a, 65.5 g, 779.1 mmol) were dissolved in toluene (150 mL), heated to reflux and stirred overnight. TLC (petroleum ether: ethyl acetate=10:1) showed that the reaction was complete. The reaction solution was cooled to room temperature, concentrated, slurried in methanol, and filtered. The filter cake was washed with a small amount of methanol to obtain 184-3 (70.7 g) as a yellowish solid. LC-MS: 214.1 [M+1]$^+$.
$^1$H-NMR: (CDCl$_3$, 400 MHz): δ 1.36 (t, J=7.2 Hz, 3H), 2.26 (s, 3H), 3.72 (s, 3H), 4.25 (q, J=7.2 Hz, 2H), 5.48 (br, 1H), 6.15-6.19 (m, 1H), 7.63-7.66 (m, 1H), 9.60 (br, 1H).

Step 3:
The intermediate 184-3 (80.9 g) was dissolved in N,N-dimethylformamide (400 mL), heated to reflux and stirred for 3 days under nitrogen. LCMS showed that there was a small amount of the raw material remaining. The reaction solution was concentrated to remove the solvent, slurried in toluene, and filtered. The filter cake was slurried in ethyl acetate and filtered. The filter cake was washed with a small amount of ethyl acetate to obtain 184-4 (57.81 g) as a gray solid. LC-MS: 182.1 [M+1]$^+$.

Step 4:
The crude 184-4 (57.8 g) was dissolved in phosphorus oxychloride (196.26 g, 1.28 mol), heated to reflux and stirred for 2 h under nitrogen. TLC showed that the raw material was completely reacted. The reaction solution was cooled to room temperature and concentrated. The residue was poured into ice water, alkalized with 8M NaOH aqueous solution, and extracted with ethyl acetate. The combined organic phase was washed with saturated brine, dried over anhydrous sodium sulfate, and concentrated. The crude was purified by silica gel column chromatography to obtain 184-5 (58.7 g) as a white solid. LC-MS: 200.1 [M+1]$^+$.

Step 5:
184-5 (30.0 g, 0.15 mol), N-bromosuccinimide (29.4 g, 0.17 mol) and azobisisobutyronitrile (2.5 g, 0.015 mol) were dissolved in tetrachloromethane (400 mL), heated to reflux and stirred for 10 h under nitrogen. The reaction solution was cooled to room temperature, mixed with silica gel, and purified by silica gel column chromatography to obtain 184-6 (40.5 g) as a colorless oil. LC-MS: 278.0/280.0 [M+1]⁺.

Step 6:

Diethyl malonate (31.7 g, 197.92 mmol) was dissolved in tetrahydrofuran (300 mL), cooled to 0 to 5° C. in an ice water bath under nitrogen, added with sodium hydride (7.9 g, 197.52 mmol, 60%), stirred for 0.5 h at room temperature, added with a solution of 184-6 (40.5 g, 98.88 mmol) in tetrahydrofuran (100 mL), and reacted at room temperature overnight. TLC showed that the raw material was completely reacted. The reaction solution was quenched with water and extracted with ethyl acetate. The combined organic phase was washed with saturated brine, dried over anhydrous sodium sulfate, and concentrated. The crude was purified by silica gel column chromatography to obtain 184-7 (26.5 g) as a colorless oil. LC-MS: 358.1 [M+1]⁺.

Step 7:

184-7 (26.5 g, 74.07 mmol) was dissolved in toluene (400 mL), cooled to 0 to 5° C. in an ice-water bath under nitrogen, added with sodium hydride (3.6 g, 90 mmol, 60%), heated to reflux and stirred for 4 h. LC-MS showed that the raw material was completely reacted. The reaction solution was cooled to room temperature, cooled in an ice-water bath, quenched with water, adjusted pH to neutral with 1M hydrochloric acid, and extracted with ethyl acetate. The combined organic phase was washed with saturated brine, dried over anhydrous sodium sulfate, and concentrated. The crude was slurried in methanol and filtered. The filter cake was washed and dried to obtain 184-8 (12.0 g, crude) as an earthy yellow solid. LC-MS: 240.1 [M+1]⁺.

Step 8:

184-8 (6.00 g), 1-methyl-4-(4,4,5,5-tetramethyl-1,3,2-dioxaborolan-2-yl)-1H-pyrazole (182-3a, 6.25 g, 30.04 mmol), sodium carbonate (5.30 g, 50 mmol) and Pd(dppf)₂ (1.02 g, 1.25 mmol) were dissolved in 1,4-dioxane/water (50 mL/10 mL), and heated to 100° C. to react overnight. LC-MS showed that the raw material was completely reacted. The reaction solution was cooled to room temperature, and filtered through celite. The filter cake was washed with ethyl acetate. The filtrate was layered. The aqueous phase was adjusted pH to neutral with 1M hydrochloric acid, and extracted with ethyl acetate. The combined organic phase was washed with saturated brine, and dried over anhydrous sodium sulfate, and concentrated. The crude was purified by silica gel column chromatography to obtain 184-9 (3.85 g) as a brown solid. LC-MS: 214.1 [M+1]⁺.

Step 9:

184-9 (1.50 g, 7.03 mmol), trimethylsilyl cyanide (3.00 g, 30.24 mmol), ammonium fluoride (2.86 g, 77.21 mmol) and ammonium carbonate (7.77 g, 80.86 mmol) were dissolved in a mixed solvent of 30% aqueous ammonia (10 mL) and ethanol (30 mL), and heated to 60° C. to react for 8 h under nitrogen. The reaction solution was cooled to room temperature, concentrated, adjusted pH to neutral with 1M hydrochloric acid, and extracted with ethyl acetate. The combined organic phase was washed with saturated brine, dried over anhydrous sodium sulfate, and concentrated. The crude was purified by silica gel column chromatography to obtain SP-27 (1.25 g) as a yellowish solid. LC-MS: 284.1 [M+1]⁺.

Example 186 Synthesis of Spiro Ring SP-28

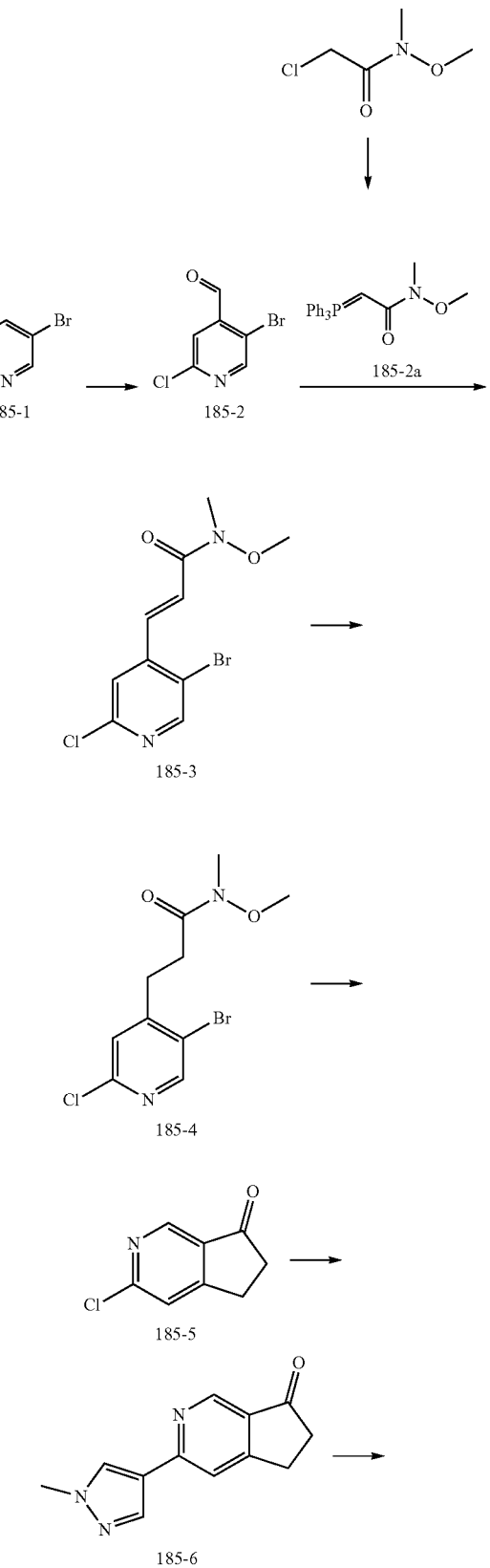

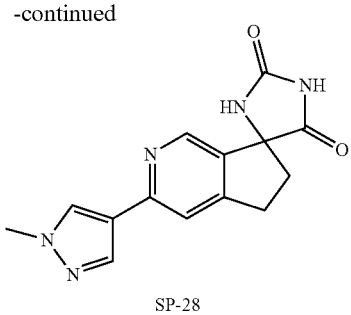

SP-28

Step 1:

2-chloro-N-methoxy-N-methylacetamide (20.0 g, 145.39 mmol) was dissolved in acetonitrile (250 mL), added with triphenylphosphine (43.0 g, 163.94 mmol) at room temperature, and warmed to 80° C. to react for 30 h. LCMS detected that the reaction was complete. The reaction solution was concentrated to dryness, dissolved in dichloromethane (150 mL), added with 2N lithium diisopropylamide (100 mL), stirred for 2 h and layered. The combined organic phase was washed with saturated brine, dried over anhydrous sodium sulfate, and concentrated to obtain 185-2a (48.0 g) as a brown oil.

Step 2:

5-Bromo-2-chloropyridine (185-1, 10.0 g, 51.96 mmol) was dissolved in tetrahydrofuran (150 mL) under nitrogen, added dropwise with lithium diisopropylamide (19.0 ml, 19 mmol, 1.0M) at −65° C., stirred for 20 min, slowly added with dry N,N-dimethylformamide (10 mL), and slowly warmed to room temperature to react overnight. TLC detected that the reaction was complete. The reaction solution was quenched by adding saturated aqueous ammonium chloride solution dropwise, and extracted with ethyl acetate. The combined organic phase was washed with saturated brine, dried over anhydrous sodium sulfate, and concentrated. The crude was purified by silica gel column chromatography to obtain 185-2 (2.6 g) as a reddish brown solid.

Step 3:

185-2 (5.2 g, 23.59 mmol) was dissolved in toluene (100 ml), added with the prepared 185-2a (9.5 g) at room temperature, heated to 100° C. and refluxed for 3 h. TLC detected that the reaction was complete. The reaction solution was concentrated. The crude was purified by silica gel column chromatography to obtain 185-3 (3.3 g) as a white solid. LC-MS: 305.0 [M+1]$^+$.

Step 4:

The solid 185-3 (2.2 g, 7.20 mmol) was dissolved in ethyl acetate (70 mL), and added with Rh/Al$_2$O$_3$ (440 mg, 20% w/w) at room temperature. After atmosphere was replaced with hydrogen 3 times, the reaction mixture was heated to 40° C. to react for 3 h. The resultant was further added with Rh/Al$_2$O$_3$ (220 mg, 20% w/w) to continually react for 3 h, and further added with Rh/Al$_2$O$_3$ (220 mg, 20% w/w) to continually react for 3 h. LCMS detected that the reaction was basically complete. The reaction solution was cooled to room temperature and filtered. The filtrate was concentrated to obtain 185-4 (2.0 g) as a yellow oil. LC-MS: 307.0 [M+1]$^+$.

Step 5:

The crude 185-4 (2.0 g) was dissolved in dry tetrahydrofuran (70 ml). After atmosphere was replaced with nitrogen 3 times, the reaction mixture was added with n-butyl lithium (3.2 ml, 8.0 mmol, 2.5M) dropwise at −70° C., and reacted at −70° C. for 2 h. LCMS monitored that the reaction was complete. The reaction solution was quenched by dropwise addition of saturated ammonium chloride solution, and extracted with ethyl acetate. The combined organic phase was washed with saturated brine, dried over anhydrous sodium sulfate, and concentrated. The crude was purified by silica gel column chromatography to obtain 185-5 (950 mg) as a white solid. LC-MS: 168.1 [M+1]$^+$. 1H-NMR: (CDCl$_3$, 400 MHz): δ 2.72-2.75 (m, 2H), 3.15-3.18 (m, 2H), 7.47 (d, J=1.2 Hz, 1H), 8.74 (s, 1H).

Step 6:

The solid 185-5 (1.1 g, 6.56 mmol) was dissolved in 1,4-dioxane (30 ml) and water (5 ml), and added with 1-methyl-4-(4,4,5,5-tetramethyl-1,3,2-dioxaborolan-2-yl)-1H-pyrazole (182-3a, 2.6 g, 13.54 mmol), [1,1'-bis(diphenylphosphino)ferrocene]palladium dichloride (270 mg, 0.33 mmol) and sodium carbonate (2.1 g, 19.81 mmol) at room temperature. After atmosphere was replaced with nitrogen 3 times, the reaction mixture was heated to 100° C. to react for 3 h. LCMS monitored that the reaction was complete. The reaction solution was cooled to room temperature, added with ethyl acetate, and filtered. The filtrate was washed with saturated brine, dried over anhydrous sodium sulfate, and concentrated. The crude was purified by silica gel column chromatography to obtain a solid. The solid was slurried in a mixture (dichloromethane/petroleum ether=1/10) and filtered. The filter cake was washed and dried to obtain 185-6 (1.09 g) as a yellowish solid. LC-MS: 214.1 [M+1]$^+$. $^1$H-NMR: (DMSO-d$_6$, 400 MHz): δ 2.62-2.63 (m, 2H), 3.09-3.12 (m, 2H), 3.88 (s, 3H), 7.84 (s, 1H), 8.10 (s, 1H), 8.39 (s, 1H), 8.75 (s, 1H).

Step 7:

The crude 185-6 (500 mg) was dissolved in ethanol (30 ml) and water (10 ml), added with trimethylsilyl cyanide (1.0 g, 10.08 mmol), ammonium fluoride (1.0 g, 27.0 mmol) and ammonium carbonate (2.5 g, 26.02 mmol) at room temperature, and heated to 60° C. to react for 16 h. LCMS monitored that the reaction was complete. The reaction solution was concentrated to dryness, adjusted pH to 6-7 with 1N hydrochloric acid, and extracted with a mixture (dichloromethane/isopropanol=3.5/1). The combined organic phase was washed with saturated brine, dried over anhydrous sodium sulfate, and concentrated. The crude was slurried in a mixture (dichloromethane/methanol=10/1) and filtered. The filter cake was washed and dried to obtain SP-28 (400 mg) as a yellow solid. LC-MS: 284.1 [M+1]$^+$. $^1$H-NMR: (DMSO-d$_6$, 400 MHz): δ 2.14-2.21 (m, 1H), 2.48-2.52 (m, 1H), 3.00 (t, J=6.8 Hz, 2H), 3.86 (s, 3H), 7.61 (s, 1H), 7.98 (s, 1H), 8.27 (d, J=8.4 Hz, 2H), 8.48 (s, 1H), 10.87 (s, 1H).

Example 187 Synthesis of Spiro Ring SP-29

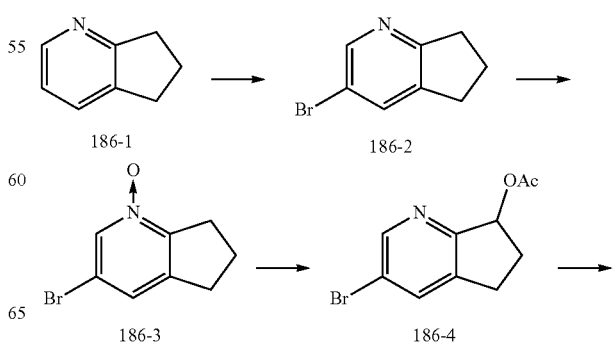

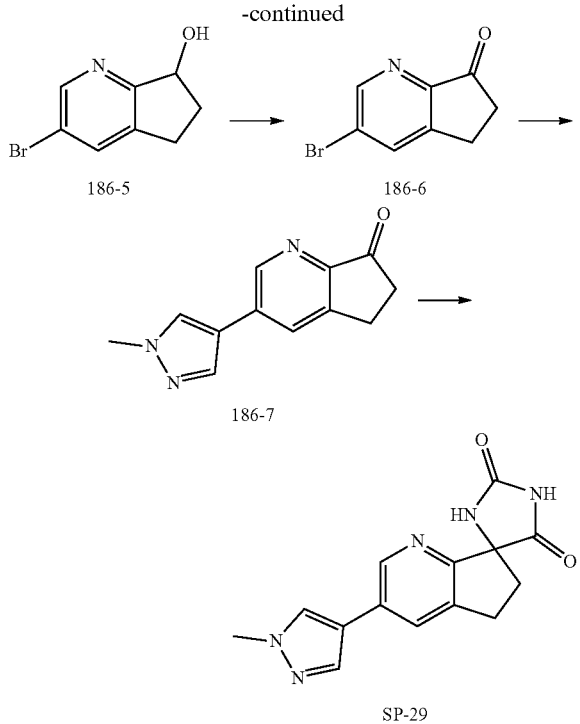

Step 1:

A mixture of 6,7-dihydro-5H-cyclopenta[b]pyridine (186-1, 20.0 g, 0.168 mol) and aluminum trichloride (56.0 g, 0.42 mol) was heated to 100° C., added with bromine (32.0 g, 0.2 mol) within 2 h, and reacted at this temperature for 15 min. The reaction solution was cooled to room temperature, poured into ice water, adjusted pH with 2M aqueous sodium hydroxide to 14, and extracted with methyl tert-butyl ether. The combined organic phase was washed with saturated brine, dried over anhydrous sodium sulfate, and concentrated. The crude was purified by silica gel column chromatography to obtain 186-2 (7.73 g) as a light brown solid. $^1$H-NMR: (CDCl$_3$, 400 MHz): δ 2.12-2.18 (m, 2H), 2.91-2.97 (m, 4H), 7.60-7.61 (m, 1H), 8.37-8.38 (m, 1H).

Step 2:

186-2 (7.13 g, 36.0 mmol) was dissolved in dichloromethane (140 mL), decreased to 0° C. in an ice bath, added in batches with m-chloroperoxybenzoic acid (85%, 14.8 g, 72.9 mmol), and warmed to room temperature to react for 1 h. The reaction solution was cooled in an ice bath, added dropwise with 2M aqueous sodium hydroxide solution, adjusted pH to 14, and extracted with dichloromethane. The combined organic phase was washed with saturated brine, dried over anhydrous sodium sulfate, and concentrated. The crude was purified by silica gel column chromatography to obtain 186-3 (5.38 g) as a brown solid. LC-MS: 214.1 [M+1]$^+$. $^1$H-NMR: (CDCl$_3$, 400 MHz): δ 2.16-2.22 (m, 2H), 3.02 (t, J=7.6 Hz, 2H), 3.09 (t, J=8.0 Hz, 2H), 7.26 (s, 1H), 8.18 (s, 1H).

Step 3:

The solid 186-3 (5.38 g, 25.13 mmol) was dissolved in acetic anhydride (35 mL) and heated to 90° C. to react overnight. The reaction solution was cooled to room temperature and concentrated. The crude was poured into water, alkalized with saturated aqueous sodium bicarbonate solution, and extracted with ethyl acetate. The combined organic phase was washed with saturated brine, dried over anhydrous sodium sulfate, and concentrated. The crude was purified by silica gel column chromatography to obtain 186-4 (3.62 g) as a red oil.

Step 4:

186-4 (3.62 g, 14.14 mmol) was dissolved in methanol/water (45 mL/45 mL), added with potassium carbonate (4.88 g, 35.30 mmol), and reacted at room temperature for 2 h. The reaction solution was concentrated and extracted with ethyl acetate. The combined organic phase was washed with saturated brine, dried over anhydrous sodium sulfate, and concentrated to obtain 186-5 (2.74 g) as a red solid. LC-MS: 214.1 [M+1]$^+$. $^1$H-NMR: (CDCl$_3$, 400 MHz): 2.04-2.11 (m, 1H), 2.53-2.60 (m, 1H), 2.79-2.87 (m, 1H), 3.00-3.07 (m, 1H), 3.84 (br, 1H), 5.16 (t, J=7.2 Hz, 1H), 7.71 (s, 1H), 8.49 (s, 1H).

Step 5:

186-5 (2.34 g, crude) was dissolved in dimethylsulfoxide (45 mL), added in batches with 2-iodoxybenzoic acid (6.12 g, 21.86 mmol), and stirred at room temperature for 2 h. LCMS detected that the reaction was complete. The reaction solution was poured into water and extracted with ethyl acetate. The combined organic phase was washed with saturated brine, dried over anhydrous sodium sulfate, and concentrated. The crude was purified by silica gel column chromatography to obtain 186-6 (2.19 g) as a solid. LC-MS: 212.1 [M+1]$^+$. $^1$H-NMR: (CDCl$_3$, 400 MHz): δ 2.75-2.78 (m, 2H), 3.15-3.18 (m, 2H), 8.04-8.05 (m, 1H), 8.79-8.80 (m, 1H).

Step 6:

186-6 (2.24 g, 10.56 mmol), 1-methyl-4-(4,4,5,5-tetramethyl-1,3,2-dioxaborolane-2-yl)-H-pyrazole (182-3a, 2.64 g, 12.69 mmol), sodium carbonate (3.36 g, 31.70 mmol) and [1,1'-bis(diphenylphosphino)ferrocene]palladium dichloride dichloromethane complex (432 mg, 0.53 mmol) were dispersed in dioxane/water (22 mL/11 mL) under nitrogen, and heated to reflux for 2 h. TLC showed that the reaction was complete. The reaction solution was cooled to room temperature, diluted with water and extracted with ethyl acetate. The combined organic phase was washed with saturated brine, dried over anhydrous sodium sulfate, and concentrated. The crude was purified by silica gel column chromatography to obtain 186-7 (1.53 g) as a yellow solid. LC-MS: 214.1 [M+1]$^+$. $^1$H-NMR: (CDCl$_3$, 400 MHz): δ 2.78 (t, J=6.0 Hz, 2H), 3.17 (t, J=5.6 Hz, 2H), 4.00 (s, 3H), 7.81 (s, 1H), 7.88 (s, 2H), 8.88 (s, 1H).

Step 7:

186-7 (1.0 g, 4.69 mmol), ammonium fluoride (2.0 g, 54.00 mmol), ammonium carbonate (4.96 g, 51.62 mmol) and trimethylsilyl cyanide (2.33 g, 23.48 mmol) were dispersed in 30% aqueous ammonia (13 mL) and ethanol (33 mL), and heated to 60° C. to react overnight. The reaction solution was cooled to room temperature, concentrated, and extracted with dichloromethane. The combined organic phase was washed with saturated brine, dried over anhydrous sodium sulfate, and concentrated. The crude was purified by silica gel column chromatography to obtain SP-29 (1.3 g) as a white solid. LC-MS: 284.1 [M+1]$^+$. $^1$H-NMR: (DMSO-d$_6$, 400 MHz): δ 2.16-2.22 (m, 1H), 2.57-2.61 (m, 1H), 2.98 (t, J=7.6 Hz, 2H), 3.86 (s, 3H), 7.89-7.90 (m, 1H), 7.94 (d, J=0.8 Hz, 1H), 8.24 (s, 1H), 8.37 (s, 1H), 8.63-8.64 (m, 1H), 10.78 (s, 1H).

Example 188 Synthesis of Amide AN-23

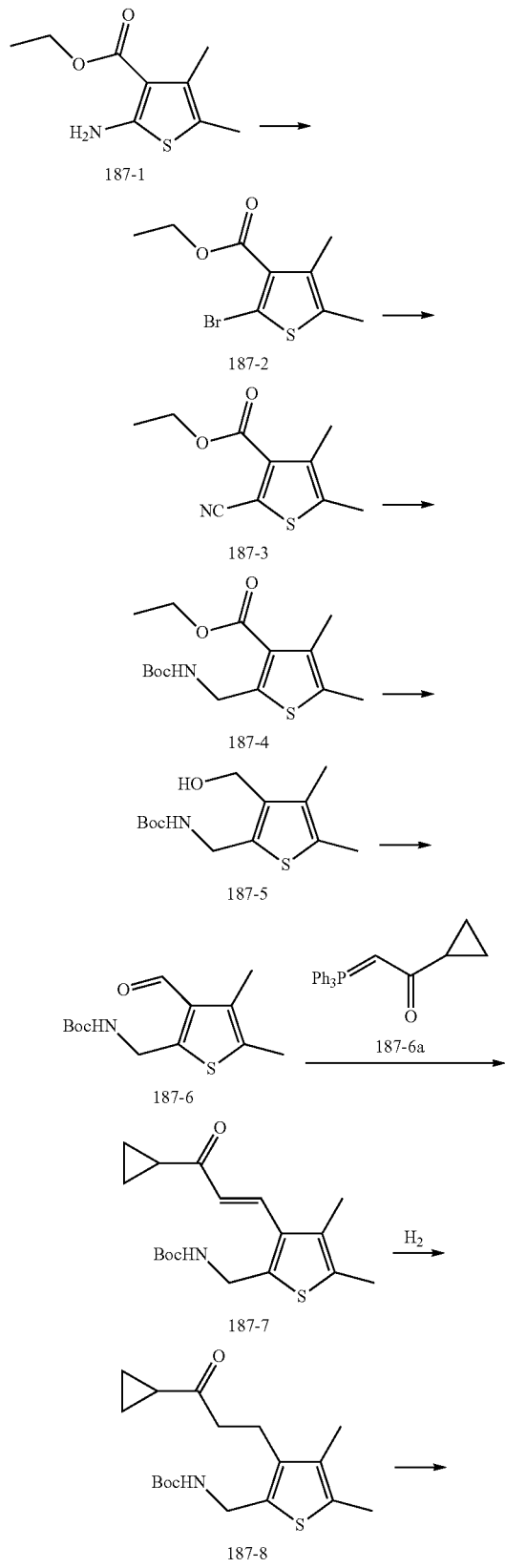

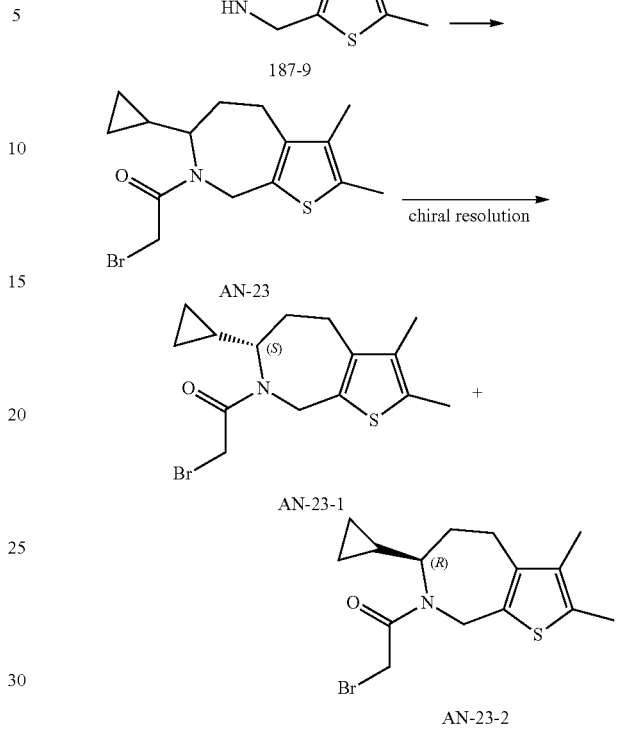

Step 1:

Copper bromide (23.6 g, 164.5 mmol) and tert-butyl nitrite (17.6 g, 170.7 mmol) were dissolved in anhydrous acetonitrile (105 mL) in sequence, heated to 30° C., added dropwise with a solution of ethyl 2-amino-4,5-dimethylthiophene-3-carboxylate (187-1, 21.0 g, 105.4 mmol) in acetonitrile (105 mL) under stirring and raised to an internal temperature of about 50° C. The reaction solution was heated to 60° C. to react for 1 h, cooled to room temperature, and concentrated. The residue was added with water and extracted with ethyl acetate. The combined organic phase was washed with water and saturated brine, dried over anhydrous sodium sulfate, and concentrated. The crude was purified by silica gel column chromatography to obtain 187-2 (19.52 g) as a yellow liquid. $^{1}$H-NMR (400 MHz, CDCl$_3$ (4.36 (q, J=7.2 Hz, 2H), 2.28 (d, J=0.8 Hz, 3H), 2.22 (d, J=0.6 Hz, 3H), 1.39 (t, J=7.2 Hz, 3H).

Step 2:

187-2 (5.0 g, 19.0 mmol) and cuprous cyanide (2.4 g, 26.7 mmol) were dissolved successively in N-methylpyrrolidone (24 mL) under nitrogen, and heated to 155° C. to react for 9 h. The reaction solution was cooled to room temperature, poured with 200 ml of water and 60 ml of ethyl acetate to precipitate a solid, and filtered. The filter cake was washed with ethyl acetate until no product point was shown (TLC monitoring). The filtrate was layered and the aqueous phase was extracted. The combined organic phase was washed with water and saturated brine, dried over anhydrous sodium sulfate, and concentrated. The crude was purified by silica gel column chromatography to obtain 187-3 (2.7 g) as a white solid. $^{1}$H-NMR (400 MHz, CDCl$_3$ δ 4.43 (q, J=7.2 Hz, 2H), 2.44 (d, J=0.4 Hz, 3H), 2.36 (d, J=0.4 Hz, 3H), 1.45 (t, J=7.2 Hz, 3H).

Step 3:

Raney Ni (400 mg), 187-3 (1.41 g, 6.74 mmol) and di-tert-butyl dicarbonate (2.21 g, 10.13 mmol) were successively dissolved in ethanol (60 mL), and hydrogenated at room temperature overnight. The reaction solution was filtered through celite and washed with ethanol. The filtrate was concentrated. The crude was purified by silica gel column chromatography to obtain 187-4 (1.94 g) as a colorless liquid. $^1$H NMR (400 MHz, CDCl$_3$ (5.36 (s, 1H), 4.57 (d, J=6.2 Hz, 2H), 4.35 (q, J=7.2 Hz, 2H), 2.31 (s, 3H), 2.26 (s, 3H), 1.46 (s, 9H), 1.40 (t, J=7.2 Hz, 3H).

Step 4:

187-4 (1.94 g, 6.19 mmol) was dissolved in anhydrous tetrahydrofuran (30 mL), decreased to −30° C., added with lithium aluminum tetrahydrogen (500 mg, 13.18 mmol) in batches, raised to 0° C. to stir for 30 min. TLC showed that the raw material was completely reacted. The reaction solution was added with water (0.5 mL), 15% sodium hydroxide solution (0.5 mL) and water (1.5 mL) successively, and filtered. The filter cake was washed with ethyl acetate. The filtrate was concentrated. The crude was purified by silica gel column chromatography to obtain 187-5 (1.51 g) as a purple liquid. $^1$H NMR (400 MHz, CDCl$_3$ δ 5.06 (s, 1H), 4.54 (s, 2H), 4.38 (d, J=6.2 Hz, 2H), 3.17 (s, 1H), 2.31 (s, 3H), 2.11 (d, J=0.5 Hz, 3H), 1.41 (s, 9H).

Step 5:

187-5 (1.51 g, 5.56 mmol) was dissolved in dimethyl sulfoxide (19 mL), added with 2-iodoxybenzoic acid (3.13 g, 11.18 mmol) in batches, and reacted at room temperature for 1.5 h. TLC showed that the raw material was completely reacted. The reaction solution was diluted with water and ethyl acetate, and filtered to remove insoluble materials. The filtrate was layered. The combined organic phase was washed with saturated brine, dried over anhydrous sodium sulfate, and concentrated to obtain 187-6 (1.7 g) as a yellow liquid. The crude was used directly in the next step.

Step 6:

The crude 187-6 (1.7 g, calculated as 5.57 mmol) and the phosphorus reagent 187-6a (2.87 g, 8.33 mmol) were dissolved in anhydrous tetrahydrofuran (40 mL) successively, and heated to reflux overnight. The reaction solution was cooled to room temperature, and concentrated. The crude was purified by silica gel column chromatography to obtain 187-7 (1.5 g) as a yellow liquid.

Step 7:

187-7 (1.50 g, 4.47 mmol) was dissolved in ethyl acetate (25 mL), added with Pd/C (content 10%, 750 mg), and hydrogenated at room temperature overnight. The reaction solution was filtered through celite, and the filter cake was washed with ethyl acetate. The filtrate was dried over anhydrous sodium sulfate, and concentrated to obtain 187-8 (1.33 g) as an off-white solid. $^1$H-NMR (400 MHz, CDCl$_3$ δ 4.87 (s, 1H), 4.35 (d, J=5.5 Hz, 2H), 2.77 (d, J=7.4 Hz, 2H), 2.73-2.67 (m, 2H), 2.29 (s, 3H), 2.01 (s, 3H), 1.88 (s, 1H), 1.44 (s, 9H), 1.00-1.04 (m, 2H), 0.91-0.81 (m, 2H).

Step 8:

187-8 (1.01 g, 2.99 mmol) was dissolved in 1,4-dioxane (7 mL), added dropwise with 6N hydrochloric acid (5 mL, 30 mmol), and reacted at room temperature for 4.5 h. The reaction solution was quenched with saturated sodium carbonate solution dropwise, and extracted with ethyl acetate. The combined organic phase was washed with water and saturated brine, dried over anhydrous sodium sulfate, and concentrated to obtain a brown liquid (708 mg).

The crude in the previous step (708 mg) was dissolved in 1,2-dichloroethane (10 mL), added dropwise with acetic acid (6 drops), stirred at room temperature for 2 h, added with sodium cyanoborohydride (283 mg, 4.49 mmol) in batches, stirred for 5 min, added with anhydrous methanol (5 mL), and reacted at room temperature overnight. The reaction solution was quenched with saturated sodium bicarbonate solution, and concentrated to remove the organic solvent. The residue was extracted with dichloromethane. The combined organic phase was washed with water and saturated brine, dried over anhydrous sodium sulfate, and concentrated. The crude was purified by silica gel column chromatography to obtain 187-9 (a brown solid, 457 mg).

LC-MS: 222.2 [M+1]$^+$.

Step 9:

187-9 (457 mg, 2.07 mmol) was dissolved in anhydrous dichloromethane (12 mL), added dropwise with bromoacetyl bromide (1.25 g, 6.19 mmol), and reacted at room temperature for 2 h. The reaction solution was quenched by adding saturated sodium bicarbonate solution dropwise, and extracted with dichloromethane. The combined organic phase was washed with water and saturated brine, dried over anhydrous sodium sulfate, and concentrated. The crude was purified by silica gel column chromatography to obtain AN-23 (520 mg) as a yellow oil. $^1$H-NMR (400 MHz, CDCl$_3$ δ 4.63 (d, J=18.2 Hz, 1H), 4.50 (d, J=17.4 Hz, 1H), 4.11 (m, 1H), 3.90 (d, J=10.9 Hz, 1H), 3.88 (s, 1H), 3.69 (d, J=10.9 Hz, 1H), 2.72 (dd, J=17.1, 7.0 Hz, 1H), 2.28 (s, 3H), 2.27-2.16 (m, 2H), 2.06 (dd, J=16.1, 9.1 Hz, 1H), 1.94 (s, 3H), 1.01-0.87 (m, 1H), 0.65-0.49 (m, 2H), 0.47-0.31 (m, 2H), HPLC purity 98%.

Chiral resolution was performed to obtain AN-23-1 and AN-23-2: Preparative column was NANOMICRO OD-5H, filler particle size (5 μm), inner diameter (30 mm), length (250 mm), flow rate: 30 mL/min, mobile phase: 95% n-hexane+5% ethanol, isogradient elution, wavelength 254 nm, peak time is 10.308 min for peak 1, and 20.407 min for peak 2.

Example 189 Synthesis of Amide AN-24

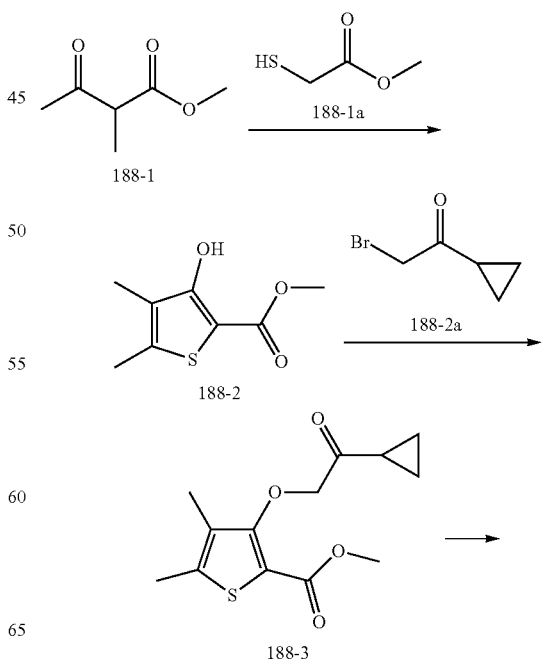

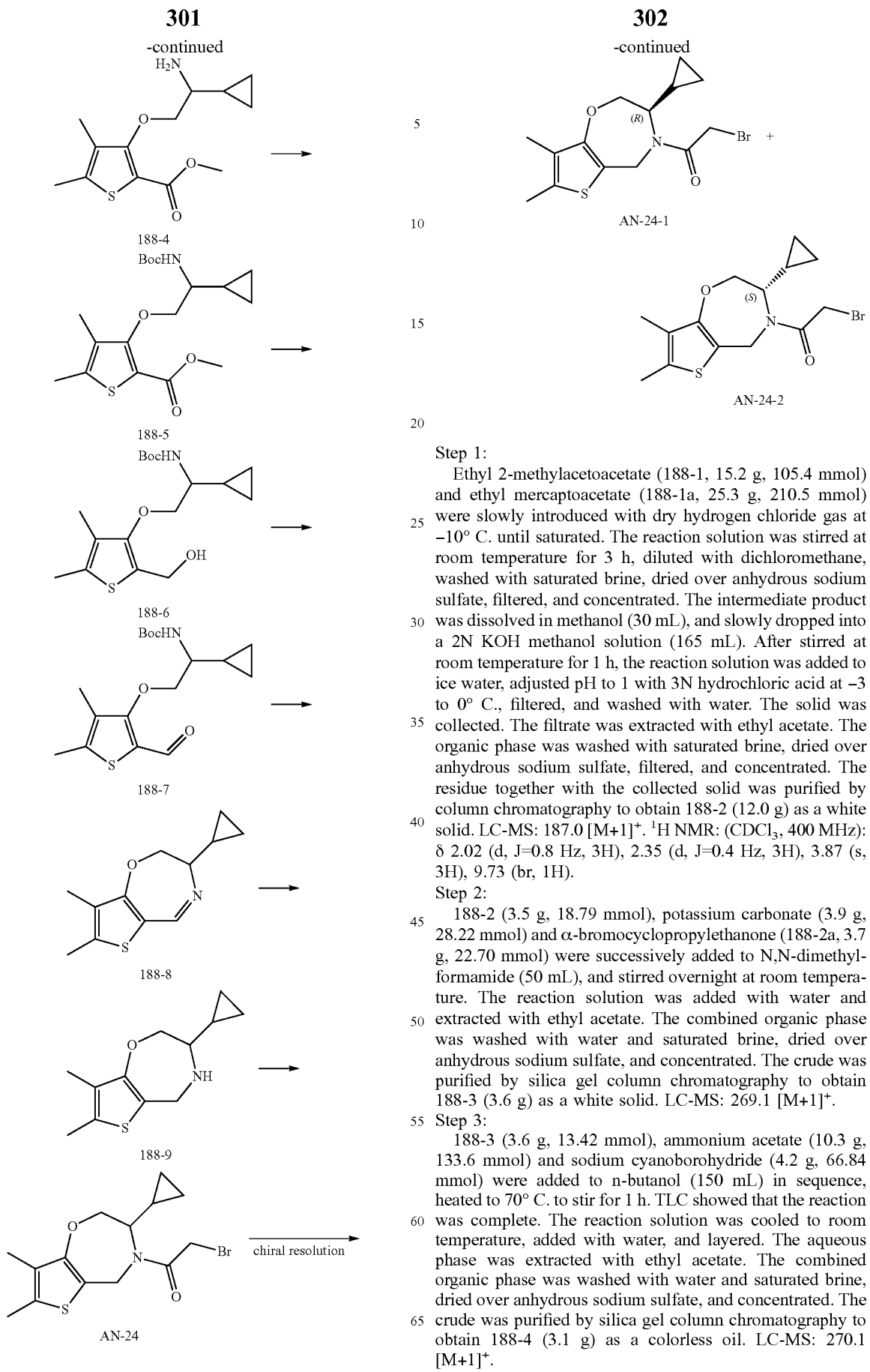

Step 1:

Ethyl 2-methylacetoacetate (188-1, 15.2 g, 105.4 mmol) and ethyl mercaptoacetate (188-1a, 25.3 g, 210.5 mmol) were slowly introduced with dry hydrogen chloride gas at −10° C. until saturated. The reaction solution was stirred at room temperature for 3 h, diluted with dichloromethane, washed with saturated brine, dried over anhydrous sodium sulfate, filtered, and concentrated. The intermediate product was dissolved in methanol (30 mL), and slowly dropped into a 2N KOH methanol solution (165 mL). After stirred at room temperature for 1 h, the reaction solution was added to ice water, adjusted pH to 1 with 3N hydrochloric acid at −3 to 0° C., filtered, and washed with water. The solid was collected. The filtrate was extracted with ethyl acetate. The organic phase was washed with saturated brine, dried over anhydrous sodium sulfate, filtered, and concentrated. The residue together with the collected solid was purified by column chromatography to obtain 188-2 (12.0 g) as a white solid. LC-MS: 187.0 [M+1]$^+$. $^1$H NMR: (CDCl$_3$, 400 MHz): δ 2.02 (d, J=0.8 Hz, 3H), 2.35 (d, J=0.4 Hz, 3H), 3.87 (s, 3H), 9.73 (br, 1H).

Step 2:

188-2 (3.5 g, 18.79 mmol), potassium carbonate (3.9 g, 28.22 mmol) and α-bromocyclopropylethanone (188-2a, 3.7 g, 22.70 mmol) were successively added to N,N-dimethylformamide (50 mL), and stirred overnight at room temperature. The reaction solution was added with water and extracted with ethyl acetate. The combined organic phase was washed with water and saturated brine, dried over anhydrous sodium sulfate, and concentrated. The crude was purified by silica gel column chromatography to obtain 188-3 (3.6 g) as a white solid. LC-MS: 269.1 [M+1]$^+$.

Step 3:

188-3 (3.6 g, 13.42 mmol), ammonium acetate (10.3 g, 133.6 mmol) and sodium cyanoborohydride (4.2 g, 66.84 mmol) were added to n-butanol (150 mL) in sequence, heated to 70° C. to stir for 1 h. TLC showed that the reaction was complete. The reaction solution was cooled to room temperature, added with water, and layered. The aqueous phase was extracted with ethyl acetate. The combined organic phase was washed with water and saturated brine, dried over anhydrous sodium sulfate, and concentrated. The crude was purified by silica gel column chromatography to obtain 188-4 (3.1 g) as a colorless oil. LC-MS: 270.1 [M+1]$^+$.

Step 4:

188-4 (3.1 g, 11.51 mmol) and triethylamine (1.8 g, 17.79 mmol) were dissolved in dichloromethane (40 mL), cool to 0 to 5° C. in an ice bath, slowly added dropwise with a solution of di-tert-butyl dicarbonate (2.8 g, 12.83 mmol) in dichloromethane (10 mL), and stirred at room temperature for 2 h. TLC showed that the reaction was complete. The reaction solution was added with water and layered. The aqueous phase was extracted with ethyl acetate. The combined organic phase was washed with 1N hydrochloric acid and saturated brine, dried over anhydrous sodium sulfate, and concentrated to obtain 188-5 (3.9 g) as a colorless oil. LC-MS: 392.1 [M+Na]$^+$.

Step 5:

188-5 (3.9 g) was dissolved in tetrahydrofuran (80 mL), cooled to 0 to 5° C. in an ice bath, added with lithium aluminum tetrahydrogen (600 mg, 15.81 mmol) in batches, and stirred at this temperature for 4 h. TLC showed that the reaction was complete. The reaction solution was slowly added dropwise with 0.6 ml of water, 0.6 mL of 15% sodium hydroxide aqueous solution and 1.8 mL of water, stirred at room temperature for 10 min, and filtered through celite. The filtrate was concentrated to obtain 188-6 (2.5 g, crude) as a colorless oil. LC-MS: 364.2 [M+Na]$^+$.

Step 6:

188-6 (2.5 g, crude) was dissolved in dichloromethane (80 mL), added with manganese dioxide (12.7 g, 146.1 mmol) at room temperature, and heated to reflux for 2 h. The reaction solution was cooled to room temperature. TLC (Petroleum ether: ethyl acetate=5:1) showed that the reaction was complete. The reaction solution was filtered through celite pad. The filtrate was concentrated. The crude was purified by silica gel column chromatography to obtain 188-7 (1.4 g) as a white solid. LC-MS: 362.2 [M+Na]$^+$.

Step 7:

188-7 (1.4 g, 4.12 mmol) was dissolved in dichloromethane (15 mL), added with trifluoroacetic acid (5 mL), and stirred at room temperature for 2 h. TLC detected that the reaction was complete. The resultant was added with ice water, neutralized with an aqueous sodium carbonate solution, and extracted with dichloromethane. The organic phase was washed with saturated brine, dried over anhydrous sodium sulfate, and concentrated to obtain 188-8 as a yellow oil. The crude was directly used in the next reaction. LC-MS: 222.1 [M+1]$^+$.

Step 8:

The crude 188-8 was dissolved in methanol (20 mL), cooled to 0° C., added with sodium borohydride (180 mg, 4.76 mmol) in batches. The reaction solution was reacted at 0° C. for 1 h. LCMS detected that the reaction was complete. The reaction solution was slowly added with water, stirred for 0.5 h, and extracted with ethyl acetate. The combined organic phase was washed with water and saturated brine, dried over anhydrous sodium sulfate, and concentrated to obtain 188-9 (980 mg) as a yellow oil. LC-MS: 224.1 [M+1]$^+$.

Step 9:

The crude 188-9 (980 mg) was dissolved in dichloromethane (20 mL), cooled to about 0° C. under nitrogen, added with a solution of bromoacetyl bromide (3.6 g, 17.84 mmol) in dichloromethane, and slowly warmed to room temperature to react. TLC detected that the reaction was complete. The reaction solution was poured into ice water and extracted with dichloromethane. The organic phase was washed with saturated brine, dried over anhydrous sodium sulfate, and concentrated. The crude was purified by silica gel column chromatography to obtain AN-24 (1.6 g) as a colorless oil. LC-MS: 344.0 [M+1]$^+$.

Chiral resolution was performed to obtain AN-24-1 and AN-24-2: Preparative column was NANOMICRO OD-5H, filler particle size (5 μm), inner diameter (30 mm), length (250 mm), flow rate: 30 mL/min, mobile phase: 95% n-hexane+5% ethanol, isogradient elution, wavelength 254 nm, peak time is 11.10 min for peak 1, and 21.10 min for peak 2.

Example 190 Synthesis of Amide AN-25

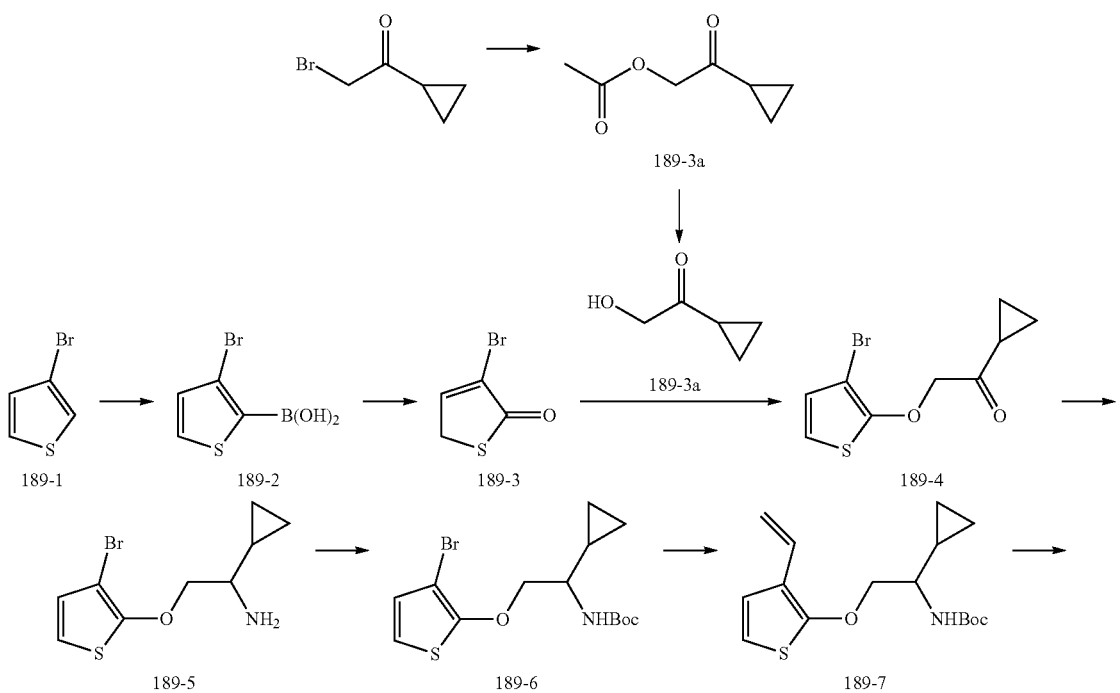

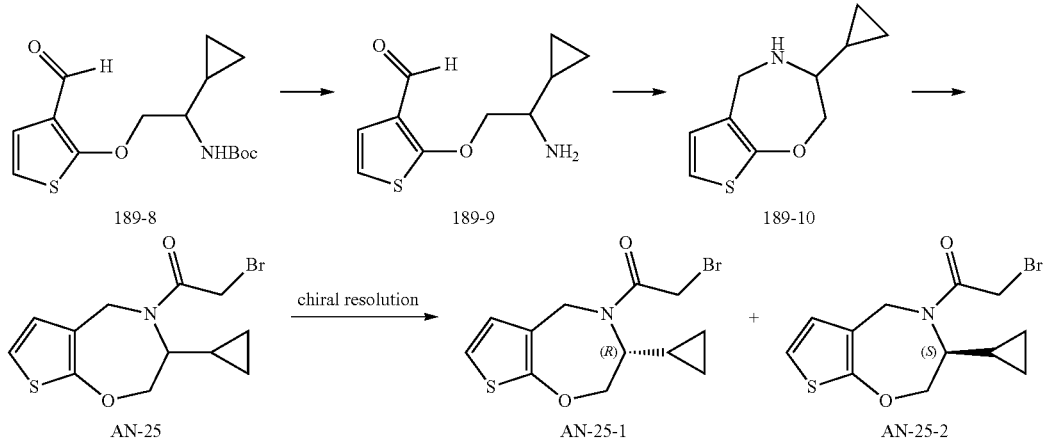

Step 1:

α-Bromocyclopropylethanone (16.2 g, 99.38 mmol) was dissolved in N,N-dimethylformamide (80 mL), added with potassium acetate (19.6 g, 199.7 mmol) at room temperature, and heated to 50° C. to react for 1 h. TLC detected that the reaction was complete. The reaction solution was cooled to room temperature, added with water and extracted with ethyl acetate. The combined organic phase was washed with saturated brine, dried over anhydrous sodium sulfate, and concentrated to obtain 189-3a (16.7 g) as a yellow oil. $^1$H NMR: (CDCl$_3$, 400 MHz): δ 0.95-0.97 (m, 2H), 1.09-1.13 (m, 2H), 1.90-1.96 (m, 1H), 2.16 (s, 3H), 4.82 (s, 2H).

Step 2:

189-3a (16.7 g) was dissolved in methanol (60 mL) and water (60 mL), added with sodium carbonate solid (10.6 g, 100.0 mmol), and reacted at room temperature overnight. TLC detected that the reaction was complete. The reaction solution was added with water and extracted with ethyl acetate. The combined organic phase was washed with saturated brine, dried over anhydrous sodium sulfate, and concentrated. The crude was purified by silica gel column chromatography to obtain 189-3b (5.4 g) as a yellow oil. $^1$H NMR: (CDCl$_3$, 400 MHz): (0.99-1.04 (m, 2H), 1.14-1.18 (m, 2H), 1.83-1.89 (m, 1H), 3.18 (br, 1H), 4.41 (2, 1H).

Step 3:

3-Bromothiophene 189-1 (20.0 g, 122.68 mmol) was dissolved in tetrahydrofuran (200 mL), cooled to about 0° C. under nitrogen, added dropwise with LDA (74 mL, 148.0 mmol, 2.0M) within about 0.5 h, stirred at 0° C. for 1 h, added dropwise with a solution of trimethyl borate (25.5 g, 245.4 mmol) in tetrahydrofuran (20 mL), and slowly warmed to room temperature to react for 2 h. The reaction solution was cooled to 0° C., quenched by adding water dropwise, acidized with 1N hydrochloric acid, and extracted with ethyl acetate. The combined organic phase was washed with saturated brine, dried over anhydrous sodium sulfate, and concentrated to obtain 189-2 (29.0 g) as a yellowish solid.

Step 4:

189-2 (29.0 g) was dissolved in dichloromethane (300 mL), added with saturated sodium bicarbonate aqueous solution (125 mL) and then with 30% hydrogen peroxide (27 mL), and reacted at room temperature for 1 h. TLC detected that the reaction was complete. The reaction mixture was filtered through celite pad. The filtrate was extracted with a mixture (dichloromethane/methanol=10/1). The combined organic phase was washed with saturated brine. The brine phase and the aqueous phase were combined and extracted with a mixture (dichloromethane/isopropanol=3.5/1). The combined organic phase was washed with saturated brine, dried over anhydrous sodium sulfate, and concentrated. The crude was purified by silica gel column chromatography to obtain 189-3 (9.5 g) as a brown-yellow solid. LC-MS: 178.9 [M+1]$^+$. $^1$H NMR: (CDCl$_3$, 400 MHz): δ 4.02 (d, J=3.2 Hz, 2H), 7.67 (t, J=2.8 Hz, 1H).

Step 5:

Diisopropyl azodicarboxylate (13.6 g, 67.26 mmol) was added dropwise to a solution of triphenylphosphine (17.6 g, 67.10 mmol) in dichloromethane (80 mL) cooled to −10° C. under nitrogen, stirred for 10 min, added dropwise with a solution of 189-3b (6.7 g, 66.92 mmol) in dichloromethane (15 mL), stirred at −10° C. for 20 min, added dropwise with a solution of 189-3 (5.0 g, 27.93) in dichloromethane, and slowly warmed to room temperature to react for 1 h. TLC detected that the raw material was basically reacted. The reaction solution was diluted with petroleum ether and directly applied to a column. Purification by column chromatography gave 189-4 (4.2 g) as a red-brown oil. $^1$H NMR: (CDCl$_3$, 400 MHz): δ 1.00-1.05 (m, 2H), 1.12-1.18 (m, 2H), 2.27-2.23 (m, 1H), 4.75 (s, 2H), 6.70-6.72 (m, 1H), 6.75-6.77 (m, 1H).

Step 6:

189-4 (5.1 g, 19.53 mmol) and ammonium acetate (15.05 g, 195.3 mmol) were dissolved in methanol (60 mL), added with sodium cyanoborohydride (6.14 g, 97.65 mmol), and reacted at room temperature overnight. TLC detected that the reaction was basically complete. The reaction solution was concentrated. The residue was dissolved in water and extracted with ethyl acetate. The combined organic phase was washed with saturated brine, and dried over anhydrous sodium sulfate to obtain 189-5 (4.5 g) as a red-brown oil. LC-MS: 262.0 [M+1]$^+$.

Step 7:

189-5 (4.5 g) was dissolved in dichloromethane (80 mL), added with N,N-diisopropyl ethylamine (4.2 g, 32.5 mmol), stirred for 5 min, cooled to about 0° C., added dropwise with a solution of Boc anhydride (5.3 g, 24.2 mmol) in dichloromethane (15 mL), and warmed to room temperature to stir for 2 h. TLC detected that the reaction was complete. The reaction solution was concentrated. The crude was purified by silica gel column chromatography to obtain 189-6 (2.7 g) as a yellowish oil. LC-MS: 384.0 [M+Na]$^+$.

Step 8:

189-6 (2.7 g, 7.45 mmol) was dissolved in 1,4-dioxane (50 mL) and water (12 mL), and added in sequence with potassium vinyltrifluoroborate (3.0 g, 22.4 mmol), N,N-diisopropylethylamine (3.8 g, 29.4 mmol) and [1,1'-bis (diphenylphosphino)ferrocene]palladium dichloride dichloromethane complex (5% catalytic amount) as a catalyst at room temperature. After atmosphere was replaced with nitrogen 3 times, the reaction mixture was heated to 100° C. to react for 6 h. LCMS detected that the reaction was complete. The reaction solution was cooled to room temperature and concentrated. The crude was purified by silica gel column chromatography to obtain 189-7 (1.55 g) as a yellowish oil. $^1$H NMR: (CDCl$_3$, 400 MHz): δ 0.31-0.34 (m, 1H), 0.44-0.48 (m, 1H), 0.54-0.60 (m, 2H), 1.14-1.18 (m, 1H), 1.45 (s, 9H), 3.17-3.21 (m, 1H), 4.15-4.22 (m, 2H), 4.98 (br, 1H), 6.66-6.67 (m, 1H), 6.73-6.74 (m, 1H).

Step 9:

189-7 (1.55 g, 5.01 mmol) was dissolved in acetone (60 mL) and water (30 mL), added with an aqueous solution of N-methylmorpholine-N-oxide (1.2 g, 10.24 mmol) and potassium osmate dihydrate (50 mg) in sequence, and reacted at room temperature for 1 h. TLC detected that the reaction was complete. The reaction solution was added with sodium periodate (2.2 g, 10.28 mmol), and reacted at room temperature for 1 h. TLC detected that the reaction was complete. The reaction solution was filtered. The filtrate was concentrated. The crude was purified by silica gel column chromatography to obtain 189-8 (1.2 g) as a yellowish oil. LC-MS: 334.1 [M+Na]$^+$.

Step 10:

189-8 (1.2 g, 3.85 mmol) was dissolved in dichloromethane (20 mL), added with trifluoracetic acid (4 mL), and reacted for 1 h at room temperature. TLC detected that the reaction was complete. The reaction solution was neutralized with saturated sodium carbonate aqueous solution and extracted with dichloromethane. The combined organic phase was washed with saturated brine, dried over anhydrous sodium sulfate, and concentrated to obtain 189-9 (700 mg) as a yellow oil. LC-MS: 194.1 [M+1]$^+$.

Step 11:

189-9 (450 mg, 2.32 mmol) was dissolved in methanol (10 mL), cooled to about 0° C., added with sodium borohydride (175 mg, 4.64 mmol), and reacted at 0° C. for 1 h. LCMS detected that the reaction was complete. The reaction solution was added with water, stirred for 0.5 h and extracted with ethyl acetate. The combined organic phase was washed with saturated brine, dried over anhydrous sodium sulfate, and concentrated to obtain 189-10 (490 mg) as a yellow oil. LC-MS: 196.1 [M+1]$^+$. $^1$H NMR: (DMSO-d$_6$, 400 MHz): δ 0.33-0.38 (m, 2H), 0.45-0.48 (m, 2H), 0.75-0.84 (m, 1H), 2.35-2.39 (m, 1H), 3.61-3.79 (m, 3H), 3.91-3.95 (m, 1H), 4.28, 4.31 (dd, J$_1$=12.0 Hz, J$_2$=2.0 Hz, 1H), 6.65-6.68 (m, 2H).

Step 12:

189-10 (490 mg) was dissolved in dichloromethane (10 mL). The mixture was slowly added dropwise to a solution of bromoacetyl bromide (2.0 g, 9.91 mmol) in dichloromethane (10 mL), and reacted for 2 h at room temperature. TLC detected that the reaction was complete. The reaction solution was neutralized with saturated sodium carbonate aqueous solution and extracted with dichloromethane. The combined organic phase was washed with saturated brine, dried over anhydrous sodium sulfate, and concentrated. The crude was dissolved in ethyl acetate, added with sodium carbonate aqueous solution, stirred for 1 h and layered. The organic phase was washed with saturated brine, dried over anhydrous sodium sulfate, and concentrate. The crude was purified by silica gel column chromatography to obtain AN-25 (640 mg) as a yellowish viscous oil. LC-MS: 316.0/318.0 [M+1]$^+$.

Chiral resolution was performed to obtain AN-25-1 and AN-25-2: Preparative column was NANOMICRO OD-5H, filler particle size (5 μm), inner diameter (30 mm), length (250 mm), flow rate: 30 mL/min, mobile phase: 95% n-hexane+5% ethanol, isogradient elution, wavelength 254 nm, peak time is 17.953 min for peak 1, and 22.417 min for peak 2.

Example 191 Synthesis of Amide AN-26

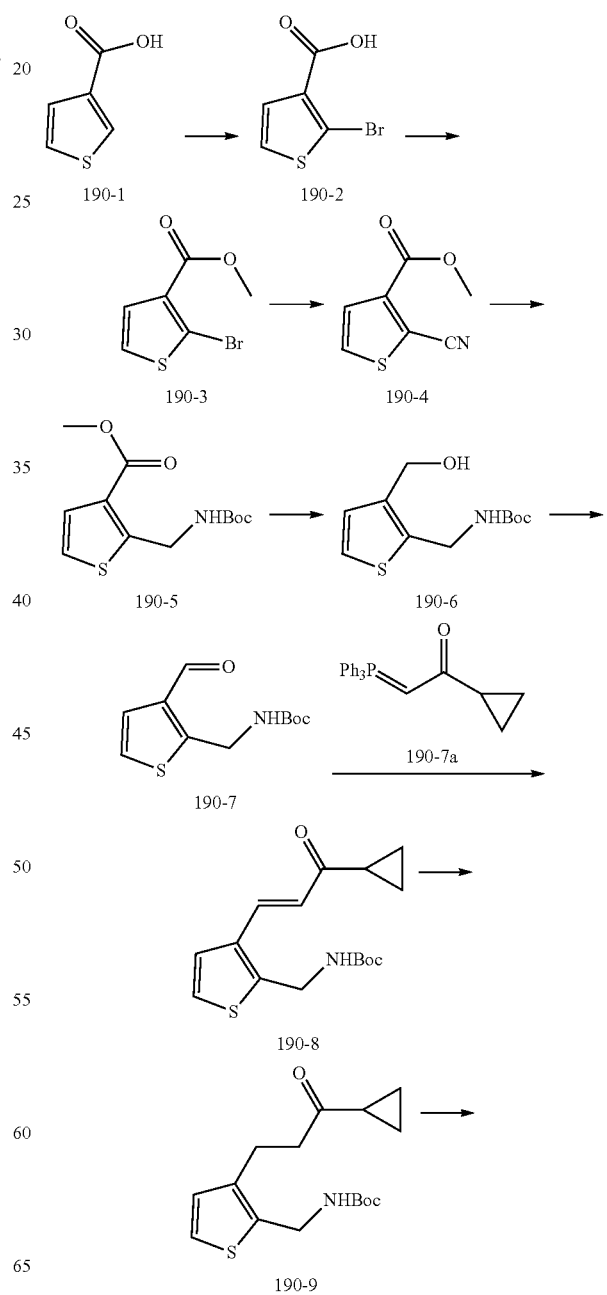

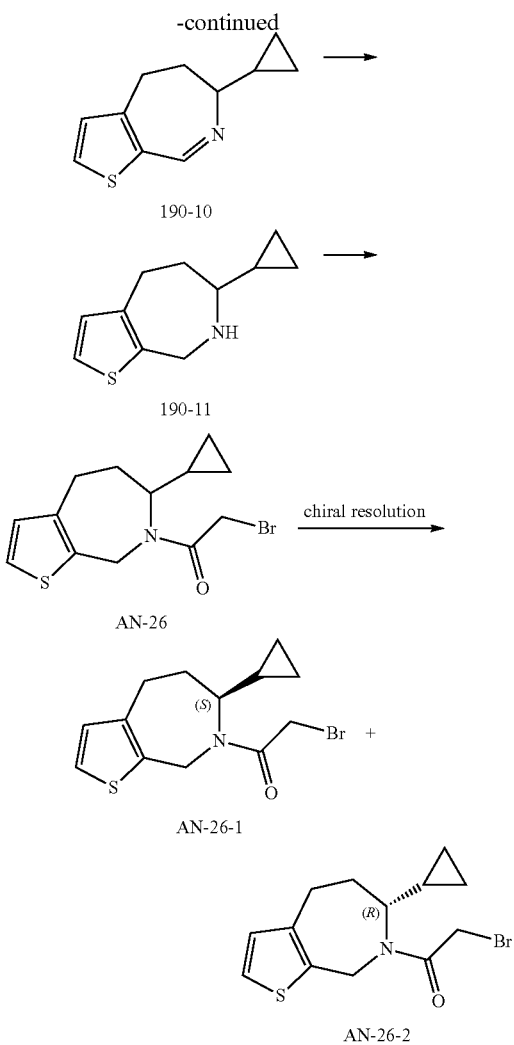

190-10

190-11

AN-26

AN-26-1

AN-26-2 chiral resolution

Step 1:

The 3-thiophenecarboxylic acid (190-1, 20.0 g, 156 mmol) was dissolved in tetrahydrofuran (150 mL), added dropwise with a tetrahydrofuran solution of n-butyllithium (126 mL, 315 mmol, 2.5M) in a dry ice bath at −78° C. under nitrogen, stirred for 0.5 h at −78° C., added slowly with liquid bromine (8.6 mL, 168 mmol) while keeping the temperature not exceeding −60° C., and slowly warmed to room temperature overnight. LCMS detected that half of the raw material reacted. The reaction solution was quenched with dilute hydrochloric acid and extracted with ethyl acetate. The combined organic phase was washed with water and saturated brine, dried over anhydrous sodium sulfate, and concentrated to obtain a crude 190-2, which was directly used in the next step. LC-MS: 205.0 [M−1]⁻.

Step 2:

190-2 was dissolved in N,N-dimethylformamide (100 mL), added with potassium carbonate (64.0 g, 463 mmol) and methyl iodide (20 mL, 321 mmol), and stirred at room temperature for 1 h. TLC detected that the reaction was complete. The reaction solution was added with saturated brine and extracted with ethyl acetate. The combined organic phase was washed with water and saturated brine, dried over anhydrous sodium sulfate, and concentrated to obtain a crude 190-3, which was used directly in the next step.

Step 3:

190-3 (29 g, 31.2 mmol) and cuprous cyanide (18 g, 196.83 mmol, 1.5 eq) were heated to 155° C. in N-methylpyrrolidone (300 mL) to react for 9 h. TLC detected that there is some of the raw material remaining. The reaction solution was cooled to room temperature, added with water and methyl tert-butyl ether, stirred vigorously, and filtered through celite pad. The filter cake was washed. The filtrate was layered. The organic phase was washed with water. The aqueous phase was extracted again with methyl tert-butyl ether once. The combined organic phase was washed, dried, and concentrated. The crude was purified by column chromatography to obtain 3.7 g of 190-4 as a yellowish solid. ¹H NMR: (CDCl₃, 400 MHz): 3.96 (s, 3H), 7.58 (q, J=3.6 Hz, 1H).

Step 4:

190-4 (3.5 g, 20.94 mmol) was dissolved in methanol (300 mL), added with Boc anhydride (13.9 g, 63.69 mmol) and Raney nickel (800 mg), and catalytically hydrogenated overnight at room temperature. TLC showed that the reaction was not complete. Raney nickel (400 mg) was further added, and the catalytic hydrogenation was continued for 5 h. TLC detected that the reaction was complete. The reaction solution was filtered through celite pad, and the filter cake was washed. The filtrate was concentrated. The crude was purified by silica gel column chromatography to obtain 190-5 (4.2 g) as a yellow oil. ¹H NMR: (CDCl₃, 400 MHz): δ 1.46 (s, 9H), 3.88 (s, 3H), 4.72 (d, J=6.4 Hz, 2H), 5.50 (br, 1H), 7.12 (d, J=5.6 Hz, 1H), 7.41 (d, J=5.6 Hz, 1H).

Step 5:

Lithium aluminum tetrahydrogen (900 mg, 23.72 mmol) was dissolved in dry tetrahydrofuran (20 mL), cool to about 0° C. under nitrogen, added dropwise with a solution of 190-5 (4.2 g, 15.48 mmol) in tetrahydrofuran (80 mL), and reacted at 0° C. for 0.5 h. TLC detected that the reaction was complete. The reaction solution was added with 0.9 mL of water, 0.9 mL of 15% sodium hydroxide aqueous solution and 2.7 mL of water in sequence, stirred vigorously for 0.5 h, and filtered with celite pad. The filter cake was washed. The filtrate was concentrated. The residue was dissolved with ethyl acetate, dried over anhydrous sodium sulfate and concentrated. The crude was purified by silica gel column chromatography to obtain 190-6 (3.2 g) as a yellowish oil.

Step 6:

190-6 (3.2 g, 13.15 mmol) was dissolved in dichloromethane (100 mL), added with manganese dioxide solid (34.0 g, 391 mmol), and heated to reflux for 2 h. TLC detected that the reaction was complete. The reaction solution was cooled to room temperature and filtered through celite pad. The filter cake was washed. The filtrate was concentrated to obtain 190-7 (2.6 g) as a yellowish oil, which was directly used in the next step. 1H NMR: (CDCl₃, 400 MHz): δ 1.46 (s, 9H), 3.88 (s, 3H), 4.74 (d, J=6.0 Hz, 2H), 5.43 (br, 1H), 7.21 (d, J=5.6 Hz, 1H), 7.42 (d, J=5.2 Hz, 1H), 10.03 (s, 1H).

Step 7:

190-7 (2.6 g) and Wittig reagent (190-7a, 4.1 g, 11.9 mmol) were heated in tetrahydrofuran (50 mL) to reflux for 2 h. TLC detected that the reaction was basically complete. The reaction solution was concentrated. The residue was slurried with petroleum ether/ethyl acetate (5 v/1 v). The combined filtrate was concentrated. The crude was purified by column chromatography to obtain 190-8 (3.0 g) as a yellow oil. LC-MS: 330.1 [M+Na]⁺.

Step 8:

190-8 (3.0 g, 9.76 mol) was dissolved in ethyl acetate (100 mL), and added with 10% Pd/C (1.0 g). After atmosphere was replaced with hydrogen three times, the reaction mixture was stirred at room temperature overnight under hydrogen. TLC detected that most of the raw material was not reacted. 1 g of 10% Pd/C was further added, and the reaction continued for 3 h. TLC detected that there was about 10% of the raw material remaining. The hydrogen balloon was replaced, and the reaction continued for 1 h. TLC detected that the reaction was complete. The reaction mixture was filtered through celite pad, and the filter cake was washed. The filtrate was concentrated to obtain 190-9 (3.2 g) as a yellowish oil. The crude was directly used in the next step. LC-MS: 332.1 [M+Na]+.

Step 9:

190-9 (2.9 g) was dissolved in dichloromethane (45 mL), added with a solution of trifluoroacetic acid (14 mL) in dichloromethane (14 mL), and reacted at room temperature for 30 min. TLC detected that the reaction was complete. The reaction solution was diluted with dichloromethane, neutralized with saturated sodium carbonate aqueous solution, and layered. The aqueous phase was extracted twice with dichloromethane/isopropanol (3.5 v/1 v). The combined organic phase was dried over anhydrous sodium sulfate and concentrated to obtain 190-10 (1.9 g) as a yellow oil. LC-MS: 192.1 [M+1]+.

Step 10:

190-10 (1.9 g) was dissolved in 1,2-dichloromethane (50 mL), added with sodium triacetoxyborohydride (4.8 g, 22.65 mmol), and heated to 70° C. to react for 2 h. TLC detected that the reaction was complete. The reaction solution was cooled to room temperature and concentrated. The crude was diluted with water and extracted with dichloromethane. The combined organic phase was washed with water and saturated brine, dried over anhydrous sodium sulfate, and concentrated to obtain 190-11 (0.75 g) as a gray solid. LC-MS: 194.1 [M+1]+.

Step 11:

190-11 (750 mg) was dissolved in dichloromethane (20 mL), added with bromoacetyl bromide (3.1 g, 15.36 mmol), and reacted at room temperature overnight. TLC detected that the reaction was complete. The reaction solution was quenched with saturated sodium carbonate aqueous solution and layered. The organic phase was concentrated. The residue was dissolved in ethyl acetate and washed with saturated sodium carbonate aqueous solution. The organic phase was dried over anhydrous sodium sulfate and concentrated. The crude was purified by silica gel column chromatography to obtain AN-26 (800 mg) as a colorless oil. LC-MS: 336.0 [M+Na]+.

Chiral resolution was performed to obtain AN-26-1 and AN-26-2: Preparative column was Daicel AD-H, filler particle size (5 μm), inner diameter (30 mm), length (250 mm), flow rate: 30 mL/min, mobile phase: 95% n-hexane+5% ethanol, isogradient elution, wavelength 254 nm, peak time is 18.534 min for peak 1, and 30.857 min for peak 2.

Example 192 Synthesis of Amide AN-27

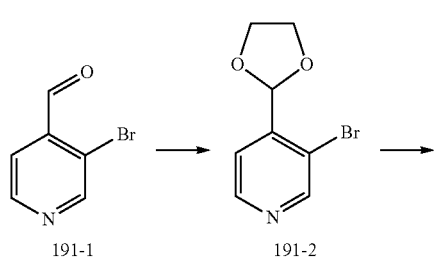

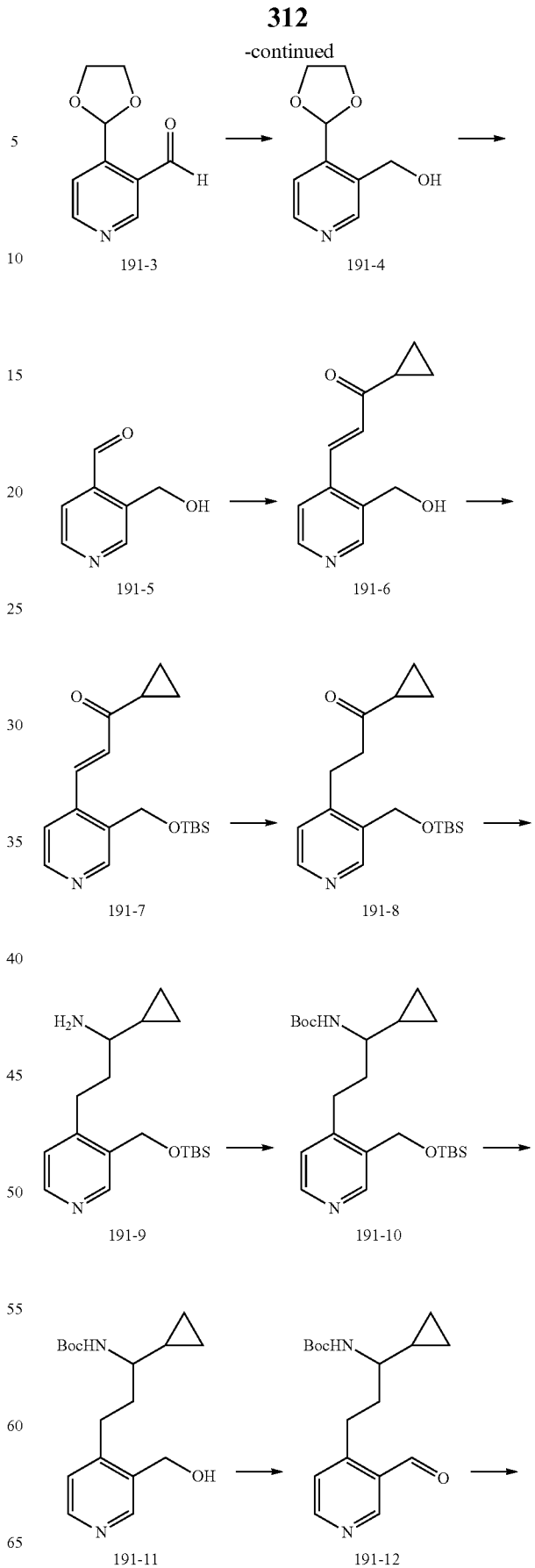

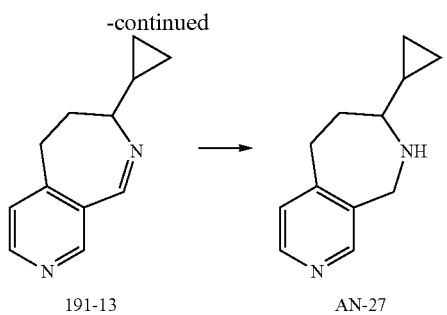

191-13     AN-27

Step 1:

3-Bromopyridine-4-aldehyde (191-1, 10.0 g, 53.76 mmol), ethylene glycol (6.7 g, 107.53 mmol) and p-toluenesulfonic acid (900 mg, 5.38 mmol) were heated in toluene (200 mL) and refluxed to separate the water for 3 h. TLC detected that the reaction was complete. The reaction solution was cooled to room temperature, poured into an iced saturated sodium carbonate aqueous solution, and layered. The organic phase was washed with saturated brine, dried over anhydrous sodium sulfate, and concentrated to obtain 191-2 (13.1 g) as a yellowish oil. The crude was directly used for the next reaction.

Step 2:

191-2 (6.0 g) was dissolved in tetrahydrofuran (100 mL), cooled to about −70° C. under nitrogen, and added dropwise with n-butyl lithium solution (11.5 mmol, 28.70 mmol, 2.5M), reacted at −70° C. for 1 h, added dropwise with tetrahydrofuran solution of N,N-dimethylformamide (9.5 g, 130.45 mmol), reacted for 1 h, slowly raised to room temperature to react for 1 h. TLC detected that the reaction was complete. The reaction solution was quenched with saturated ammonium chloride solution, extracted with ethyl acetate. The organic phase was washed with saturated brine, dried over anhydrous sodium sulfate, and concentrated. The crude was purified by silica gel column chromatography to obtain 191-3 (1.3 g) as a yellow oil.

Step 3:

191-3 (2.1 g, 11.73 mmol) was dissolved in methanol (30 mL), cooled to 0° C., added with sodium borohydride solid (669 mg, 17.6 mmol) in batches, and stirred at 0° C. for 0.5 h. TLC detected that the reaction was complete. The reaction solution was quenched with water and extracted with ethyl acetate. The organic phase was washed with saturated brine, dried over anhydrous sodium sulfate, and concentrated to obtain 191-4 (2.3 g) as a yellow oil. LC-MS: 182.1 [M+1]$^+$.

Step 4:

191-4 (2.3 g) was dissolved in 3N hydrochloric acid (30 mL), and heated to 80° C. to react for 3 h. TLC detected that the reaction was complete. The reaction solution was cooled to room temperature, neutralized with saturated sodium carbonate aqueous solution, and extracted with dichloromethane/isopropanol (3.5V/1V). The organic phase was washed with saturated brine, dried over anhydrous sodium sulfate, and concentrated to obtain 191-5 (1.5 g) as a yellow-brown solid.

Step 5:

191-5 (1.5 g) and Wittig reagent (190-7a, 3.8 g, 10.95 mmol) were heated in tetrahydrofuran (50 mL) to reflux for 1 h. TLC detected that the reaction was complete. The reaction solution was cooled to room temperature and concentrated to obtain a crude 191-6, which was directly used for the next reaction. LC-MS: 204.1 [M+1]$^+$.

Step 6:

191-6 was dissolved in N,N-dimethylformamide (30 mL), added with imidazole (2.2 g, 32.85 mmol) at room temperature, stirred for 5 min, added with tert-butyldimethylchlorosilane (2.5 g, 16.43 mmol), and heated to 60° C. to react for 2 h. TLC detected that the reaction was basically complete. The reaction solution was cooled to room temperature, quenched with water and extracted with ethyl acetate. The organic phase was washed with saturated brine, dried over anhydrous sodium sulfate, and concentrated. The crude was purified by silica gel column chromatography to obtain 191-7 (2.9 g) as a yellow-brown oil.

Step 7:

191-7 (2.9 g, 9.13 mmol) was dissolved in ethyl acetate (60 mL), added with Pd/C (500 mg), and hydrogenated at room temperature for 0.5 h. TLC detected that the reaction was complete. The reaction solution was filtered through celite pad, and the filter cake was washed. The filtrate was concentrated to obtain 191-8 (2.65 g) as a yellowish oil. LC-MS: 320.2 [M+1]$^+$.

Step 8:

191-8 (2.65 g) and ammonium acetate (6.4 g, 82.9 mmol) were dissolved in n-butanol (50 mL), added with sodium cyanoborohydride (2.6 g, 41.5 mmol), and heated to 70° C. to react for 2 h. TLC detected that the reaction was complete. The reaction solution was cooled to room temperature, added with water, stirred for 0.5 h, and layered. The n-butanol phase was concentrated to dryness to obtain 191-9, which was directly used in the next reaction. LC-MS: 321.1 [M+1]$^+$.

Step 9:

191-9 was dissolved in tetrahydrofuran (30 mL), added with 2N sodium hydroxide aqueous solution (15 mL, 30.0 mmol), cooled to about 0° C., added dropwise with Boc anhydride (4.0 g, 18.33 mmol), warmed to room temperature and stirred to react for 2 h. TLC detected that the reaction was basically complete. The reaction mixture was added with water and extracted with ethyl acetate. The organic phase was washed with saturated brine, dried over anhydrous sodium sulfate, and concentrated. The crude was purified by silica gel column chromatography to obtain 191-10 (1.3 g) as a brown solid. LC-MS: 421.3 [M+1]$^+$.

Step 10:

191-10 (1.3 g, 3.09 mmol) was dissolved in tetrahydrofuran (30 mL), added with tetrabutylammonium fluoride monohydrate (1.0 g. 3.09 mmol), and stirred at room temperature for 1 h. TLC detected that the reaction was complete. The reaction solution was added with water and extracted with ethyl acetate. The organic phase was washed with saturated brine, dried over anhydrous sodium sulfate, and concentrated to obtain 191-11 (1.1 g) as a brown oil.

Step 11:

191-11 (1.1 g) was dissolved in dichloromethane (50 mL), added with manganese dioxide (4.6 g, 52.91 mmol) at room temperature, and heated to reflux for 2 h. TLC detected that the reaction was basically complete. The reaction solution was cooled to room temperature, and filtered through celite pad. The filtered cake was washed. The filtrate was concentrated to obtain 191-12 (1.1 g) as a brown oil.

Step 12:

191-12 (1.1 g) was dissolved in dichloromethane (15 mL), added with trifluoracetic acid (5 mL), and stirred for 1 h at room temperature. TLC detected that the reaction was complete. The reaction solution was concentrated at room temperature, diluted with ice water, neutralized with saturated sodium carbonate solution, and extracted with ethyl acetate. The organic phase was washed with saturated brine, dried over anhydrous sodium sulfate, and concentrated to obtain 191-13 (530 mg) as a brown viscous oil.

Step 13:

191-13 (530 mg, 2.85 mmol) was dissolved in methanol (10 mL), cooled to about 0° C., added with sodium borohydride solid (108 mg, 2.85 mmol) in batches, and reacted at 0° C. for 0.5 h. TLC detected that the reaction was basically complete. The reaction solution was added with water, reacted at room temperature for 0.5 h, and extracted with dichloromethane/isopropanol (3.5V/1V). The organic phase was washed with saturated brine, dried over anhydrous sodium sulfate, and concentrated to obtain a yellow oil, which was purified to obtain AN-27 (200 mg) as a yellow oil. LC-MS: 189.1 [M+1]$^+$.

Example 193 Synthesis of Amide AN-28

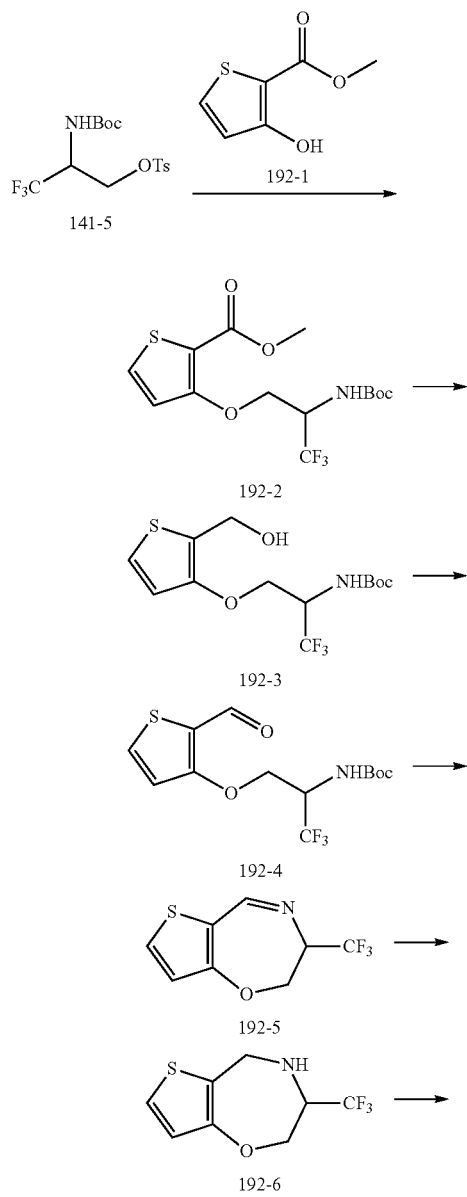

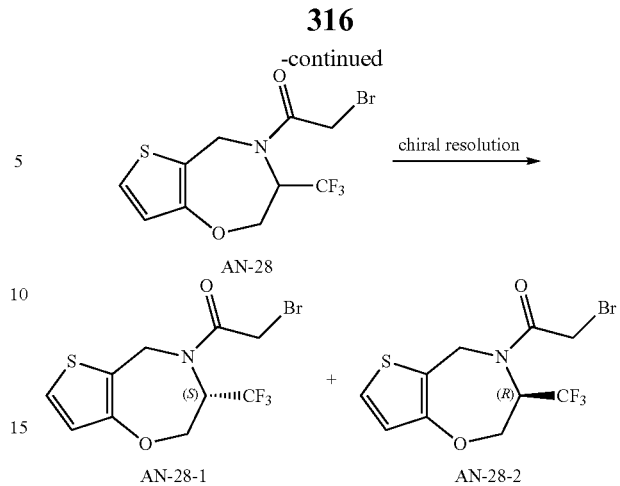

Step 1:

141-5 (12.6 g, 32.87 mmol) was dissolved in N,N-dimethylformamide (130 mL) under nitrogen, added with methyl 3-hydroxy-2-thiophenecarboxylate (192-1, 10.4 g, 65.75 mmol) and potassium carbonate (13.6 g, 98.4 mmol), and reacted at room temperature for 3 days. TLC detected that the reaction was complete. The reaction solution was added with water and extracted with ethyl acetate. The combined organic phase was washed with water and saturated brine, dried over anhydrous sodium sulfate, and concentrated. The crude was purified by silica gel column chromatography to obtain 192-2 (7.1 g) as a white solid. LC-MS: 392.1 [M+Na]$^+$.

Step 2:

LiAlH$_4$ (1.17 g, 30.83 mmol) was dispersed in dry tetrahydrofuran (80 m) under nitrogen, cooled in an ice bath, and added dropwise at the low temperature with 192-2 (7.6 g, 20.58 mmol, dissolved in 20 ml of tetrahydrofuran), and reacted at room temperature for 1 h. TLC detected that the reaction was complete. The reaction solution was added dropwise with 1.2 ml of water, 1.2 ml of 15% sodium hydroxide, 3.6 ml of water, added with anhydrous sodium sulfate, stirred for 30 min, and filtered. The filtrate was concentrated to obtain 192-3 (5.39 g) as a yellowish solid. LC-MS: 364.1 [M+Na]$^+$.

Step 3:

192-3 (5.39 g, crude) was dissolved in dichloromethane (160 mL) under nitrogen, added with manganese dioxide (27.5 g, 316.3 mmol), and reacted for 1 h at room temperature. TLC detected that the reaction was complete. The reaction solution was filtered through celite pad. The filtrate was concentrated to obtain 192-4 (5.2 g) as a yellow solid. LC-MS: 362.0 [M+Na]$^+$. $^1$H NMR: (CDCl$_3$, 400 MHz): δ 1.46 (s, 9H), 3.86 (s, 3H), 4.17-4.20 (m, 1H), 4.48-4.56 (m, 2H), 5.01 (d, J=9.6 Hz, 1H), 6.81 (d, J=5.6 Hz, 1H), 7.43 (d, J=5.6 Hz, 1H).

Step 4:

192-4 (5.0 g) was dissolved in dichloromethane (50 mL), cooled to about 0° C. in an ice water bath, added dropwise with trifluoracetic acid (40 mL), and reacted for 1 h at room temperature. TLC detected that the reaction was complete. The reaction solution was added with dichloromethane, added dropwise with a saturated sodium bicarbonate aqueous solution to adjust pH to be weakly alkaline and layered. The combined organic phase was washed with saturated sodium bicarbonate aqueous solution and saturated brine, dried over anhydrous sodium sulfate and concentrated to obtain 192-5 (2.83 g) as a yellow solid. LC-MS: 222.1 [M+1]$^+$.

Step 5:

192-5 (2.83 g) was dissolved in methanol (30 mL) under nitrogen, added with sodium borohydride (0.97 g, 25.64 mmol), and reacted overnight at room temperature. LCMS detected that the reaction was complete. The reaction solution was quenched with water, stirred for 30 min and extracted with ethyl acetate. The combined organic phase was washed with water and saturated brine, dried over anhydrous sodium sulfate, and concentrated. The crude was purified by silica gel column chromatography to obtain 192-6 (2.72 g) as a yellow solid. LC-MS: 224.1 [M+1]$^+$.

Step 6:

192-6 (2.72 g, 12.19 mmol) was dissolved in dichloromethane (60 mL) under nitrogen, cooled to about 0° C. in an ice water bath, added dropwise with bromoacetyl bromide (9.86 g, 48.79 mmol, 10 ml, diluted with methyl chloride), and reacted overnight at room temperature. TLC detected that the reaction was complete. The reaction solution was poured into ice water, adjusted pH with sodium bicarbonate to weakly alkaline and layered. The combined organic phase was washed with water and saturated brine, dried over anhydrous sodium sulfate, and concentrated. The crude was diluted with ethyl acetate, alkalized with saturated sodium bicarbonate aqueous solution, stirred for 30 min and layered. The combined organic phase was washed with water and saturated brine, dried over anhydrous sodium sulfate, and concentrated. The crude was purified by silica gel column chromatography to obtain AN-28 (3.16 g) as a white solid. LC-MS: 344.0 (M+1)$^+$.

Chiral resolution was performed to obtain AN-28-1 and AN-28-2: Preparative column was NANOMICRO OD-5H, filler particle size (5 μm), inner diameter (30 mm), length (250 mm), flow rate: 30 m/min, mobile phase: 70% n-hexane+30% isopropanol, isogradient elution, wavelength 254 nm, peak time is 18.523 min for peak 1, and 23.813 min for peak 2.

Example 194 Synthesis of Amide AN-29

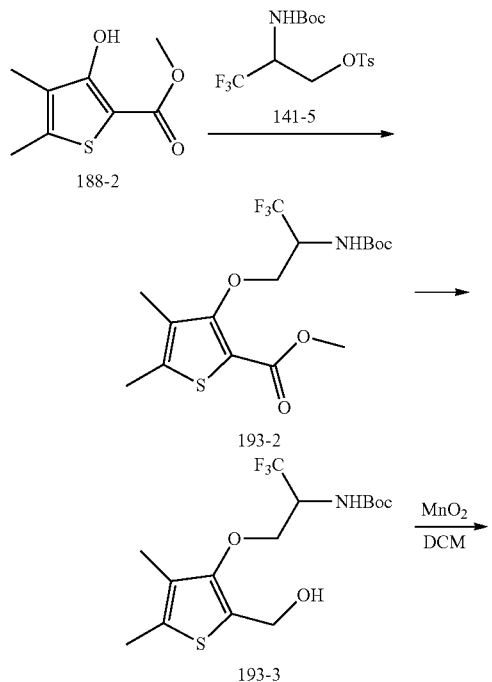

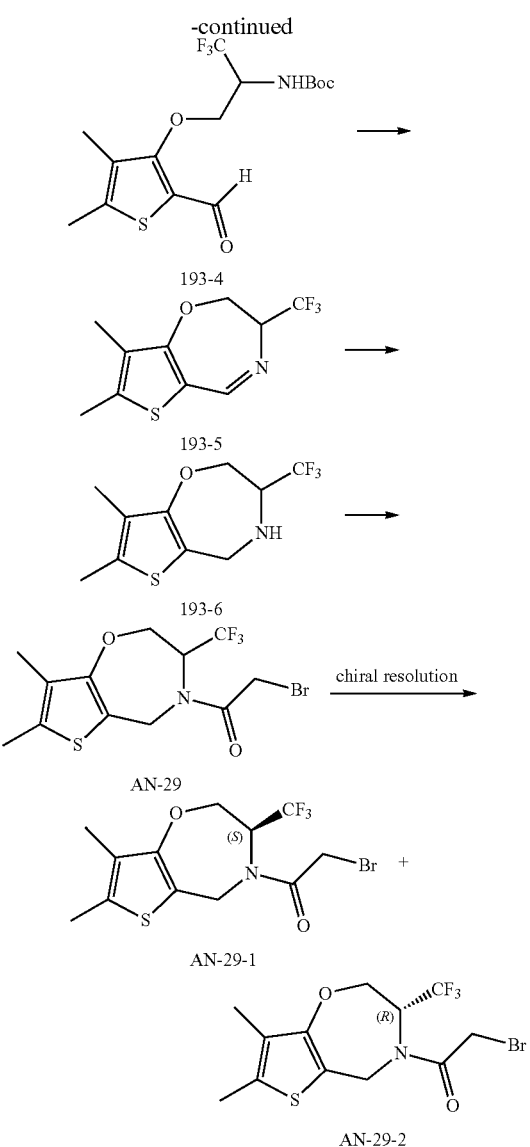

Step 1:

188-2 (7.3 g, 39.20 mmol) was dissolved in N,N-dimethylformamide (120 ml), added with potassium carbonate (8.1 g, 58.61 mmol) and 141-5 (7.5 g, 19.56 mmol), stirred at room temperature for 4 days. TLC detected that the reaction was complete. The reaction solution was poured into ice water and extracted with ethyl acetate. The combined organic phase was washed with water and saturated brine, dried over anhydrous sodium sulfate, and concentrated. The crude was purified by silica gel column chromatography to obtain 193-2 (3.0 g) as a white solid. LC-MS: 420.1 [M+Na]$^+$. $^1$H-NMR: (CDCl$_3$, 400 MHz): δ 1.48 (s, 9H), 2.01 (s, 3H), 2.33 (s, 3H), 3.84 (s, 3H), 4.21-4.24 (m, 1H), 4.40-4.43 (m, 1H), 4.52 (br, 1H), 6.06 (d, J=8.8 Hz, 1H).

Step 2:

193-2 (5.3 g, 13.34 mmol) was dissolved in tetrahydrofuran (60 mL), added with lithium aluminum tetrahydrogen (0.76 g, 20.03 mmol) in batches under nitrogen, and stirred at this temperature for 2 h. TLC showed that the reaction was complete. The reaction solution was slowly added dropwise with water (0.68 mL), 15% sodium hydroxide aqueous solution (0.8 mL) and water (2.4 mL) in sequence, stirred at room temperature for 10 min, and filtered through celite pad. The filtrate was concentrated to obtain 193-3 (4.9 g) as a white solid. The crude was used directly in the next step. LC-MS: 392.1 [M+Na]$^+$, $^1$H-NMR: (CDCl$_3$, 400 MHz): δ 1.48 (s, 9H), 1.99 (s, 4H), 2.28 (s, 3H), 4.15 (s, 2H), 4.54 (br, 1H), 4.63 (d, J=5.2 Hz, 2H), 5.5 (d, J=9.2 Hz, 1H).

Step 3:

193-3 (4.90 g) was dissolved in dichloromethane (100 mL), added with manganese dioxide (22.95 g, 264.0 mmol), and heated to reflux for 2 h. TLC showed that the reaction was complete. The reaction solution was cooled to room temperature and filtered through celite pad. The filtrate was concentrated. The crude was purified by silica gel column chromatography to obtain 193-4 (4.2 g, 86% yield in two steps) as a white solid. LC-MS: 390.1 [M+Na]$^+$, $^1$H NMR: (CDCl$_3$, 400 MHz): δ 1.47 (s, 9H), 2.01 (s, 3H), 2.38 (s, 3H), 4.33-4.41 (m, 2H), 4.62 (br, 1H), 5.38 (d, J=9.6 Hz, 1H), 9.81 (s, 1H).

Step 4:

193-4 (3.7 g, 10.07 mmol) was dissolved in dichloromethane (12 mL), added with trifluoracetic acid (6 mL), and stirred for 0.5 h at room temperature. TLC showed that the reaction was complete. The reaction solution was alkalized with saturated aqueous sodium bicarbonate solution, and extracted with ethyl acetate. The combined organic phase was washed with water and saturated brine, dried over anhydrous sodium sulfate, and concentrated to obtain 193-5 (2.4 g) as a yellowish oil. The crude was used directly in the next step.

Step 5:

193-5 (2.4 g) was dissolved in methanol (40 mL), added with sodium borohydride (550 mg, 14.54 mmol) under nitrogen, and stirred overnight at room temperature. LCMS showed that a small amount of the raw material did not react. The reaction solution was added with water and extracted with ethyl acetate. The combined organic phase was washed with water and saturated brine, dried over anhydrous sodium sulfate, and concentrated. The crude was purified by silica gel column chromatography to obtain 193-6 (2.1 g) as a yellowish solid. LC-MS: 252.1 [M+H]$^+$, $^1$H-NMR: (CDCl$_3$, 400 MHz): δ 1.94 (s, 3H), 2.24 (s, 3H), 3.65-3.69 (m, 1H), 3.82-3.86 (m, 1H), 3.96-4.01 (m, 1H), 4.10, 4.14 (m, 1H), 4.55 (dd, J$_1$=12.4 Hz, J$_2$=2.8 Hz, 1H).

Step 6:

193-6 (2.1 g, 8.36 mmol) was dissolved in dichloromethane (80 mL). After atmosphere was replaced with nitrogen three times, the solution was cooled to 0 to 5° C., added with bromoacetyl bromide (6.75 g, 33.44 mmol) in one time, and stirred overnight at room temperature. TLC showed that a small amount of the raw material did not react. The reaction solution was cooled to 0 to 5° C., quenched with water and layered. The aqueous phase was extracted with dichloromethane. The combined organic phase was concentrated, diluted with ethyl acetate, washed with saturated Na$_2$CO$_3$ aqueous solution, washed with saturated brine, dried over anhydrous sodium sulfate, and concentrated. The crude was purified by silica gel column chromatography to obtain AN-29 (2.9 g) as a white solid. LC-MS: 372.0 [M+1]$^+$.

Chiral resolution was performed to obtain AN-29-1 and AN-29-2: Preparative column was Daicel AD-H, filler particle size (5 μm), inner diameter (30 mm), length (250 mm), flow rate: 30 mL/min, mobile phase: 95% n-hexane+5% ethanol, isogradient elution, wavelength 254 nm, peak time is 10.240 min for peak 1, and 19.173 min for peak 2.

Example 195 Synthesis of Intermediate 195-9

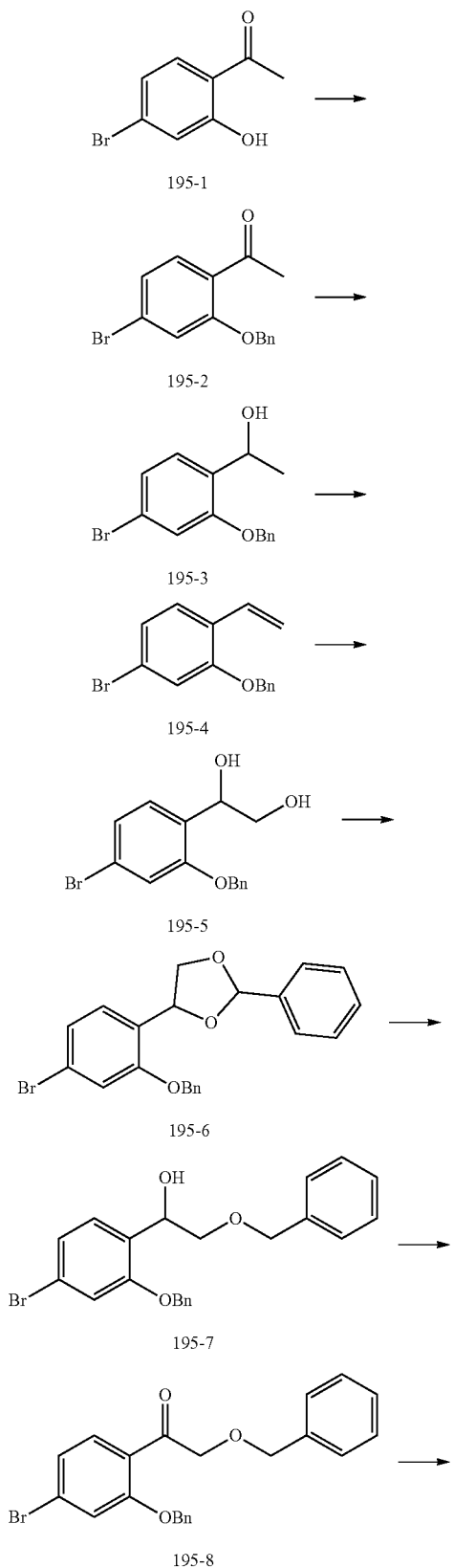

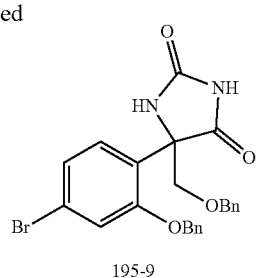

195-9

Step One:

4-bromo-2-hydroxyacetophenone (195-1, 20.0 g, 93.0 mmol) and potassium carbonate (25.7 g, 185.9 mmol) were dissolved in N,N-dimethylformamide, added dropwise with benzyl bromide (19.1 g, 111.7 mmol) at room temperature, and reacted at room temperature overnight. TLC showed that the reaction was complete. The reaction solution was quenched with water, and filtered. The filter cake was washed with water, dried to obtain 195-2 (29.5 g) as a white solid. LC-MS: 327.1 [M+Na]$^+$.

Step Two:

195-2 (15.0 g) was dissolved in a mixed solvent of dichloromethane (50 mL) and methanol (50 mL), added with sodium borohydride (4.7 g, 124.2 mmol) in batches under ice bath, and reacted in the ice bath for 1 h. TLC showed that the reaction was complete. The reaction solution was quenched with ice water and extracted with dichloromethane. The combined organic phase was washed with water and saturated brine, dried over anhydrous sodium sulfate, and concentrated to obtain 195-3 (15.0 g) as a white solid.

Step Three:

195-3 (15.0 g, crude) and p-toluenesulfonic acid (930 mg, 4.9 mmol) were dissolved in toluene and heated to reflux for 3 h. TLC showed that the reaction was complete. The reaction solution was cooled to room temperature, quenched with water and extracted with ethyl acetate. The combined organic phase was washed with water and saturated brine, dried over anhydrous sodium sulfate, and concentrated to obtain 195-4 (14.1 g).

Step Four:

195-4 (14.1 g) and N-methylmorpholine N-oxide (17.0 g, 145.1 mmol) were dissolved in a mixed solvent of acetone (50 m) and water (50 mL), added with potassium osmate dihydrate (1.78 g, 4.84 mmol), and stirred at room temperature for 3 h. TLC showed that the reaction was complete. The reaction solution was quenched with water and extracted with ethyl acetate. The combined organic phase was washed with water and saturated brine, dried over anhydrous sodium sulfate, and concentrated. The crude was purified by silica gel column chromatography to obtain 195-5 (6.5 g) as a white solid. LC-MS: 345.0 [M+Na]$^+$. $^1$H NMR: (CD$_3$OD, 400 MHz): δ 3.27-3.33 (m, 1H), 3.52-3.57 (m, 1H), 4.71 (t, J=6.0 Hz, 1H), 4.92-4.96 (m, 1H), 5.15 (d, J=3.2 Hz, 2H), 5.20 (d, J=4.4 Hz, 1H), 7.14 (dd, J$_1$=8.0 Hz, J$_2$=1.6 Hz, 1H), 7.23 (d, J=1.6 Hz, 1H), 7.32-7.47 (m, 6H).

Step Five:

195-5 (6.5 g, 20.1 mmol) and benzaldehyde dimethyl acetal (3.7 g, 24.3 mmol) were dissolved in toluene (50 mL), added with p-toluenesulfonic acid (173 mg, 1.0 mmol), and stirred at room temperature overnight. TLC showed that the reaction was complete. The reaction solution was quenched with water and extracted with ethyl acetate. The combined organic phase was washed with water and saturated brine, dried over anhydrous sodium sulfate, and concentrated to obtain 195-6 (8.1 g). LC-MS: 411.0 [M+1]$^+$.

Step Six:

195-6 (8.1 g) was dissolved in toluene (50 mL), cooled to 0° C. in an ice bath, added with diisobutylaluminum hydride (49 mg, 49 mmol), and stirred at room temperature overnight. TLC showed that the reaction was complete. The reaction solution was quenched with water and extracted with ethyl acetate. The combined organic phase was washed with water and saturated brine, dried over anhydrous sodium sulfate, and concentrated. The crude was purified by silica gel column chromatography to obtain 195-7 (3.7 g) as a white solid. LC-MS: 413.1 [M+1]$^+$. $^1$H NMR: (CD$_3$OD, 400 MHz): δ 3.33-3.38 (m, 1H), 3.52 (dd, J$_1$=10.0 Hz, J$_2$=2.8 Hz, 1H), 4.45 (s, 2H), 5.07-5.10 (m, 1H), 5.13 (s, 2H), 5.38 (d, J=4.8 Hz, 1H), 7.14, 7.16 (dd, J$_1$=8.4 Hz, J$_2$=2.0 Hz, 1H), 7.22-7.43 (m, 12H).

Step Seven:

195-7 (3.7 g, 8.95 mmol) was dissolved in dichloromethane (30 mL), added with Dess-Martine (4.56 g, 10.75 mmol), and stirred overnight at room temperature. TLC showed that the reaction was complete. The reaction solution was quenched with water and extracted with ethyl acetate. The combined organic phase was washed with water and saturated brine, dried over anhydrous sodium sulfate, and concentrated. The crude was purified by silica gel column chromatography to obtain 195-8 (3.4 g) as a white solid. LC-MS: 411.0 [M+1]$^+$. $^1$H NMR: (CD$_3$OD, 400 MHz): δ 4.45 (s, 2H), 4.61 (s, 2H), 5.25 (s, 2H), 7.23-7.52 (m, 12H), 7.64-7.66 (m, 1H).

Step Eight:

195-8 (3.4 g, 8.27 mmol) was dissolved in a mixed solvent of ammonia (30 mL) and ethanol (80 mL), added with trimethylsilyl cyanide (7.4 g, 74.59 mmol), ammonium fluoride (7.4 g, 199.8 mmol) and ammonium carbonate (17.0 g, 176.9 mmol) at room temperature, and heated to 80° C. to react overnight. TLC showed that the reaction was complete. The reaction solution was cooled to room temperature, quenched with water and extracted with ethyl acetate. The combined organic phase was washed with water and saturated brine, dried over anhydrous sodium sulfate, and concentrated to obtain 195-9 (3.5 g). LC-MS: 481.1 [M+1]$^+$.

Example 196 Synthesis of SYY-B110

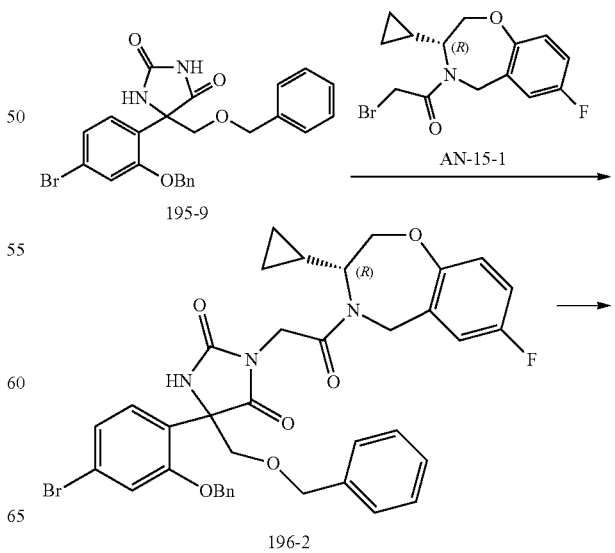

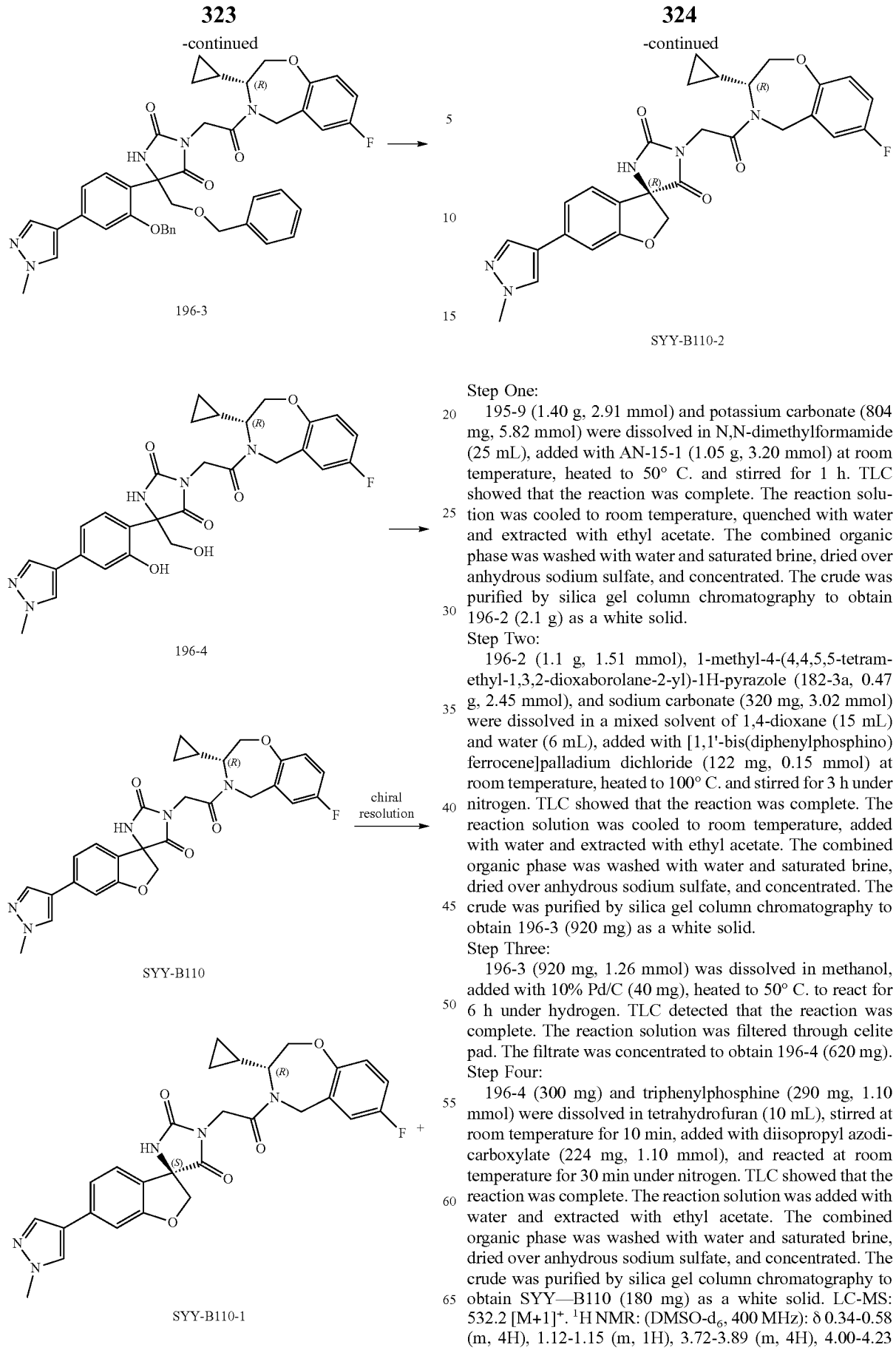

Step One:

195-9 (1.40 g, 2.91 mmol) and potassium carbonate (804 mg, 5.82 mmol) were dissolved in N,N-dimethylformamide (25 mL), added with AN-15-1 (1.05 g, 3.20 mmol) at room temperature, heated to 50° C. and stirred for 1 h. TLC showed that the reaction was complete. The reaction solution was cooled to room temperature, quenched with water and extracted with ethyl acetate. The combined organic phase was washed with water and saturated brine, dried over anhydrous sodium sulfate, and concentrated. The crude was purified by silica gel column chromatography to obtain 196-2 (2.1 g) as a white solid.

Step Two:

196-2 (1.1 g, 1.51 mmol), 1-methyl-4-(4,4,5,5-tetramethyl-1,3,2-dioxaborolane-2-yl)-1H-pyrazole (182-3a, 0.47 g, 2.45 mmol), and sodium carbonate (320 mg, 3.02 mmol) were dissolved in a mixed solvent of 1,4-dioxane (15 mL) and water (6 mL), added with [1,1'-bis(diphenylphosphino)ferrocene]palladium dichloride (122 mg, 0.15 mmol) at room temperature, heated to 100° C. and stirred for 3 h under nitrogen. TLC showed that the reaction was complete. The reaction solution was cooled to room temperature, added with water and extracted with ethyl acetate. The combined organic phase was washed with water and saturated brine, dried over anhydrous sodium sulfate, and concentrated. The crude was purified by silica gel column chromatography to obtain 196-3 (920 mg) as a white solid.

Step Three:

196-3 (920 mg, 1.26 mmol) was dissolved in methanol, added with 10% Pd/C (40 mg), heated to 50° C. to react for 6 h under hydrogen. TLC detected that the reaction was complete. The reaction solution was filtered through celite pad. The filtrate was concentrated to obtain 196-4 (620 mg).

Step Four:

196-4 (300 mg) and triphenylphosphine (290 mg, 1.10 mmol) were dissolved in tetrahydrofuran (10 mL), stirred at room temperature for 10 min, added with diisopropyl azodicarboxylate (224 mg, 1.10 mmol), and reacted at room temperature for 30 min under nitrogen. TLC showed that the reaction was complete. The reaction solution was added with water and extracted with ethyl acetate. The combined organic phase was washed with water and saturated brine, dried over anhydrous sodium sulfate, and concentrated. The crude was purified by silica gel column chromatography to obtain SYY—B110 (180 mg) as a white solid. LC-MS: 532.2 [M+1]$^+$. $^1$H NMR: (DMSO-d$_6$, 400 MHz): δ 0.34-0.58 (m, 4H), 1.12-1.15 (m, 1H), 3.72-3.89 (m, 4H), 4.00-4.23

(m, 2H), 4.38-4.78 (m, 5H), 4.90-5.02 (m, 1H), 6.87-7.27 (m, 6H), 7.86-7.88 (m, 1H), 8.14-8.16 (m, 1H), 9.06-9.09 (m, 1H).

Chiral resolution was performed to obtain SYY-B110-1 and SYY-B110-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 23.166 min for peak 1, and 62.642 min for peak 2.

Example 197 Synthesis of SYY-B112

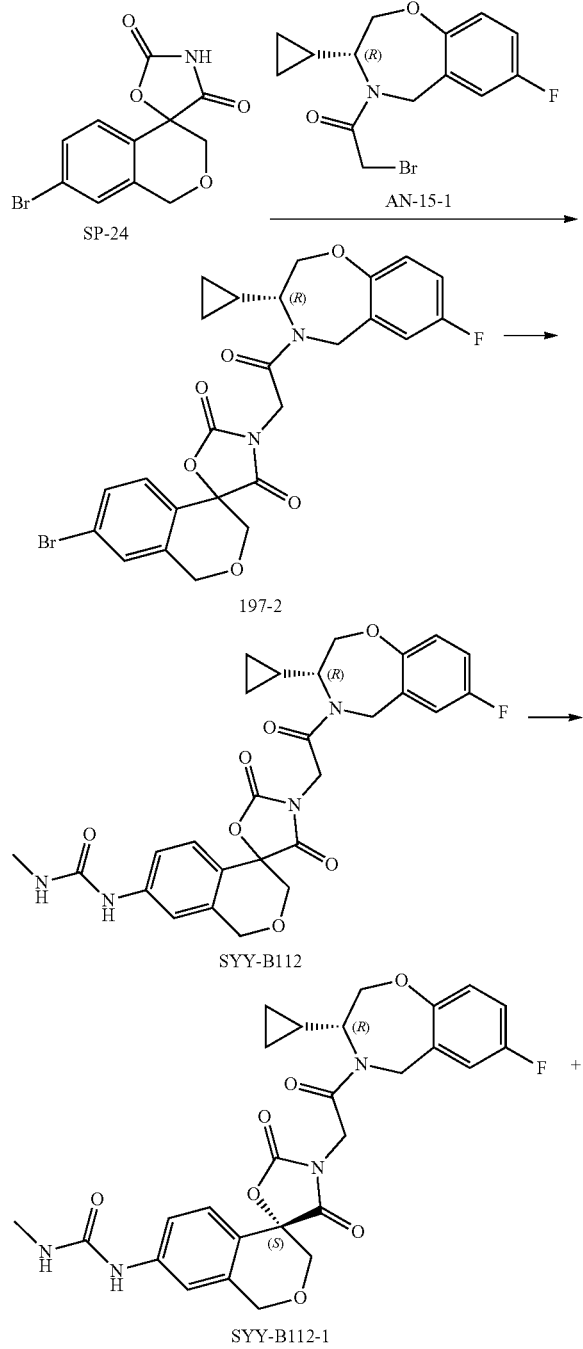

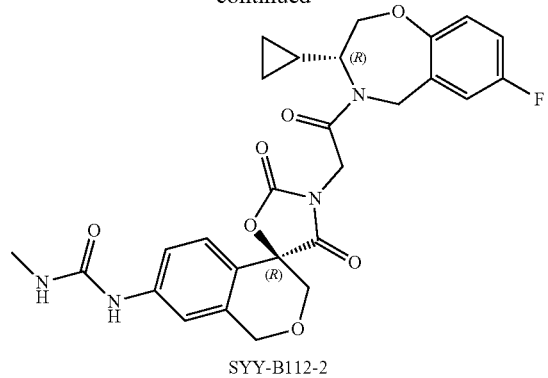

Step 1:

The spiro ring intermediate SP-24 (400 mg, 1.34 mmol) was dissolved in dry N,N-dimethylformamide (20 ml), added with the amide fragment AN-15-1 (400 mg, 1.22 mmol) and potassium carbonate (338 mg, 2.44 mmol) at room temperature, and stirred overnight at room temperature to complete the reaction. The reaction solution was added with water (100 ml), stirred for 10 min and filtered. The filter cake was washed with water and petroleum ether, dissolved with ethyl acetate, washed with water and saturated brine, dried over anhydrous sodium sulfate, and concentrated to obtain 197-2 (560 mg). LC-MS: 545.1 [M+1]$^+$.

Step 2:

197-2 (560 mg) was dissolved in dry 1,4-dioxane (20 ml), added with methyl urea (163 mg, 2.20 mmol), tri(dibenzylideneacetone)dipalladium (50 mg, 0.06 mmol), 4,5-bis(diphenylphosphino)-9,9-dimethylxanthene (64 mg, 0.11 mmol) and cesium carbonate (711 mg, 2.20 mmol) at room temperature, heated to 100° C. and stirred for 40 min under nitrogen. TLC showed that the reaction was complete. The reaction solution was cooled to room temperature, poured into ice water and extracted with ethyl acetate. The combined organic phase was washed with water and saturated brine, dried over anhydrous sodium sulfate, and concentrated. The crude was purified by silica gel column chromatography to obtain SYY—B112 (208 mg). LC-MS: 539.2 [M+1]$^+$. $^1$H NMR: (DMSO-d$_6$, 400 MHz): δ 0.36-0.58 (m, 4H), 1.25-1.38 (m, 1H), 2.63 (m, 3H), 3.77-4.51 (m, 6H), 4.55-5.06 (m, 5H), 6.13-6.15 (m, 1H), 6.92-7.05 (m, 2H), 7.20-7.37 (m, 4H), 8.76 (m, 1H).

Chiral resolution was performed to obtain SYY-B112-1 and SYY-B112-2: Preparative column was Daicel AD-H, filler particle size (5 μm), inner diameter (30 mm), length (250 mm), flow rate: 30 m/min, mobile phase: 70% n-hexane+30% isopropanol, isogradient elution, wavelength 254 nm, peak time is 19.372 min for peak 1, and 25.430 min for peak 2.

Example 198 Synthesis of SYY-B116-1

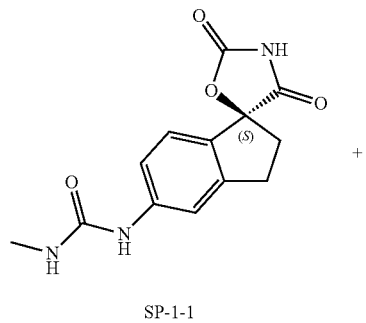

SP-1-1

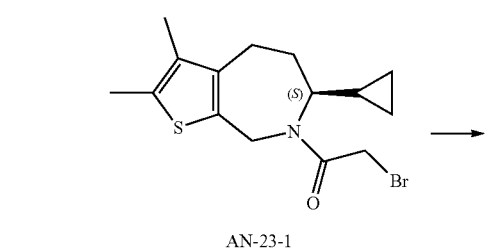

AN-23-1

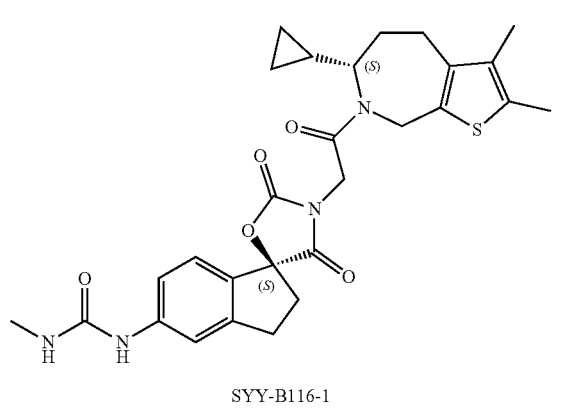

SYY-B116-1

The spiro ring intermediate SP-1-1 (38 mg, 0.14 mmol) and potassium carbonate (39 mg, 0.28 mmol) were dissolved in N,N-dimethylformamide (1 mL), stirred for 5 min, added with the amide fragment AN-23-1 (43 mg, 0.13 mmol), and reacted at room temperature for 6 h. The reaction solution was poured into 15 ml of water and extracted with ethyl acetate. The combined organic phase was washed with water and saturated brine, dried over anhydrous sodium sulfate, and concentrated. The crude was purified by silica gel column chromatography to obtain SYY-B116-1 (51 mg) as a white solid. LC-MS: 559.2 [M+Na]+; $^1$H NMR (400 MHz, DMSO-$d_6$) δ 8.66 (s, 1H), 7.51 (s, 1H), 7.27-7.21 (m, 2H), 6.04-6.07 (m, 1H), 4.90-3.59 (m, 6H), 3.13-2.91 (m, 2H), 2.75-2.56 (m, 5H), 2.44-1.97 (m, 6H), 1.89-1.91 (m, 3H), 1.22-1.20 (m, 1H), 0.52-0.31 (m, 4H).

Example 199 Synthesis of SYY-B116-2

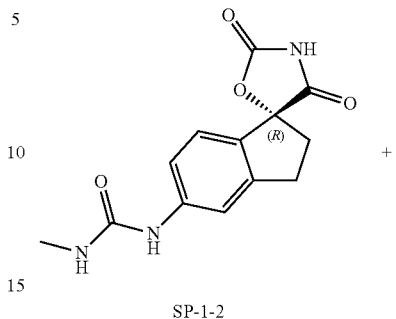

SP-1-2

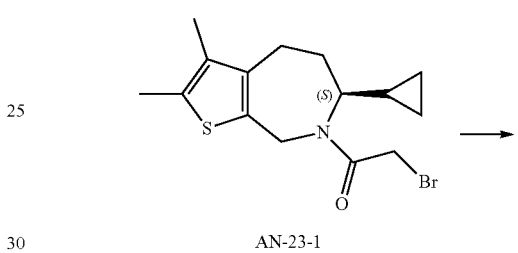

AN-23-1

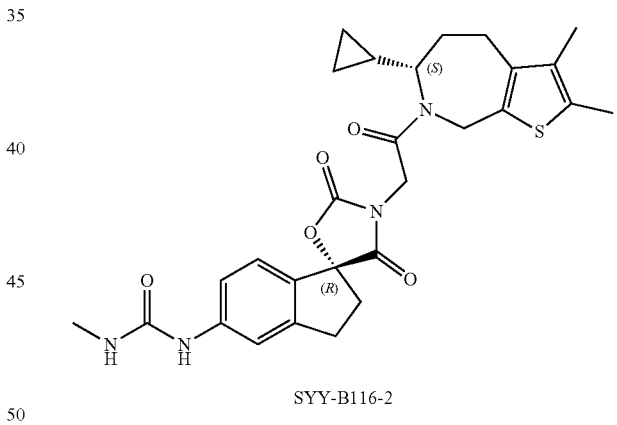

SYY-B116-2

The spiro ring intermediate SP-1-2 (38 mg, 0.14 mmol) and potassium carbonate (43 mg, 0.31 mmol) were dissolved in N,N-dimethylformamide (1 mL), stirred for 5 min, added with the amide fragment AN-23-1 (42 mg, 0.12 mmol), and reacted at room temperature overnight. The reaction solution was poured into 15 ml of water and extracted with ethyl acetate. The combined organic phase was washed with water and saturated brine, dried over anhydrous sodium sulfate, and concentrated. The crude was purified by silica gel column chromatography to obtain SYY-B116-2 (60 mg) as a white solid. LC-MS: 559.2 [M+Na]*. $^1$H NMR (400 MHz, DMSO-$d_6$) δ 8.67 (m, 1H), 7.51 (m, 1H), 7.25-7.17 (m, 2H), 6.04-6.07 (m, 1H), 4.87-3.58 (m, 6H), 3.11-2.91 (m, 2H), 2.71-2.55 (m, 5H), 2.48-2.33 (m, 1H), 2.23-1.99 (m, 5H), 1.90 (s, 3H), 1.22-1.20 (m, 1H), 0.54-0.32 (m, 4H).

Example 200 Synthesis of SYY-B118-2

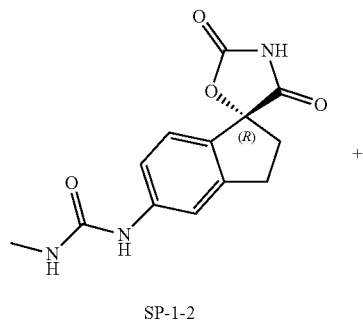

SP-1-2

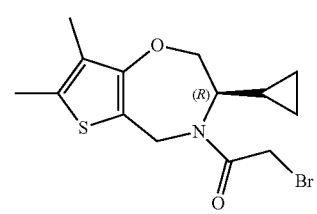

AN-24-1

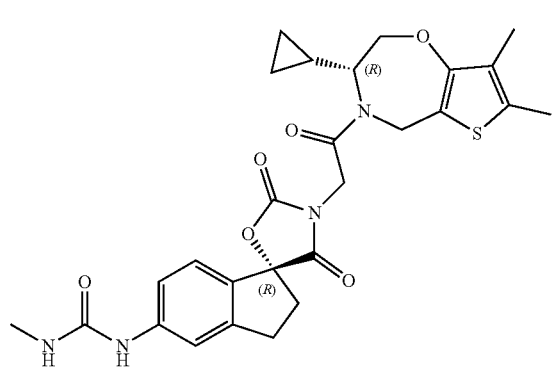

SYY-B118-2

The spiro ring intermediate SP-1-2 (64 mg, 0.23 mmol) and the amide fragment AN-24-1 (80 mg, 0.23 mmol), potassium carbonate (96 mg, 0.7 mmol) were stirred in N,N-dimethylformamide (3 mL) at room temperature for 2 h. TLC detected that the reaction was complete. The reaction solution was added with water and extracted with ethyl acetate. The organic phase was washed with saturated brine, dried over anhydrous sodium sulfate, and concentrated. The crude was purified to obtain SYY-B118-2 (50 mg) as an off-white solid. LC-MS: 539.1 [M+H]$^+$; $^1$H-NMR: (DMSO-d$_6$, 400 MHz): δ 0.35-0.64 (m, 4H), 1.09-1.13 (m, 1H), 1.85-1.87 (m, 3H), 2.20-2.22 (m, 3H), 2.43-2.48 (m, 1H), 2.57-2.64 (m, 5H), 2.93-3.14 (m, 2H), 3.89-3.99 (m, 1H), 4.19-4.99 (m, 5H), 6.06-6.10 (m, 1H), 7.19-7.27 (m, 2H), 7.54 (m, 1H), 8.70-8.71 (m, 1H).

Example 201 Synthesis of SYY-B120-1

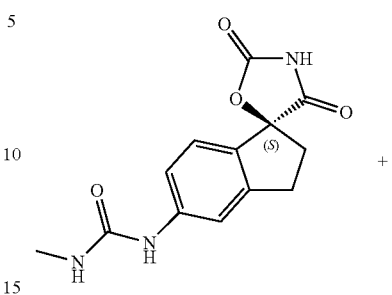

SP-1-1

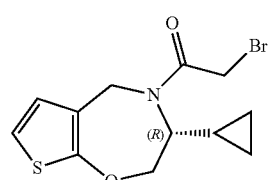

AN-25-1

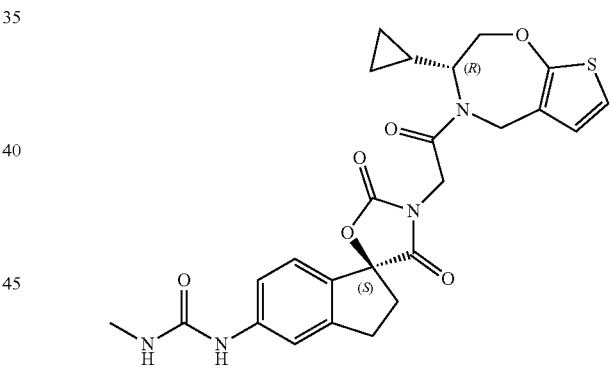

SYY-B120-1

The spiro ring intermediate SP-1-1 (37 mg, 0.134 mmol) was dissolved in N,N-dimethylformamide (4 mL), added with potassium carbonate (27 mg, 0.195 mmol) and the amide fragment AN-25-1 (40 mg, 0.126 mmol) in sequence, and reacted at room temperature overnight. TLC detected that the reaction was complete. The reaction solution was added with water and extracted with ethyl acetate. The combined organic phase was washed with saturated brine, dried over anhydrous sodium sulfate, and concentrated. The crude was purified to obtain SYY-B120-1 (42 mg) as an off-white solid. LC-MS: 511.2 [M+H]$^+$; $^1$H NMR: (DMSO-d$_6$, 400 MHz): δ 0.31-0.58 (m, 4H), 1.17-1.32 (m, 1H), 2.43 (m, 1H), 2.54-2.62 (m, 4H), 2.90-3.11 (m, 2H), 3.80-5.12 (m, 7H), 6.14 (m, 1H), 6.75 (m, 2H), 7.24 (m, 2H), 7.52 (m, 1H), 8.79 (m, 1H).

Example 202 Synthesis of SYY-B120-2

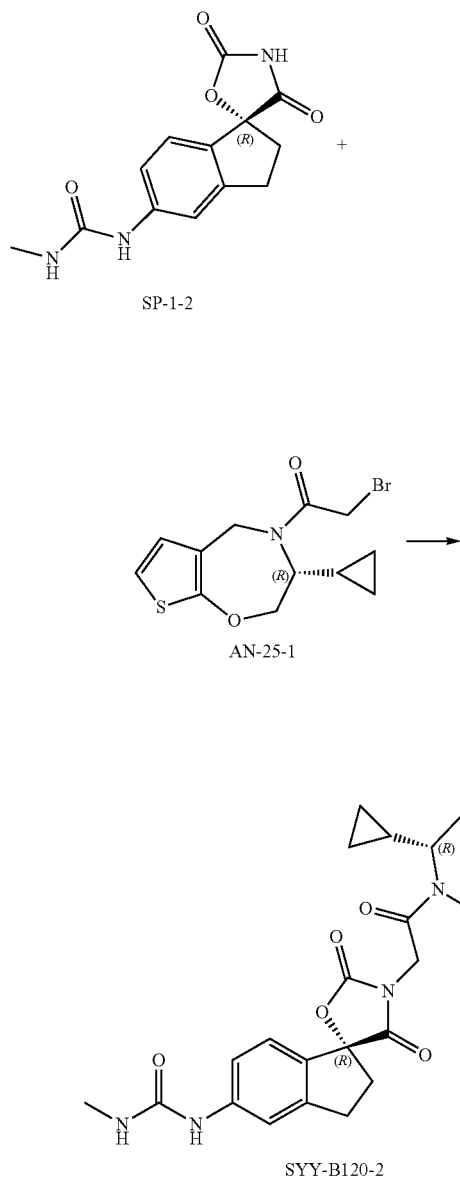

Example 203 Synthesis of SYY—B122

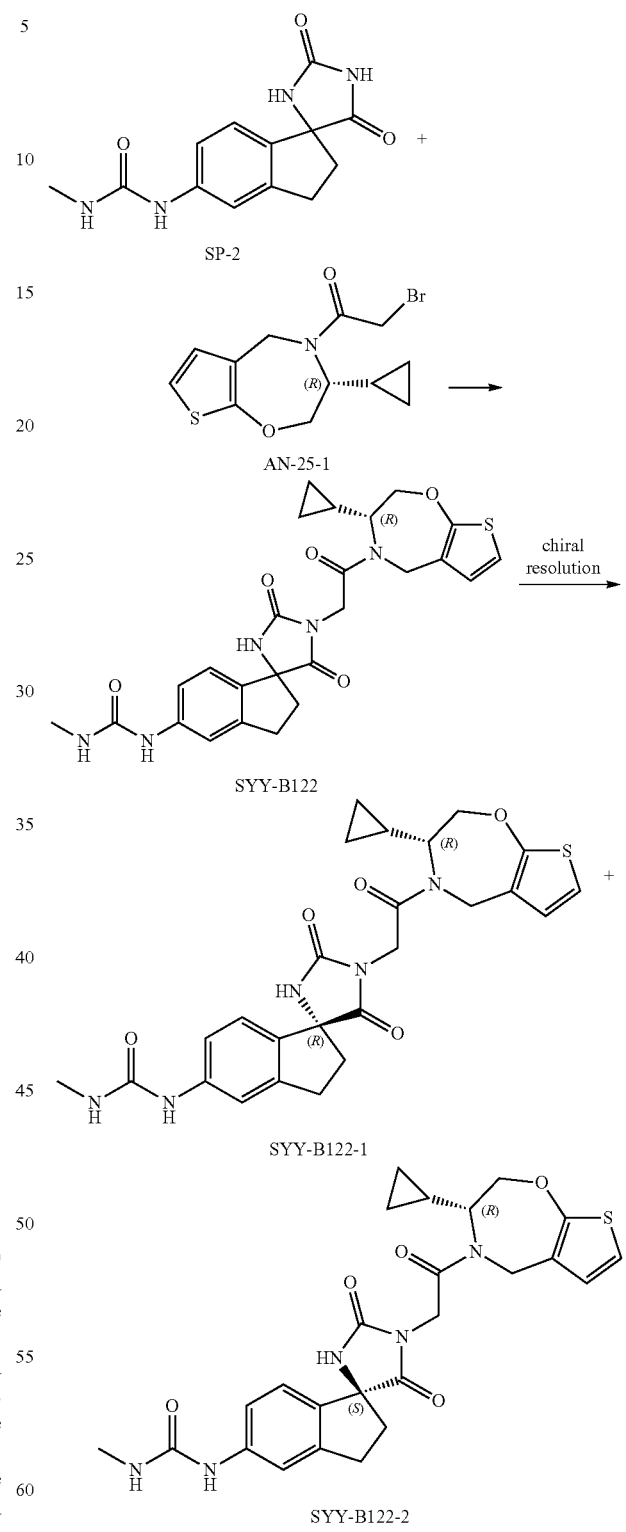

The spiro ring intermediate SP-1-2 (37 mg, 0.134 mmol) was dissolved in N,N-dimethylformamide (4 mL), added with potassium carbonate (27 mg, 0.195 mmol) and the amide fragment AN-25-1 (40 mg, 0.126 mmol) in sequence, and reacted at room temperature overnight. TLC detected that the reaction was complete. The reaction solution was added with water and extracted with ethyl acetate. The combined organic phase was washed with saturated brine, dried over anhydrous sodium sulfate, and concentrated. The crude was purified to obtain SYY-B120-2 (47 mg) as an off-white solid. LC-MS: 511.2 [M+H]$^+$; $^1$H NMR: (DMSO-d$_6$, 400 MHz): δ 0.31-0.58 (m, 4H), 1.17-1.32 (m, 1H), 2.41-2.46 (m, 1H), 2.56-2.63 (m, 4H), 2.91-3.12 (m, 2H), 3.79-3.97 (m, 1H), 4.15-4.52 (m, 4H), 4.68-5.11 (m, 2H), 6.11-6.12 (m, 1H), 6.68-6.76 (m, 2H), 7.18-7.25 (m, 2H), 7.52 (m, 1H), 8.76-8.78 (m, 1H).

The spiro ring intermediate SP-2 (91 mg, 0.332 mmol) was dissolved in N,N-dimethylformamide (5 mL), added with potassium carbonate (66 mg, 0.478 mmol) and the amide fragment AN-25-1 (100 mg, 0.316 mmol) in sequence, and reacted at room temperature overnight. TLC detected that the reaction was complete. The reaction solution was added with water and extracted with ethyl acetate. The combined organic phase was washed with saturated brine, dried over anhydrous sodium sulfate, and concentrated. The crude was purified to obtain SYY—B122 (150 mg) as yellowish solid. LC-MS: 510.2[M+1]+. ¹H NMR: (DMSO-d₆, 400 MHz): δ 50.28-0.56 (m, 4H), 1.15-1.28 (m, 1H), 2.09-2.16 (m, 1H), 2.43-2.46 (m, 1H), 2.61-2.62 (m, 3H), 2.88-2.98 (m, 2H), 3.82 (m, 1H), 4.10-5.07 (m, 6H), 6.00-6.01 (m, 1H), 6.69-6.76 (m, 2H), 7.03-7.18 (m, 2H), 7.41 (m, 1H), 8.55 (m, 1H), 8.68-8.72 (m, 1H).

Chiral resolution was performed to obtain SYY-B122-1 and SYY-B122-2: Preparative column was NANOMICRO OD-5H, filler particle size (5 μm), inner diameter (30 mm), length (250 mm), flow rate: 30 mL/min, mobile phase: 70% n-hexane+30% isopropanol, isogradient elution, wavelength 254 nm, peak time is 13.052 min for peak 1, and 18.095 min for peak 2.

Example 204 Synthesis of SYY-B124

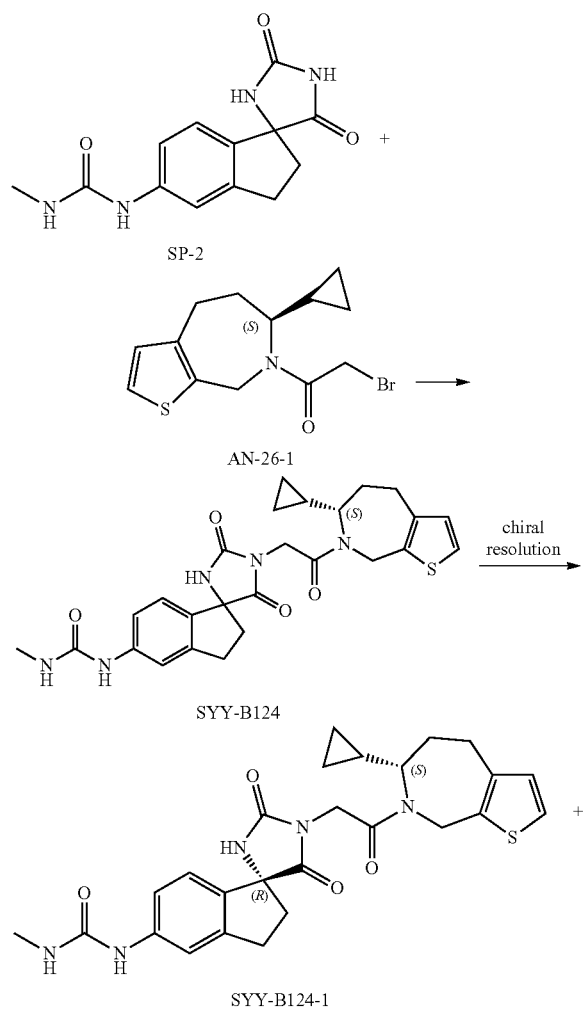

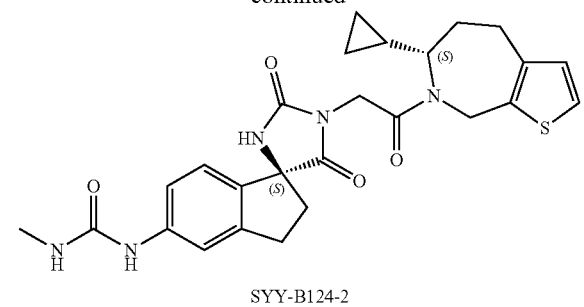

SYY-B124-2

The spiro ring intermediate SP-2 (135 mg, 0.49 mmol) was dissolved in N,N-dimethylformamide (5 mL), added with the amide fragment AN-26-1 (140 mg, 0.44 mmol) and potassium carbonate (93 mg, 0.67 mmol), and reacted at room temperature overnight. TLC detected that the reaction was complete. The reaction solution was added with water and extracted with ethyl acetate. The combined organic phase was washed with water and saturated brine, dried over anhydrous sodium sulfate, and concentrated. The crude was purified to obtain SYY—B124 (140 mg) as a white solid. LC-MS: 530.2 [M+Na]+; ¹H NMR: (DMSO-d₆, 400 MHz): δ 0.26-0.59 (m, 4H), 1.21-1.28 (m, 1H), 1.96-2.09 (m, 3H), 2.28-2.45 (m, 2H), 2.60-2.62 (m, 3H), 2.81-2.95 (m, 3H), 3.54-3.89 (m, 2H), 4.16-4.35 (m, 1H), 4.63-5.00 (m, 2H), 5.98-6.02 (m, 1H), 6.76-6.82 (m, 1H), 7.03-7.25 (m, 3H), 7.40-7.41 (m, 1H), 8.53-8.67 (m, 2H).

Chiral resolution was performed to obtain SYY-B124-1 and SYY-B124-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 10.024 min for peak 1, and 39.011 min for peak 2.

Example 205 Synthesis of SYY-B126-1

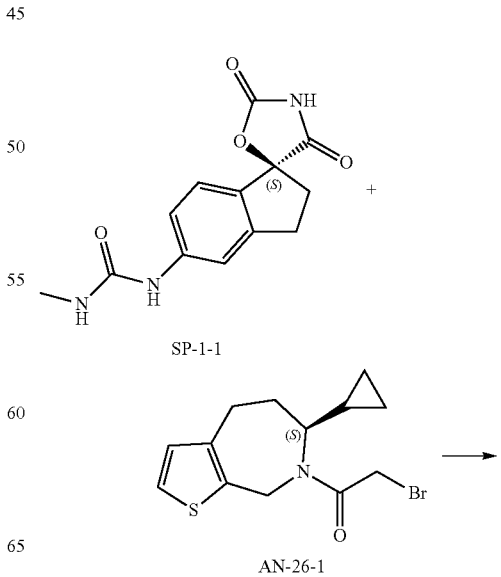

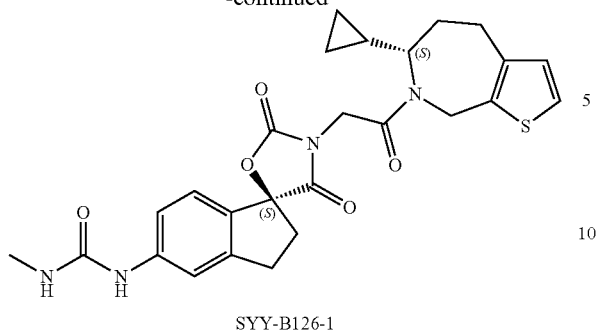

SYY-B126-1

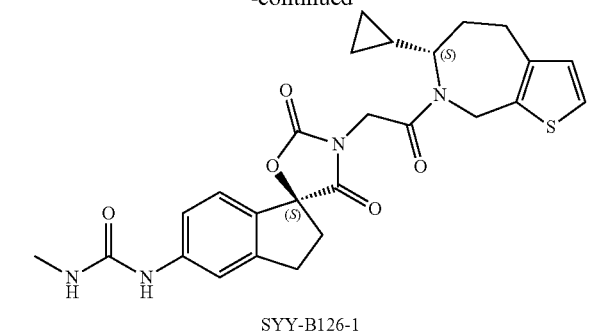

SYY-B126-1

The spiro ring intermediate SP-1-1 (75 mg, 0.27 mmol) was dissolved in N,N-dimethylformamide (3 mL), added with the amide fragment AN-26-1 (78 mg, 0.25 mmol) and potassium carbonate (52 mg, 0.38 mmol), and reacted at room temperature overnight. TLC detected that the reaction was complete. The reaction solution was added with water and extracted with ethyl acetate. The combined organic phase was washed with water and saturated brine, dried over anhydrous sodium sulfate, and concentrated. The residue was purified to obtain SYY-B126-1 (75 mg) as a white solid. LC-MS: 509.2 (M+1)$^+$. $^1$H NMR: (DMSO-d$_6$, 400 MHz): δ 0.28-0.54 (m, 4H), 1.22-1.31 (m, 1H), 1.96-2.07 (m, 2H), 2.34-2.45 (m, 2H), 2.55-2.62 (m, 4H), 2.86-3.07 (m, 3H), 3.57-3.94 (m, 2H), 4.35-5.05 (m, 3H), 6.06 (m, 1H), 6.77-6.85 (m, 1H), 7.19-7.28 (m, 3H), 7.52 (m, 1H), 8.68 (m, 1H).

Example 206 Synthesis of SYY-B126-2

The spiro ring intermediate SP-1-2 (75 mg, 0.27 mmol) was dissolved in N,N-dimethylformamide (3 mL), added with the amide fragment AN-26-1 (78 mg, 0.25 mmol) and potassium carbonate (52 mg, 0.38 mmol), and reacted at room temperature overnight. TLC detected that the reaction was complete. The reaction solution was added with water and extracted with ethyl acetate. The combined organic phase was washed with water and saturated brine, dried over anhydrous sodium sulfate, and concentrated. The residue was purified to obtain SYY-B126-2 (75 mg) as a white solid. LC-MS: 509.2 (M+1)$^+$. $^1$H NMR: (DMSO-d$_6$, 400 MHz): δ 0.29-0.55 (m, 4H), 1.22-1.31 (m, 1H), 1.96-2.07 (m, 2H), 2.31-2.45 (m, 2H), 2.52-2.62 (m, 4H), 2.84-3.11 (m, 3H), 3.55-3.91 (m, 2H), 4.33-4.58 (m, 1H), 4.71-5.04 (m, 2H), 6.04-6.07 (m, 1H), 6.78-6.84 (m, 1H), 7.17-7.27 (m, 3H), 7.51-7.52 (m, 1H), 8.67-8.69 (m, 1H).

Example 207 Synthesis of SYY-B130

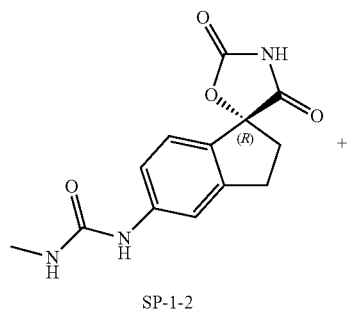

SP-1-2

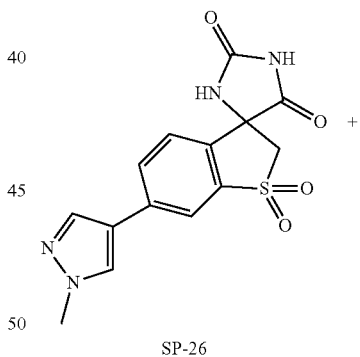

SP-26

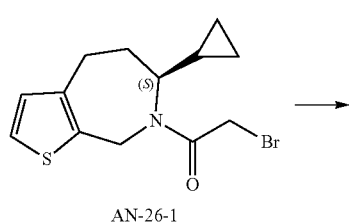

AN-26-1

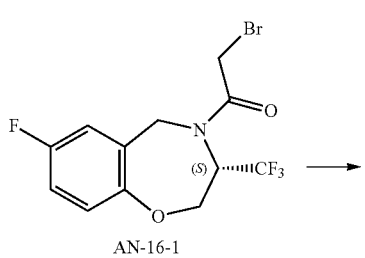

AN-16-1

337
-continued

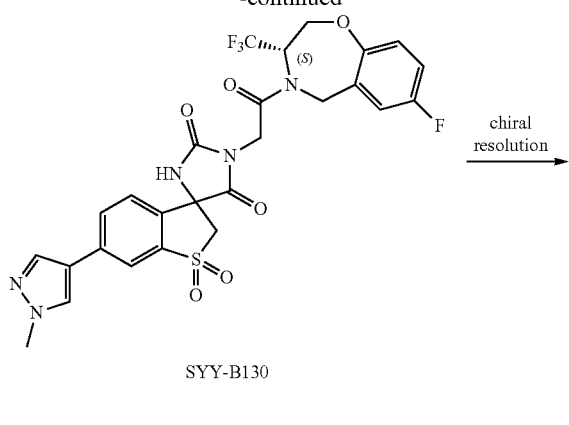

SYY-B130

+

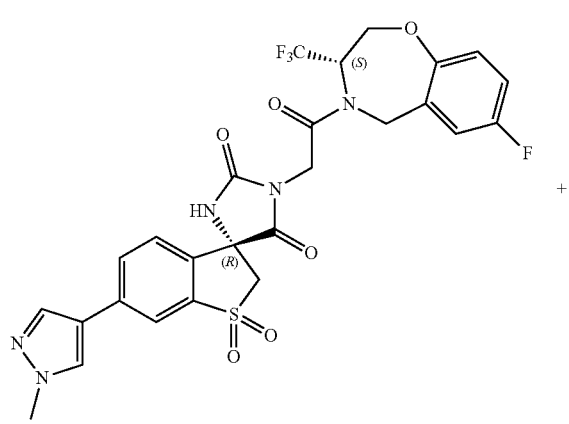

SYY-B130-1

338
-continued

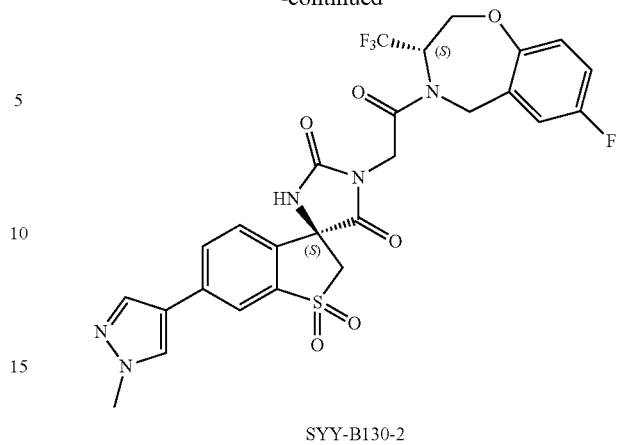

SYY-B130-2

The spiro ring intermediate SP-26 (122 mg, 0.367 mmol) and potassium carbonate (106 mg, 0.767 mmol) were dissolved in N,N-dimethylformamide (2 mL), stirred for 20 min, added with the amide fragment AN-16-1 (100 mg, 0.281 mmol), and reacted at room temperature overnight. The reaction solution was poured into water and extracted with ethyl acetate. The combined organic phase was washed with water and saturated brine, dried over anhydrous sodium sulfate, and concentrated. The crude was purified by silica gel column chromatography to obtain SYY—B130 (166 mg) as a yellow solid. LC-MS: 608.2 $[M+H]^+$. $^1$H NMR (400 MHz, DMSO-$d_6$) δ 9.29-9.33 (m, 1H), 8.39 (m, 1H), 8.13-7.97 (m, 3H), 7.61-7.57 (m, 1H), 7.25-6.93 (m, 3H), 5.55-5.53 (m, 1H), 5.12-5.00 (m, 5H), 4.27-3.79 (m, 6H).

Chiral resolution was performed to obtain SYY-B130-1 and SYY-B130-2: Preparative column was Daicel AD-H, filler particle size (5 μm), inner diameter (30 mm), length (250 mm), flow rate: 30 m/min, mobile phase: 60% n-hexane+40% isopropanol, isogradient elution, wavelength 254 nm, peak time is 35.245 min for peak 1, and 49.580 min for peak 2.

Example 208 Synthesis of SYY-B170-1 and SYY-B170-2

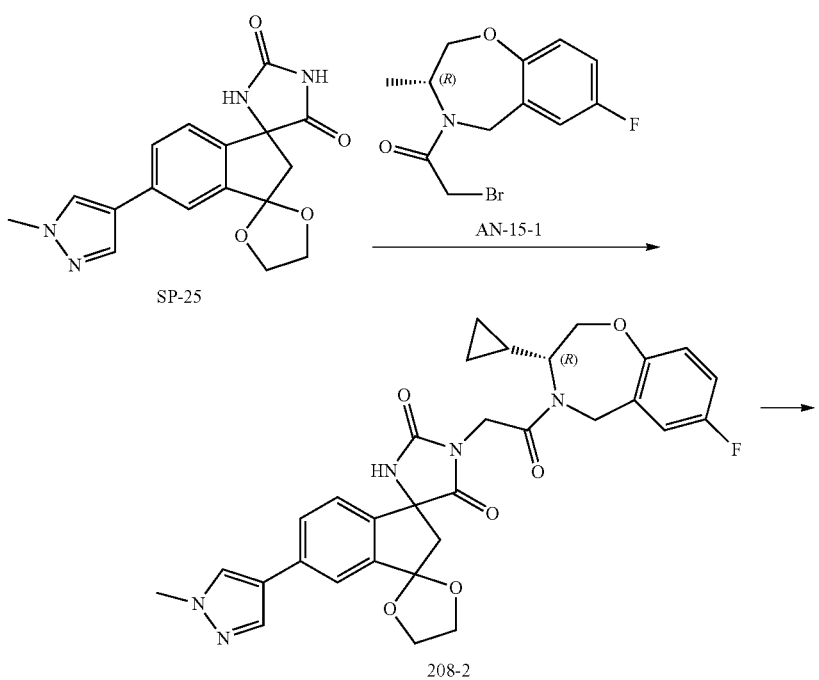

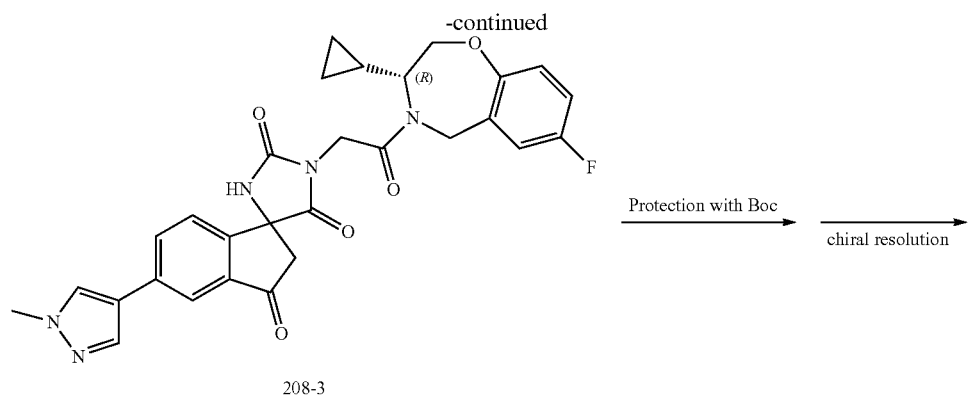
208-3
Protection with Boc →  chiral resolution →
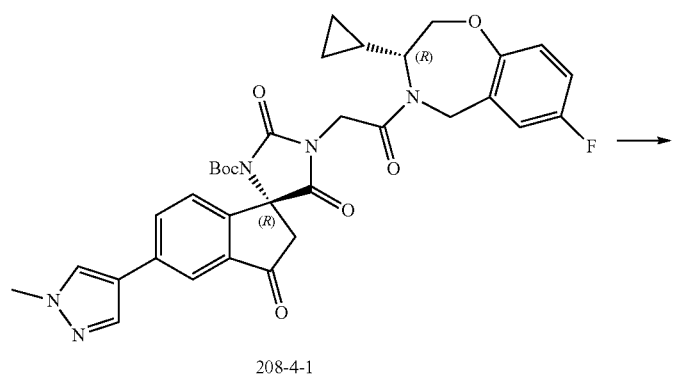
208-4-1
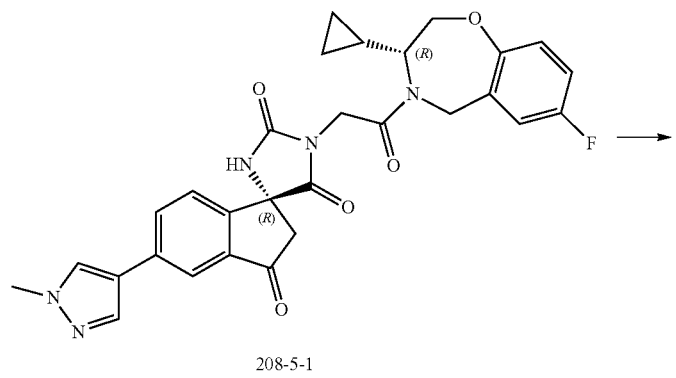
208-5-1
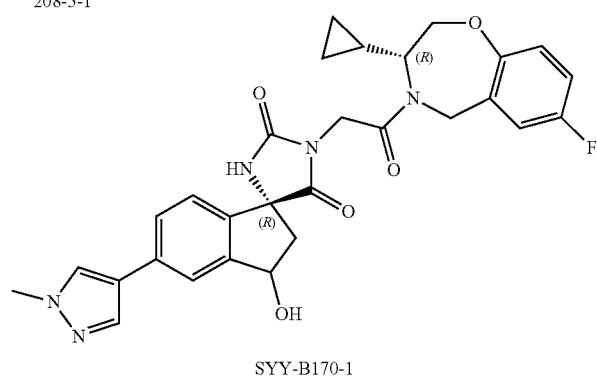
SYY-B170-1

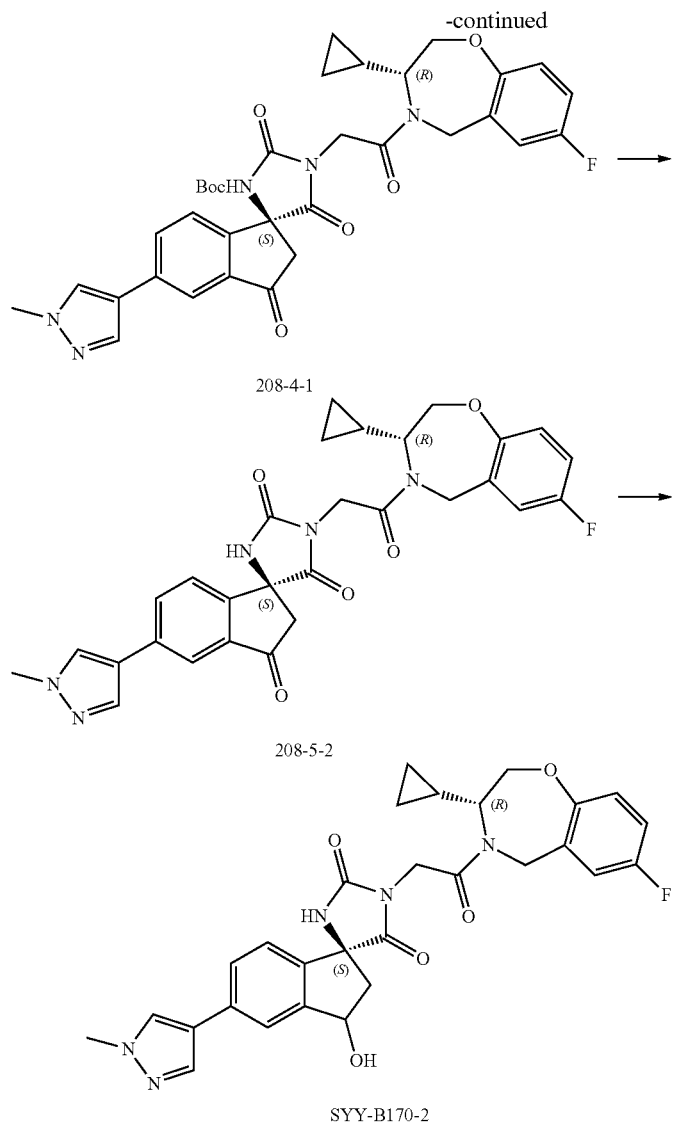

208-4-1

208-5-2

SYY-B170-2

Step 1:

The spiro ring intermediate SP-25 (500 mg, 1.47 mmol), the amide fragment AN-15-1 (528 mg, 1.61 mmol), and potassium carbonate (444 mg, 3.21 mmol) were dissolved in N,N-dimethylformamide (10 mL), and reacted at room temperature overnight. TLC detected that the reaction was complete. The reaction solution was added with water and extracted with ethyl acetate. The combined organic phase was washed with water and saturated brine, dried over anhydrous sodium sulfate, and concentrated. The crude was purified by silica gel column chromatography to obtain 208-2 (720 mg) as a yellow solid.

Step 2:

208-2 (720 mg, 1.22 mmol) was dissolved in tetrahydrofuran (15 mL), added with 6N hydrochloric acid (1 mL, 0.6 mmol), and reacted at room temperature overnight. TLC detected that the reaction was complete. The reaction solution was concentrated to obtain 208-3 (700 mg) as a yellow solid.

Step 3:

208-3 (700 mg) was dissolved in tetrahydrofuran (20 mL), added with 4-dimethylaminopyridine (catalytic amount) and di-tert-butyl dicarbonate (422 mg, 1.93 mmol), and reacted at room temperature overnight. The reaction solution was concentrated. The crude was purified by silica gel column chromatography to obtain 208-4 (770 mg) as a white solid.

Chiral resolution was performed to obtain 208-4-1 and 208-4-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 33.650 min for peak 1, and 38.393 min for peak 2.

Step 4:

208-4-1 (370 mg, 0.57 mmol) was dissolved in dichloromethane (6 mL), added with TFA (1.2 mL), and reacted for 2 h at room temperature. TLC detected that the reaction was complete. The reaction solution was concentrated to dryness at 30° C. to obtain a crude 208-5-1 (370 mg), which was directly used in the next reaction. 208-5-1 was dissolved in methanol (6 mL) to precipitate a solid, added with tetrahydrofuran (6 mL), cooled to 0° C., and added with sodium borohydride solid (34 mg, 0.9 mmol). The reaction solution became clear. TLC detected that the reaction was complete.

The reaction solution was added with water, stirred for 0.5 h, and extracted with ethyl acetate. The combined organic phase was washed with water and saturated brine, dried over anhydrous sodium sulfate, and concentrated. The residue was purified to obtain SYY-B170-1 (20 mg) as a yellowish solid. LC-MS: 546.2 [M+1]⁺. $^1$H NMR: (DMSO-$d_6$, 400 MHz): δ 0.33-0.58 (m, 4H), 1.13-1.22 (m, 1H), 2.23-2.33 (m, 1H), 2.42-2.45 (m, 1H), 3.75-3.85 (m, 4H), 4.03-4.25 (m, 2H), 4.33-4.78 (m, 3H), 4.92-5.02 (m, 1H), 5.24-5.30 (m, 1H), 5.52-5.57 (m, 1H), 6.88-7.27 (m, 4H), 7.50-7.54 (m, 2H), 7.85-7.87 (m, 1H), 8.15-8.17 (m, 1H), 8.73-8.75 (m, 1H).

Step 5:

208-4-2 (290 mg, 0.57 mmol) was dissolved in dichloromethane (6 mL), added with trifluoroacetic acid (1.2 mL), and reacted for 2 h at room temperature. TLC detected that the reaction was complete. The reaction solution was concentrated to dryness at 30° C. to obtain a crude 208-5-2 (370 mg), which was directly used in the next reaction. 208-5-2 was dissolved in methanol (6 mL) to precipitate a solid, added with tetrahydrofuran (6 mL), cooled to 0° C., and added with sodium borohydride solid (34 mg, 0.9 mmol). The reaction solution became clear. TLC detected that the reaction was complete. The reaction solution was added with water, stirred for 0.5 h, and extracted with ethyl acetate. The combined organic phase was washed with water and saturated brine, dried over anhydrous sodium sulfate, and concentrated. The residue was purified to obtain SYY-B170-2 (15 mg) as a yellowish solid. LC-MS: 546.2 [M+1]⁺. $^1$H NMR: (DMSO-$d_6$, 400 MHz): δ 0.32-0.61 (m, 4H), 1.13-1.22 (m, 1H), 2.26-2.32 (m, 1H), 2.43-2.47 (m, 1H), 3.76-3.84 (m, 4H), 4.02-4.25 (m, 2H), 4.33-4.76 (m, 3H), 4.93-5.03 (m, 1H), 5.269 (q, J=6.8 Hz, 1H), 5.53-5.55 (d, J=7.2 Hz, 1H), 6.89-7.27 (m, 4H), 7.51-7.53 (m, 2H), 7.86 (m, 1H), 8.16 (m, 1H), 8.73-8.77 (m, 1H).

Example 209 Synthesis of SYY-B132-1

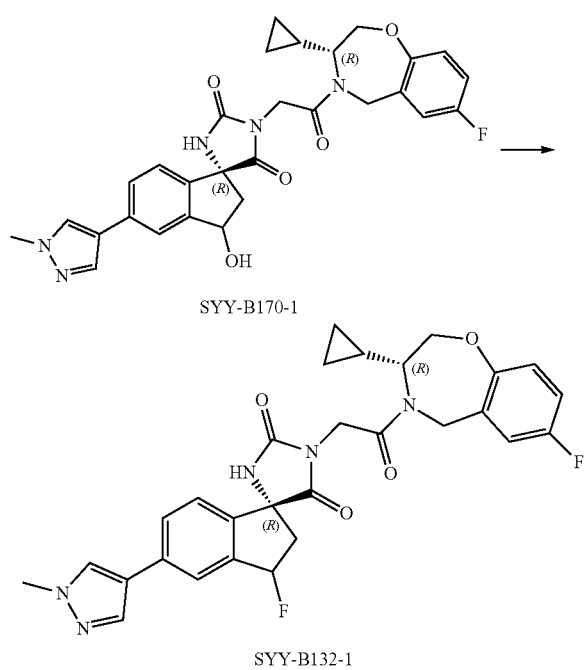

SYY-B170-1

SYY-B132-1

SYY-170-1 (120 mg, 0.22 mmol) was dissolved in dichloromethane (10 mL), cooled to about −70° C. under nitrogen, added with a solution of diethylaminosulfur trifluoride (83 mg, 0.51 mmol) in dichloromethane (5 mL), and reacted at −70° C. for 2 h. TLC detected that a small amount of raw materials did not react completely. The reaction solution was added with saturated sodium bicarbonate aqueous solution and extracted with dichloromethane. The combined organic phase was washed with water and saturated brine, dried over anhydrous sodium sulfate, and concentrated. The crude was purified to obtain SYY-B132-1 (42 mg) as an off-white solid. LC-MS: 548.3 [M+1]⁺. $^1$H NMR: (DMSO-$d_6$, 400 MHz): δ 0.32-0.56 (m, 4H), 1.10-1.15 (m, 1H), 2.24-2.37 (m, 1H), 2.98-3.16 (m, 1H), 3.70-3.85 (m, 4H), 3.97-4.23 (m, 2H), 4.31-5.00 (m, 4H), 6.00-6.18 (m, 1H), 6.85-7.34 (m, 4H), 7.71 (m, 2H), 7.92-7.94 (m, 1H), 8.21-8.23 (m, 1H), 9.00-9.02 (m, 1H).

Example 210 Synthesis of SYY-B132-2

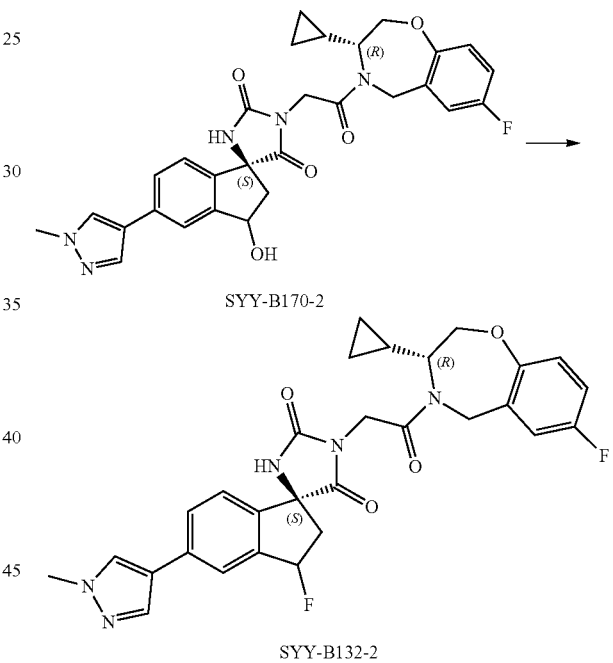

SYY-B170-2

SYY-B132-2

SYY-170-2 (140 mg, 0.26 mmol) was dissolved in dichloromethane (5 mL), cooled to about −70° C. under nitrogen, added with a solution of diethylaminosulfur trifluoride (83 mg, 0.51 mmol) in dichloromethane (5 mL), and reacted at −70° C. for 2 h. TLC detected that a small amount of the raw material did not react completely. The reaction solution was added with saturated sodium bicarbonate aqueous solution and extracted with dichloromethane. The combined organic phase was washed with water and saturated brine, dried over anhydrous sodium sulfate, and concentrated. The crude was purified to obtain SYY-B132-2 (31 mg) as an off-white solid. LC-MS: 548.3 [M+1]⁺. $^1$H NMR: (DMSO-$d_6$, 400 MHz): δ 0.27-0.54 (m, 4H), 1.08-1.16 (m, 1H), 2.25-2.36 (m, 1H), 2.98-3.02 (m, 1H), 3.70-3.84 (m, 4H), 3.98-4.22 (m, 2H), 4.30-5.00 (m, 4H), 6.02-6.19 (m, 1H), 6.85-7.31 (m, 4H), 7.69-7.72 (m, 2H), 7.93 (m, 1H), 8.22 (m, 1H), 9.00-9.03 (m, 1H).

Example 211 Synthesis of SYY-B136-1 and SYY-B137-1

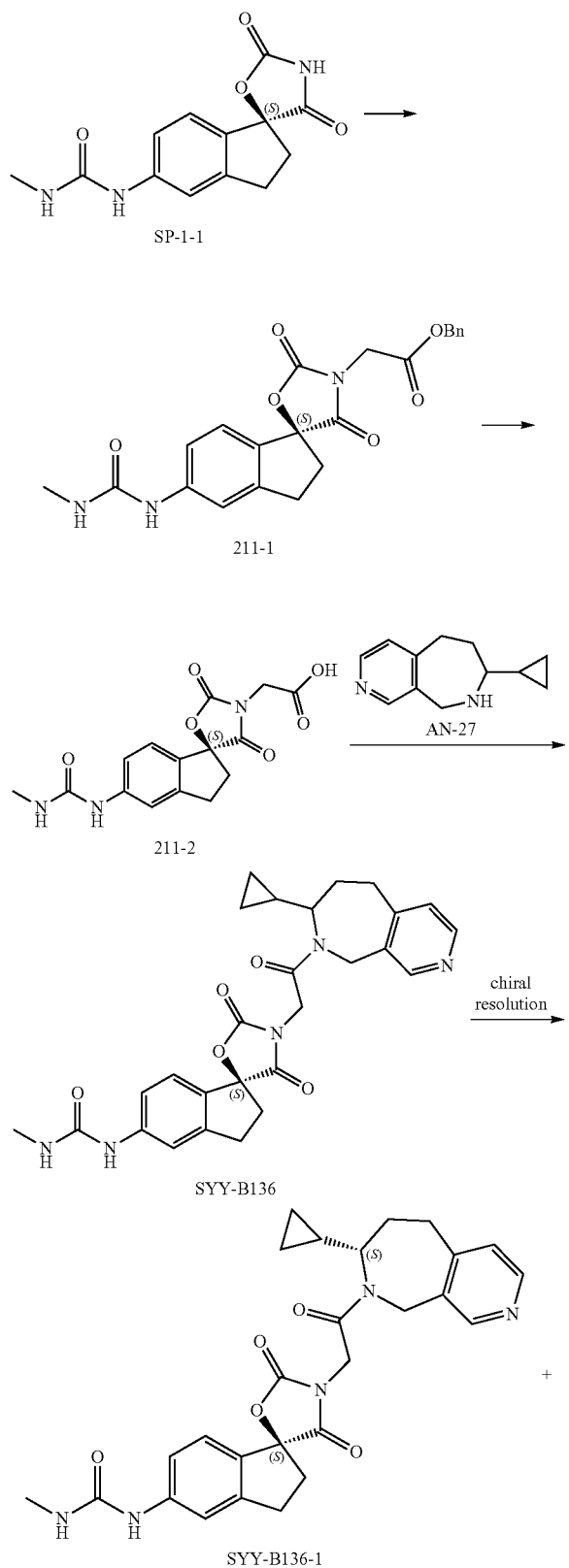

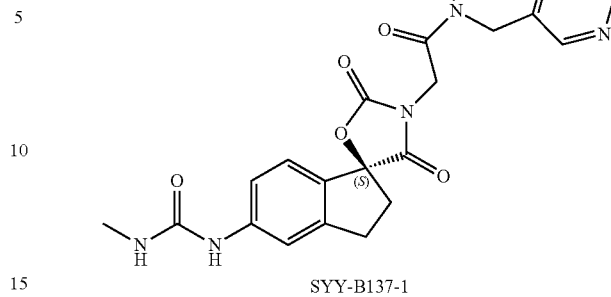

Step 1:

The spiro ring intermediate SP-1-1 (200 mg, 0.73 mmol) was dissolved in N,N-dimethylformamide (5 mL), added with potassium carbonate (201 mg, 1.46 mmol), reacted at room temperature for 0.5 h, added with benzyl bromoacetate (174 mg, 0.76 mmol), and reacted at room temperature for 2 h. TLC detected that the reaction was complete. The reaction solution was added with water and extracted with ethyl acetate. The organic phase was washed with saturated brine, dried over anhydrous sodium sulfate, and concentrated to obtain 211-1 (370 mg) as a yellow oil. The crude was directly used in the next step.

Step 2:

211-1 (370 mg) was dissolved in methanol (10 mL), and added with Pd/C (100 mg). After atmosphere was replaced with hydrogen 3 times, the reaction mixture was stirred at room temperature to react overnight. TLC detected that the reaction was complete. The reaction solution was filtered through celite pad. The filtrate was concentrated to obtain 211-2 (270 mg) as a yellowish solid.

Step 3:

211-2 (270 mg) and amides fragment AN-27 (100 mg, 0.53 mmol) were dissolved in N,N-dimethylformamide (5 mL), and added with N,N-diisopropylethylamine (137 mg, 1.06 mmol). After stirring for 5 min, the resultant was added with HATU (2-(7-azabenzotriazol-1-yl)-N,N,N',N'-tetramethyluronium hexafluorophosphate) (302 mg, 0.8 mmol), reacted at room temperature for 2 h. TLC detected that the reaction was complete. The reaction solution was added with water and extracted with ethyl acetate. The organic phase was washed with saturated brine, dried over anhydrous sodium sulfate, and concentrated. The crude was purified to obtain SYY—B136 (180 mg) as a white solid. LC-MS: 504.2 [M+1]$^+$; $^1$H NMR: (DMSO-d$_6$, 400 MHz): δ 0.36-0.55 (m, 4H), 1.39-1.51 (m, 1H), 1.99-2.10 (m, 2H), 2.35-2.45 (m, 1H), 2.52-2.87 (m, 5H), 2.92-3.14 (m, 3H), 3.48-3.89 (m, 1H), 4.33-4.92 (m, 4H), 6.04-6.06 (m, 1H), 7.15-7.24 (m, 3H), 7.51 (m, 1H), 8.28-8.48 (m, 2H), 8.67 (m, 1H).

Chiral resolution was performed to obtain SYY-B136-1 and SYY-B137-1: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 20.95 min for peak 1, and 31.04 min for peak 2.

Example 212 Synthesis of Compounds SYY-B136-2 and SYY-B137-2

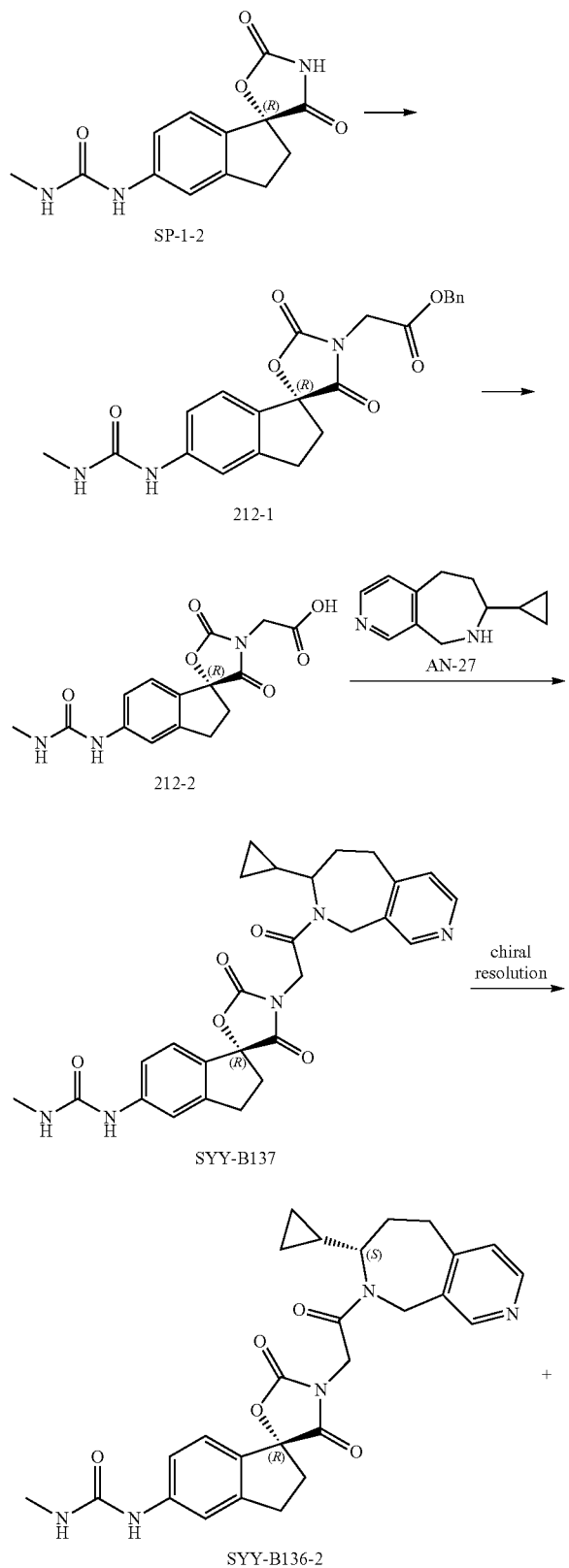

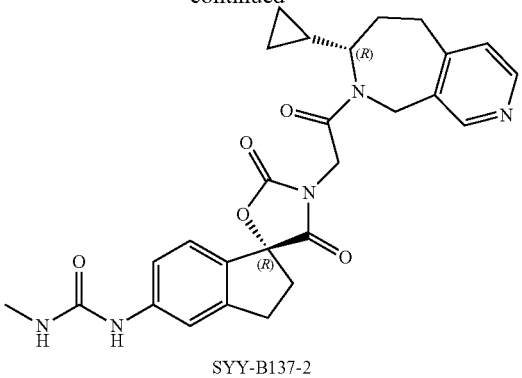

Step 1:

The spiro ring intermediate SP-1-2 (200 mg, 0.73 mmol) was dissolved in N,N-dimethylformamide (5 mL), added with potassium carbonate (201 mg, 1.46 mmol), reacted at room temperature for 0.5 h, added with benzyl bromoacetate (174 mg, 0.76 mmol), and stirred at room temperature for 2 h. TLC detected that the reaction was complete. The reaction solution was added with water and extracted with ethyl acetate. The organic phase was washed with saturated brine, dried over anhydrous sodium sulfate, and concentrated to obtain 212-1 (340 mg) as a yellow oil. The crude was directly used in the next step.

Step 2:

212-1 (340 mg) was dissolved in methanol (10 mL), and added with 10% Pd/C (100 mg). After atmosphere was replaced with hydrogen 3 times, the reaction mixture was stirred at room temperature to react overnight. TLC detected that the reaction was complete. The reaction solution was filtered through celite pad. The filtrate was concentrated to obtain 212-2 (250 mg) as a yellowish solid.

Step 3:

212-2 (250 mg) and the amide fragment AN-27 (100 mg, 0.53 mmol) were dissolved in N,N-dimethylformamide (5 mL), added with N,N-diisopropylethylamine (137 mg, 1.06 mmol), stirred for 5 min, added with HATU (2-(7-azabenzotriazol-1-yl)-N,N,N',N'-tetramethyluronium hexafluorophosphate) (302 mg, 0.8 mmol, 1.5 eq.), and reacted at room temperature for 2 h. TLC detected that the reaction was complete. The reaction solution was added with water and extracted with ethyl acetate. The organic phase was washed with saturated brine, dried over anhydrous sodium sulfate, and concentrated. The crude was purified by Pre-TLC to obtain SYY—B137 (190 mg) as a white solid. LC-MS: 504.2 [M+1]$^+$; $^1$H NMR: (DMSO-d$_6$, 400 MHz): δ 0.38-0.55 (m, 4H), 1.22-1.39 (m, 1H), 1.98-2.10 (m, 2H), 2.37-2.45 (m, 1H), 2.52-2.78 (m, 5H), 2.93-3.11 (m, 3H), 3.44-3.81 (m, 1H), 3.84-4.36 (m, 1H), 4.49-4.92 (m, 3H), 6.05-6.08 (m, 1H), 7.04-7.23 (m, 3H), 7.50-7.51 (m, 1H), 8.29-8.48 (m, 2H), 8.67-8.69 (m, 1H).

Chiral resolution was performed to obtain SYY-B136-2 and SYY-B137-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 31.74 min for peak 1, and 41.83 min for peak 2.

Example 213 Synthesis of SYY-B138

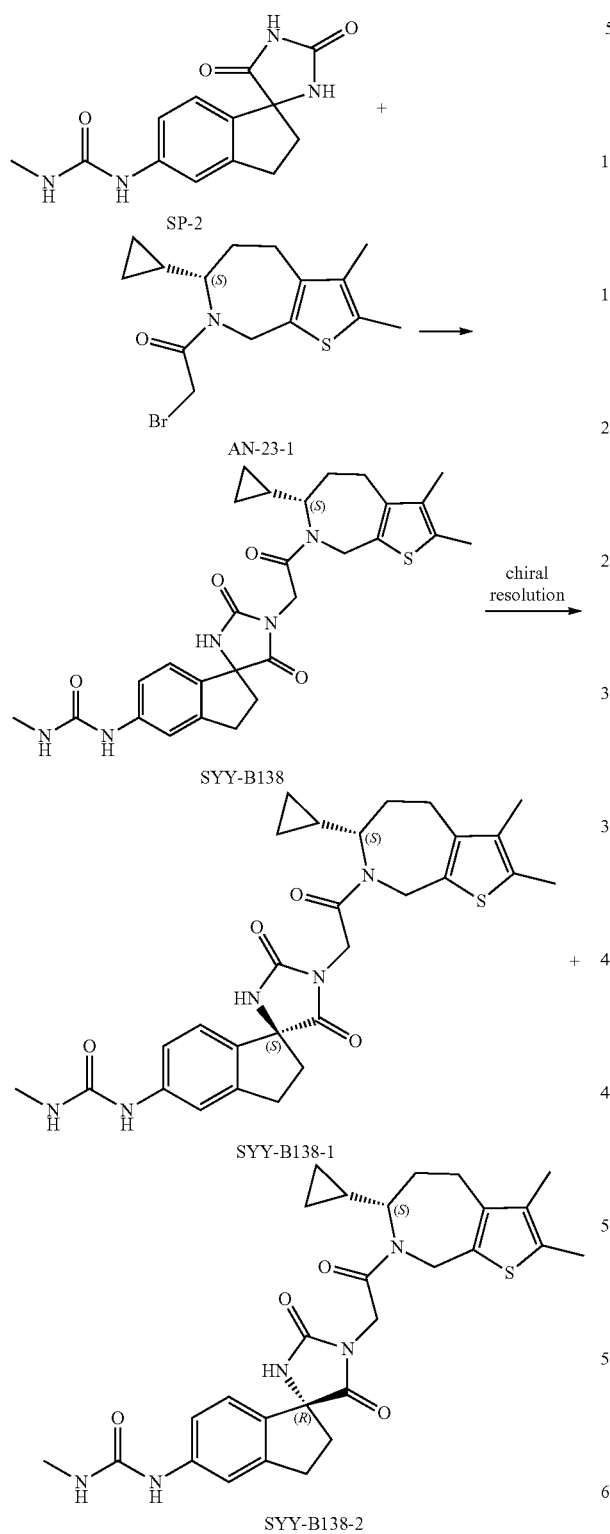

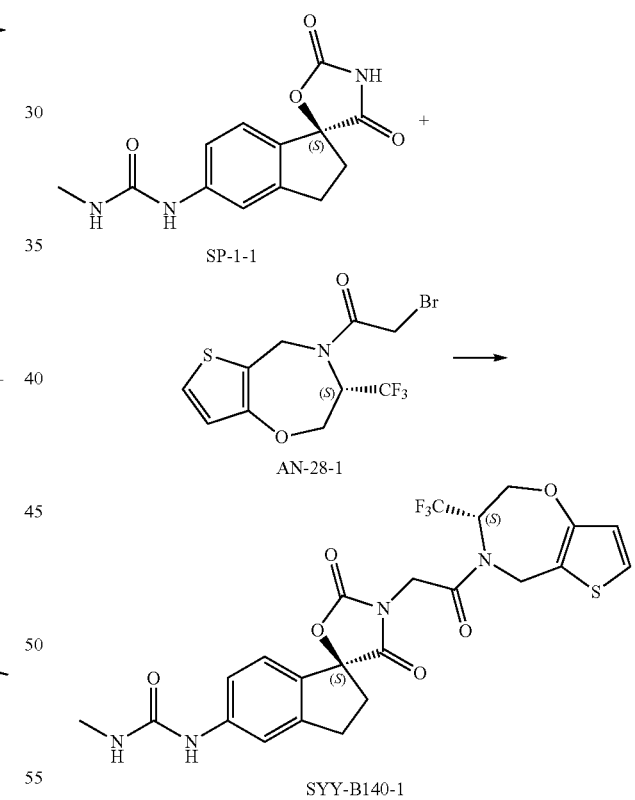

reacted at room temperature overnight. The reaction solution was poured into water and extracted with ethyl acetate. The combined organic phase was washed with water and saturated brine, dried over anhydrous sodium sulfate, and concentrated. The crude was purified by silica gel column chromatography to obtain SYY—B138 (158 mg) as a yellow solid. LC-MS: 536.2 [M+1]$^+$. $^1$H NMR: (DMSO-d$_6$, 400 MHz): δ 0.31-0.57 (m, 4H), 1.07-1.19 (m, 1H), 1.90-1.91 (m, 3H), 2.05-2.33 (m, 7H), 2.43-2.48 (m, 1H), 2.62-2.74 (m, 4H), 2.90-2.96 (m, 2H), 3.57-3.91 (m, 2H), 4.17-4.35 (m, 1H), 4.60-4.84 (m, 2H), 5.98-6.02 (m, 1H), 7.03-7.06 (m, 1H), 7.13-7.18 (m, 1H), 7.41-7.43 (m, 1H), 8.53-8.68 (m, 2H).

Chiral resolution was performed to obtain SYY-B138-1 and SYY-B138-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 8.051 min for peak 1, and 33.764 min for peak 2.

Example 214 Synthesis of SYY-B140-1

Step 1:
SP-1-1 (48 mg, 0.174 mol) was dissolved in N,N-dimethylformamide (5 mL) under nitrogen, added with potassium carbonate (36 mg, 0.260 mol), added with AN-28-1 (60 mg, 0.174 mol) under stirring at room temperature, and reacted at room temperature overnight. TLC detected that the reaction was complete. The reaction solution was added with water and extracted with ethyl acetate. The combined organic phase was washed with water and saturated brine, dried over anhydrous sodium sulfate, and concentrated. The The spiro ring intermediate SP-2 (93 mg, 0.34 mmol) and potassium carbonate (97 mg, 0.70 mmol) were dissolved in N,N-dimethylformamide (1.5 mL), stirred for 5 min, added with the amide fragment AN-23-1 (96 mg, 0.28 mmol), and crude was purified to obtain SYY-B140-1 (50 mg) as a white solid. LC-MS: 539.2 [M+1]+. 1H NMR: (DMSO-d6, 400 MHz): δ 2.43-2.44 (m, 1H), 2.48-2.52 (m, 4H), 2.93-3.11 (m, 2H), 3.97-5.23 (m, 6H), 5.63-5.73 (m, 1H), 6.08-6.09 (m, 1H), 6.67-6.71 (m, 1H), 7.20-7.33 (m, 3H), 7.52 (s, 1H), 8.72 (s, 1H).

Example 215 Synthesis of SYY-B140-2

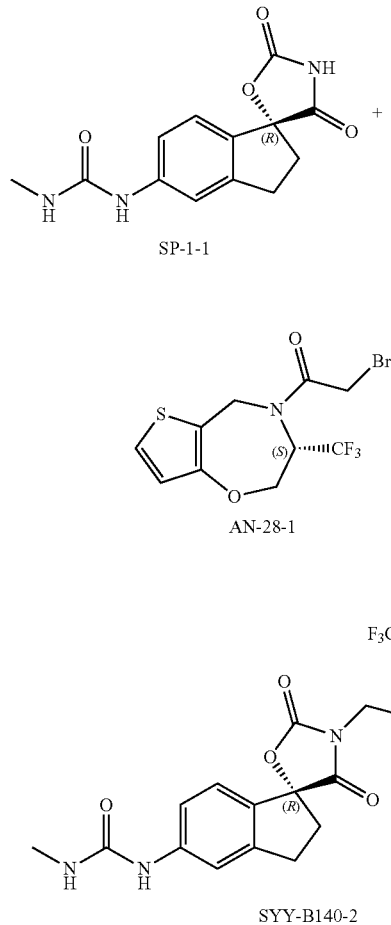

Example 216 Synthesis of SYY-B142

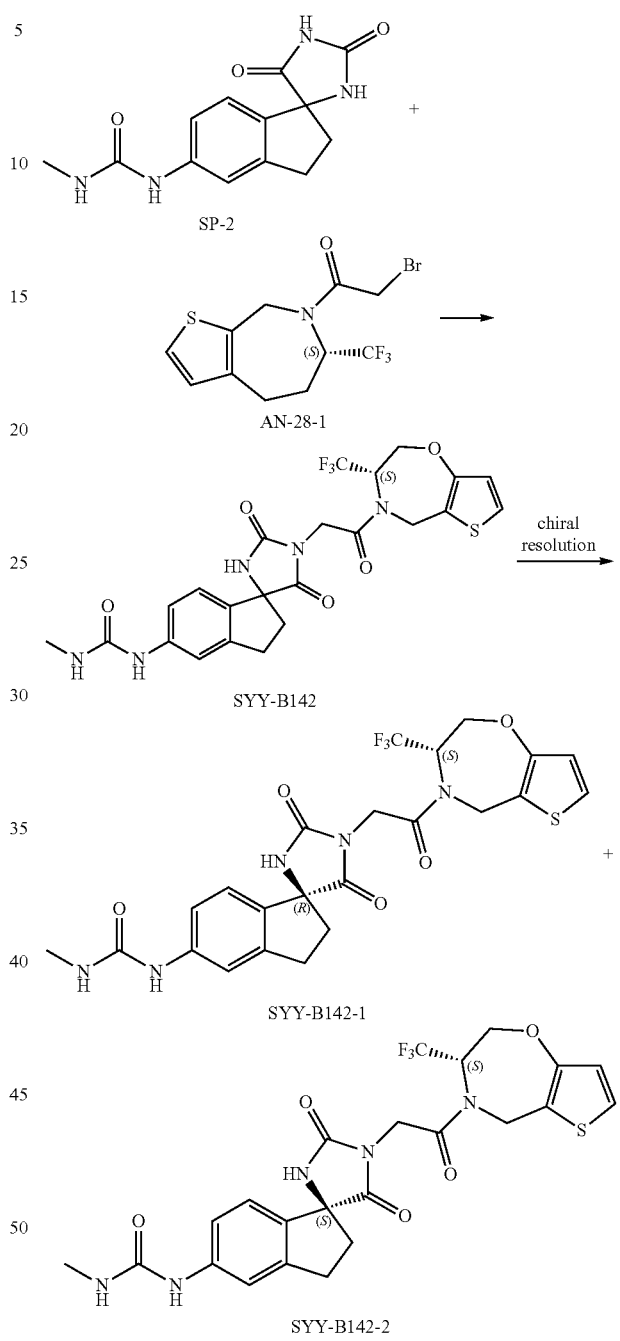

Step 1:

SP-1-2 (48 mg, 0.174 mol) was dissolved in N,N-dimethylformamide (5 mL) under nitrogen, added with potassium carbonate (36 mg, 0.260 mol), added with AN-28-1 (60 mg, 0.174 mol) under stirring at room temperature, and reacted at room temperature overnight. TLC detected that the reaction was complete. The reaction solution was added with water and extracted with ethyl acetate. The combined organic phase was washed with water and saturated brine, dried over anhydrous sodium sulfate, and concentrated. The crude was purified to obtain SYY-B140-2 (60 mg) as a white solid. LC-MS: 539.2 [M+1]+. 1H NMR: (DMSO-d6, 400 MHz): δ 2.37-2.47 (m, 1H), 2.58-2.63 (m, 4H), 2.91-3.12 (m, 2H), 3.99-5.03 (m, 6H), 5.66-5.74 (m, 1H), 6.08-6.09 (m, 1H), 6.67-6.71 (m, 1H), 7.21-7.33 (m, 3H), 7.52 (s, 1H), 8.73 (s, 1H).

The spiro ring intermediate SP-2 (123 mg, 0.448 mol) was dissolved in N,N-dimethylformamide (10 mL) under nitrogen, added with potassium carbonate (84 mg, 0.608 mol), added the with the amide fragment AN-28-1 (140 mg, 0.407 mol) under stirring at room temperature, and reacted at room temperature overnight. TLC detected that the reaction was complete. The reaction solution was added with water and extracted with ethyl acetate. The combined organic phase was washed with water and saturated brine, dried over anhydrous sodium sulfate, and concentrated. The crude was purified to obtain SYY—B142 (150 mg) as a white solid. LC-MS: 538.1 [M+1]+. 1H NMR: (DMSO-d6, 400 MHz): δ

2.10-2.19 (m, 1H), 2.44-2.50 (m, 4H), 2.90-2.94 (m, 2H), 3.88-5.18 (m, 6H), 5.61-5.66 (m, 1H), 5.98-6.01 (m, 1H), 6.67 (m, 1H), 7.03-7.31 (m, 3H), 7.41 (m, 1H), 8.54 (m, 1H), 8.72-8.76 (m, 1H).

Chiral resolution was performed to obtain SYY-B142-1 and SYY-B142-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 10.505 min for peak 1, and 48.704 min for peak 2.

Example 217 Synthesis of SYY—B144

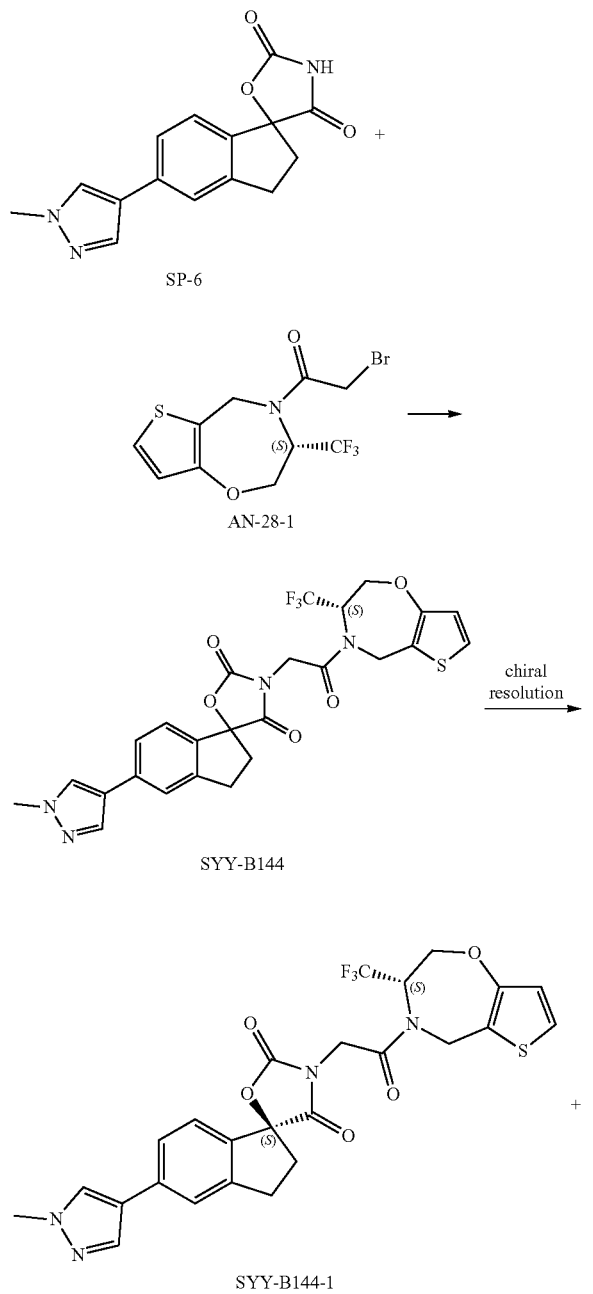

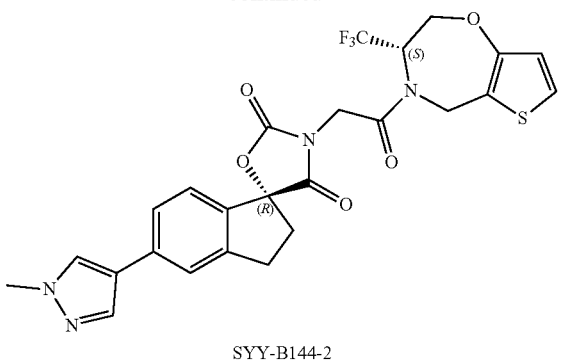

Step 1:

The spiro ring intermediate SP-6 (126 mg, 0.445 mol) was dissolved in N,N-dimethylformamide (10 mL) under nitrogen, added with potassium carbonate (84 mg, 0.608 mmol), added with AN-28-1 (140 mg, 0.407 mol) under stirring at room temperature, and reacted at room temperature overnight. TLC detected that the reaction was complete. The reaction solution was added with water and extracted with ethyl acetate. The combined organic phase was washed with water and saturated brine, dried over anhydrous sodium sulfate, and concentrated. The crude was purified to obtain SYY—B144 (200 mg) as a white solid. LC-MS: 547.1 $(M+1)^+$. LC-MS: 547.1 $(M+1)^+$. $^1$H NMR: (DMSO-$d_6$, 400 MHz): δ 2.48-2.64 (m, 2H), 3.03-3.16 (m, 2H), 3.85 (s, 3H), 4.01-5.23 (m, 6H), 5.69 (br, 1H), 6.69 (m, 1H), 7.26-7.58 (m, 4H), 7.89 (s, 1H), 8.16 (s, 1H).

Chiral resolution was performed to obtain SYY-B144-1 and SYY-B144-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 42.326 min for peak 1, and 52.483 min for peak 2.

Example 218 Synthesis of SYY—B146

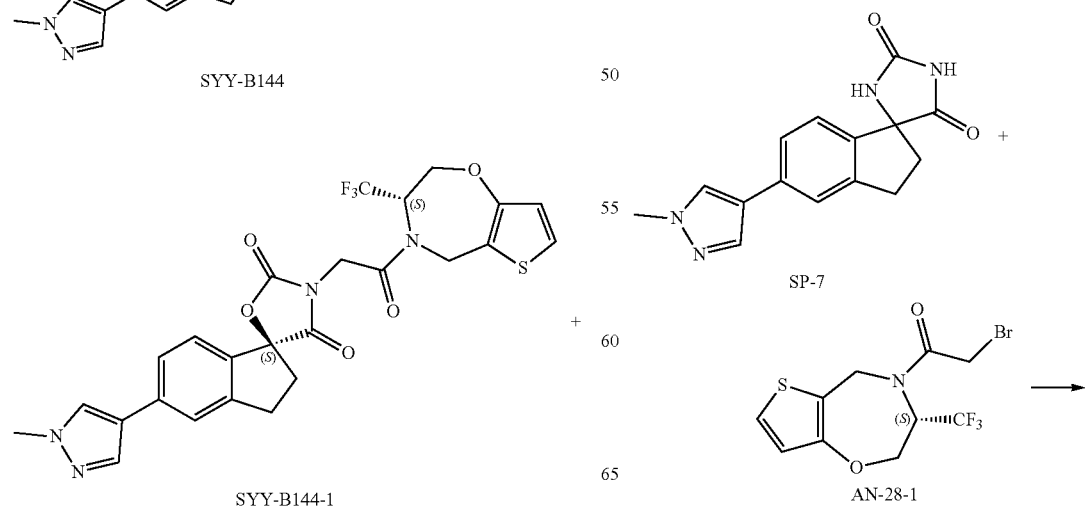

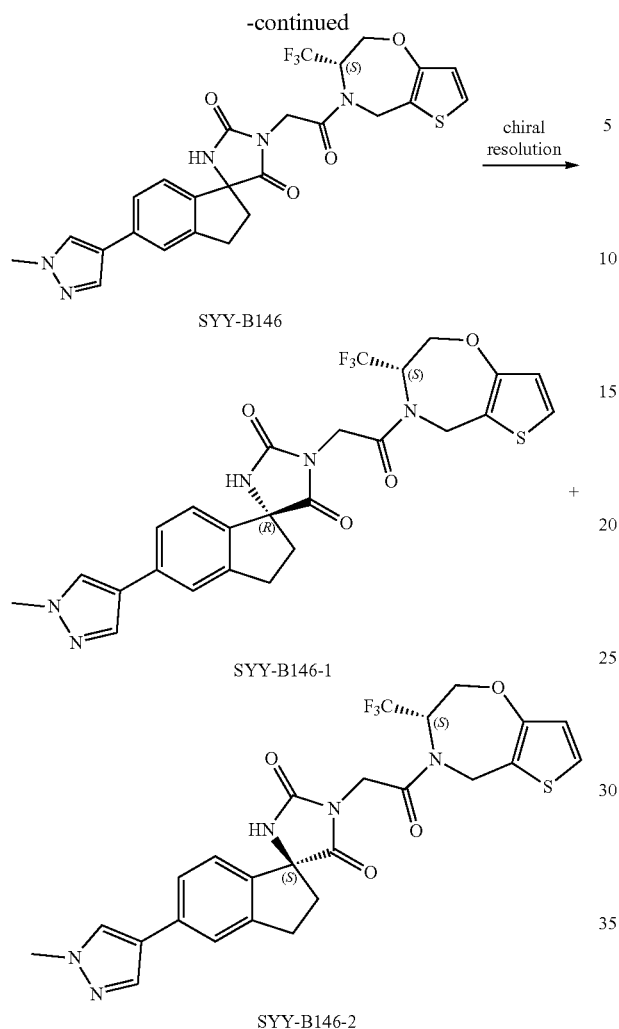

SYY-B146

SYY-B146-1

SYY-B146-2

The spiro ring intermediate SP-7 (126 mg, 0.446 mmol) was dissolved in N,N-dimethylformamide (10 mL) under nitrogen, added with potassium carbonate (84 mg, 0.608 mmol), added with the amide fragment AN-28-1 (140 mg, 0.407 mmol) under stirring at room temperature, reacted at room temperature overnight. TLC detected that the reaction was complete. The reaction solution was added with water and extracted with ethyl acetate. The combined organic phase was washed with water and saturated brine, dried over anhydrous sodium sulfate, and concentrated. The crude was purified to obtain SYY—B146 (150 mg) as a white solid. LC-MS: 546.1 (M+1)$^+$. $^1$H NMR: (DMSO-d$_6$, 400 MHz): δ 2.13-2.24 (m, 1H), 2.51-2.58 (m, 1H), 3.00 (m, 2H), 3.84-3.92 (m, 4H), 4.47-5.18 (m, 5H), 5.63 (br, 1H), 6.67 (m, 1H), 7.20-7.31 (m, 2H), 7.43-7.49 (m, 2H), 7.84 (m, 1H), 8.12 (m, 1H), 8.81-8.84 (m, 1H).

Chiral resolution was performed to obtain SYY-B146-1 and SYY-B146-2: Preparative column was Daicel AD-H, filler particle size (5 μm), inner diameter (30 mm), length (250 mm), flow rate: 30 mL/min, mobile phase: 50% n-hexane+50% ethanol, isogradient elution, wavelength 254 nm, peak time is 33.8 min for peak 1, and 40.4 min for peak 2.

Example 219 Synthesis of SYY-B148-1 and SYY-B148-2

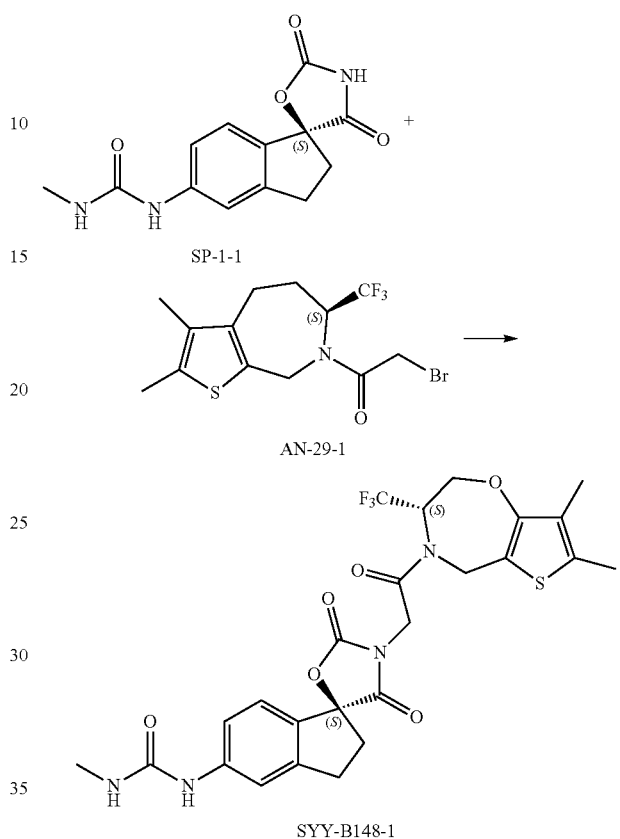

SP-1-1

AN-29-1

SYY-B148-1

The spiro ring intermediate SP-1-1 (50 mg, 0.182 mmol) and potassium carbonate (37 mg, 0.268 mmol) were dissolved in N,N-dimethylformamide (3 mL), stirred for 0.5 h, then added with the amide fragment AN-29-1 (82 mg, 0.220 mmol), and reacted at room temperature overnight. The reaction solution was added with water and extracted with ethyl acetate. The combined organic phase was washed with water and saturated brine, dried over anhydrous sodium sulfate, and concentrated. The crude was purified by silica gel column chromatography to obtain SYY-B148-1 (50 mg) as a white solid. LC-MS: 567.2 [M+1]$^+$. $^1$H NMR: (DMSO-d$_6$, 400 MHz): δ 1.86 (s, 3H), 2.17-2.21 (m, 3H), 2.43-2.46 (m, 1H), 2.56-2.62 (m, 4H), 2.92-3.11 (m, 2H), 3.97-5.10 (m, 6H), 5.61-5.73 (m, 1H), 6.01-6.09 (m, 1H), 7.19-7.25 (m, 2H), 7.53 (s, 1H), 8.70 (s, 1H).

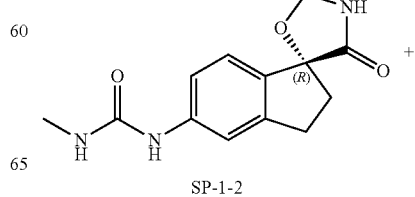

SP-1-2

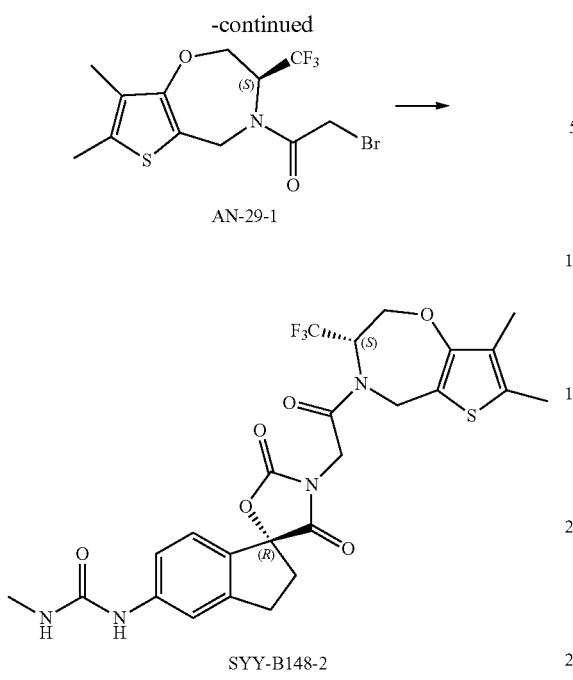

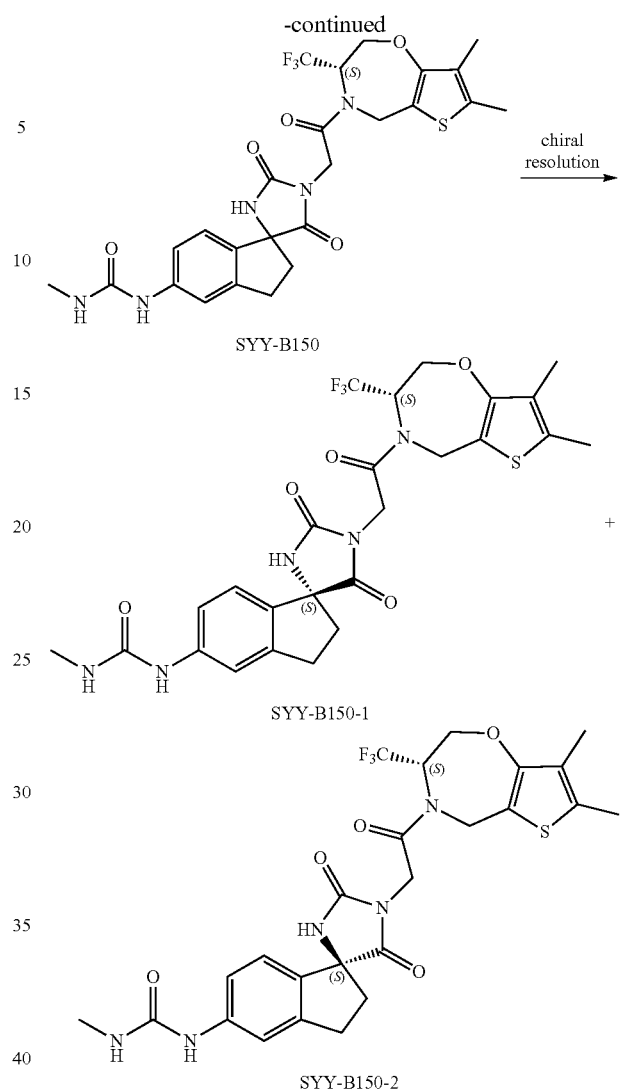

The spiro ring intermediate SP-1-2 (50 mg, 0.182 mmol) and potassium carbonate (37 mg, 0.268 mmol) were dissolved in N,N-dimethylformamide (3 mL), stirred for 0.5 h, then added with the amide fragment AN-29-1 (82 mg, 0.220 mmol), and reacted at room temperature overnight. The reaction solution was added with water and extracted with ethyl acetate. The combined organic phase was washed with water and saturated brine, dried over anhydrous sodium sulfate, and concentrated. The crude was purified by silica gel column chromatography to obtain SYY-B148-2 (65 mg) as a white solid. LC-MS: 567.2 [M+1]$^+$. $^1$H NMR: (DMSO-d$_6$, 400 MHz): δ 1.85-1.87 (m, 3H), 2.18-2.21 (m, 3H), 2.43-2.46 (m, 1H), 2.56-2.62 (m, 4H), 2.91-3.12 (m, 2H), 4.00-5.10 (m, 6H), 5.62-5.74 (m, 1H), 6.04-6.08 (m, 1H), 7.19-7.26 (m, 2H), 7.53 (s, 1H), 8.70 (s, 1H).

Example 220 Synthesis of SYY-B150

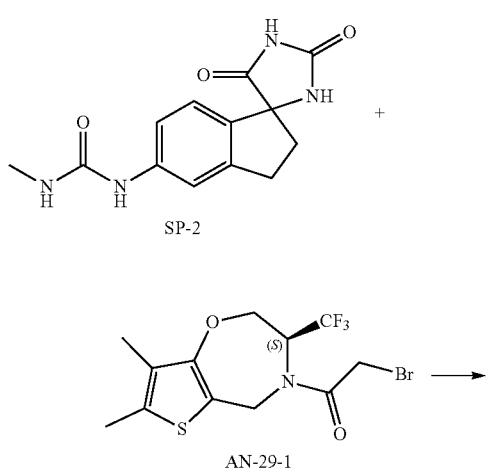

The spiro ring intermediate SP-2 (100 mg, 0.364 mmol) and potassium carbonate (124 mg, 0.897 mmol) were dissolved in N,N-dimethylformamide (5 mL), stirred for 0.5 h at room temperature, then added with AN-29-1 (147 mg, 0.395 mmol), and stirred at room temperature for 2 h. TLC showed that the reaction was complete. The reaction solution was added with water and extracted with ethyl acetate. The combined organic phase was washed with water and saturated brine, dried over anhydrous sodium sulfate, and concentrated. The crude was purified by silica gel column chromatography to obtain SYY—B150 (156 mg) as a yellowish solid. LC-MS 564.2 [M−1]$^−$; $^1$H NMR: (DMSO-d$_6$, 400 MHz): δ 1.84-1.86 (m, 3H), 2.10-2.21 (m, 4H), 2.44-2.48 (m, 1H), 2.61 (d, J=4.4 Hz, 3H), 2.87-2.97 (m, 2H), 3.87-5.05 (m, 6H), 5.58-5.64 (m, 1H), 5.96-6.02 (m, 1H), 7.03-7.17 (m, 2H), 7.42 (s, 1H), 8.54 (s, 1H), 8.74-8.77 (m, 1H).

Chiral resolution was performed to obtain SYY-B150-1 and SYY-B150-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 7.624 min for peak 1, and 29.843 min for peak 2.

Example 221 Synthesis of SYY-B152

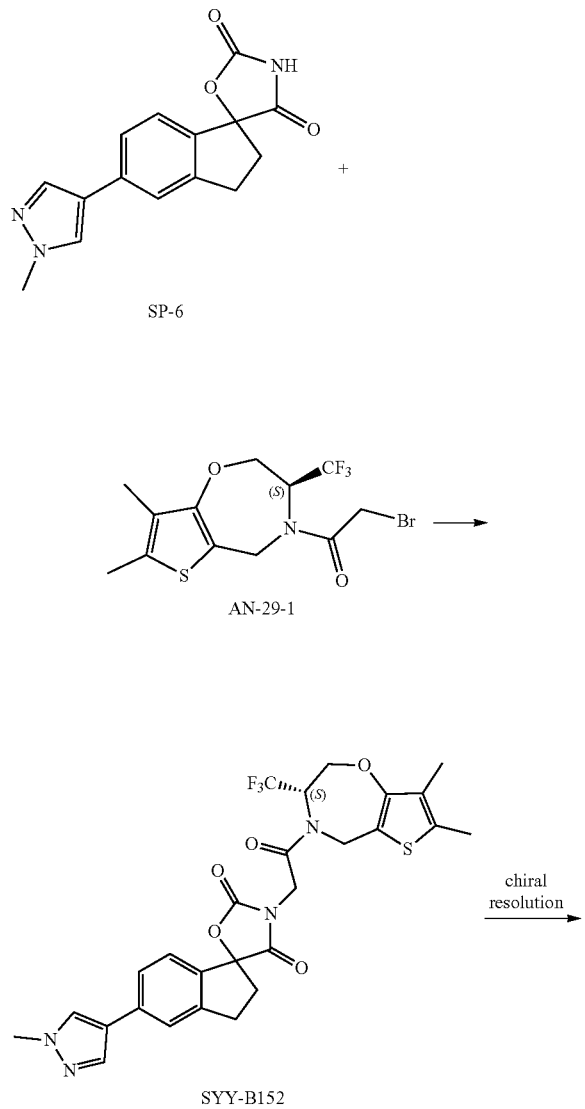

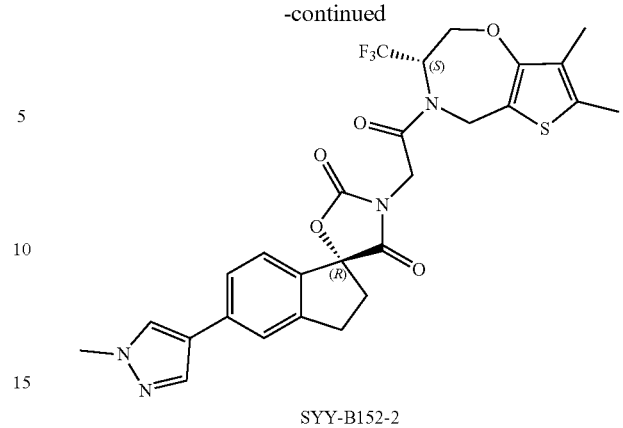

The spiro ring intermediate SP-6 (117 mg, 0.413 mol) was dissolved in N,N-dimethylformamide (10 mL) under nitrogen, added with potassium carbonate (78 mg, 0.564 mol), added with the amide fragment AN-29-1 (140 mg, 0.376 mol) under stirring at room temperature, and reacted at room temperature overnight. TLC detected that the reaction was complete. The reaction solution was added with water and extracted with ethyl acetate. The combined organic phase was washed with water and saturated brine, dried over anhydrous sodium sulfate, and concentrated. The crude was purified to obtain SYY—B152 (220 mg) as a white solid. LC-MS: 575.2 (M+1)$^+$. $^1$H-NMR: (DMSO-d$_6$, 400 MHz): δ 1.85-1.87 (m, 3H), 2.19-2.21 (m, 3H), 2.51-2.68 (m, 2H), 2.99-3.20 (m, 2H), 3.85 (s, 3H), 4.01-5.10 (m, 6H), 5.60-5.75 (m, 1H), 7.40-7.42 (m, 1H), 7.51-7.58 (m, 2H), 7.88-7.89 (m, 1H), 8.16-8.17 (m, 1H).

Chiral resolution was performed to obtain SYY-B152-1 and SYY-B152-2: Preparative column was Daicel AD-H, filler particle size (5 μm), inner diameter (30 mm), length (250 mm), flow rate: 30 m/min, mobile phase: 60% n-hexane+40% isopropanol, isogradient elution, wavelength 254 nm, peak time is 28.659 min for peak 1, and 35.103 min for peak 2.

Example 222 Synthesis of SYY-B154

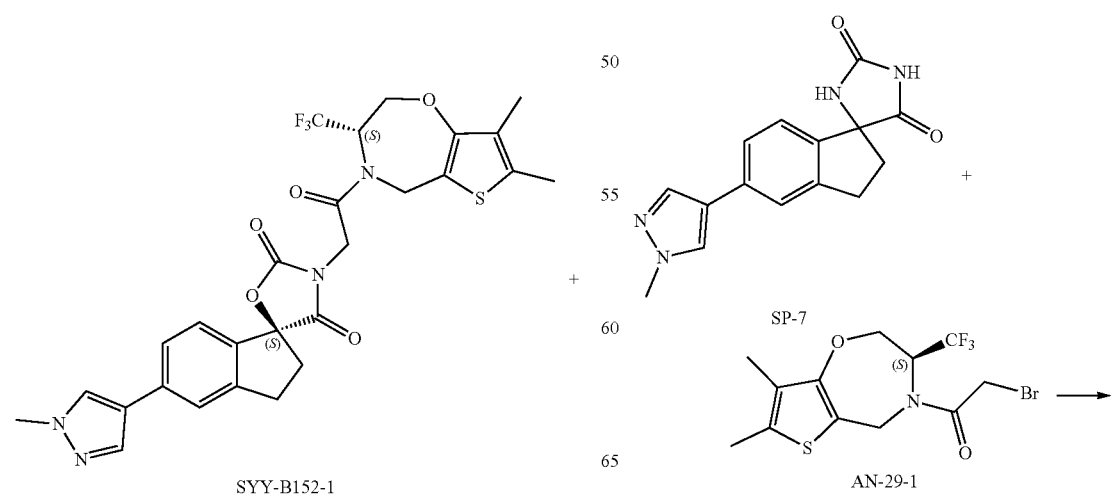

Example 223 Synthesis of SYY—B155

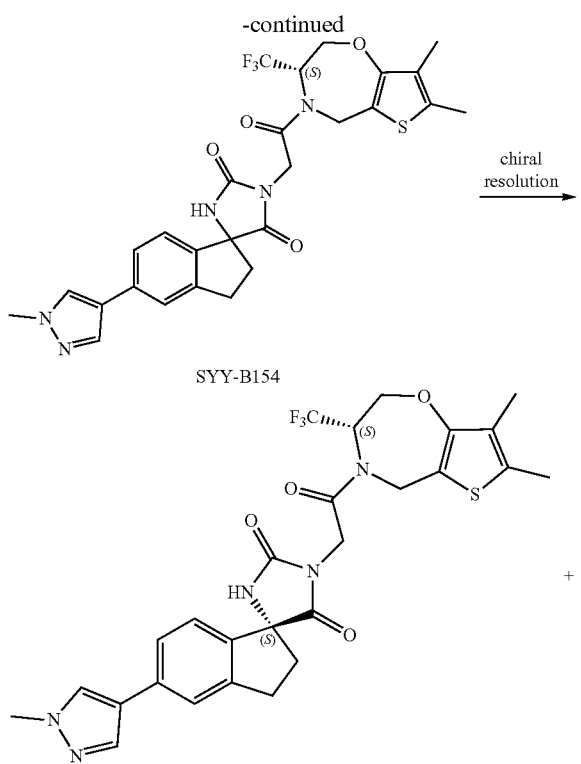

SYY-B154

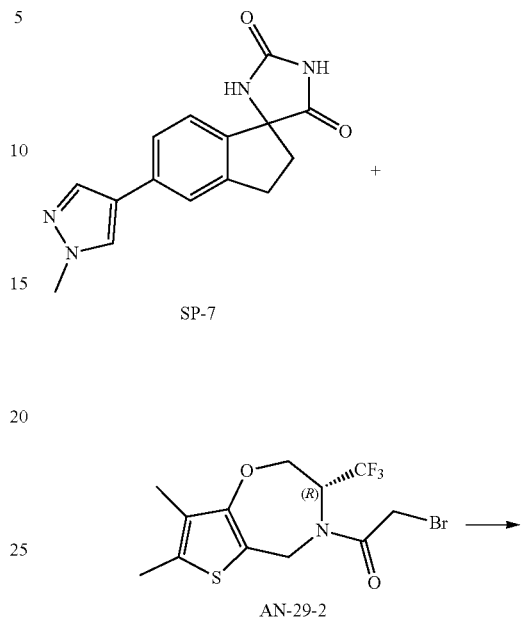

SP-7

SYY-B154-1

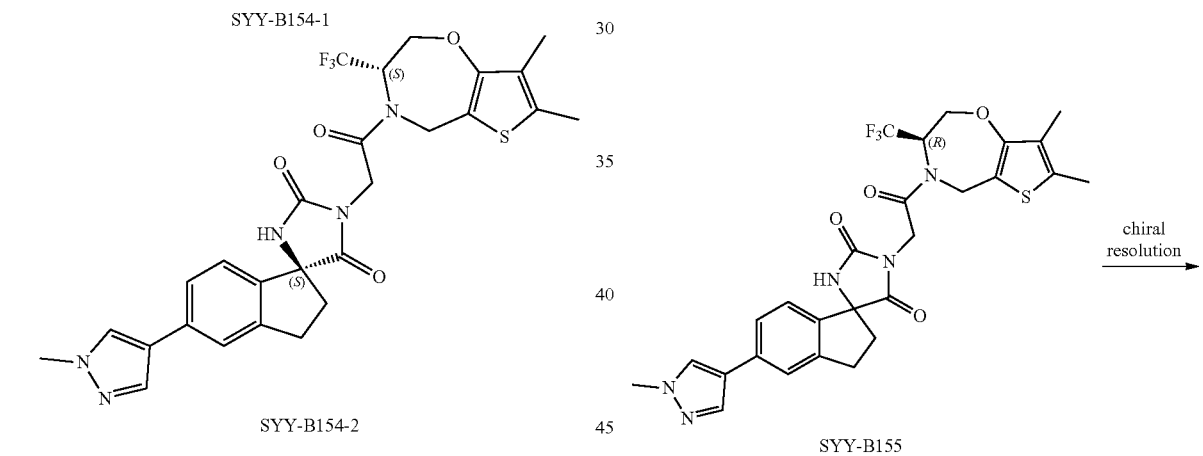

SYY-B154-2

SYY-B155

The spiro ring intermediate SP-7 (117 mg, 0.414 mol) was dissolved in N,N-dimethylformamide (10 mL) under nitrogen, added with potassium carbonate (78 mg, 0.564 mol), added with AN-29-1 (140 mg, 0.377 mol) under stirring at room temperature, and reacted at room temperature overnight. TLC detected that the reaction was complete. The reaction solution was added with water and extracted with ethyl acetate. The combined organic phase was washed with water and saturated brine, dried over anhydrous sodium sulfate, and concentrated. The crude was purified to obtain SYY—B154 (150 mg) as a yellowish solid. LC-MS: 574.2 (M+1)$^+$.

Chiral resolution was performed to obtain SYY-B154-1 and SYY-B154-2: Preparative column was Daicel AD-H, filler particle size (5 μm), inner diameter (30 mm), length (250 mm), flow rate: 30 mL/min, mobile phase: 60% n-hexane+40% isopropanol, isogradient elution, wavelength 254 nm, peak time is 11.173 min for peak 1, and 18.061 min for peak 2.

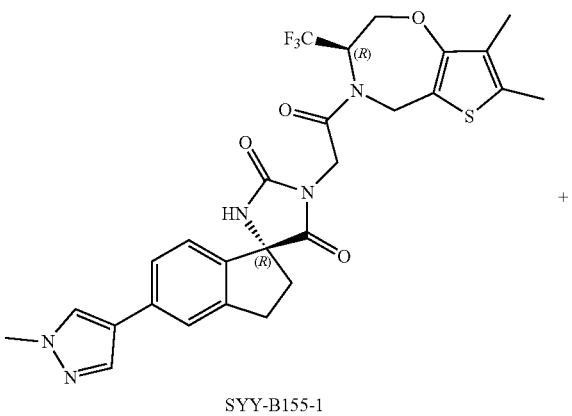

SYY-B155-1

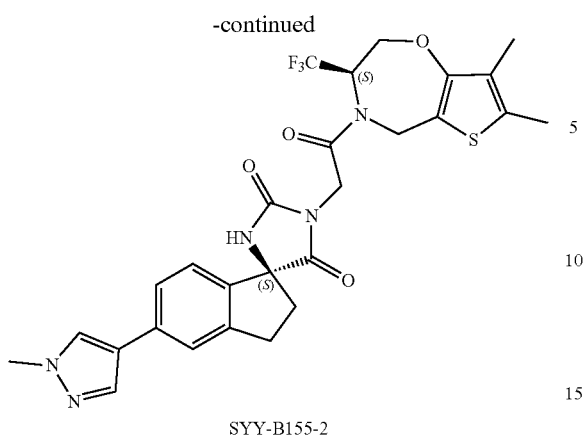

SYY-B155-2

The spiro ring intermediate SP-7 (120 mg, 0.425 mmol) was dissolved in N,N-dimethylformamide (10 mL) under nitrogen, added with potassium carbonate (75 mg, 0.543 mmol), added with AN-29-2 (134 mg, 0.361 mmol) under stirring at room temperature, and reacted at room temperature overnight. TLC detected that the reaction was complete. The reaction solution was added with water and extracted with ethyl acetate. The combined organic phase was washed with water saturated brine, dried over anhydrous sodium sulfate, and concentrated. The crude was purified to obtain SYY—B155 (180 mg) as a yellowish solid. LC-MS: 574.2 $(M+1)^+$.

Chiral resolution was performed to obtain SYY-B155-1 and SYY-B155-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 25.5 min for peak 1, and 46.6 min for peak 2.

Example 224 Synthesis of SYY-B156

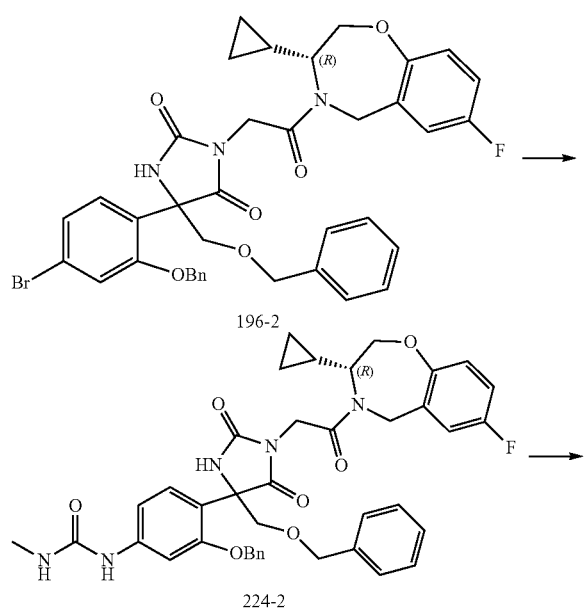

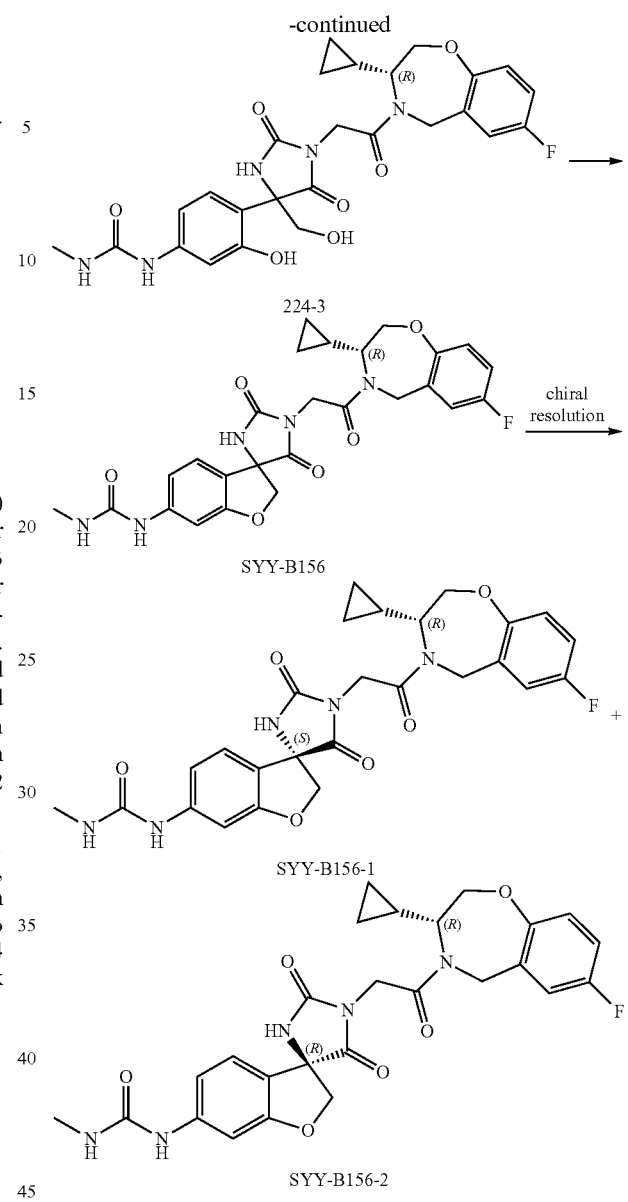

Step One:

The intermediate 196-2 (1.0 g, 1.37 mmol), methylurea (210 mg, 2.83 mmol) and cesium carbonate (1.12 g, 3.44 mmol) were dissolved in dioxane (15 mL), added with $Pd_2(dba)_3$ (73 mg, 0.08 mmol) and XanPhos (46 mg, 0.08 mmol) at room temperature, heated to 100° C. and stirred for 3 h under nitrogen. TLC showed that the reaction was complete. The reaction solution was cooled to room temperature, added with water and extracted with ethyl acetate. The combined organic phase was washed with water and saturated brine, dried over anhydrous sodium sulfate, and concentrated. The crude was purified by silica gel column chromatography to obtain 224-2 (460 mg) as a white solid.

Step Two:

224-2 (460 mg, 0.64 mmol) was dissolved in methanol, added with Pd/C (40 mg), and reacted at room temperature for 3 h under hydrogen. TLC detected that the reaction was complete. The reaction solution was filtered through celite pad. The filtrate was concentrated to obtain 224-3 (270 mg).

Step Three:

224-3 (270 mg) and triphenylphosphine (261 mg, 1.00 mmol) were dissolved in tetrahydrofuran (10 mL), added with DIAD (201 mg, 1.00 mmol), and reacted at room temperature overnight under nitrogen. TLC showed that the reaction was complete. The reaction solution was added with water and extracted with ethyl acetate. The combined organic phase was washed with water and saturated brine, dried over anhydrous sodium sulfate, and concentrated. The crude was purified by silica gel column chromatography to obtain SYY—B156 (210 mg) as a white solid. LC-MS: 524.2 [M+1]$^+$. $^1$H NMR: (DMSO-d$_6$, 400 MHz): δ 0.32-0.57 (m, 4H), 1.10-1.12 (m, 1H), 2.60-2.61 (m, 3H), 3.70-3.79 (m, 1H), 3.99-4.23 (m, 2H), 4.32-4.76 (m, 5H), 4.89-5.01 (m, 1H), 6.00-6.04 (m, 1H), 6.73-7.22 (m, 6H), 8.65-8.67 (m, 1H), 9.00-9.02 (m, 1H).

Chiral resolution was performed to obtain SYY-B156-1 and SYY-B156-2: Preparative column was Daicel AD-H, filler particle size (5 μm), inner diameter (30 mm), length (250 mm), flow rate: 30 mL/min, mobile phase: 60% n-hexane+40% ethanol, isogradient elution, wavelength 254 nm, peak time is 11.518 min for peak 1, and 20.135 min for peak 2.

Example 225 Synthesis of SYY—B161

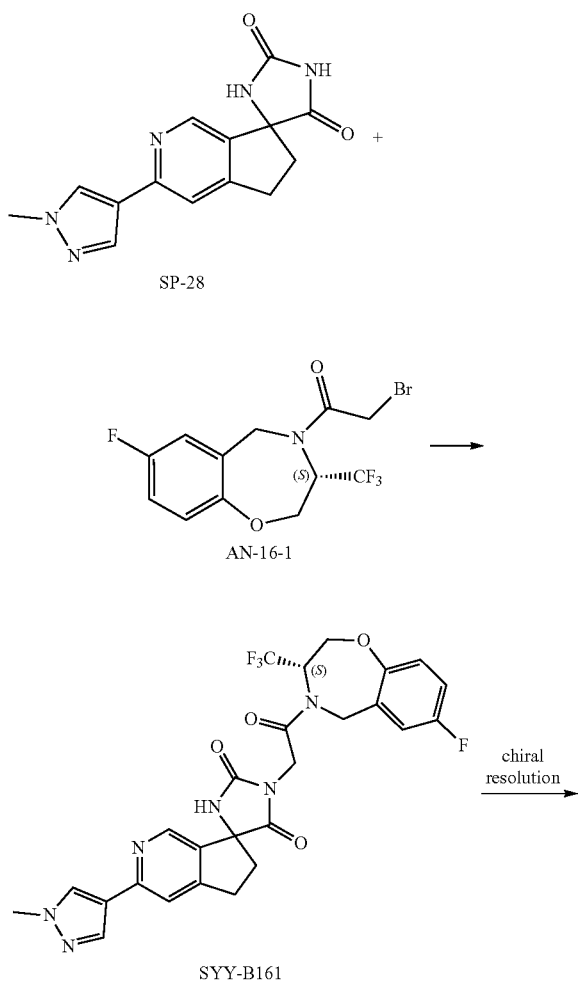

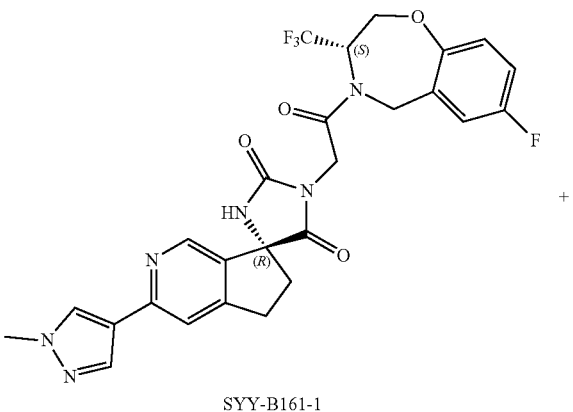

The spiro ring intermediate SP-28 (175 mg, 0.62 mmol) was dissolved in N,N-dimethylformamide (10 mL), added with the amide fragment AN-16-1 (200 mg, 0.56 mmol) and potassium carbonate (117 mg, 0.85 mmol), and reacted at room temperature overnight. TLC detected that the raw material was completely reacted. The reaction solution was added with water and extracted with ethyl acetate. The combined organic phase was washed with saturated brine, dried over anhydrous sodium sulfate, and concentrated. The crude was purified to obtain SYY—B161 (260 mg) as a white solid. LC-MS: 559.2 (M+1)$^+$. $^1$H NMR: (DMSO-d$_6$, 400 MHz): δ 2.18-2.24 (m, 1H), 2.51-2.54 (m, 1H), 3.01-3.02 (m, 2H), 3.80-4.23 (m, 4H), 4.48-5.10 (m, 5H), 5.53 (m, 1H), 6.94-7.22 (m, 3H), 7.61 (m, 1H), 7.98 (m, 1H), 8.26 (m, 1H), 8.36 (m, 1H), 8.92-8.94 (m, 1H).

Chiral resolution was performed to obtain SYY-B161-1 and SYY-B161-2: Preparative column was NANOMICRO OD-5H, filler particle size (5 μm), inner diameter (30 mm), length (250 mm), flow rate: 30 mL/min, mobile phase: 60% n-hexane+40% ethanol, isogradient elution, wavelength 254 nm, peak time is 14.263 min for peak 1, and 33.038 min for peak 2.

Example 226 Synthesis of SYY-B163

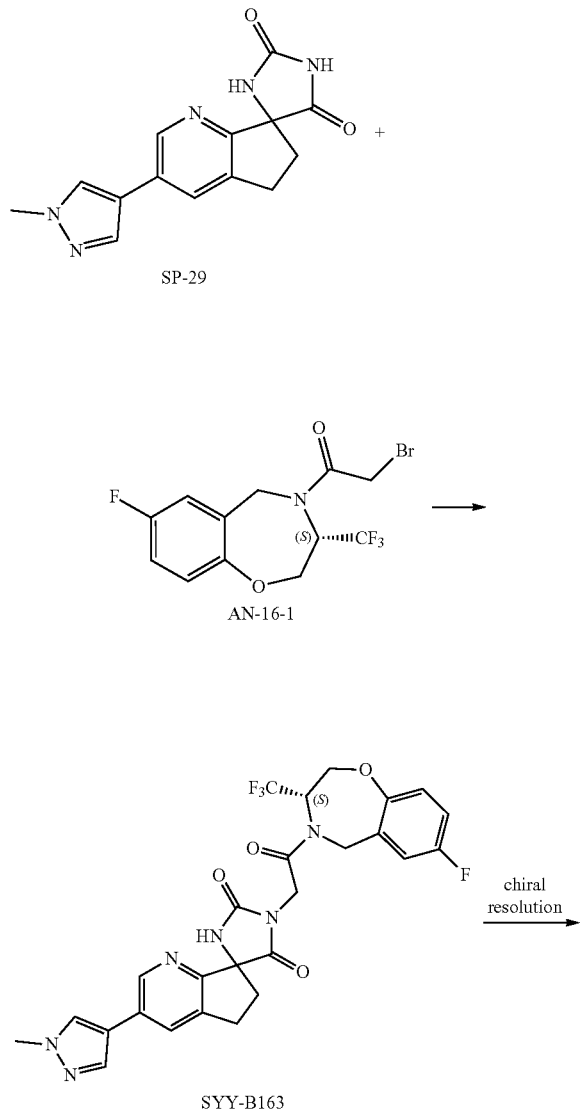

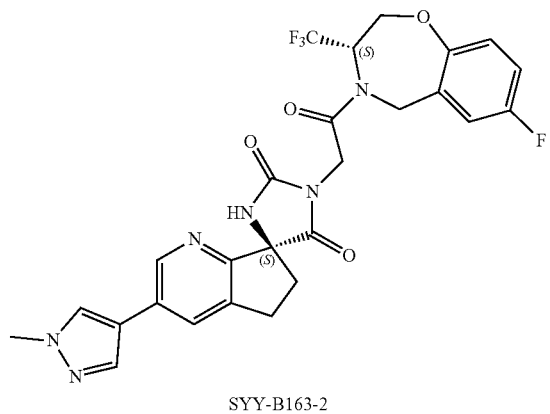

The spiro ring intermediate SP-29 (150 mg, 0.53 mmol) and potassium carbonate (100 mg, 0.72 mmol) were dissolved in N,N-dimethylformamide (4 mL), stirred for 20 min, added with the amide fragment AN-16-1 (171 mg, 0.48 mmol), and reacted at room temperature for 3 h. TLC detected that the raw material was completely reacted. The reaction solution was poured into water to precipitate a solid, which was filtered. The filter cake was washed with water, and dried to obtain 270 mg of SYY—B163 as a white solid. LC-MS: 559.2 (M+1)$^+$. $^1$H NMR: (DMSO-d$_6$, 400 MHz): δ 2.18-2.25 (m, 1H), 2.54-2.65 (m, 1H), 2.97-3.03 (m, 2H), 3.78-4.20 (m, 4H), 4.47-5.06 (m, 5H), 5.43-5.55 (m, 1H), 6.94-7.24 (m, 3H), 7.92 (m, 2H), 8.24 (m, 1H), 8.62 (m, 1H), 8.79 (m, 1H).

Chiral resolution was performed to obtain SYY-B163-1 and SYY-B163-2: Preparative column was NANOMICRO OD-5H, filler particle size (5 μm), inner diameter (30 mm), length (250 mm), flow rate: 30 mL/min, mobile phase: 60% n-hexane+40% ethanol, isogradient elution, wavelength 254 nm, peak time is 16.179 min for peak 1, and 26.537 min for peak 2.

Example 227 Synthesis of SYY-B165

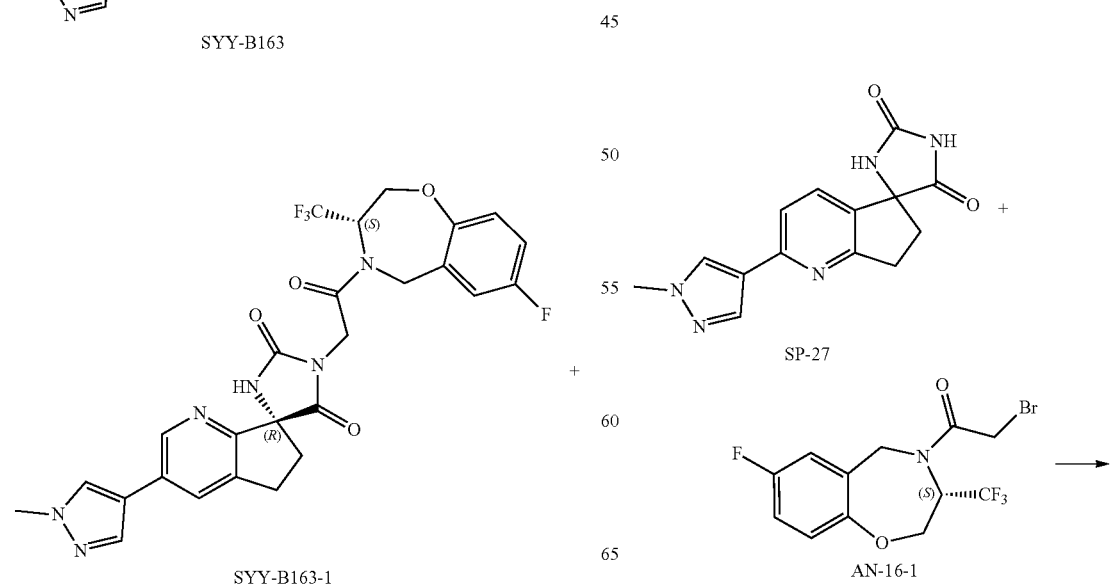

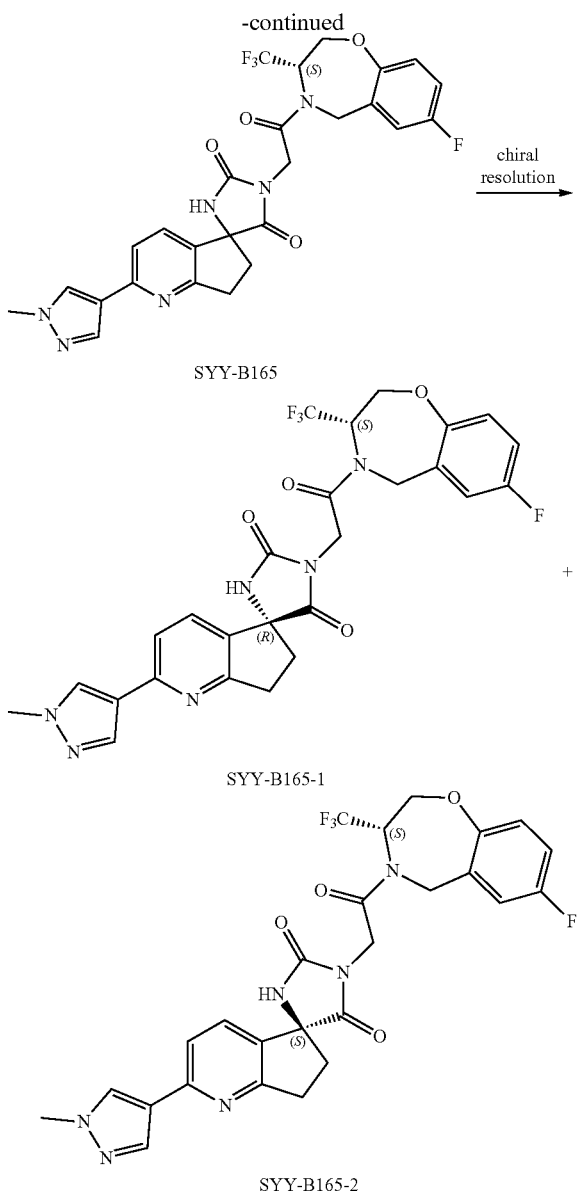

SYY-B165

SYY-B165-1

SYY-B165-2

The spiro ring intermediate SP-27 (165 mg, 0.58 mmol) and potassium carbonate (111 mg, 0.80 mmol) were dissolved in N,N-dimethylformamide (4 mL), stirred for 20 min, added with the amide fragment AN-16-1 (186 mg, 0.52 mmol), and reacted at room temperature overnight. TLC detected that the raw material was completely reacted. The reaction solution was poured into water and extracted with ethyl acetate. The combined organic phase was washed with saturated brine, dried over anhydrous sodium sulfate, and concentrated. The crude was purified by silica gel column chromatography to obtain SYY—B165 (270 mg) as a yellowish solid. LC-MS: 559.2 (M+1)$^+$. $^1$H NMR: (DMSO-d$_6$, 400 MHz): δ 2.19-2.22 (m, 1H), 2.53-2.55 (m, 1H), 3.02-3.05 (m, 2H), 3.78-4.22 (m, 4H), 4.48-5.08 (m, 5H), 5.48-5.57 (m, 1H), 6.92-7.21 (m, 3H), 7.52-7.60 (m, 2H), 7.97-7.98 (m, 1H), 8.28-8.29 (m, 1H), 8.88-8.90 (m, 1H).

Chiral resolution was performed to obtain SYY-B165-1 and SYY-B165-2: Preparative column: NANOMICRO OD-5H, filler particle size (5 μm), inner diameter (30 mm), length (250 mm), flow rate: 30 mL/min, mobile phase: 60% n-hexane+40% ethanol, isogradient elution, wavelength 254 nm, peak time is 14.691 min for peak 1, and 26.624 min for peak 2.

Example 228

Histone Acetyltransferase (p300) Activity Assay

The effect of small molecule compounds in different concentrations on the activity of histone acetyltransferase p300 was detected by radioisotope experimental technology, and IC$_{50}$ (50% of the highest inhibitory concentration) of the compound was calculated by fitting with GraphPad Prism 5.0 software. P300 enzyme (commercially available from BPS Corporation, Cat. No. 50071) catalyzed the reaction of a cofactor, [$^3$H] labeled acetyl coenzyme A ([$^3$H]—Ac-CoA) (available from PerkinElmer Corporation, Cat. No. NET290) and a histone substrate peptide, which has a sequence of ARTKQTARKSTGGKAPRKQLA-GG-K(Biotin)-NH$_2$, to transfer the isotope [$^3$H]-labeled acetyl on the cofactor [$^3$H]—Ac-CoA to the histone lysine substrate. The reaction was finally terminated with Ac-CoA (Sigma, Cat. No. A2056) without isotope labeling. If the activity of the acetyltransferase p300 was inhibited, the isotope signal cannot be detected on the substrate polypeptide. Therefore, the inhibitory activity of the compound against the acetyltransferase p300 was evaluated.

In the enzyme reaction system, 200 nL of a diluted compound (100% DMSO) was first transferred to a test plate using Echo, where the final concentration of the compound in the enzyme reaction system ranges from 0.25 to 5000 nM. Then 10 μL/well of p300 protein (final concentration of 0.05 nM) was transferred therein, and incubated with the compound for 15 min at room temperature. Then 10 μL/well of a substrate mixture (final concentrations of histone peptide and [$^3$H]—Ac-CoA were 600 nM and 250 nM, respectively) was added to start the enzyme-catalyzed reaction, and incubated at room temperature for 60 min. Then 10 L/well of a 250 μM cold Ac-CoA solution was added to stop the reaction. Finally 25 μL/well of the reaction solution was transferred to a 384-well Flashplate (Perkin Elmer, Cat. No. SMP410A001PK), and incubated at room temperature for 1 h. The resultant was washed with double distilled water+ 0.1% Tween-20 three times. The signal value was read by using Microbeta. The data was analyzed by using GraphPad Prism 5.0 software to obtain IC$_{50}$.

The positive control drug was A-485 developed by Abbvie Pharmaceuticals Corporation (Reference: Abbvie Inc., WO2016044770; Nature, 2017; ACS Med. Chem. Lett., 2018, 9, 28-33).

| Compound | Inhibition rate |
|---|---|
| A-485 | IC$_{50}$ = 21 nM |
| SYY-B014-2 | IC$_{50}$ = 12 nM |
| SYY-B015-1 | IC$_{50}$ = 12 nM |
| SYY-B015-2 | IC$_{50}$ = 3.7 nM |
| SYY-B017-1 | IC$_{50}$ = 640 nM |
| SYY-B017-2 | IC$_{50}$ = 270 nM |
| SYY-B018-1 | IC$_{50}$ = 3.3 nM |
| SYY-B018-2 | IC$_{50}$ = 0.67 nM |
| SYY-B019-1 | IC$_{50}$ = 2.7 nM |
| SYY-B019-2 | IC$_{50}$ = 2.0 nM |
| SYY-B020-1 | IC$_{50}$ = 200 nM |
| SYY-B020-2 | IC$_{50}$ = 45 nM |
| SYY-B021-1 | IC$_{50}$ = 3 nM |
| SYY-B021-2 | IC$_{50}$ = 3 nM |
| SYY-B022-1 | IC$_{50}$ = 54 nM |

-continued

| Compound | Inhibition rate |
|---|---|
| SYY-B022-2 | $IC_{50}$ = 12 nM |
| SYY-B023-1 | $IC_{50}$ = 4 nM |
| SYY-B023-2 | $IC_{50}$ = 2 nM |
| SYY-B024-1 | $IC_{50}$ = 47 nM |
| SYY-B024-2 | $IC_{50}$ = 24 nM |
| SYY-B025-1 | $IC_{50}$ = 1.6 nM |
| SYY-B025-2 | $IC_{50}$ = 1.1 nM |
| SYY-B026-1 | $IC_{50}$ = 22 nM |
| SYY-B026-2 | $IC_{50}$ = 18 nM |
| SYY-B027-1 | $IC_{50}$ = 9.1 nM |
| SYY-B027-2 | $IC_{50}$ = 3.1 nM |
| SYY-B028-1 | $IC_{50}$ = 1.1 μM |
| SYY-B028-2 | $IC_{50}$ = 55 nM |
| SYY-B029-1 | $IC_{50}$ = 4.1 nM |
| SYY-B029-2 | $IC_{50}$ = 1.4 nM |
| SYY-B030-1 | $IC_{50}$ = 230 nM |
| SYY-B030-2 | $IC_{50}$ = 230 nM |
| SYY-B031-1 | $IC_{50}$ = 1.8 nM |
| SYY-B031-2 | $IC_{50}$ = 1.9 nM |
| SYY-B032-1 | $IC_{50}$ = 100 nM |
| SYY-B032-2 | $IC_{50}$ = 37 nM |
| SYY-B033 | $IC_{50}$ = 4.8 nM |
| SYY-B034 | $IC_{50}$ > 0.1 μM |
| SYY-B035-1 | $IC_{50}$ < 5 nM |
| SYY-B035-2 | $IC_{50}$ < 5 nM |
| SYY-B036-1 | $IC_{50}$ = 180 nM |
| SYY-B036-2 | $IC_{50}$ = 1.5 μM |
| SYY-B037-1 | $IC_{50}$ = 1.5 nM |
| SYY-B037-2 | $IC_{50}$ > 0.1 μM |
| SYY-B038-1 | $IC_{50}$ = 1.0 nM |
| SYY-B038-2 | $IC_{50}$ > 0.1 μM |
| SYY-B039-1 | $IC_{50}$ = 1.9 nM |
| SYY-B039-2 | $IC_{50}$ = 1.2 nM |
| SYY-B040-1 | $IC_{50}$ = 130 nM |
| SYY-B040-2 | $IC_{50}$ = 160 nM |
| SYY-B041-1 | $IC_{50}$ = 4.3 nM |
| SYY-B041-2 | $IC_{50}$ = 3.4 nM |
| SYY-B043 | $IC_{50}$ < 5 nM |
| SYY-B045 | $IC_{50}$ < 5 nM |
| SYY-B044 | $IC_{50}$ > 50 nM |
| SYY-B046 | $IC_{50}$ > 50 nM |
| SYY-B057-1 | $IC_{50}$ = 8.9 nM |
| SYY-B057-2 | $IC_{50}$ = 2.4 nM |
| SYY-B074 | $IC_{50}$ < 10 nM |
| SYY-B077 | $IC_{50}$ < 5 nM |
| ZB-P-29 | $IC_{50}$ < 10 nM |
| ZB-P-28 | $IC_{50}$ < 10 nM |
| SYY-B083 | $IC_{50}$ < 20 nM |
| SYY-B084 | $IC_{50}$ < 20 nM |
| SYY-B085 | $IC_{50}$ < 20 nM |
| SYY-B086 | $IC_{50}$ < 10 nM |
| ZB-P-21 | $IC_{50}$ < 20 nM |
| SYY-B092 | $IC_{50}$ < 20 nM |
| SYY-B093 | $IC_{50}$ < 20 nM |
| SYY-B094 | $IC_{50}$ < 100 nM |
| SYY-B099 | $IC_{50}$ < 20 nM |
| SYY-B100-1 | $IC_{50}$ = 20.6 nM |
| SYY-B100-2 | $IC_{50}$ = 16.8 nM |
| SYY-B081-1 | $IC_{50}$ < 200 nM |
| SYY-B081-2 | $IC_{50}$ = 6.8 nM |
| SYY-B088 | $IC_{50}$ < 10 nM |
| SYY-B090-1 | $IC_{50}$ = 1.37 nM |
| SYY-B090-2 | $IC_{50}$ = 1.58 nM |
| SYY-B095-1 | $IC_{50}$ = 11.7 nM |
| SYY-B096-2 | $IC_{50}$ = 7.4 nM |
| SYY-B097-1 | $IC_{50}$ = 42.3 nM |
| SYY-B097-2 | $IC_{50}$ = 4.0 nM |
| SYY-B102-1 | $IC_{50}$ = 13.9 nM |
| SYY-B102-2 | $IC_{50}$ = 0.55 nM |
| SYY-B104 | $IC_{50}$ < 20 nM |
| SYY-B106 | $IC_{50}$ < 20 nM |
| SYY-B108 | $IC_{50}$ < 50 nM |
| ZB-P-30 | $IC_{50}$ < 10 nM |
| ZB-P-31 | $IC_{50}$ < 5 nM |
| SYY-B110 | $IC_{50}$ < 10 nM |
| SYY-B112 | $IC_{50}$ < 10 nM |
| SYY-B116-1 | $IC_{50}$ = 140 nM |

-continued

| Compound | Inhibition rate |
|---|---|
| SYY-B116-2 | $IC_{50}$ = 2.0 nM |
| SYY-B118-2 | $IC_{50}$ = 6.6 nM |
| SYY-B120 | $IC_{50}$ < 5 nM |
| SYY-B122 | $IC_{50}$ < 10 nM |
| SYY-B124 | $IC_{50}$ < 20 nM |
| SYY-B126-2 | $IC_{50}$ = 0.5 nM |
| SYY-B130 | $IC_{50}$ < 10 nM |
| SYY-B136-1 | $IC_{50}$ < 10 nM |
| SYY-B140-2 | $IC_{50}$ = 7.0 nM |
| SYY-B156 | $IC_{50}$ < 30 nM |
| SYY-B161 | $IC_{50}$ < 100 nM |
| SYY-B163 | $IC_{50}$ < 20 nM |
| SYY-B165 | $IC_{50}$ < 20 nM |
| SYY-B170-2 | $IC_{50}$ < 20 nM |
| SYY-B132-2 | $IC_{50}$ < 10 nM |
| SYY-B136-2 | $IC_{50}$ < 10 nM |
| SYY-B142 | $IC_{50}$ < 50 nM |
| SYY-B144 | $IC_{50}$ < 50 nM |

Example 229

Cell Growth Inhibition Experiment

The human mantle cell lymphoma (MCL) cell line MAVER-1 (from ATCC, CRL-3008) was cultured with RPMI 1640 medium (Gibco, available from Life Technologies Corporation, 22400-089) containing 1000 fetal bovine serum (Gibco, available from Life Technologies, 10099-141) and 1% antibiotics (penicillin and streptomycin, available from Life Technologies Corporation, 10378016) in a $CO_2$ cell incubator (37° C., 5% $CO_2$). In the cell growth inhibition experiment, MAVER-1 cells in exponential growth phase were seeded on a 96-well plate (purchased from Corning Company, 3599) in a volume of 100 μL/well and a cell density of 1*10E5 cells/well. After seeded, the plate was placed in a $CO_2$ incubator to culture for 1 h. 100 μL of a compound at different concentrations diluted in 3-fold gradient or DMSO were added in a 96-well plate containing the cells. The final concentration of the compound ranges from 0.3 to 10000 nM, and the final concentration of DMSO is 0.05% as control group. The cells were treated with the compound for 5 days. Cell viability was measured using CellTiter-Glo reagent (purchased from Promega, G7572): the cells treated with the compound for 5 days was added with CellTiter-Glo reagent at 20 μL/well, incubated at room temperature for 10 min, transferred to a white 96-well plate (OptiPlate-96, purchased from PerkinElmer, 605299) by 80 μL. Subsequently, the luminescence signal was detected by using a multifunctional microplate reader EnVision (purchased from PerkinElmer) at a wavelength of 400-700 nm. The data was analyzed by using GraphPad Prism 5.0 software to obtain $IC_{50}$.

Human castration resistant prostate cancer cell line 22Rv1 and LNCaP clone FGC (22Rv1 cell line was from ATCC, CRL-2505, LNCaP clone FGC cell line was purchased from Cell Bank of the Chinese Academy of Sciences) were cultured with RPMI 1640 medium (Gibco, available from Life Technologies Corporation, 22400-089) containing 10% fetal bovine serum (Gibco, available from Life Technologies, 10099-141) and 1% antibiotics (penicillin and streptomycin, available from Life Technologies Corporation, 10378016) in a $CO_2$ cell incubator (37° C., 5% $CO_2$). In the cell growth inhibition experiment, 22Rv1 and LNCaP clone FGC cells in exponential growth phase were seeded on a 96-well plate (purchased from Corning Company, 3599)

with a volume of 150 μL/well and a cell density of 1,500 cells/well. After seeded, the plate was placed in a $CO_2$ incubator to incubate overnight to allow the cells to adhere. On the next day, 50 μL of a compound at different concentrations diluted in 3-fold gradient or DMSO were added in a 96-well plate containing the cells. The final concentration of the compound ranges from 0.3 to 10000 nM, and the final concentration of DMSO is 0.05% as control group. The cells were treated by the compound for 5 days. Cell viability was measured using CellTiter-Glo reagent (purchased from Promega, G7572): the cell treated with the compound for 5 days was added with CellTiter-Glo reagent at 40 μL/well, incubated at room temperature for 10 min, transferred to a white 96-well plate (OptiPlate-96, purchased from PerkinElmer, 605299) by 70 μL. Subsequently, the luminescence signal was detected using a multifunctional microplate reader EnVision (purchased from PerkinElmer) at a wavelength of 400-700 nm. The data was analyzed by using GraphPad Prism 5.0 software to obtain $IC_{50}$.

The positive control drug was A-485 developed by Abbvie Pharmaceuticals Corporation (Reference: Abbvie Inc., WO2016044770; Nature, 2017; ACS Med. Chem. Lett., 2018, 9, 28-33).

| Compound | Cell line MAVER-1 ($IC_{50}$) | Cell line 22Rv1 ($IC_{50}$) | Cell line LNCaP clone FGC ($IC_{50}$) |
|---|---|---|---|
| A-485 | 206 nM | 384 nM | 215 nM |
| SYY-B003 | 112 nM | 258 nM | 164 nM |
| SYY-B014-2 | / | / | 78 nM |
| SYY-B015-1 | 104 nM | 345 nM | 168 nM |
| SYY-B015-2 | 18 nM | 33 nM | 15 nM |
| SYY-B018-1 | 49 nM | 88 nM | 73 nM |
| SYY-B018-2 | 6 nM | 5 nM | 6 nM |
| SYY-B019-1 | 40 nM | 205 nM | 186 nM |
| SYY-B019-2 | 17 nM | 5 nM | 9 nM |
| SYY-B021-1 | 32 nM | 107 nM | 63 nM |
| SYY-B021-2 | 22 nM | 24 nM | 13 nM |
| SYY-B023-1 | 23 nM | 50 nM | 65 nM |
| SYY-B023-2 | 12 nM | 3 nM | 4 nM |
| SYY-B024-2 | 116 nM | 77 nM | 53 nM |
| SYY-B025-1 | 44 nM | 79 nM | 67 nM |
| SYY-B025-2 | 9 nM | 9 nM | 11 nM |
| SYY-B026-2 | 254 nM | 358 nM | 132 nM |
| SYY-B027-1 | / | 40 nM | 48 nM |
| SYY-B027-2 | 13 nM | 23 nM | 14 nM |
| SYY-B029-1 | 66 nM | 146 nM | 82 nM |
| SYY-B029-2 | 15 nM | / | 13 nM |
| SYY-B031-1 | 61 nM | 210 nM | 91 nM |
| SYY-B031-2 | 18 nM | 23 nM | 66 nM |
| SYY-B033 | / | 127 nM | 78 nM |
| SYY-B035-1 | / | <300 nM | / |
| SYY-B035-2 | / | <300 nM | / |
| SYY-B037-1 | / | 64 nM | 13 nM |
| SYY-B038-1 | / | 13 nM | 6 nM |
| SYY-B039-1 | / | 74 nM | 52 nM |
| SYY-B039-2 | / | 36 nM | 15 nM |
| SYY-B041-1 | / | <100 nM | <100 nM |
| SYY-B041-2 | / | <100 nM | <100 nM |
| SYY-B043 | / | <50 nM | / |
| SYY-B045 | / | <100 nM | / |
| SYY-B057-2 | 65 nM | 10.5 nM | / |
| SYY-B074 | <20 nM | / | / |
| SYY-B077 | <20 nM | <20 nM | / |
| ZB-P-29 | <10 nM | <10 nM | / |
| ZB-P-28 | <10 nM | <10 nM | / |
| SYY-B083 | <50 nM | <100 nM | / |
| SYY-B084 | <20 nM | <100 nM | / |
| SYY-B085 | <10 nM | <50 nM | / |
| SYY-B086 | 20 nM | <20 nM | / |
| ZB-P-21 | <50 nM | <100 nM | / |
| SYY-B092 | <20 nM | / | / |
| SYY-B093 | <20 nM | <20 nM | / |
| SYY-B099 | / | 121 nM | / |

The invention claimed is:

1. A compound represented by formula Ig or Ih, a pharmaceutically acceptable salt, stereoisomer, enantiomer, diastereomer, atropisomer, racemate, polymorphs, solvate or isotopically labeled compound thereof:

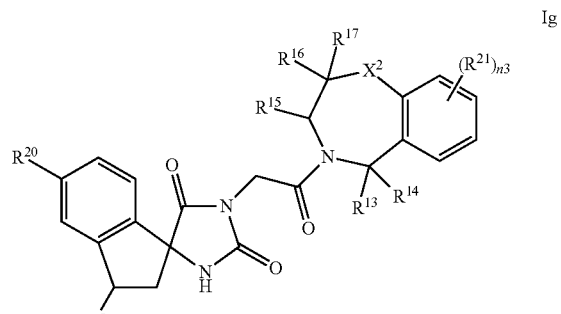

Ig

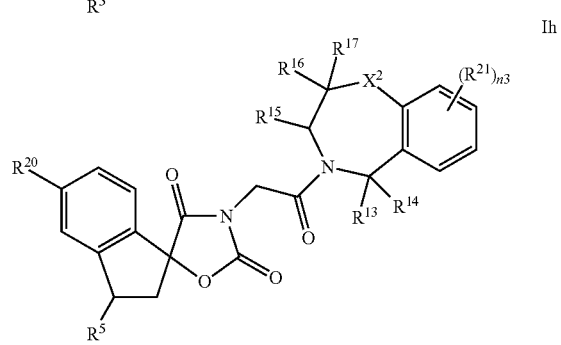

Ih wherein
$R^5$ is hydrogen, halogen or $C_1$-$C_6$ alkyl;
$X^2$ is independently —$C(R^2)(R^3)$—, —O—, —$N(R^4)$—, or —$S(O)_{n1}$—;
$R^2$ and $R^3$ are each independently hydrogen, deuterium, $C_1$-$C_6$ alkyl, $C_1$-$C_6$ haloalkyl, or $C_3$-$C_6$ cycloalkyl;
$R^4$ is independently hydrogen, $C_1$-$C_6$ alkyl, $C_3$-$C_6$ cycloalkyl, —C(=O)($C_1$-$C_6$ alkyl), —$S(O)_2$($C_1$-$C_6$ alkyl), —C(=O)($C_3$-$C_6$ cycloalkyl), or —$S(O)_2$($C_3$-$C_6$ cycloalkyl);
$R^{13}$ and $R^{14}$ are each independently hydrogen, deuterium, $C_1$-$C_6$ alkyl, $C_1$-$C_6$ haloalkyl, or $C_3$-$C_6$ cycloalkyl;
$R^{16}$ and $R^{17}$ are each independently hydrogen, deuterium, $C_1$-$C_6$ alkyl, $C_1$-$C_6$ haloalkyl, or $C_3$-$C_6$ cycloalkyl;
$R^{15}$ is independently hydrogen, $C_1$-$C_6$ alkyl substituted with 0 to 2 $R^a$s, $C_1$-$C_6$ haloalkyl, or $M^a$;
wherein, $R^a$ is independently $C_1$-$C_6$ alkyl, $C_2$-$C_6$ alkenyl, $C_2$-$C_6$ alkynyl, halogen, $C_1$-$C_6$ haloalkyl, $C_1$-$C_6$ haloalkoxy, —CN, hydroxyl, —$OM^e$, —$SM^e$, —$S(O)_2$ $M^e$, —$C(O)NM^fM^g$, —$NM^fM^g$, —$N(M^e)C(O)M^h$, —$N(M^e)S(O)_2M^h$, —$N(M^e)C(O)OM^h$, —$N(M^e)C(O)$ $NM^fM^g$, or $M^b$ at each occurrence;
$R^{20}$ is independently hydrogen, halogen, —OH, —CN, —COOH, $C_1$-$C_6$ alkyl, $C_1$-$C_6$ alkoxy, $C_1$-$C_6$ haloalkoxy, $C_2$-$C_{10}$ alkoxyalkyl, $C_4$-$C_{20}$ alkoxyalkylalkynyl, $C_2$-$C_{10}$ haloalkoxyalkyl, $C_1$-$C_6$ hydroxyalkyl, $C_3$-$C_{10}$ hydroxyalkylalkynyl, $C_2$-$C_{10}$ hydroxyalkynyl, —B($R^b$)($R^d$), —S(O)$_{n1}R^c$, —N($R^c$)$_2$, —C(=O)N($R^c$)$_2$, —NHC(=O)$R^c$, —NHC(=O)O$R^c$, —NHC(=O)C(=O)N($R^c$)$_2$, —NHC(=O)C(=O)O$R^c$, —NHC(=O)N($R^c$)$_2$, —NHC(=O)N$R^c$C(=O)N($R^c$)$_2$, —NHC(=O)N$R^c$S(O)$^2$O$R^c$, —NHC(=O)N$R^c$S(O)$_2$N($R^c$)$_2$, —NHC(=S)N($R^c$)$_2$—NHC(=NC≡N)N$R^c$, NHC(=NC≡N)S$R^c$, —NHS(O)$_{n1}R^c$, $M^c$, —($C_1$-$C_6$ alkylene)-B($R^b$)($R^d$), —($C_1$-$C_6$ alkylene)-S(O)$_{n1}R^c$, —($C_1$-$C_6$ alkylene)-N($R^c$)$_2$, —($C_1$-$C_6$ alkylene)-C(=O)N($R^c$)$_2$, —($C_1$-$C_6$ alkylene)-NHC(=O)$R^c$, —($C_1$-$C_6$ alkylene)-NHC(=O)O$R^c$, —($C_1$-$C_6$ alkylene)-NHC(=O)C(=O)N($R^c$)$_2$, —($C_1$-$C_6$ alkylene)-NHC(=O)N($R^c$)$_2$, —($C_1$-$C_6$ alkylene)-NHC(=O)N$R^c$C(=O)N($R^c$)$_2$, —($C_1$-$C_6$ alkylene)-NHC(=O)N$R^c$S(O)$_2$O$R^c$, —($C_1$-$C_6$ alkylene)-NHC(=O)N$R^c$S(O)$_2$N($R^c$)$_2$, —($C_1$-$C_6$ alkylene)-NHC(=S)N($R^c$)$_2$, —($C_1$-$C_6$ alkylene)-NHC(=N—C≡N)N$R^c$, —($C_1$-$C_6$ alkylene)-NHC(=N—C≡N)S$R^c$, —($C_1$-$C_6$ alkylene)-NHS(O)$_{n1}R^c$, —($C_1$-$C_6$ alkylene)-$M^c$, —CH=CH—($C_1$-$C_6$ alkyl), —CH=CH-$M^c$, —O$M^c$, —S$M^c$, or —N($R^c$)$M^c$ at each occurrence;

$R^b$ and $R^d$ are each independently hydrogen, hydroxyl, or $C_1$-$C_6$ alkyl;

$R^c$ is independently hydrogen, $C_1$-$C_6$ alkyl, $C_6$-$C_{10}$ aryl, 5-10 membered heteroaryl, 3-10 membered non-aromatic heterocyclic group, $C_3$-$C_{10}$ cycloalkyl, or $C_5$-$C_{10}$ cycloalkenyl, which are each independently unsubstituted or substituted with 1 or 2 groups of amino, hydroxyl, methoxy, $C_1$-$C_6$ alkyl, $C_3$-$C_{10}$ cycloalkyl, or CN when $R^c$ is not hydrogen;

$M^a$, $M^b$ and $M^c$ are each independently $C_6$-$C_{10}$ aryl, $C_5$-$C_{10}$ heteroaryl, $C_3$-$C_{10}$ non-aromatic heterocyclic group, $C_3$-$C_{10}$ cycloalkyl, or $C_3$-$C_{10}$ cycloalkenyl, which are each independently unsubstituted or substituted with 1-2 $M^d$;

$M^d$ is independently $C_1$-$C_6$ alkyl, $C_2$-$C_6$ alkenyl, $C_2$-$C_6$ alkynyl, halogen, $C_1$-$C_6$ haloalkyl, —CN, oxo, —O$M^e$, —OC(O)$M^h$, —OC(O)N$M^f M^g$, —S$M^e$, —S(O)$_2 M^e$, —S(O)$_2$N$M^f M^g$, —C(O)$M^e$, —C(O)-5-10-membered monocyclic heterocyclic ring, —C(O)-5-10-membered monocyclic heteroaryl, —C(O)O$M^e$, —C(O)N$M^f M^g$, —N$M^f M^g$, —N($M^e$)C(O)$M^h$, —N($M^e$)S(O)$_2 M^h$, —N($M^e$)C(O)O$M^h$, —N($M^e$)C(O)N$M^f M^g$, —($C_1$-$C_6$ alkylene)-O$M^e$, —($C_1$-$C_6$ alkylene)-OC(O)$M^h$, —($C_1$-$C_6$ alkylene)-OC(O)N$M^f M^g$, —($C_1$-$C_6$ alkylene)-S(O)$_2 M^e$, —($C_1$-$C_6$ alkylene)-S(O)$_2$N$M^f M^g$, —($C_1$-$C_6$ alkylene)-C(O)$M^e$, —($C_1$-$C_6$ alkylene)-C(O)O$M^e$, —($C_1$-$C_6$ alkylene)-C(O)N$M^f M^g$, —($C_1$-$C_6$ alkylene)-N$M^f M^g$, —($C_1$-$C_6$ alkylene)-N($M^e$)C(O)$M^h$, —($C_1$-$C_6$ alkylene)-N($M^e$)S(O)$_2 M^h$, —($C_1$-$C_6$ alkylene)-N($M^e$)C(O)O$M^h$, —($C_1$-$C_6$ alkylene)-N($M^e$)C(O)N$M^f M^g$, or —($C_1$-$C_6$ alkylene)-CN at each occurrence;

$R^{21}$ is each independently $C_1$-$C_6$ alkyl, halogen, $C_1$-$C_6$ haloalkyl, $C_1$-$C_6$ haloalkoxy, $C_3$-$C_6$ cycloalkyl, —O$M^e$, —OC(O)$M^h$, —OC(O)N$M^f M^g$, —S$M^e$, —S(O)$_2 M^e$, —S(O)$_2$N$M^f M^g$, —C(O)$M^e$, —C(O)O$M^e$, —C(O)N$M^f M^g$, —N$M^f M^g$, —N($M^e$)C(O)$M^h$, —N($M^e$)S(O)$_2 M^h$, —N($M^e$)C(O)O$M^h$ or —N($M^e$)C(O)N$M^f M^g$ at each occurrence;

$M^e$, $M^f$, and $M^g$ are independently hydrogen, $C_1$-$C_6$ alkyl, $C_1$-$C_6$ haloalkyl, or $C_3$-$C_6$ cycloalkyl at each occurrence; and $M^h$ is independently $C_1$-$C_6$ alkyl, $C_1$-$C_6$ haloalkyl, or $C_3$-$C_6$ cycloalkyl at each occurrence;

n1 is independently 0, 1 or 2 at each occurrence;

n3 is independently 0, 1, 2 or 3 at each occurrence.

2. The compound according to claim 1, or a pharmaceutically acceptable salt, stereoisomer, enantiomer, diastereomer, atropisomer, racemate, polymorphs, solvate or isotopically labeled compound thereof, wherein, the compound is selected from the group consisting of the compounds represented by formulae Ii and Ij:

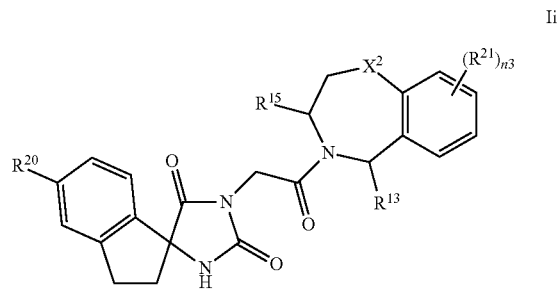

Ii

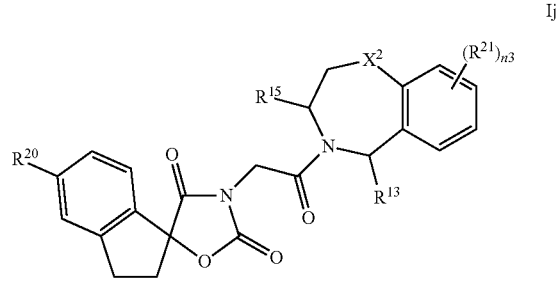

Ij wherein $R^{13}$ is hydrogen, $C_1$-$C_6$ alkyl, or $C_3$-$C_6$ cycloalkyl;

$X^2$ is $CH_2$, O, —S(O)$_{n1}$—, or —N($R^4$)—;

$R^{15}$, $R^{20}$, $R^{21}$, $R^4$, n1 and n3 are the same as defined in the formulae Ig and Ih of claim 1.

3. The compound according to claim 1, or a pharmaceutically acceptable salt, stereoisomer, enantiomer, diastereomer, atropisomer, racemate, polymorphs, solvate or isotopically labeled compound thereof, wherein, the compound is selected from the group consisting of the compounds represented by formulae Ik and Il:

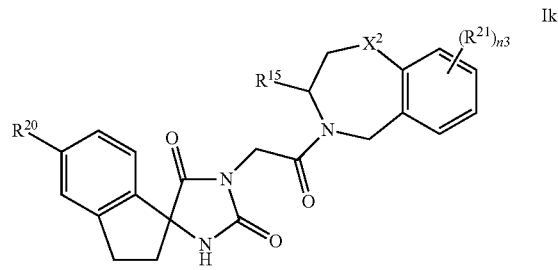

Ik

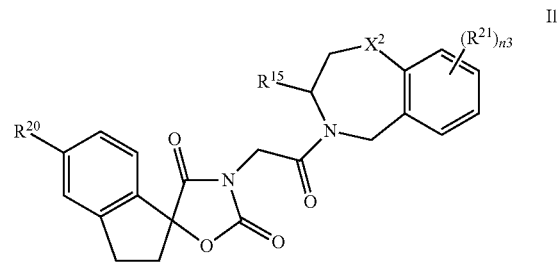

Il wherein $X^2$ is $CH_2$, O, S or —N(Me)-;

$R^{21}$ is $C_1$-$C_6$ alkyl, halogen, $C_1$-$C_6$ haloalkyl, $C_1$-$C_6$ haloalkoxy, $C_1$-$C_6$ alkoxy, or $C_3$-$C_6$ cycloalkyl;

n3 is 0, 1 or 2;

$R^{15}$ is $C_1$-$C_6$ alkyl, $C_3$-$C_6$ cycloalkyl, or $C_1$-$C_6$ haloalkyl;

$R^{20}$ is the same as defined in the formulae Ig and Ih of claim 1.

4. The compound according to claim 3, or a pharmaceutically acceptable salt, stereoisomer, enantiomer, diastereomer, atropisomer, racemate, polymorphs, solvate or isotopically labeled compound thereof, wherein, $X^2$ is $CH_2$, O, S or —N(Me)-;

$R^{21}$ is halogen;

n3 is 0, 1 or 2;

$R^{15}$ is cyclopropyl, methyl, ethyl, propyl, isopropyl, or $CF_3$;

$R^{20}$ is

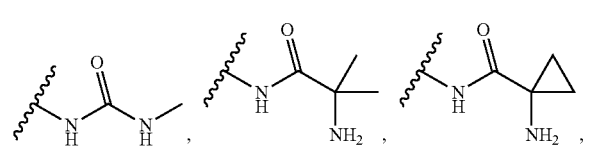

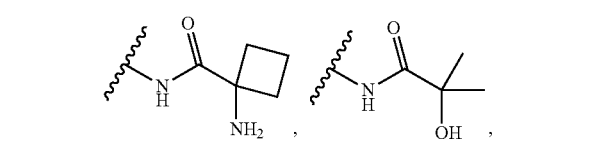

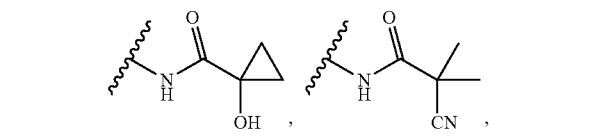

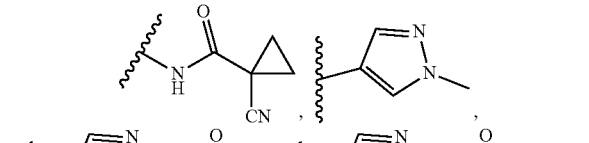

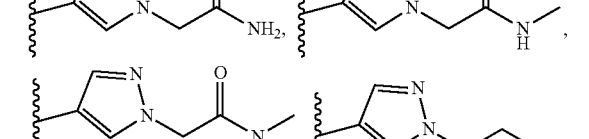

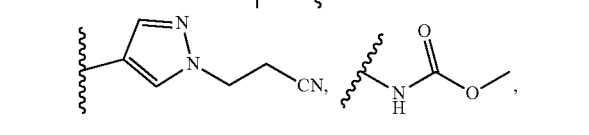

or —NHC(=O)($C_1$-$C_6$ alkyl).

5. A compound represented by formula Im, In, Io, or Ip, or a pharmaceutically acceptable salt, stereoisomer, enantiomer, diastereomer, atropisomer, racemate, polymorphs, solvate or isotopically labeled compound thereof:

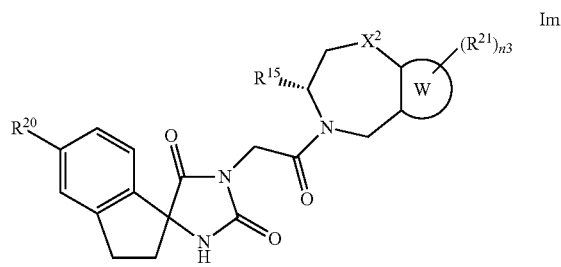

Im

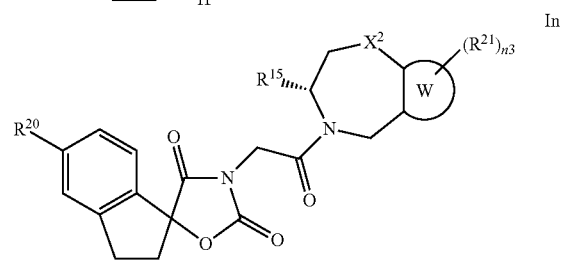

In

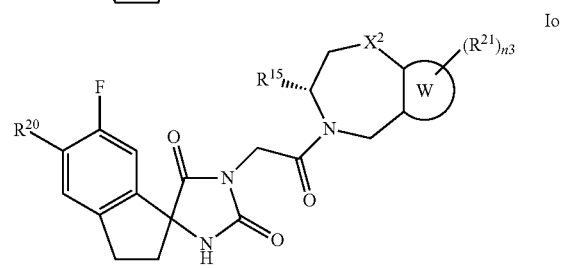

Io

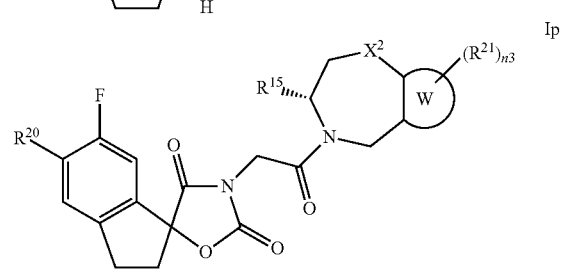

Ip wherein $X^2$ is $CH_2$, O, —S(O)$_{n1}$—, or —N($R^4$)—;

$R^4$ is independently hydrogen, $C_1$-$C_6$ alkyl, $C_3$-$C_6$ cycloalkyl, —C(=O)($C_1$-$C_6$ alkyl), —S(O)$_2$($C_1$-$C_6$ alkyl), —C(=O)($C_3$-$C_6$ cycloalkyl), or —S(O)$_2$($C_3$-$C_6$ cycloalkyl);

$R^{15}$ is independently hydrogen, $C_1$-$C_6$ alkyl substituted with 0 to 2 $R^a$s, $C_1$-$C_6$ haloalkyl, or $M^a$;

wherein, $R^a$ is independently $C_1$-$C_6$ alkyl, $C_2$-$C_6$ alkenyl, $C_2$-$C_6$ alkynyl, halogen, $C_1$-$C_6$ haloalkyl, $C_1$-$C_6$ haloalkoxy, —CN, hydroxyl, —$OM^e$, —$SM^e$, —S(O)$_2$$M^e$, —C(O)N$M^f M^g$, —N$M^f M^g$, —N($M^e$)C(O)$M^h$, —N($M^e$)S(O)$_2 M^h$, —N($M^e$)C(O)O$M^h$, —N($M^e$)C(O)N$M^f M^g$, or $M^b$ at each occurrence:

$R^{20}$ is independently hydrogen, halogen, —OH, —CN, —COOH, $C_1$-$C_6$ alkyl, $C_1$-$C_6$ alkoxy, $C_1$-$C_6$ haloalkoxy, $C_2$-$C_{10}$ alkoxyalkyl, $C_4$-$C_{20}$ alkoxyalkylalkynyl, $C_2$-$C_{10}$ haloalkoxyalkyl, $C_1$-$C_6$ hydroxyalkyl, $C_3$-$C_{10}$ hydroxyalkylalkynyl, $C_2$-$C_{10}$ hydroxyalkynyl, —B($R^b$)($R^d$), —S(O)$_{n1}R^c$, —N($R^c$)$_2$, —C(=O)N($R^c$)$_2$, —NHC(=O)$R^c$, —NHC(=O)O$R^c$, —NHC(=O)C(=O)N($R^c$)$_2$, —NHC(=O)C(=O)O$R^c$, —NHC(=O)N($R^c$)$_2$, —NHC(=O)N$R^c$C(=O)N($R^c$)$_2$, —NHC(=O)N$R^c$S(O)$_2$O$R^c$, —NHC(=O)N$R^c$S(O)$_2$N($R^c$)$_2$, —NHC(=S)N($R^c$)$_2$—NHC(=NC≡N)N$R^c$, —NHC (=NC≡N)SR$^c$, —NHS(O)$_{n1}$R$^c$, M$^c$, —(C$_1$-C$_6$ alkylene)-B(R$^b$)(R$^d$), —(C$_1$-C$_6$ alkylene)-S(O)$_{n1}$R$^c$, —(C$_1$-C$_6$ alkylene)-N(R$^c$)$_2$, —(C$_1$-C$_6$ alkylene)-C(=O)N(R$^c$)$_2$, —(C$_1$-C$_6$ alkylene)-NHC(=O)R$^c$, —(C$_1$-C$_6$ alkylene)-NHC(=O)OR$^c$, —(C$_1$-C$_6$ alkylene)-NHC(=O)C(=O)N(R$^c$)$_2$, —(C$_1$-C$_6$ alkylene)-NHC(=O)N(R$^c$)$_2$, —(C$_1$-C$_6$ alkylene)-NHC(=O)NR$^c$C(=O)N(R$^c$)$_2$, —(C$_1$-C$_6$ alkylene)-NHC(=O)NR$^c$S(O)$_2$OR$^c$, —(C$_1$-C$_6$ alkylene)-NHC(=O)NR$^c$S(O)$_2$N(R$^c$)$_2$, —(C$_1$-C$_6$ alkylene)-NHC(=S)N(R$^c$)$_2$, —(C$_1$-C$_6$ alkylene)-NHC(=N-CEN)NR$^c$, —(C$_1$-C$_6$ alkylene)-NHC(=N—C≡N)SR$^c$, —(C$_1$-C$_6$ alkylene)-NHS(O)$_{n1}$R$^c$, —(C$_1$-C$_6$ alkylene)-M$^c$, —CH=CH—(C$_1$-C$_6$ alkyl), —CH=CH-M$^c$, —OM$^c$, —SM$^c$, or —N(R$^c$)M$^c$ at each occurrence:

R$^b$ and R$^d$ are each independently hydrogen, hydroxyl, or C$_1$-C$_6$ alkyl;

R$^c$ is independently hydrogen, C$_1$-C$_6$ alkyl, C$_6$-C$_{10}$ aryl, 5-10 membered heteroaryl, 3-10 membered non-aromatic heterocyclic group, C$_3$-C$_{10}$ cycloalkyl, or C$_5$-C$_{10}$ cycloalkenyl, which are each independently unsubstituted or substituted with 1 or 2 groups of amino, hydroxyl, methoxy, C$_1$-C$_6$ alkyl, C$_3$-C$_{10}$ cycloalkyl, or CN when R$^c$ is not hydrogen;

M$^a$, M$^b$ and M$^c$ are each independently C$_6$-C$_{10}$ aryl, C$_5$-C$_{10}$ heteroaryl, C$_3$-C$_{10}$ non-aromatic heterocyclic group, C$_3$-C$_{10}$ cycloalkyl, or C$_3$-C$_{10}$ cycloalkenyl, which are each independently unsubstituted or substituted with 1-2 M$^d$;

M$^d$ is independently C$_1$-C$_6$ alkyl, C$_2$-C$_6$ alkenyl, C$_2$-C$_6$ alkynyl, halogen, C$_1$-C$_6$ haloalkyl, —CN, oxo, —OM$^e$, —OC(O)M$^h$, —OC(O)NM$^f$M$^g$, —SM$^e$, —S(O)$_2$M$^e$, —S(O)$_2$NM$^f$M$^g$, —C(O)M$^e$, —C(O)-5-10-membered monocyclic heterocyclic ring, —C(O)-5-10-membered monocyclic heteroaryl, —C(O)OM$^e$, —C(O)NM$^f$M$^g$, —NM$^f$M$^g$, —N(M$^e$)C(O)M$^h$, —N(M$^e$)S(O)$_2$M$^h$, —N(M$^e$)C(O)OM$^h$, —N(M$^e$)C(O)NM$^f$M$^g$, —(C$_1$-C$_6$ alkylene)-OM$^e$, —(C$_1$-C$_6$ alkylene)-OC(O)M$^h$, —(C$_1$-C$_6$ alkylene)-OC(O)NM$^f$M$^g$, —(C$_1$-C$_6$ alkylene)-S(O)$_2$M$^e$, —(C$_1$-C$_6$ alkylene)-S(O)$_2$NM$^f$M$^g$, —(C$_1$-C$_6$ alkylene)-C(O)M$^e$, —(C$_1$-C$_6$ alkylene)-C(O)OM$^e$, —(C$_1$-C$_6$ alkylene)-C(O)NM$^f$M$^g$, —(C$_1$-C$_6$ alkylene)-NM$^f$M$^g$, —(C$_1$-C$_6$ alkylene)-N(M$^e$)C(O)M$^h$, —(C$_1$-C$_6$ alkylene)-N(M$^e$)S(O)$_2$M$^h$, —(C$_1$-C$_6$ alkylene)-N(M$^e$)C(O)OM$^h$, —(C$_1$-C$_6$ alkylene)-N(M$^e$)C(O)NM$^f$M$^g$, or —(C$_1$-C$_6$ alkylene)-CN at each occurrence:

R$^{21}$ is each independently C$_1$-C$_6$ alkyl, halogen, C$_1$-C$_6$ haloalkyl, C$_1$-C$_6$haloalkoxy, C$_3$-C$_6$ cycloalkyl, —OM$^e$, —OC(O)M$^h$, —OC(O)NM$^f$M$^g$, —SM$^e$, —S(O)$_2$M$^e$, —S(O)$_2$NM$^f$M$^g$, —C(O)M$^e$, —C(O)OM$^e$, —C(O)NM$^f$M$^g$, —NM$^f$M$^g$, —N(M$^e$)C(O)M$^h$, —N(M$^e$)S(O)$_2$M$^h$, —N(M$^e$)C(O)OM$^h$ or —N(M$^e$)C(O)NM$^f$M$^g$ at each occurrence:

M$^e$, M$^f$, and M$^g$ are independently hydrogen, C$_1$-C$_6$ alkyl, C$_1$-C$_6$ haloalkyl, or C$_3$-C$_6$ cycloalkyl at each occurrence; and M$^h$ is independently C$_1$-C$_6$ alkyl, C$_1$-C$_6$ haloalkyl, or C$_3$-C$_6$ cycloalkyl at each occurrence;

n1 is independently 0, 1 or 2 at each occurrence;

n3 is are independently 0, 1, 2 or 3 at each occurrence,

W is a benzene ring or a C$_5$-C$_6$ heteroaromatic ring.

6. A compound, or a pharmaceutically acceptable salt, stereoisomer, enantiomer, diastereomer, atropisomer, racemate, polymorphs, solvate or isotopically labeled compound thereof, wherein, the compound is selected from the group consisting of

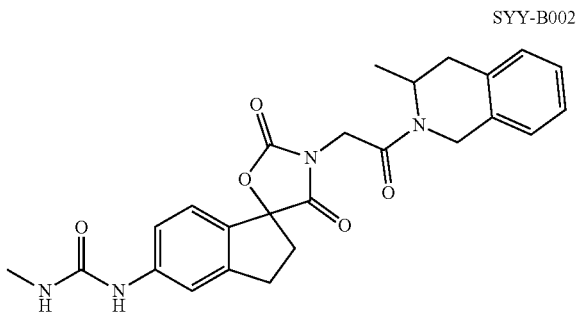
SYY-B002

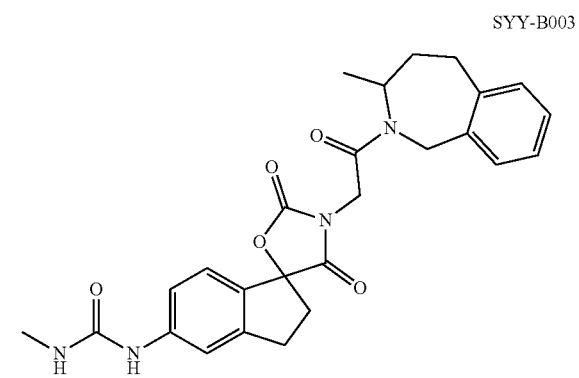
SYY-B003

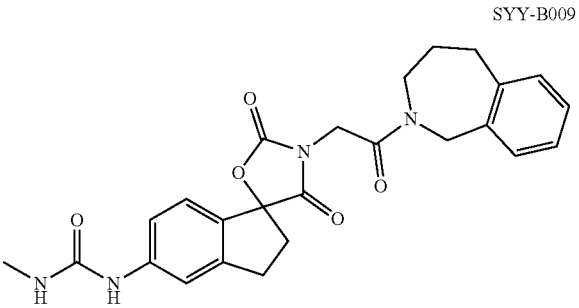
SYY-B009

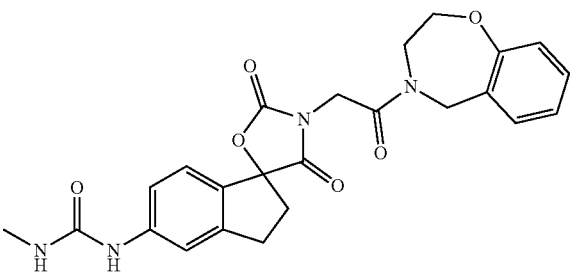
SYY-B010

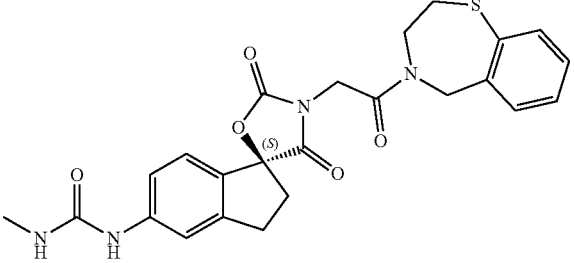
SYY-B012-1

-continued
SYY-B012-2
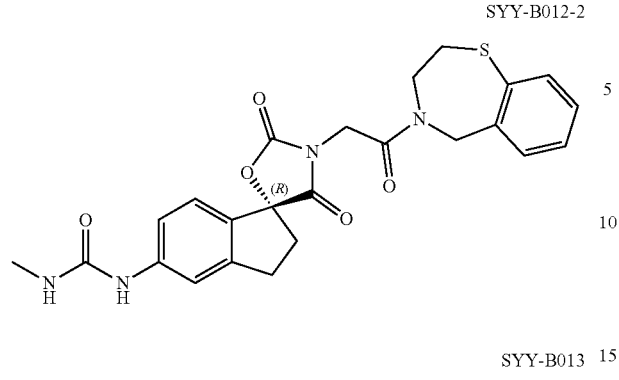
SYY-B013
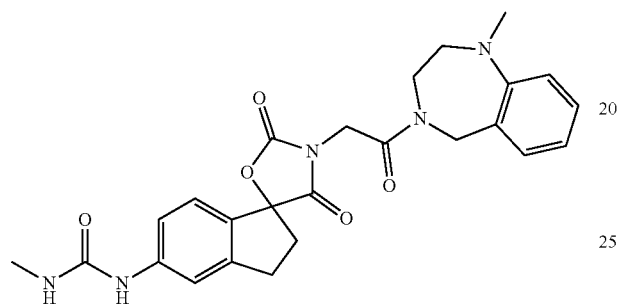
SYY-B014-1
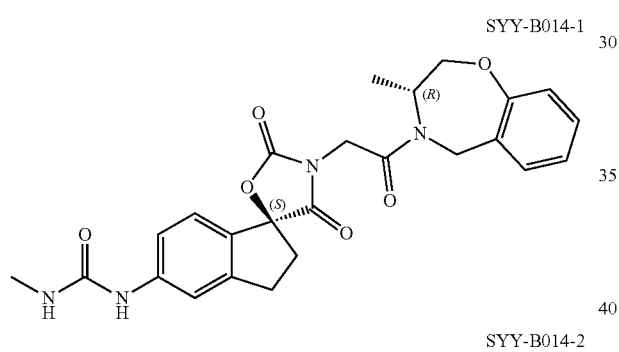
SYY-B014-2
SYY-B015-1
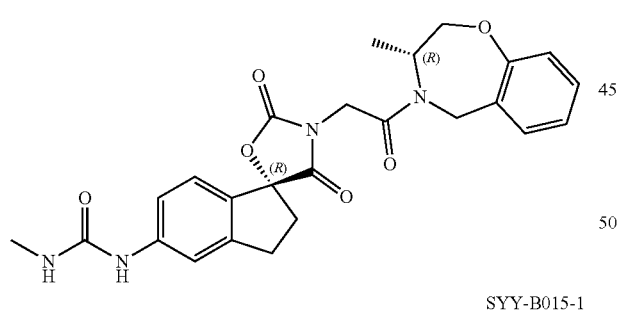
-continued
SYY-B015-2
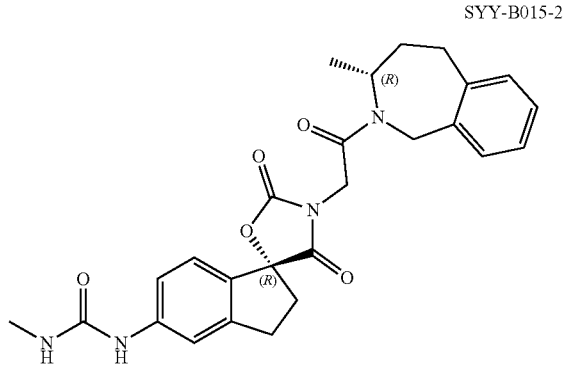
SYY-B016-1
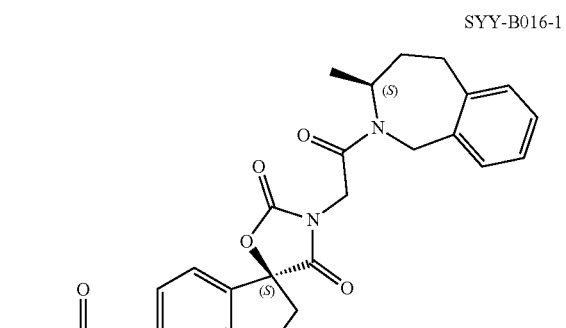
SYY-B016-2
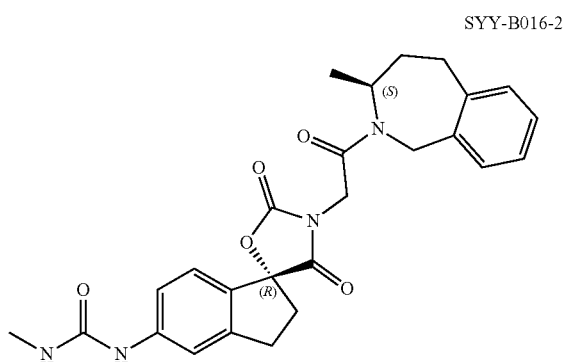
SYY-B017-1
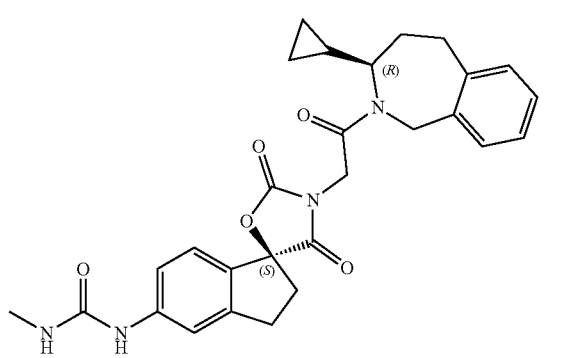

SYY-B017-2
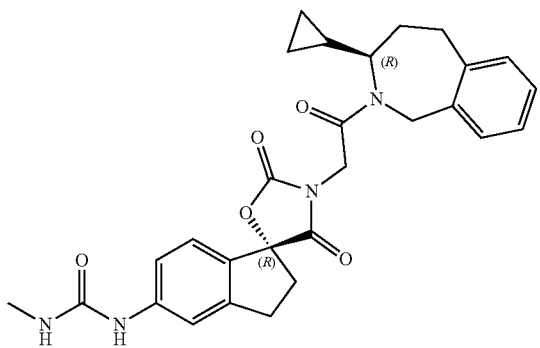
SYY-B018-1
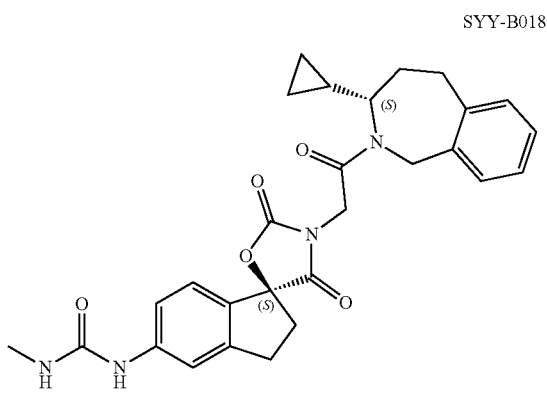
SYY-B018-2
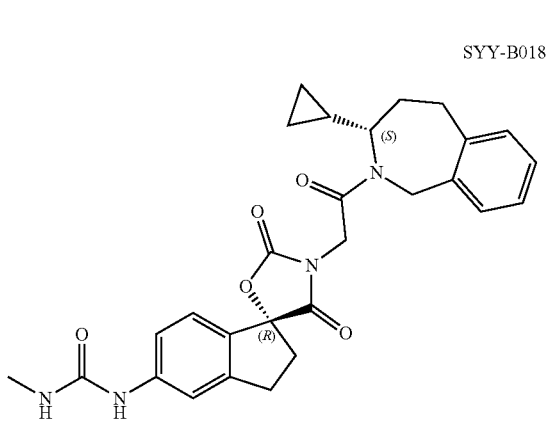
SYY-B019-1
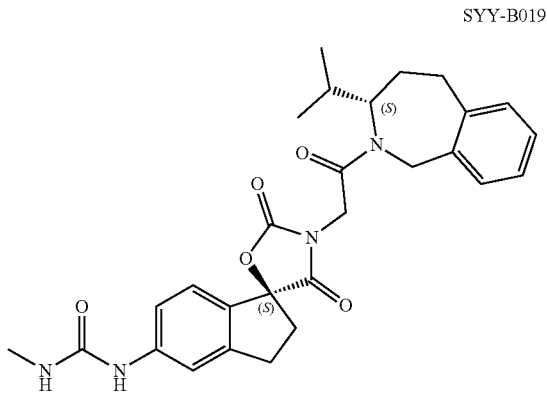
SYY-B019-2
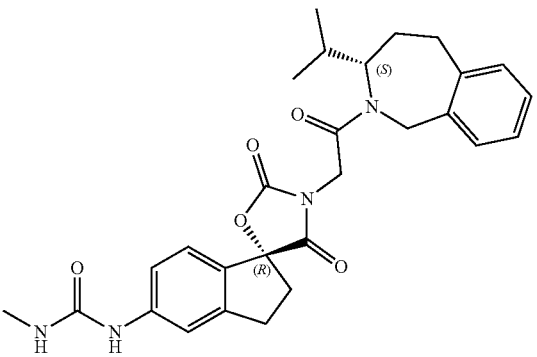
SYY-B020-1
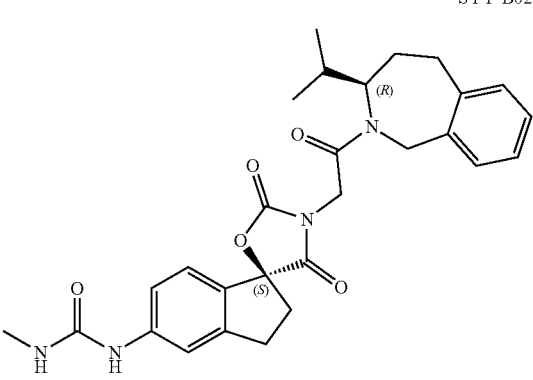
SYY-B020-2
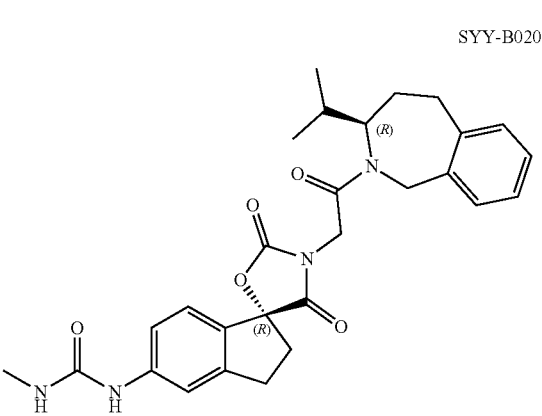
SYY-B021-1
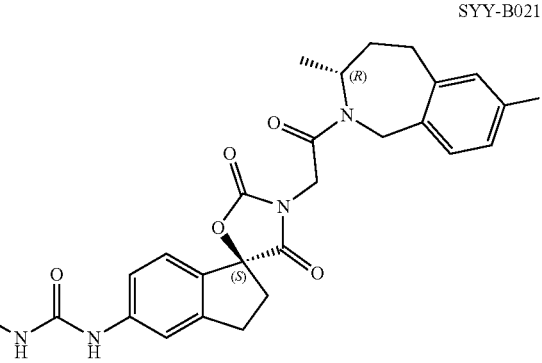

SYY-B021-2
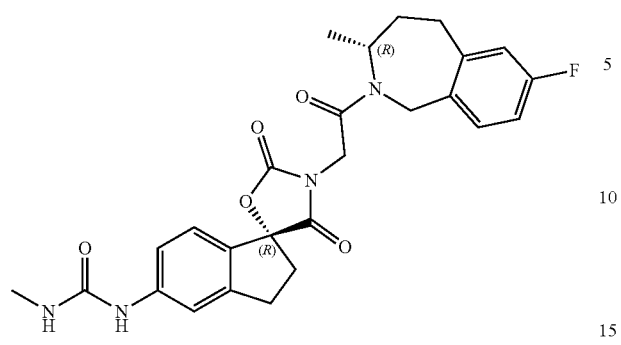
SYY-B023-2
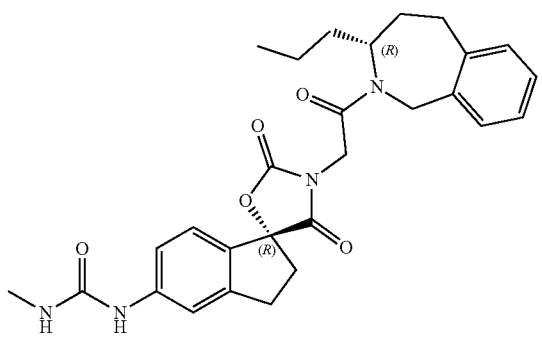
SYY-B022-1
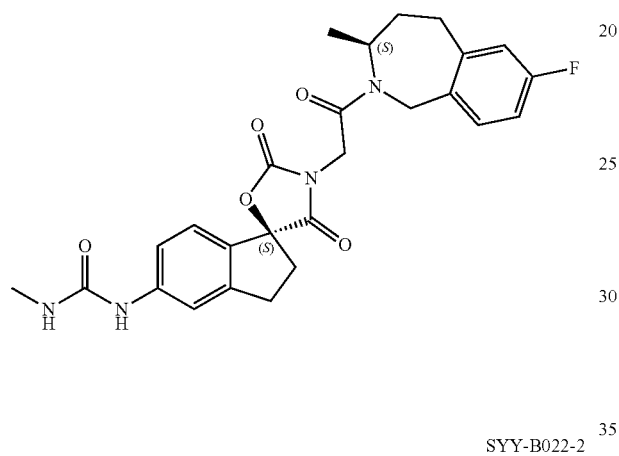
SYY-B024-1
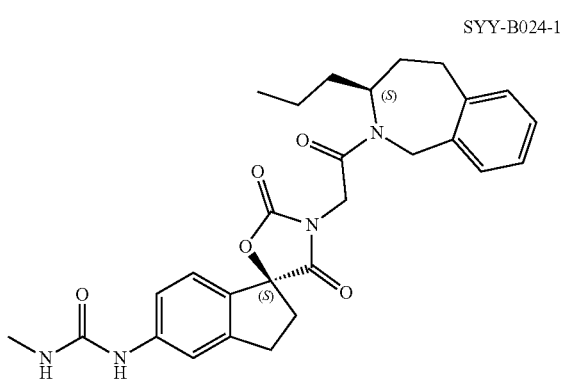
SYY-B022-2
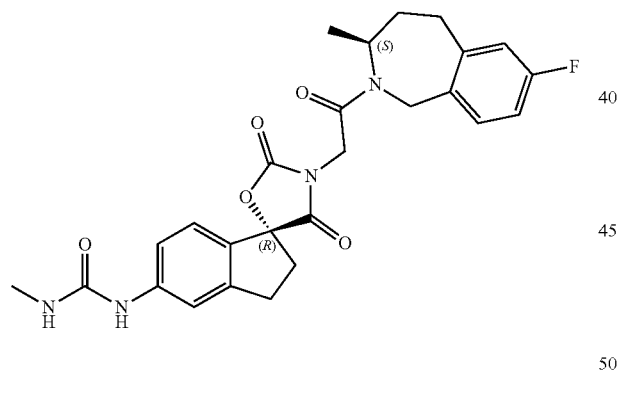
SYY-B024-2
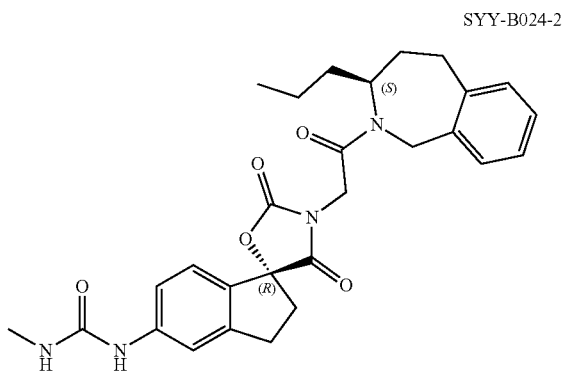
SYY-B023-1
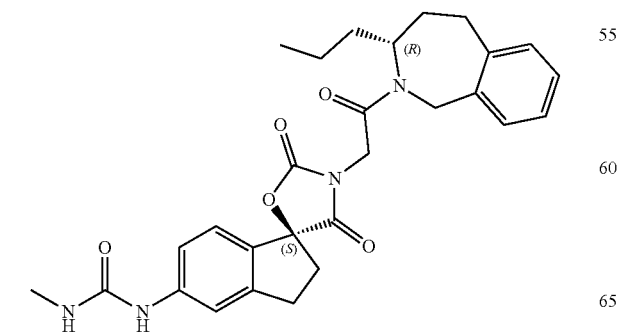
SYY-B025-1
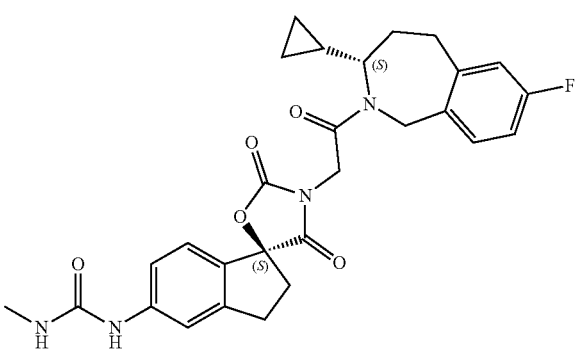

387
-continued
SYY-B025-2
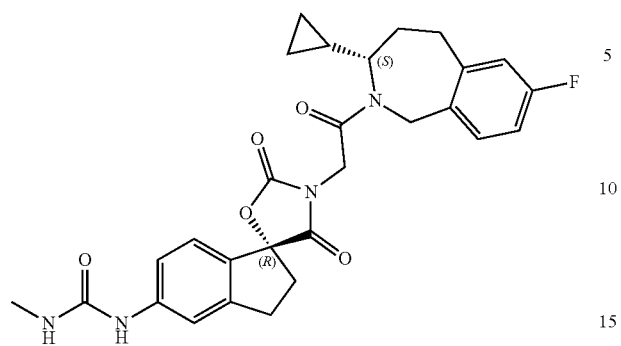
SYY-B026-1
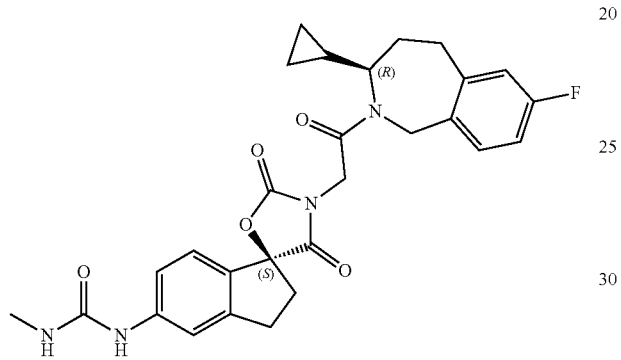
SYY-B026-2
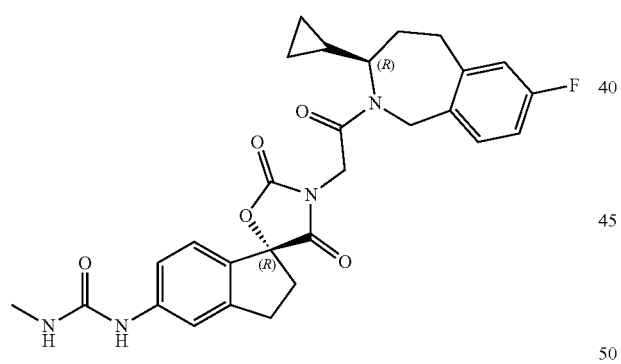
SYY-B027-1
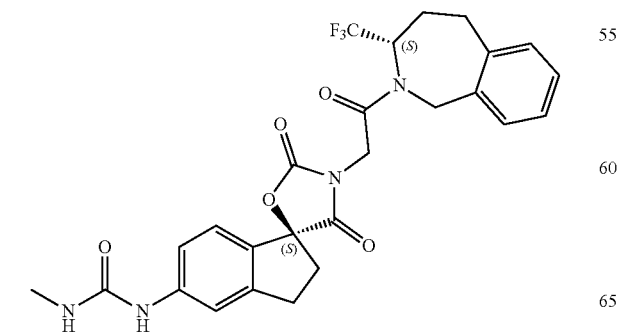
388
-continued
SYY-B027-2
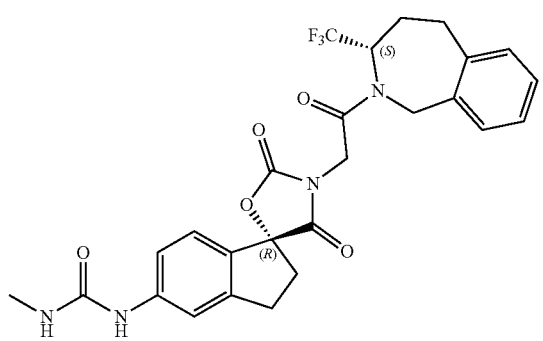
SYY-B028-1
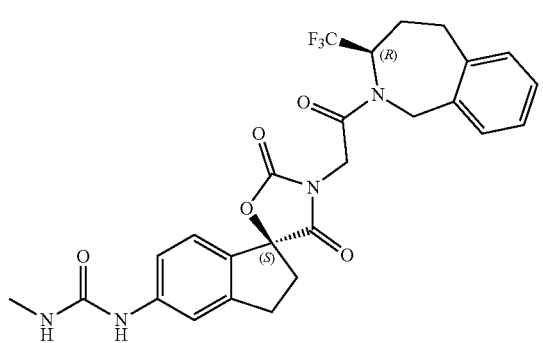
SYY-B028-2
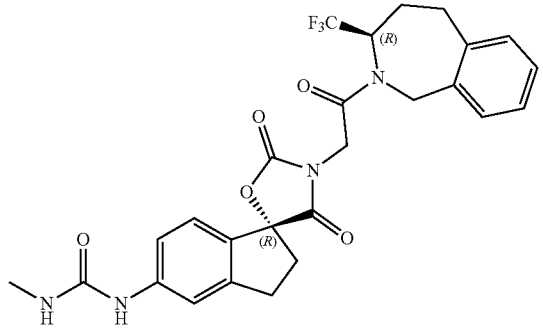
SYY-B029-1
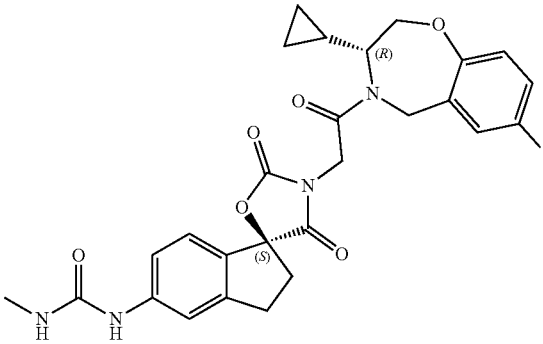

-continued
SYY-B029-2
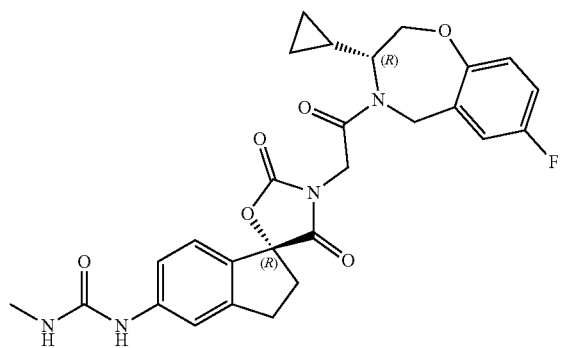
SYY-B030-1
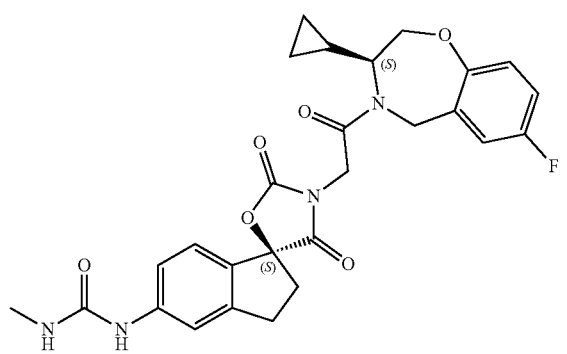
SYY-B030-2
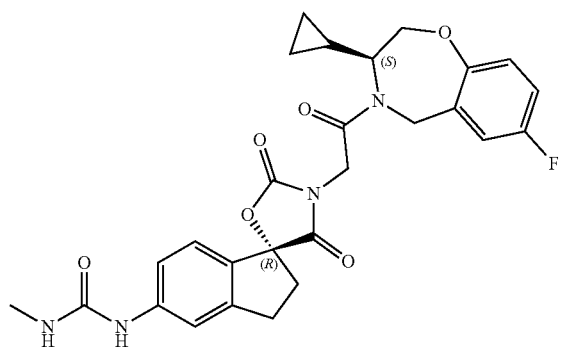
SYY-B031-1
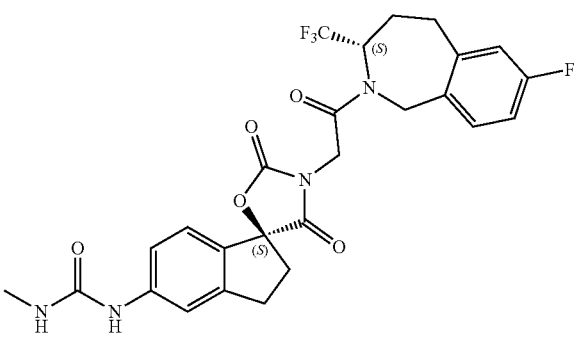
-continued
SYY-B031-2
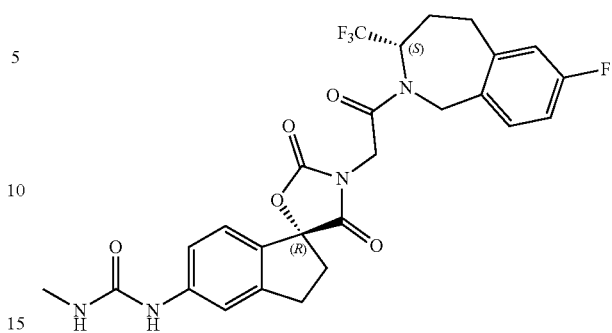
SYY-B032-1
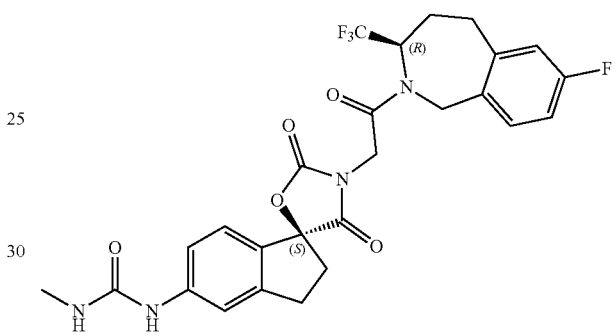
SYY-B032-2
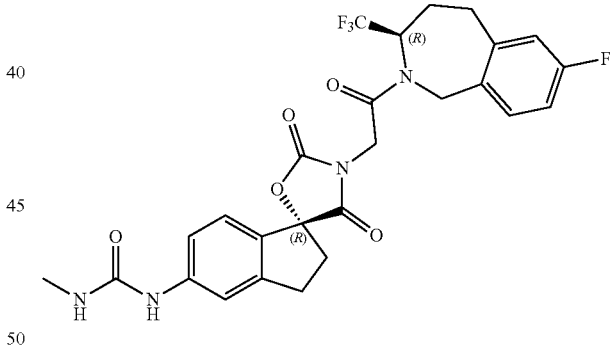
SYY-B033-1
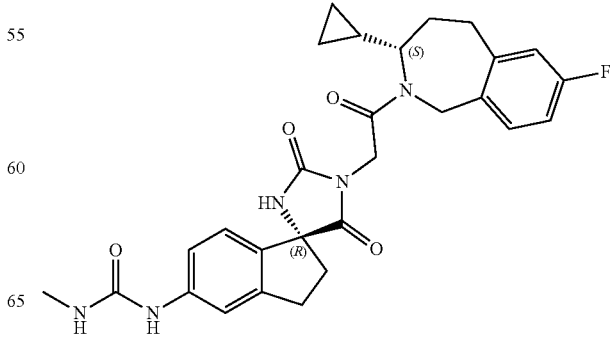

SYY-B033-2
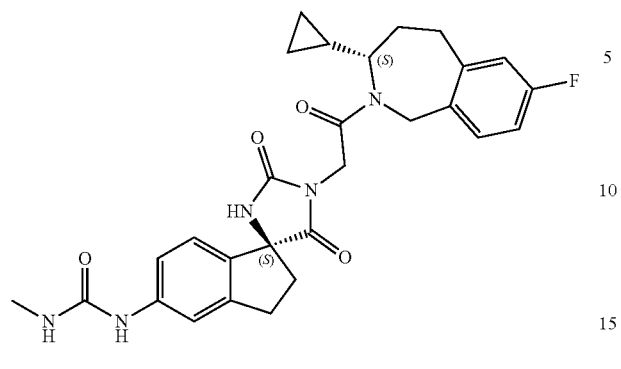
SYY-B035-2
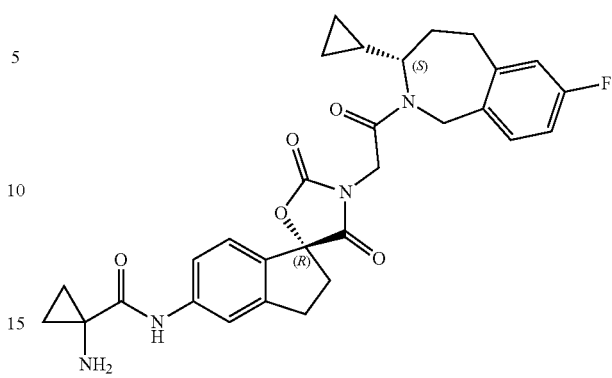
SYY-B034-1
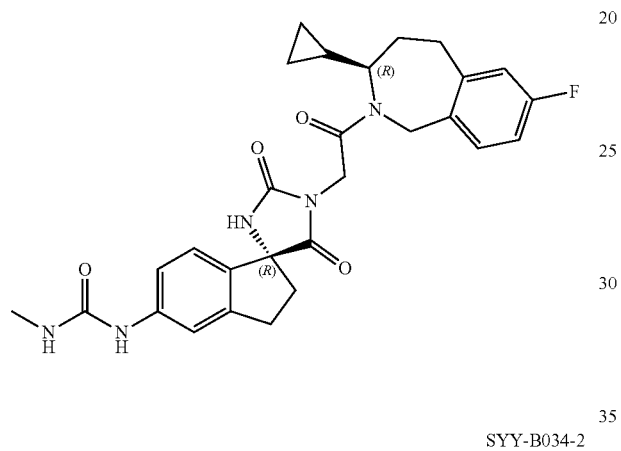
SYY-B036-1
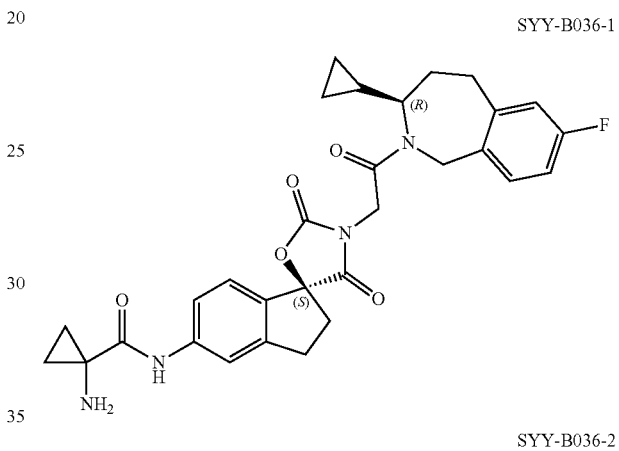
SYY-B034-2
SYY-B036-2
SYY-B035-1
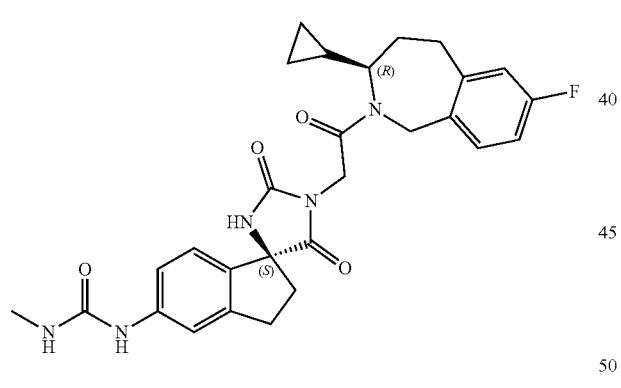
SYY-B037-1
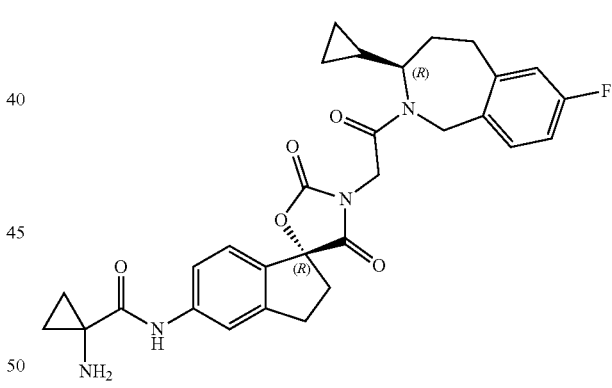
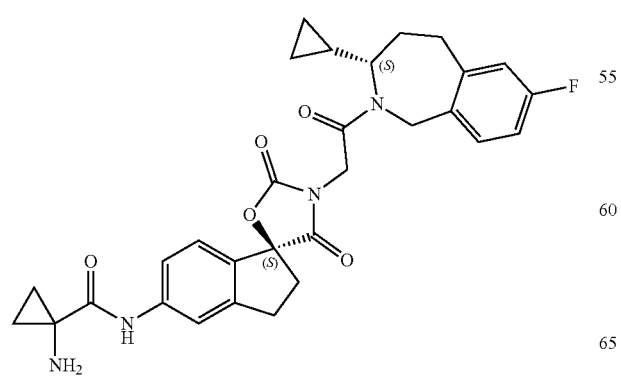

SYY-B037-2
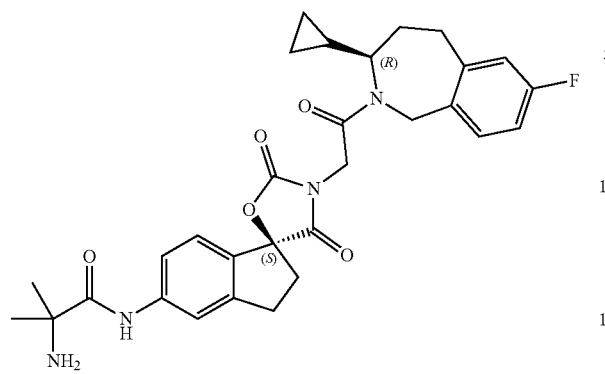
SYY-B038-1
SYY-B038-2
SYY-B039-1
SYY-B039-2
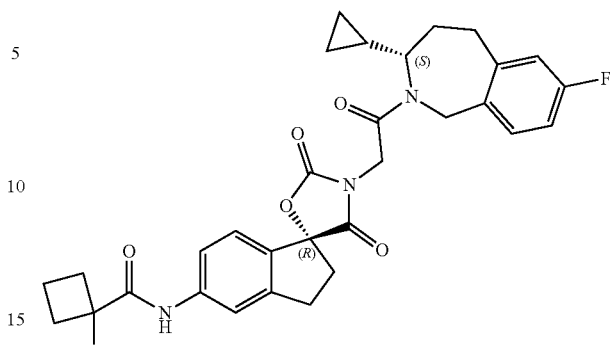
SYY-B040-1
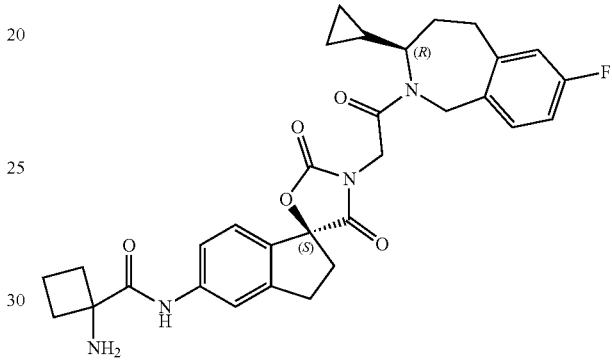
SYY-B040-2
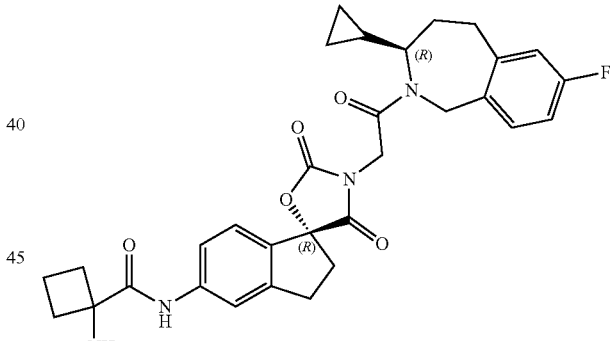
SYY-B041-1
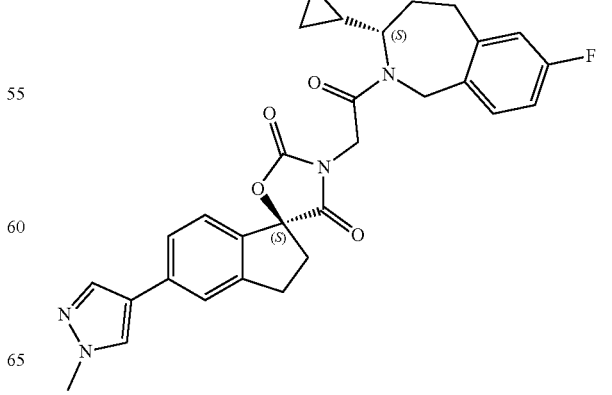

SYY-B041-2
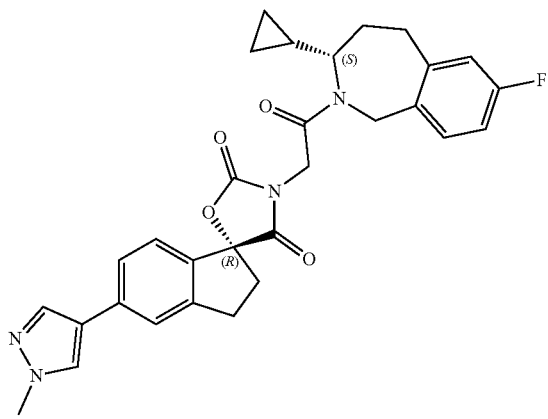
SYY-B043-1
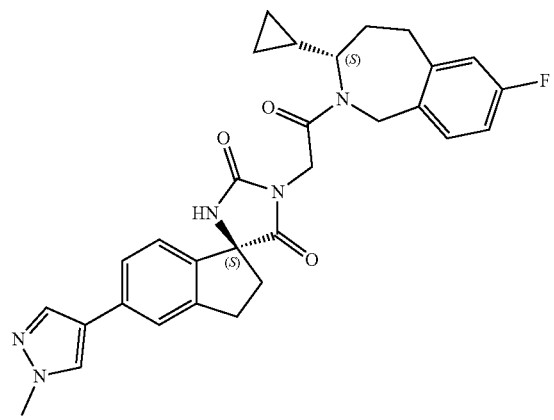
SYY-B042-1
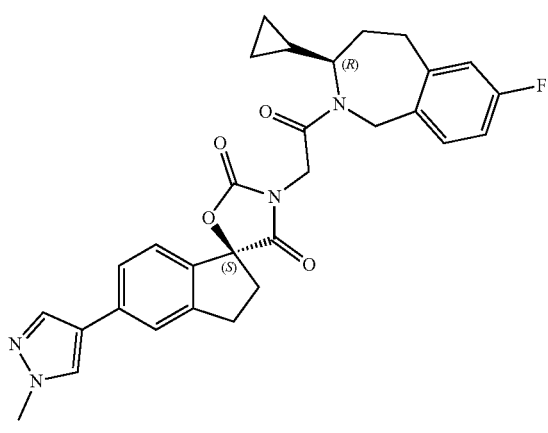
SYY-B043-2
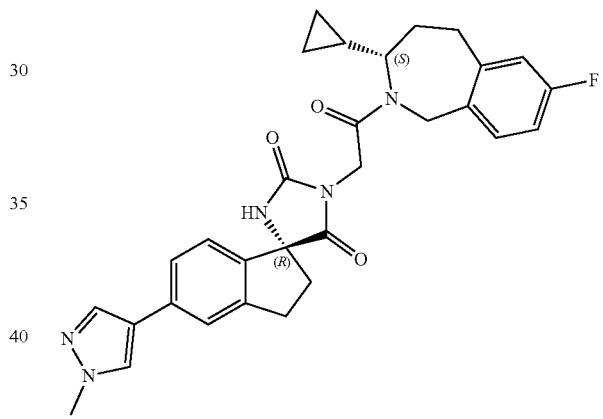
SYY-B042-2
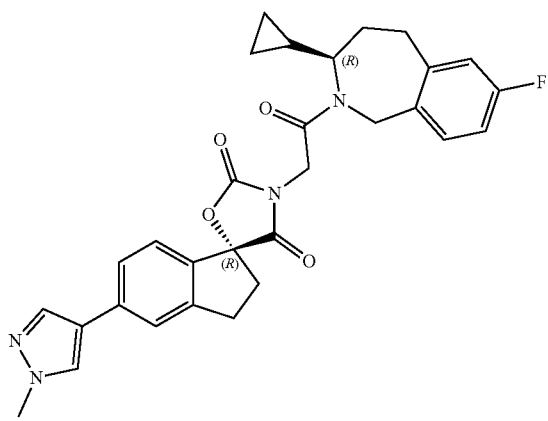
SYY-B044-1
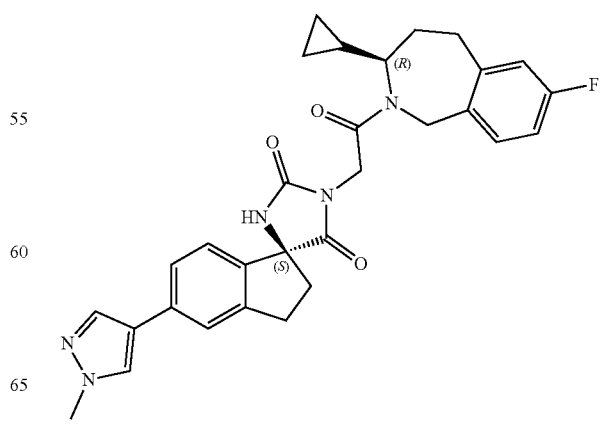

397
-continued
SYY-B044-2
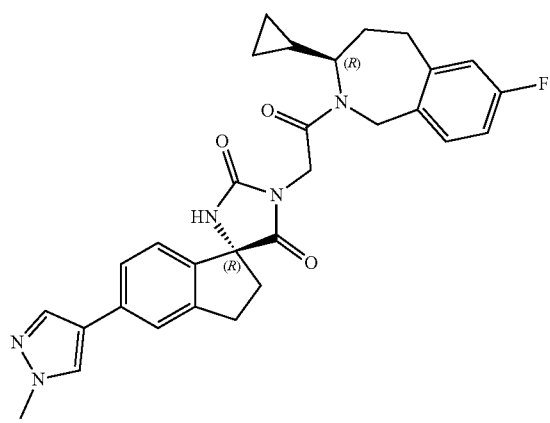
SYY-B045
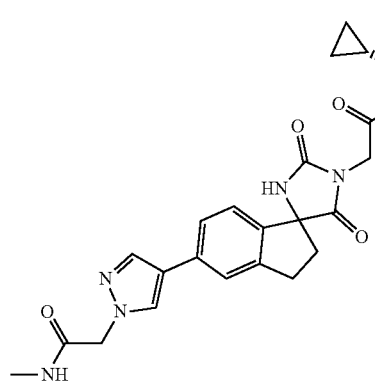
SYY-B046-1
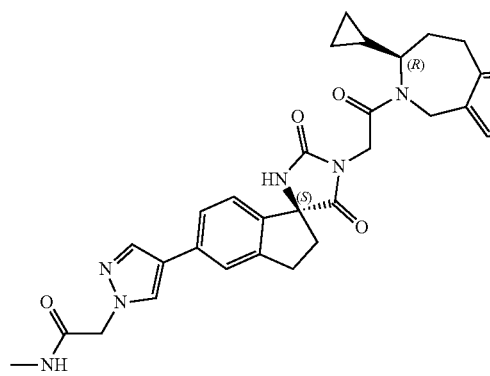
SYY-B046-2
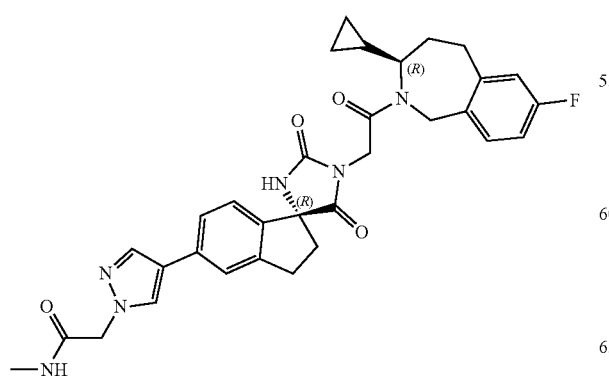
398
-continued
ZB-P-01
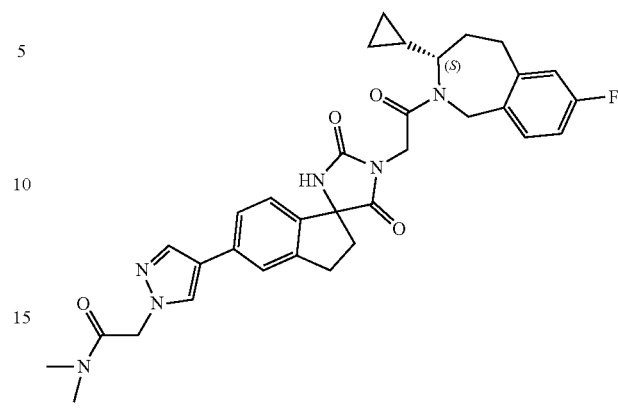
ZB-P-02
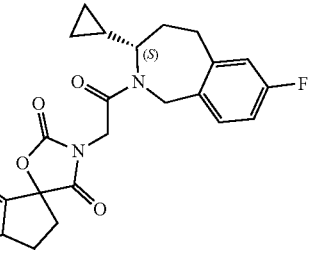
ZB-P-03
ZB-P-04
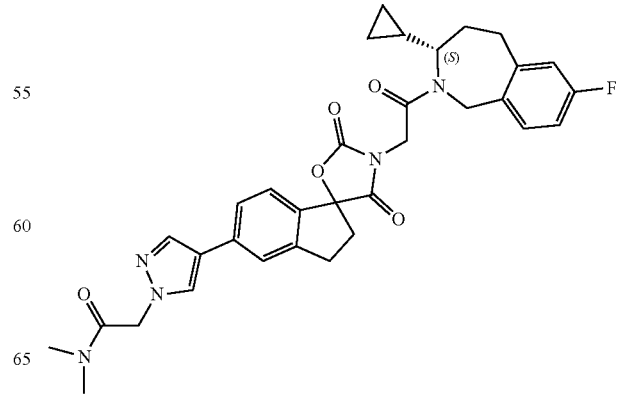

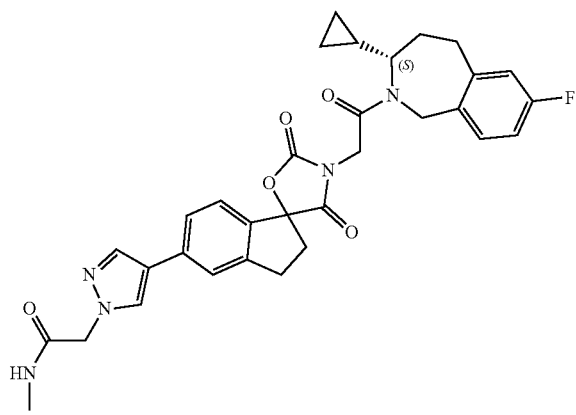
ZB-P-05
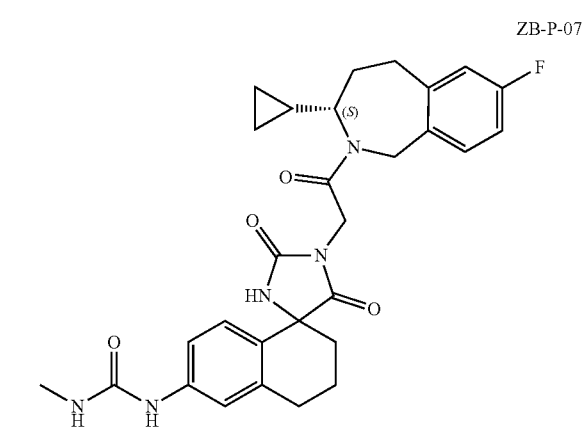
ZB-P-06
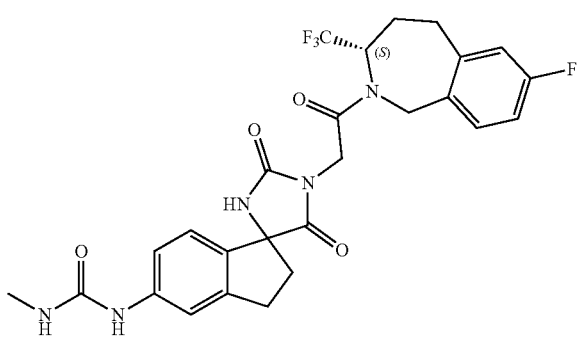
ZB-P-07
ZB-P-08
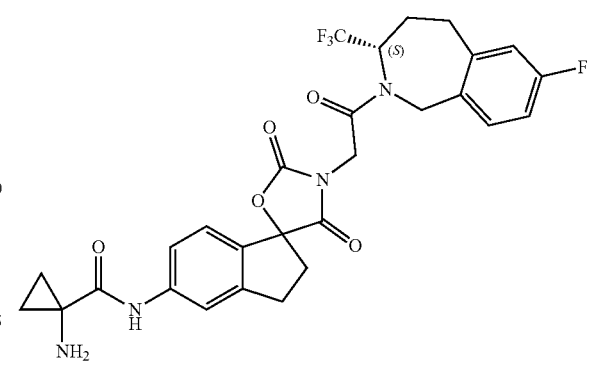
ZB-P-09
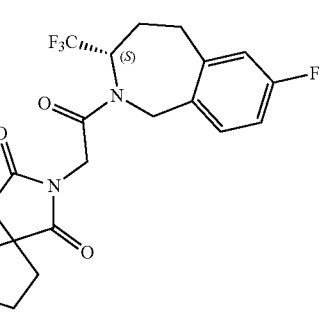
ZB-P-10
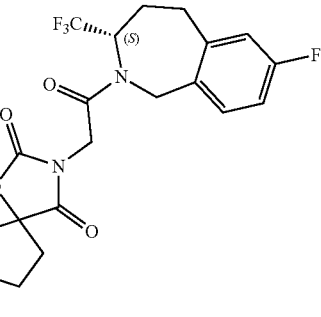
ZB-P-11
ZB-P-12
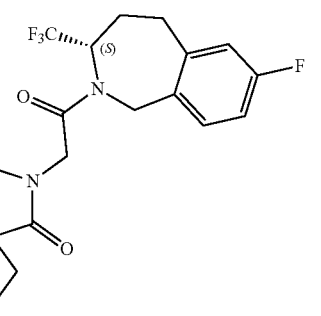

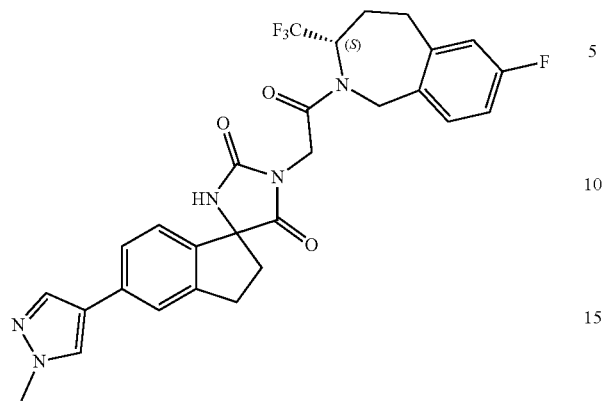
ZB-P-13
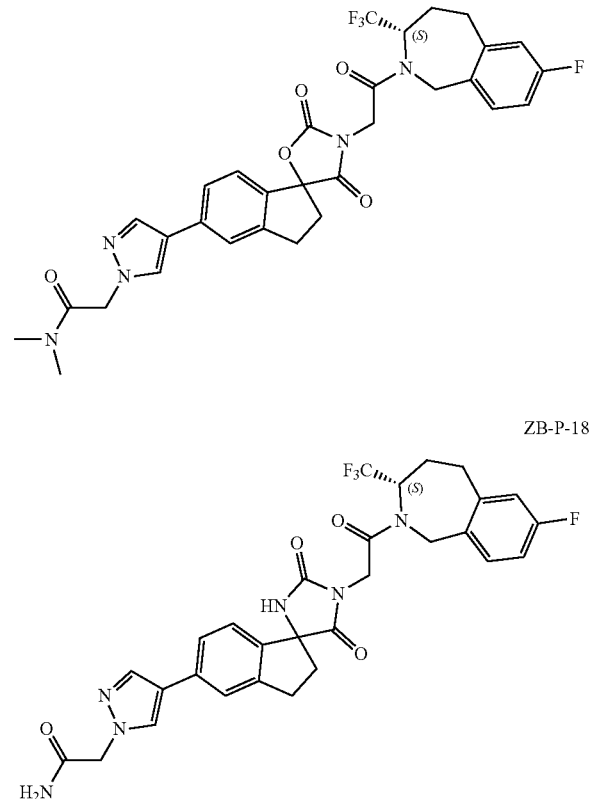
ZB-P-17
ZB-P-14
ZB-P-18
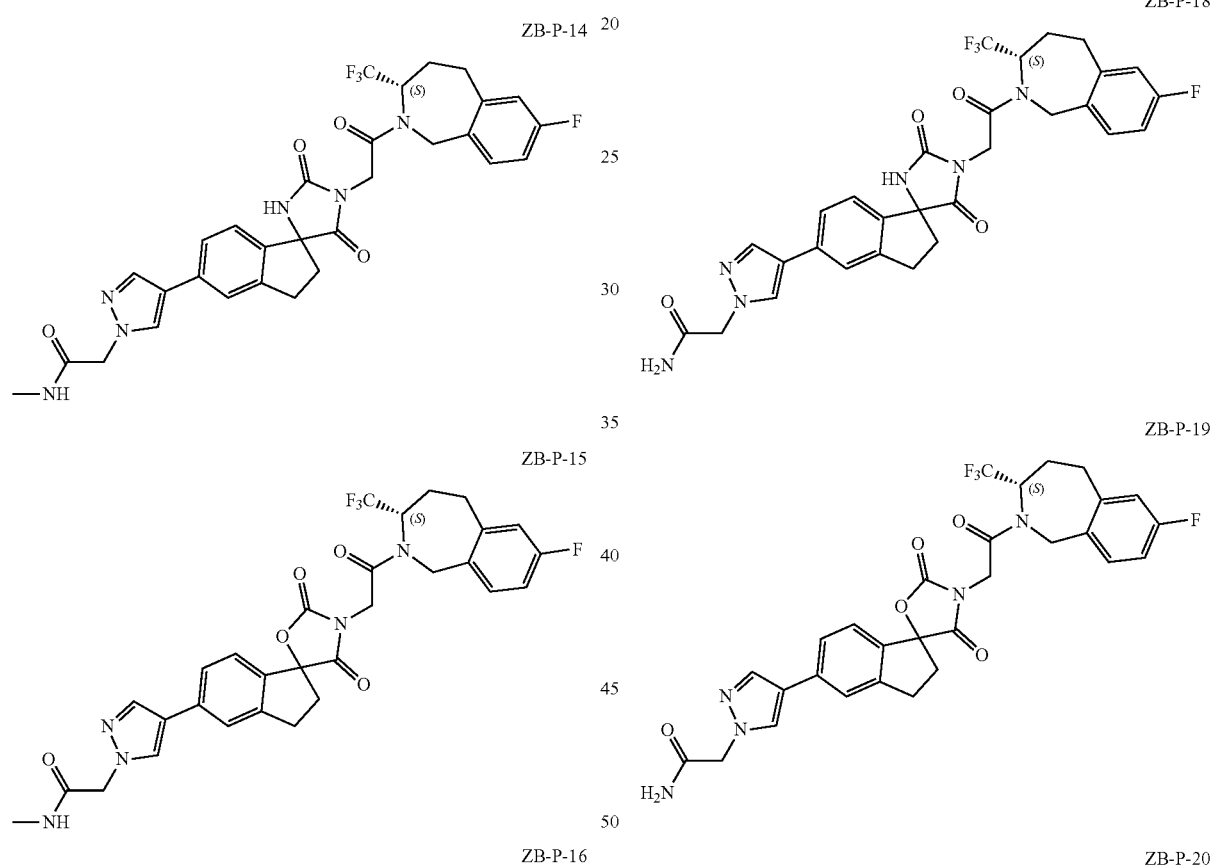
ZB-P-15
ZB-P-19
ZB-P-16
ZB-P-20
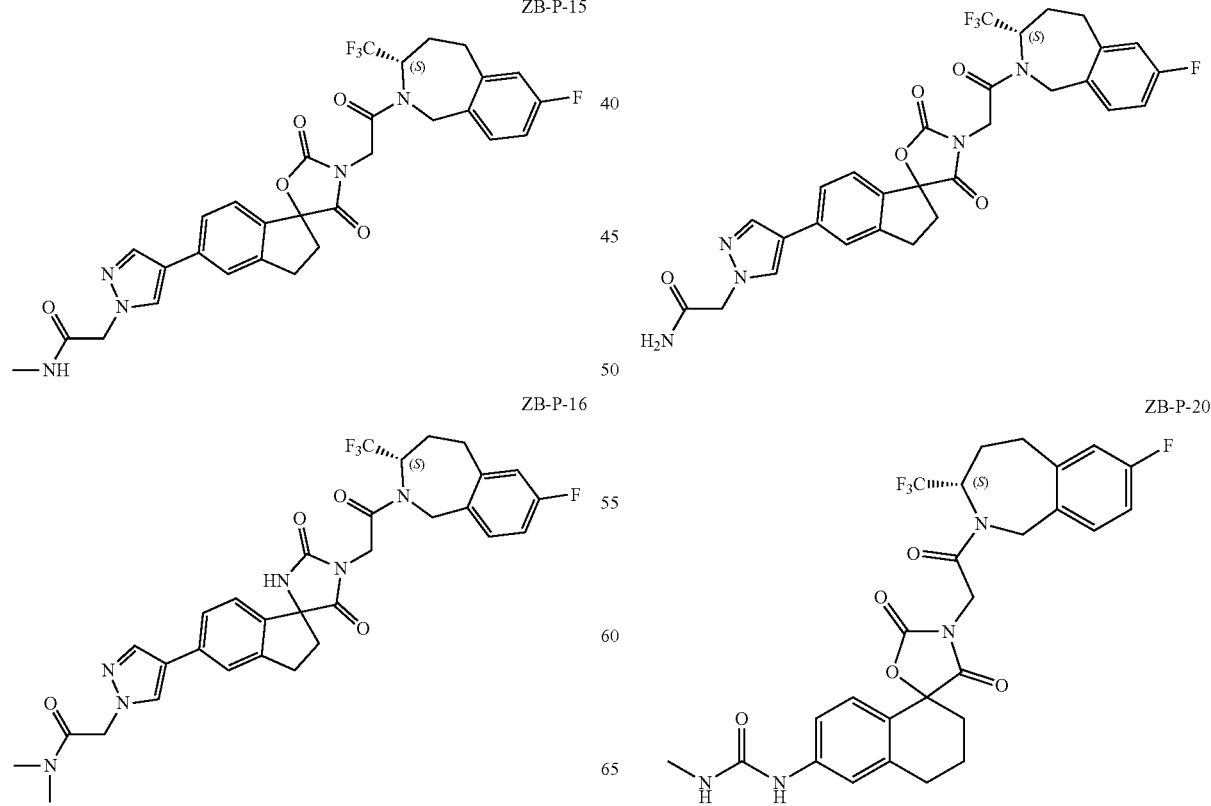

SYY-B033
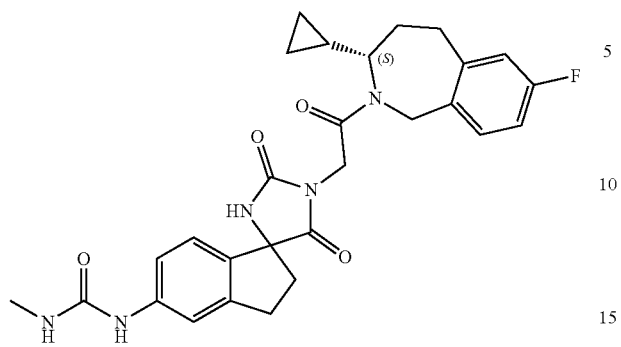
SYY-B043
SYY-B045
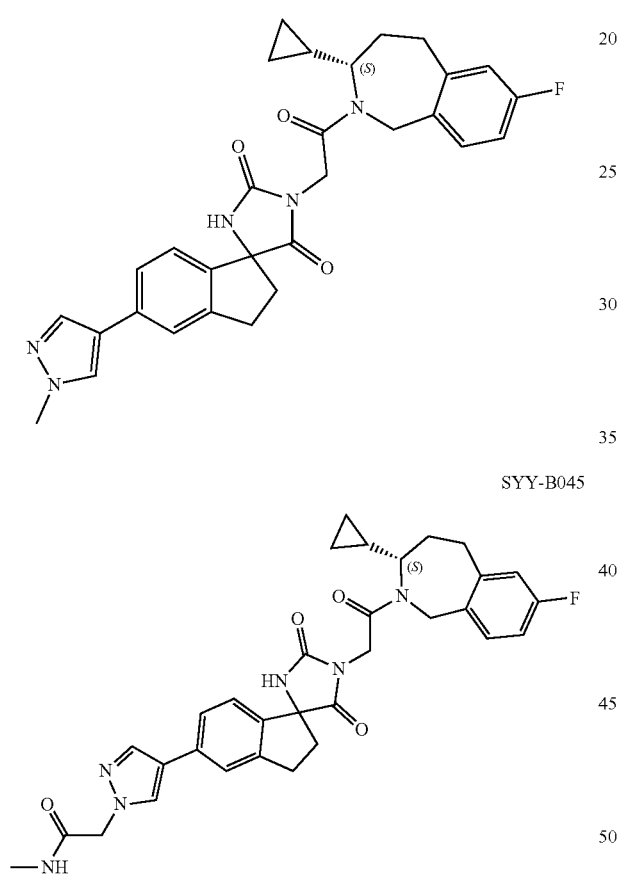
ZB-P-21
ZB-P-22
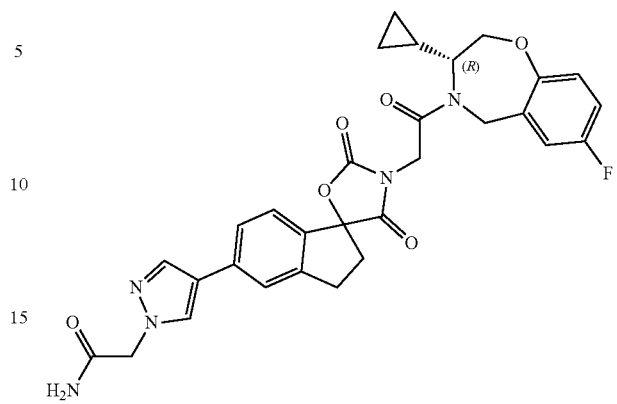
ZB-P-23
ZB-P-24
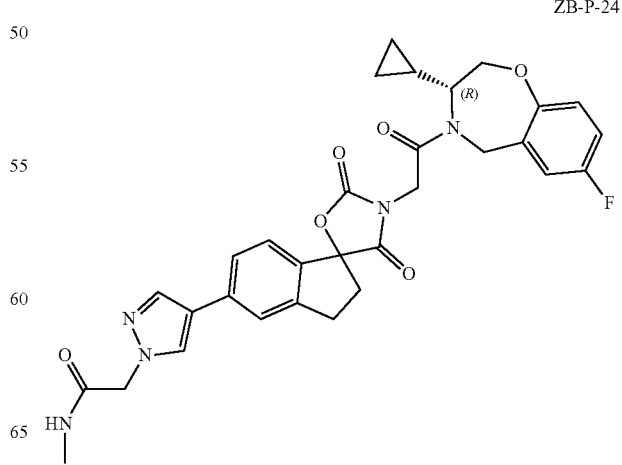

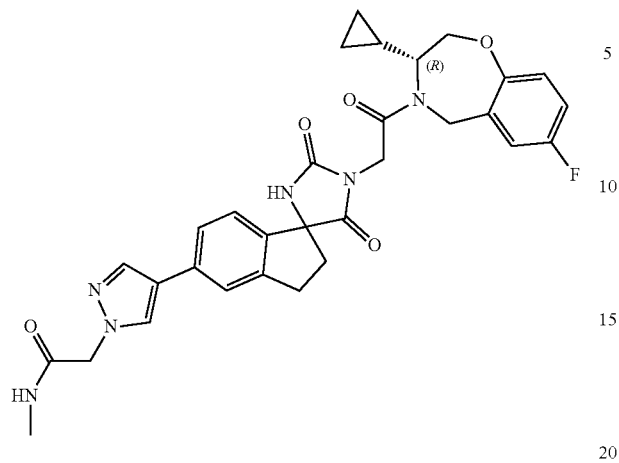
ZB-P-25
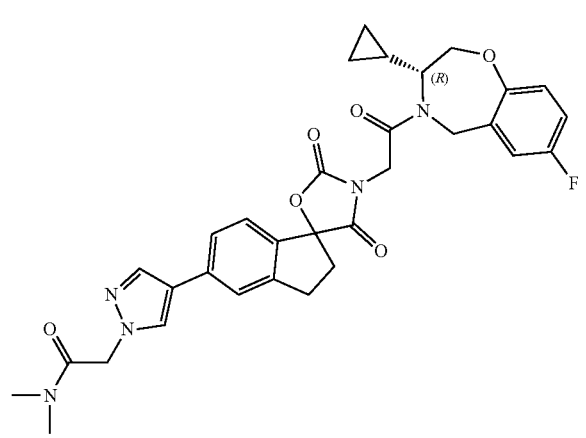
ZB-P-26
ZB-P-27
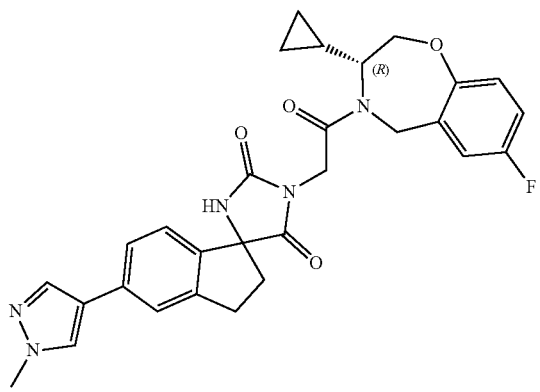
ZB-P-28
ZB-P-29
SYY-B045-1
SYY-B045-2
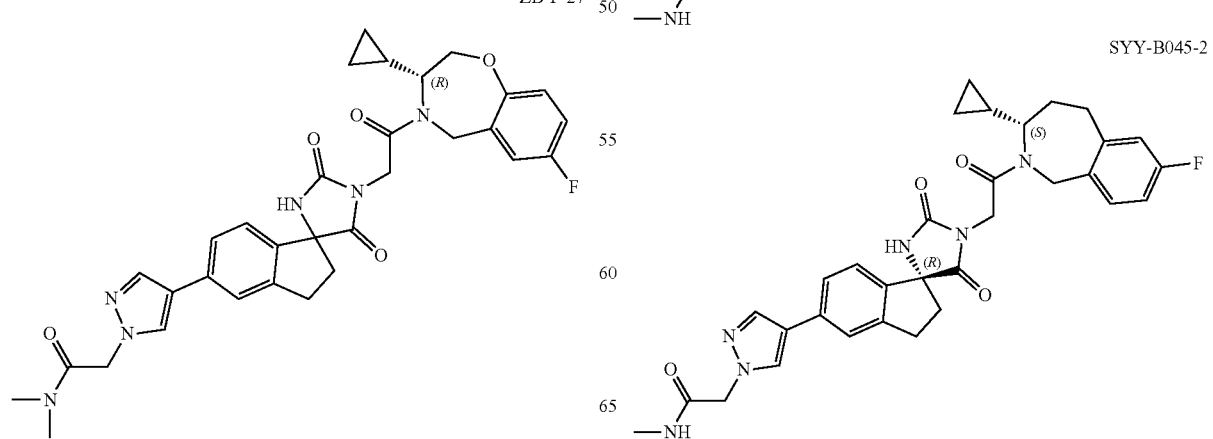

407
-continued
ZB-P-30
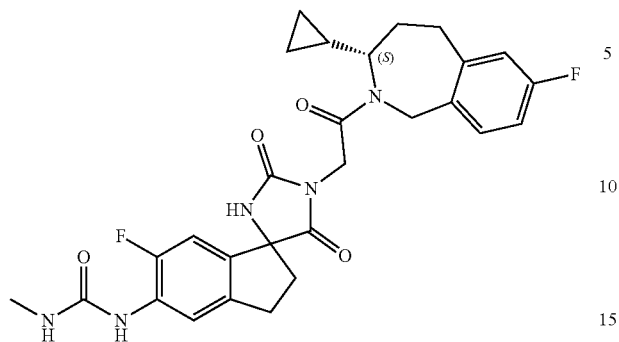
ZB-P-31
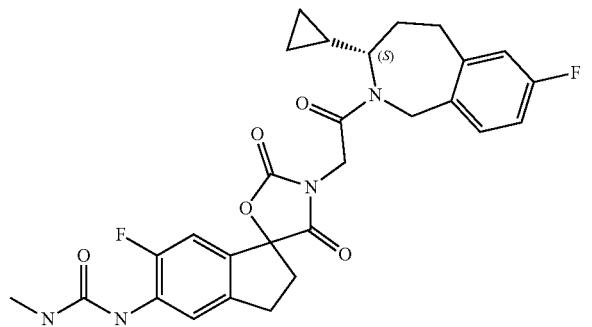
ZB-P-32
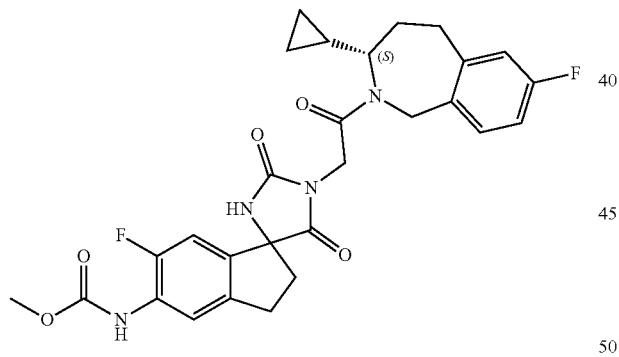
ZB-P-33
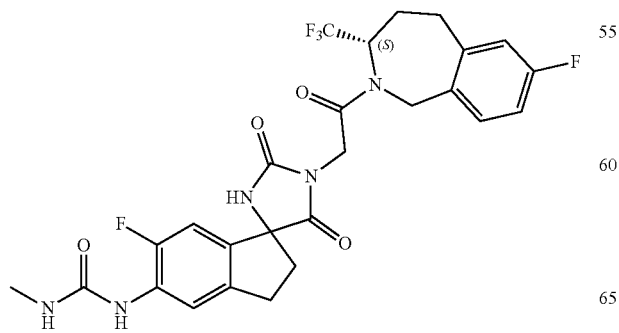
408
-continued
ZB-P-34
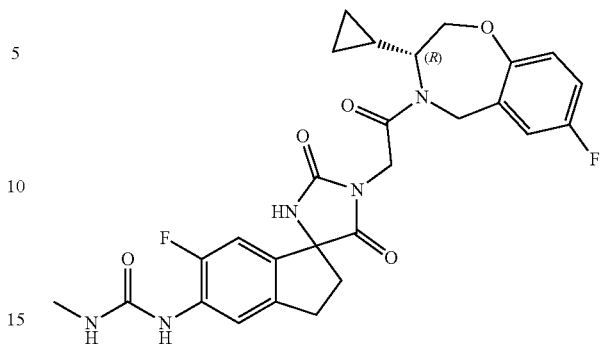
ZB-P-35
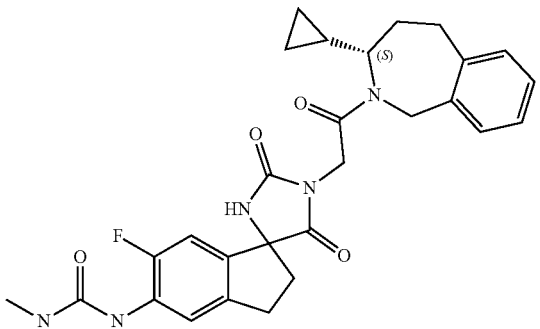
ZB-P-36
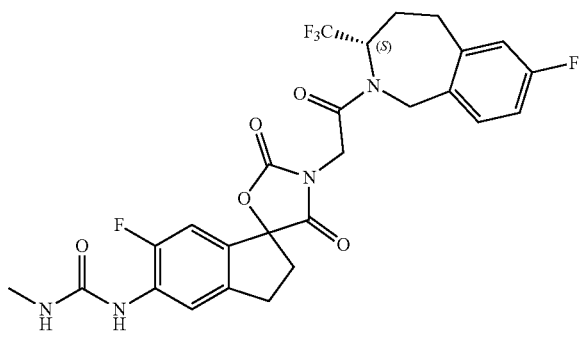
ZB-P-37
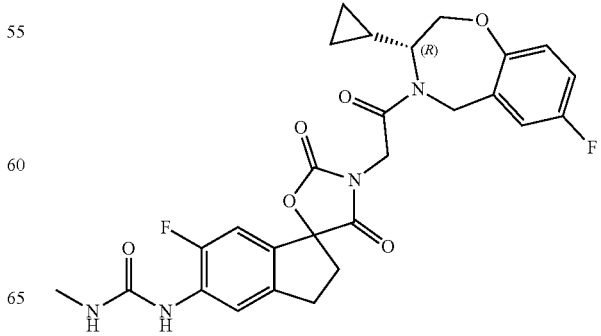

409
-continued
ZB-P-38
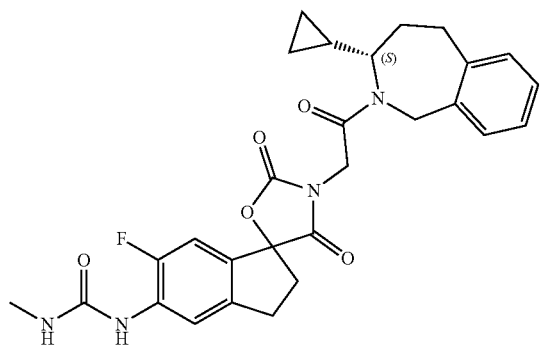
ZB-P-39
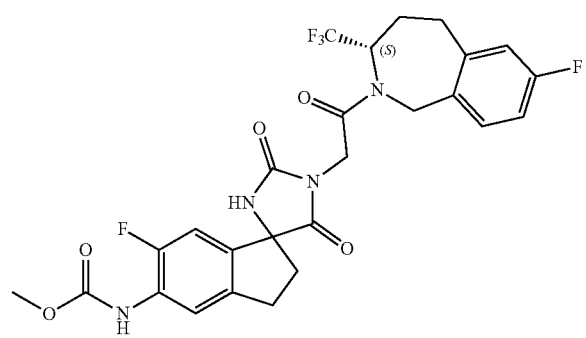
ZB-P-40
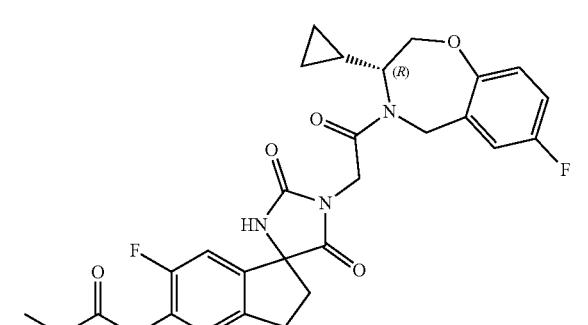
ZB-P-41
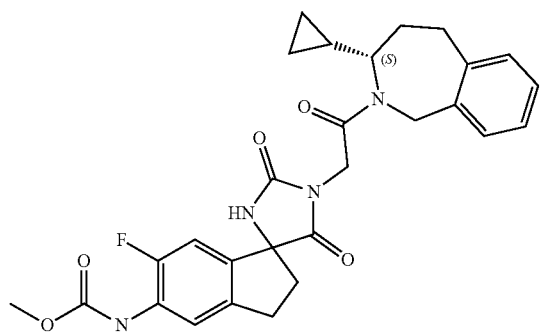
410
-continued
ZB-P-42
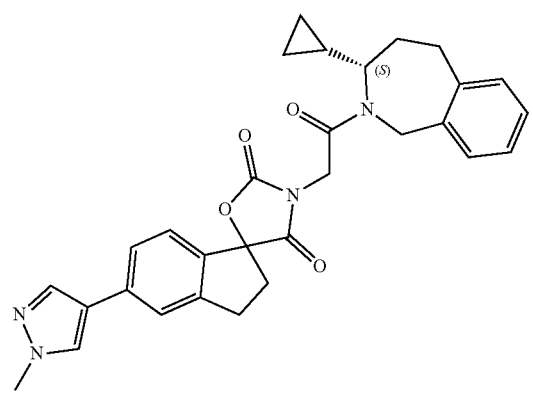
ZB-P-43
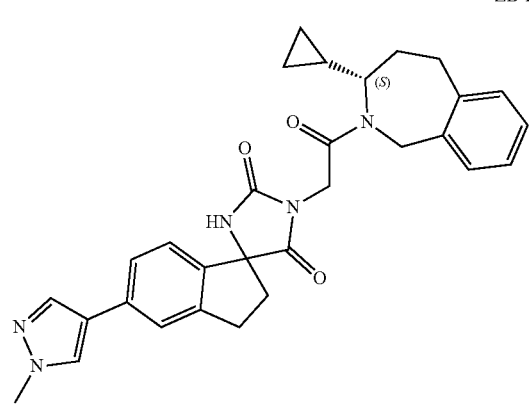
ZB-P-44
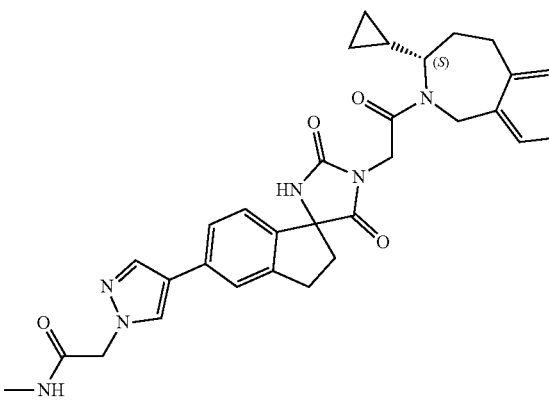
ZB-P-12-1
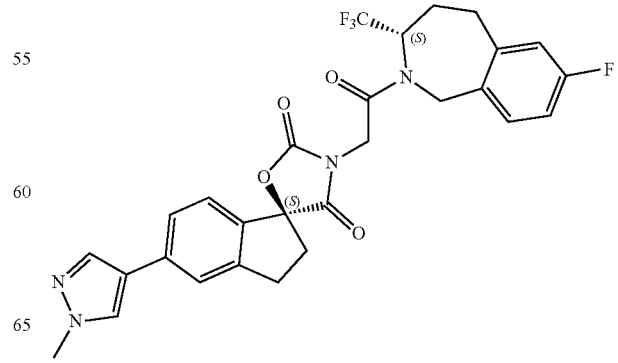

ZB-P-12-2
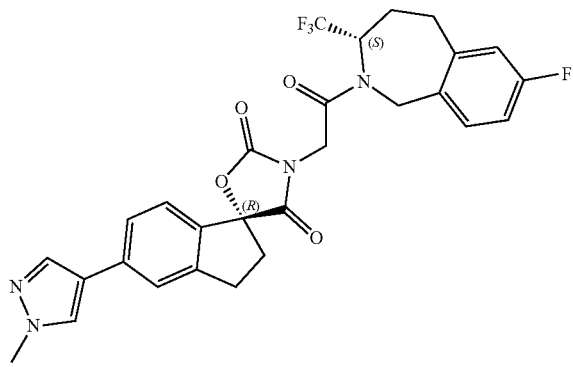
ZB-P-14-1
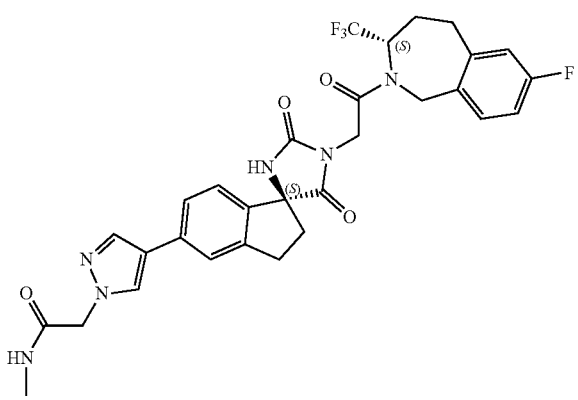
ZB-P-14-2
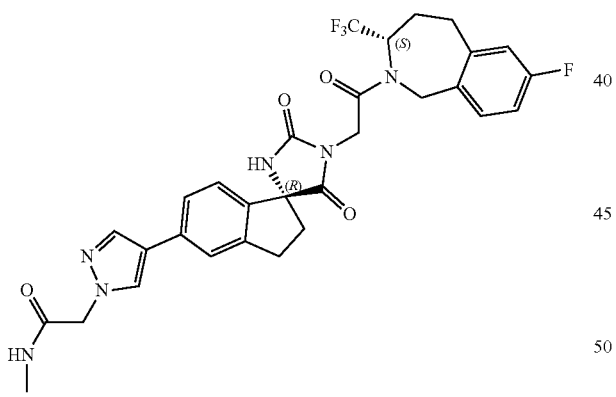
ZB-P-32-1
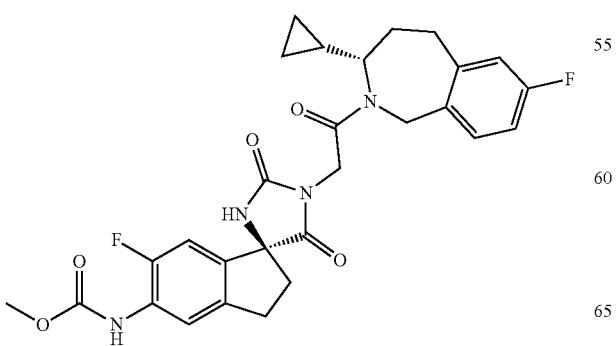
ZB-P-32-2
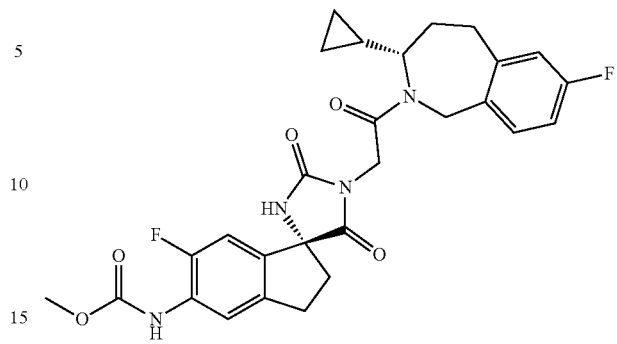
SYY-B041
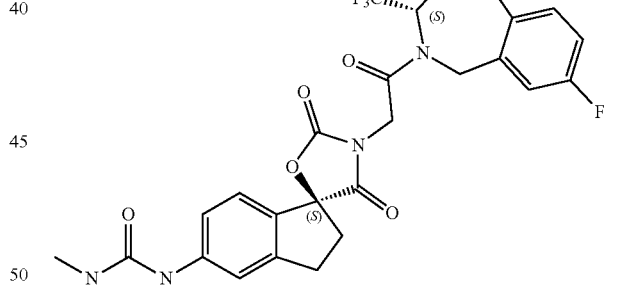
SYY-B057-1
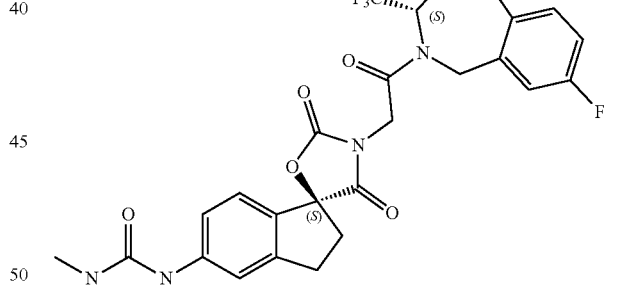
SYY-B057-2
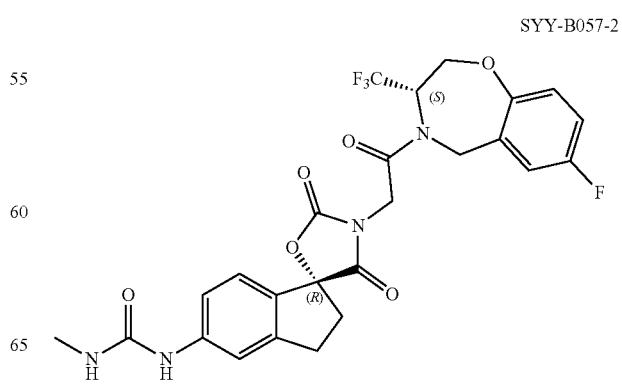

-continued
SYY-B074
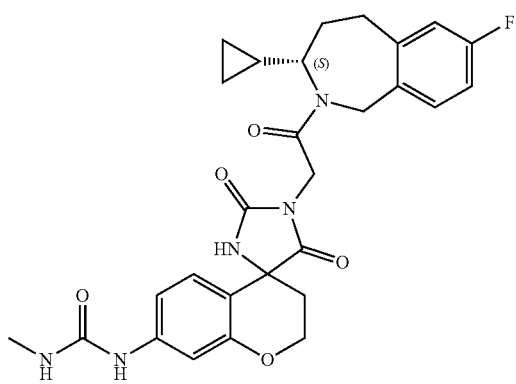
SYY-B077
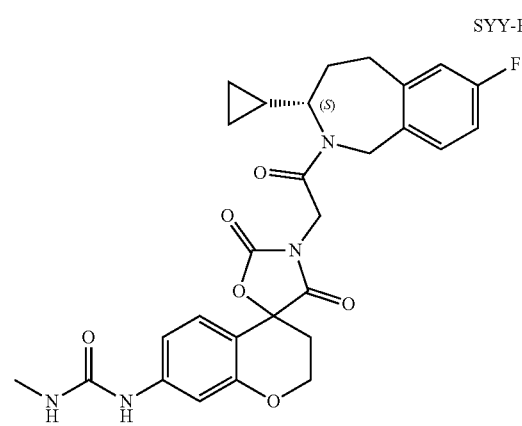
SYY-B083
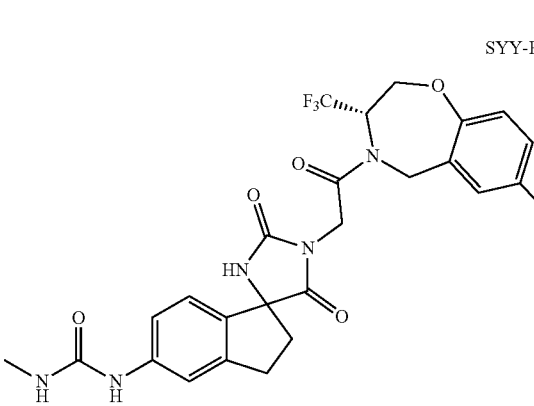
SYY-B084
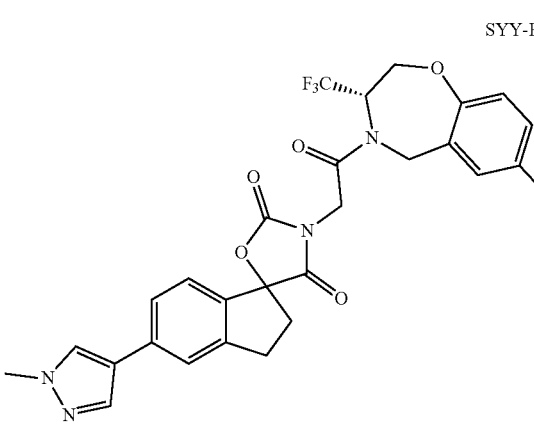
-continued
SYY-B085
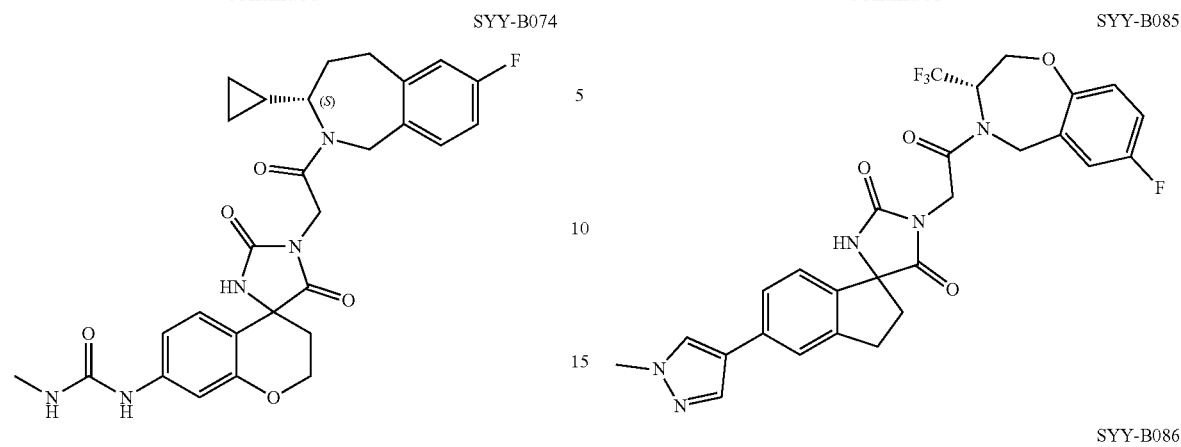
SYY-B086
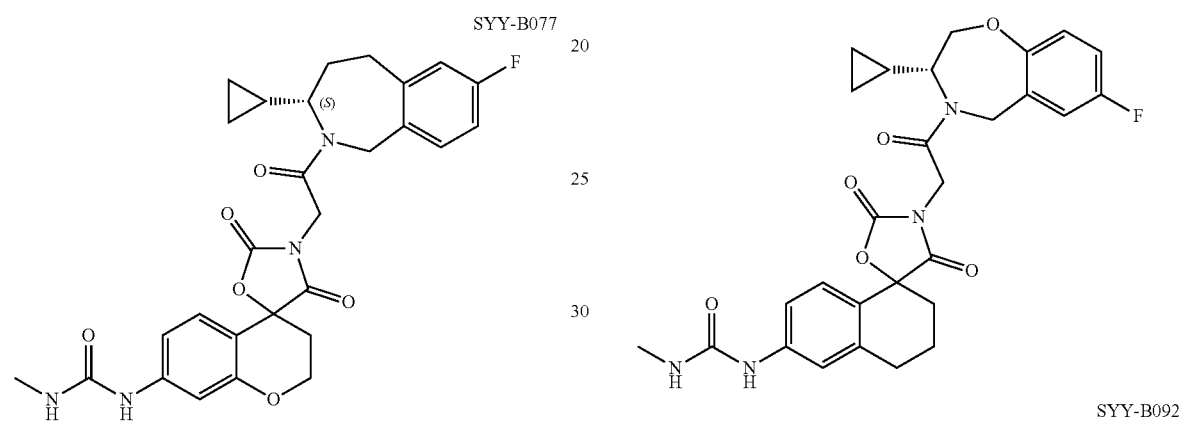
SYY-B092
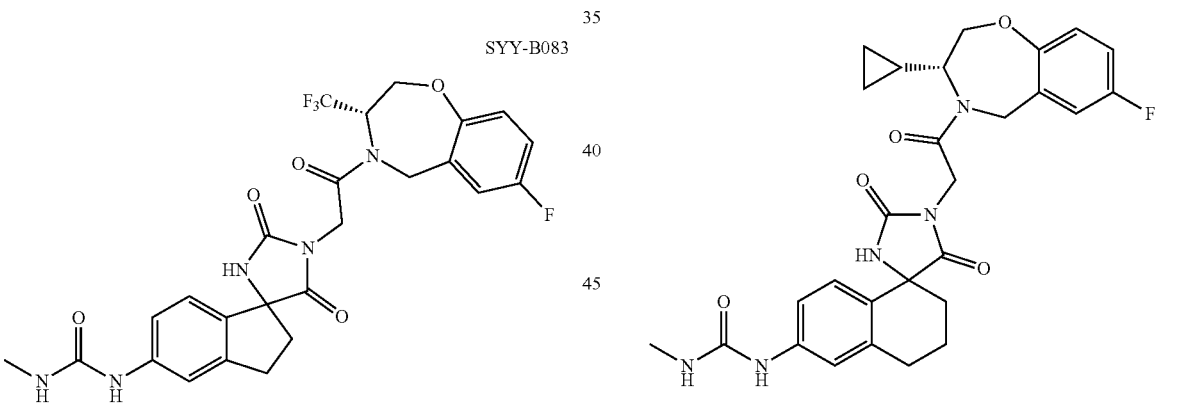
SYY-B093
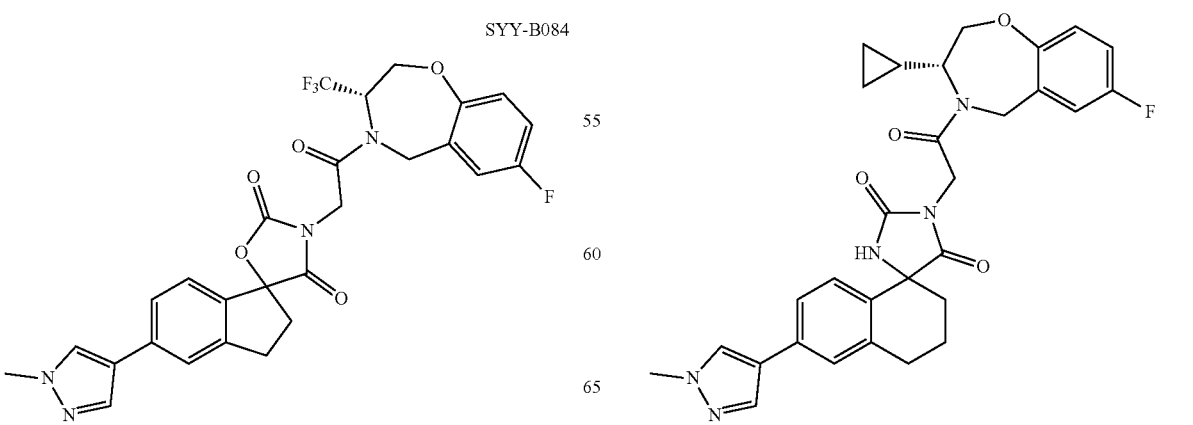

SYY-B094
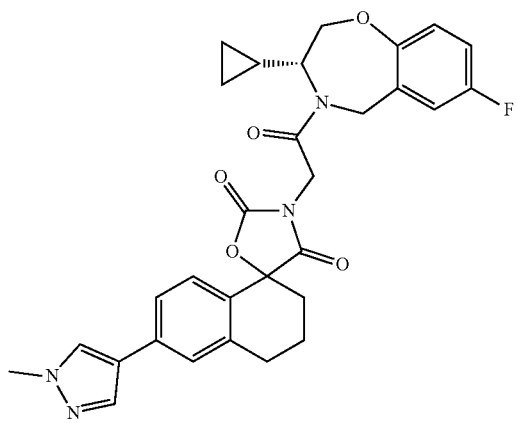
SYY-B099
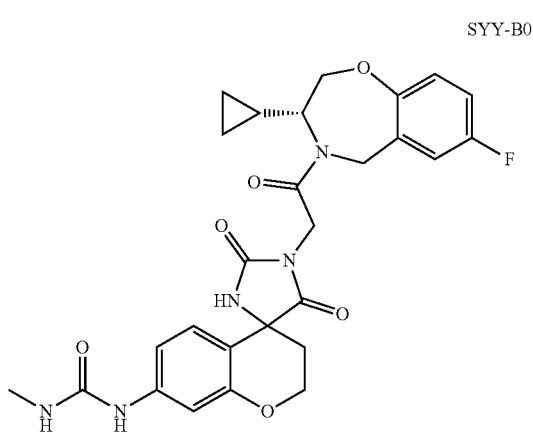
SYY-B100-1
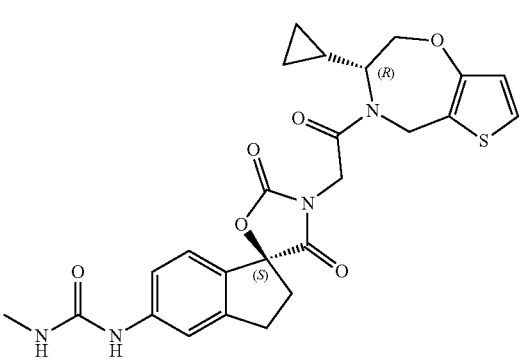
SYY-B100-2
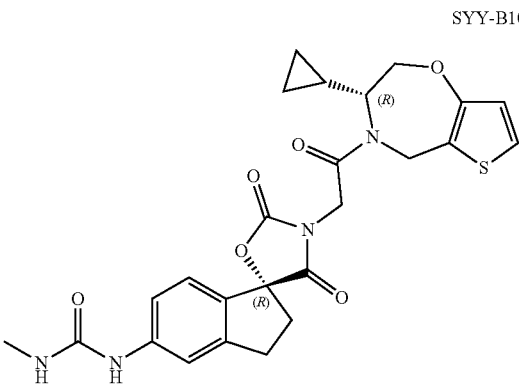
ZB-P-21-1
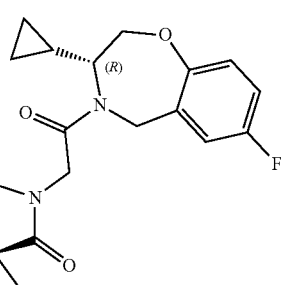
ZB-P-21-2
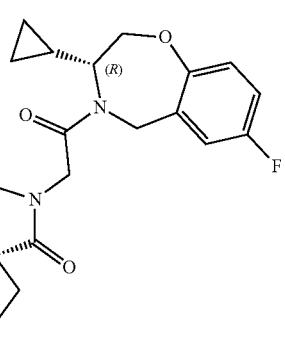
ZB-P-28-1
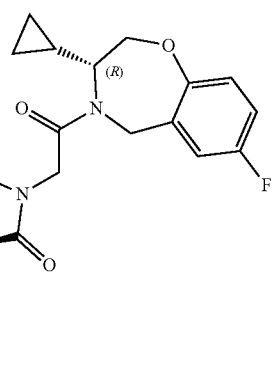
ZB-P-28-2
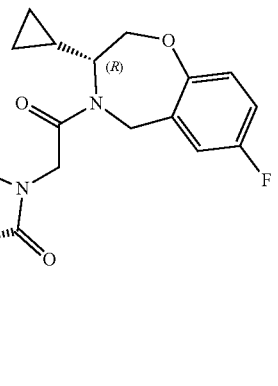

-continued
ZB-P-29-1
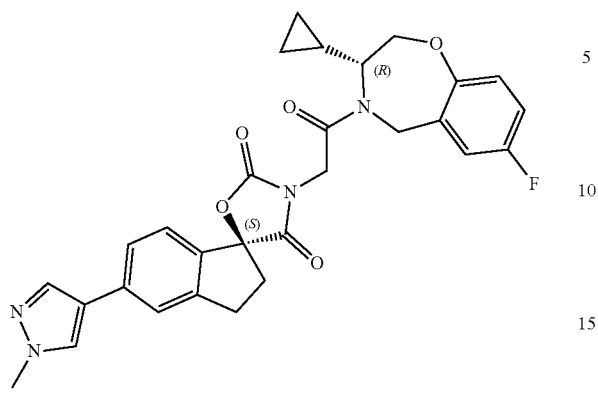
ZB-P-29-2
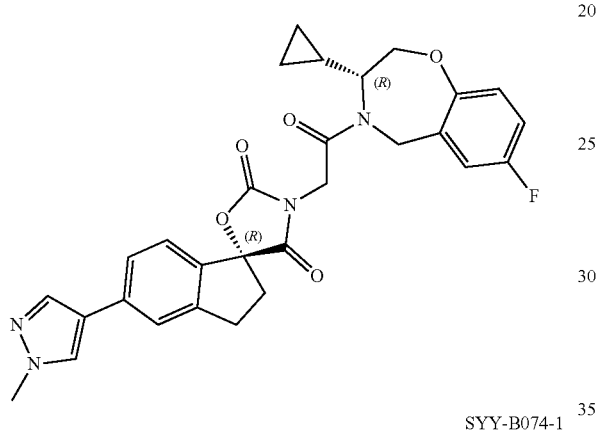
SYY-B074-1
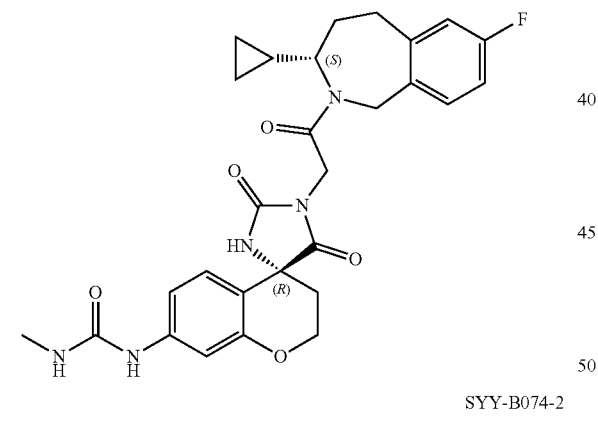
SYY-B074-2
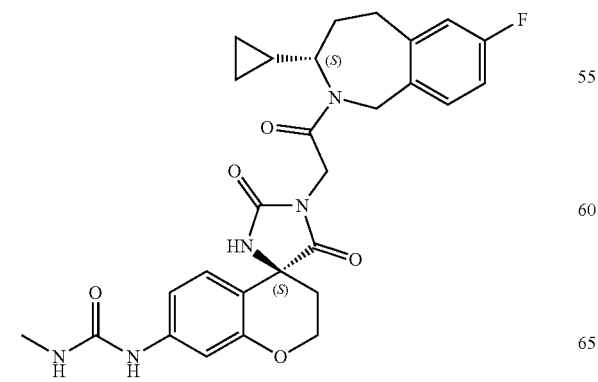
-continued
SYY-B077-1
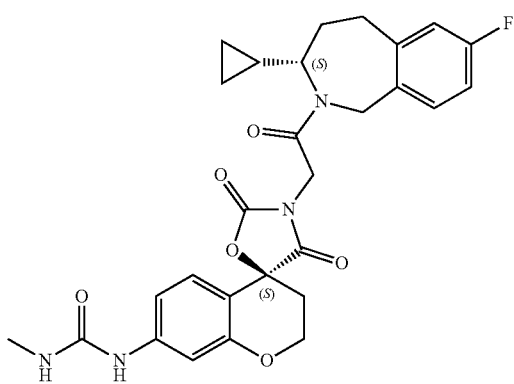
SYY-B077-2
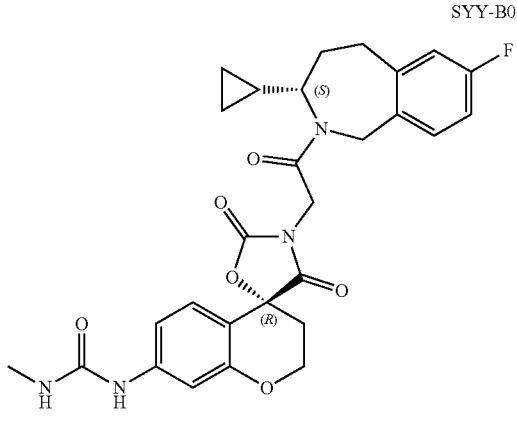
SYY-B083-1
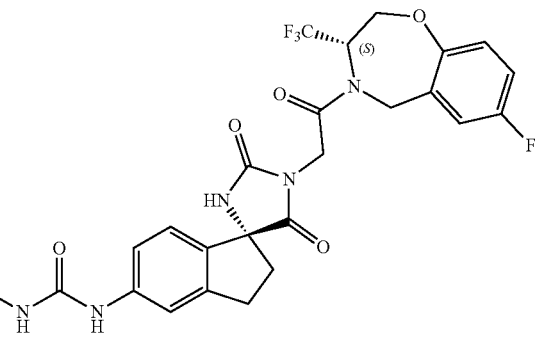
SYY-B083-2
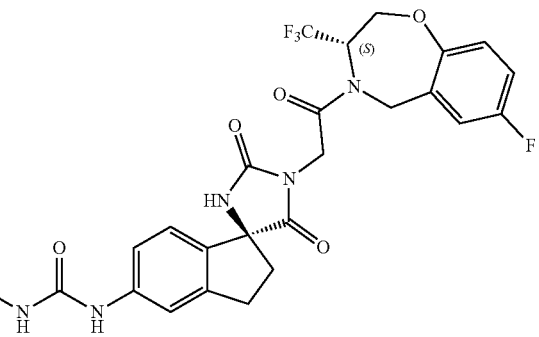

SYY-B084-1
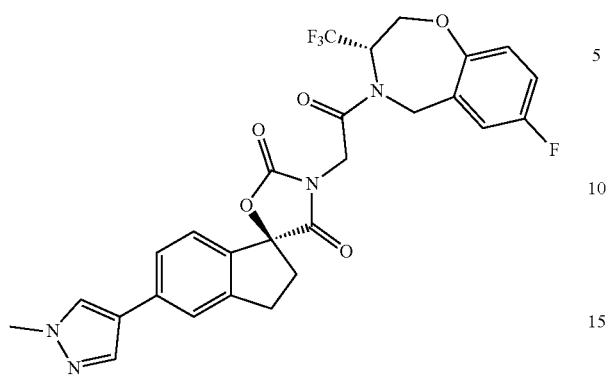
SYY-B086-1
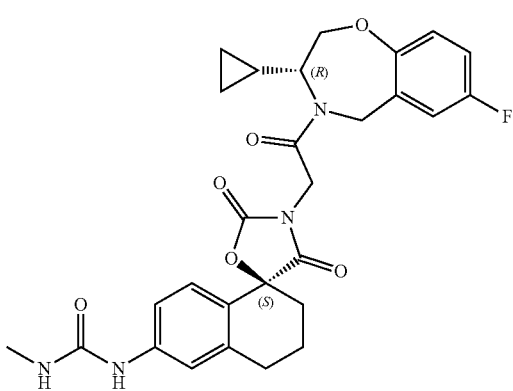
SYY-B084-2
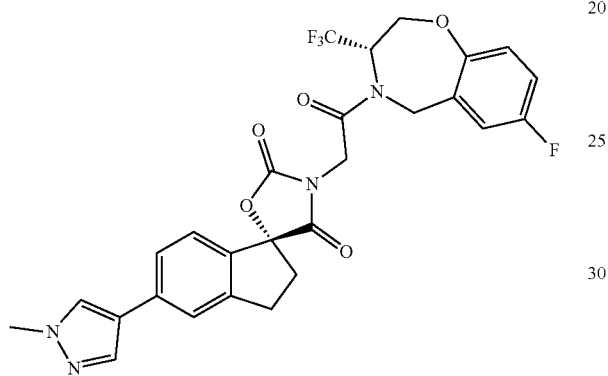
SYY-B086-2
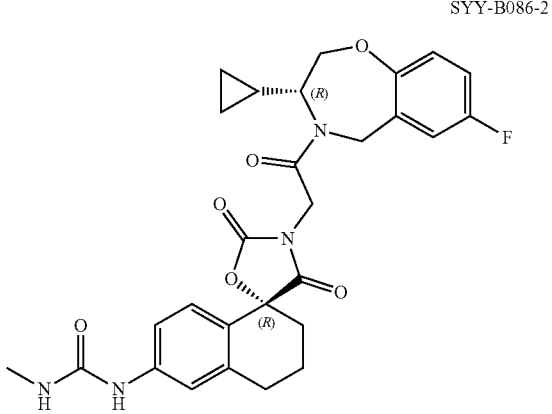
SYY-B085-1
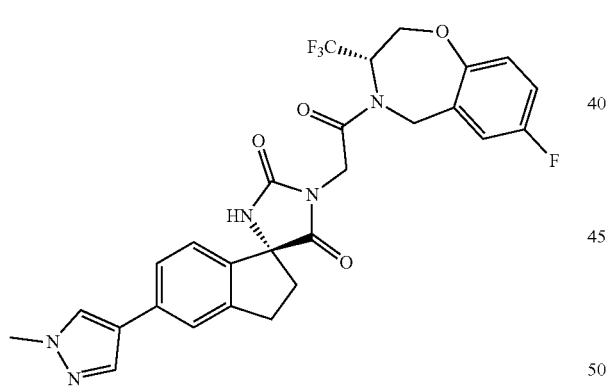
SYY-B092-1
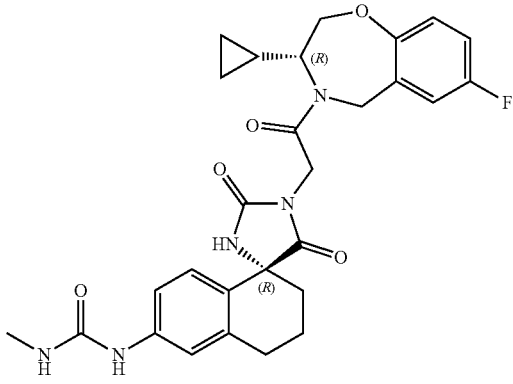
SYY-B085-2
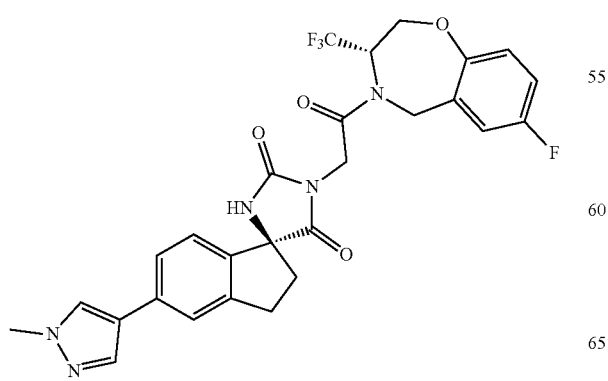
SYY-B092-2
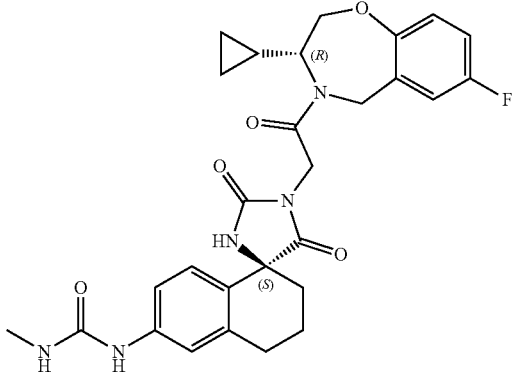

-continued
SYY-B093-1
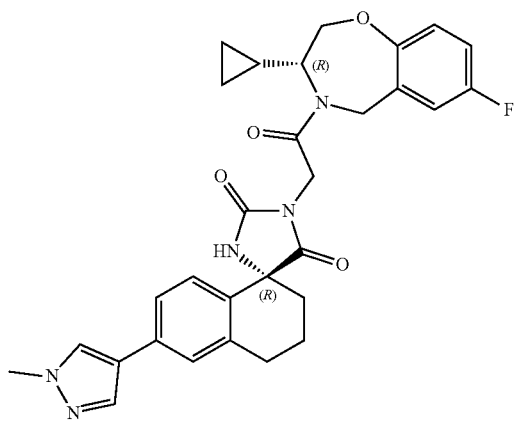
SYY-B093-2
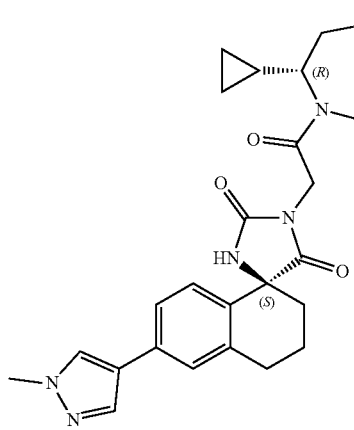
SYY-B094-1
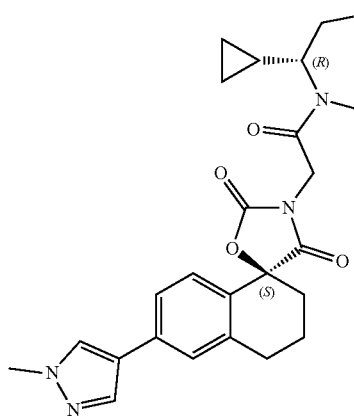
-continued
SYY-B094-2
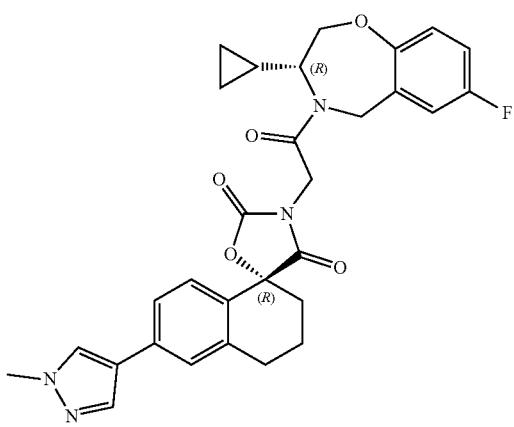
SYY-B099-1
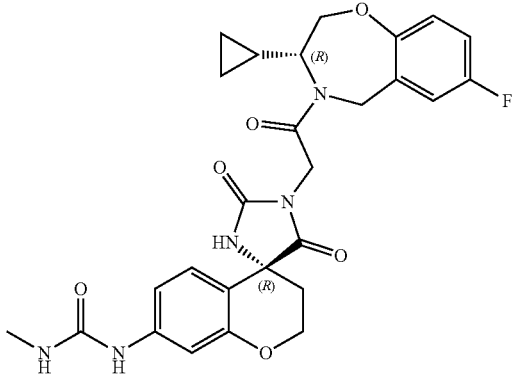
SYY-B099-2
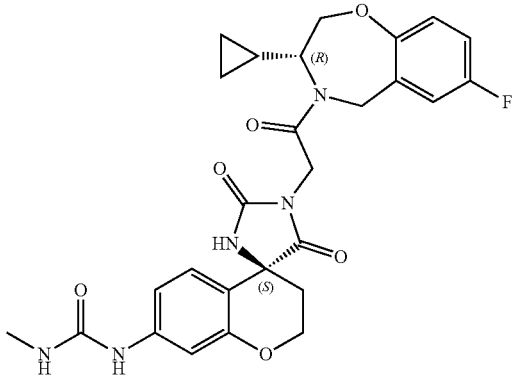
SYY-B081-1
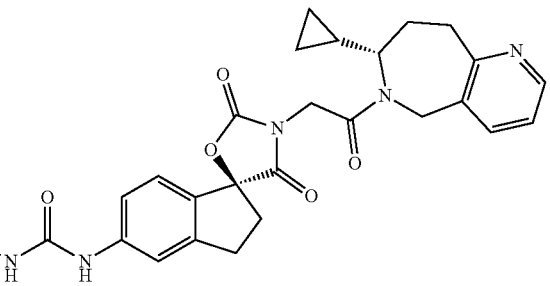

423
-continued
SYY-B081-2
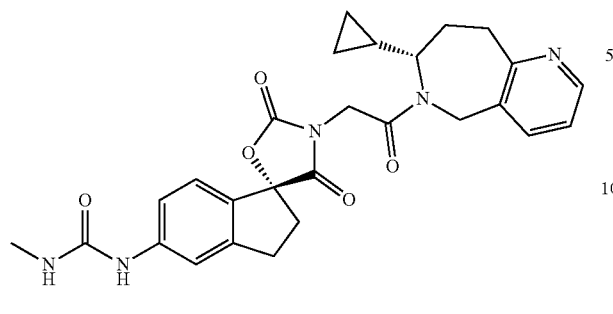
SYY-B088
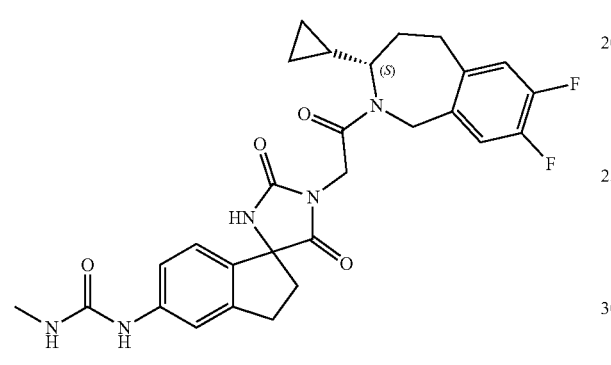
SYY-B088-1
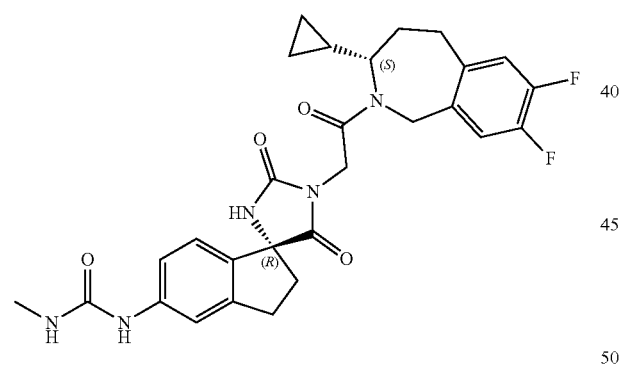
SYY-B088-2
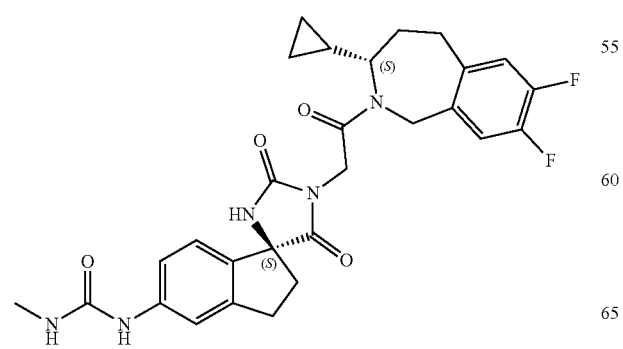
424
-continued
SYY-B090-1
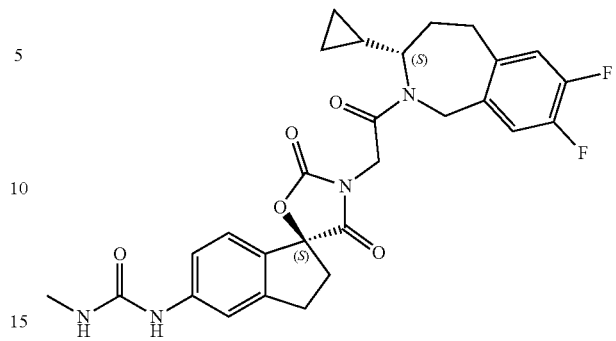
SYY-B090-2
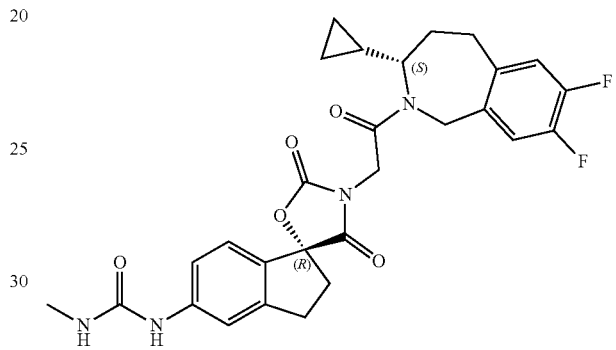
SYY-B095
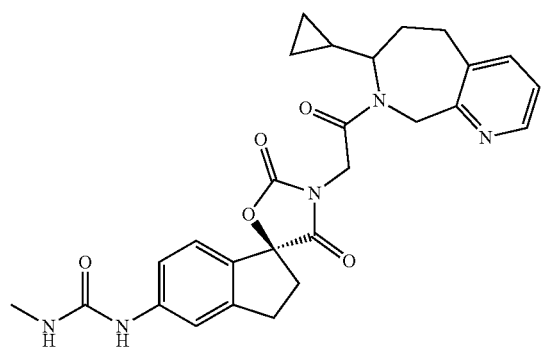
SYY-B095-1
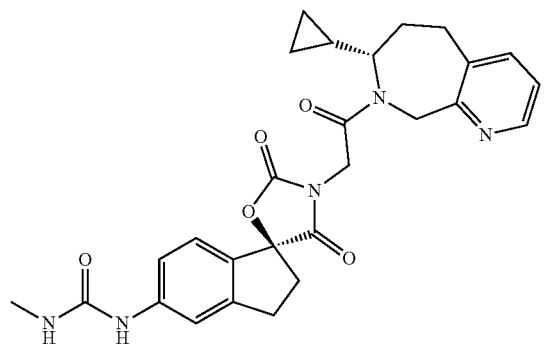

SYY-B095-2

SYY-B096

SYY-B096-1

SYY-B096-2

SYY-B097-1

SYY-B097-2

SYY-B102-1

SYY-B102-2

-continued
SYY-B104
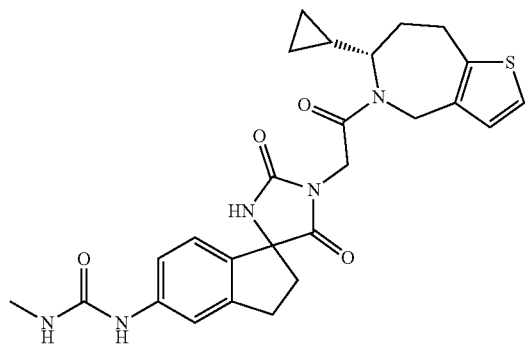
SYY-B104-1
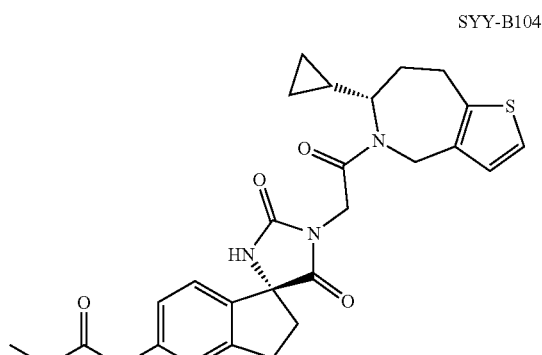
SYY-B104-2
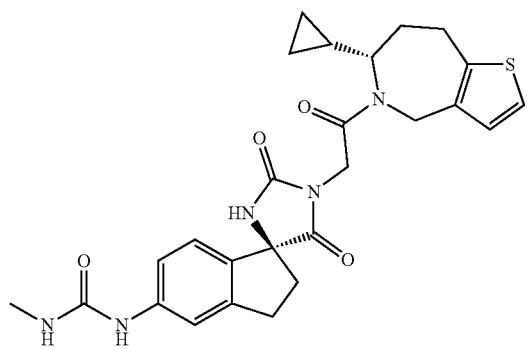
SYY-B106
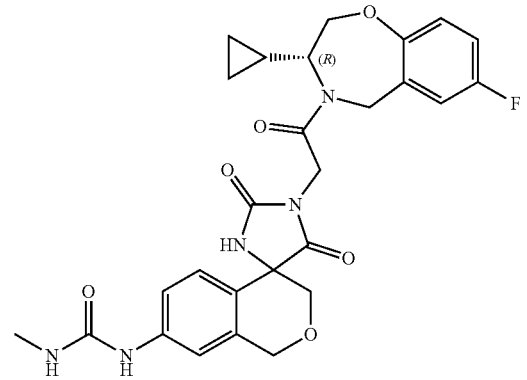
-continued
SYY-B106-1
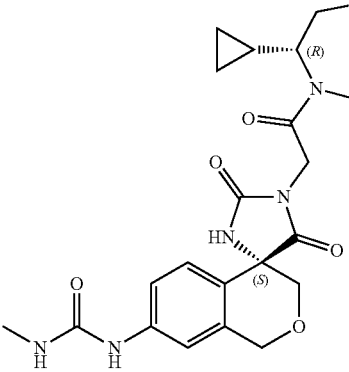
SYY-B106-2
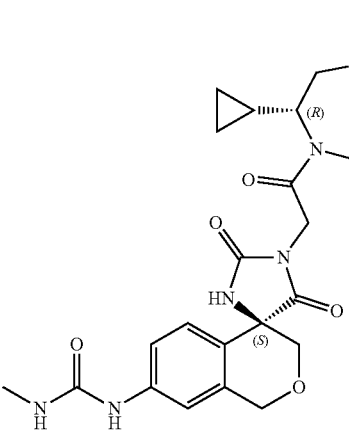
SYY-B108
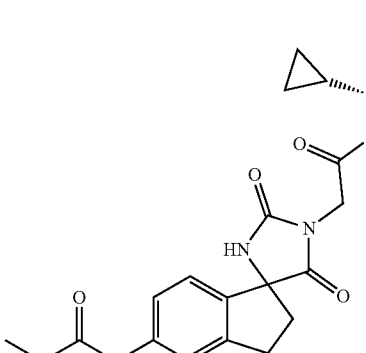
SYY-B108-1
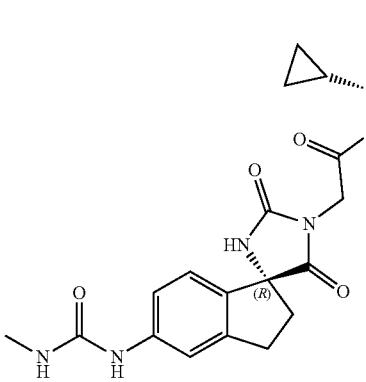

SYY-B108-2
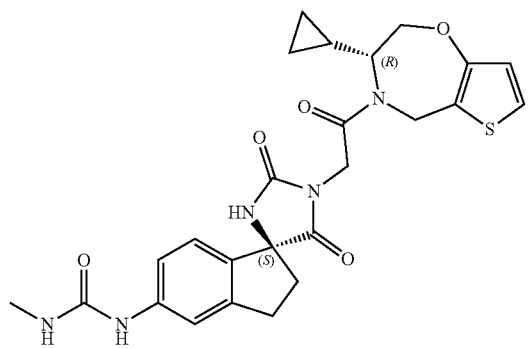
ZB-P-30-1
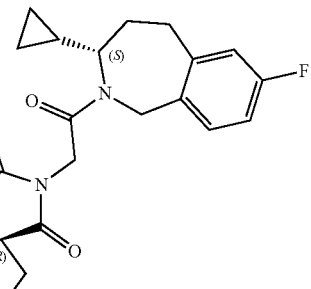
SYY-B082-1
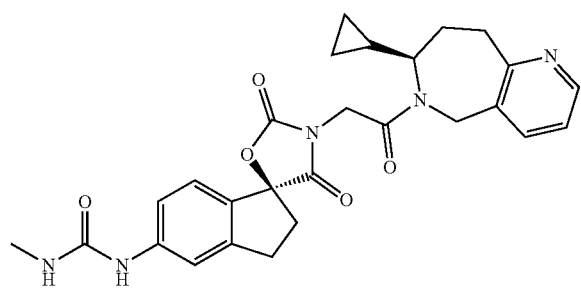
ZB-P-30-2
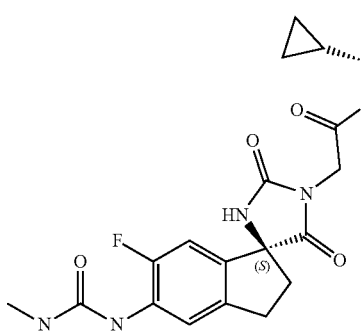
SYY-B082-2
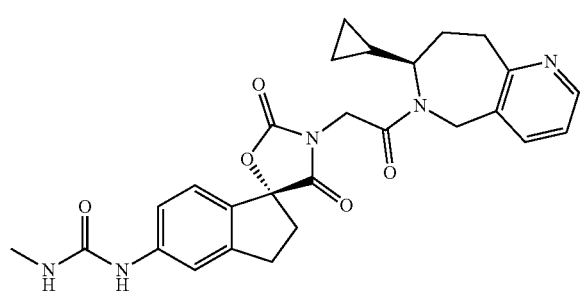
ZB-P-31-1
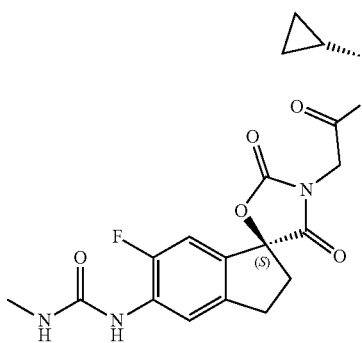
SYY-B098-1
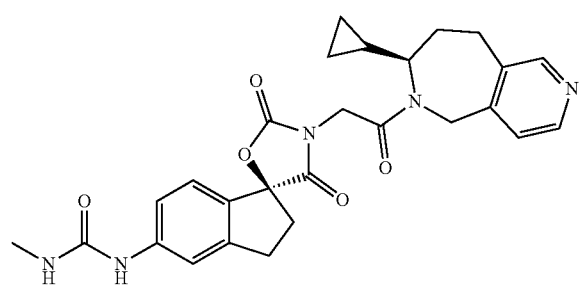
ZB-P-31-2
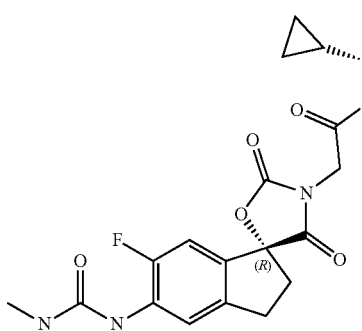
SYY-B098-2
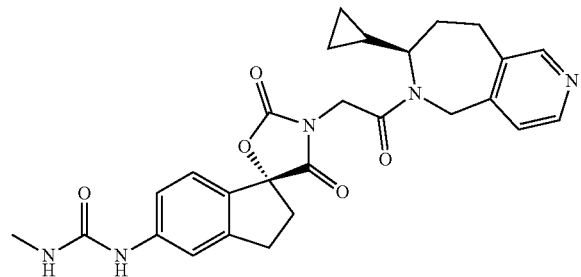

431
-continued
SYY-B110
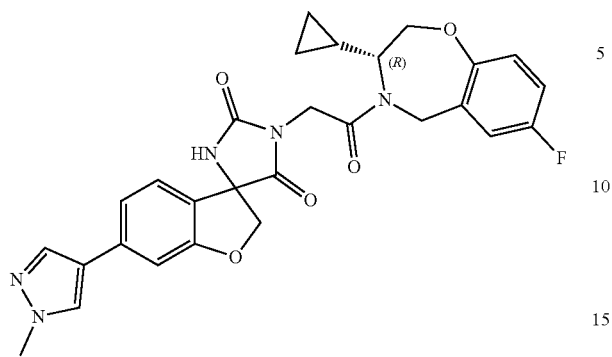
SYY-B110-1
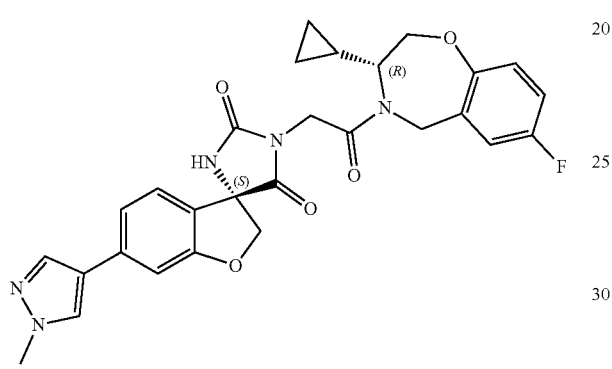
SYY-B110-2
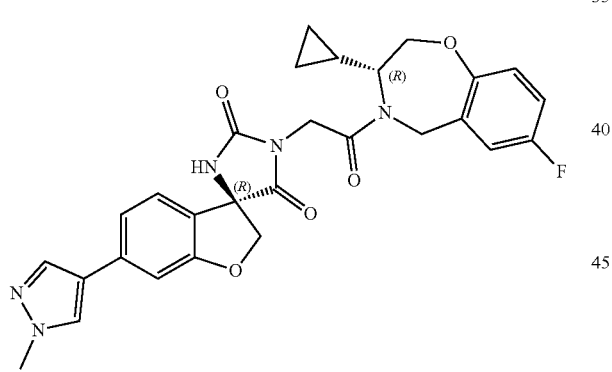
SYY-B112
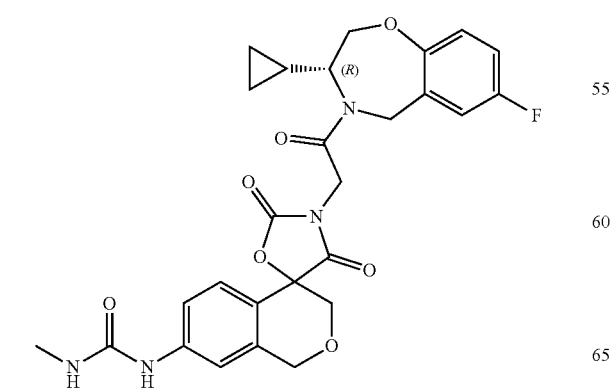
432
-continued
SYY-B112-1
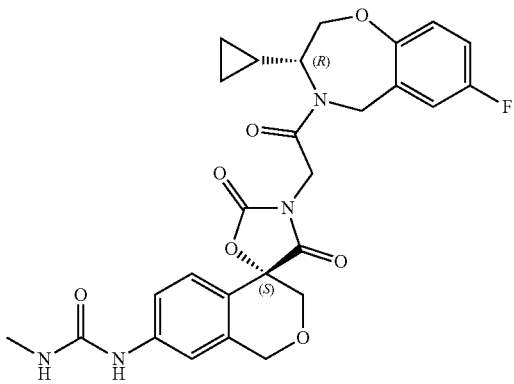
SYY-B112-2
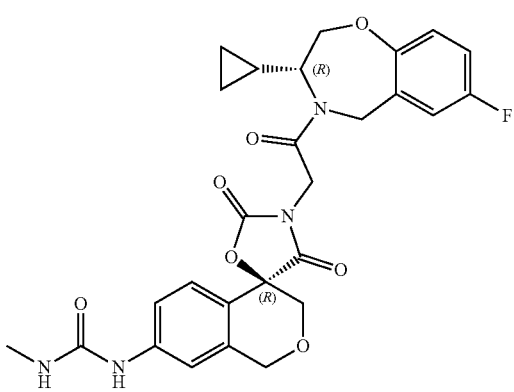
SYY-B116-1
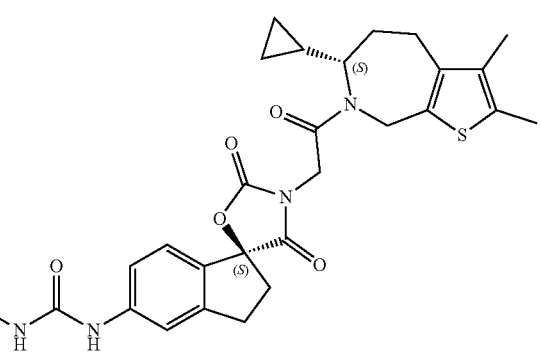
SYY-B116-2
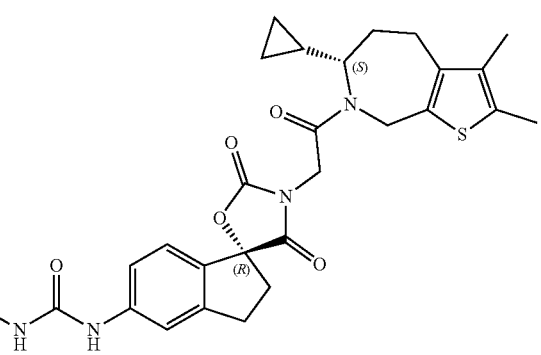

433
-continued
SYY-B118-2
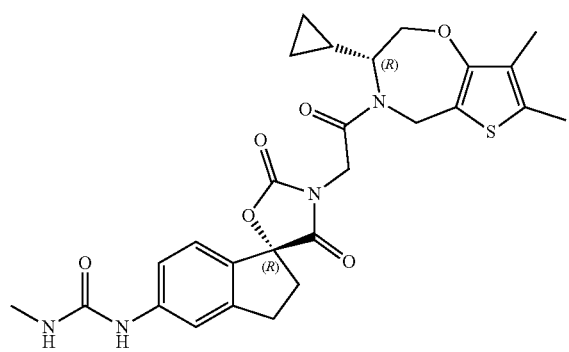
SYY-B120-1
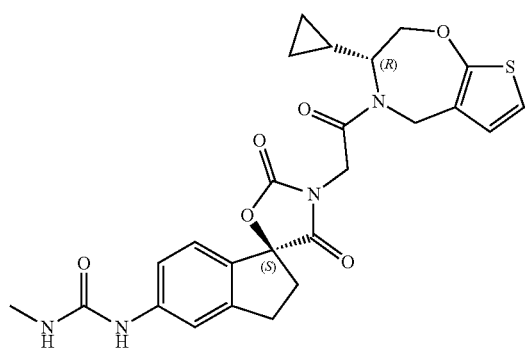
SYY-B120-2
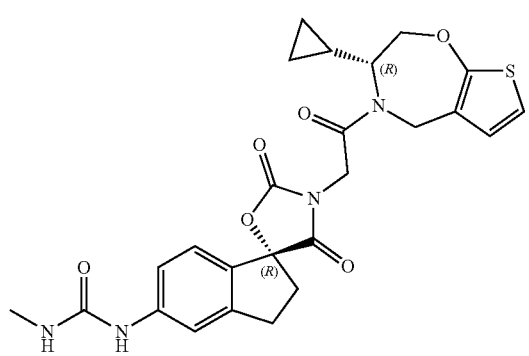
SYY-B122
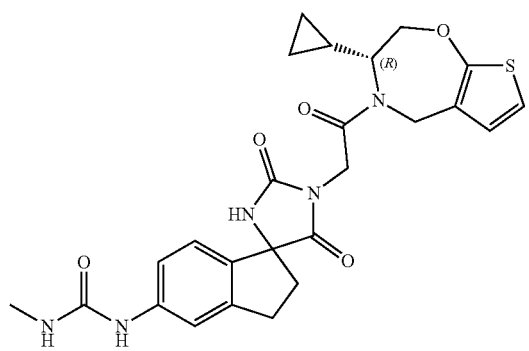
434
-continued
SYY-B122-1
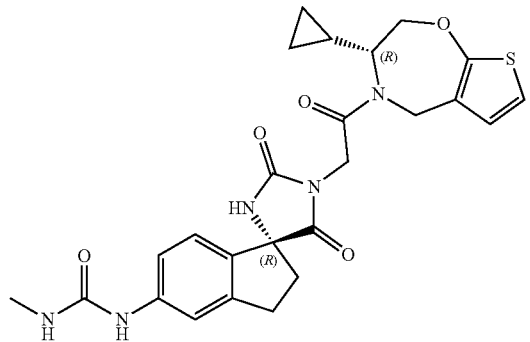
SYY-B122-2
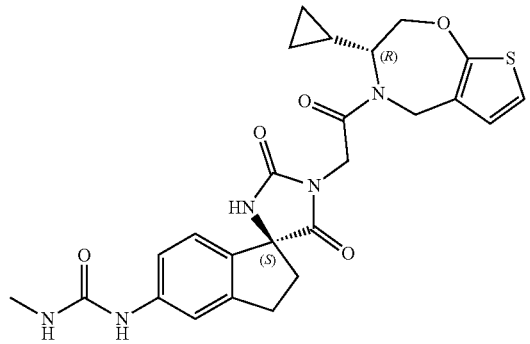
SYY-B124
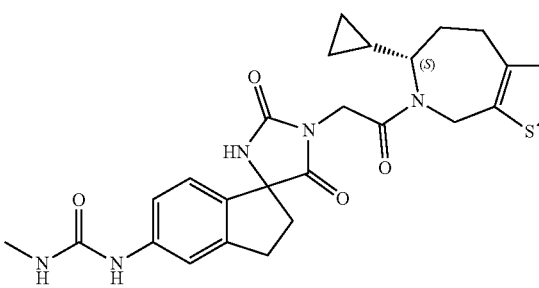
SYY-B124-1
SYY-B124-2
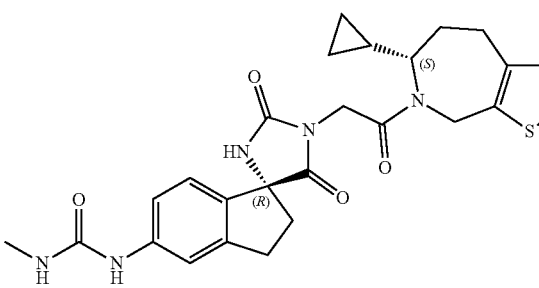

SYY-B126-1
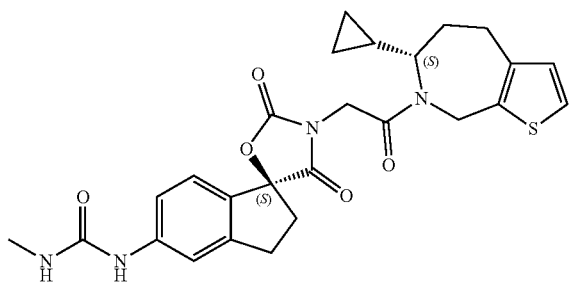
SYY-B126-2
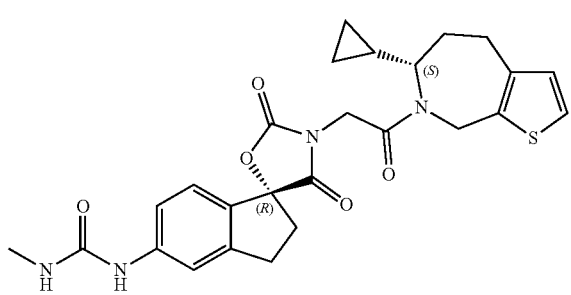
SYY-B130
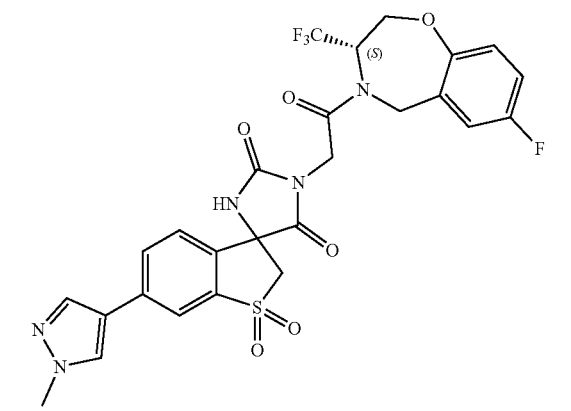
SYY-B130-1
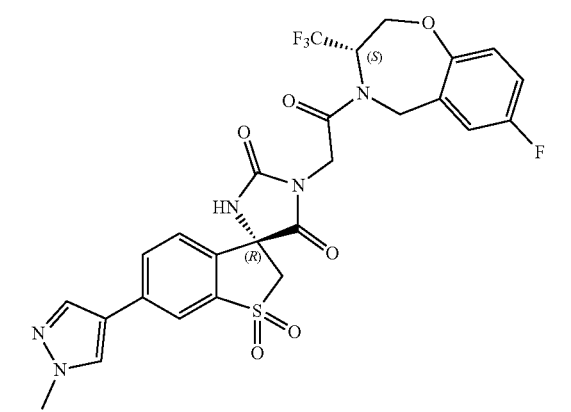
SYY-B130-2
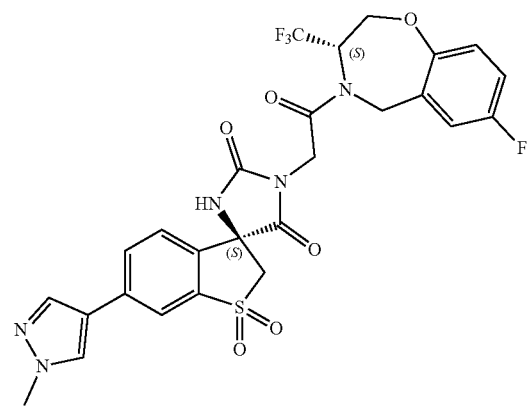
208-3
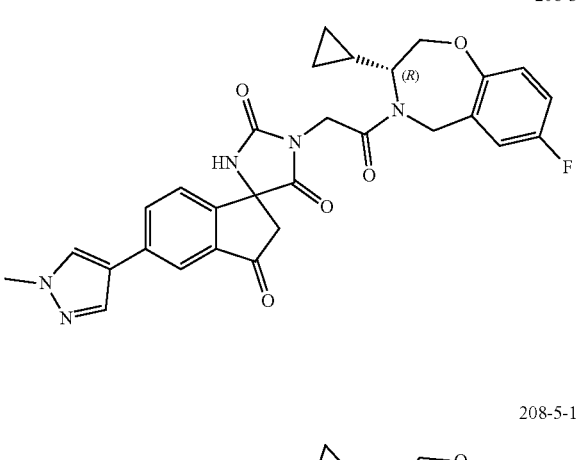
208-5-1
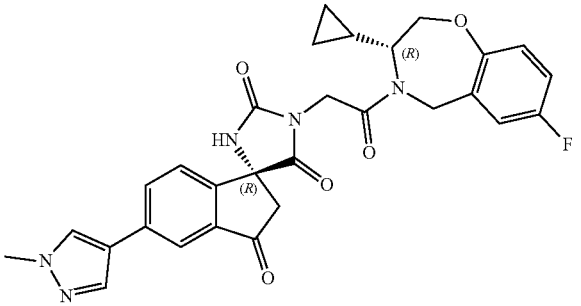
208-5-2
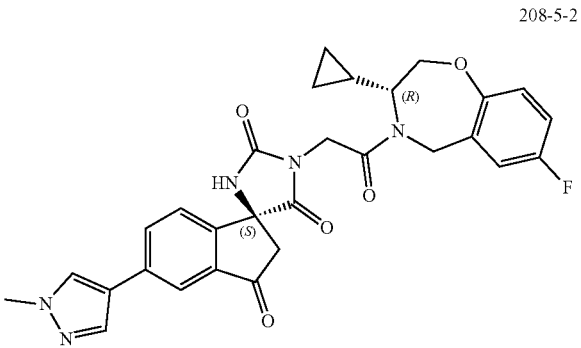

437
-continued
SYY-B170-1
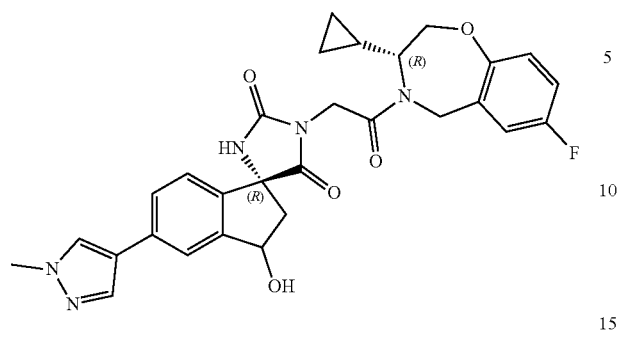
SYY-B170-2
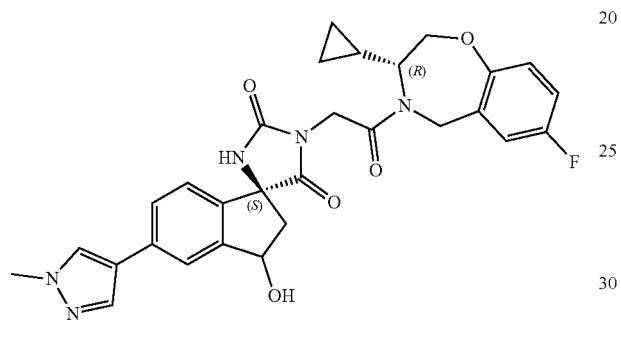
SYY-B132-1
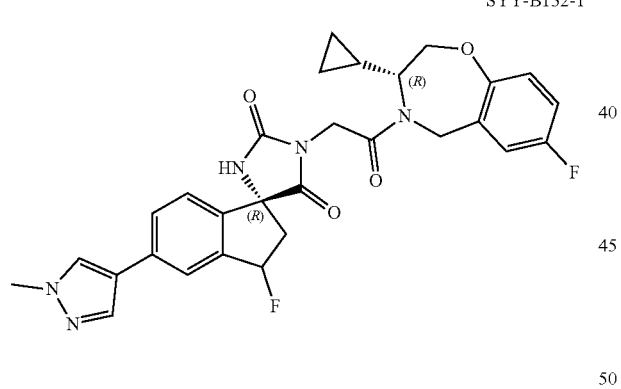
SYY-B132-2
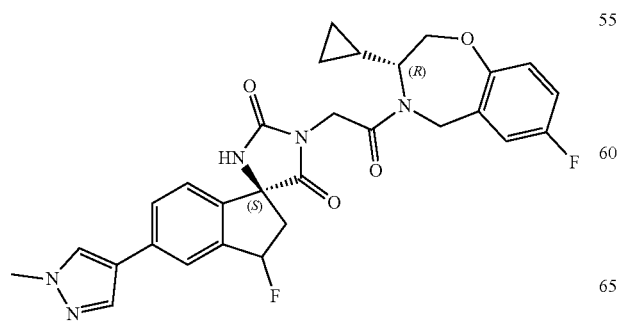
438
-continued
SYY-B136
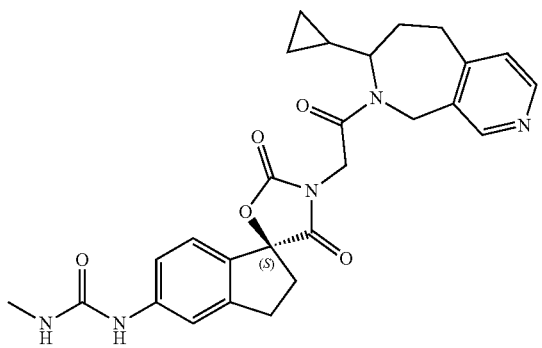
SYY-B136-1
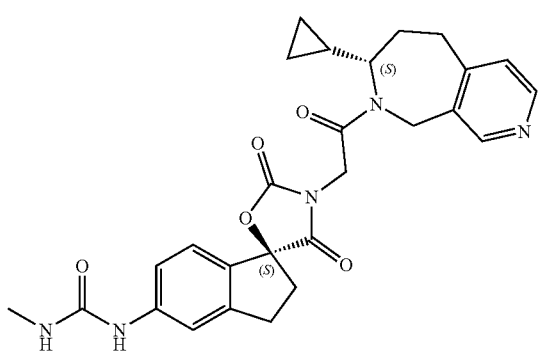
SYY-B136-2
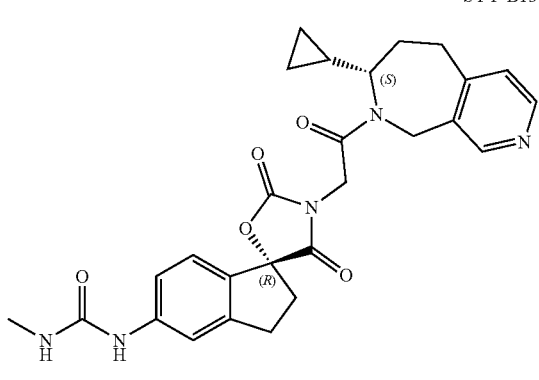
SYY-B137
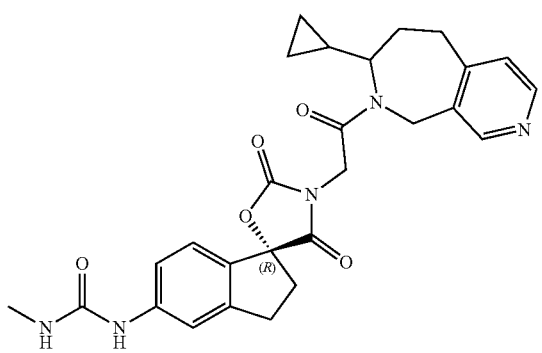

439
-continued
SYY-B137-1
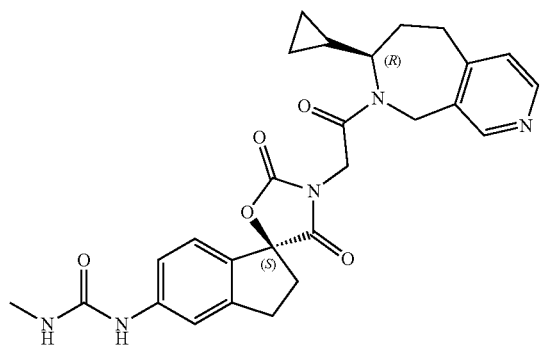
SYY-B137-2
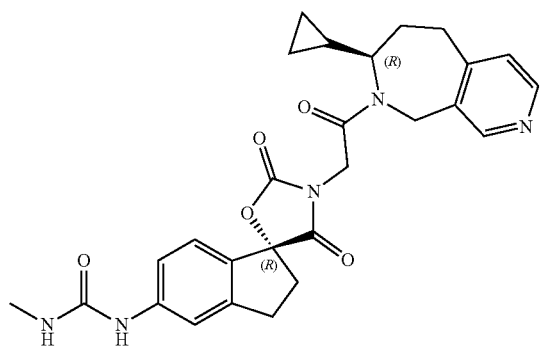
SYY-B138
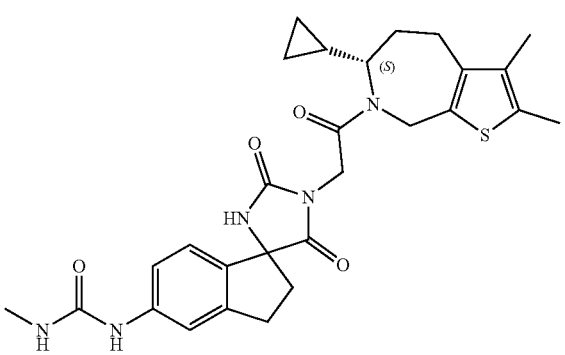
SYY-B138-1
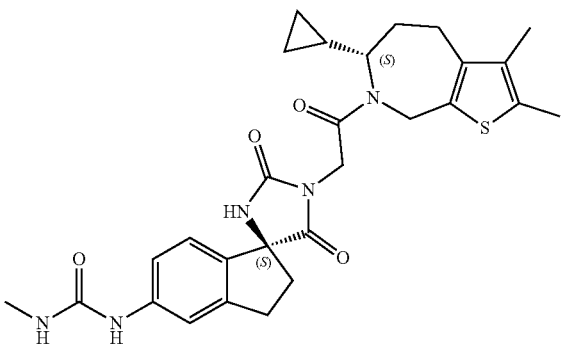
440
-continued
SYY-B138-2
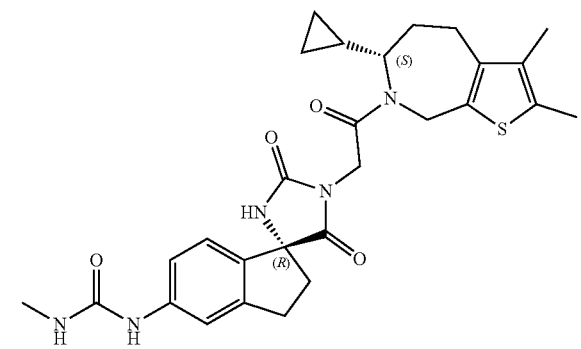
SYY-B140-1
SYY-B140-2
SYY-B142
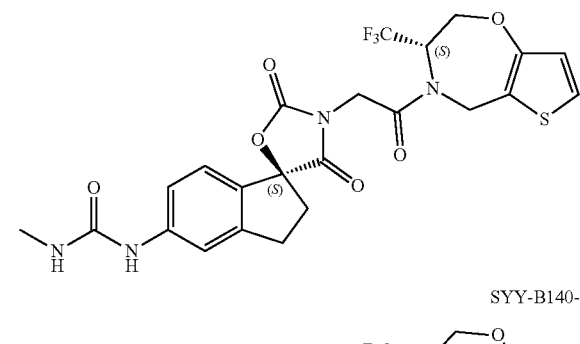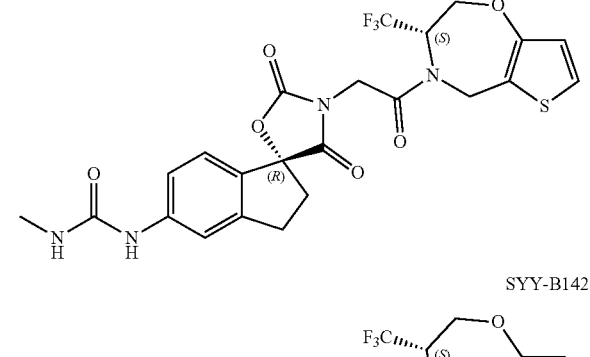
SYY-B142-1
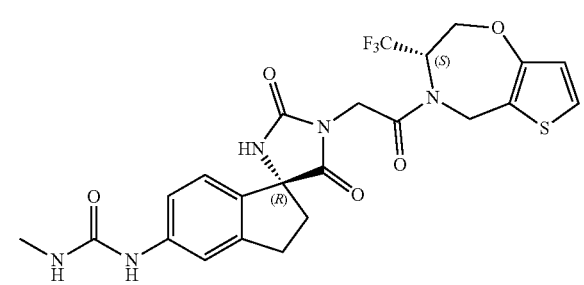

441 -continued
SYY-142-2
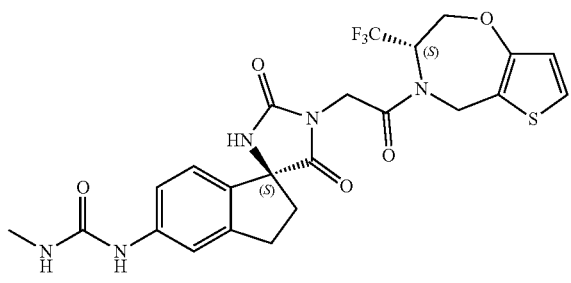
SYY-B144
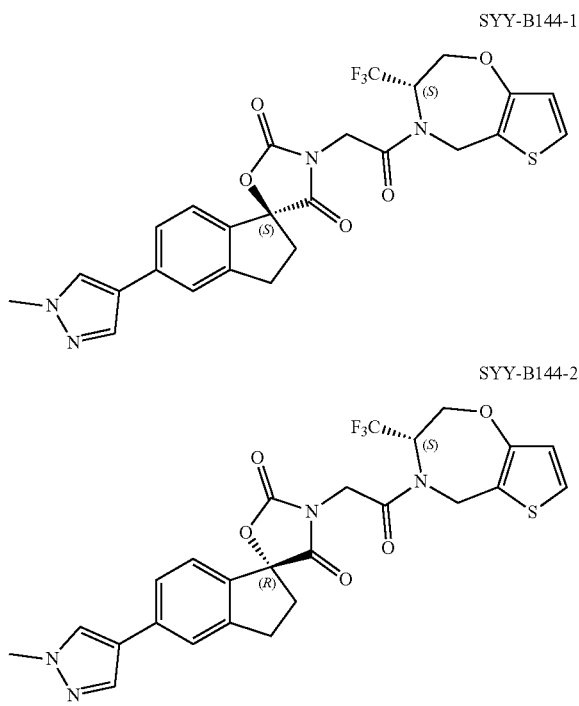
SYY-B144-1
SYY-B144-2
SYY-B146
442 -continued
SYY-B146-1
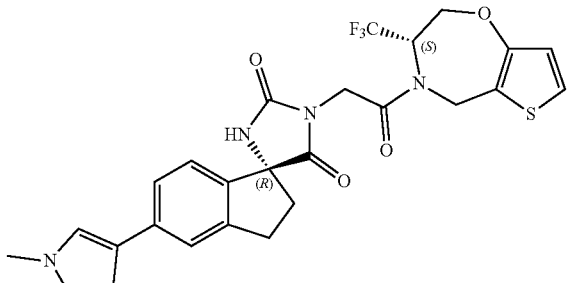
SYY-B146-2
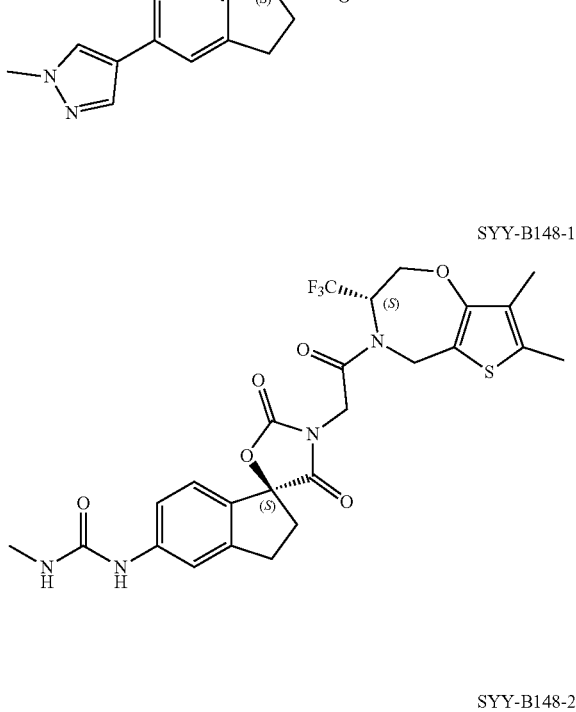
SYY-B148-1
SYY-B148-2
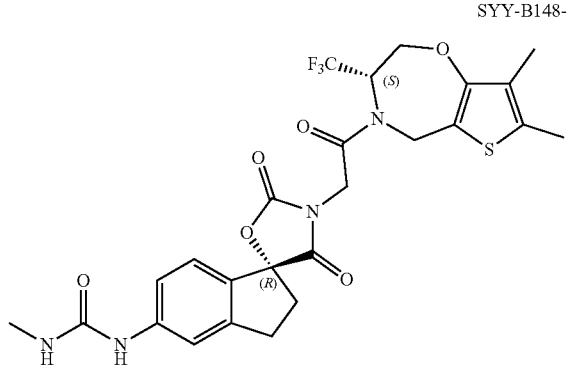

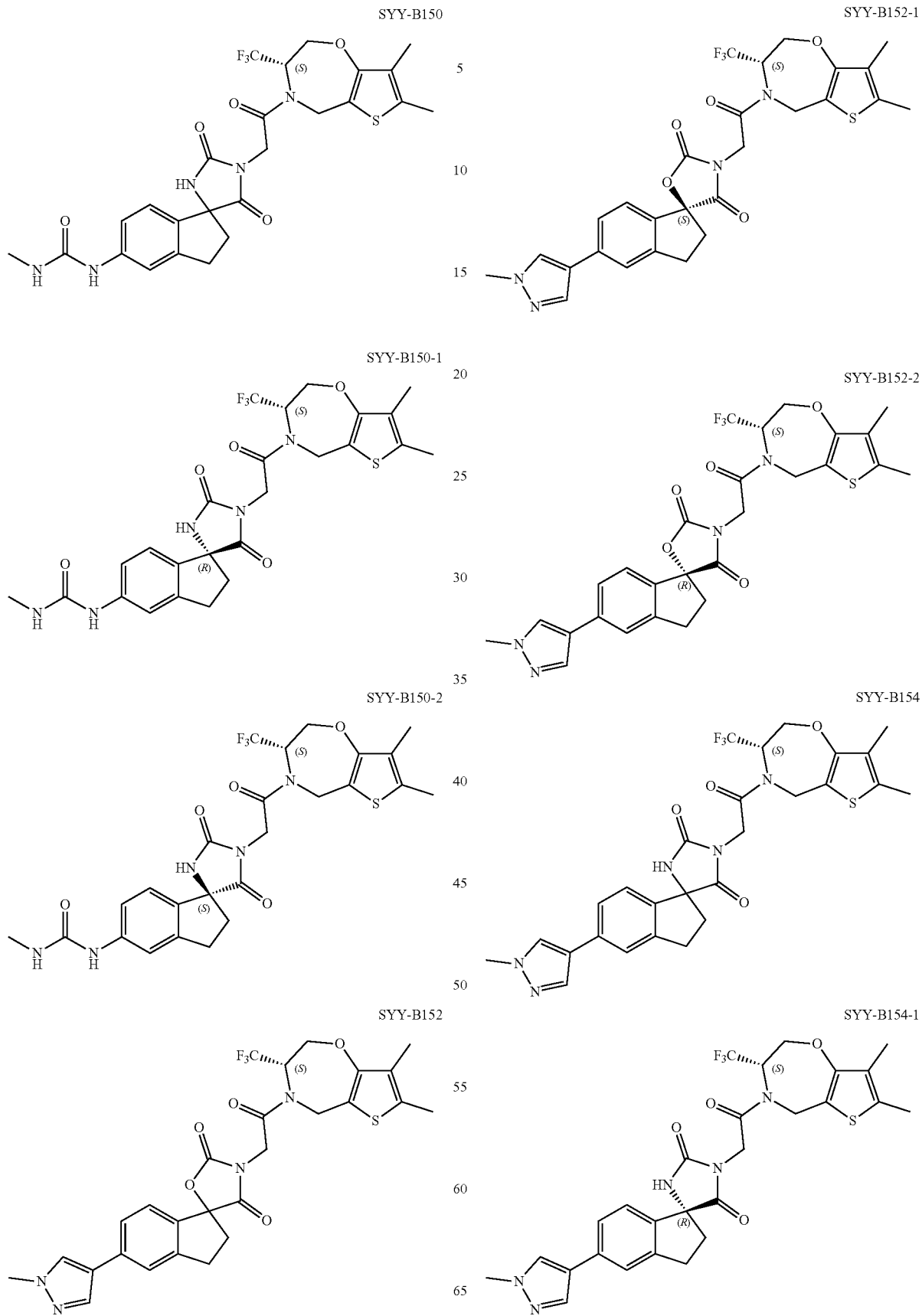

445
-continued
SYY-B154-2
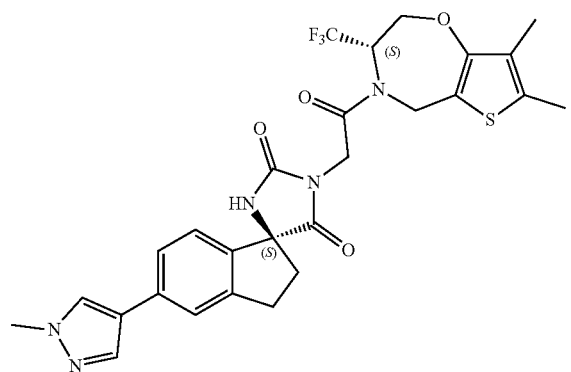
SYY-B155
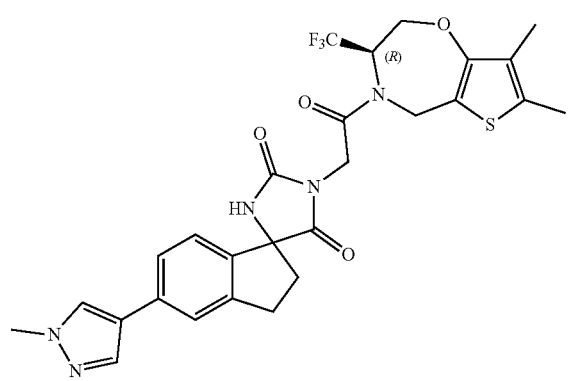
SYY-B155-1
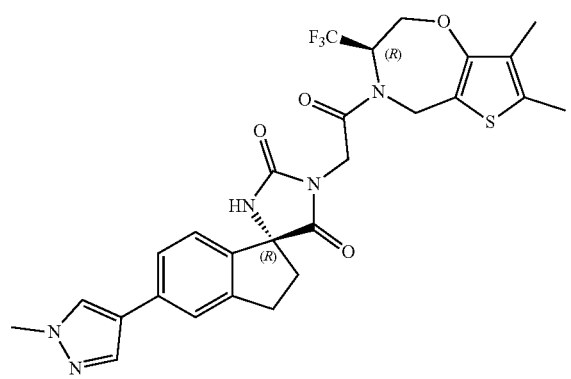
SYY-B155-2
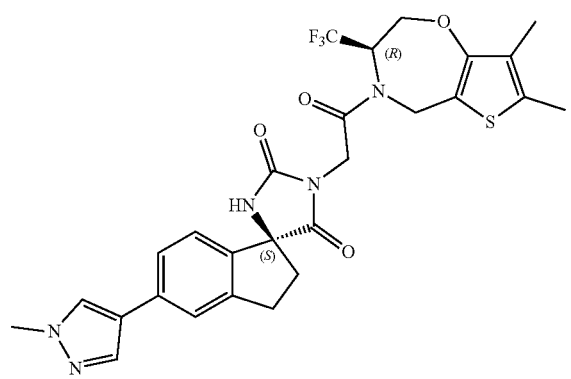
446
-continued
SYY-B156
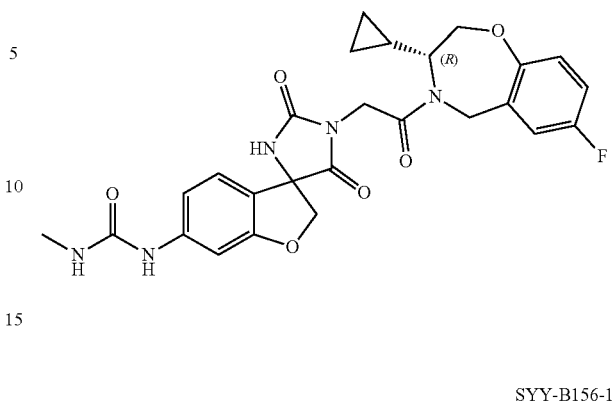
SYY-B156-1
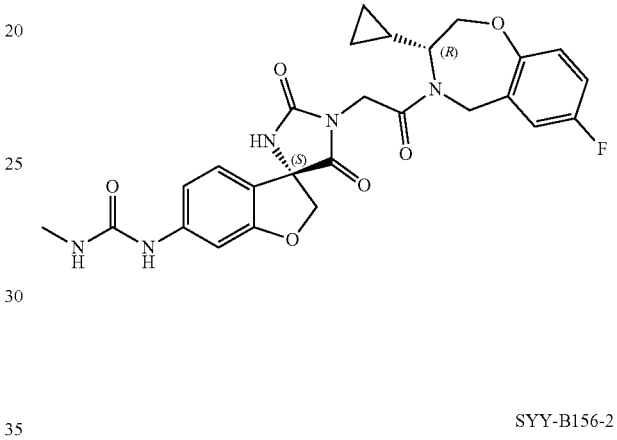
SYY-B156-2
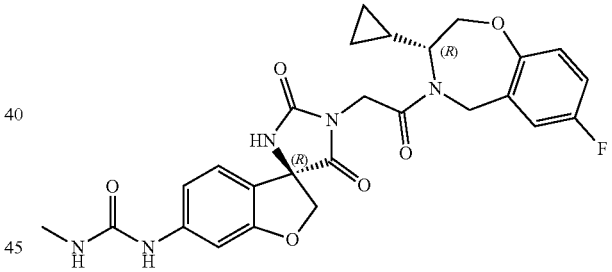
SYY-B161
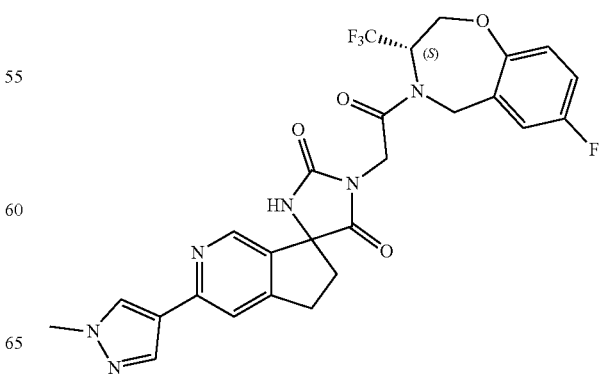

447
-continued
SYY-B161-1
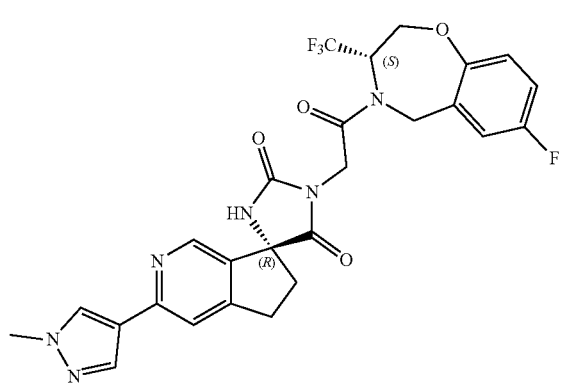
SYY-B161-2
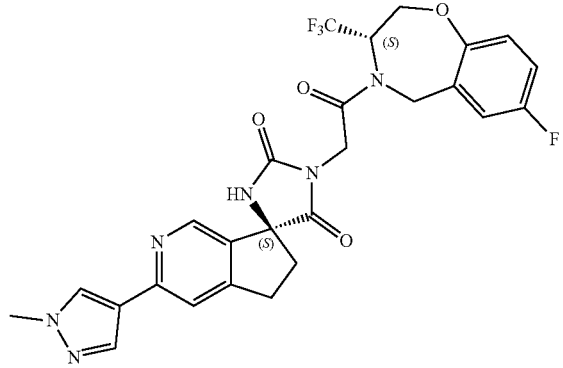
SYY-B163
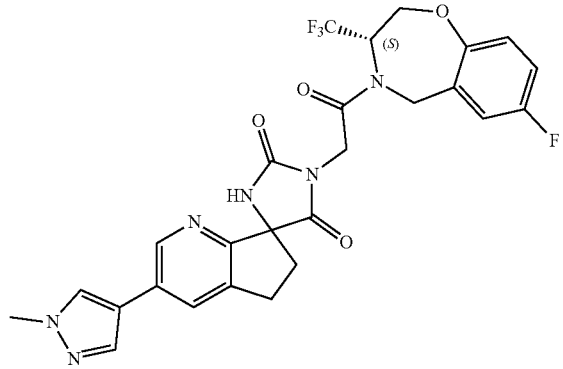
SYY-B163-1
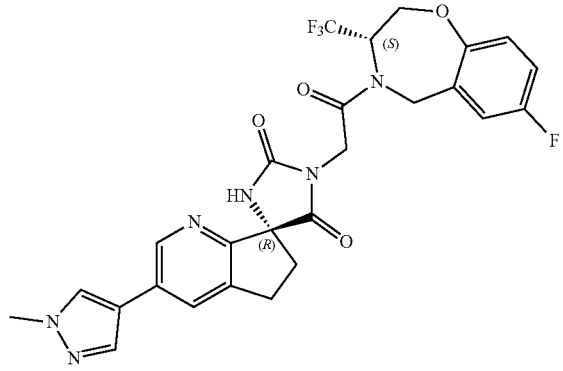
448
-continued
SYY-B163-2
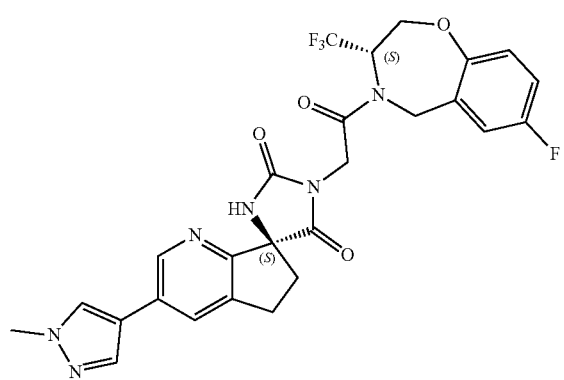
SYY-B165
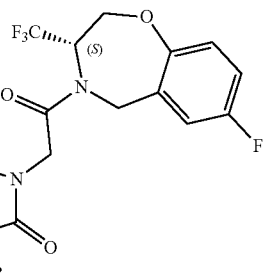
SYY-B165-1
(image continues)
and
SYY-B165-2
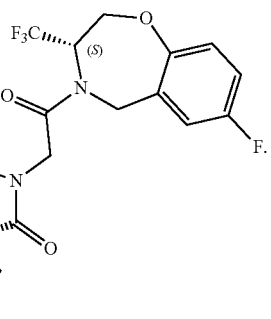
7. A pharmaceutical composition comprising a therapeutically effective amount of the compound according to claim 1, or a pharmaceutically acceptable salt, stereoisomer, enantiomer, diastereomer, atropisomer, racemate, polymorphs, solvate or isotopically labeled compound, and a pharmaceutically acceptable carrier, diluent or excipient.

8. The pharmaceutical composition according to claim 7, wherein the pharmaceutical composition further comprises at least one therapeutic agent.

9. A method of treating a disease, disorder or condition in a subject, comprising:
    administrating the compound, a pharmaceutically acceptable salt, stereoisomer, enantiomer, diastereomer, atropisomer, racemate, polymorphs, solvate or isotopically labeled compound thereof according to claim 1 to the subject,
    wherein the disease, disorder or condition is selected from the group consisting of acoustic neuroma, acute leukemia, basal cell carcinoma, cholangiocarcinoma, bladder cancer, brain cancer, breast cancer, bronchial cancer, Burkitt's lymphoma, cervical cancer, chondrosarcoma, chordoma, choriocarcinoma, chronic leukemia, colon cancer, colorectal cancer, craniopharyngioma, cystadenocarcinoma, diffuse large B-cell lymphoma, undesirable proliferative changes, embryonic cancer, endometrial cancer, epithelial cancer, erythroleukemia, esophageal cancer, estrogen receptor-positive breast cancer, essential thrombocythemia, Ewing's Sarcoma, fibrosarcoma, follicular lymphoma, germ cell testicular cancer, glioma, glioblastoma, gliosarcoma, heavy chain disease, hemangioblastoma, liver cancer, hepatocellular carcinoma, hormone-insensitive prostate cancer, leiomyosarcoma, liposarcoma, lung cancer, lymphatic endothelial sarcoma, lymphangiosarcoma, lymphoblastic leukemia, Lymphoma, lymphoma medullary carcinoma, medulloblastoma, melanoma, meningioma, mesothelioma, multiple myeloma, Myelogenous leukemia, myeloma, myxosarcoma, neuroblastoma, NUT midline carcinoma, non-small cell lung cancer, oligodendroglioma, oral cancer, osteogenic sarcoma, ovarian cancer, pancreatic cancer, papillary adenocarcinoma, papillary cancer, pineal gland tumor, polycythemia vera, prostate cancer, rectal cancer, renal cell carcinoma, retinoblastoma, rhabdomyosarcoma, sarcoma, sebaceous carcinoma, seminoma, skin cancer, stomach cancer, squamous cell carcinoma, synovial tumor, spiroma, thyroid cancer, primary macroglobulinemia, testicular tumor, uterine cancer and nephroblastoma,
    alternatively, the disease, disorder or condition is selected from the group consisting of a metabolic disease, a neurodegenerative disease and an inflammation.

10. A method of treating a disease, disorder or condition in a subject, comprising:
    administrating the pharmaceutical composition according to claim 7 to the subject, wherein the disease, disorder or condition is selected from the group consisting of acoustic neuroma, basal cell carcinoma, cholangiocarcinoma, bladder cancer, brain cancer, breast cancer, bronchial cancer, Burkitt's lymphoma, cervical cancer, chondrosarcoma, chordoma, choriocarcinoma, chronic leukemia, chronic lymphocytic leukemia, chronic myeloid leukemia, chronic myelogenous leukemia, colon cancer, colorectal cancer, craniopharyngioma, cystadenocarcinoma, diffuse large B-cell lymphoma, undesirable proliferative changes, embryonic cancer, endometrial cancer, epithelial cancer, erythroleukemia, esophageal cancer, estrogen receptor-positive breast cancer, essential thrombocythemia, Ewing's Sarcoma, fibrosarcoma, follicular lymphoma, germ cell testicular cancer, glioma, glioblastoma, gliosarcoma, heavy chain disease, hemangioblastoma, liver cancer, hepatocellular carcinoma, hormone-insensitive prostate cancer, leiomyosarcoma, liposarcoma, lung cancer, lymphatic endothelial sarcoma, lymphangiosarcoma, lymphoblastic leukemia, Lymphoma, lymphoma, medullary carcinoma, medulloblastoma, melanoma, meningioma, mesothelioma, multiple myeloma, Myelogenous leukemia, myeloma, myxosarcoma, neuroblastoma, NUT midline carcinoma, non-small cell lung cancer, oligodendroglioma, oral cancer, osteogenic sarcoma, ovarian cancer, pancreatic cancer, papillary adenocarcinoma, papillary cancer, pineal gland tumor, polycythemia vera, prostate cancer, rectal cancer, renal cell carcinoma, retinoblastoma, rhabdomyosarcoma, sarcoma, sebaceous carcinoma, seminoma, skin cancer, stomach cancer, squamous cell carcinoma, synovial tumor, spiroma, thyroid cancer, primary macroglobulinemia, testicular tumor, uterine cancer and nephroblastoma,
    alternatively, the disease, disorder or condition is selected from the group consisting of a metabolic disease, a neurodegenerative disease and an inflammation.

11. The pharmaceutical composition according to claim 8, wherein the at least one therapeutic agent comprised in the pharmaceutical composition is selected from the group consisting of anticancer agents, immunomodulators, antiallergic agents, antiemetics, pain relievers, cytoprotective agents, and combinations thereof.

12. A pharmaceutical composition comprising a therapeutically effective amount of the compound according to claim 6, or a pharmaceutically acceptable salt, stereoisomer, enantiomer, diastereomer, atropisomer, racemate, polymorphs, solvate or isotopically labeled compound thereof, and a pharmaceutically acceptable carrier, diluent or excipient.

13. A method of treating a disease, disorder or condition in a subject, comprising
    administrating the compound, a pharmaceutically acceptable salt, stereoisomer, enantiomer, diastereomer, atropisomer, racemate, polymorphs, solvate or isotopically labeled compound thereof according to claim 6 to the subject,
    wherein the disease, disorder or condition is selected from the group consisting of acoustic neuroma, acute leukemia, basal cell carcinoma, cholangiocarcinoma, bladder cancer, brain cancer, breast cancer, bronchial cancer, Burkitt's lymphoma, cervical cancer, chondrosarcoma, chordoma, choriocarcinoma, chronic leukemia, colon cancer, colorectal cancer, craniopharyngioma, cystadenocarcinoma, diffuse large B-cell lymphoma, undesirable proliferative changes, embryonic cancer, endometrial cancer, epithelial cancer, erythroleukemia, esophageal cancer, estrogen receptor-positive breast cancer, essential thrombocythemia, Ewing's Sarcoma, fibrosarcoma, follicular lymphoma, germ cell testicular cancer, glioma, glioblastoma, gliosarcoma, heavy chain disease, hemangioblastoma, liver cancer, hepatocellular carcinoma, hormone-insensitive prostate cancer, leiomyosarcoma, liposarcoma, lung cancer, lymphatic endothelial sarcoma, lymphangiosarcoma, lymphoblastic leukemia, Lymphoma, lymphoma, medullary carcinoma, medulloblastoma, melanoma, meningioma, mesothelioma, multiple myeloma, Myelogenous leukemia, myeloma, myxosarcoma, neuroblastoma, NUT midline carcinoma, non-small cell lung cancer, oligodendroglioma, oral cancer, osteogenic sarcoma, ovarian cancer, pancreatic cancer, papillary adenocarcinoma, papillary cancer, pineal gland tumor, polycythemia vera, prostate cancer, rectal cancer, renal cell carcinoma, retinoblastoma, rhabdomyosarcoma, sarcoma, sebaceous carcinoma, seminoma, skin cancer, stomach cancer, squamous cell carcinoma, synovial tumor, spiroma, thyroid cancer, primary macroglobulinemia, testicular tumor, uterine cancer and nephroblastoma, alternatively, the disease, disorder or condition is selected from the group consisting of a metabolic disease, a neurodegenerative disease and an inflammation.

14. A method of treating a disease, disorder or condition in a subject, comprising
administrating the pharmaceutical composition according to claim 12 to the subject, wherein the disease, disorder or condition is selected from the group consisting of acoustic neuroma, acute leukemia, basal cell carcinoma, cholangiocarcinoma, bladder cancer, brain cancer, breast cancer, bronchial cancer, Burkitt's lymphoma, cervical cancer, chondrosarcoma, chordoma, choriocarcinoma, chronic leukemia, chronic lymphocytic leukemia, chronic myeloid leukemia, chronic myelogenous leukemia, colon cancer, colorectal cancer, craniopharyngioma, cystadenocarcinoma, diffuse large B-cell lymphoma, undesirable proliferative changes, embryonic cancer, endometrial cancer, epithelial cancer, erythroleukemia, esophageal cancer, estrogen receptor-positive breast cancer, essential thrombocythemia, Ewing's Sarcoma, fibrosarcoma, follicular lymphoma, germ cell testicular cancer, glioma, glioblastoma, gliosarcoma, heavy chain disease, hemangioblastoma, liver cancer, hepatocellular carcinoma, hormone-insensitive prostate cancer, leiomyosarcoma, liposarcoma, lung cancer, lymphatic endothelial sarcoma, lymphangiosarcoma, lymphoblastic leukemia, Lymphoma, lymphoma, medullary carcinoma, medulloblastoma, melanoma, meningioma, mesothelioma, multiple myeloma, Myelogenous leukemia, myeloma, myxosarcoma, neuroblastoma, NUT midline carcinoma, non-small cell lung cancer, oligodendroglioma, oral cancer, osteogenic sarcoma, ovarian cancer, pancreatic cancer, papillary adenocarcinoma, papillary cancer, pineal gland tumor, polycythemia vera, prostate cancer, rectal cancer, renal cell carcinoma, retinoblastoma, rhabdomyosarcoma, sarcoma, sebaceous carcinoma, seminoma, skin cancer, stomach cancer, squamous cell carcinoma, synovial tumor, spiroma, thyroid cancer, primary macroglobulinemia, testicular tumor, uterine cancer and nephroblastoma, alternatively, the disease, disorder or condition is selected from the group consisting of a metabolic disease, a neurodegenerative disease and an inflammation.

15. A pharmaceutical composition comprising a therapeutically effective amount of the compound according to claim 5, or a pharmaceutically acceptable salt, stereoisomer, enantiomer, diastereomer, atropisomer, racemate, polymorphs, solvate or isotopically labeled compound thereof, and a pharmaceutically acceptable carrier, diluent or excipient.

16. A method of treating a disease, disorder or condition in a subject, comprising
administrating the compound, a pharmaceutically acceptable salt, stereoisomer, enantiomer, diastereomer, atropisomer, racemate, polymorphs, solvate or isotopically labeled compound thereof according to claim 5 to the subject,
wherein the disease, disorder or condition is selected from the group consisting of acoustic neuroma, acute leukemia, basal cell carcinoma, cholangiocarcinoma, bladder cancer, brain cancer, breast cancer, bronchial cancer, Burkitt's lymphoma, cervical cancer, chondrosarcoma, chordoma, choriocarcinoma, chronic leukemia, chronic lymphocytic leukemia, chronic myeloid leukemia, chronic myelogenous leukemia, colon cancer, colorectal cancer, craniopharyngioma, cystadenocarcinoma, diffuse large B-cell lymphoma, undesirable proliferative changes, embryonic cancer, endometrial cancer, epithelial cancer, erythroleukemia, esophageal cancer, estrogen receptor-positive breast cancer, essential thrombocythemia, Ewing's Sarcoma, fibrosarcoma, follicular lymphoma, germ cell testicular cancer, glioma, glioblastoma, gliosarcoma, heavy chain disease, hemangioblastoma, liver cancer, hepatocellular carcinoma, hormone-insensitive prostate cancer, leiomyosarcoma, liposarcoma, lung cancer, lymphatic endothelial sarcoma, lymphangiosarcoma, lymphoblastic leukemia, Lymphoma, lymphoma, medullary carcinoma, medulloblastoma, melanoma, meningioma, mesothelioma, multiple myeloma, Myelogenous leukemia, myeloma, myxosarcoma, neuroblastoma, NUT midline carcinoma, non-small cell lung cancer, oligodendroglioma, oral cancer, osteogenic sarcoma, ovarian cancer, pancreatic cancer, papillary adenocarcinoma, papillary cancer, pineal gland tumor, polycythemia vera, prostate cancer, rectal cancer, renal cell carcinoma, retinoblastoma, rhabdomyosarcoma, sarcoma, sebaceous carcinoma, seminoma, skin cancer, stomach cancer, squamous cell carcinoma, synovial tumor, spiroma, thyroid cancer, primary macroglobulinemia, testicular tumor, uterine cancer and nephroblastoma, alternatively, the disease, disorder or condition is selected from the group consisting of a metabolic disease, a neurodegenerative disease and an inflammation.

17. A method of treating a disease, disorder or condition in a subject, comprising
administrating the pharmaceutical composition according to claim 15 to the subject, wherein the disease, disorder or condition is selected from the group consisting of acoustic neuroma, acute leukemia, basal cell carcinoma, cholangiocarcinoma, bladder cancer, brain cancer, breast cancer, bronchial cancer, Burkitt's lymphoma, cervical cancer, chondrosarcoma, chordoma, choriocarcinoma, chronic leukemia, colon cancer, colorectal cancer, craniopharyngioma, cystadenocarcinoma, diffuse large B-cell lymphoma, undesirable proliferative changes, embryonic cancer, endometrial cancer, epithelial cancer, erythroleukemia, esophageal cancer, estrogen receptor-positive breast cancer, essential thrombocythemia, Ewing's Sarcoma, fibrosarcoma, follicular lymphoma, germ cell testicular cancer, glioma, glioblastoma, gliosarcoma, heavy chain disease, hemangioblastoma, liver cancer, hepatocellular carcinoma, hormone-insensitive prostate cancer, leiomyosarcoma, liposarcoma, lung cancer, lymphatic endothelial sarcoma, lymphangiosarcoma, lymphoblastic leukemia, Lymphoma, lymphoma, medullary carcinoma, medulloblastoma, melanoma, meningioma, mesothelioma, multiple myeloma, Myelogenous leukemia, myeloma, myxosarcoma, neuroblastoma, NUT midline carcinoma-(—NM), non-small cell lung cancer, oligodendroglioma, oral cancer, osteogenic sarcoma, ovarian cancer, pancreatic cancer, papillary adenocarcinoma, papillary cancer, pineal gland tumor, polycythemia vera, prostate cancer, rectal cancer, renal cell carcinoma, retinoblastoma, rhabdomyosarcoma, sarcoma, sebaceous carcinoma, seminoma, skin cancer, stomach cancer, squamous cell carcinoma, synovial tumor, spiroma, thyroid cancer, primary macroglobulinemia, testicular tumor, uterine cancer and nephroblastoma, alternatively, the disease, disorder or condition is selected from the group consisting of a metabolic disease, a neurodegenerative disease and an inflammation.

\* \* \* \* \*

UNITED STATES PATENT AND TRADEMARK OFFICE
CERTIFICATE OF CORRECTION

PATENT NO. : 12,172,989 B2
APPLICATION NO. : 17/075206
DATED : December 24, 2024
INVENTOR(S) : Bing Zhou et al.

It is certified that error appears in the above-identified patent and that said Letters Patent is hereby corrected as shown below:

On the Title Page

Item (30) reads:
"Foreign Application Priority Data
Apr. 20, 2018 (CN) ............ 201810360078
Aug. 31, 2018 (CN) ............ 201811012724"

Should read:
--Foreign Application Priority Data
Apr. 20, 2018 (CN) ............ 201810360078.2
Aug. 31, 2018 (CN) ............ 201811012724.2--

In the Claims

Claim 1, Line 38 reads:
"$(R^c)_2$, -NHC(=O)NR$^c$S(O)$^2$OR$^c$, -NHC(=O)"

Should read:
--$(R^c)_2$, -NHC(=O)NR$^c$S(O)$_2$OR$^c$, -NHC(=O)--

Claim 1, Line 40 reads:
"(=NC≡N)NR$^c$, NHC(=NC≡N)SR$^c$, -NHS(O)$_{n1}$R$^c$,"

Should read:
--(=NC≡N)NR$^c$, -NHC(=NC≡N)SR$^c$, -NHS(O)$_{n1}$R$^c$,--

Claim 5, Line 45 reads:
"$(R^c)_2$, -(C$_1$-C$_6$ alkylene)-NHC(=N-CEN)NR$^c$,"

Signed and Sealed this
Thirteenth Day of May, 2025

Coke Morgan Stewart
*Acting Director of the United States Patent and Trademark Office*

CERTIFICATE OF CORRECTION (continued)
U.S. Pat. No. 12,172,989 B2

Should read:
--(R$^c$)$_2$, -(C$_1$-C$_6$ alkylene)-NHC(=N-C≡N)NR$^c$,--

Claim 5, Line 49 reads:
"-SM$^c$, or -N(R$^c$)M$^c$ at each occurrence:"

Should read:
-- -SM$^c$, or -N(R$^c$)M$^c$ at each occurrence;--

Claim 6, Line 196 figure SYY-B106-2 reads:

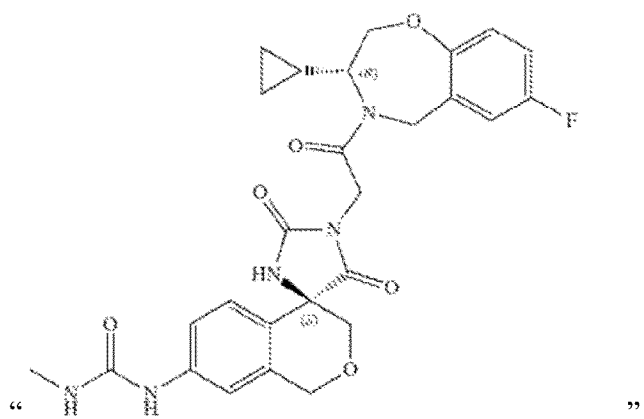

"                                              "

Should read:

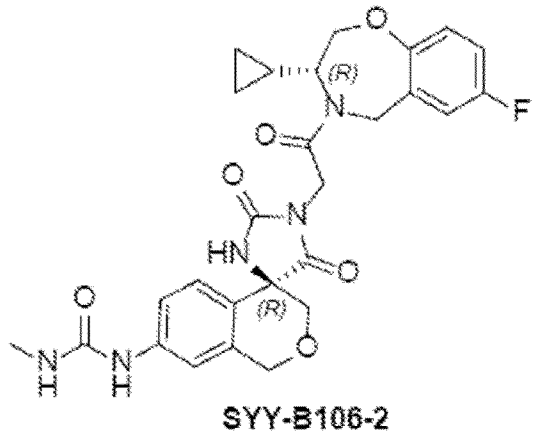

--                                             --

Claim 9, Line 27 reads:
"lymphoma medullary carcinoma, medulloblastoma,"

Should read:
--lymphoma, medullary carcinoma, medulloblastoma,--

Claim 17, Line 27 reads:
"midline carcinoma-(-NM), non-small cell lung can-"

CERTIFICATE OF CORRECTION (continued)
U.S. Pat. No. 12,172,989 B2

Should read:
--midline carcinoma, non-small cell lung can- --